(12) United States Patent
Burgess et al.

(10) Patent No.: US 6,989,232 B2
(45) Date of Patent: Jan. 24, 2006

(54) PROTEINS AND NUCLEIC ACIDS ENCODING SAME

(75) Inventors: Catherine E. Burgess, Wethersfield, CT (US); Pamela B. Conley, Palo Alto, CA (US); William M. Grosse, Branford, CT (US); Matthew Hart, San Francisco, CA (US); Ramesh Kekuda, Stamford, CT (US); Richard A. Shimkets, West Haven, CT (US); Kimberly A. Spytek, New Haven, CT (US); Edward Szekeres, Jr., Branford, CT (US); James E. Tomlinson, Burlingame, CA (US); James N. Topper, Los Altos, CA (US); Ruey-Bin Yang, San Mateo, CA (US)

(73) Assignees: Millennium Pharmaceuticals, Inc., Cambridge, MA (US); Curagen Corporation, New Haven, CT (US)

(*) Notice: Subject to any disclaimer, the term of this patent is extended or adjusted under 35 U.S.C. 154(b) by 339 days.

(21) Appl. No.: 09/939,853

(22) Filed: Aug. 27, 2001

(65) Prior Publication Data

US 2004/0039163 A1 Feb. 26, 2004

Related U.S. Application Data

(60) Provisional application No. 60/228,191, filed on Aug. 25, 2000, provisional application No. 60/267,300, filed on Feb. 8, 2001, provisional application No. 60/269,961, filed on Feb. 20, 2001, and provisional application No. 60/277,337, filed on Mar. 20, 2001.

(51) Int. Cl.
*C12Q 1/68* (2006.01)

(52) U.S. Cl. ............... 435/6; 435/252.3; 435/320.1; 435/325; 435/252.33; 514/44; 536/23.1; 536/23.5

(58) Field of Classification Search ............... 536/23.1, 536/23.5, 23.2; 514/44; 435/6, 320.1, 325, 435/252.3, 252.33
See application file for complete search history.

(56) References Cited

U.S. PATENT DOCUMENTS 4,350,764 A * 9/1982 Baxter et al. ............... 435/69.4

FOREIGN PATENT DOCUMENTS

| EP | 1033401 | 6/2000 |
|----|---------|--------|
| EP | 1033405 | 6/2000 |
| EP | 1074617 | 7/2001 |
| WO | WO 00/09552 | 2/2000 |

OTHER PUBLICATIONS

GenBank Accession No. AC026539 (Apr. 27, 2000).*
Pharmacia P–L Biochemicals 1984 Product Reference Guide (pp. 36–37).*
Adams et al, Nature 377 (Suppl), 3 (1995).*
Nakayama et al, Genomics 51(1), 27(1998).*
Mahairas et al, Accession No. B45150 (Oct. 21, 1997).*
Wallace et al, Methods Enzymol. 152: 432 (1987).*
GenBank Accession No.: CAB01233 (Jun. 20, 2001).
SWALL (SPTR) Accession No.: Q9N4G7 (Oct. 1, 2000).
GenBank Accession No.: Z77666 (Jun. 20, 2001).
GenBank Accession No.: XM_038002 (Oct. 16, 2001).
GenBank Accession No.: XM_039746 (Oct. 16, 2001).
GenBank Accession No.: AAF51854 (Oct. 4, 2000).
GenBank Accession No.: AAF52569 (Oct. 4, 2000).
GenBank Accession No.: AAF53188 (Oct. 4, 2000).
GenBank Accession No.: AAF55108 (Oct. 5, 2000).
GenBank Accession No.: AAF58048 (Oct. 4, 2000).
GenBank Accession No.: AAF59281 (Oct. 4, 2000).
GenBank Accession No.: AE003598 (Oct. 4, 2000).
GenBank Accession No.: AE003619 (Oct. 4, 2000).
GenBank Accession No.: AE003636 (Oct. 4, 2000).
GenBank Accession No.: AE003706 (Oct. 5, 2000).
GenBank Accession No.: AE003808 (Oct. 4, 2000).
GenBank Accession No.: AE003842 (Oct. 4, 2000).
SWALL (SPTR) Accession No.: Q9V419 (May 1, 2000).
SWALL (SPTR) Accession No.: Q9V7K1 (May 1, 2000).
SWALL (SPTR) Accession No.: Q9VFF2 (May 1, 2000).
SWALL (SPTR) Accession No.: Q9VK90 (May 1, 2000).
SWALL (SPTR) Accession No.: Q9VLW2 (May 1, 2000).
SWALL (SPTR) Accession No.: Q9VNR8 (May 1, 2000).
GenBank Accession No.: U72744 (Feb. 1, 1997).
Alderborn, et al. (2000). "Determination of single–nucleotide polymorphisms by real–time pyrophosphate DNA sequencing." *Genome Res.* 10(8): 1249–1258.
Alessi, et al. (1997). "3–Phosphoinositide–dependent protein kinase–1 (PDK1): structural and functional homology with the Drosophila DSTPK61 kinase." *Curr. Biol.* 7(10): 776–789.
Alessi, et al. (1997). "Characterization of a 3–phosphoinositide–dependent protein kinase which phosphorylates and activates protein kinase Balpha." *Curr. Biol.* 7(4): 261–269.
GenBank Accession No.: AAC50357 (Sep. 12, 2000).
GenBank Accession No.: U30473 (Sep. 12, 2000).
SWALL (SPTR) Accession No.: Q13239 (Nov. 1, 1996).
GenBank Accession No.: AAC48618 (Aug. 22, 1996).

(Continued)

*Primary Examiner*—James Martinell
(74) *Attorney, Agent, or Firm*—Millennium Pharmaceuticals, Inc.

(57) ABSTRACT

Disclosed herein are nucleic acid sequences that encode novel polypeptides. Also disclosed are polypeptides encoded by these nucleic acid sequences, and antibodies, which immunospecifically-bind to the polypeptide, as well as derivatives, variants, mutants, or fragments of the aforementioned polypeptide, polynucleotide, or antibody. The invention further discloses therapeutic, diagnostic and research methods for diagnosis, treatment, and prevention of disorders involving any one of these novel human nucleic acids and proteins.

38 Claims, No Drawings

OTHER PUBLICATIONS

GenBank Accession No.: AAC50646 (Aug. 22, 1996).
GenBank Accession No.: U23028 (Aug. 22, 1996).
GenBank Accession No.: AL035424 (Nov. 23, 1999).
GenBank Accession No.: CAB39994 (Nov. 23, 1999).
SWALL (SPTR) Accession No.: Q9C0H6 (Oct. 16, 2001).
SWALL (SPTR) Accession No.: Q9Y3J5 (Oct. 16, 2001).
Burn, et al. (1996). "Generation of a transcriptional map for a 700–kb region surrounding the polycystic kidney disease type 1 (PKD1) and tuberous sclerosis type 2 (TSC2) disease genes on human chromosome 16p3.3." *Genome Res.* 6(6): 525–537.
GenBank Accession No.: AK003661 (Jul. 5, 2001).
GenBank Accession No.: AK005100 (Jul. 5, 2001).
GenBank Accession No.: AK007036 (Jul. 5, 2001).
GenBank Accession No.: AK010359 (Jul. 5, 2001).
GenBank Accession No.: AK018438 (Jul. 5, 2001).
GenBank Accession No.: AK018708 (Jul. 5, 2001).
GenBank Accession No.: AK020837 (Jul. 5, 2001).
GenBank Accession No.: BAB22923 (Jul. 5, 2001).
GenBank Accession No.: BAB23818 (Jul. 5, 2001).
GenBank Accession No.: BAB24835 (Jul. 5, 2001).
GenBank Accession No.: BAB26879 (Jul. 5, 2001).
GenBank Accession No.: BAB31212 (Jul. 5, 2001).
GenBank Accession No.: BAB31359 (Jul. 5, 2001).
GenBank Accession No.: BAB32223 (Jul. 5, 2001).
SWALL (SPTR) Accession No.: Q9SN75 (May 1, 2000).
GenBank Accession No.: AL132955 (Nov. 30, 1999).
GenBank Accession No.: CAB61989 (Nov. 30, 1999).
GenBank Accession No.: AAB46616 (Feb. 10, 1997).
GenBank Accession No.: P33527 (Mar. 1, 2001).
GenBank Accession No.: D64005 (Oct. 8, 1999).
GenBank Accession No.: AAB17690 (Oct. 30, 1996).
GenBank Accession No.: U19516 (Oct. 30, 1996).
GenBank Accession No.: AAB83979 (Nov. 6, 1997).
GenBank Accession No.: AAB83983 (Nov. 6, 1997).
GenBank Accession No.: AF022853 (Nov. 8, 1997).
SWALL (SPTR) Accession No.: Q9UQ99 (May 1, 2000).
GenBank Accession No.: AJ251892 (Dec. 22, 1999).
GenBank Accession No.: CAB64381 (Dec. 22, 1999).
SWALL (SPTR) Accession No.: Q9U111 (May 1, 2000).
Gubb and Garcia–Bellido (1982). "A genetic analysis of the determination of cuticular polarity during development in Drosophila melanogaster." *J. Embryol. Exp. Morphol.* 68: 37–57.
GenBank Accession No.: AAD55929 (Sep. 21, 1999).
GenBank Accession No.: AF148265 (Sep. 21, 1999).
SWALL (SPTR) Accession No.: Q9RPT3 (May 1, 2000).
GenBank Accession No.: AAB59366 (Aug. 3, 1993).
GenBank Accession No.: CAA32889 (Mar. 31, 1995).
GenBank Accession No.: BAA28955 (Jun. 20, 1998).
GenBank Accession No.: AB036840 (Jul. 15, 2000).
GenBank Accession No.: AB036841 (Jul. 15, 2000).
GenBank Accession No.: BAB00617 (Jul. 15, 2000).
GenBank Accession No.: BAB00618 (Jul. 15, 2000).
SWALL (SPTR) Accession No.: Q9NDQ8 (Oct. 1, 2000).
SWALL (SPTR) Accession No.: Q9NDQ9 (Oct. 1, 2000).
Hoyt (1994). "Cellular roles of kinesin and related proteins." *Curr. Opin. Cell Biol.* 6(1): 63–68.
GenBank Accession No.: AAF17300 (Dec. 14, 1999).
GenBank Accession No.: AF108229 (Dec. 14, 1999).
SWALL (SPTR) Accession No.: Q9U541 (May 1, 2000).
Hurd and Saxton (1996). "Kinesin mutations cause motor neuron disease phenotypes by disrupting fast axonal transport in Drosophila." *Genetics* 144(3): 1075–1085.
SWALL (SPTR) Accession No.: Q9H875 (Mar. 1, 2000).
SWALL (SPTR) Accession No.: Q9H955 (Mar. 1, 2000).
GenBank Accession No.: AK001921 (Feb. 22, 2000).
GenBank Accession No.: AK021895 (Sep. 29, 2000).
GenBank Accession No.: AK023057 (Sep. 29, 2000).
GenBank Accession No.: AK023964 (Sep. 29, 2000).
GenBank Accession No.: BAB14382 (Sep. 29, 2000).
GenBank Accession No.: BAB14742 (Sep. 29, 2000).
SWALL (SPTR) Accession No.: Q55909 (Nov. 1, 1997).
GenBank Accession No.: BAA10672 (Jul. 4, 2001).
GenBank Accession No.: AK025645 (Sep. 29, 2000).
GenBank Accession No.: BAB15201 (Sep. 29, 2000).
SWALL (SPTR) Accession No.: Q9H6Q3 (May 1, 2001).
SWALL (SPTR) Accession No.: Q9CQZ1 (Jun. 1, 2001).
SWALL (SPTR) Accession No.: Q9CVQ1 (Jun. 1, 2001).
SWALL (SPTR) Accession No.: Q9CW36 (Jun. 1, 2001).
SWALL (SPTR) Accession No.: Q9CWV6 (Jun. 1, 2001).
SWALL (SPTR) Accession No.: Q9CXA5 (Jun. 1, 2001).
SWALL (SPTR) Accession No.: Q9CY32 (Jun. 1, 2001).
SWALL (SPTR) Accession No.: Q9D1E2 (Jun. 1, 2001).
SWALL (SPTR) Accession No.: Q9D1Z9 (Jun. 1, 2001).
GenBank Accession No.: O15438 (Aug. 20, 2001).
GenBank Accession No.: BAA28146 (Feb. 13, 1999).
GenBank Accession No.: AAA36741 (Sep. 15, 1994).
GenBank Accession No.: M25631 (Sep. 15, 1994).
GenBank Accession No.: CAA76658 (May 12, 1999).
GenBank Accession No.: AAD01430 (Jun. 22, 1999).
GenBank Accession No.: AAA61178 (Jan. 14, 1995).
GenBank Accession No.: CAA28370 (Mar 21, 1995).
GenBank Accession No.: P07996 (Aug. 20, 2001).
GenBank Accession No.: AAF02111 (Jan. 24, 2001).
GenBank Accession No.: AC009755 (Jan. 24, 2001).
GenBank Accession No.: AAC12836 (Apr. 5, 2000).
GenBank Accession No.: AC004238 (Apr. 5, 2000).
SWALL (SPTR) Accession No.: O64760 (Aug. 1, 1998).
SWALL (SPTR) Accession No.: Q9SRU3 (May 1, 2001).
GenBank Accession No.: AL050318 (Jul. 20, 2001).
GenBank Accession No.: CAB75365 (Jul. 20, 2001).
SWALL (SPTR) Accession No.: Q9H135 (May 1, 2001).
GenBank Accession No.: AAC27662 (Jul. 28, 1998).
GenBank Accession No.: AB054031 (Jul. 27, 2001).
GenBank Accession No.: BAB32487 (Jul. 27, 2001).
SWALL (SPTR) Accession No.: Q99PT4 (Jun. 1, 2001).
SWALL (SPTR) Accession No.: Q99PU2 (Jun. 1, 2001).
GenBank Accession No.: BAB32495 (Jun. 27, 2001).
GenBank Accession No.: Z92844 (Nov. 23, 1999).
Moore and Endow (1995). "Kinesin proteins: a phylum of motors for microtubule–based motility." *Bioessays* 18(3): 207–219.
GenBank Accession No.: AAD09622 (Jul. 14, 1999).
GenBank Accession No.: AF111168 (Jul. 14, 1999).
GenBank Accession No.: O95432 (May 1, 1999).
GenBank Accession No.: AB033062 (Nov. 11, 1999).
GenBank Accession No.: AB046863 (Feb. 22, 2001).
GenBank Accession No.: AB051474 (Feb. 7, 2001).
GenBank Accession No.: BAA86550 (Nov. 11, 1999).
GenBank Accession No.: BAB13469 (Feb. 22, 2001).
GenBank Accession No.: BAB21778 (Feb. 7, 2001).
SWALL (SPTR) Accession No.: Q9ULI4 (May 1, 2000).
SWALL (SPTR) Accession No.: Q9HCC9 (Mar. 1, 2000).
GenBank Accession No.: AAF81717 (Jul. 5, 2000).

GenBank Accession No.: AAF81719 (Jul. 5, 2000).
GenBank Accession No.: AF252281 (Jul. 4, 2000).
GenBank Accession No.: AF252283 (Jul. 4, 2000).
GenBank Accession No.: BAA13758 (Feb. 7, 1999).
Online Inheritance in Man OMIM: 116806 (Jun. 16, 1994).
Online Inheritance in Man OMIM: 127600 (Jun. 4, 1986).
Online Inheritance in Man OMIM: 171190 (Jun. 29, 1988).
Online Inheritance in Man OMIM: 175100 (Jun. 2, 1986).
Online Inheritance in Man OMIM: 176705 (Aug. 6, 1991).
Online Inheritance in Man OMIM: 176807 (Feb. 7, 1992).
Online Inheritance in Man OMIM: 178000 (Jun. 2, 1986).
Online Inheritance in Man OMIM: 184757 (Jun. 21, 1994).
Online Inheritance in Man OMIM: 232200 (Jun. 3, 1986).
Online Inheritance in Man OMIM: 300011 (Feb. 4, 1996).
Online Inheritance in Man OMIM: 300189 (May 18, 1999).
Online Inheritance in Man OMIM: 311800 (Jun. 24, 1986).
Online Inheritance in Man OMIM: 314250 (Jun. 4, 1986).
Online Inheritance in Man OMIM: 314580 (Jun. 4, 1986).
Online Inheritance in Man OMIM: 601014 (Jan. 23, 1996).
Online Inheritance in Man OMIM: 601462 (Oct. 9, 1996).
Online Inheritance in Man OMIM: 603030 (Sep. 11, 1998).
Online Inheritance in Man OMIM: 604050 (Jul. 22, 1999).
Online Inheritance in Man OMIM: 604054 (Jul. 22, 1999).
GenBank Accession No.: AAC25416 (Jul. 2, 1998).
SWALL (SPTR) Accession No.: O88563 (Jul. 15, 1999).
GenBank Accession No.: AAA82756 (Aug. 31, 1995).
SWALL (SPTR) Accession No.: Q60898 (Nov. 1, 1996).
GenBank Accession No.: U29056 (Dec. 4, 1995).
GenBank Accession No.: AP003044 (Jan. 26, 2001).
GenBank Accession No.: BAB19328 (Jan. 26, 2001).
SWALL (SPTR) Accession No.: Q9FP22 (May 1, 2000).
GenBank Accession No.: AAC25186 (Dec. 12, 2000).
GenBank Accession No.: AF068754 (Dec. 12, 2000).
GenBank Accession No.: AAD10191 (Jan. 28, 1999).
GenBank Accession No.: AF102777 (Jan. 28, 1999).
SWALL (SPTR) Accession No.: Q9Z1T6 (May 30, 2000).
GenBank Accession No.: AL158075 (Jun. 21, 2001).
GenBank Accession No.: AL050320 (Apr. 4, 2001).
GenBank Accession No.: CAC36074 (Apr. 4, 2001).
SWALL (SPTR) Accession No.: Q9BQL4 (Jun. 1, 2000).
SWALL (SPTR) Accession No.: Q9U3B7 (May 1, 2000).

GenBank Accession No.: AAC48313 (Apr. 17, 1998).
SWALL (SPTR) Accession No.: Q23832 (Nov. 1, 1996).
GenBank Accession No.: U42213 (Apr. 17, 1998).
GenBank Accession No.: AAH01130 (Jul. 12, 2001).
GenBank Accession No.: AAH05999 (Jul. 12, 2001).
GenBank Accession No.: BC005999 (Jul. 12, 2001).
SWALL (SPTR) Accession No.: Q9BQ24 (Jun. 1, 2001).
GenBank Accession No.: AAB80938 (Oct. 13, 1997).
GenBank Accession No.: AF022908 (Oct. 13, 1997).
SWALL (SPTR) Accession No.: O35379 (Jan. 1, 1998).
SWALL (SPTR) Accession No.: O76007 (Nov. 1, 1998).
GenBank Accession No.: AJ011654 (Oct. 14, 1998).
GenBank Accession No.: CAA09726 (Oct. 14, 1998).
GenBank Accession No.: AAF36018 (Nov. 3, 2001).
GenBank Accession No.: AC024201 (Nov. 3, 2001).
GenBank Accession No.: AAC72122 (Sep. 26, 2001).
GenBank Accession No.: AC005278 (Sep. 26, 2001).
SWALL (SPTR) Accession No.: Q9ZVS7 (May 1, 1999).
Wijnholds, et al. (1997). "Increased sensitivity to anticancer drugs and decreased inflammatory response in mice lacking the multidrug resistance–associated protein." *Nat. Med.* *3*(11): 1275–1279.
GenBank Accession No.: AL133463 (Mar. 15, 2001).
GenBank Accession No.: CAC16127 (Mar. 15, 2001).
SWALL (SPTR) Accession No.: Q9H599 (Mar. 1, 2001).
SWALL (SPTR) GenBank Accession No.: O74339 (Nov. 1, 1998).
GenBank Accession No.: AL031174 (Feb. 1, 2000).
GenBank Accession No.: CAA20110 (Feb. 1, 2000).
Klein, et al. "Selection for genes encoding secreted proteins and receptors" *Proc. Natl. Acad. Sci. USA* 93:7108–7113.
International Search Report for PCT US 01/26510, mailed Sep. 12, 2002.
Nagase, et al. (1999). "Prediction of the coding sequences of unidentified human genes. XV. The complete sequences of 100 new cDNA clones from brain which code for large proteins in vitro." *DNA Research.* *6:*337–345.
International Search Report for PCT/US01/26510. Mailed on Mar. 5, 2003.

* cited by examiner

PROTEINS AND NUCLEIC ACIDS ENCODING SAME

RELATED APPLICATIONS

This application claims priority from Provisional Applications U.S. Ser. No. 60/228,191, filed Aug. 25, 2000, U.S. Ser. No. 60/267,300, filed Feb. 8, 2001, U.S. Ser. No. 60/269,961, filed Feb. 20, 2001, and U.S. Ser. No. 60/277,337, filed Mar. 20, 2001, each of which is incorporated by reference in its entirety.

FIELD OF THE INVENTION

The invention generally relates to novel nucleic acids and polypeptides encoded thereby.

BACKGROUND OF THE INVENTION

Eukaryotic cells are subdivided by membranes into multiple functionally distinct compartments that are referred to as organelles. Each organelle includes proteins essential for its proper function. These proteins can include sequence motifs often referred to as sorting signals. The sorting signals can aid in targeting the proteins to their appropriate cellular organelle. In addition, sorting signals can direct some proteins to be exported, or secreted, from the cell.

One type of sorting signal is a signal sequence, which is also referred to as a signal peptide or leader sequence. The signal sequence is present as an amino-terminal extension on a newly synthesized polypeptide chain. A signal sequence can target proteins to an intracellular organelle called the endoplasmic reticulum ("ER").

The signal sequence takes part in an array of protein-protein and protein-lipid interactions that result in translocation of a polypeptide containing the signal sequence through a channel in the ER. After translocation, a membrane-bound enzyme, named a signal peptidase, liberates the mature protein from the signal sequence.

The ER functions to separate membrane-bound proteins and secreted proteins from proteins that remain in the cytoplasm. Once targeted to the ER, both secreted and membrane-bound proteins can be further distributed to another cellular organelle called the Golgi apparatus. The Golgi directs the proteins to other cellular organelles such as vesicles, lysosomes, the plasma membrane, mitochondria and microbodies.

Secreted and membrane-bound proteins are involved in many biologically diverse activities. Examples of known secreted proteins include human insulin, interferon, interleukins, transforming GENX-beta, human growth hormone, erythropoietin, and lymphokines. Only a limited number of genes encoding human membrane-bound and secreted proteins have been identified.

The invention generally relates to nucleic acids and polypeptides encoded by them. More specifically the invention relates to nucleic acids encoding cytoplasmic, nuclear, membrane bound, and secreted polypeptides, as well as vectors, host cells, antibodies, and recombinant methods for producing these nucleic acids and polypeptides.

SUMMARY OF THE INVENTION

The invention is based in part upon the discovery of nucleic acid sequences encoding novel polypeptides. The novel nucleic acids and polypeptides are referred to herein as NOVX, or NOV1, NOV2, NOV3, NOV4, NOV5, NOV6, NOV7, NOV8, NOV9, NOV10, NOV11, NOV12, NOV13, NOV14, NOV15 and NOV16 nucleic acids and polypeptides. These nucleic acids and polypeptides, as well as variants, derivatives, homologs, analogs and fragments thereof, will hereinafter be collectively designated as "NOVX" nucleic acid or polypeptide sequences.

In one aspect, the invention provides an isolated NOVX nucleic acid molecule encoding a NOVX polypeptide that includes a nucleic acid sequence that has identity to the nucleic acids disclosed in SEQ ID NOS: 1, 8, 10, 12, 18, 20, 26, 28, 34, 36, 42, 44, 50, 52, 54, 60, 62, 64, 70, 72, 74, 76, 82, 89, 91, 99 and 101. In some embodiments, the NOVX nucleic acid molecule will hybridize under stringent conditions to a nucleic acid sequence complementary to a nucleic acid molecule that includes a protein-coding sequence of a NOVX nucleic acid sequence. The invention also includes an isolated nucleic acid that encodes a NOVX polypeptide, or a fragment, homolog, analog or derivative thereof. For example, the nucleic acid can encode a polypeptide at least 80% identical to a polypeptide comprising the amino acid sequences of SEQ ID NOS: 2, 9, 11, 19, 27, 35, 43, 51, 53, 61, 63, 65, 71, 73, 75, 83, 90, 92, 100 and 102. The nucleic acid can be, for example, a genomic DNA fragment or a cDNA molecule that includes the nucleic acid sequence of any of SEQ ID NOS: 1, 8, 10, 12, 18, 20, 26, 28, 34, 36, 42, 44, 50, 52, 54, 60, 62, 64, 70, 72, 74, 76, 82, 89, 91, 99 and 101.

Also included in the invention is an oligonucleotide, e.g., an oligonucleotide which includes at least 6 contiguous nucleotides of a NOVX nucleic acid (e.g., SEQ ID NOS: 1, 8, 10, 12, 18, 20, 26, 28, 34, 36, 42, 44, 50, 52, 54, 60, 62, 64, 70, 72, 74, 76, 82, 89, 91, 99 and 101) or a complement of said oligonucleotide.

Also included in the invention are substantially purified NOVX polypeptides (SEQ ID NOS: 2, 9, 11, 19, 27, 35, 43, 51, 53, 61, 63, 65, 71, 73, 75, 83, 90, 92, 100 and 102). In certain embodiments, the NOVX polypeptides include an amino acid sequence that is substantially identical to the amino acid sequence of a human NOVX polypeptide.

The invention also features antibodies that immunoselectively bind to NOVX polypeptides, or fragments, homologs, analogs or derivatives thereof.

In another aspect, the invention includes pharmaceutical compositions that include therapeutically- or prophylactically-effective amounts of a therapeutic and a pharmaceutically-acceptable carrier. The therapeutic can be, e.g., a NOVX nucleic acid, a NOVX polypeptide, or an antibody specific for a NOVX polypeptide. In a further aspect, the invention includes, in one or more containers, a therapeutically- or prophylactically-effective amount of this pharmaceutical composition.

In a further aspect, the invention includes a method of producing a polypeptide by culturing a cell that includes a NOVX nucleic acid, under conditions allowing for expression of the NOVX polypeptide encoded by the DNA. If desired, the NOVX polypeptide can then be recovered.

In another aspect, the invention includes a method of detecting the presence of a NOVX polypeptide in a sample. In the method, a sample is contacted with a compound that selectively binds to the polypeptide under conditions allowing for formation of a complex between the polypeptide and the compound. The complex is detected, if present, thereby identifying the NOVX polypeptide within the sample.

The invention also includes methods to identify specific cell or tissue types based on their expression of a NOVX.

Also included in the invention is a method of detecting the presence of a NOVX nucleic acid molecule in a sample by contacting the sample with a NOVX nucleic acid probe or primer, and detecting whether the nucleic acid probe or primer bound to a NOVX nucleic acid molecule in the sample.

In a further aspect, the invention provides a method for modulating the activity of a NOVX polypeptide by contacting a cell sample that includes the NOVX polypeptide with a compound that binds to the NOVX polypeptide in an amount sufficient to modulate the activity of said polypeptide. The compound can be, e.g., a small molecule, such as a nucleic acid, peptide, polypeptide, peptidomimetic, carbohydrate, lipid or other organic (carbon containing) or inorganic molecule, as further described herein.

Also within the scope of the invention is the use of a therapeutic in the manufacture of a medicament for treating or preventing disorders or syndromes including, e.g., those described for the individual NOVX nucleotides and polypeptides herein, and/or other pathologies and disorders of the like.

The therapeutic can be, e g., a NOVX nucleic acid, a NOVX polypeptide, or a NOVX-specific antibody, or biologically-active derivatives or fragments thereof.

For example, the compositions of the present invention will have efficacy for treatment of patients suffering from the diseases and disorders disclosed above and/or other pathologies and disorders of the like. The polypeptides can be used as immunogens to produce antibodies specific for the invention, and as vaccines. They can also be used to screen for potential agonist and antagonist compounds. For example a cDNA encoding NOVX may be useful in gene therapy, and NOVX may be useful when administered to a subject in need thereof. By way of non-limiting example, the compositions of the present invention will have efficacy for treatment of patients suffering from the diseases and disorders disclosed above and/or other pathologies and disorders of the like.

The invention further includes a method for screening for a modulator of disorders or syndromes including, e.g., the diseases and disorders disclosed above and/or other pathologies and disorders of the like. The method includes contacting a test compound with a NOVX polypeptide and determining if the test compound binds to said NOVX polypeptide. Binding of the test compound to the NOVX polypeptide indicates the test compound is a modulator of activity, or of latency or predisposition to the aforementioned disorders or syndromes.

Also within the scope of the invention is a method for screening for a modulator of activity, or of latency or predisposition to an disorders or syndromes including, e.g., the diseases and disorders disclosed above and/or other pathologies and disorders of the like by administering a test compound to a test animal at increased risk for the aforementioned disorders or syndromes. The test animal expresses a recombinant polypeptide encoded by a NOVX nucleic acid. Expression or activity of NOVX polypeptide is then measured in the test animal, as is expression or activity of the protein in a control animal which recombinantly-expresses NOVX polypeptide and is not at increased risk for the disorder or syndrome. Next, the expression of NOVX polypeptide in both the test animal and the control animal is compared. A change in the activity of NOVX polypeptide in the test animal relative to the control animal indicates the test compound is a modulator of latency of the disorder or syndrome.

In yet another aspect, the invention includes a method for determining the presence of or predisposition to a disease associated with altered levels of a NOVX polypeptide, a NOVX nucleic acid, or both, in a subject (e.g., a human subject). The method includes measuring the amount of the NOVX polypeptide in a test sample from the subject and comparing the amount of the polypeptide in the test sample to the amount of the NOVX polypeptide present in a control sample. An alteration in the level of the NOVX polypeptide in the test sample as compared to the control sample indicates the presence of or predisposition to a disease in the subject. Preferably, the predisposition includes, e.g., the diseases and disorders disclosed above and/or other pathologies and disorders of the like. Also, the expression levels of the new polypeptides of the invention can be used in a method to screen for various cancers as well as to determine the stage of cancers.

In a further aspect, the invention includes a method of treating or preventing a pathological condition associated with a disorder in a mammal by administering to the subject a NOVX polypeptide, a NOVX nucleic acid, or a NOVX-specific antibody to a subject (e.g., a human subject), in an amount sufficient to alleviate or prevent the pathological condition, in preferred embodiments, the disorder, includes, e.g., the diseases and disorders disclosed above and/or other pathologies and disorders of the like.

In yet another aspect, the invention can be used in a method to identity the cellular receptors and downstream effectors of the invention by any one of a number of techniques commonly employed in the art. These include but are not limited to the two-hybrid system, affinity purification, co-precipitation with antibodies or other specific-interacting molecules.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

The present invention provides novel nucleotides and polypeptides encoded thereby. Included in the invention are the novel nucleic acid sequences and their polypeptides. The sequences are collectively referred to as "NOVX nucleic acids" or "NOVX polynucleotides" and the corresponding encoded polypeptides are referred to as "NOVX polypeptides" or "NOVX proteins." Unless indicated otherwise, "NOVX" is meant to refer to any of the novel sequences disclosed herein. Table A provides a summary of the NOVX nucleic acids and their encoded polypeptides.

TABLE A

Sequences and Corresponding SEQ ID Numbers

| NOVX | Internal Identification | SEQ ID NO (nt) | SEQ ID NO (aa) | Homology |
|---|---|---|---|---|
| NOV1 | 24CS017 | 1 | 2 | Kinesin like protein; Overlaps genomic clone with KIAA1236-like protein, predicted secreted |
| NOV2 | 24CS059; CG56403-01; 146556340 | 8 | 9 | Novel Nuclear Protein-like protein |
| NOV3 | 24SC113; CG56383-01 | 10, 12 | 11 | LIM-domain-containing Prickle-like, secreted-like protein |
| NOV4 | 24SC128; CG56824-01; 13374351; 13374350; 13374349 | 18, 20 | 19 | hypothetical protein similar to Y71F9B.2 PROTEIN - *Caenorhabditis elegans*-like protein |
| NOV5 | 24SC239; 13374166; 13374167; 13374355; 13374356; 13374357; 13374358; 13374359; 13374360; 13374361; 13374362 | 26, 28 | 27 | CG8441 PROTEIN-like protein |
| NOV6 | 24SC300 | 34, 36 | 35 | eEIF-2B epsilon subunit-like protein |
| NOV7 | 24SC526; 13374363; 13374364; 13374365; 13374366 | 42, 44 | 43 | heat shock factor binding protein 1-like protein |
| NOV8 | 24SC714; 13373973; 13373974 | 50 | 51 | putative secreted protein-like protein |
| NOV9 | 6CS060; 13374352; 13374353; 13374354 | 52, 54 | 53 | Kelch-like protein-like protein |
| NOV10 | 100340173; 1373975; 1373976; 1373977; 1373978 | 60, 62, 64 | 61, 63, 65 | hypothetical 22.2 kDa protein SLR0305-like protein; Transmembrane |
| NOV11 | 87938450; | 70 | 71 | transposase-like protein |
| NOV12 | 87917235; 13373979; CG92002-01 | 72 | 73 | Novel Leucine Zipper Containing Type II membrane like protein-like protein |
| NOV13 | 87919652; | 74, 76 | 75 | P07948 tyrosine-protein kinase LYN-like protein |
| NOV14 | 87935554; | 82 | 83 | O15438 canalicular multispecific organic anion transporter 2-like protein; multidrug resistance |
| NOV15a | 100399281 | 89 | 90 | novel intracellular thrombospondin domain containing protein-like protein |
| NOV15b | CG57356-01; 159518754 | 91 | 92 | novel intracellular thrombospondin domain containing protein-like protein |
| NOV16a | 101330077 | 99 | 100 | FYVE finger-containing phosphoinositide kinase-like protein |
| NOV16b | CG57248-01; 100391903 | 101 | 102 | FYVE finger-containing phosphoinositide kinase-like protein |

NOVX nucleic acids and their encoded polypeptides are useful in a variety of applications and contexts. The various NOVX nucleic acids and polypeptides according to the invention are useful as novel members of the protein families according to the presence of domains and sequence relatedness to previously described proteins. Additionally, NOVX nucleic acids and polypeptides can also be used to identify proteins that are members of the family to which the NOVX polypeptides belong.

The NOVX genes and their corresponding encoded proteins are useful for preventing, treating or ameliorating medical conditions, e.g., by protein or gene therapy. Pathological conditions can be diagnosed by determining the amount of the new protein in a sample or by determining the presence of mutations in the new genes. Specific uses are described for each of the sixteen genes, based on the tissues in which they are most highly expressed. Uses include developing products for the diagnosis or treatment of a variety of diseases and disorders.

For example, NOV1 is homologous to a kinesin-like superfamily of proteins. Thus, the NOV1 nucleic acids, polypeptides, antibodies and related compounds according to the invention will be useful in therapeutic and diagnostic applications implicated in, for example; cancer (e.g. renal and/or gastric cancer), neurodegenerative diseases, diseases of vesicular transport, and infectious diseases, and/or other pathologies, diseases and disorders.

Also, NOV2 is homologous to the Novel Nuclear Protein-like family of proteins. Thus NOV2 nucleic acids, polypeptides, antibodies and related compounds according to the invention will be useful in therapeutic and diagnostic applications implicated in, for example; cancer and/or other pathologies, diseases and disorders.

Further, NOV3 is homologous to a family of LIM-domain-containing Prickle-like proteins. Thus, the NOV3 nucleic acids and polypeptides, antibodies and related compounds according to the invention will be useful in therapeutic and diagnostic applications implicated in, for example; dystonia-parkinsonism syndrome; dyskeratosis, hereditary benign intraepithelial; developmental disorders, diseases of cytoskeletal function, cancer (e.g. gastric uterine, lung and/or renal cancer), neurodegenerative diseases (e.g. Alzheimer's disease, multiple sclerosis and stroke) and/or other pathologies, diseases and disorders.

Also, NOV4 is homologous to the hypothetical protein similar to Y71F9B.2 PROTEIN—Caenorhabditis elegans-like family of proteins. Thus, NOV4 nucleic acids, polypeptides, antibodies and related compounds according to the invention will be useful in therapeutic and diagnostic applications implicated in, for example; heart disease, stroke, autoimmune disease, infectious disease, and cancer (e.g. renal and/or breast cancer) and/or other pathologies, diseases and disorders.

Additionally, NOV5 is homologous to the CG8441 PROTEIN-like family of proteins. Thus NOV5 nucleic acids, polypeptides, antibodies and related compounds according to the invention will be useful in therapeutic and diagnostic applications implicated in, for example; cancer (e.g. breast and/or ovarian cancer) and/or other pathologies, diseases and disorders.

Also, NOV6 is homologous to the eEIF-2B epsilon subunit-like family of proteins. Thus NOV6 nucleic acids, polypeptides, antibodies and related compounds according to the invention will be useful in therapeutic and diagnostic applications implicated in, for example; cancer (e.g. breast and/or ovarian cancer) and/or other pathologies, diseases and disorders.

Further, NOV7 is homologous to members of the heat shock factor binding protein l-like family of proteins. Thus, the NOV7 nucleic acids, polypeptides, antibodies and related compounds according to the invention will be useful in therapeutic and diagnostic applications implicated in, for example; cancer (e.g. breast and/or ovarian cancer) and/or other pathologies, diseases and disorders.

Still further, NOV8 is homologous to the putative secreted protein-like protein family of proteins. Thus, NOV8 nucleic acids and polypeptides, antibodies and related compounds according to the invention will be useful in therapeutic and diagnostic applications implicated in, for example; cancer (e.g. liver, lung, ovarian and/or colon cancer), inflammatory diseases and/or other pathologies, diseases and disorders.

Additionally, NOV9 is homologous to the Kelch-like protein-like family of proteins. Thus, NOV9 nucleic acids and polypeptides, antibodies and related compounds according to the invention will be useful in therapeutic and diagnostic applications implicated in Menkes disease, myoglobinuria/hemolysis due to PGK deficiency, and Wieacker-Wolff syndrome, neurological disorders, development-related pathologies and/or other various pathologies, diseases and disorders.

NOV10a, NOV10b and NOV10c are homologous to a hypothetical 22.2 kDa protein SLR0305-like protein family of proteins and the Type IIIb plasma membrane-like family of proteins. Thus, the NOV10 nucleic acids, polypeptides, antibodies and related compounds according to the invention will be useful in therapeutic and diagnostic applications implicated in, for example; ACTH deficiency; Convulsions, familial febrile, 1; Duane syndrome; congenital Adrenal hyperplasia due to 11-beta-hydroxylase deficiency; glucocorticoid-remediable Aldosteronism; congenital Hypoaldosteronism due to CMO I deficiency; congenital Hypoaldosteronism due to CMO II deficiency; susceptibility to Nijmegen breakage syndrome; Low renin hypertension; Anemia, Ataxia-telangiectasia, Autoimmume disease, Immunodeficiencies, kidney cancer, proliferative disease, immune-mediated disease, allergy, asthma, and psoriasis and/or other pathologies, diseases and disorders.

NOV11 is homologous to a transposase-like protein family of proteins. Thus, the NOV11 nucleic acids, polypeptides, antibodies and related compounds according to the invention will be useful in, for example; potential therapeutic applications such as the following: (i) a protein therapeutic, (ii) a small molecule drug target, (iii) an antibody target (therapeutic, diagnostic, drug targeting/cytotoxic antibody). (iv) a nucleic acid useful in gene therapy (gene delivery/gene ablation), (v) an agent promoting tissue regeneration in vitro and in vivo, and (vi) a biological defense weapon, and/or transposase-related pathologies, diseases and disorders.

Also, NOV12 is homologous to the Novel Leucine Zipper Containing Type II membrane like protein-like family of proteins. Thus NOV12 nucleic acids, polypeptides, antibodies and related compounds according to the invention will be useful in therapeutic and diagnostic applications implicated in, for example; prostate cancer, lung cancer, diabetes, abnormal wound healing, congenital slow-channel myosthenic syndrome, asthma, IBD, contact hypersensitivity, infection disease, allorejection, autoimmunity, inflammation and/or other pathologies, diseases and disorders.

Further, NOV13 is homologous to a family of P07948 tyrosine-protein kinase LYN-like proteins. Thus, the NOV13 nucleic acids and polypeptides, antibodies and related compounds according to the invention will be useful in therapeutic and diagnostic applications implicated in, for example; breast cancer, diabetes and/or other pathologies, diseases and disorders.

Also, NOV14 is homologous to the O15438 canalicular multispecific organic anion transporter 2-like family of proteins. Thus, NOV14 nucleic acids, polypeptides, antibodies and related compounds according to the invention will be useful in therapeutic and diagnostic applications implicated in, for example, detoxification, drug resistance, multidrug resistance, inflammatory disease, cancer, liver disease and/or other pathologies, diseases and disorders.

Additionally, NOV15 is homologous to the novel intracellular thrombospondin domain containing protein-like family of proteins. Thus NOV15 nucleic acids, polypeptides, antibodies and related compounds according to the invention will be useful in therapeutic and diagnostic applications implicated in, for example; systemic lupus erythematosus, autoimmune disease, asthma, emphysema, scleroderma, allergy, ARDS; fertility, breast cancer, liver differentiation, hypogonadism; angiogenesis, vasc ularization in CNS tissue undergoing repair/regeneration, CNS-related cancers, diseases of the thyroid gland, immunological disease, diseases of the thyroid gland and pancreas as well as other metabolic and neuroendocrine diseases and/or other pathologies, diseases and disorders.

Also, NOV16a and NOV16b are homologous to the FYVE finger-containing phosphoinositide kinase-like family of proteins. Thus NOV16 nucleic acids, polypeptides, antibodies and related compounds according to the invention will be useful in therapeutic and diagnostic applications implicated in, for example; diabetes, obesity, fertility, signaling and/or other pathologies, diseases and disorders.

The NOVX nucleic acids and polypeptides can also be used to screen for molecules, which inhibit or enhance NOVX activity or function. Specifically, the nucleic acids and polypeptides according to the invention may be used as targets for the identification of small molecules that modulate or inhibit, e.g., neurogenesis, cell differentiation, cell proliferation, hematopoiesis, wound healing and angiogenesis.

In one embodiment of the present invention, NOVX or a fragment or derivative thereof may be administered to a subject to treat or prevent a disorder associated with decreased expression or activity of NOVX. Examples of such disorders include, but are not limited to, cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; neurological disorders such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, akathesia, amnesia, catatonia, diabetic neuropathy, tardive dyskinesia, dystonias, paranoid psychoses, postherpetic neuralgia, and Tourette's disorder; and disorders of vesicular transport such as cystic fibrosis, glucose-galactose malabsorption syndrome, hypercholesterolemia, diabetes mellitus, diabetes insipidus, hyper- and hypoglycemia, Grave's disease, goiter, Cushing's disease, Addison's disease, gastrointestinal disorders including ulcerative colitis, gastric and duodenal ulcers, other conditions associated with abnormal vesicle trafficking including acquired immunodeficiency syndrome (AIDS), allergic reactions, autoimmune hemolytic anemia, proliferative glomerulonephritis, inflammatory bowel disease, multiple sclerosis, myasthenia gravis, rheumatoid arthritis, osteoarthritis, scleroderma, Chediak-Higashi syndrome, Sjogren's syndrome, systemic lupus erythiematosus, toxic shock syndrome, traumatic tissue damage and viral, bacterial, fungal, helminthic, and protozoal infections, as well as additional indications listed for the individual NOVX clones.

The NOVX nucleic acids and proteins of the invention are useful in potential diagnostic and therapeutic applications and as a research tool. These include serving as a specific or selective nucleic acid or protein diagnostic and/or prognostic marker, wherein the presence or amount of the nucleic acid or the protein are to be assessed. These also include potential therapeutic applications such as the following: (i) a protein therapeutic, (ii) a small molecule drug target, (iii) an antibody target (therapeutic, diagnostic, drug targeting/cytotoxic antibody), (iv) a nucleic acid useful in gene therapy (gene delivery/gene ablation), (v) an agent promoting tissue regeneration in vitro and in vivo, and (vi) a biological defense weapon.

Additional utilities for the NOVX nucleic acids and polypeptides according to the invention are disclosed herein.

NOV1

A disclosed NOV1 nucleic acid of 1065 nucleotides (also referred to as 24CS017) encoding a novel kinesin-like protein is shown in Table 1A. An open reading frame was identified beginning with an ATG initiation codon at nucleotides 1–3 and ending with a TAA codon at nucleotides 1063–1065. The start and stop codons are shown in bold letters in Table 1A.

TABLE 1A

NOV1 nucleotide sequence.

(SEQ ID NO:1)
ATGACGGGGCTGCTCCTCCTCAGCCTCCAGTCAGGCTGTGTGGCAGCGATCACCTCCATGTCGATGGAGTGTCTGTG

CAGTTTGGGAGCGAGGCTCTGCCTCTCTCGGTCTACCCTTGGGAGTGAAATAGTGACCGTCCCTTTGAGCCCGAGAG

CTGGGGAGAAGGCCGTGCCTGTTAACAGCTGCCTGGACCCTCTCTGGAGAGCAGCAGAGAGAGGCGGGGCTGGAGGA

GATGTTGCCAAGAACCTAAGGGTGAAAGTCATGCTTCGCATCTGTTCCACCTTGGCTCGAGATACTTCAGAATCCAG

CTCTTTCTTAAAGGTGGACCCACGGAAGAAGCAGATCACCTTGTACGATCCCCTGACTTGTGGAGGTCAAAATGCCT

TCCAAAAGAGAGGCAACCAGGTTCCTCCAAAGATGTTTGCCTTCGATGCAGTTTTTCCACAAGACGCTTCTCAGGCT

GAAGTGTGTGCAGGCACCGTGGCAGAGGTGATCCAGTCTGTGGTCAACGGGCAGATGGCTGCGTGTTCTGTTTCGG

CCACGCCAAACTGGGAAAATCCTACACCATGATCGGAAAGGATGATTCCATGCAGAACCTGGGCATCATTCCCTGTG

CCATCTCTTGGCTCTTCAAGCTCATAAACGAACGCAAGGAAAAGACCGGCGCCCGTTTCTCAGTCCGGGTTTCCGCC

TABLE 1A-continued

NOV1 nucleotide sequence.

GTGGAAGTGTGGGGGAAGGAGGAGAACCTGCGGGACCTGCTGTCGGAGGTGGCCACGGGCAGCCTGCAGGACGGCCA

GTCCCCGGGCGTGTACCTCTGTGAGGACCCCATCTGCGGCACGCAGCTGCAGAACCAGAGCGAGCTGCGGGCCCCCA

CCGCAGAGAAGGCTGCCTTTTTCCTGGATGCCGCCATTGCCTCCCGCAGGAGCCACCAACAGGACTGTGATGAGGAC

GACCACCGCAACTCACACGTGTTCTTCACACTGCACATCTACCAGTACCGGATGGAGAAGAGCGGGAAAGGGGGAAT

TCTGCTTTCGATTTGGAATCTGAAAGTAGGGAGAAATCTTGAAAACAAGGAAACAGTTCATTAA

A disclosed NOV1 polypeptide (SEQ ID NO:2) encoded by SEQ ID NO:1 has 354 amino acid residues and is presented in Table 1B using the one-letter amino acid code. SignalP, Psort and/or Hydropathy results predict that NOV1 has a signal peptide and is likely to be localized extracellularly with a certainty of 0.4562. In an alternative embodiment, NOV1 is likely to be localized to the endoplasmic reticulum membrane with a certainty of 0.1000, or to the endoplastic reticulum lumen with a certainty of 0.1000, or to the microbody (peroxisome) with a certainty of 0.1000. The most likely cleavage site for a NOV1 peptide is between amino acids 16 and 17, i.e., at the dash between amino acids VAA-IT. NOV1 has a molecular weight of 38525.7 Daltons.

parameter that describes the number of hits one can "expect" to see just by chance when searching a database of a particular size. It decreases exponentially with the Score (S) that is assigned to a match between two sequences. Essentially, the E value describes the random background noise that exists for matches between sequences.

The Expect value is used as a convenient way to create a significance threshold for reporting results. The default value used for blasting is typically set to 0.0001. In BLAST 2.0, the Expect value is also used instead of the P value (probability) to report the significance of matches. For example, an E value of one assigned to a hit can be interpreted as meaning that in a database of the current size one might expect to see one match with a similar score

TABLE 1B

Encoded NOV1 protein sequence.

(SEQ ID NO:2)

MTGLLLLSLQSGCVAA/ITSMSMECLSCLGARLCLSRSTLGSEIVTVPLSPRAGEKAVPVNSCLDPLWRAAERGGAGGD

VAKNLRVKVMLRICSTLARDTSESSSFLKVDPRKKQITLYDPLTCGGQNAFQKRGNQVPPKMFAFDAVFPQDASQAEVC

AGTVAEVIQSVVNGADGCVFCFGHAKLGKSYTMIGKDDSMQNLGIIPCAISWLFKLINERKEKTGARFSVRVSAVEVWG

KEENLRDLLSEVATGSLQDGQSPGVYLCEDPICGTQLQNQSELRAPTAEKAAFFLDAAIASRRSHQQDCDEDDHRNSHV

FFTLHIYQYRMEKSGKGGILLSIWNLKVGRNLENKETVH

In all BLAST alignments herein, the "E-vaLue" or "Expect" value is a numeric indication of the probability that the aligned sequences could have achieved their similarity to the BLAST query sequence by chance alone, within the database that was searched. The Expect value (E) is a simply by chance. An E value of zero means that one would not expect to see any matches with a similar score simply by chance. See, e.g., BLAST educational information provided by the National Center for Biotechnology Information (NCBI), Bethesda, Md.

TABLE 1C

BLASTP results for NOV1

| Gene Index/<br>Identifier | Protein/Organism | Length<br>(aa) | Identity<br>(%) | Positives<br>(%) | Expect |
|---|---|---|---|---|---|
| Q9ULI4;<br>AB033062;<br>BAA86550.1 | KIAA1236 PROTEIN<br>(FRAGMENT) *homo sapiens*<br>6/2001 | 1481 | 155/222<br>(70%) | 185/222<br>(83%) | 4e-87 |
| Q99PU2;<br>KIF26B;<br>BAB32487 | KINESIN SUPERFAMILY<br>PROTEIN 26B (FRAGMENT).<br>KIF26B, *mus musculus*<br>6/2001 | 130 | 122/145<br>(84%) | 126/145,<br>(87%) | 7e-64 |
| Q99PT4;<br>AB054031;<br>BAB32495.1; | KINESIN SUPERFAMILY<br>PROTEIN 26A (FRAGMENT).<br>KIF26A, *mus musculus*<br>6/2001 | 147 | 106/147<br>(72%) | 130/147,<br>(88%) | 2e-58 |
| Q9VLW2; | CG14535 PROTEIN. | 302 | 69/165 | 99/165, | 9e-28 |

TABLE 1C-continued

BLASTP results for NOV1

| Gene Index/ Identifier | Protein/Organism | Length (aa) | Identity (%) | Positives (%) | Expect |
|---|---|---|---|---|---|
| AE003619; AAF52569.1 | *drosophila melanogaster* 6/2001 | | (42%) | (60%) | |
| Q9U541; AF108229; AAF17300.1 | VAB-8L. *caenorhabditis elegans* 6/2001 | 1066 | 61/191 (32%) | 98/191, (51%) | 1e–18 |

The homology of these and other sequences is shown graphically in the ClustalW analysis shown in Table 1D. In the ClustalW alignment of the NOV1 protein, as well as all other ClustalW analyses herein, the black outlined amino acid residues indicate regions of conserved sequence (i.e., regions that may be required to preserve structural or functional properties), whereas non-highlighted amino acid residues are less conserved and can potentially be mutated to a much broader extent without altering protein structure or function.

TABLE 1D

ClustalW Analysis of NOV1

1) Novel NOV1 (SEQ ID NO:2)
2) BAA86550.1 partial sequence used (SEQ IS NO:3)
3) KIF26B (SEQ ID NO:4)
4) KIF26A (SEQ ID NO:5)
5) CG14535 (SEQ ID NO:6)
6) VAB-8L - partial sequence used (SEQ ID NO:7)

```
NOV1        MTGLLLLSLQSGCVAAITSMSMECLCSLGARLCLSRSTLGSEIVTVPLSP  50
BAA86550.1  --------------------------------------------------   1
KIF26B      --------------------------------------------------   1
KIF26A      --------------------------------------------------   1
CG14535     ----------------------------------------MATTSTSNMS  10
VAB-8L      --------------------------------------------------   1

NOV1        RAGEKAVPVNSCLDPLWRAAERGGAGGDVAKNLRVKVMLRICSTLARDTS  100
BAA86550.1  --------------------------------------------------   1
KIF26B      --------------------------------------------------   1
KIF26A      --------------------------------------------------   1
CG14535     RNGGFCGALQRAPPPMPPRLIRRLSSRECTGVGKVKVMLRVADRDRNSGG   60
VAB-8L      ---------------------------------------MEACSSKTSLL  11

NOV1        ESSSFLKVDPRKKQITLYDP-LTCGGQNAFQKRGNQVP--PKMFAFDAVF  147
BAA86550.1  -------------QVILYDP-AAGPPGSAGFRRAATAAV-PKMFAFDAVF   35
KIF26B      --------------------------------------------------   1
KIF26A      --------------------------------------------------   1
CG14535     TEPDFMALDKKKRQVTLTDPRTACPPPQAAQERAPMVAA-PKMFAFDNLF  109
VAB-8L      LHSPLRTIPKLRLCASISSEDVAHGRCSLTDQHLQIEGKNYSKTTFDHIF   61

NOV1        PQDASQAEVCAGTVAEVIQSVVNGADGCVFCFGHAKLGKSYTMIGKDDSM  197
BAA86550.1  PQDSEQAEVCSGTVADVLQSVVSGADGCIFSFGHMSLGKSYTMIGKDSSP   85
KIF26B      -------------------------------PAPTGKSYTMIGKDDSM   17
KIF26A      -----------------------------------GKSYTMIGKDSSP   13
CG14535     TGEDKQSDVCASALSEVIPAVLEGSDGCLLAMGYPATGKAQIVLGELGGG  159
VAB-8L      RTDATQDDMYTAFLSDTINSVFAGNDATVLAMGAKTNGKDERLYGNSVSR  111

NOV1        Q------------NLGIIPCAISWLFKLINERKEKTGARFSVRVSAVEVW  235
BAA86550.1  Q------------SLGIVPCAISWLFRLIEERRERTGIRFSVRVSAVEVC  123
KIF26B      Q------------NLGIIPCAISWLFKLINERKEKTGARFSVRISAVEVW   55
KIF26A      Q------------SLGIVPCAISQLFRLIDERKERLGTRFSIRVSAVEVC   51
CG14535     SGSGSASGSGVACSLGAAPCAIAWLYKCIQERRQKSGARFSVRVSAVGVS  209
VAB-8L      N------------GLVQMATTQLMNALDDNKD-SEERIQVRMSAIMVS  146

NOV1        GKE---ENLRDLLSEVATGSLQDGQSPGVYLCEDPICGTQLQNQSELRAP  282
BAA86550.1  GRD---CSLRDLIAEVAPGSLQDTQSPGVYLREDPVCGAQLQNQSELRAP  170
KIF26B      GKE---ENLRDLLSEVATGSLQDGQSPGVYLCEDP-------------   87
KIF26A      GHD---QSLRDLIAEBASGSLQDYQSPGVYLREDPVCGTQLQNQNELRAP   98
CG14535     ATKPDALSQDLIRSHAAEYGVYSHIKPNALFIHSELLFFWSQYWN-----  254
VAB-8L      QNE---SSIVDLLSPFNP----DPRHRVVKIVDDARTGVFIDNESEIRVE  189
```

TABLE 1D-continued

ClustalW Analysis of NOV1

```
NOV1         TAEKAAFELDAAIASRRSHQQDCDEDDHRNSHVFFTLHIYQYRMEKSGKG  332
BAA86550.1   TAEKAAFYLDAALAARSTSRAGCGEDARRSSHMLFTLHVYQYRMEKCGRG  220
KIF26B       -AEKAAFLLDAAIASRRSNQQDCDEDDHRHSHMLFTLHIYQYRM------  130
KIF26A       TAEKAAFYLDAALAARSTSRAGCGEEARRSSHMLFTLHVYQYRVEKCGQ-  147
CG14535      -SGSDYGYTESDDSPGIYLRDDFLAVQRNYVHPPPSVRPFSSTQRSPDA-  302
VAB-8L       TIDQALFYLNTAVDHRMIQD----EHTHRTSHVFISLSLYSYKMGDKMQG  235

NOV1         G-------------------------------------------ILLSIWN--  340
BAA86550.1   GMSGGRSRLHLIDLGSCEAAAGRAGEAAGGPLCLSLSALGSVILALVNGA     270
KIF26B       ----------------------------------------------------  130
KIF26A       ----------------------------------------------------  147
CG14535      ----------------------------------------------------  302
VAB-8L       G----RRRLCFLDMGIGERNSTNGG--------MTMPALGSILLAMVQRN    273

NOV1         -----------------LKVG---------------RNLENKETVH----    354
BAA86550.1   KHVPYRDHRLTMLLRESLATAGCRTTMIAHVSDAPAQHAETLSTVQLAAR    320
KIF26B       ----------------------------------------------------  130
KIF26A       ----------------------------------------------------  147
CG14535      ----------------------------------------------------  302
VAB-8L       KHIPSRDSSVCQLIRCALSTSRFTTFVFSFG----AKSDDNENIAHLACK    319

NOV1         -----------------------------------------------     354
BAA86550.1   IHRLRRKKAKYASSSSGGESSCEEGRARRPPHLRPFHPRTVALDPD ...   370
KIF26B       -----------------------------------------------     130
KIF26A       -----------------------------------------------     147
CG14535      -----------------------------------------------     302
VAB-8L       IARTRAKSMVGHGRKSSGTMSTGTMESNSSSCG------TTTITPG ...   363
```

Other BLAST results include sequences from the Patp database, which is a proprietary database that contains sequences published in patents and patent publications. Patp results include those listed in Table 1E.

TABLE 1E

Patp BLASTP Analysis for NOV1

| Sequences producing High-scoring Segment Pairs | Protein/ Organism | Length (aa) | Identity (%) | Positive (%) | E Value |
|---|---|---|---|---|---|
| patp: AAY51328 | Human KLIMP protein- H. sapiens | 1103 | 29 | 48 | 1.6e-11 |
| Patp: AAB36227 | Human kinesin-like protein HKLP | 1816 | 29 | 49 | 8.2e-11 |
| patp: AAB94768 | Human protein SEQ ID NO: 15849- H. sapiens | 664 | 29 | 50 | 6.3e-10 |
| Patp: AAY06618 | Thermomyces lanuginosus Kinesin motor protein TL-gamma- Thermomyces lanuginosus | 784 | 26 | 46 | 1.4e-09 |
| Patp: AAY01632 | Amino acid sequence of centromere-associated protein-E - Xenopus sp | 2954 | 38 | 58 | 1.8e-08 |
| Patp: AAG21666 | Arabidopsis thaliana protein fragment SEQ ID NO: 24303- Arabidopsis thaliana | 452 | 30 | 57 | 2.7e-08 |

The presence of identifiable domains in NOV1, as well as all other NOVX proteins, was determined by searches using software algorithms such as PROSITE, DOMAIN, Blocks, Pfam, ProDomain, and Prints, and then determining the Interpro number by crossing the domain match (or numbers) using the Interpro website (maintained by the European Bioinformatics Institute, Hinxton, Cambridge, UK). DOMAIN results for NOV1 as disclosed in Tables 1F, were collected from the Conserved Domain Database (CDD) with Reverse Position Specific BLAST analyses. This BLAST analysis software samples domains found in the Smart and Pfam collections.

Table 1F lists the domain description from DOMAIN analysis results against NOV1. This indicates that the NOV1 sequence has properties similar to those of other proteins known to contain these domains. In a sequence alignment herein, fully conserved single residues are calculated to determine percent homology, and conserved and "strong" semi-conserved residues are calculated to determine percent positives. The "strong" group of conserved amino acid residues may be any one of the following groups of amino acids: STA, NEQK, NHQK, NDEQ, QHRK, MILV, MILF, HY, FYW.

TABLE 1F

Domain Analysis of NOV1

Prodom analysis

| Sequences producing High-scoring Segment Pairs. | High Score | Smallest Sum Probability P(N) |
|---|---|---|
| prdm:361 p36 (52) KINH(7) KINN(2) KF1(2) // PROTEIN M . . . | 189 | 3.2e-15 |
| prdm:12025 p36 (2) CYT1(2) 7/ PROBABLE B-TYPE CYTOCHROME . . . | 55 | 0.76 |
| prdm:29378 p36 (1) RPSW_STRCO /1 RNA POLYMERASE SIGMA FAC . . . | 57 | 0.93 |
| prdm:14019 p36 (2) CIK6(2) // CHANNEL VOLTAGE-GATED POTA . . . | 49 | 0.998 |
| prdm:44434 p36 (1) ERY1_SACER // ERYTHRONOLIDE SYNTHASE, . . . | 49 | 0.998 |

>prdm:361 p36 (52) KINH(7) KINN(2) KF1(2) // PROTEIN MOTOR ATP-BINDING
MICROTUBULES COILED COIL KINESIN-LIKE CELL KINESIN MITOSIS, 170 aa.
Identities = 43/108 (39%), Positives = 66/108 (61%)
for NOV1: 139 to 246, and Sbjct: 61 to 166

>prdm:12025 p36 (2) CYT1(2) // PROBABLE B-TYPE CYTOCHROME TRICARBOXYLIC ACID CYCLE
ELECTRON TRANSPORT HEME TRANSMEMBRANE, 48 aa.
Identities = 13/21 (61%), Positives = 15/21 (31%)

>prdm:29378 p36 (1) RPSW_STRCO // RNA POLYMERASE SIGMA FACTOR WHIG. TRANSCRIPTION
REGULATION; SIGMA FACTOR; DNA-DIRECTED RNA POLYMERASE; DNA-BINDING. 81 aa.
Identities = 14/42 (33%), Positives = 21/42 (50%)

>prdm:14019 p36 (2) CIK6(2) // CHANNEL VOLTAGE-GATED POTASSIUM PROTEIN KV1.6 IONIC
TRANSMEMBRANE ION TRANSPORT GLYCOPROTEIN, 40 aa.
Identities = 9/19 (47%), Positives = 13/19 (68%)

>prdm:44434 p36 (1) ERY1_SACER // ERYTHRONOLIDE SYNTHASE, MODULES 1 AND 2 (EC
2.3.1.94) (ORF 1) (6-DEOXYERYTHRONOLIDE B SYNTHASE I) (DEBS 1). TRANSFERASE;
ACYLTRANSFERASE; ANTIBIOTIC BIOSYNTHESIS; NADP; PHOSPHOPANTETHEINE;
MULTIFUNCTIONAL ENZYME, 55 aa.
Identities = 14/35 (40%), Positives = 16/35 (45%)

BLOCKS analysis

| AC# | Description | Strength | Score |
|---|---|---|---|
| BL00411C | Kinesin motor domain proteins. | 1642 | 1283 |
| BL00411B | Kinesin motor domain proteins. | 1185 | 1156 |
| BL00411D | Kinesin motor domain proteins. | 1217 | 1107 |
| BL00853G | Beta-eliminating lyases pyridoxal-phosphate a | 1858 | 1105 |
| BL00509B | Ras GTPase-activating proteins. | 1280 | 1073 |
| BL01227A | Uncharacterized protein family U2E0012 protei | 1059 | 1072 |
| BL00094F | C-s cytosine-specific DNA methylases proteins | 1186 | 1045 |
| BL01240E | Purine and other phosphorylases family 2 prot | 1350 | 1039 |
| BL00487G | IMP dehydrogenase/GMP reductase proteins. | 1525 | 1029 |
| BL00411A | Kinesin motor domain proteins. | 1284 | 1019 |
| BL00370B | PEP-utilizing enzymes phosphorylation site pr | 1554 | 1015 |
| BL00838C | Interleukins -4 and -13 proteins. | 1661 | 1011 |
| BL00486A | DNA mismatch repair proteins mutS family prot | 1290 | 1010 |

TABLE 1F-continued

Domain Analysis of NOV1

| ProSite analysis | NOV1 aa position |
|---|---|
| Pattern-ID: ASN_GLYCOSYLATION PS00001 (Interpro) | 275 |
| Pattern-DE: N-glycosylation site, Pattern: N[^P][ST]]^P] | |
| Pattern-ID: GLYCOSAMINOGLYCAN PS00002 (Interpro) | 329 |
| Pattern-DE: Glycosaminoglycan attachment site, Pattern: SG.G | |
| Pattern-ID: PKC_PHOSPHO_SITE PS00005 (Interpro) | 49, 226, 297, 329 |
| Pattern-DE: Protein kinase C phosphorylation site | |
| Pattern: [ST].[RK] | |
| Pattern-ID: CK2_PHOSPHO_SITE PS00006 (Interpro) | 61, 116, 152, 160, 230, 252 |
| Pattern-DE: Casein kinase II phosphorylation site | |
| Pattern: [ST].{2}[DE] | |
| Pattern-ID: MYRISTYL PS00008 (Inrerpro) | 12, 29, 73, 124, 171, |
| Pattern-DE: N-myristoylation site | 201, 222, 256, 333 |
| Pattern: G[^EDRKGPFYW].{2}[STAGCN][P] | |
| Pattern-ID: ATP_GTP_A PS00017 (Interpro) | 180 |
| Pattern-DE: ATP/GTP-binding site motif A (P-loop) | |
| Pattern: [AG].{4}GK[ST] | |

The disclosed NOV1 nucleic acid encoding a kinesin-like protein includes the nucleic acid whose sequence is provided in Table 1A, or a fragment thereof. The invention also includes a mutant or variant nucleic acid any of whose bases may be changed from the corresponding base shown in Table 1A while still encoding a protein that maintains its kinesin-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 60% percent of the bases may be so changed.

The disclosed NOV1 protein of the invention includes the kinesin-like protein whose sequence is provided in Table 1B. The invention also includes a mutant or variant protein any of whose residues may be changed from the corresponding residue shown in Table 1B while still encoding a protein that maintains its kinesin-like activities and physiological functions, or a functional fragment thereof. In the mutant or variant protein, up to about 60% percent of the residues may be so changed.

The invention further encompasses antibodies and antibody fragments, such as $F_{ab}$ or $(F_{ab})_2$, that bind immunospecifically to any of the proteins of the invention. Also encompassed within the invention are peptides and polypeptides comprising sequences having high binding affinity for any of the proteins of the invention, including such peptides and polypeptides that are fused to any carrier partcle (or biologically expressed on the surface of a carrier) such as a bacteriophage particle.

Kinesin family proteins are microtubule-based motor proteins that drive the transport of molecular component within the cell. Translocation of components within the cell is critical for maintaining cell structure and function.

Kinesin defines a ubiquitous, conserved family of over 50 proteins that can be classified into at least 8 subfamilies based on primary amtino acid sequence, domain structure, velocity of movement, and cellular function. See review in: Moore and Endow (1996) Bioessays 18:207–219; and Hoyt (1994) Curr. Opin. Cell Biol. 6:63–68). The prototypical kinesin molecule is involved in the transport of membrane-bound vesicles amd organelles. This function is particularly important for axonal transport in neurons. Protein-containing vesicles are constantly transported from the neuronal cell body along microtubules that span the length of the axon leading to the synaptic terminal. Failure to supply the synaptic terminal with these vesicles blocks the transmission of neural signals. In the fruit fly Drosophila melanogaster, for example, mutations in kinesin cause severe disruption of axonal transport in larval nerves which leads to progressive paralysis. See Hurd and Saxton (1996) Genetics 144:1075–1085. This phenotype mimics the pathology of some vertebrate motor neuron diseases, such as amyotrophic lateral sclerosis (ALS). In addition to axonal transport, kinesin is also important in all cell types for the transport of vesicles from the Golgi complex to the endoplasmic reticulum. This role is critical for maintaining the identity and functionality of these secretory organelles.

Members of the more divergent subfamilies of kinesin are called kinesin-related proteins (KRPs), many of which function during mitosis in eukaryotes as divergent as yeast and human (Hoyt, supra). Some KRPs are required for assembly of the mitotic spindle. In vivo and in vitro analyses suggest that these KRPs exert force on microtubules that comprise the mitotic spindle, resulting in the separation of spindle poles. Phosphorylation of KRP is required for this activity. Failure to assemble the mitotic spindle results in abortive mitosis and chromosomal aneuploidy, the latter condition being characteristic of cancer cells. In addition, a unique KRP, centromere protein E. localizes to the kinetochore of human mitotic chromosomes and may play a role in their segregation to opposite spindle poles.

As described earlier, NOV1 shares extensive sequence homologies with kinesin family proteins, including kinesin superfamily protein 26A and 26B, and With kinesin-like proteins, including human kinesin-like motor protein (KLIMP), human kinesin-like protein (HKLP) and Thermomyces lanuginosus Kinesin motor protein TLgamma. The structural similarities indicate that NOV1 may function as a member of kinesin family proteins. Therefore, NOV1, like kinesin family proteins and kinesin-related proteins, may be associated with cancer, neurological disorders and disorders of vehicular transport. Accordingly, the NOV1 nucleic acids and proteins identified here may be useful in potential therapeutic applications implicated in (but not limited to) various pathologies and disorders as indicated herein. For example, a cDNA encoding the kinesin-like protein NOV1 may be useful in gene therapy, and the kinesin-like protein NOV1 may be useful when administered to a subject in need thereof. The NOV1 nucleic acid encoding kinesin-like protein, and the kinesin-like protein of the invention, or fragments thereof, may further be useful in diagnostic applications, wherein the presence or amount of the nucleic acid or the protein are to be assessed. Additional disease indications and tissue expression for NOV1 is presented in Example 2.

Based on the tissues in which NOV1 is most highly expressed specific uses include developing products for the diagnosis or treatment of a variety of diseases and disorders.

NOV1 nucleic acids and polypeptides are further useful in the generation of antibodies that bind immuno-specifically to the novel NOV1 substances for use in therapeutic or diagnostic methods. These antibodies may be generated according to methods known in the art, using prediction from hydrophobicity charts, as described in the "Anti-NOVX Antibodies" section below. The disclosed NOV1 protein has multiple hydrophilic regions, each of which can be used as an immunogen. In one embodiment, a contemplated NOV1 epitope is from about amino acids 50 to 80. In another embodiment, a NOV1 epitope is from about amino acids 100 to 150. In additional embodiments, NOV1 epitopes are from about amino acids 190 to 200, from about amino acids 205 to 275 and from about amino acids 280 to 330. These novel proteins can be used in assay systems for functional analysis of various human disorders, which will help in understanding of pathology of the disease and development of new drug targets for various disorders.

NOV2

A disclosed NOV2 nucleic acid of 7560 nucleotides (also referred to as 24CS059, CG56403-01 and 146556340) encodina a novel nuclear protein-like protein is shown in Table 2A. An open reading frame was identified beginning, with an ATG initiation codon at nucleotides 7170–7172 and ending with a TGA codon at nucleotides 7476–7478. A putative untranslated region upstream from the initiation codon and downstream from the termination codon is underlined in Table 2A, and the start and stop codons are in bold letters.

TABLE 2A

NOV2 nucleotide sequence.

(SEQ ID NO:8)
GTATTCTCAGAGCTGCCAGGAGTGCATCGAGCCTGTAATTTCCTGTTCTCTGAATCCCCCATCTTTCTGCAGCTCCAAGCTT

TGTGTCCCACAGCCTGTGACTCTGTGCTAACAAATCGCTATTGTCCAGTGGGGCGAATGGTGGCTGGAACTAAAGAATTGCT

GTCTGGTTTCTATTCAAATCCAGGTAGCGAGATATATGAATGGACTTTTCGAATCGTCATGTGAATAACGTCTGCTCGGCAT

GAAGGCTCAGAGCCATGCTAGGAAGGATTAACTCGTAGGCTGACCACTAACATCCTTTGTGGTACGAGGGAGAAACATTCCC

AAGTATCATTTTATTCACACTTAATTTTCTATCCCATACCCCCAAAATAAGGCTAGCTATTTAATTAGTTGGCTGCTTTTCT

CTTAATTTTTAGTGTTTCTGTTGATAATGTGTAAGTTTGGGAAAATGCTAAGTAGCTTTTCACTTAGAACACTGTTATTTTC

TCTTTAAAGTTTTCTACCTTACATTTATTATAGCATAGTTATCTTTATAGCATAGATGCAGAAAGTAAGAGAGAGCTTGTTT

TTTCAAGAAAACAACCCTTTAAAATACTTTCCAACCCATGAAGGGAAAAATCCTCCTTTTTTCCCCCAAGTGCATTCTACTT

ATTACTTTGCATTTTTCTCCCAAAGTCCAAATTTATGCAAAGAAAATAGAAACAAGTTCAAATGCAATGCATTAACCAAATA

AAACAAGTCTGCTTCAAATTAGGAACCAACCTAAGCATTTGTAAAGTGTAGCAGAATCAGAATTCTTTTAAAAATTAGATTT

GGAACCTGAACTATATAATTCATAATTCTCATTTTTCTGTGGAAAATTATTTTATCTTTCTCCTGTATACCTGAAAAAATGT

CCATAGGCTTAAAGGGTCATGCTTTTACATTCCTTCCATATCACAGGTACTATGAAGTAAGGAGACTTTTAGGTTTCTTTTT

GTCTTAAACTCAGACAGCTTTGTAAGCAGTAGTGTGTAGATTACAAGAGTTAGACAAAAGCAGGCGCGACTGAGAAGAGTTG

GTGGGGGAGAAGCTTGGGGCACTTCCTGTCACTCAACACATTCCAGATCACTAAAAAATTTCCACACCCTCTGCATTCCCCC

TTGCCCACTCCAGTTCCCGGTATTTTCTGATTCCATATGTTGTGGTATTTACCATACTTCTCTCCCTCACTAGGCTCTGGCA

AGACTGCTTCAGAGGGGATGCATTCCTTTAGATTGCACAAAGCGGAGCTGGGAAAATGGCTGGCAGTTTCAGAATCTAGTCA

TABLE 2A-continued

NOV2 nucleotide sequence.

CGATCGCACGCATGAGCACCTCACACATCCATGTCCCTACCCGCCCCCCGCTCCCGCCCCTGCAGCTGGCTGACCTGTCTC

ACCCACTGCTGGCCTATCGAACGGCCAGGACTGTCTGGTTTTGGCTCGTGCCTTTGTCCATGTCTGGCTTAGTTCCTCTCTG

TCTATGCTTGCCTCTACCCCCACCGCCCCAGGCGGCACAAGTGTTTGGCCACACAAAACTAGAGATAGAAAAGGTGGTAAAA

ACTTCAAACTTTTCTAAATTCTCCAACAGTTTATTTCTTGTGAATTTCTTCCTTCTTTAAATACTCCATTTTAAGAAAACAA

AAAAATTAATTATCTAAAGGCAAAGAATGGAAAGCAACCTTTGTGTTCCTTATAATAACTGACTTCATAACTCTCTCCAGCT

GCGTTATGGGATGTGTATAAAAAGCTTCTGTTCTGAGAACAAAGGAGCACGTGCAGAAATGAGACGAAAAAATCCACTGACA

GTATTCCATTACACAAATTACTTAAAAGATTTTAGTCAAGCCCCTCAACAGATTCAATTTTAAAATGGCTTTTAGTTAAAAA

AAAAAAATTGAAAGTGCTTACCCAGTAAAAGAACCGAAGTAGTCCTGAACTGTTACGTAAGACTTTTTACAGTTGGATCTTT

GTCAAAAGGGGATGGGGGTGATGGGAGAAAGCAGCAACGACAATCAAAAAAGTTCGAGCTGCTGTGGCTAGAGGACAACTTC

TGTGTTTCCAGATAGGATTCTTGCTGTAGAAATGGAACTTCCAGCCAGCACAGCATCCTGTCCCAGTAGAGAAATGAGTTTG

TCAGTTAAAACAAAAAAAAAATTAGATACTGGAACCCAGGCTAGACGAGGTATTGAACCGCGCCAGATTTCCTTGCAGCCCT

GTCTGCTCAGCTCGCATTGAACTATATATGACCCAGATGATGGACAGAAGCACATTTAGTCATGTGCACACTGGAAGAAAGC

GGATTTGCTGGTCCCTGGCAGTGCAGGGGTTTGTCTTCTGATTGGGCTGTGCCCTGATCGGTGAAATGTGAAGCCCTCACCA

TTCAGAGGCCGTAATTCAGGACTGGCAGTTTGAGTGTCTGGCTGCCTCTAGTCACTGAGAGACTTTGAAGGTGTTGCTTTTG

TTTGGTGGCATTACCCACCCAGAGGTTGCTTACACCTCTCTACTTGTGTCAGAAGAAATACTAGTCTTTCTGAAATACAAAT

AGGCAGCCGATTTTTCCTGAATCCTAAATCACCCTATTGTTGATAAACTTGGCTCTAACTGAAACCAATTATTTGATTTGAA

AATTTATTGTGATCCTAACCAAGCTTCATATCCAGACCAACCCTTGGTCTTGATTTTATAGGTTTGATAAGGTAAAAATAAA

AGTGGCATATTTGACTTTGAAGCCTCTATATGATATAAATTGCTCTTAATGAAAATTGGATAGATGGACAACAGAGAAGTGA

AGTTTTAGATTCTGGAGTGTTTGGATGTATGAGGAAGAAGCTTTATGTCTTTTTATCCCCTTTGTGAGACTGTCACTCTTGT

CCCAGTCCTAGTCACATTAGGGGTTGCTGGGGGGGGAAGCTATGAAAGCATGGACCCTACTGAGCTGTGACATAGCCTTTA

ATCATGCAAGACAGCCACGGTCTGCTCTCTTCAGTCTGTCTGAACTAGGGTCCTTGGGGTTTATTTTCCATCTTTCTGAGCC

ACTGGGAAACCAGGTCATTATACAGGACTGTCATTTGTGACATTTTTGTTTAGTACATGGCAGTTGCTTTGTTTATTTAATG

CAAGTTGACACTTCTTTAAAGTTTCAAAACAGTAAAGTTGTTTTGTGAGACCTTGACTCTGATATATGAAATCTACTCTACA

TGGACCAATCATTTTTTTCCGTGGACTTTCTTGTCTCTTTAGAAATTAGCTTATAGAGTCCTAAATTGATACTTAAACATAC

CAATAGTTCTGTTTATTTCTTGCCTTTCTCACAGTTGTTGAAATAATTCCATCTGTCTCTTTTGCTGTAAATTTTGGGTTTG

GATGTTTGTACTTGGAATTTTTTAGATGTTGACTATATTATGCAGCACCTTCCATATGAGGACTACCCCAGAATTATTCTCT

TGTCTTAACCCGAGAAAAGCTGTTTTGATGCACTATTAGATATAAGAATGTTCGAAAGAAGAGGAGATGAGCACTCTCTTGC

TTTTTGTAAGCCACAAGACAATCTTTTTTTTTCTAAGTTGTGGTAAGGTATATGTAACATAAAATTGACTGTTGTAATAAT

TTTTAAGTGTATAGTTCTGTGGTGTTAAGTGCATTCACGTTGTTTTGCAGCCTTCACCACCATCCATCCACCACAGAACTCT

TCTCCTCTTGCAAAACTGAAATTCTCTACCTACCTGTTAAACACTAACTTGCCATTCTTCCCTCCCCCAGGCCCTGGGGACA

ACCATCATTCTACTTTCTCTTTGATTTTTTGTTTTTTGTTTTTGGAGACGGAATTTTACTCTTGTTGCCCAAGCTGGGATGC

AATGGCACTGTCTTGGCTCACTGCAACTTCCGCCTCCTGGGTTCAAGCAATTCTCCTTCCTCAGCCTCCTGAGTAGCTGGGA

CTACAGGTGCCCACCACCACGCCTGGCTAGTTTTTGTATTTTTAGTAGACACGGGGTTTCACCATGTTGGCCAGGCTGGTCT

CGAACTCGTGATCTCAAGTGATCCACCCACCTTGGCCTCCCAAAATCCTAGAATTACAGGCATGAGCCCACCGTGCCTAGCC

TCTGTCTGTTTGCTTTTTGACTACTCTAGATACCTCATATAAGTGGAATAATACAAGATGTGTTCCCTTTTGACAGGCTTAT

TTCACTTAGCATGGTGTCCTCAAGGTTCATGCATGTTGTCGCATGTCAGAATTTCCTTACGTTTTAAGGCTGAATAATATAC

CATTGCATGTGTATACTACTGTCTTAGTCCCTTTAGTGTTGCTGTAAAGGAATACCTGAGGCTGGGTAATTTATAAAGAAAA

GAGGTTTATTTGGCTCATGGTTCTGCAAGCTGTACAAGAAGCATGGCACCAGCTTCTGGTGAGGGCCTCAAGCTGCCTCCAT

TABLE 2A-continued

NOV2 nucleotide sequence.

TCATGGCACAAGGTGAAAGGGAGCTGGTGTGTGCAGAGATCACATGGTAGGAGAGGAGGAGGCAAGAGAGAGAAGAAGGAGG

TGCCAGACTACTTTAAAACCATCAGCTTTTGCAGGGAGTTATAGAGCCAGCACTCACTGACTACTGCAAGAATGGCACCAAG

ACATTCATGAGGGATCTGCCTTCATGACCCAGACACCTCCCACCAGGCCCCACCACCAACATAAGGGGTTAGATTTCAGCAT

GAGACTCAATGAGGGGGAGCAAACAAATTACATCCAAACTGTAGCAACCACATTTTGTTTATCCATTCATCTGTCAATGGA

CACTTAAGTAGCTTCCACTTTTTTGCTATCAAGACAGTTTTTCTTGACTATTCTTAAAATCATGTGAGGGCTTCTTTACAGA

GCTGTTCTGACCCATCTCAGAAGCTCTTTTCACTTTATAAGTTGTAAGGGTTTTGATGGGCCTTTTAACTCTAGAGACCAGC

TAGTCCCTAACATCAGGTTTGCTAGAGAAGGGAAGATTCTTTCCAGCCTTCCTGGATGACACCTAATACATACTATATTCCT

AGTAATTCTGTTATACTTAAGATTTATGGGTTCATCTTTCCTGTTACACTGTGAGCCCTTCCTGGGCTGGGACGATGGCCAG

TTTCTCTTGAGTTGTGCCTTGTGCCTCTGTATAGGCACAGGGCCTATTATGAAGTAGATATCAATAAATATTAGTTGGAAAA

AATGTGAATTAGTAAATAATAATTTGTATTGGGTTTTTATGTGCCAGATGTTTTGAATACATTTAGCTAATTTAATCTTCAA

AACAGTCCTTTCAGATACATATTGTTATCTTCATTTAATAGATGAGGGAACTTGTCAAAGGCCTCAGAGATGTAAAATGTAT

AACTGGGATTTGAACCTTTGTTCAAATTGCTTGTTCTCGCTTGACTCAAGAGCCATTATGTTAGAGGCAGACTTCATAGTCA

GTTGATGATCAGTGGGTTTGGAAACATGAAATTTAGCTCAGGCATCGGCTCCAAATTAAATACTCTTTCATTGGGCATTAGG

AACTATACCCTTCTGATATGGCTCATGAATGGATGCTCAGAGGAAAGCTTGGCTCGTTAGTTACTTGGACCTTTTATAGGGA

CTTTAGCTGAACAACTAATTGCTGAACTCAGTTGGCAAAGGCTCTTCTGTGGGTAAATCCTCTTTCACATGTTATTTTGAAA

GTGCAGTTAAATTCTAACATACATGATGTGGCCCTGGAATGGATGCATCAGTTTTCTTTATTCTGTTTGTTTGGCAGGTGTG

TGTGTGTGTGTGTGTGTGTGTGTGTGTACAAAAAAAAAAAATGTATGTATAAAAGCAACCAGTATCTAGGTATCAG

GAACAAAACAAAGGTTTTTATGGAGCTTACATTCTAATGGGGAGACAGAAAAATGAATTCTCAAAGTACTATGAAGTGAAAC

ATGAAGCTACACTGTGAAGAAAATAGGGTAGTGTGGTGATGGAGAATGACTGACTGGTGGGATGTGGTGGATTGGGAGACAT

CTTGAATGAGGAAGTATCGGGCTATGCCTCTCTGAGGAACCAAAGTATGCAAGCTGAGAGCCAAGTCATGACATGAAGAACC

TCAGCCTACAAAGAGCCAGAAGAATGAACTGGGTAGTGGCAACAAGAAATGCAAGAGCTCTCATGTGGGATTGAGCTTAGTG

TGCTTGAGGAGCCAAAAGGGTAGTATGGCTAAAATGGAGTGAATGCAAGTAGGGGTGATGTTGGAGAGGTGGGATGGGGCCC

TATCACATAGGACCTTGTAAGCTATAGTAAGAAATTTGGGTTTTTTCCAAGTGTATTTTTTCCCAAATTTGTTTTTTTCCCC

CCAAATAGTAGGACATTGGAAGGTTTTAAGCAGAATGGTAACTTGTTCTGCAGGCCGAAGAAGTCCTTGTGTGCAGTTCTTG

TCTATGTTTAGTCCTCTGAGGCCCCCTTGACACTATCTTTAACTGGGGTTCCTCCCAAGCTGAGAATCTTGCCAAGGTTCTC

ACATGTCAGTGGCCACCTTTGAGTGTCCTAGAAGAATCATATTTCTTTTATAACCATTTTGGGGCTAACATTGGTTTCATTG

CCCTTTCCACAACAGAGAGGGTTTGTTCAACGAGAGCTTCTTCCAGCATTTTCATACATCACTGTTGCCTGGGTAGGGTTTT

GCAGCCTGATTCTCTGTATTAATTTAGGATAAAATTCAGTTATTAATTAGACCTGATCTTTCTTTGTCAATAATTTAGAAGC

ATATGTCCTCGGCACATAATGTTGGCTGACTGTTTGGTTAATAATATGTTCTTGAAGACATACTTCTGGAAATCTGAAATTG

ATAAGTGAAGAGGAACTTTCTTACTATTCATAAATAAGGTTGTATTCAGCTATTCTGACTCTAGTAGGGTTAATTGCTAACA

TTTGACCTACATTATTTTATTTTTTCAATTTCTCAAAAACTCTGAAAAGTATAGGCCAGGGGCCTTGGCTCATGCCTGTAAT

GCCAGTGCTTTGGGACGCCATGGTGGAAGGATTGCTTGAGGCCAGGAGTTCGAGACCAGCCTTAGCAACATAGTAAGACCCC

CATATCTACAAAAAATAAATTTGCCTGGCTTGATGATATGTGCCTGTAGTTCTAGTTACTTGTGAGGGTGAGGAGAGAGGGT

CACTTGAGTGCAGGAGTTCAAGGCTGCAGTGAGCTATGATGATGCCACCATACTCCAGGATGGTGACAGAGACTCTGTCTCT

TAAAAACAACAACAAAACAAACCTCTGACAAATACAGAAAATAACAGCATACACCTGATAGTCCCATTTTATAGGCAAGTG

ACATCTAGTATTTTCATAGTAAAATATCATGTAGTGTCATCTGATACTTTCTTCTTTTTACTAAAAAAAAAAAAAAGTTACT

TGCAAGCTACTCAGTTGATTTCACAGCTTACTGAAGGGGCAGCCAGAACTTTGGAAAGCACAAAAGGTGAGAAAACTGAGGC

TABLE 2A-continued

NOV2 nucleotide sequence.

TCTGGTGGTTAAATGACTTGTCCAGTGTCACATAGCAAGGAAGAGGCAGAGCTGAGACTTGAACCAGAGCTTGATTCCAAAG

TTCTTGCTCGTACTAT

The NOV2 nucleic acid was identified on chromosome 9 by comparing the sequence to public databases. The NOV2 nucleic acid maps to the 9q33–34 locus, a region associated with endotoxin hyporesponsiveness (OMIM 603030), adrenocortical insufficiency without ovarian defect (OMIM 184757) and other diseases/disorders. Single nucleotide polymorphisms were identified for NOV2, as described in Example 3. It was found that NOV2 had homology to the nucleic acid sequences shown in the BLASTN data listed in Table 2B.

complete the gene sequence. The DNA sequence was then manually corrected for apparent inconsistencies thereby obtaining the sequences encoding the full-length protein.

A disclosed NOV2 polypeptide (SEQ ID NO:9) encoded by SEQ ID NO:8 has 102 amino acid residues and is presented in Table 2C using the one-letter amino acid code. SignalP, Psort and/or Hydropathy results predict that NOV2 has no known signal peptide and is likely to be localized in

TABLE 2B

BLASTN results for NOV2

| Gene Index/ Identifier | Protein/ Organism | Begin– End | Length (nt) | Identity (%) | Expect |
|---|---|---|---|---|---|
| AL158075 | Human DNA sequence from clone RP11-348K2 on chromosome 9q33.1-34.13, complete sequence. 6/2001. Strand = Plus/Minus | [1–7560] [3799–4086] [4584–4654] [5736–5773] [6954–7071] [7003–7071] | 102867 | 7560/7560 (100%) | 0.0 |
| AK021895 | Homo sapiens cDNA FLJ11833 fis, clone HEMBA1006579. 9/2000. | [1–2237] | 2237 | 2234/2237 (100%) | 0.0 |

BLASTN homology of NOV2 to the GenBank Acc. No. AL158075 genomic clone in Table 2B depicts a proposed exon and intron structure for the NOV2 gene, which is most likely encoded on the AL158075 clone minus strand. The NOV2 nucleic acid is likely to be expressed in 10 week embryo and whole embryo, mainly head, based on its the nucleus with a certainty of 0.300. In alternative embodiments, a NOV2 polypeptide is located in the mitochondrial matrix space with a certainty of 0.100, in a lysosome (lumen) with a certainty of 0.100, or in a microbody (peroxisome) with a certainty of 0.0101. NOV2 has a molecular weight of 11700.6 Daltons.

TABLE 2C

Encoded NOV2 protein sequence.

(SEQ ID NO:9)
MMMPPYSRMVTETLSLKKQQQNKPLTNTENNSIHLIVPFYRQVTSSIFIVKYHVVSSDTFFFLLKKKKSYLQATQLISQLT

EGAAARTLESTKGEKTEALVVK homology to GenBank Acc. No. AK021895. GenBank AK021895 disclosed in September 2000, has homology to the 5' untranslated NOV2 sequence.

Exons were predicted by homology and the intron/exon boundaries were determined using standard genetic rules, as described in Example 1. Exons were further selected and refined by means of similarity determination using multiple BLAST (for example, tBlastN, BlastX, and BlastN) searches, and, in some instances, GeneScan and Grail. Expressed sequences from both public and proprietary databases were also added when available to further define and No sequences were found in the EMBL, PIR or GenBank databases that had homology to the NOV2 polypeptide in an unfiltered BLASTP search (expectation value=1.0 for input parameter).

The presence of identifiable domains in NOV2, as well as all other NOVX proteins, was determined by searches using software algorithms such as PROSITE, DOMAIN, Blocks, Pfam, ProDomain, and Prints, and then determining the Interpro number by crossing the domain match (or numbers) using the Interpro website (maintained by the European Bioinformatics Institute, Hinxton, Cambridge, UK). DOMAIN results for NOV2 as disclosed in Tables 1E, were collected from the Conserved Domain Database (CDD) with Reverse Position Specific BLAST analyses. This BLAST analysis software samples domains found in the Smart and Pfam collections.

Table 2D lists the domain description from DOMAIN analysis results against NOV2. Table 2E provides the percent homologies of NOV2 to the domains found in the BLASP analyses. Homology to one or more domains indicates that the NOV2 sequence has properties similar to those of other proteins known to contain these domains, and is a likely phosphoprotein.

TABLE 2D

Domain Analysis of NOV2

PRODOM Protein Domain Analysis

| Sequences producing High-scoring Segment Pairs: | High Score | Smallest Sum Probability P(N) |
|---|---|---|
| prdm:38396 p36(1) DRTS_PLAFK-DIHYDROFOLATE REDUCTASE . . . | 51 | 0.37 |
| prdm:48689 p36(1) Y360_MYCGE-HYPOTHETICAL PROTEIN MG3 . . . | 51 | 0.37 |
| prdm:55080 p36(1) DPOM_PODAN-PROBABLE DNA POLYMERASE . . . | 61 | 0.69 |
| prdm:16122 p36(2) PHAC(1) PHBC(1)-POLYMERASE SYNTHAS . . . | 46 | 0.84 |
| prdm:24351 p36(1) RS6_HAEIN-30S RIBOSOMAL PROTEIN S6 . . . .. | 46 | 0.84 |

BLOCKS Protein Domain Analysis

| AC# | Description | Strength | Score |
|---|---|---|---|
| BL00243G | Integrins beta chain cysteine-rich domain pro | 1511 | 1011 |
| BL00951C | ER lumen protein retaining receptor proteins. | 1661 | 1002 |
| BL01081 | Bacterial regulatory proteins, tetR family pr | 1354 | 1002 |
| BL00126A | 3'5'-cyclic nucleotide phosphodiesterases pro | 1312 | 1000 |
| BL00764A | Endonuclease III iron-sulfur binding region p | 1181 | 1000 |

| ProSite Protein Domain Analysis | AA of NOV2 (SEQ ID NO:4) |
|---|---|
| Pattern-ID: ASN_GLYCOSYLATION PS00001 (Interpro) | 30 |
| Pattern-DE: N-glycosylation site | |
| Pattern: N[^P][ST][^P] | |
| Pattern-ID: CAMP_PHOSPHO_SITE PS00004 (Interpro) | 66 |
| Pattern-DE: cAMP- and cgMP-dependent protein kinase phosphorylation site | |
| Pattern: [RK]{2}.[ST] | |
| Pattern-ID: PKC_PHOSPHO_STTE PS00005 (Interpro) | 15, 90 |
| Pattern-DE: Protein kinase C phosphorylation site | |
| Pattern: [ST].[RK] | |
| Pattern-ID: CK2_PHOSPHO_SITE PS00006 (Interpro) | 26, 91 |
| Pattern-DE: Casein kinase II phosphorylation site | |
| Pattern: [ST].{2}[DE] | |
| Pattern-ID: MYRISTYL PS00008 (Interpro) | 83 |
| Pattern-DE: N-myristoylation site | |
| Pattern: G[^EDRKHPFYW].{2}[STAGCN][^P] | |

TABLE 2E

ProDom results for NOV2

| ProDom Identifier | Protein/Organism | Length (nt) | Identity (%) | Positive (%) | Expect |
|---|---|---|---|---|---|
| prdm:38396 | p36 (1) DRTS_PLAFK- DIHYDROFOLATE REDUCTASE (EC 1.5.1.3) / THYMIDYLATE SYNTHASE (EC 2.1.1.45) (DHFR-TS). MULTIFUNCTIONAL ENZYME; OXIDOREDUCTASE; TRANSFERASE; NADP; METHYLTRANSFERASE; NUCLEOTIDE BIOSYNTHESIS; ONE-CARBON METABOLISM | 52 | 11/41 (26%) | 24/41 (58%) | 0.46 |
| prdm:48689 | p36 Y360_MYCGE-HYPOTHETICAL PROTEIN MG360 | 38 | 14/34 (41%) | 19/34 (55%) | 0.46 |
| prdm:55080 | p36 (1) DPOM_PODAN-PROBABLE DNA POLYMERASE (EC 2.7.7.7) DNA-DIRECTED DNA POLYMERASE | 135 | 14/60 (23%) | 28/60 (46%) | 1.2 |
| prdm:16122 | p36 (2) PHAC(1) PHHC(1)-POLYMERASE SYNTRASE PHA POLY 3-HYDROXYALKAKOATE PHA-POLYMERASE POLYHYDROXYALKANOIC ACID BIOSYNTHESIS TRANSFERASE | 55 | 14/37 (37%) | 20/37 (54%) | 1.8 |
| prdm 24351 | 36 (1) RS6_HAEIN // 30S RIBOSOMAL PROTEIN S6. RIBOSOMAL PROTEIN; RRNA-BINDING | 35 | 10/23 (43%) | 14/23 (60%) | 1.8 |

Other BLAST results include sequences from the Patp database, which is a proprietary database that contains sequences published in patents and patent publications. Patp results include those listed in Table 2F.

Such modifications include, by way of nonlimiting example, modified bases, and nucleic acids whose sugar phosphate backbones are modified or derivatized. These modifications are carried out at least in part to enhance the chemical

TABLE 2F

Patp alignments of NOV2

| PatP Identifier | Protein/Organism | Length (nt) | Identity (%) | Positive (%) | Expect |
|---|---|---|---|---|---|
| AAB43292 | Human ORFX oORF3056 polypeptide sequence SEQ ID NO:6112, PN = WO200058473-A2 | 110 | 69/101 (68%) | 77/101 (76%) | 3.4e-29 |
| AAG02872 | Human secreted protein, SEQ ID NO: 6953, PN = EP1033401-A2 | 144 | 60/101 (59%) | 73/101 (72%) | 1.1e-25 |
| AAR97079 | Respiratory Syncytial Virus antigenic fragment 30 | 61 | 15/30 (50%) | 17/30 (56%) | 2.1 |
| AAR97084 | Respirarory Syncytial Virus antigenic fragment 35 | 51 | 15/30 (50%) | 17/30 (56%) | 2.1 |
| AAR97080 | Respiratory Syncytial Virus antigenic fragment 31 | 59 | 15/30 (50%) | 17/30 (56%) | 2.1 |
| AAR97081 | Respiratory Syncytial Virus antigenic fragment 32 | 57 | 15/30 (50%) | 17/30 (56%) | 2.1 |
| AAR97082 | Respiratory Syncytial Virus antigenic fragment 33 | 55 | 15/30 (50%) | 17/30 (56%) | 2.1 |
| AAR97083 | Respiratory Syncytial Virus antigenic fragment 34 | 55 | 15/30 (50%) | 17/30 (56%) | 2.1 |

The disclosed NOV2 nucleic acid encoding a nuclear protein-like protein includes the nucleic acid whose sequence is provided in Table 2A, or a fragment thereof. The invention also includes a mutant or variant nucleic acid any of whose bases may be changed from the corresponding base shown in Table 2A while still encoding a protein that maintains its nuclear protein-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. stability of the modified nucleic acid, such that they may be used, for example, as antisense binding nucleic acids in therapeutic applications in a subject. In the mutant or variant nucleic acids, and their complements, up to about 67% percent of the bases may be so changed.

The disclosed NOV2 protein of the invention includes the nuclear protein-like protein whose sequence is provided in Table 2B. The invention also includes a mutant or variant protein any of whose residues may be changed from the corresponding residue shown in Table 2B while still encoding a protein that maintains its nuclear protein-like activities and physiological functions, or a functional fragment thereof. In the mutant or variant protein, up to about 66% percent of the residues may be so changed.

The invention further encompasses antibodies and antibody fragments, such as $F_{ab}$ or $(F_{ab})_2$, that bind immuno-specifically to any of the proteins of the invention.

The above defined information for this invention suggests that this nuclear protein-like protein (NOV2) may function as a member of a nuclear protein family. Therefore, the NOV2 nucleic acids and proteins identified here may be useful in potential therapeutic applications implicated in (but not limited to) various pathologies and disorders as indicated herein. The potential therapeutic applications for this invention include, but are not limited to: cancer research tools, for all tissues and cell types composing (but not limited to) those defined here, including cancerous and normal tissue, endotoxin hyporesponsiveness (OMIM 603030), adrenocortical insufficiency without ovarian defect (OMIM 184757) and other diseases/disorders.

The NOV2 nucleic acids and proteins of the invention are useful in potential therapeutic applications implicated in cancer including but not limited to and/or other pathologies and disorders. For example, a cDNA encoding the nuclear protein-like protein (NOV2) may be useful in cancer therapy, and the nuclear protein-like protein (NOV2) may be useful when administered to a subject in need thereof. By way of nonlimiting example, the compositions of the present invention will have efficacy for treatment of patients suffering from diseases including but not limited to endotoxin hyporesponsiveness and cancer. The NOV2 nucleic acid encoding nuclear protein-like protein, and the nuclear protein-like protein of the invention, or fragments thereof, may further be useful in diagnostic applications, wherein the presence or amount of the nucleic acid or the protein are to be assessed.

NOV2 nucleic acids and polypeptides are further useful in the generation of antibodies that bind immuno-specifically to the novel NOV2 substances for use in therapeutic or diagnostic methods. These antibodies may be generated according to methods known in the art, using prediction from hydrophobicity charts, as described in the "Anti-NOVX Antibodies" section below. The disclosed NOV2 protein has multiple hydrophilic regions, each of which can be used as an immunogen. In one embodiment, a contemplated NOV2 epitope is from about amino acids 10 to 38. In another embodiment, a NOV2 epitope is from about amino acids 55 to 102. These novel proteins can be used in assay systems for functional analysis of various human disorders, which will help in understanding of pathology of the disease and development of new drug targets for various disorders.

NOV3

A disclosed NOV3 nucleic acid of 7380 nucleotides (also referred to as 24SC113) encoding a novel LIM-domain containing Prickle-like protein is shown in Table 3A. An open reading frame was identified beginning with an ATG initiation codon at nucleotides 1991 to 1993 and ending with a TGA codon at nucleotides 2951 to 2953. The start and stop codons are in bold letters in Table 3A.

TABLE 3A

NOV3 nucleotide sequence.

(SEQ ID NO:10)
GTGAGTCAGGGAGGAGAAAGGTAGGCTGCTTGGGCCGGTGGCCTTTTGTTCTTGCAATTCTCTTCTTCTC

CCTAATTTCTGGTTCATTGCCTCTTTAGACAAGTCTCCAGAAGTTCTTCCTTGAAAGTCCAGGCTCAGGA

ACTCTCAGCCACTGAAGATAAAGGCCACATTAGTCCCTTTTTCTGGGAAGCCGTGTATCATTACGCATCA

GGAGAATGCAGGGGTCCTGGTCCACCCTACAGTCATAGCTTGAGGCTATATTCCCAGCAGGCTCTCCCCA

CGGGAAGGGGCCCCAGCAGCTCCCAGTTTCCATTCTGCCAGTTTTACTGCTGCTATAAAAAGAGCCTGCT

GTGTGACTGCCTTAGCAAAAGTCCTGCCTTAGAAAAAGCAATGAGAGGTGTTGGCTTAGTGCAGGTCACT

TGCCCACCCCTGAATCAGTCCCTGGGTGCCAGGAGAGCAGATTTTTTTTGCTGGCCTATGTTGGGCCCCA

GATCAGCTTTTGCCCCACCCAAAGCTCACGGCCTGAAGATGGCAGGGAAATGGTGTCCCACAGGGAGAGG

AAGTCCTATAACCAGAAGAGGGCAGAGATGATGAGAAGGCAGAACCCCTGGGGCTGTGGGAGGCTCCCTT

AGTACGCAGTGTGGCCAGGCTATATAAACCTGGCGCAGGCCTGTCACAGGGAGGAATCGTACCTCTTCCT

TCCCTGATGAAATTAAGCAAAGGGTACTTACGCTCCCAGAGGGGCAGTAGCTTTGGCAATACCGTGTCTA

GGTTTTTCTTTACCGAAAGCAGATTTTTCCTTAACAAGAGTTGAAATCCACATTTTTATTTCCCACTAAG

TCTGTTGAGACTGCTTTAACGGAATAGCACAGACTGGGTGGCCTCTGAGTAACAGAAATGTATTGCTGAC

AGTTCTGAAAGCTGGGAAGTTCAAACTCAAGGCACCAGCAAATGCAGTGTCTGCTGAGGGCCTGTTTTTT

GTTTCCTGGATGATACTTTCTGGCAGAGTCATCATATAGTGGAAGGAGCAAACAGGCTCCCTTGGGCCTC

TGTTATAAGGGCACTAATCTCATTCATGAGGTATCCACTCTCATGACCTAGTCACCTCCCAAAAAGCTCC

ATCTCCTAATGCCATCACTTTAGGATTTAGGTGTTAAACTTAGGAGTTCTGAAGAAAACATTCACCATAG

CATCCACTGAGTTGCTGCTGTGACTTACCCATTGGAATAGCATATGCTAGTAATGGGATTCACTCGATCT

ATCTACACACAAAGAGCCCTGTCATACACCAGGCCATGTTCCAGGTCCTGGAGATGCTGTAGAAACTCAA

TGAGTCTGTCCTCATAGAGCTTCACTTTTAGCGGGGAGAGAAATAATAAACAGATGCATGTATATACTG

TABLE 3A-continued

NOV3 nucleotide sequence.

TTGTAATGTAAAGCGGTATTAATGCTATCAAGAAAACTCCAGCAGGTAAGGGTGGAGAGTAATGGAGAAT

CACTATTTAGTGTGGATAGGAAGACTTCTCAGAGGAGTTGGCTTTTGAGCAGATGCCTAACTAGAGTGAA

GGAGATAGTGTCAATGTCATGGTTGAGAATAAGACTTCCTGGGTACAGATCTCGTCTCTGGTTCCTAGTT

ATGTTACCCTGCCAAGTTACTTAGCCTCATCTGCCTCTACTTTCTCATGTGAAAACTGCAAATAATATTA

GAAAGCTAGCTCAAGGAGCTGAGTGATTAAATGAGTTTACATATATAAAGCTCTTAAAGCAGTACATGAT

CATACGTTAATATTACTATTGCTATTTGTCAGGGGGAAATGTGTCCCAGGCAGAAGGATTCATAGACAAG

CCATTTTAACCTAGAGTCTTTGTGCTTGGAGCAAATGAGTTAAGGCGCATACTGGTACAACAAGGACTTC

TCGTAATAGGACGTGAATACCATTTACATAAGGGTCTGATTGTTGATTTATTGACAGTTTATCCTGCCGC

ACCTGGAATCCTGAGACAAACCAAGGTGCTATGTGTTTCACGTCCCAGTGCAGAGCTCTGAGCAGCTCAT

CAGCCTCTCCAATGTCTCTCATTTTTTTAGGTATCGACCAAGGTCAAATGACCTATGATGGCCAACACTG

GCATGCCACTGAGACCTGTTTCTGCTGTGCTCACTGCAAGAAATCCCTCCTGGGGCGGCCATTCCTCCCG

AAGCAGGGCCAGATATTCTGCTCACGGGCCTGCAGTGCTGGGGAAGACCCCAATGGTTCTGACTCCTCTG

ATTCCGCCTTCCAGAACGCCAGGGCCAAGGAGTCCCGGCGCAGTGCCAAAATTGGCAAGAACAAGGGCAA

GACGGAGGAGCCCATGCTGAACCAGCACAGCCAGCTGCAAGTGAGTTCTAACCGGCTGTCAGCCGACGTA

GACCCCCTGTCACTGCAGATGGACATGCTCAGCCTGTCCAGCCAGACACCCAGCCTCAACCGGGACCCCA

TCTGGAGGAGCCGGGAAGAGCCCTACCATTATGGGAACAAGATGGAGCAGAACCAGACCCAGAGCCCTCT

GCAGCTCCTCAGCCAGTGCAACATCAGAACTTCCTACAGTCCAGGAGGGCAAGGGGCTGGGGCCCAGCCC

GAAATGTGGGGCAAGCACTTCAGCAACCCCAAAAGGAGCTCGTCACTGGCCATGACAGGACATGCTGGCA

GCTTCATCAAGGAATGCCGAGAAGACTATTACCCGGGGAGGCTGAGATCTCAGGAGAGCTACAGTGATAT

GTCTAGTCAGAGTTTCAGTGAGACCCGAGGCAGCATCCAAGTCCCCAAATATGAGGAGGAAGAGGAAGAG

GAAGGGGGCTTGTCCACTCAGCAGTGTCGGACCCGTCATCCCATCAGTTCCCTGAAATACACAGAGGACA

TGACGCCCACAGAGCAGACCCCTCGGGGCTCCATGGAATCCCTGGCCCTGTCTAATGCAACAGGTAGGTT

CTGTTCACCTTGAAAACAGATAGAAAGGGGGTAGTCTCTGGGTGACTGGATGCTGGTCCCCAGGAATTTT

TTTTTTTTTGAAATGGAGTCTCGCTCTGTCCCCAGGCTGGAGTGCAGTGGCACGATCTCCGCTCACTG

CAAGCTCCACCTCCCGGGTTCACGCCATTCTCCTGCCTCAGCCTCACGAGTAGTTGGGACTACAGGTGCC

CGCCACCATGCCTGGCTAATTTTTTTGTATTTTTAGTACACACGTGTTTCACCGTGTTAGCCGGGATGTT

CTCGATCTCCTGACCTCGTGATCCACCTGCCTCGGCCTCCCAAAGTGGTAGGATTACAGGCGTGAGCCAC

CGTGCCCAGCCTGGTCCTCCGGATTTTAATGTTGTTTCTGCCACGTGCCCTCTTCTAATAGGCTGCTGAG

GAAGGTAAACCCAAGTTTGAGATGGCTTCTATCTTTGATGGGCTTCCCTGTAAACAAAGCCTGAGACAGG

TCCAGATGCCTGTGATGTACTGAGGGAGTGCTCTCAGGAGAAGGGGAGTGAGAGAAAGAGGACAGAGCAT

GGGGAGGAGCCAAGTGAGGAATGGTGTCTTCACTGGGGTCTGGCTTCTGCCTGATCCCACAGGGGACTCT

GATGGATGAGTTGCACTATAGAATCAATTGCTTCTTGTGACGAAGGGGCTGATGTTTTGTACCATCGTGT

TAGTTGGTCATCAGCTTTGGGCTGCTGAGGAGTGACAAAGGGATGAGATAGTGGATGTGGGCTTGGGGCA

AGGCAGCTCCTGTTGGCCAAAGGCAGCATTAAAGAAAGAAAATACTATGGTCTGAATGTTTTCCCCAAAA

TTCTTAAATTAAGATCCTAAATCCCAAGGTGATGGCATTAGGAGAAGGGGCCTTTTGGGAGGTGATTAAG

TCATGAGAGTGGAGACCTCATGAATGGGATTAATGCCCTTATAAAAGAGGTCCAAGGGAACTTGTTTGCC

CCTTGTACCATATGAAGGTGGAGAAGGTGTAGCTGTGAGCTGATGGCAGTACTCACAGCACCTGGAGCCC

AGTTGCCCCAGCGTGGTGCTGCCTGGGGCACCAAAGCATCCATGACAGCTTCTGAGACTGTTCTGAACCT

GTTTCTCACCAGGGAACTGGCTTCAAAGTGCAGATAAAGACATAAGAAATGTTTGGCTAGACAAGGAGAA

TABLE 3A-continued

NOV3 nucleotide sequence.

GACAGGCAGGCTGAAAAGAACAGAAGTAGAGAGAGAGAGATAATGGCATGCTTCTCTCTCCAGTGAAGTT

GTCCAGCTGGTTTTGTGTGCGTGGGAAGACTGATGTTGGCCAGGCATGGTGGCTCATGCCTGTAATTTCA

GCACTTTGGGGAGGCCAAGGCAGGAGGATCACTTGAGGCCAGGAGTTGGAGACCAGCCTGGGCAACCATA

GTGAGACTCTGTCTCTACAAACATATATGTGTGTGTATATATATAAAATATATAGCGTGTGTATATATAT

ATCATATATAATATATATTGTGTGTATATATAATATATAAATATATATGATATAATATATACAAATGTGT

TATATATATATATATAAATTAGCTGGACTTGGTGGCACATGCTCATAGTCCCAGCTACTTAGGAGACTAA

AGCAGGAGGATCACTTGAGCCCAGGAAGTTGAGGCTGAACTAAGCAATGATCCCACCTCTGCACTCCAGC

CTGGGCAGCAGAGTGACAACCTGTCTCTAGAAAAAAAAAAAAAAAAATTTAATATTATTGATTTAATATT

TTAAACATTATTTAAAAAATATTTTTAAATGTGGGAAAAAATAGAGTAACGTAGATTTTCTCTGTGATAG

TGCTACTTAAAGCAGAATCTGAGGATAACACTGGCTGAGAACTATCACCCATCAGCAGTGAGATTAGTAC

TTAACACCTATCAGCAGCGAGATTAGTACTGAAACTGGAAGTGTTAGAAACTTATAGCAGTTCGATGTTG

CGGTGCCATCCAAGTGCGTTTTCAGCAGGCTTGTCTTATTGATCAGGTTATAGACCCATCAGGGTGTTAT

AGAACTCACATACTGAGCTCTTTGTGCTTTGTGCTGTGTCTCAGACATGCTCAGCAGGGCCATATGTCGG

TCCACAAGGGATTGAAAATGAAAACAAACTGGTCCTTCACCACTGATAGCTTGAGAAGAGTAGCGCTCTA

AGATGTGCTAAGTATATCTGCCCCTTTGTGGGCAAGGTACCAGAGGAGGGAGATATACGTCTGCCCCTTA

CAGCAAGGATTCCATAGCCGATGGTGTCTGGATAGAGACTGTGATAATGTTAGCCCCATTTGAAGGGGAC

GGCCACTGCTCAGCTCCAGCTGCTTGTTGCCATGTGCTGGGATATTTATGTATCCACCTAACCTTTATAT

AGCTCTTGCAATGTGTCAAACATTGTTCTGAGCACGTCATAAATATTAGCTTGCTTAATTACATTGTCAT

AACACTGTGAGGGAGGAATATTGTTATGATTCTCATTTCAGAGTTGAAGAAACAGAAATGGAGAGGTTGA

GGGACTCACCCAAAGTCACTCAGCTTTCAGAGTGGTAGAGCAGGGATTTGAACCTGTGCATATGATTTCA

GAACCTTGCTCTTAATCACACCAGGCTGCCAGTCTAATACAAGCCCCATCCTGTCAGATCTTCCAGTTTT

TCCAGAGAAGTTAAAAATGTGGATTTTTAAAAATATGAAATCTATTTCAACACTGCTAGACAAACAAAAT

GAGGCTCTGAGTTGTAGCTTGTCCATGCAGTGGGTTTTACTTTCTATCCTCCTCAAATACATCCACATCT

GTGTTCCCATTTGTCCAAGAACAAAGAGTAGATATCCTCATCCCCATGTTTCAGATGGAAAAAAAAAAA

AAAATGAGGCCTTGGTGACTAAGCGCCTTGCCTGATGTCTTAGAAGGGAGCAATTAGTGCAGAGTGATGA

CTGCCTGCTTCCAGCCCAGGTTATGTTATTCTCGAAAGATTTATGTGCTATAATTATTTAAGAGGACAGC

AGATAAATATACTTCAGCCTCTGAAGAAGAGTTTCTCAAAGCTAGACCACCTGCATTAGAATCATGGG

TGTGCTTGATTCAAACATAGGCTCCTGGGCCTCCCCCTAACCCCTTGCATCAGAACTCTACAGAGGTGGG

GCCCAGGAATCTGCATGTTAAGCAGATCTCTGCTGAGGCTGATGTGCACCATTGTCTGAGGGGAGATGTG

CCTGGGTTTGTCTGCTCTGACTGTATCATCCTCACGTTGTGGCTCATGAGGAAATCAGAAGGGCTAGAGG

TTGAGGAATGCTGGAAAGGGCAAGTGAGGAAGACACTCAATTTCCATTCCTAAGGAGGGAGTGGACGCGG

TTTCCATTCCTAAAGAAGACATCATGGGAGATTTACTCTCATGATTTTCTAGGATCCTTGGGCAAAGCAA

CTAATGCCCCTTTGCCTCAGATTTTTGGGAAGCAACCCTGGCCATGCCTGATAAAACTGAGGGAAAAAAA

CTCCTGAGATCAGCACTGTCTAATATGGCAGCCATATGGGCTGTGGAAATTTAAACGAATTAAAATTAA

ATGAAATTAAAATTTCAGGCCATTAGTTGCACTAGACACATTTTAAGTACTCAACAGCAATGGCCTGAAG

TTTAAATTTTATTTAATTTTAATTCTTTTAAATTTCAATAGCCTCCTGTGGCTAGAGGTGACCCTGCTAG

AAGGTGCAGATGACAGAGTGAACTGATAAGATGGGCACGATATTAAGCCATCATTAGTCTCTGAAGTTCT

TACATGAGCCCTAATTTTTTGTCTTTCTAATTAATTAATAGTTAGGATTACTGGTTCTGGAGTCACACTT

TABLE 3A-continued

NOV3 nucleotide sequence.

GCTGGGATGAGATCAAGCCTTCATCATTTAGGAGTTGTGTGGCCTTGAACAAGTCACTTAAACTCTGCAA

AACTCAATTTCCTCATCCATGGAATTTTGTGAATAAGTGGATAAAGGTGTTCCTGTAGTACTTCCTTTGT

ATAGCTTTGGTGAGGGTTAAATGATAATTGCGTTTAAAATCATTAATATAGTCTTTGACACATATGACCT

TCTATAATGGTTACCTGCGACTTTTTATTATTATTAATTCTTTCTCCTCCCAAACACACTGATTCAAGTT

TTGACCTGTTGTGGCTACTAACTTCTCCCACCATCCACCAGCTGTGCAGGTTTGCATTTTAGATTTGAAA

ATACTCCTGCATGGGCCAGGCGTGGTGGCTCACACCTGTAATCTCAACACTTTGGGAGGCCAAGGCAGGT

GGATCACTTGAGGCCAGAAGTTCAAGACCAGCCTTGCCAACGTGGCAAAACCCCGTCTCTACTAAAAATA

CAGAAATTAGCCAGGCATGGTGGTGCATGACTGTAGTTCCAGCTTTTTGGGAGGCTGAGGCACAAGAATC

ACTTGAACCCAGGAGGCGGAGGTTTCAGTG

The NOV3 nucleic acid was identified on chromosome 3. This information was assigned using OMIM, the electronic northern bioinformatic tool implemented by CuraGen Corporation, public ESTs, public literature references and/or genomic clone homologies. This was executed to derive the chromosomal mapping of the SeqCalling assemblies, Genomic clones, literature references and/or EST sequences that were included in the invention.

A disclosed NOV3 polypeptide (SEQ ID NO:11) encoded by SEQ ID NO:10 has 320 amino acid residues and is presented in Table 3B using the one-letter amino acid code. SignalP results predict that NOV3 contains no known signal peptide. Psort and/or Hydropathy results predict that NOV3 is likely to be localized extracellularly with a certainty of 0.3700. In an alternative embodiment, NOV3 is likely to be localized to the lysosome lumen with a certainty of 0.1900, or to the endoplastic reticulum membrane with a certainty of 0.1000, or to the endoplastic reticulum lumen with a certainty of 0.1000. NOV3 has a molecular weight of 35510.0 Daltons.

TABLE 3B

Encoded NOV3 protein sequence.

(SEQ ID NO:11)
MCFTSQCRALSSSSASPMSLIFLGIDQGQMTYDGQHWHATETCFCCAHCKKSLLGRPFLPKQGQIFCSRACSAGEDPNGSD

SSDSAFQNARAKESRRSAKIGKNKGKTEEPMLNQHSQLQVSSNRLSADVDPLSLQMDMLSLSSQTPSLNRDPIWRSREEPY

HYGNKMEQNQTQSPLQLLSQCNIRTSYSPGGQGAGAQPEMWGKHFSNPKRSSSLAMTGHAGSFIKECREDYYPGRLRSQES

YSDMSSQSFSETRGSIQVPKYEEEEEEEGGLSTQQCRTRHPISSLKYTEDMTPTEQTPRGSMESLALSNATGRFCSP

The reverese complement for NOV3 is presented in Table 3C.

TABLE 3C

Reverse complement of the NOV3 sense strand.

(SEQ ID NO:12)
CACTGAAACCTCCGCCTCCTGGGTTCAAGTGATTCTTGTGCCTCAGCCTCCCAAAAAGCTGGAACTACAGTCATGCACCAC

CATGCCTGGCTAATTTCTGTATTTTTAGTAGAGACGGGGTTTTGCCACGTTGGCAAGGCTGGTCTTGAACTTCTGGCCTCA

AGTGATCCACCTGCCTTGGCCTCCCAAAGTGTTGAGATTACAGGTGTGAGCCACCACGCCTGGCCCATGCAGGAGTATTTT

CAAATCTAAAATGCAAACCTGCACAGCTGGTGGATGGTGGGAGAAGTTAGTAGCCACAACAGGTCAAAACTTGAATCAGTG

TGTTTGGGAGGAGAAAGAATTAATAATAATAAAAAGTCGCAGGTAACCATTATAGAAGGTCATATGTGTCAAAGACTATAT

TAATGATTTTAAACGCAATTATCATTTAACCCTCACCAAAGCTATACAAAGGAAGTACTACAGGAACACCTTTATCCACTT

ATTCACAAAATTCCATGGATGAGGAAATTGAGTTTTGCAGAGTTTAAGTGACTTGTTCAAGGCCACACAACTCCTAAATGA

TGAAGGCTTGATCTCATCCCAGCAAGTGTGACTCCAGAACCAGTAATCCTAACTATTAATTAATTAGAAAGACAAAAAATT

AGGGCTCATGTAAGAACTTCAGAGACTAATGATGGCTTAATATCGTGCCCATCTTATCAGTTCACTCTGTCATCTGCACCT

TABLE 3C-continued

Reverse complement of the NOV3 sense strand.

TCTAGCAGGGTCACCTCTAGCCACAGGAGGCTATTGAAATTTAAAAGAATTAAAATTAAATAAAATTTAAACTTCAGGCCA
TTGCTGTTGAGTACTTAAAATGTGTCTAGTGCAACTAATGGCCTGAAATTTTAATTTCATTTAATTTTAATTCGTTTAAAT
TTCCACAGCCCCATATGGCTGCCATATTAGACAGTGCTGATCTCAGGAGTTTTTTTCCCTCAGTTTTATCAGGCATGGCCA
GGGTTGCTTCCCAAAAATCTGAGGCAAAGGGGCATTAGTTGCTTTGCCCAAGGATCCTAGAAAATCATGAGAGTAAATCTC
CCATGATGTCTTCTTTAGGAATGGAAACCGCGTCCACTCCCTCCTTAGGAATGGAAATTGAGTGTCTTCCTCACTTGCCCT
TTCCAGCATTCCTCAACCTCTAGCCCTTCTGATTTCCTCATGAGCCACAACGTGAGGATGATACAGTCAGAGCAGACAAAC
CCAGGCACATCTCCCCTCAGACAATGGTGCACATCAGCCTCAGCAGAGATCTGCTTAACATGCAGATTCCTGGGCCCCACC
TCTGTAGAGTTCTGATGCAAGGGGTTAGGGGGAGGCCCAGGAGCCTATGTTTGAATCAAGCACACCCATGATTCTAATGCA
GGTGGTCTAGCTTTGAGAAACTCTTCTTCAGAGGCTGAAGTATATATTTATCTGCTGTCCTCTTAAATAATTATAGCACAT
AAATCTTTCGAGAATAACATAACCTGGGCTGGAAGCAGGCAGTCATCACTCTGCACTAATTGCTCCCTTCTAAGACATCAG
GCAAGGCGCTTAGTCACCAAGGCCTCATTTTTTTTTTTTTTTCCATCTGAAACATGGGGATGAGGATATCTACTCTTTGT
TCTTGGACAAATGGGAACACAGATGTGGATGTATTTGAGGAGGATAGAAAGTAAAACCCACTGCATGGACAAGCTACAACT
CAGAGCCTCATTTTGTTTGTCTAGCAGTGTTGAAATAGATTTCATATTTTTAAAAATCCACATTTTTAACTTCTCTGGAAA
AACTGGAAGATCTGACAGGATGGGCTTGTATTAGACTGGCAGCCTGGTGTGATTAAGAGCAAGGTTCTGAAATCATATGC
ACAGGTTCAAATCCCTGCTCTACCACTCTGAAAGCTGAGTGACTTTGGGTGAGTCCCTCAACCTCTCCATTTCTGTTTCTT
CAACTCTGAAATGAGAATCATAACAATATTCCTCCCTCACAGTGTTATGACAATGTAATTAAGCAAGCTAATATTTATGAC
GTGCTCAGAACAATGTTTGACACATTGCAAGAGCTATATAAAGGTTAGGTGGATACATAAATATCCCAGCACATGGCAACA
AGCAGCTGGAGCTGAGCAGTGGCCGTCCCCTTCAAATGGGCTAACATTATCACAGTCTCTATCCAGACACCATCGGCTAT
GGAATCCTTGCTGTAAGGGGCAGACGTATATCTCCCTCCTCTGGTACCTTGCCCACAAAGGGGCAGATATACTTAGCACAT
CTTAGAGCGCTACTCTTCTCAAGCTATCAGTGGTGAAGGACCAGTTTGTTTTCATTTTCAATCCCTTGTGGACCGACATAT
GGCCCTGCTGAGCATGTCTGAGACACAGCACAAAGCACAAAGAGCTCAGTATGTGAGTTCTATAACACCCTGATGGGTCTA
TAACCTGATCAATAAGACAAGCCTGCTGAAAACGCACTTGGATGGCACCGCAACATCGAACTGCTATAAGTTTCTAACACT
TCCAGTTTCAGTACTAATCTCGCTGCTGATAGGTGTTAAGTACTAATCTCACTGCTGATGGGTGATAGTTCTCAGCCAGTG
TTATCCTCAGATTCTGCTTTAAGTAGCACTATCACAGAGAAAATCTACGTTACTCTATTTTTTCCCACATTTAAAAATATT
TTTTAAATAATGTTTAAAATATTAAATCAATAATATTAAATTTTTTTTTTTTTTTCTAGAGACAGGTTGTCACTCTGCT
GCCCAGGCTGGAGTGCAGAGGTGGGATCATTGCTTAGTTCAGCCTCAACTTCCTGGGCTCAAGTGATCCTCCTGCTTTAGT
CTCCTAAGTAGCTGGGACTATGAGCATGTGCCACCAAGTCCAGCTAATTTATATATATATATATAACACATTTGTATATAT
TATATCATATATATTTATATATTATATATACACACAATATATATTATATATGATATATATATACACACGCTATATATTTTA
TATATATACACACACATATATGTTTGTAGAGAGAGAGTCTCACTATGGTTGCCCAGGCTGGTCTCCAACTCCTGGCCTCAA
GTGATCCTCCTGCCTTGGCCTCCCCAAAGTGCTGAAATTACAGGCATGAGCCACCATGCCTGGCCAACATCAGTCTTCCCA
CGCACACAAAACCAGCTGGACAACTTCACTGGAGAGAGAAGCATGCCATTATCTCTCTCTCTCTACTTCTGTTCTTTTCAG
CCTGCCTGTCTTCTCCTTGTCTAGCCAAACATTTCTTATGTCTTTATCTGCACTTTGAAGCCAGTTCCCTGGTGAGAAACA
GGTTCAGAACAGTCTCAGAAGCTGTCATGGATGCTTTGGTGCCCCAGGCAGCACCACGCTGGGGCAACTGGGCTCCAGGTG
CTGTGAGTACTGCCATCAGCTCACAGCTACACCTTCTCCACCTTCATATGGTACAAGGGCAAACAAGTTCCCTTGGACCT
CTTTTATAAGGGCATTAATCCCATTCATGAGGTCTCCACTCTCATGACTTAATCACCTCCCAAAAGGCCCCTTCTCCTAAT
GCCATCACCTTGGGATTTAGGATCTTAATTTAAGAATTTTGGGGAAAACATTCAGACCATAGTATTTTCTTTCTTTAATGC
TGCCTTTGGCCAACAGGAGCTGCCTTGCCCCAAGCCCACATCCACTATCTCATCCCTTTGTCACTCCTCAGCAGCCCAAAG
CTGATGACCAACTAACACGATGGTACAAAACATCAGCCCCTTCGTCACAAGAAGCAATTGATTCTATAGTGCAACTCATCC
ATCAGAGTCCCCTGTGGGATCAGGCAGAAGCCAGACCCCAGTGAAGACACCATTCCTCACTTGGCTCCTCCCCATGCTCTG

TABLE 3C-continued

Reverse complement of the NOV3 sense strand.

```
TCCTCTTTCTCTCACTCCCCTTCTCCTGAGAGCACTCCCTCAGTACATCACAGGCATCTGGACCTGTCTCAGGCTTTGTTT

ACAGGGAAGCCCATCAAAGATAGAAGCCATCTCAAACTTGGGTTTACCTTCCTCAGCAGCCTATTAGAAGAGGGCACGTGG

CAGAAACAACATTAAAATCCGGAGGACCAGGCTGGGCACGGTGGCTCACGCCTGTAATCCTACCACTTTGGGAGGCCGAGG

CAGGTGGATCACGAGGTCAGGAGATCGAGAACATCCCGGCTAACACGGTGAAACACGTGTGTACTAAAAATACAAAAAAAT

TAGCCAGGCATGGTGGCGGGCACCTGTAGTCCCAACTACTCGTGAGGCTGAGGCAGGAGAATGGCGTGAACCCGGGAGGTG

GAGCTTGCAGTGAGCGGAGATCGTGCCACTGCACTCCAGCCTGGGGACAGAGCGAGACTCCATTTCAAAAAAAAAAAAAA

TTCCTGGGGACCAGCATCCAGTCACCCAGAGACTACCCCCTTTCTATCTGTTTTCAAGGTGAACAGAACCTACCTGTTGCA

TTAGACAGGGCCAGGGATTCCATGGAGCCCCGAGGGGTCTGCTCTGTGGGCGTCATGTCCTCTGTGTATTTCAGGGAACTG

ATGGGATGACGGGTCCGACACTGCTGAGTGGACAAGCCCCCTTCCTCTTCCTCTTCCTCCTCATATTTGGGGACTTGGATG

CTGCCTCGGGTCTCACTGAAACTCTGACTAGACATATCACTGTAGCTCTCCTGAGATCTCAGCCTCCCCGGGTAATAGTCT

TCTCGGCATTCCTTGATGAAGCTGCCAGCATGTCCTGTCATGGCCAGTGACGAGCTCCTTTTGGGGTTGCTGAAGTGCTTG

CCCCACATTTCGGGCTGGGCCCCAGCCCCTTGCCCTCCTGGACTGTAGGAAGTTCTGATGTTGCACTGGCTGAGGAGCTGC

AGAGGGCTCTGGGTCTGGTTCTGCTCCATCTTGTTCCCATAATGGTAGGGCTCTTCCCGGCTCCTCCAGATGGGGTCCCGG

TTGAGGCTGGGTGTCTGGCTGGACAGGCTGAGCATGTCCATCTGCAGTGACAGGGGGTCTACGTCGGCTGACAGCCGGTTA

GAACTCACTTGCAGCTGGCTGTGCTGGTTCAGCATGGGCTCCTCCGTCTTGCCCTTGTTCTTGCCAATTTTGGCACTGCGC

CGGGACTCCTTGGCCCTGGCGTTCTGGAAGGCGGAATCAGAGGAGTCAGAACCATTGGGTCTTCCCCAGCACTGCAGGCC

CGTGAGCAGAATATCTGGCCCTGCTTCGGGAGGAATGGCCGCCCCAGGAGGGATTTCTTGCAGTGAGCACAGCAGAAACAG

GTCTCAGTGGCATGCCAGTGTTGGCCATCATAGGTCATTTGACCTTGGTCGATACCTAAAAAAATGAGAGACATTGGAGAG

GCTGATGAGCTGCTCAGAGCTCTGCACTGGGACGTGAAACACATAGCACCTTGGTTTGTCTCAGGATTCCAGGTGCGGCAG

GATAAACTGTCAATAAATCAACAATCAGACCCTTATGTAAATGGTATTCACGTCCTATTACGAGAAGTCCTTGTTGTACCA

GTATGCGCCTTAACTCATTTGCTCCAAGCACAAAGACTCTAGGTTAAAATGGCTTGTCTATGAATCCTTCTGCCTGGGACA

CATTTCCCCCTGACAAATAGCAATAGTAATATTAACGTATGATCATGTACTGCTTTAAGAGCTTTATATATGTAAACTCAT

TTAATCACTCAGCTCCTTGAGCTAGCTTTCTAATATTATTTGCAGTTTTCACATGAGAAAGTAGAGGCAGATGAGGCTAAG

TAACTTGGCAGGGTAACATAACTAGGAACCAGAGACGAGATCTGTACCCAGGAAGTCTTATTCTCAACCATGACATTGACA

CTATCTCCTTCACTCTAGTTAGGCATCTGCTCAAAAGCCAACTCCTCTGAGAAGTCTTCCTATCCACACTAAATAGTGATT

CTCCATTACTCTCCACCCTTACCTGCTGGAGTTTTCTTGATAGCATTAATACCGCTTTACATTACAACAGTATATACATGC

ATCTGTTTATTATTTCTCTCCCCCGCTAAAAGTGAAGCTCTATGAGGACAGACTCATTGAGTTTCTACAGCATCTCCAGGA

CCTGGAACATGGCCTGGTGTATGACAGGGCTCTTTGTGTGTAGATAGATCGAGTGAATCCCATTACTAGCATATGCTATTC

CAATGGGTAAGTCACAGCAGCAACTCAGTGGATGCTATGGTGAATGTTTTCTTCAGAACTCCTAAGTTTAACACCTAAATC

CTAAAGTGATGGCATTAGGAGATGGAGCTTTTTGGGAGGTGACTAGGTCATGAGAGTGGATACCTCATGAATGAGATTAGT

GCCCTTATAACAGAGGCCCAAGGGAGCCTGTTTGCTCCTTCCACTATATGATGACTCTGCCAGAAAGTATCATCCAGGAA

CAAAAAACAGGCCCTCAGCAGACACTGCATTTGCTGGTGCCTTGAGTTTGAACTTCCCAGCTTTCAGAACTGTCAGCAATA

CATTTCTGTTACTCAGAGGCCACCCAGTCTGTGCTATTCCGTTAAAGCAGTCTCAACAGACTTAGTGGGAAATAAAAATGT

GGATTTCAACTCTTGTTAAGGAAAAATCTGCTTTCGGTAAAGAAAAACCTAGACACGGTATTGCCAAAGCTACTGCCCCTC

TGGGAGCGTAAGTACCCTTTGCTTAATTTCATCAGGGAAGGAAGAGGTACGATTCCTCCCTGTGACAGGCCTGCGCCAGGT

TTATATAGCCTGGCCACACTGCGTACTAAGGGAGCCTCCCACAGCCCCAGGGGTTCTGCCTTCTCATCATCTCTGCCCTCT

TCTGGTTATAGGACTTCCTCTCCCTGTGGGACACCATTTCCCTGCCATCTTCAGGCCGTGAGCTTTGGGTGGGCAAAAGC

TGATCTGGGGCCCAACATAGGCCAGCAAAAAAAATCTGCTCTCCTGGCACCCAGGGACTGATTCAGGGGTGGGCAAGTGAC
```

TABLE 3C-continued

Reverse complement of the NOV3 sense strand.

CTGCACTAAGCCAACACCTCTCATTGCTTTTTCTAAGGCAGGACTTTTGCTAAGGCAGTCACACAGCAGGCTCTTTTTATA

GCAGCAGTAAAACTGGCAGAATGGAAACTGGGAGCTGCTGGGGCCCCTTCCCGTGGGGAGAGCCTGCTGGGAATATAGCCT

CAAGCTATGACTGTAGGGTGGACCAGGACCCCTGCATTCTCCTGATGCGTAATGATACACGGCTTCCCAGAAAAAGGGACT

AATGTGGCCTTTATCTTCAGTGGCTGAGAGTTCCTGAGCCTGGACTTTCAAGGAAGAACTTCTGGAGACTTGTCTAAAGAG

GCAATGAACCAGAAATTAGGGAGAAGAAGAGAATTGCAAGAACAAAAGGCCACCGGCCCAAGCAGCCTACCTTTCTCCTCC

CTGACTCAC

The full NOV3 amino acid sequence of the protein of the invention was found to have 59 to 120 amino acid residues (49%) identical to, and 80 to 120 amino acid residues (66%) similar to, the 1011 amino acid residue SPTREMBL-ACC:Q9NDQ8 PRICKLE 2 from Ciona intestinalis. In additional searches of the public databases, NOV3 has homology to the amino acid sequences shown in the BLASTP data listed in Table 3D.

TABLE 3D

BLAST results for NOV3

| Matching Entry (in SwissProt + SpTrEMBL) | Description | Length (aa) | Identity (%) | Positives (%) | Expect |
|---|---|---|---|---|---|
| Q9NDQ8; AB036841; BAB00618.1 | PRICKLE 2. ciona intestinalis 6/2001 | 1011 | 59/122 (48%) | 78/122 (64%) | 1e−23 |
| Q9NDQ9; AB036840; BAB00617.1 | PRICKLE 1. ciona intestinalis. prickle 1 6/2001 | 1066 | 58/122 (48%) | 77/122 (63%) | 1e−22 |
| Q9U1I1; AJ251892; CAB64381.1 | LIM-DOMAIN PROTEIN (ESN PROTEIN). drosophila melanogaster 6/2001 | 785 | 47/69 (53%) | 60/89 (67%) | 2e−20 |
| O76007; AJ011654; CAA09726.1 | TRIPLE LIM DOMAIN PROTEIN. homo sapiens 6/2001 | 615 | 38/61 (62%) | 49/61 (80%) | 4e−20 |
| Q9V4I9; AE003842; AAF59281.1 | CG11084 PROTEIN drosophila melanogaster 6/2001 | 1268 | 47/105 (45%) | 62/105 (59%) | 8e−20 |

The homology of these and other sequences is shown graphically in the ClustalW analysis shown in Table 3E. In the ClustalW alignment of the NOV3 protein, as well as all other ClustalW analyses herein, the black outlined amino acid residues indicate regions of conserved sequence (i.e., regions that may be required to preserve structural or functional properties), whereas non-highlighted amino acid residues are less conserved and can potentially be mutated to a much broader extent without altering protein structure or function.

TABLE 3E

ClustalW Analysis of NOV3

1) Novel NOV3 (SEQ ID NO:11)

2) Q9DQ8 (SEQ ID NO:13)

3) Q9DQ9 (SEQ ID NO:14)

4) Q9U1I1 (SEQ ID NO:15)

5) O76007 (SEQ ID NO:16)

6) Q9V4I9 c-ter fragment (SEQ ID NO:17)

TABLE 3E-continued

ClustalW Analysis of NOV3

```
NOV3     1                                                         MTMPAAATEQ  10
Q9DQ8    1                                                         MTMPAAATEQ  10
Q9DQ9    1                                                         MTMPAAATEQ  10
Q9U1I1   1   -----MQQAP-------QQQQHPHP----PSSSYYTQTES--------ELLQIEAGGTGL  36
O76007   1                                                         MFARGSRRRR  10
Q9V4I9 241   EEESPEQEAPKPALPPKQKQQRPVPPLPPPPANRVTQDQGTQPAAPQVPLQPLTAGDLQF 300

NOV3    11   TRGTMPSNIDEKS-------------AGLDQDIVIRGP-----------------  35
Q9DQ8   11   TRGTMPSNIDEKS-------------AGLDQDIVIRGP-----------------  35
Q9DQ9   11   TRGTMPSNIDEKS-------------AGLDQDIVIRGP-----------------  35
Q9U1I1  37   TFASHSQR--PES-------------AISQVASTAHLDVPSAASS----------  66
O76007  11   SGRAPPEAEDEDR-------------GQPCNSCREQCPGFLLHG-----------  41
Q9V4I9 301   LNLSLRQRSLERSMKPFKDAHDISFTFNELDTSAEPEVATGAAQQESNECRTPLTQISYL 360

NOV3    35   ------------------------------------------------------------  35
Q9DQ8   35   ------------------------------------------------------------  35
Q9DQ9   35   ------------------------------------------------------------  35
Q9U1I1  66   ----------------------GSGGSAVSGGSGG-----APESAGRFVS---PLQR--  93
O76007  41   ------------------------------------------------------------  41
Q9V4I9 361   QKIPTLPRHFSPSGQGLATPPALGSGGMGLPSSSSASALYAAQAAAGILPTSPLPLQRHQ 420

NOV3    35   -----TENRVR------------------------RRQSRRQAS--------VRHNR--  55
Q9DQ8   35   -----TENRVR------------------------RRQSRRQAS-  -----VRHNR--  55
Q9DQ9   35   -----TENRVR------------------------RRQSRRQAS--------VRHNR--  55
Q9U1I1  93   -----RHCQPP-------------SHLPLNSVASPLRTASYKSAAAVAGHGFHHSHHQ-- 133
O76007  41   WRKICQHCKCP------------------------REEHAVHAVPVDLERIMCRLIS--  74
Q9V4I9 421   QYLPPHHQQHPGAGMGPGPGSGAAAGPPLGPQYSPGCSANPKYSNAQLPPPPHHHHQLSP 480

NOV3    55   -------------------------------NSASDEENDGDSGCALEEYAWVPPNLT  82
Q9DQ8   55   -------------------------------NSASDEENDGDSGCALEEYAWVPPNLT  82
Q9DQ9   55   -------------------------------NSASDEENDGDSGCALEEYAWVPPNLT  82
Q9U1I1 133   -------------------------------QLDFQRNSQSDDSGCALEEYTWVPPGLR 162
O76007  74   -------------------------------DFQRHSISDDDSGCASEEYAWVPPGLK 101
Q9V4I9 481   ALSTPSPPSLLHHPAGGTSSASAHAPFLGGPHMDMRQSHSDDDSGCALEEYTWVPPGLR 540

NOV3    83   PDQVRYYFISLPEDKVPLVDSIGDKYRVRQLLHQLPPHDDKVCYCNDLSDEEKRELRLFS 142
Q9DQ8   83   PDQVRYYFTSLPEDKVPLVDSIGDKYRVRQLLHQLPPHDDKVCYCNDLSDEEKRELRIFS 142
Q9DQ9   83   PDQVRYYFTSLPEDKVPLVDSIGDKYRVRQLLHQLPPHDDKVCYCNDLSDEEKRELRIFS 142
Q9U1I1 163   PDQVRLYFSQLPDDKVPYVNSPGEKYRVKQLLHQLPPQDNVRYCHSLSDEEKRELRIFS 222
O76007 102   PEQVYQFFSCLPEDKVPYVNSPGEKYRIKQLLHQLPPHDSEAQYCTALEEBEKKELRAFS 161
Q9V4I9 541   PDQVRLYFSQTPDDKVPYVNSPGEQYRVRQLLHQLPHDNSVRYCHSLTDEERKELRLFS 600

NOV3   143   EQRKKDYLGCGKIRILPLNTEGTPCSECGILVKGGDIVAVASRAEPGMCWHPACFVCSVC 202
Q9DQ8  143   EQRKKDYLGCGKIRILPLNTEGTPCSECGILVKGGDIVAVASRAEPGMCWHPACFVCSVC 202
Q9DQ9  143   EQRKKDYLGCGKIRILPLNTEGTPCSECGILVKGGDIVAVASRAEPGMCWHPACFVCSVC 202
Q9U1I1 223   AQRKREALGRCAVRLLSDERP----CKGCEEPLSGGDIVVFAQRLGAQLCWHPGCFVCSVC 279
O76007 162   QQRKRENLGRCIVRRFPVTITGAICEECGKQIGGDIAVFASRAGLGACWHPQCFVCTTC 221
Q9V4I9 601   TQRKRDALGRCNVRQLMSARP----CDGCDDLISTGDIAVFATRLGPNASWHPACEACSVC 657

NOV3     2   RELLVDLFYFYQDGRLYCGRHHAETLKPRCSACDEIIFSDECTEAEGRHWHMDHFCCFEC 262
Q9DQ8    2   RELLVDLFYFYQDGRLYCGRHHAETLKPRCSACDEIIFSDECTEAEGRHWHMDHFCCFEC 262
Q9DQ9    2   RELLVDLFYFYQDGRLYCGRHHAETLKPRCSACDEIIFSDECTEAEGRHWHMDHFCCFEC 262
Q9U1I1 280   KELLVDLIYFQRDCNLYCGRHHAETQKPRCSACDEIIFSDECTEAEGRITWHMKHFACQEC 339
O76007 222   QELLVDLIYFVHVGKVYCGRHHAFCLRPRCQACDEIIFSPECTEAEGRHWHMDHFCCFEC 281
Q9V4I9 658   RELLCDLIYFHRDCRMYCGRHHAETLKPRCSACDEIILADECTEAEGRAWHMNHFACHEC 717

NOV3   263   DQVLGGQRYIMRLGKPNCTQCFEALYAEYCDMCGDLIGLDAGQMQYEGQHWHATDNCFCC 322
Q9DQ8  263   DQVLGGQRYIMRLGKPNCTQCFEALYAEYCDMCGDLIGLDAGQMQYEGQHWHATDNCFCC 322
Q9DQ9  263   DQVLGGQRYIMRLGKPNCTQCFEALYAEYCDMCGDLIGLDAGQMQYEGQHWHATDNCFCC 322
Q9U1I1 340   EHQLGGQRYHCCACFLTMFAEYCLYCGEVIGVDQGQMSHDGQHWHATDQCFSC 399
O76007 282   EASLGGQRYVMRQSRPHCCACYEARHAEYCDGCGEHIGLDQGQMAYEGQHWHASDRFCC 341
Q9V4I9 718   DKQLGGQRYIMREGKPYCLHCFDAMFAEYCLYCGEAIGVDQGQMSHDGQHWHATDECFSC 777

NOV3   323   NRCRKSLLGRPFLPKHGRIFCSKACSLGEDPGHSESDSQHSSSQYENPQLPTSHNVRRSL 382
Q9DQ8  323   NRCRKSLLGRPFLPKHGRIFCSKACSLGEDPGHSESDSQHSSSQYENPQLPTSHNVRRSL 382
Q9DQ9  323   NRCRKSLLGRPFLPKHGRIFCSKACSLGEDPGHSESDSQHSSSQYENPQLPTSHNVRRSL 382
Q9U1I1 400   CTCRCSLLGRPFLPRRCTIYCSIACSKGEPPTPSDTSSG--------------------- 438
O76007 342   SRCGRALLCGRPCPSPRGLIFCSRACSLGSEP-TAPGPSRRSWS----------------- 383
Q9V4I9 778   NTCRCSLLGRAFLPRRGAILYCSIACSKGEPPTPSDSSGTGMYT------------------ 820

NOV3   383   NLDNLSIHDKPWEDKGELSPASNNVFIDAADMYPISAAVAASTRYSKGHTRPSHPYLDGM 442
Q9DQ8  383   NLDNLSIHDKPWEDKGELSPASNNVFIDAADMYPISAAVAASTRYSKGHTRPSHPYLDGM 442
Q9DQ9  383   NLDNLSIHDKPWEDKGELSPASNNVFIDAADMYPISAAVAASTRYSKGHTRPSHPYLDGM 442
Q9U1I1 400   ---------------------------PQLRPTHRASTSSQIAKSPRRGGER------ 463
O76007 342   ---------------AG------------PVTAPLAAST--------------- 395
Q9V4I9 778   ---------------------------TPTPPIQRVRTPHQAPLPARIPSSH------ 845
```

TABLE 3E-continued

ClustalW Analysis of NOV3

```
NOV3    443 DPVNAEMVTENDAGFKGAATSRKTVTDSVTSPTSTVSSRTTSKNGVQFPQNTYNSTDSSG 502
Q9DQ8   443 DPVNAEMVTENDAGFKGAATSRKTVTDSVTSPTSTVSSRTTSKNGVQFPQNTYNSTDSSG 502
Q9DQ9   443 DPVNAEMVTENDAGFKGAATSRKTVTDSVTSPTSTVSSRTTSKNGVQFPQNTYNSTDSSG 502
Q9U1I1  463 ---------ERDPGRKAHHGHPKATGSAGDLLERQERQRMEAAG---------------- 498
O76007  395 ----------ASFS-----------AVKG-----ASETTTKC----------------- 411
Q9V4I9  845 ---------ASSSPPMSPQQQQQHQATFNQAMYQMQSQQMEAAGGLVDQSKSYAASDS-- 894

NOV3    503 YNSSSTLDAIEHQQNAALKAAMGSNYSYGKSKQTPCSKRPQNGEDCHVSATEFTPEHPAA 562
Q9DQ8   503 YNSSSTLDAIEHQQNAALKAAMGSNYSYGKSKQTPCSKRPQNGEDCHVSATEFTPEHPAA 562
Q9DQ9   503 YNSSSTLDAIEHQQNAALKAAMGSNYSYGKSKQTSCSKRPQNGEDCHVSATEFTPEHPAA 562
Q9U1I1  498 ----------------------------------VADLLLGGCVPC----------MPRP 514
O76007  411 ---------------------------------TSTELAPATCPE------EPSRELRGA 432
Q9V4I9  894 -D-----------------A--G----------VVKDLEHGGHMGCG----DLTDESGGR 920

NOV3    563 PRASPPTLIGSRKLAPEIKKTIDSLTKATEIDNKSPPVNVASMLPKSAVPIPAPRARYAP 622
Q9DQ8   563 PRASPPTIIGSRKLAPEIKKTIDSLTKATEIDNKSPPVNVASMLPKSAVPIPAPRARYAP 622
Q9DQ9   563 PRASPPTIIGSRKLAPEIKKTIDSLTKATEIDNKSPPVNVASMLPKSAVPIPAPRARYAP 622
Q9U1I1  515 AHPPPIDLTELGIS-------------------------------LDN-ICAGDK 537
O76007  433 PHRHSMPELGLR-----------------------------------SVPEPPESPGQP 457
Q9V4I9  921 ASSTSQNLSPLNSPG------------------DFQPHFLPKPMELQRQLENPHTASMP 962

NOV3    623 SLTPSPPSTAASELTSPWMHKSHARTDSPPDSREFPSPPVPVRSPPTESKEHSSPLQRSV 682
Q9DQ8   623 SLTPSPPSTAASELTSPWMHKSHARTDSPPDSREFPSPPVPVRSPPTESKEHSSPLQRSV 682
Q9DQ9   623 SLTPSPPSTAASELTSPWMHKSHARTDSPPDSREFPSPPVPVRSPPTESKEHSSPLQRSV 682
Q9U1I1  538 SIFGDTQTLTNSMPDMLLSKADDSHSYSQTDKINLNSPS--------------NSDLTQS 583
O76007  458 NLRPD-------D---S-----AFGRQSTPRVS--FRDPLVSEGGP-----------RRTL 490
Q9V4I9  963 ELAGKLVAPPAHMQGLSQLHAVSSHQFQQHEYADILEPPPPPPGEIPE----LPTPNLSVA 1019

NOV3    683 SERLANKRRSREPISLPEQTISEHPRLRSDDKHVSVENDKTSPELKSILKKSRNPSKSFR 742
Q9DQ8   683 SERLANKRRSREPISLPEQTISEHPRLRSDDKHVSVENDKTSPELKSILKKSRNPSKSFR 742
Q9DQ9   683 SERLANKRRSREPISLPEQTISEHPRLRSDDKHVSVENDKTSPELKSILKKSRNPSKSFR 742
Q9U1I1  584 TQELANELELD-NEPVRELPHDGYEQLFANNRNQEHPAEQYD-----DEQLDNRPMK--- 634
O76007  491 SAPPAQRRRPRSPP----------PRAPSRRRHHHNHHHH---------HNRHPSR---- 528
Q9V4I9  1020 STALPPELMGSPTHSAGDRSLNTPMSTQSASHAPPHPVSILGA-SSSSPMSGEPAKK-- 1076

NOV3    743 NRERGSLSGSLDRLEEFHRKSDVMKYASDDEDGAGFGDAQGDFSSFQRGQRLYSSARFPE 802
Q9DQ8   743 NRERGSLSGSLDRLEEFHRKSDVMKYASDDEDGAGFGDAQGDFSSFQRGQRLYSSARFPE 802
Q9DQ9   743 NRERGSLSGSLDRLEEFHRKSDVMKYASDDEDGAGFGDAQGDFSSFQRGQRLYSSARFPE 802
Q9U1I1  634 -------EVRFHSVQDTMSRSK--SYTDN-------------------------SNARR-- 659
O76007  528 ------------------RR----HYQCDAGSGS-----DSE------------------ 543
Q9V4I9  1076 ---K--GVRFEGIPDTLPRST--SYSGNGAGTSGGGERERD-----RDKDKEGGGRHGH 1123

NOV3    8   EVTEKPRSQNQGGRPRSQHRTRFKDNSALD----RTHSALNLDELDCAIARRNPKPGKTC 858
Q9DQ8   8   EVTEKPRSQNQGGRPRSQHRTRFKDNSALD----RTHSALNLDELDCAIARRNPKPGKTC 858
Q9DQ9   8   EVTEKPRSQNQGGRPRSQHRTRFKDNSALRPNAQRSQFREQKLELDCAIARRNPKPGKTC 862
Q9U1I1  659 ----RRRRRNQSRSSSEMQINQTNLRLHN-------------------------A 685
O76007  543 -----------------------------------------------------SC 545
Q9V4I9  1124 GHSSRRRRRKSSSSSSHHRSGSGHRSHST---------------------------TRA 1156

NOV3    859 SKLSGKSTCSKKLKRTRSTDFAFERSAATPTSSRKNRRTKRFVEDEPEDGWCSTCTSSND 918
Q9DQ8   859 SKLSGKSTCSKKLKRTRSTDFAFERSAATPTSSRKNRRTKRFVEDEPEDGWCSTCTSSND 918
Q9DQ9   859 SKLSGKSTCSKKLKRTRSTDFAFERSAATPTSSRKNRRTKRFVEDEPEDGWCSTCSSSD 922
Q9U1I1  686 QTQVGTTPLN-------------LLNN-------------LDNCDVASICSTCSSSS 717
O76007  546 S--------------------S---------SPSSS--SS------ESSEDDGFF-------- 563
Q9V4I9  1157 DTYAPAQPLSSYQGPPSVLQAANLVHESPSRQQRERERERERESPESDVCSTVSSSSS 1216

NOV3    919 DSDYERWDGLGTSPPTSPLSAMRRGSAPVGVRVNMTRRQPPHPFLANADSALAASAAGFN 978
Q9DQ8   919 DSDYERWDGLGTSPPTSPLSAMRRGSAPVGVRVNMTRRQPPHPFLANADSALAASAAGFN 978
Q9DQ9   923 DSDYERWDGLGTSPPTSPLSAMRRGSAPVGVRVNMTRRQPPHPFLANADSALAASAAGFN 982
Q9U1I1  718 SDMD-----DYVY------------------RLPARKHYGGVFVAYVPNDALAY 748
O76007  563 ----------LG-------------------ERIPLPPHLCRPMPAQDTAMETFN 589
Q9V4I9  1217 SSEDY----MMMY-----------------QLPQRRHYGGVRVSYVPNDALAY 1248

NOV3    979 SMGVYRPSMPRNFS-----------------------------TTSHMRYRRRQ- 10
Q9DQ8   979 SNGVYRPSMPRNFS-----------------------------TTSHMRYRRRQ- 10
Q9DQ9   983 SNGVYRPSMPRNFFFHHVAYALQAETAEKALYRHVTTNAVTKTSEIDRKSSETKSWRSQD 1042
Q9U1I1  749 ER---KKKMAQDSSL--------A-----------------PGAGNASVGGAP 773
O76007  590 SP---SLSLPRDSR--------------------------------AGMPRQARD- 609
Q9V4I9  1249 DR---KRKPSE-------------------------------------LGGD- 1260

NOV3    10  ----------QKKHCIVM------ 1011
Q9DQ8   10  ----------QKKHCIVM------ 1011
Q9DQ9   1043 ASYLPRGGSKARESAPIVDTNTSA 1066
Q9U1I1  774 AIM------HESKNCTIS------ 785
O76007  609 ----------KNCIVA------ 615
Q9V4I9  1260 ----------KDKNCTIS------ 1268
```

Other BLAST results include sequences from the Patp database, which is a proprietary database that contains sequences published in patents and patent publications. Patp results include those listed in Table 3F.

TABLE 3F

Patp Alignment of NOV3

| Sequences producing High-scoring Segment Pairs | Protein/ Organism | Length (as) | Identity (%) | Positive (%) | Expect |
|---|---|---|---|---|---|
| patp: AAW83952 | Polypeptide encoded by gene 2 clone HDTAY29- H. sapiens | 159 | 44 | 67 | 1.4e−07 |
| Patp: AAY57563 | Human testin (HTES)- H. sapiens | 421 | 44 | 67 | 3.4e−05 |
| patp. AAB93751 | Human protein SEQ ID NO: 13416- H. sapiens | 464 | 44 | 67 | 3.4e−05 |
| Patp: AAB42119 | Human ORFX ORF1883 polypeptide- H. sapiens | 464 | 44 | 67 | 4.0e−05 |
| Patp: AAG01529 | Human secreted protein- H. sapiens | 126 | 30 | 44 | 5.8e−05 |
| Patp AAY84378 | Amino acid sequence of a human LIM domain protein homologue- H. sapiens | 280 | 32 | 50 | 0.00077 |

The results of a domain search indicate that the NOV3 protein contains the protein domain (as defined by Interpro) named IPR001781 at amino acid positions 43 to 76. Table 3G lists the domain description from further DOMAIN analysis results against NOV3. This indicates that NOV3 has properties similar to those of other proteins known to contain these domains and similar to the properties of these domains.

TABLE 3G

Domain Analysis of NOV3

PRODOM ANALYSIS

| Sequences producing High-scoring Segment Pairs: | High Score | Smallest Sum Probability P(N) |
|---|---|---|
| Nprdm: 21599 p36 (1) TES2__MOUSE // TESTIN 2 (TES2) (CONTAIN . . . | 127 | 1.8e−08 |
| prdm: 39635 p36 (1) ZYX__MOUSE // ZYXIN. REPEAT; LIM MOTIF; . . . | 68 | 0.048 |
| prdm: 67 p36 (155) LIM1 (10) LIM3 (8) PAXI(8) // PROTEIN . . . | 67 | 0.061 |
| prdm: 55854 p36 (1) HMW1__MYCGE // CYTADHERENCE HIGH MOLECU . . . | 72 | 0.15 |
| prdm: 7588 p36 (3) SLI3 (2) LRG1 (1) // PROTEIN LIM MOTIF . . . | 61 | 0.25 | prdm: 21599 p36 (1) TES2__MOUSE // TESTIN 2 (TES2) (CONTAINS TESTIN 1 (TES1)). LIM MOTIF; METAL-BINDING; ZINC; ALTERNATIVE SPLICING, 66 aa.
Expect = 1.8e−08, Identities = 19/43 (44%), Positives = 29/43 (67%)
for NOV3 aa residues 29 to 71; and LIM Domain residues 19 to 61
>prdm: 39635 p36 (1) ZYX__MOUSE // ZYXIN. REPEAT; LIM MOTIF; METAL-BINDING; ZINC; CELL ADHESION, 44 aa.
Identities = 13/34 (38%), Positives = 19/34 (55%)
>prdm: 67 p36 (155) LIM1 (10) LIM3 (8) PAXI (8) // PROTEIN LIM MOTIF METAL-BINDING ZINC REPEAT HOMEOBOX NUCLEAR DNA-BINDING DEVELOPMENTAL, 68 aa.
Identities = 14/37 (37%), Positives = 20/37 (54%)
>prdm: 55854 p36 (1) HMW1__MYCGE // CYTADHERENCE HIGH MOLECULAR WEIGHT PROTEIN 1 (CYTADHERENCE ACCESSORY PROTEIN 1). STRUCTURAL PROTEIN, 107 aa.
Identities = 18/67 (26%), Positives = 37/67 (55%)
>prdm: 7588 p36 (3) SLI3 (2) LRG1 (1) // PROTEIN LIM MOTIF METAL-BINDING ZINC REPEAT SKELETAL MUSCLE LIM-PROTEIN SLIM, 67 aa.
Identities = 20/55 (36%), Positives = 30/55 (54%)

BLOCKS ANALYSIS

| AC# | Description | Strength | Score | AA# |
|---|---|---|---|---|
| BL00115R | Eukaryotic RNA polymerase II heptapeptide rep | 2074 | 1110 | 124 |
| BL00911C | Dihydroorotate dehydrogenase proteins. | 1314 | 1050 | 201 |
| BL01137D | Uncharacterized protein family UPF0006 protei | 1297 | 1048 | 126 |
| BL00576D | General diffusion Gram-negative porins protei | 1391 | 1047 | 172 |
| BL01182C | Glycosyl hydrolases family 35 proteins. | 1577 | 1046 | 73 |

TABLE 3G-continued

Domain Analysis of NOV3

| ProSite Analysis | | NOV3 aa position |
|---|---|---|
| Pattern-ID: | ASN_GLYCOSYLATION PS00001 (Interpro) | 78, 171, 312 |
| Pattern-DE: | N-glycosylation site, Pattern: N[^P][ST][^P] | |
| Patcern-ID: | CAMP_PHOSPHO_SITE PS00004 (Interpro) | 211 |
| Pattern-DE: | cAMP- and cGMP-dependent protein kinase phosphorylation site | |
| Pattern. | [RK]{2}.[ST] | |
| Pattern-ID: | PKC_PHOSPHO_SITE PS00005 (Interpro) | 95, 98, 123, 287, 300, 314 |
| Pattern-DE: | Protein kinase C phosphorylation site | |
| Pattern: | [ST].[RK] | |
| Pattern-ID: | CK2_PHOSPHO_SITE PS00006 (Interpro) | 72, 157, 243, 251, 295 |
| Pattern-DE: | Casein kinase II phosphorylation site | |
| Pattern: | [ST].{2}[DE] | |
| Pattern-ID: | TYR_PHOSPHO_SITE PS00007 (Interpro) | 156, 227 |
| Pattern-DE: | Tyrosine kinase phosphorylation site | |
| Pattern: | [RK].{2,3}[DE].{2,3}Y | |
| Pattern-ID: | MYRISTYL PS00008 (Interpro) | 24, 63, 79, 192, 272, 303 |
| Pattern-DE: | N-myristoylation site | |
| Pattern: | G[^EDRKHPFYW].{2}[STAGCN][^P] | |
| Pattern-ID: | LEUCINE_ZIPPER PS00029 (Interpro) | 119 |
| Pattern-DE: | Leucine zipper pattern | |
| Pattern: | L.{6}L.{6}L.{6}L | |

The LIM domain is a zinc finger structure that is present in several types of proteins, including homeodomain transcription factors, kinases and proteins that consist of several LIM domains. Proteins containing LIM domains have been discovered to play important roles in a variety of fundamental biological processes including cytoskeleton organization, cell lineage specification and organ development, but also for pathological functions such as oncogenesis, leading to human disease. The LIM domain has been demonstrated to be a protein-protein interaction motif that is critically involved in these processes. The recent isolation and analysis of more LIM domain-containing proteins from several species have confirmed and broadened our knowledge about LIM protein function. Furthermore, the identification and characterization of factors that interact with LIM domains illuminates mechanisms of combinatorial developmental regulation.

LIM domain containing proteins generally have two tandem copies of a domain, called LIM (for Lin-11 Isl-1 Mec-3) in their N-terminal section. Zyxin and paxillin are exceptions in that they contains respectively three and four LIM domains at their C-terminal extremity. In apterous, isl-1, LH-2, lin-11, lim-1 to lim-3, lmx-1 and ceh-14 and mec-3 there is a homeobox domain some 50 to 95 amino acids after the LIM domains. In the LIM domain, there are seven conserved cysteine residues and a histidine. The arrangement followed by these conserved residues is C-x(2)-C-x(16,23)-H-x(2)-[CH]-x(2)-C-x(2)-C-x(16,21)-C-x(2,3)-[CHD]. The LIM domain binds two zinc ions. LIM does not bind DNA, rather it seems to act as interface for protein-protein interaction.

The Prickle gene in *Drosophila* belongs to a family of "tissLue polarity" genes that control the orientation of bristles and hairs in the adult cuticle. (See Gubb and Garcia-Bellido, J. *Embryol. Exp. Morphol.* 68:37–57 (1982)) These "tissue polarity genes play important roles in the organization of the cytoskeleton. Prickle has been shown to be involved in hereditary benign intraepithelial dyskeratosis (OMIM Entry: 127600). Characteristic histologic changes of the prickle cell layer of the mucosa include numerous round, waxy-looking, eosinophilic cells that appear to be engulfed by normal cells. The conjunctiva and oral mucous membranes are affected. The oral lesion, which grossly resembles leukoplakia, is not precancerous. The eye lesions resemble pterygia (see OMIM 178000). The only symptoms are produced by involvement of the cornea, resulting in impairment of vision.

The human homolog of *Drosophila* discs large-3 (DLG3) is a protein related to Prickle and LIM. See, OMIM Entry 300189. Mutations of the 'discs large' (dlg) tumor suppressor locus in *Drosophila* lead to imaginal disc neoplasia and a prolonged larval period followed by death. *Drosophila* dlg and related proteins form a subfamily of the membrane-associated guanylate kinase (MAGUK) protein family and are important components of specialized cell junctions. See DLGI (OMIM 601014). A partial cDNA encoding NEDLG (neuroendocrine DLG) was isolated by searching an EST database for sequences related to dig and DLGI. See, Makino et al. (1997). Northern blot analysis revealed that NEDLG is highly expressed in neuronal and endocrine tissues. Immunolocalization studies indicated that the protein was expressed mainly in nonproliferating cells, such as neurons, cells in Langerhans islets of the pancreas, myocytes of heart muscles, and the prickle and functional layer cells of the esophageal epithelium. In a yeast 2-hybrid assay, NEDLG interacted with the C-terminal region of the APC (OMIM 175100) tumor suppressor protein. Therefore, NEDLG may negatively regulate cell proliferation through its interaction with the APC protein. By fluorescence in situ hybridization, Makino et al. (1997) mapped the NEDLG gene to Xq13. Using radiation hybrid panels, Stathakis et al. (1998) refined the map position to Xq13.1. DLG3 is located within the dystonia-parkinsonism syndrome (DYT3; OMIM 314250) locus.

The disclosed NOV3 nucleic acid encoding a LIM-domain-containing Prickle-like secreted protein includes the nucleic acid whose sequence is provided in Table 3A, or a fragment thereof. The invention also includes a mutant or variant nucleic acid any of whose bases may be changed from the corresponding base shown in Table 3A while still encoding a protein that maintains its LIM-domain-containing Prickle-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 17% percent of the bases may be so changed.

The disclosed NOV3 protein of the invention includes the LIM-domain-containing Prickle-like protein whose sequence is provided in Table 3B. The invention also includes a mutant or variant protein any of whose residues may be changed from the corresponding residue shown in Table 3B while still encoding a protein that maintains its LIM-domain-containing Prickle-like activities and physiological functions, or a functional fragment thereof. In the mutant or variant protein, up to about 16% percent of the residues may be so changed.

The invention further encompasses antibodies and antibody fragments, such as Fab, (Fab)2 or single chain FV constructs, that bind immunospecifically to any of the proteins of the invention. Also encompassed within the invention are peptides and polypeptides comprising sequences having high binding affinity for any of the proteins of the invention, including such peptides and polypeptides that are fused to any carrier partcle (or biologically expressed on the surface of a carrier) such as a bacteriophage particle.

The protein similarity information, expression pattern, and map location for the novel LIM-domain-containing Prickle-like NOV3 protein and nucleic acid disclosed herein suggest that this novel LIM-domain-containing Prickle-like protein may have important structural and/or physiological functions characteristic of the LIM-domain-containing Prickle-like protein family. For example, NOV3 may be important for the proper organization of cytoskeleton, or in the treatment of dystonia-parkinsonism syndrome; hereditary benign intraepithelial dyskeratosis; developmental disorders and other diseases, disorders and conditions of the like. Accordingly, NOV3 nucleic acids and proteins may have potential diagnostic and therapeutic applications in treating disorders that involve cytoskeleton malfunctions. These include serving as a specific or selective nucleic acid or protein diagnostic and/or prognostic marker, wherein the presence or amount of the nucleic acid or the protein are to be assessed, as well as potential therapeutic applications such as the following: (i) a protein therapeutic, (ii) a small molecule drug target, (iii) an antibody target (therapeutic, diagnostic, drug targeting/cytotoxic antibody), (iv) a nucleic acid useful in gene therapy (gene delivery/gene ablation), and (v) a composition promoting tissue regeneration in vitro and in vivo (vi) biological defense weapon.

Based on the tissues in which NOV3 is most highly expressed, including kidney and ovary, specific uses include developing products for the diagnosis or treatment of a variety of diseases and disorders. Additional disease indications and tissue expression for NOV3 is presented in Example 2.

The nucleic acids and proteins of the invention are useful in potential diagnostic and therapeutic applications implicated in, but not limited to, various diseases and disorders described below and/or other pathologies. For example, the compositions of the present invention will have efficacy for treatment of patients suffering from: dystonia-parkinsonism syndrome; dyskeratosis, hereditary benigh intraepithelial; developmental disorders and other diseases, disorders and conditions of the like. A cDNA encoding the LIM-domain-containing Prickle-like protein NOV3 may be useful in gene therapy, and the Prickle-like protein NOV3 may be useful when administered to a subject in need thereof.

These materials are further useful in the generation of antibodies that bind immunospecifically to the novel substances of the invention for use in therapeutic or diagnostic methods.

NOV3 nucleic acids and polypeptides are further useful in the generation of antibodies that bind immuno-specifically to the novel NOV3 substances for use in therapeutic or diagnostic methods. These antibodies may be generated according to methods known in the art, using prediction from hydrophobicity charts, as described in the "Anti-NOVX Antibodies" section below. The disclosed NOV3 protein has multiple hydrophilic regions, each of which can be used as an immunogen. In one embodiment, a contemplated NOV3 epitope is from about amino acids 25 to 50. In another embodiment, a NOV3 epitope is from about amino acids 55 to 140. In additional embodiments, NOV3 epitopes are from about amino acids 145 to 180, from about amino acids 180 to 225, and from about amino acids 250 to 280. These novel proteins can be used in assay systems for functional analysis of various human disorders, which will help in understanding of pathology of the disease and development of new drug targets for various disorders.

NOV4

A disclosed NOV4 nucleic acid of 1278 nucleotides (also referred to as CG56824-01) encoding a novel lipid metabolism-like protein is shown in Table 4A. An open reading frame was identified beginning with an ATG initiation codon at nucleotides 184 to 186 and ending with a TGA codon at nucleotides 1195 to 1197. Putative untranslated regions upstream from the initiation codon and downstream from the termination codon are underlined in Table 4A, and the start and stop codons are in bold letters.

TABLE 4A

NOV4 nucleotide sequence.

(SEQ ID NO:18)

CTCTTCGTGGCCCAACGCCCCAATCCTTGCGTGTCCTTGCAGTCCCACCCCACACTCAGCCTTGTGTCCCTCGATCCAGT

CTCCGACTTCCATTTCCCACCCTAAACCGCCTACCCGGTGTCTGTTCCCCGCCCGGTTGTCCTCGCCCTGCTGCGCTGAG

TGTCCCCTGTTAGCCTCGACCCCATGGCGCTGCAGACGCTGCAGAGCTCGTGGGTGACCTTCCGCAAGATCCTGTCTCAC

TTCCCCGAGGAGCTGAGTCTGGCTTTCGTCTACGGCTCCGGGGTGTACCGCCAGGCAGGGCCCAGTTCAGACCAGAAGAA

TGCTATGCTGGACTTTGTGTTCACAGTAGATGACCCTGTCGCATGGCATTCAAAGAACCTGAAGAAAAATTGGAGTCACT

TABLE 4A-continued

NOV4 nucleotide sequence.

ACTCTTTCCTAAAAGTTTTAGGGCCCAAGATTATCACGTCCATCCAGAATAACTATGGCGCTGGAGTTTACTACAATTCA

TTGATCATGTGTAATGGTAGGCTTATCAAATATGGAGTTATTAGCACTAACGTTCTGATTGAAGATCTCCTCAACTGGAA

TAACTTATACATTGCTGGACGACTCCAAAAACCGGTGAAAATTATCTCAGTGAACGAGGATGTCACTCTTAGATCAGCCC

TCGATAGAAATCTGAAGAGTGCTGTGACCGCTGCTTTCCTCATGCTCCCCGAAAGCTTTTCTGAAGAAGACCTCTTCATA

GAGATTGCCGGTCTCTCCTATTCAGGTGACTTTCGGATGGTGGTTGGAGAAGATAAAACAAAAGTGTTGAATATTGTGAA

GCCCAATATAGCCCACTTTCGAGAGCTCTATGGCAGCATACTACAGGAAAATCCTCAAGTGGTGTATAAAAGCCAGCAAG

GCTGGCTGGAGATAGATAAAAGCCCAGAAGGACAGTTCACTCAGCTGATGACATTGCCCAAAACCTTACAGCAACAGATA

AATCATATTATGGACCCTCCTGGAAAAAACAGAGATGTGGAAGAAACTTTATTCCAAGTGGCTCATGATCCCGACTGTGG

AGATGTGGTGCGACTAGGGCTTTCAGCAATCGTGAGACCGTCTAGTATAAGACAGAGCACGAAAGGCATTTTTACTGCTG

GCCTGAAGAAGTCAGTGATTTATAGTTCACTAAAACTGCACAAAATGTGGAAAGGGTGGCTGAGGAAAACATCCTGATTT

TGCTTGCTTTTATATATGTTATGTGTAGATGAATAAAGTGTTTGATCCTTTTTGACAAAAAAAAAAAAAAAAAAAAAAA

In a search of public sequence databases, the NOV4 nucleic acid sequence has 96 of 101 bases (95%) identical to a human cDNA clone NT2RP3003346. Public nucleotide databases include all GenBank databases and the GeneSeq patent database.

A disclosed NOV4 polypeptide (SEQ ID NO:19) encoded by SEQ ID NO:18 has 337 amino acid residues and is presented in Table 4B using the one-letter amino acid code. SignalP, Psort and/or Hydropathy results predict that NOV4 has a signal peptide. The most likely cleavage site is between amino acid positions 14 and 15, i.e., at the dash between TFR-KI. NOV4 is likely to be localized to the mitochondrial matrix space with a certainty of 0.6567. In alternative embodiments, NOV4 is localized to the mitochondrial inner membrane with a certainty of 0.3497, to the mitochondrial intermembrane space with a certainty of 0.3497, or the mitochondrial outer membrane with a certainty of 0.3497. NOV4 has a molecular weight of 38,078.6 Daltons.

sequence was cloned by the polymerase chain reaction (PCR) using the primer set NOV4-2, shown in Table 17A. The PCR product derived by exon linking, covering the entire NOV4 open reading frame, was cloned into the pCR2.1 vector from Invitrogen to provide clone 110189::COR24SC128.698230.M23.

TABLE 4B

Encoded NOV4 protein sequence.

(SEQ ID NO:19)

MALQTLQSSWVTFRKILSHFPEELSLAFVYGSGVYRQAGPSSDQKNAMLDFVFTVDDPVAWHSKNLKK

NWSHYSFLKVLGPKIITSIQNNYGAGVYYNSLIMCNGRLIKYGVISTNVLIEDLLNWNNLYIAGRLQK

PVKIISVNEDVTLRSALDRNLKSAVTAAFLMLPESFSEEDLFIEIAGLSYSGDFRMVVGEDKTKVLNI

VKPNIAHFRELYGSILQENPQVVYKSQQGWLEIDKSPEGQFTQLMTLPKTLQQQINHIMDPPGKNRDV

EETLFQVAHDPDCGDVVRLGLSAIVRPSSIRQSTKGIFTAGLKKSVIYSSLKLHKMWKGWLRKTS

The NOV4 nucleic acid was tentatively localized to human chromosome 3. The cDNA coding for the NOV4

The reverse complement for NOV4 is presented in Table 4C.

TABLE 4C

NOV4 reverse complement (SEQ ID NO:20)

TTTTTTTTTTTTTTTTTTTTTTGTCAAAAAGGATCAAACACTTTATTCATCTACACATAACATATATAAAAGCAAGCA

TABLE 4C-continued

NOV4 reverse complement

```
AAATCAGGATGTTTTCCTCAGCCACCCTTTCCACATTTTGTGCAGTTTTAGTGAACTATAAATCACTGACTTCTTCAG

GCCAGCAGTAAAAATGCCTTTCGTGCTCTGTCTTATACTAGACGGTCTCACGATTGCTGAAAGCCCTAGTCGCACCAC

ATCTCCACAGTCGGGATCATGAGCCACTTGGAATAAAGTTTCTTCCACATCTCTGTTTTTTCCAGGAGGGTCCATAAT

ATGATTTATCTGTTGCTGTAAGGTTTTGGGCAATGTCATCAGCTGAGTGAACTGTCCTTCTGGGCTTTTATCTATCTC

CAGCCAGCCTTGCTGGCTTTTATACACCACTTGAGGATTTTCCTGTAGTATGCTGCCATAGAGCTCTCGAAAGTGGGC

TATATTGGGCTTCACAATATTCAACACTTTTGTTTTATCTTCTCCAACCACCATCCGAAAGTCACCTGAATAGGAGAG

ACCGGCAATCTCTATGAAGAGGTCTTCTTCAGAAAAGCTTTCGGGGAGCATGAGGAAAGCAGCGGTCACAGCACTCTT

CAGATTTCTATCGAGGGCTGATCTAAGAGTGACATCCTCGTTCACTGAGATAATTTTCACCGGTTTTGGAGTCGTCC

AGCAATGTATAAGTTATTCCAGTTGAGGAGATCTTCAATCAGAACGTTAGTGCTAATAACTCCATATTTGATAAGCCT

ACCATTACACATGATCAATGAATTGTAGTAAACTCCAGCGCCATAGTTATTCTGGATGGACGTGATAATCTTGGGCCC

TAAAACTTTTAGGAAAGAGTAGTGACTCCAATTTTTCTTCAGGTTCTTTGAATGCCATGCGACAGGGTCATCTACTGT

GAACACAAAGTCCAGCATAGCATTCTTCTGGTCTGAACTGGGCCCTGCCTGGCGGTACACCCCGGAGCCGTAGACGAA

AGCCAGACTCAGCTCCTCGGGGAAGTGAGACAGGATCTTGCGGAAGGTCACCCACGAGCTCTGCAGCGTCTGCAGCGC

CATGGGGTCGAGGCTAACAGGGGACACTCAGCGCAGCAGGGCGAGGACAACCGGGCGGGGAACAGACACCGGGTAGGC

GGTTTAGGGTGGGAAATGGAAGTCGGAGACTGGATCGAGGGACACAAGGCTGAGTGTGGGGTGGGACTGCAAGGACAC

GCAAGGATTGGGGCGTTGGGCCACGAAGAG
```

In a search of public sequence databases, the NOV4 amino acid sequence has 90 of 214 amino acid residues (42%) identical to, and 137 residues (214%) positive with, the 274 amino acid residue *C. elegans* Y71F9B.2 protein. Public amino acid databases include the GenBank databases, SwissProt, PDB and PIR.

It was also found that NOV4 had homology to the amino acid sequences shown in the BLASTP data listed in Table 4D.

TABLE 4D

BLAST results for NOV4

| Gene Index/<br>Identifier | Protein/Organism | Length<br>(aa) | Identity<br>(%) | Positives<br>(%) | Expect |
|---|---|---|---|---|---|
| Q9CW36;<br>AK005100;<br>BAB23818.1 | 1500001M20R1K<br>PROTEIN<br>(FRAGMENT).<br>*mus musculus.*<br>6/2001 | 367 | 271/332<br>(82%) | 304/332,<br>(92%) | 1e−160 |
| O74339;<br>AL031174;<br>CAA20110.1 | HYPO-<br>THETICAL<br>44.3 KDA<br>PROTEIN<br>C1A4.06C IN<br>CHROMOSOME<br>II.<br>*schizosac-<br>charomyces<br>pombe.*<br>3/2001 | 383 | 119/325<br>(37%) | 174/325,<br>(54%) | 2e−47 |
| Q9N4G7;<br>AC024201;<br>AAF36018.1 | Y71F9B.2<br>PROTEIN<br>*caenorhabditis<br>elegans.*<br>10/2000 | 274 | 111/320<br>(35%) | 169/320,<br>(53%) | 5e−47 |
| Q9VFF2; | CG3641 | 647 | 109/269 | 152/269, | 2e−44 |

TABLE 4D-continued

BLAST results for NOV4

| Gene Index/<br>Identifier | Protein/Organism | Length<br>(aa) | Identity<br>(%) | Positives<br>(%) | Expect |
|---|---|---|---|---|---|
| AE003706;<br>AAF55108.1 | PROTEIN.<br>*drosophila<br>melanogaster.*<br>5/2000 |  | (41%) | (57%) |  |
| Q9SN75;<br>AL132955;<br>CAB61989.1 | HYPO-<br>THETICAL<br>37.4 KDA<br>PROTEIN.<br>*arabidopsis<br>thaliana.*<br>5/2000 | 332 | 102/314<br>(32%) | 170/314,<br>(54%) | 7e−41 |

The homology of these and other sequences is shown graphically in the ClustalW analysis shown in Table 4E. In the ClustalW alignment of the NOV4 protein, as well as all other ClustalW analyses herein, the black outlined amino acid residues indicate regions of conserved sequence (i.e., regions that may be required to preserve structural or functional properties), whereas non-highlighted amino acid residues are less conserved and can potentially be mutated to a much broader extent without altering protein structure or function.

TABLE 4E

ClustalW Analysis of NOV4

1) NOV4 (SEQ ID NO:19)
2) Q9CW36 (SEQ ID NO:21)
3) O74339 (SEQ ID NO:22)
4) Q9N4G7 (SEQ ID NO:23)
5) Q9VFF2 (SEQ ID NO:24)
6) Q9SN75 (SEQ ID NO:25)

```
NOV4     1   ------------------GTGRKRGPHDRELRAQFRHSTVCPTGGPPAHGAAGLHSSGVG  42
Q9CW36   1   ------------------GTGRKRGPHDRELRAQFRHSTVCPTGGPPAHGAAGLHSSGVG  42
O74339   1   MIFGKTHFLSYNILRYSTKRWMNRHSYSHHAKCTVAQLLKQNLLTFENQRIQPEEELKEN  60
Q9N4G7   1   ------------------------------------------------------MDEY    4
Q9VFF2   1   -------------------------------------------------------MLDLY  5
Q9SN75   1   -----------------------------------------------------METTQKD  7

NOV4    43   LRRILAHFPEDLSLAFAYGSAVYRQAGPSAHQEN--------PMLDLVFTVDDPVAWHAM  94
Q9CW36  43   LRRILAHFPEDLSLAFAYGSAVYRQAGPSAHQEN--------PMLDLVFTVDDPVAWHAM  94
O74339  61   LTKVVNYFQAPIDVAVGYGSGVFRQAGYSQKEN---------PMIDFIFQVEDPVKWHKI 111
Q9N4G7   5   RELISVLPLETVEYAFAYGSGAIQQNEDKSEK----------MVDFVIVTKNAQEFHRD  54
Q9VFF2   6   RRTVARFPLGSVSYMFAYGSGVKQQEGYGKVGNGNNLRPPPGYVVDLVFCVRDARGEHAE  65
Q9SN75   8   ELSSFLSVLPPVDFCCVYGSTLHPNNQ-DKSK----------MVDYILGVSDPIKWHSA  55

NOV4    95   NLKKNWSHYS--FLKLLGPRISSIQNNYGAGVYFNPLIRCDGK--LIKYGVISTGTLIE 150
Q9CW36  95   NLKKNWSHYS--FLKLLGPRISSIQNNYGAGVYFNPLIRCDGK--LIKYGVISTGTLIE 150
O74339 112   NLQQNPSHYS--FVKNFGPGFVSTLQESFGTGVYYNTHVEVEGN--IIKYGVYSKKDVYE 167
Q9N4G7  55   NILKNPQHYS--LLRLMGPKMIEKIQCNFAARVYNNTHVKVGKR--KIKYGVISYENVKQ 110
Q9VFF2  66   NLHRHPDHYS--ALRHLGPNFVAKYQERLGAGVYCNTLVPLPDVGITIKYGVVSQEELLE 123
Q9SN75  56   NLKMNSDHYASWMVHLGGARLITNVADKVGVGVHENPFVNWNDR--KLKYGVVRMHDLVQ 113

NOV4   151   DLLNWNNLYIAGRLQKPVK-IVSMNENMALRAALDKNLRSAVITACMLPESFSEEDLFI 209
Q9CW36 151   DLLNWNNLYIAGRLQKPVK-IVSMNENMALRAALDKNLRSAVITACMLPESFSEEDLFI 209
O74339 168   DLKHWNTMYLAGRFQKPVV-ILKGEDE--FYKENSYNLSSALHVLADRETEFDLYK 224
Q9N4G7 111   DLLDWRWIYIYSGRLHKPVLEVIKPRQD--MCDLVTENRRSALHSSLLLLPESFTLKQLFH 168
Q9VFF2 124   DLLDWRHLYLAGRLHKPVTNLVNPSDNPPLKAALERNLVSALQVALLLLPEKFTAYGLFH 183
Q9SN75 114   DILDWKRFYLSGRLQKPVHMLYDNLD---IEDVNSVNKRAATSAALLLPSKFTEEDLYA 170

NOV4   210   ELAGLSYSGDFRM-VIGEEKSKVLNIVKPNVGHFREIYESILQKDPQVVYKMHQG----- 263
Q9CW36 210   ELAGLSYSGDFRM-VIGEEKSKVLNIVKPNVGHFREIYESILQKDPQVVYKMHQG----- 263
O74339 225   TIVSLSYLGDIRMSFFAENPRKVENIVSKQIAFFRKLYLPLLYAEPG-VHFIESSE---- 279
Q9N4G7 169   KLVGLSYTGDFRM-VVGEDKNKINKIVEGNYEELLRVYEP--------------------- 207
Q9VFF2 184   TIAGLSYKGDFRM-IFGENKQKVHNIVSPQINDEFALYQPSLGQLSDYVAVNMKGQEPGS 242
Q9SN75 171   KICSLSYMGDLRM-FFAEDTNKVNKIVKGQFDLEQSMYKPFLEECETKNLLRFSSAEAS- 228

NOV4   263   -----QLEIDKSPEGQFTQLMTLPRTLQQQIN---------------------------- 290
Q9CW36 263   -----QLEIDKSPEGQFTQLMTLPRTLQQQIN---------------------------- 290
O74339 279   ----VLKSMDPSDNSRYLSFHQN--ITKDSIS---------------------------- 305
Q9N4G7 207   -----LMNDD-----------------ARLS----------------------------- 216
Q9VFF2 243   RKPAIIFEQDKSSSATCQHLRQLPRELQKRLQRNAACRGDYTQVVNHLSMASQLPEVLQA 302
Q9SN75 228   ---HTKLVQDSSLSATRSLVSSLPASVRSQMG----------------------------KS 259

NOV4   290   ----HIMD--------------------------------PPGRNRD---- 301
Q9CW36 290   ----HIMD--------------------------------PPGRNRD---- 301
O74339 305   ----RLLN--------------------------------GLPLN----- 314
Q9N4G7 216   ----VIFS--------------------------------LAHRH----- 225
Q9VFF2 303   SVNDIIMSSDDNSSDSNSSSDERQRKRKLKKHSKDVDKSKKKKSKHHKEKRRHKEKKRS 362
Q9SN75 260   LGEKKFVS--------------------------------ETGRVMG---- 274

NOV4   301   ----------VEETLLQVAQDPDCGDVVRLAIS-------------------------S 325
Q9CW36 301   ----------VEETLLQVAQDPDCGDVVRLAIS-------------------------S 325
O74339 314   ----------LVKILGLKPDTSSFEKCAELMLIN------------------------Q 339
Q9N4G7 225   -------------------------DVAATVETAIG-----------------------G 237
Q9VFF2 363   KHEEEPPVPYTQPPHLINASPPDVATNNEDSFGPALPPHLRKTQQPELPEQSQPAPQPQA 422
Q9SN75 274   --------------EVCISSREEAAKCMEKVMR-------------------------R 294

NOV4   326   IVRPSSIR--------------------------------------------------- 333
Q9CW36 326   IVRPSSIR--------------------------------------------------- 333
O74339 340   ISTRSLLIS-------------------------------------------------- 348
Q9N4G7 238   IIRPVSLS--------------------------------------------------- 245
Q9VFF2 423   MIGPVLPSNLTREKSPTKEAEAEDDDDLAGTFGPLPNASQVALEERALALKLAALEGGGL 482
Q9SN75 295   RVMVSSGR--------------------------------------------------- 302

NOV4   333   -----------------------------QSTKGLFTACMKK----------------- 346
Q9CW36 333   -----------------------------QSTKGLFTACMKK----------------- 346
O74339 348   -----------------------------KSIKKLTSFSILT---------------- 361
Q9N4G7 245   -----------------------------QTAKNAFSACVTR---------------- 258
Q9VFF2 483   GTSTDQDVREEWMLELPDVGLKSGLAALSNMKRTFYQCKERPDFSDRSSWTKTPQSEADA 542
Q9SN75 302   -----------------------------QAVSGFLAACAIN---------------- 315
```

TABLE 4E-continued

ClustalW Analysis of NOV4

```
NOV4     346 -----------------SVIY---------SSRK------------------------ 354
Q9CW36   346 -----------------SVIY---------SSRK------------------------ 354
O74339   361 -----------------QSIKG--------IFTAR----------------------- 371
Q9N4G7   258 -----------------SLIY---------SMAK------------------------ 266
Q9VFF2   543 AASGPKSLSSKELEQMAQVKYEQQRDDEQESMAKRHKKKHKREESLVELHQKKLRKEQRE 602
Q9SN75   315 -----------------ATMY---------LSQK------------------------ 323

NOV4     354 --------------------------LNKMWKGWMSKAS----              367
Q9CW36   354 --------------------------LNKMWKGWMSKAS----              367
O74339   371 --------------------------CHSFRWYMSMRS----              383
Q9N4G7   266 --------------------------MSKFLKSK--------              274
Q9VFF2   603 KPERRPFSRDVDLKLNKIDKNQTKQIVDKAKILNTKFSRGQAKYL             647
Q9SN75   323 --------------------------MRKAWNSRA-------               332
```

Table 4F lists the domain description from DOMAIN analysis results against NOV4. This indicates that the NOV4 sequence has properties similar to those of other proteins known to contain this domain.

TABLE 4F

Domain Analysis of NOV4

ProDom Protein Domain Analysis prdm:50749 p36 (1) YG1W_YEAST//HYPOTHETICAL 44.2 KD PROTEIN IN RME1-TFC4 INTERGENIC REGION. HYPOTHETICAL PROTEIN, 385 aa.
Expect = 2.1e-41, Identities = 85/209 (40%), Positives = 117/209 (55%)
for NOV4: 16 to 222; Sbjct: 116 to 324
Expect = 2.1e-41, Identities = 19/39 (48%), Positives = 28/39 (71%)
for NOV4: 290 to 328; Sbjct: 344 to 382 prdm:29671 p36 (1) PMFF_PROMI//PUTATIVE MINOR FIMBRIAL SUBUNIT PMFF PRECURSOR. FIMBRIA; SIGNAL, 53 aa.
Expect = 0.64, Identities = 15/48 (31%), Positives = 27/48 (56%)
for NOV4: 157 to 202; Sbjct: 6 to 53 prdM:16833 p36 (2) VL96(2)//L96 PROTEIN REPEAT DNA PACKAGING DNA-BINDING, 61 aa.
Expect = 2.2, Identities = 11/32 (34%), Positives = 18/32 (56%)
for NOV4: 21 to 52; Sbjct: 9 to 40 prdm:2442 p36 (10) INVO(10)//INVOLUCRIN KERATINOCYTE REPEAT, 65 aa.
Expect = 4.7, Identities = 14/40 (35%), Positives = 20/40 (50%)
for NOV4: 242 to 276; Sbjct: 8 to 47 prdm:15830 p36 (2) GLG1(1) GLG2(1)//GLYCOGEN SYNTHESIS INITIATOR PROTEIN BIOSYNTHESIS GLG1 GLG2, 51 aa.
Expect = 6.0, Identities = 10/23 (43%), Positives = 14/23 (60%)
for NOV4: 254 to 276; Sbjct: 22 to 44

BLOCKS Protein Domain Analysis

| AC# | Description | Strength | Score |
|---|---|---|---|
| BL00115R | 0 Eukaryotic RNA polymerase II heptapeptide rep | 2074 | 1110 |
| BL00911C | 0 Dihydroorotate dehydrogenase proteins. | 1314 | 1050 |
| BL01137D | 0 Uncharacterized protein family UPF0006 protei | 1297 | 1048 |
| BL00576B | 0 General diffusion Gram-negative porins protei | 1391 | 1047 |
| BL01182C | 0 Glycosyl hydrolases family 35 proteins. | 1577 | 1046 |

| ProSite Protein Domain Analysis | | NOV4 aa position |
|---|---|---|
| Pattern-ID: | ASN_GLYCOSYLATION PS00001 (Interpro) | 69 |
| Pattern-DE: | N-glycosylation site | |
| Pattern: | N[^P] [ST] [^P] | |
| | | |
| Pattern-ID: | CAMP_PHOSPHO_SITE PS00004 (Interpro) | 334 |
| Pattern-DE: | cAMP- and cGMP-dependent protein kinase phosphorylation site | |
| Pattern: | [RK] {2}.[ST] | |
| | | |
| Pattern-ID: | PKC_PHOSPHO_SITE PS00005 (Interpro) | 12, 148, 301, 305, 322 |
| Pattern-DE: | Protein kinase C phosphorylation site | |

TABLE 4F-continued

Domain Analysis of NOV4

| Pattern: | [ST].[RK] | |
|---|---|---|
| Pattern-ID: | CK2_PHOSPHO_SITE PS00006 (Interpro) | 54, 142, 151, 171 |
| Pattern-DE: | Casein kinase II phosphorylation site | |
| Pattern: | [ST].{2}[DE] | |
| Pattern-ID: | MYRISTYL PS00008 (Interpro) | 94, 111, 183, 308 |
| Pattern-DE: | N-myristoylation site | |
| Pattern: | G[^EDRKHPFYW].{2}[STAGCN][^P] | |

Other BLAST results include sequences from the Patp database, which is a proprietary database that contains sequences published in patents and patent publications. A BLASTP analysis of the patp database showed that NOV4 has 85 of 209 aa residues (40%) identical to, and 117 of 209 aa residues (55%) positive with, the 385 aa *Saccharomyces cerevisiae* Lipid metabolism protein encoded by the open reading frame YGR046w (patp:AAB19189, Expect=1.6e−40). Patp results include those listed in Table 4G.

TABLE 4G

Patp alignments of NOV4

| Sequences producing High-scoring Segment Pairs: | High Score | Smallest Sum Prob. P (N) |
|---|---|---|
| patp:AAB19189 Lipid metabolism protein encoded by the open reading frame YGR046w—*Saccharomyces cerevisiae*, 385 aa. | 374 | 1.6e−40 |

The disclosed NOV4 nucleic acid encoding a lipid metabolism associated protein-like protein includes the nucleic acid whose sequence is provided in Table 4A, or a fragment thereof. The invention also includes a mutant or variant nucleic acid any of whose bases may be changed from the corresponding base shown in Table 4A while still encoding a protein that maintains its lipid metabolism-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 45% percent of the bases may be so changed.

The disclosed NOV4 protein of the invention includes the lipid metabolism-like protein whose sequence is provided in Table 4B. The invention also includes a mutant or variant protein any of whose residues may be changed from the corresponding residue shown in Table 4B while still encoding a protein that maintains its lipid metabolism-like activities and physiological functions, or a functional fragment thereof. In the mutant or variant protein, up to about 58% percent of the residues may be so changed.

The invention further encompasses antibodies and antibody fragments, such as $F_{ab}$ or $(F_{ab})_2$ that bind immunospecifically to any of the proteins of the invention.

The above defined information for this invention suggests that this lipid metabolism-like protein (NOV4) may function as a member of a v family". Therefore, the NOV4 nucleic acids and proteins identified here may be useful in potential therapeutic applications implicated in (but not limited to) various pathologies and disorders as indicated below. The potential therapeutic applications for this invention include, but are not limited to: cardiovascular disease research tools, for all tissues and cell types composing (but not limited to) those defined here Based on the tissues in which NOV4 is most highly expressed; including duodenum, small intestine, uterus, thymus, CAEC, liver, breast, lung, kidney; specific uses include developing products for the diagnosis or treatment of a variety of diseases and disorders. Additional disease indications and tissue expression for NOV4 is presented in Example 2.

The NOV4 nucleic acids and proteins of the invention are useful in potential therapeutic applications implicated in cancer including but not limited to heart disease, stroke and/or other pathologies and disorders. For example, a cDNA encoding the lipid metabolism-like protein (NOV4) may be useful in cardiovascular disease therapy, and the lipid metabolism-like protein (NOV4) may be useful when administered to a subject in need thereof. By way of nonlimiting example, the compositions of the present invention will have efficacy for treatment of patients suffering from cardiovascular disease including but not limited to heart disease, hypertension, diabetes, stroke and renal failure. The NOV4 nucleic acid encoding lipid metabolism-like protein, and the lipid metabolism-like protein of the invention, or fragments thereof, may further be useful in diagnostic applications, wherein the presence or amount of the nucleic acid or the protein are to be assessed.

NOV4 nucleic acids and polypeptides are further useful in the generation of antibodies that bind immuno-specifically to the novel NOV4 substances for use in therapeutic or diagnostic methods. These antibodies may be generated according to methods known in the art, using prediction from hydrophobicity charts, as described in the "Anti-NOVX Antibodies" section below. The disclosed NOV4 protein has multiple hydrophilic regions, each of which can be used as an immunogen. In one embodiment, a contemplated NOV4 epitope is from about amino acids 1 to 20 In another embodiment, a NOV4 epitope is from about amino acids 30 to 55. In additional embodiments, NOV4 epitopes are from about amino acids 60 to 75, from about amino acids 80–95, from about amino acids 120 to 160, from about amino acids 185–290 and from about amino acids 300–337. These novel proteins can be used in assay systems for functional analysis of various human disorders, which will help in understanding of pathology of the disease and development of new drug targets for various disorders.

NOV5

In another embodiment, the novel sequence is NOV5 (alternatively referred to herein as 24SC239), which includes the 983 nucleotide sequence (SEQ ID NO:26) shown in Table 5A. A NOV5 ORF begins with a Kozak consensus ATG initiation codon at nucleotides 66–68 and ends with a TGA codon at nucleotides 551–553. Putative untranslated regions upstream from the initiation codon and downstream from the termination codon are underlined in Table 5A, and the start and stop codons are in bold letters.

TABLE 5A

NOV5 Nucleotide Sequence (SEQ ID NO:26)
CCGCGGCTGTGTCGTCATACTTGCGCGCCGACGCCGCCGCTCGCTTGTGAAACTGGAAGGCTGCCATGGCTAGCCCAGC

CGCCTCCTCGGTGCGACCACCGAGGCCCAAGAAAGAGCCGCAGACGCTCGTCATCCCCAAGAATGCGGCGGAGGAGCAG

AAGCTCAAGCTGGAGCGGCTCATGAAGAACCCGGACAAAGCAGTTCCAATTCCAGAGAAAATGAGTGAATGGGCACCTC

GACCTCCCCCAGAATTTGTCCGAGATGTCATGGGTTCAAGTGCTGGGGCCGGCAGTGGAGAGTTCCACGTGTACAGACA

TCTGCGCCGGAGAGAATATCAGCGACAGGACTACATGGATGCCATGGCTGAGAAGCAAAAATTGGATGCAGAGTTTCAG

AAAAGACTGGAAAAGAATAAAATTGCTGCAGAGGAGCAGACCGCAAAGCGCCGGAAGAAGCGCCAGAAGTTAAAAGAGA

AGAAATTACTGGCAAAGAAGATGAAACTTGAACAGAAGAAACAAGAAGGACCCGGTCAGCCCAAGGAGCAGGGGTCCAG

CAGCTCTGCGGAGGCATCTGGAACAGAGGAGGAGGAGGAAGTGCCCAGTTTCACCATGGGGCGATGACAATGTTTGCCA

CAGCCTCTGCCTGGAACCTGGCTCGTGCTGTGACCAGAAGGGAAAGGCGGCTGTTTGGCTCTTTCTCCCCCGCAAGGAC

CCGCTGACCCGCTGGATGGAGAGCAAAGGAGACCCCTCCCGAGCCGCTCACAGTCCTGTATTTGGCAGGTTTGGGAGCC

TGAGGGGCCATCTCCCTGACACTCAGAGGCACTGCCTTGCAGACACCATCCGTGCTCCTGGTAAAGGGGACAGAGAGC

CTCACCTTGCCACATATTTGAACAGTGATGAGTTTGGGGCTGGTTTCTGGGAAGGGAACGTTTATTTAGTAAAGAGCAG

AACACCCTTAAAAAAAAAAAAAAAAAAAAAAAAAAAA

The NOV5 protein (SEQ ID NO:27) encoded by SEQ ID NO:26 is 184 amino acids in length and is presented using the one-letter code in Table 5B. The Psort profile for NOV5 predicts that this sequence has no known signal peptide and is likely to be localized at the nucleus with a certainty of 0.9883. In alternative embodiments, a NOV5 polypeptide is located to the mitochondrial matrix space with a certainty of 0.1000, or the lysosome (lumen) with a certainty of 0.1000. The NOV5 protein has a molecular weight of 20996.9 Daltons.

TABLE 5B

NOV5 protein sequence (SEQ ID NO:27)
MASPAASSVRPPRPKKEPQTLVIPKNAAEEQKLKLERLMKNPDKAVPIPEKMSEWAPRPPPEFVRDVMGSSAGAGSGEF

HVYRHLRRREYQRQDYMDAMAEKQKLDAEFQKRLEKNKIAAEEQTAKRRKKRQKLKEKKLLAKKMKLEQKKQEGPGQPK

EQGSSSSAEASGTEEEEEVPSFTMGR

The reverse complement for NOV5 is presented in Table 5C.

TABLE 5C

NOV5 reverse complement (SEQ ID NO:28)
TTTTTTTTTTTTTTTTTTTTTTTTTAAGGGTGTTCTGCTCTTTACTAAATAAACGTTCCCTTCCCAGAAACCAGCCCC

TABLE 5C-continued

NOV5 reverse complement

```
AAACTCATCACTGTTCAAATATGTGGCAAGGTGAGGCTCTCTGTCCCCCTTTACCAGGAGCACGGATGGTGTCTGCAAG

GCAGTGCCTCTGAGTGTCAGGGAGATGGCCCCTCAGGCTCCCAAACCTGCCAAATACAGGACTGTGAGCGGCTCGGGAG

GGGTCTCCTTTGCTCTCCATCCAGCGGGTCAGCGGGTCCTTGCGGGGAGAAAGAGCCAAACAGCCGCCTTTCCCTTCT

GGTCACAGCACGAGCCAGGTTCCAGGCAGAGGCTGTGGCAAACATTGTCATCGCCCCATGGTGAAACTGGGCACTTCCT

CCTCCTCCTCTGTTCCAGATGCCTCCGCAGAGCTGCTGGACCCCTGCTCCTTGGGCTGACCGGGTCCTTCTTGTTTCTT

CTGTTCAAGTTTCATCTTCTTTGCCAGTAATTTCTTCTCTTTTAACTTCTGGCGCTTCTTCCGGCGCTTTGCGGTCTGC

TCCTCTGCAGCAATTTTATTCTTTTCCAGTCTTTTCTGAAACTCTGCATCCAATTTTTGCTTCTCAGCCATGGCATCCA

TGTAGTCCTGTCGCTGATATTCTCTCCGGCGCAGATGTCTGTACACGTGGAACTCTCCACTGCCGGCCCCAGCACTTGA

ACCCATGACATCTCGGACAAATTCTGGGGAGGTCGAGGTGCCCATTCACTCATTTTCTCTGGAATTGGAACTGCTTTG

TCCGGGTTCTTCATGAGCCGCTCCAGCTTGAGCTTCTGCTCCTCCGCCGCATTCTTGGGGATGACGAGCGTCTGCGGCT

CTTTCTTGGGCCTCGGTGGTCGCACCGAGGAGGCGGCTGGGCTAGCCATGGCAGCCTTCCAGTTTCACAAGCGAGCGGC

GGCGTCGGCGCGCAAGTATGACGACACAGCCGCGG
```

BLASTP results for NOV5 are shown in Table 5D.

TABLE 5D

BLAST results for NOV5

| Matching Entry (in SwissProt + SpTrEMBL) | Description | aa Length | % Identity | % Positive | E Value |
|---|---|---|---|---|---|
| Q9H875; AK023964; BAB14742.1 | CDNA FLJ13902 FIS, CLONE THYRO1001793. *homo sapiens*. 3/2001 | 184 | 184/184 (100%) | 184/184, (100%) | 1e–102 |
| Q9CWV6; AK010359; BAB26879.1 | 8430424D23RIK PROTEIN. *mus musculus*. 6/2001 | 186 | 170/106 (91%) | 174/186, (94%) | 4e–89 |
| Q9CY32; AK010359; BAB26879.1 | 8430424D23RIK PROTEIN. *mus musculus*. 6/2001 | 186 | 170/186 (91%) | 174/186, (94%) | 4e–89 |
| Q9CXA5; | 8430424D23RIK | 148 | 133/148 | 136/148, | 2e–67 |
| AK018438; BAB31212.1 | PROTEIN. *mus musculus*. 6/2001 | | (90%) | (92%) | |
| Q9V7K1; AE003808; AAF58048.1 | CG8441 PROTEIN. *drosophila melanogaster* 5/2000 | 253 | 75/158 (47%) | 99/158, (63%) | 3e–30 |

A multiple sequence alignment is given in Table 5E, with the NOV5 protein of the invention being shown on lines 1 in a ClustalW analysis comparing NOV5 with related protein sequences of Table 5D.

TABLE 5E

Information for the ClustalW proteins:

1. SEQ ID NO:27, NOV5
2. SEQ ID NO:29, Q9H875 CDNA FLJ13902 FIS, CLONE THYRO1001793. *homo sapiens*. 3/2001
3. SEQ ID NO:30, Q9CWV6 8430424D23RIK PROTEIN, *mus musculus* 6/2001
4. SEQ ID NO:31, Q9CY32 8430424D23RIK PROTEIN, *mus musculus* 6/2001
5. SEQ ID NO:32, Q9CXA5 8430424D23RIK PROTEIN, *mus musculus* 6/2001
6. SEQ ID NO:33, Q9V7K CG8441 PROTEIN, *drosophila melanogaster*. 5/2000

```
NOV5     1  -------MASP---------AAASVRPPRPKKEPQTLVIPKNAAEEQKLKLERLMKNPDK  44
Q9H875   1  -------MASP---------AAASVRPPRPKKEPQTLVIPKNAAEEQKLKLERLMKNPDK  44
Q9CWV6   1  -------MASP---------AAASVRPPRPKKEPQTLVIPKNAAEEQKLKLERLMKNPDK  44
Q9CY32   1  -------MASP---------AAASVRPPRPKKEPQTLVIPKNAAEEQKLKLERLMKNPDK  44
Q9CXA5   1  ------------------------------------------------------MKNPDK   6
Q9V7K1   1  MSLIKNLVKEPEQKAKKKKKNAGSGESDSDKKKPLRPFIKTATDLQRLKLEKLMKNPDK  60
```

TABLE 5E-continued

Information for the ClustalW proteins:

```
NOV5     45 AVPIPEKMSEWAPRP-PPEFVRDVMGSSAGAGSGEFHVYRHLRRREYQRQDYMDAMAEKQ 103
Q9H875   45 AVPIPEKMSEWAPRP-PPEFVRDVMGSSAGAGSGEFHVYRHLRRREYQRQDYMDAMAEKQ 103
Q9CWV6   45 AVPIPEKMNEWAPRA-PPEFVRDVMGSSAGAGSGEFHVYRHLRRREYQRQDYMDAMAEKQ 103
Q9CY32   45 AVPIPEKMNEWAPRA-PPEFVRDVMGSSAGAGSGEFHVYRHLRRREYQRQDYMDAMAEKQ 103
Q9CXA5    7 AVPIPEKMNEWAPRA-PPEFVRDVMGSSAGAGSGEFHVYRHLRRREYQRQDYMDAMAEKQ  65
Q9V7K1   61 PVVIPEQRRERDFMSSVPTFVRNVMGSSAGAGSGEFHVYRHLRRKEYARQKNIQNQSARE 120

NOV5    104 KLDAEFQRLEKNKIAAEEQTAKRRKKRQKLK--------EKKLLAKKMKLEQKKQ--EG 153
Q9H875  104 KLDAEFQRLEKNKIAAEEQTAKRRKKRQKLK--------EKKLLAKKMKLEQKKQ--EG 153
Q9CWV6  104 KLDAEFQRLEKNKIAAEEQTAKRRKKRQKLK--------EKKLLAKKMKLEQKKQK-EE 154
Q9CY32  104 KLDAEFQRLEKNKIAAEEQTAKRRKKRQKLK--------EKKLLAKKMKLEQKKQK-EE 154
Q9CXA5   66 KLDAEFQRLEKNKIAAEEQTAKRRKKRQKLK--------EKKLLAKKMKLEQKKQK-EE 116
Q9V7K1  121 AADEAYQQKLDDNRRAAEEKTAKKRAKRLKRKQRAKKPREDKKPLAKEASEDSNTDSEEE 180

NOV5    154 PGQPKE--------QGSSSAEASGTEEE--EEVPS-FTMGR------------------ 184
Q9H875  154 PGQPKE--------QGSSSAEASGTEEE--EEVPS-FTMGR------------------ 184
Q9CWV6  155 PSQCQE--------QHASSSDEASETEEE--EEEPSVLIMGR------------------ 186
Q9CY32  155 PSQCQE--------QHASSSDEASETEEE--EEEPSVLIMGR------------------ 186
Q9CXA5  117 PSQCQE--------QHASSSDEASETEEE--EEEPSVLIMGR------------------ 148
Q9V7K1  181 PTEEKAESSPEEGQQVASKESDDNNTQTSNEEAVNSNTEAKSAEDTNAVELDSTEATKE 240

NOV5    184 ------------                                                184
Q9H875  184 ------------                                                184
Q9CWV6  186 ------------                                                186
Q9CY32  186 ------------                                                186
Q9CXA5  148 ------------                                                148
Q9V7K1  241 SQNVDQEQDKPVP                                               253
```

ProDom results for NOV5 were collected from using a proprietary database. The results are listed in Table 5F with the statistics and domain description.

TABLE 5F

ProDom results for NOV5

ProDom Analysis

| Sequences producing High-scoring Segment Pairs: | High Score | Smallest Sum Probability P(N) |
|---|---|---|
| prdm:38062 p36 (1) INCE_CHICK//INNER CENTROMERE PROTEIN . . . | 119 | 1.1e-06 |
| prdm:26211 p36 (1) D7_DICDI//CAMP-INDUCIBLE PRESPORE PR . . . | 82 | 0.00051 |
| prdm:4957 p36 (5) CALD(5)//CALDESMON CDM MUSCLE PROTE . . . | 74 | 0.0041 |
| prdm:22005 p36 (1) INCE_CHICK//INNER CENTROMERE PROTEIN . . . | 72 | 0.0070 |

>prdm:38062 p36 (1) INCH_CHICK//INNER CENTROMERE PROTEIN (INCENP). CELL DIVISION;
MICROTUBULES; COILED COIL; CENTROMERE; MITOSIS; CELL CYCLE; NUCLEAR PROTEIN;
ALTERNATIVE SPLICING, 218 aa.
Identities = 31/94 (32%), Positives = 57/94 (60%) for NOV5: 86-179, Sbjct: 9-98
Identities = 29/97 (29%), Positives = 55/97 (56%) for NOV5: 86-182, Sbjct: 9-104
Identities = 24/79 (30%), Positives = 46/79 (58%) for NOV5: 98-176, Sbjct: 2-73

>prdm:26211 p36 (1) D7_DICDI//CAMP-INDUCIBLE PRESPORE PROTEIN D7 PRECURSOR.
SPORULATION; SIGNAL, 112 aa.
Identities = 24/90 (26%), Positives = 47/90 (52%) for NOV5: 88-177, Sbjct. 16-96
Identities = 21/76 (27%), Positives = 38/76 (50%) for NOV5: 8-152, Sbjct: 16-91

>prdm:4957 p36 (5) CALD(5)//CALDESMON CDM MUSCLE PROTEIN ACTIN-BINDING CALMODULIN-BINDING
PHOSPHORYLATION ALTERNATIVE SPLICING REPEAT, 89 aa.
Identities = 24/73 (32%), Positives = 40/73 (54%) for NOV5: 11-184, Sbjct: 8-80

>prdm:22005 p36 (1) INCE_CHICK//INNER CENTROMERE PROTEIN (INCENP). CELL DIVISION;
MICROTUBULES; COILED COIL; CENTROMERE; MITOSIS; CELL CYCLE; NUCLEAR PROTEIN;
ALTERNATIVE SPLICING, 71 aa.
Identities = 18/67 (26%), Positives = 40/67 (59%) for NOV5: 96-160, Sbjct: 2-68
Identities = 16/56 (28%), Positives = 29/56 (51%) for NOV5: 86-71, Sbjct: 16-71

TABLE 5F-continued

ProDom results for NOV5

PROSITE-Protein Domain Matches for Gene ID: NOV05

Pattern-ID: PKC_PHOSPHO_SITE PS00005 (Interpro) PDOC00005

Pattern-DE: Protein kinase C phosphorylation site

Pattern: [ST].[RK]

Pattern-ID: CK2_PHOSPHO_SITE PS00006 (Interpro) PDOC00006

Pattern-DE: Casein kinese II phosphorylation site

Pattern: [ST].{2}[DE]

Pattern-ID: MYRISTYL PS00008 (Interpro) PDOC00008

Pattern-DE: N-myristoylation site

The INCE_CHICK//INNER CENTROMERE PROTEIN (INCENP) is involved in cell division, microtubules, and centromeres. It is also involved with cell cycle through involvement with nuclear proteins and alternative splicing. The D7_DICDI//CAMP-INDUCIBLE PRESPORE PROTEIN D7 PRECURSOR is involved with cell signaling and sporulation.

BLOCKS analysis was also performed on NOV5. Protein families that NOV5 was similar to are shown in Table 5G.

TABLE 5G

BLOCKS Analysis of NOV5

| AC# | Description | Strength | Score |
| --- | --- | --- | --- |
| BL00500 0 | Thymosin beta-4 family proteins. | 1993 | 1089 |
| BL01103E 0 | Aspartate-semialdehyde dehydrogenase proteins | 1372 | 1057 |
| BL00936A 0 | Ribosomal protein L35 proteins. | 1518 | 1039 |
| BL01002C 0 | Translationally controlled tumor protein. | 1430 | 1026 |
| BL01179A 0 | Phosphotyrosine interaction domain proteins ( | 1196 | 1025 |
| BL01104C 0 | Ribosomal protein L13e proteins. | 1458 | 1022 |
| BL00412B 0 | Neuromodulin (GAP-43) proteins. | 1927 | 1006 |
| BL01252D 0 | Endogenous opioids neuropeptides precursors p | 1763 | 1005 |
| BL01118B 0 | Translation initiation factor SUI1 proteins. | 1517 | 1003 |
| BL00892B 0 | HIT family proteins. | 1500 | 1002 |

Other BLAST results include sequences from the Patp database, which is a proprietary database that contains sequences published in patents and patent publications. Patp results include those listed in Table 5H.

TABLE 5H

Patp alignments of NOV5

| Sequences producing High-scoring Segment Pairs: | % Identity | % Positive |
| --- | --- | --- |
| patp:AAB50322 Human cytoskeleton-associated protein #2 - . | 100% | 100% |
| patp:AAB94798 Human protein sequence SEQ ID NO:15925-Ho . . . | 100% | 100% |

TABLE 5H-continued

Patp alignments of NOV5

| Sequences producing High-scoring Segment Pairs: | % Identity | % Positive |
|---|---|---|
| patp:AAG42902 Arabidopsis thaliana protein fragment SEQ I . . | 45% | 57% |
| patp:AAG42903 Arabidopsis thaliana protein fragment SEQ I . . | 45% | 57% |
| patp:AAG42904 Arabidopsis thaliana protein fragment SEQ I . . | 45% | 57% |
| patp:AAG51246 Arabidopsis thaliana protein fragment SEQ I . . | 47% | 58% |
| patp:AAG51247 Arabidopsis thaliana protein fragment SEQ I . . | 47% | 58% |
| patp:AAG51248 Arabidopsis thaliana protein fragment SEQ I . . | 47% | 58% |

NOV5 is expressed in at least the following tissues: lung, ovary, prostate, tonsil, breast cancer, and ovarian cancer. This information was derived by determining the tissue sources of the sequences that were included in the invention including but not limited to SeqCalling sources, Public EST sources, Literature sources, and/or RACE sources.

The disclosed NOV5 nucleic acid encoding a novel protein includes the nucleic acid whose sequence is provided in Table 5A, or a fragment thereof. The invention also includes a mutant or variant nucleic acid any of whose bases may be changed from the corresponding base shown in Table 5A while still encoding a protein that maintains its activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 37% percent of the bases may be so changed.

The disclosed NOV5 protein of the invention includes the novel protein whose sequence is provided in Table 5B. The invention also includes a mutant or variant protein any of whose residues may be changed from the corresponding residue shown in Table 5B while still encoding a protein that maintains its activities and physiological functions, or a functional fragment thereof. In the mutant or variant protein, up to about 37% percent of the residues may be so changed.

The invention further encompasses antibodies and antibody fragments, such as $F_{ab}$ or $(F_{ab})_2$ that bind immuno-specifically to any of the proteins of the invention.

The NOV5 nucleic acids and proteins of the invention are useful in potential therapeutic applications implicated in cancer including but not limited to breast cancer, ovarian cancer, and/or other pathologies and disorders. For example, a cDNA encoding the novel protein (NOV5) may be useful in cancer therapy, and the novel protein (NOV5) may be useful when administered to a subject in need thereof. By way of nonlimiting example, the compositions of the present invention will have efficacy for treatment of patients suffering from cancer including but not limited to breast and ovarian cancer. The NOV5 nucleic acid encoding novel protein, of the invention, or fragments thereof, may further be useful in diagnostic applications, wherein the presence or amount of the nucleic acid or the protein are to be assessed.

NOV5 nucleic acids and polypeptides are further useful in the generation of antibodies that bind immuno-specifically to the novel NOV5 substances for use in therapeutic or diagnostic methods. These antibodies may be generated according to methods known in the art, using prediction from hydrophobicity charts, as described in the "Anti-NOVX Antibodies" section below. The disclosed NOV5 protein has multiple hydrophilic regions, each of which can be used as an immunogen. In one embodiment, a contemplated NOV5 epitope is from about amino acids 1 to 20. In another embodiment, a NOV5 epitope is from about amino acids 25 to 45. In additional embodiments, NOV5 epitopes are from about amino acids 50 to 55, from about amino acids 60 to 70, from about amino acids 85 to 100, and from about amino acids 105 to 175. These novel proteins can be used in assay systems for functional analysis of various human disorders, which will help in understanding of pathology of the disease and development of new drug targets for various disorders.

NOV6

In another embodiment, the EIF-2B epsilon subunit-like protein is NOV6 (alternatively referred to herein as 24SC300), which includes the 2456 nucleotide sequence (SEQ ID NO:34) shown in Table 6A. A NOV6 ORF begins with a Kozak consensus ATG initiation codon at nucleotides 836–838 and ends with a TGA codon at nucleotides 1934–1936. Putative untranslated regions upstream from the initiation codon and downstream from the termination codon are underlined in Table 6A, and the start and stop codons are in bold letters.

TABLE 6A

NOV6 Nucleotide Sequence (SEQ ID NO:34)

GAATTCCTGACTGCCACAGGTGTACAGGAAACATTTGTCTTTTGTTGCTGGAAAGCTGCTCAAATCAAAGAACA
TTTACTGAAGTCAAAGTGGTGCCGCCCTACATCTCTCAATGTGGTTCGAATAATTACATCAGAGCTCTATCGAT
CACTGGGAGATGTCCTCCGTGATGTTGATGCCAAGGCTTTGGTGCGCTCTGACTTTCTTCTGGTGTATGGGAT
GTCATCTCAAACATCAATATCACCAGAGCCCTTGAGGAACACAGGTTGAGACGGAAGCTAGAAAAAAATGTTTC
TGTGATGACGATGATCTTCAAGGAGTCATCCCCCAGCCACCCAACTCGTTGCCACGAAGACAATGTGGTAGTGG
CTGTGGATAGTACCACAAACAGGGTTCTCCATTTTCAGAAGACCCAGGGTCTCCGGCGTTTTGCATTTCCTCTG
AGCCTGTTTCAGGGCAGTAGTGATGGAGTGGAGGTTCGATATGATTTACTGGATTGTCATATCAGCATCTGTTC
TCCTCAGGTGGCACAACTCTTTACAGACAACTTTGACTACCAAACTCGAGATGACTTTGTGCGAGGTCTCTTAG
TGAATGAGGAGATCCTAGGGAACCAGATCCACATGCACGTAACAGCTAAGGAATATGGTGCCCGTGTCTCCAAC
CTACACATGTACTCAGCTGTCTGTGCTGACGTCATCCGCCGATGGGTCTACCCTCTCACCCCAGAGGCGAACTT
CACTGACAGCACCACCCAGAGCTGCACTCATTCCCGGCACAACATCTACCGAGGGCCTGAGGTCAGCCTGGGCC
ATGGCAGCATCCTAGAGGAAAATGTGCTCCTGGGCTCTGGCACTGTCATTGGCAGCAATTGCTTTATCACCAAC
AGTGTCATTGGCCCCGGCTGCCACATTGGTGAGCACAGGTGATAACGTGGTGCTGGACCAGACCTACCTGTGGC
AGGGTGTTCGAGTGGCGGCTGGAGCACAGATCCATCAGTCTCTGCTTTGTGACAATGCTGAGGTCAAGGAACGA
GTGACACTGAAACCACGCTCTGTCCTCACTTCCCAGGTGGTCGTGGGCCCAAATATCACGCTGCCTGAGGGCTC
GGTGATCTCTTTGCACCCTCCAGATGCAGAGGAAGATGAAGATGATGGCGAGTTCAGTGATGATTCTGGGGCTG
ACCAAGAAAGGACAAAGTGAAGATGAAAGGTTACAATCCAGCAGAAGTAGGAGCTGCTGGCAAGGGCTACCTC
TGGAAAGCTGCAGGCATGAACATGGAGGAAGAGGAGGAACTGCAGCAGAATCTGTGGGGACTCAAGATCAACAT
GGAAGAAGAGAGTGAAAGTGAAAGTGAGCAAAGTATGGATTCTGAGGAGCCGGACAGCCGGGGAGGCTCCCCTC
AGATGGATGACATCAAAGTGTTCCAGAATGAAGTTTTAGGAACACTACAGCGGGGCAAAGAGGAGAACATTTCT
TGTGACAATCTCGTCCTGGAAATCAACTCTCTCAAGTATGCCTATAACATAAGTCTAAAGGAGGTGATGCAGGT
ACTGAGCCACGTGGTCCTGGAGTTCCCCCTGCAACAGATGGATTCCCCGCTTGACTCAAGCCGCTACTGTGCCC
TGCTGCTTCCTCTGCTAAAGGCCTGGAGCCCTGTTTTTAGGAACTACATAAAGCGCGCAGCCGACCATTTGGAA
GCGTTAGCAGCCATTGAGGACTTCTTCCTAGAGCATGAAGCTCTTGGTATTTCCATGGCCAAGGTACTGATGGC
TTTCTACCAGCTGGAGATCCTGGCTGAGGAAACAATTCTGAGCTGGTTCAGCCAAAGAGATACAACTGACAAGG
GCCAGCAGTTGCGCAAGAATCAACAGCTGCAGAGGTTCATCCAGTGGCTAAAAGAGGCAGAAGAGGAGTCATCT
GAAGATGACTGAAGTCACACTGCCTGCTCCTTTGGGTGTGATTGAGTGCCCTCCTGGCTCCTGGGCTGGGACAA
GTGAGGAACTAGCTGCAGAGGGATGAGTGACCACCATCCAGGCTGAGACTGAAAGGAGCAGAGGCTGGAACTAC
AGTATTCTTTCCCCTGCTAGCAACCATGTGCCTCCCATCCTGACTGTGGAGTTGGGATGTGGAAGTGGGGCTGG
AACAAAGCTTCTGCCTAGGGAGGAGCTAAGCAGGCCCGGCAGTTGGAGGAAGGCCAGAGGAACAGCTTTGTGCT
CCGGCTTTCCCTCAGGGAACAGCAGAGAGCAGTTGGCTCTTTCTGCTGCTTGTATATGTTAATATTAAAAGAGA
GAGTGGTGTATTTGGTTTGTCTCCATCCCCGACTAATCAGCCAGTGAAGTATGTGACCAGAATCACATGATAGC
CTTTCCTTAACACCTGGGGGAGAGGGAGGACGGGTGTGCCAGCCACTAGGTGGTACTGTGGTACCTTGCTAATT
AACCTTTCCCATGG

The NOV6 40789.4 Dalton protein (SEQ ID NO:35) encoded by SEQ ID NO:34 is 366 amino acids in length and is presented using the one-letter code in Table 6B. The Psort profile for NOV6 predicts that this sequence has a signal peptide. The most likely cleavage site for a NOV6 peptide is between amino acids 21–22, i.e. at the dash between amino acids VSL-AP. NOV6 is likely to be localized outside the cell with a certainty of 0.6138. In alternative embodiments, a NOV6 polypeptide is located to the lysosome (lumen) with a certainty of 0.01900, the endoplasmic reticulum (membrane) with a certainty of 0.1000, or the endoplasmic reticulum (lumen) with a certainty of 0.1000.

TABLE 6B

NOV6 protein sequence (SEQ ID NO:35)

MCSWALALSLAAIALSPTVSLAPAATLVSTGDNVVLDQTYLWQGVRVAAGAQIHQSLLCDNAEVKERVTLKPRSVLTS

QVVVGPNITLPEGSVISLHPPDAEEDEDDGEFSDDSGADQEKDKVKMKGYNPAEVGAAGKGYLWKAAGMNMEEEEELQ

QNLWGLKINMEEESESESEQSMDSEEPDSRGGSPQMDDIKVFQNEVLGTLQRGKEENISCDNLVLEINSLKYAYNISL

KEVMQVLSHVVLEFPLQQMDSPLDSSRYCALLLPLLKAWSPVFRNYIKRAADHLEALAAIEDFFLEHEALGISMAKVL

MAFYQLEILAEETILSWFSQRDTTDKGQQLRKNQQLQRFIQWLKEAEEESSEDD

The reverse complement for NOV6 is presented in Table 6C.

TABLE 6C

NOV6 reverse complement (SEQ ID NO:36)

CCATGGGAAAGGTTAATTAGCAAGGTACCACAGTACCACCTAGTGGCTGGCACACCCGTCCTCCCTCTCCCCCAGGTG

TTAAGGAAAGGCTATCATGTGATTCTGGTCACATACTTCACTGGCTGATTAGTCGGGGATGGAGACAAACCAAATACA

CCACTCTCTCTTTTAATATTAACATATACAAGCAGCAGAAAGAGCCAACTGCTCTCTGCTGTTCCCTGAGGGAAAGCC

GGAGCACAAAGCTGTTCCTCTGGCCTTCCTCCAACTGCCGGGCCTGCTTAGCTCCTCCCTAGGCAGAAGCTTTGTTCC

AGCCCCACTTCCACATCCCAACTCCACAGTCAGGATGGGAGGCACATGGTTGCTAGCAGGGGAAAGAATACTGTAGTT

CCAGCCTCTGCTCCTTTCAGTCTCAGCCTGGATGGTGGTCACTCATCCCTCTGCAGCTAGTTCCTCACTTGTCCCAGC

CCAGGAGCCAGGAGGGCACTCAATCACACCCAAAGGAGCAGGCAGTGTGACTTCAGTCATCTTCAGATGACTCCTCTT

CTGCCTCTTTTAGCCACTGGATGAACCTCTGCAGCTGTTGATTCTTGCGCAACTGCTGGCCCTTGTCAGTTGTATCTC

TTTGGCTGAACCAGCTCAGAATTGTTTCCTCAGCCAGGATCTCCAGCTGGTAGAAAGCCATCAGTACCTTGGCCATGG

AAATACCAAGAGCTTCATGCTCTAGGAAGAAGTCCTCAATGGCTGCTAACGCTTCCAAATGGTCGGCTGCGCGCTTTA

TGTAGTTCCTAAAAACAGGGCTCCAGGCCTTTAGCAGAGGAAGCAGCAGGGCACAGTAGCGGCTTGAGTCAAGCGGGG

AATCCATCTGTTGCAGGGGGAACTCCAGGACCACGTGGCTCAGTACCTGCATCACCTCCTTTAGACTTATGTTATAGG

CATACTTGAGAGAGTTGATTTCCAGGACGAGATTGTCACAAGAAATGTTCTCCTCTTTGCCCCGCTGTAGTGTTCCTA

AAACTTCATTCTGGAACACTTTGATGTCATCCATCTGAGGGGAGCCTCCCCGGCTGTCCGGCTCCTCAGAATCCATAC

TTTGCTCACTTTCACTTTCACTCTCTTCTTCCATGTTGATCTTGAGTCCCCACAGATTCTGCTGCAGTTCCTCCTCTT

CCTCCATGTTCATGCCTGCAGCTTTCCAGAGGTAGCCCTTGCCAGCAGCTCCTACTTCTGCTGGATTGTAACCTTTCA

TCTTCACTTTGTCCTTTTCTTGGTCAGCCCCAGAATCATCACTGAACTCGCCATCATCTTCATCTTCCTCTGCATCTG

GAGGGTGCAAAGAGATCACCGAGCCCTCAGGCAGCGTGATATTTGGGCCCACGACCACCTGGGAAGTGAGGACAGAGC

GTGGTTTCAGTGTCACTCGTTCCTTGACCTCAGCATTGTCACAAAGCAGAGACTGATGGATCTGTGCTCCAGCCGCCA

CTCGAACACCCTGCCACAGGTAGGTCTGGTCCAGCACCACGTTATCACCTGTGCTCACCAATGTGGCAGCCGGGGCCA

ATGACACTGTTGGTGATAAAGCAATTGCTGCCAATGACAGTGCCAGAGCCCAGGAGCACATTTTCCTCTAGGATGCTG

CCATGGCCCAGGCTGACCTCAGGCCCTCGGTAGATGTTGTGCCGGGAATGAGTGCAGCTCTGGGTGGTGCTGTCAGTG

AAGTTCGCCTCTGGGGTGAGAGGGTAGACCCATCGGCGGATGACGTCAGCACAGACAGCTGAGTACATGTGTAGGTTG

GAGACACGGGCACCATATTCCTTAGCTGTTACGTGCATGTGGATCTGGTTCCCTAGGATCTCCTCATTCACTAAGAGA

CCTCGCACAAAGTCATCTCGAGTTTGGTAGTCAAAGTTGTCTGTAAAGAGTTGTGCCACCTGAGGAGAACAGATGCTG

ATATGACAATCCAGTAAATCATATCGAACCTCCACTCCATCACTACTGCCCTGAAACAGGCTCAGAGGAAATGCAAAA

CGCCGGAGACCCTGGGTCTTCTGAAAATGGAGAACCCTGTTTGTGGTACTATCCACAGCCACTACCACATTGTCTTCG

TABLE 6C-continued

NOV6 reverse complement

TGGCAACGAGTTGGGTGGCTGGGGGATGACTCCTTGAAGATCATCGTCATCACAGAAACATTTTTTTCTAGCTTCCGT

CTCAACCTGTGTTCCTCAAGGGCTCTGGTGATATTGATGTTTGAGATGACATCCCCATACACCAGAAGAAAGTCAGAG

CGCACCAAAGCCTTGGCATCAACATCACGGAGGACATCTCCCAGTGATCGATAGAGCTCTGATGTAATTATTCGAACC

ACATTGAGAGATGTAGGGCGGCACCACTTTGACTTCAGTAAATGTTCTTTGATTTGAGCAGCTTTCCAGCAACAAAAG

ACAAATGTTTCCTGTACACCTGTGGCAGTCAGGAATTC

BLASTP results for NOV6 are shown in Table 6D.

TABLE 6D

BLAST results for NOV6

| Matching Entry (in SwissProt + SpTrEMBL) | Description | aa Length | % Identity | % Positive | E Value |
| --- | --- | --- | --- | --- | --- |
| E2BE_HUMAN; U23028; AAC50646.1 | TRANSLATION INITIATION FACTOR EIF-2B EPSILON SUBUNIT (EIF-2B GDP-GTPEXCHANGE FACTOR) (FRAGMENT). homo sapiens. 7/1999 | 641 | 335/336 (100%) | 336/336, (100%) | 0.0 |
| E2BE_RABIT; U23037; AAC48618.1 | TRANSLATION INITIATION FACTOR EIF-2B EPSILON SUBUNIT (EIF-2B GDP-GTPEXCHANGE FACTOR). oryctolagus cuniculus. 7/1999 | 721 | 294/336 (88%) | 318/336, (95%) | 1e-171 |
| E2BE_RAT; U19516; AAB17690.1 | TRANSLATION INITIATION FACTOR EIF-2B EPSILON SUBUNIT (EIF-2B GDP-GTPEXCHANGE FACTOR). rattus norvegicus. 7/1999 | 716 | 292/336 (87%) | 314/336, (93%) | 1e-168 |
| O64760; AC004238; AAC12836.1 | PUTATIVE TRANSLATION INITIATION FACTOR EIF-2B-EPSILON SUBUNIT. arabidopsis thaliana. 6/2001 | 730 | 100/362 (28%) | 170/362, (47%) | 1e-34 |
| Q9SRU3; AC009755; AAF02111.1 | PUTATIVE TRANSLATION INITIATION FACTOR EIF-2B EPSILON SUBUNIT. arabidopsis thaliana. 6/2001 | 676 | 96/341 (28%) | 166/341, (49%) | 8e-29 |

A multiple sequence alignment is given in Table 6E, with the NOV6 protein of the invention being shown on lines 1 in a ClustalW analysis comparing NOV6 with related protein sequences of Table 6D.

TABLE 6E

Information for the ClustalW protein:

```
1. SEQ ID NO:35, NOV6
2. SEQ ID NO:37, E2BE_HUMAN EIF-2B GDP-GTPEXCHANGE FACTOR 7/1999
3. SEQ ID NO:38, E2BE_RABIT EIF-2B GDP-GTPEXCHANGE FACTOR 7/1999
4. SEQ ID NO:39, E2BE_RAT EIF-2B GDP-GTPEXCHANGE FACTOR 7/1999
5. SEQ ID NO:40, O64760 PUTATIVE EIF-2B-EPSILON SUBUNIT 6/2001
6. SEQ ID NO:41, Q9SRU3 PUTATIVE EIF-2B EPSILON SUBUNTI 6/2001

NOV6       1    ------------------------------------------------------------ 1
E2BE_HUMAN 1    ------------------------------------------------------------ 1
E2BE_RABIT 1    MATTVVAPPGAVSDRANKRGGGPGGGGGGGARGAEEESPPPLQAVLVADSFNRRFFPIS 60
E2BE_RAT   1    -MAATAAVPSAVGGRANKRGGGSGGGG-----TQGAEEEPPPPLQAVLVADSFDRRFFPIS 55
O64760     1    ------MGAQKKGGAAARVSEDAEVQS------------RHRLQAILLADSFATKFRPVT 42
Q9SRU3     1    ------MASRKK--RAAKISEDSEEEQS----------TTQTLQAILLADSFATKLLPLT 42
```

TABLE 6E-continued

Information for the ClustalW protein:

```
NOV6         1   --------------------EFLTATGVQETFVFCCWKAAQIKEHLLKSKWCRPTSLNVV  40
E2BE_HUMAN   1   --------------------EFLTATGVQETFVFCCWKAAQIKEHLLKSKWCRPTSLNVV  40
E2BE_RABIT  61   KDQPRVLLPLANVALIDYTLEFLTATGVQETFVFCCWKAAQIKEHLQKSKWCRPTSLNVV 120
E2BE_RAT    56   KDQPRVLLPLANVALIDYTLEFLTATGVQETFVFCCWKAAQIKEHLQKSKWCHPTSLNVV 115
O64760      43   LERPKVLLPIVNVPMIDYTLAWLESAGIEEVFVFCCAHSMQVIEYLEKSKWYSHPNLLVR 102
Q9SRU3      43   LERPNVLLPLVNIPMIDYTLAWLESAGIEEVFVFC---SMQVIDYLNNSDWYSHKDFTVK  99

NOV6        41   RIITSELYRSLGDVLR----DVDAKALVRSDFLLVYGDVISNINITRALEEHRLRRKLEK  96
E2BE_HUMAN  41   RIITSELYRSLGDVLR----DVDAKALVRSDFLLVYGDVISNINITRALEEHRLRRKLEK  96
E2BE_RABIT 121   RIITSELYRSLGDVLR----DVDAKALVRSDFLLVYGDVVSNINVTRALEEHRLRRKLEK 176
E2BE_RAT   116   RITTSDLYRSLGDVLR----DVDAKALVRSDFLLEYGDVVSNINISKALEEHRLRRKLEK 171
O64760     103   TIES-HKSISAGDALRYMYEQQTETSQIQGDFVLVSGDTVSNMPLADLIQEHRERKKKDE 161
Q9SRU3     100   TIESPQNDTSAGDALRYIYEQQIETSQIQGDFVLVNGCIVSNMPLTQLIQEHRDRKKKDE 159

NOV6        97   NVSVMTMIFKESSPS---HPTRCHEDNVVVAVDSTINRVLHFQKTQG---LRRFAEPLSL 150
E2BE_HUMAN  97   NVSVMTMIFKESSPS---HPTRCHEDNVVVAVDSTINRVLHFQKTQG---LRRFAEPLSL 150
E2BE_RABIT 177   NVSVMTMIFKESSPS---HPTRCHEDNVVVAVDSAINRILHFQKTQG---LRRFSEPLSL 230
E2BE_RAT   172   NVSVMTMVFKESSPS---HPTRCHEDNVVLAVDSTINRILHFQKTQG---LRRFSEPLGL 225
O64760     161   -KAIMTMVIKCSKSSPLTHQSRLGTDQLFIAVDPLIKQLLHYEEDKIDHPSGSVCLEKSL 220
Q9SRU3     159   -KAIMTMVIR---------QSLITDHQLFTAVNPLIKQLLYYDED-------NICEDKSL 202

NOV6       151   FQGSSDGVEVRYDLLDCHISICSPQVAQLFTDNFDYQTRDDFVRGLLVNEEILGNQIHMH 210
E2BE_HUMAN 151   FQGSSDGVEVRYDLLDCHISICSPQVAQLFTDNFDYQTRDDFVRGLLVNEEILGNQIHMH 210
E2BE_RABIT 231   FQGSGAGVEIRYDLLDCHISIVSPQVAQLFTDNFDYQTRDDFVRGLLVNEEILGNQIHMH 290
E2BE_RAT   226   FQGSGAGVEIRYDLLDCHISIVSPSVLSLFEDNFDYQHLRRHFVKGVLVDDIMGYKIFTH 285
O64760     221   LD-TNPSVLVCNDMQDCYIDICSPSVLSLFEDNFDYQHLRRHFVKGVLVDDIMGYKIFTH 279
Q9SRU3     203   LD-RNPSVLLCDDMQDCYIDICSLEVLSLFVDNFDYQHMRCDFVEGVLADDIIGYKIFTH 261

NOV6       211   VTAKEYGARVSNLHMYSAVCADVIRRWVYPLTPEANFTDSTTQSCTHSRHNIYRGPEVSL 270
E2BE_HUMAN 211   VTAKEYGARVSNLHMYSAVCADVIRRWVYPLTPEANFTDSTTQSCTHSRHNIYRGPEVSL 270
E2BE_RABIT 291   VTTREYGARVSNLHMYSAVCADVIRRWVYPLTPEANFTDSTAQSCTHSRHNIYRGPEVSL 350
E2BE_RAT   286   VTSREYGSRVSNLHMYSAVCTDVIRRWVYPLTPEVNFTDSSTQSYTHSRHNIYRGPEVSL 345
O64760     280   EIHSSYAGRIDNFRSYDTVSKDIIQRWTFPYVPDINFSG--RPLKLGRQGIYKASCVVQ 337
Q9SRU3     262   EISSCYASRIENFRSYDMVSKDIIQRRTFPYVPDMKFSG--NRTLKLERQGIYKASDATQ 319

NOV6       271   GHGSILEENVLLGSGTVIGSNCFITNSVIGPGCHIGDNVVLDQTYLWQGVRVAAGAQIHQ 330
E2BE_HUMAN 271   GHGSILEENVLLGSGTVIGSNCFITNSVIGPGCHIGDNVVLDQTYLWQGVRVAAGAQIHQ 330
E2BE_RABIT 351   GHGSILEENVLLGSGTVIGSNCSITNSVIGPGCCIGDNVVLDRAYLWKGVQVASGAQIHQ 410
E2BE_RAT   346   GHGSVLEENVLLGAGTVVGSNCSITNSVIGPNCHIGDNVVLDQAYLWQGVRVAAGAQIHQ 405
O64760     338   SRSADVGASTVIGYGTKIGHGDKIMNSVIGNGCSIGSNVVIEGSYIWNNYTIEDGCEIRN 397
Q9SRU3     320   LPSAHVGASYVIGHATNIGSGTKILNSVIGNGCSIGSNVVIQGSYIWNNVTVEDGCEIRN 379

NOV6       331   SLLCDNAEVKERVTLKPRSVLTSQVVVGPNITLPEGSVISLHPPDAEEDEDGEFSDDSG 390
E2BE_HUMAN 331   SLLCDNAEVKERVTLKPRSVLTSQVVVGPNITLPEGSVISLHPPDAEEDEDGEFSDDSG 390
E2BE_RABIT 411   SLLCDHAEVKEQVTLKPHCVLTSQVVVGPNITLPEGSVISLHPPDAEEDEDDGQFSDDSG 470
E2BE_RAT   406   SLLCDRAEVKERVILKPHCVLTSQVVVGPDIILPEGSVISLHPPDAEEDEDDGQFSDDSG 465
O64760     398   ATVCDGVKTRAGAVLQPGVVLSFNVVVGRDFVVPAYSKVSILQQPTTEDSDEELEYADSS 457
Q9SRU3     380   AIVCDEVKVCAGAIVKPGVVLSFKVVVGRDFVVPAYSQVSILRQPMEEDSDE-----E-- 432

NOV6       390   ---ADQEKDKVKMKGYNPAEVGAACKGYLWK------AAGMNEEEEELQQNLWGLKINM 441
E2BE_HUMAN 390   ---ADQEKDKVKMKGYNPAEVGAACKGYLWK------AAGMNEEEEELQQNLWGLKINM 441
E2BE_RABIT 470   ---VNQAKEKAKLKGYNPAEVGVACKGYLWK------AADMNTEKEEELRQSLWGLTINE 521
E2BE_RAT   465   ---ADQEKEKVKLKGYNPAEVGPEGQGYLWK------AEDVDEKEDEELRQSLWGLMINM 516
O64760     458   SGTADHLSGLNLQMESKASELGPDGAGYHWEVCEGAHDEEWKHSVAPIPKDKLSEITQAI 517
Q9SRU3     432   ----NLLSGVDLQMESK---LGLDGAGYIWK---QACEDEWKHSVPPIPKDKLAEIIKAI 482

NOV6       442   EEESESESEQSMDSEEPDSRGGSPQMDDIK------VFQNEVLGTLQRGKEENISCDNLV 495
E2BE_HUMAN 442   EEESESESEQSMDSEEPDSRGGSPQMDDIK------VFQNEVLGTLQRGKEENISCDNLV 495
E2BE_RABIT 522   EEESETESETSMDSEELDSRAGSPQLDDIK------VFQNEVLGTLQRGKEESISCDNLI 575
E2BE_RAT   517   EEESETESERSVDPEELDSRAGSPQLDDIR------VFQNEVLGTLQRGREENISCDNLV 570
O64760     518   DDDDTDDESVVPTSGPLKSDADSINTDVNDPNDDYYFEKPEVGTVLRAVEENIKVDLVT 577
Q9SRU3     483   DDDDTDDESVVTTSGDAN---TSINNDLFD-------FEREVDGTRLRAVEENIVADLAV 532

NOV6       496   LEINSLKYAYNVSLKEVMQVLSHVVLEFPLQQMDSPLDSSRYCALLLPLLKAWSPVFRNY 555
E2BE_HUMAN 496   LEINSLKYAYNVSLKEVMQVLSHVVLEFPLQQMDSPLDSSRYCALLLPLLKAWSPVFRNY 555
E2BE_RABIT 576   LEINSLKYAYNISLKEVMQVLSHVVLEFPLQQMDSPLEANRYCALLLPLLKAWSPVFRNY 635
E2BE_RAT   571   LEINSLKYAYNISLKEVMQVLSHVVLEFPLQQVDGVLDPNRYCALLLPLLKAWSPVFRNY 630
O64760     578   MEINGLRLSFNMESADCAGATFFSMIKLALDTPHNSG--SELYKNAASIITKWKDLLGFY 635
Q9SRU3     533   LEINSLRLSYNMESAHCAGAIFYSMMKLAVSTPHSSI--NDLYRNASSIITRWKGLLGFY 590

NOV6       556   IKRAADHLEALAAIEDFFLE-HEALGISMAKVLMAFYQL--EILAEETILSWFSQRDTTD 612
E2BE_HUMAN 556   IKRAADHLEALAAIEDFFLE-HEALGISMAKVLMAFYQL--EILAEETILSWFSQRDTTD 612
E2BE_RABIT 636   IKRAADHLEALAAIEFFLE-HEALGTCIAKVLMGFYQL--EILAEETILSWFGQRDVTD 692
E2BE_RAT   631   IKTAADHLEALAAIEDFFLE-HETLVPSLAKVLMAFYQL--EILAEETILSWFSQRDITD 687
O64760     636   AKKIDEQIEVIMKPEEMCQESHKELGPLFTQIIHLLYDK--DVLQEDAIIRWEEEKAGAD 693
Q9SRU3     591   VKKSDEQIEVISRLEEMCEESAHELGTLFAHIRYMYKEENDLLQEVAIIRWSDEKAGAD 650
```

TABLE 6E-continued

Information for the ClustalW protein:

```
NOV6        613  KGQQLRKNQQLQRFIQWLKEAEEESSEDD---------  641
E2BE_HUMAN  613  KGQQLRKNQQLQRFIQWLKEAEEESSEDD---------  641
E2BE_RABIT  693  KGRQLRKNQQLQRFIQWLKEAEEESSEDD---------  721
E2BE_RAT    688  KGQQLRKNQQLQRFIQWLKEAEEESSDDD---------  716
O64760      694  EADKVYLK-QCDTFIQWLKEASEEEDEDDEDEEEEEDN  730
Q9SRU3      651  KSDKVYLK-QCKPFITWLKETSDDEDG-----------  676
```

ProDom results for NOV6 were collected from a public database. DOMAIN results for NOV6 were collected using the PFAM HMM database. The results are listed in Table 6F with the statistics and domain description.

TABLE 6F

Domain results for NOV6

ProDom Analysis prdm:15525 p36 (2) E2BE(2)//TRANSLATION FACTOR EIF-2B INITIATION EPSILON SUBUNIT GDP-GTP EXCHANGE AMINO-ACID BIOSYNTHESIS, 311 aa.
Identities = 270/311 (86%), Positives = 290/311 (93%) for Query: 56-366 and Sbjct: 1-311

>prdm:14746 p36 (2)//FACTOR TRANSLATION EIF-2B SUBUNIT EXCHANGE INITIATION EPSILON GDP-GTP AMINO-ACID BIOSYNTHESIS, 261 aa.
Identities = 61/245 (24%), Positives = 109/245 (44%) for Query: 129-358 and Sbjct: 17-261

>prdm:3752 p36 (7) IF5(7)//INITIATION FACTOR PROTEIN EUKARYOTIC TRANSLATION EIF-5 BIOSYNTHESIS GTP-BINDING PROBABLE ALTERNATIVE, 260 aa.
Identities = 37/94 (39%), Positives = 51/94 (54%) for Query: 278-363 and Sbjct: 126-219

>prdm:48803 p36 (1) SSRP_DROME//SINGLE-STRAND RECOGNITION PROTEIN (SSRP) (CHORION-FACTOR 5). DNA-BINDING; RNA-BINDING; NUCLEAR PROTEIN, 58 aa.
Identities = 9/20 (45%), Positives = 15/20 (75%) for Query: 100-119 and Sbjct: 2-20
Identities = 10/29 (34%), Positives = 15/29 (51%) for Query: 165-193 and Sbjct: 29-56

>prdm:25633 p36 (1) FKB1_DROME//39 KD FK506-BINDING NUCLEAR PROTEIN (PEPTIDYL-PROLYL CIS-TRANSISOMERASE) (PPIASE) (EC 5.2.1.8). ISOMERASE, ROTAMASE; NUCLEAR PROTEIN, 85 aa
Identities = 27/85 (31%), Positives = 42/85 (49%), for Query: 102-186, Sbjct: 3-78

PFAM HMM Domain Analysis of NOV06

| Model | Description | Score | E-value |
| --- | --- | --- | --- |
| W2 | (InterPro) e-IF4-gamma/eIF5/eIF2-epsilon | 121.5 | 1.6e-32 |
| hormone2 | (InterPro) Peptide hormone | 10.4 | 0.76 |

Parsed for domains:

| Model | Domain | seq-f | seq-t | hnm-f | hnm-t | score | E-value |
| --- | --- | --- | --- | --- | --- | --- | --- |
| hormone2 | 1/1 | 342 | 357 .. | 13 | 28 .] | 10.4 | 0.76 |
| W2 | 1/1 | 284 | 366 . ] | 1 | 87 [ ] | 121.5 | 1.6e-32 |

PROSITE—Protein Domain Matches for Gene ID: NOV06

Pattern-ID: ASN_GLYCOSYLATION P500001 (Interpro) PDOC00001

Pattern-DE: N-glycosylation sites

Pattern: N[^P] [ST] [^P]

NOV6 Position: 85- NITL; 213-NISC; 231-NISL

Pattern-ID: PKC_PHOSPHO_SITE PS00005 (Interpro) PDOC00005

Pattern-DE: Protein kinase C phosphorylation sites

Pattern: [ST].[RK]

NOV6 Position: 69 -TLK; 225 -SLK; 233-SLK; 259-SSR; 331-SQR; 336-TDK

Pattern-ID: CK2_PHOSPHO_SITE PS00006 (Interpro) PDOC00006

TABLE 6F-continued

Domain results for NOV6

Pattern-DE: Casein kinase II phosphorylation sites

Pattern: [ST].{2} [DE]

NOV6 Position: 29-STGD; 87-TLPE; 114-SGAD; 170-SESE; 233-SLKE; 255-SPLD, 331-SQRD; 362-SSED Pattern-ID: MYRISTYL PS00008 (Interpro) PDOC00008

Pattern-DE: N-myristoylation sites

Pattern: G[^EDRKHPFYW].{2} [STAGCN] [^P]

NOV6 Position: 44-GVRVAA; 91-GSVISL; 161-GLKINM; 305-GISMAK

BLOCKS Analysis

| AC# | Description | Strength | Score |
|---|---|---|---|
| BL00260 | 0 Glucagon / GIP / secretin / VIP family protei | 1460 | 1100 |
| BL00501B | 0 Signal peptidases I serine proteins. | 1234 | 1061 |
| BL00558A | 0 Eukaryotic mitochondrial porin proteins | 1284 | 1056 |
| BL00486C | 0 DNA mismatch repair proteins mutS family prot | 1682 | 1037 |
| BL00808J | 0 ADP-glucose pyrophosphorylase proteins. | 1397 | 1036 |
| BL00992B | 0 Serum amyloid A proteins. | 1851 | 1024 |
| BL01271B | 0 Sodium:sulfate symporter family proteins. | 1480 | 1022 |
| BL00132E | 0 Zinc carboxypeptidases, zinc-binding region 1 | 1608 | 1020 |

The translation factor eif-2B initiation epsilon subunit is involved with GDP-GTP exchange, and amino acid biosynthesis. The initiation factor protein eukaryotic translation EIF-5 is thought to be involved with biosynthesis and GTP-binding. The single-strand recognition protein (SSRP) (chorion-factor 5) is involved with DNA-binding; and RNA-binding. The FK506-binding nuclear protein (peptidyl-prolyl cis-trans isomerase) (PPIASE) (EC 5.2.1.8) is a rotamase; and is involved with nuclear proteins.

Other BLAST results include sequences from the Patp database, which is a proprietary database that contains sequences published in patents and patent publications. Patp results include those listed in Table 6G.

NOV6 is expressed in at least the following tissues: placenta, small intestine, larynx, kidney, muscle, colon, tonsil, stomach, uterus, bone marrow, brain and others This information was derived by determining the tissue sources of the sequences that were included in the invention including but not limited to SeqCalling sources, Public EST sources, Literature sources, and/or RACE sources.

The disclosed NOV6 nucleic acid encoding a novel protein includes the nucleic acid whose sequence is provided in Table 6A, or a fragment thereof. The invention also includes a mutant or variant nucleic acid any of whose bases may be changed from the corresponding base shown in Table 6A while still encoding a protein that maintains its activities and physiological functions, or a fragment of such

TABLE 6G

Patp alignments of NOV6

| Sequences producing High-scoring Segment Pairs: | % Identity | % Positive |
|---|---|---|
| patp:AAB43883 Human cancer associated protein sequence | 29/96 | 55/96 |
| SEQ ID NO:1328 - Homo sapiens, 424 aa. PN = WO200055350-A1. Expect = 7.6e-06 | (30%) | (57%) |

The eIF4-gamma/eIF5/eIF2-epsilon proteins are involved with regulation of genes at the translational level, and are involved with GTP-GDP exchange. Peptide hormones are involved in many physiological processes including glucose and fat metabolism, immune system regulation, and neuronal regulation.

a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 13% percent of the bases may be so changed.

The disclosed NOV6 protein of the invention includes the novel protein whose sequence is provided in Table 6B. The invention also includes a mutant or variant protein any of whose residues may be changed from the corresponding residue shown in Table 6B while still encoding a protein that maintains its activities and physiological functions, or a functional fragment thereof. In the mutant or variant protein, up to about 13% percent of the residues may be so changed.

The invention further encompasses antibodies and antibody fragments, such as $F_{ab}$ or $(F_{ab})_2$, that bind immuno-specifically to any of the proteins of the invention.

The NOV6 nucleic acids and proteins of the invention are useful in potential therapeutic applications implicated in cancer including but not limited to breast cancer, ovarian cancer, and/or other pathologies and disorders. For example, a cDNA encoding the novel protein (NOV6) may be useful in cancer therapy, and the novel protein (NOV6) may be useful when administered to a subject in need thereof. By way of nonlimiting example, the compositions of the present invention will have efficacy for treatment of patients suffering from cancer including but not limited to breast and ovarian cancer. The NOV6 nucleic acid encoding novel protein, of the invention, or fragments thereof, may further be useful in diagnostic applications, wherein the presence or amount of the nucleic acid or the protein are to be assessed.

NOV6 nucleic acids and polypeptides are further useful in the generation of antibodies that bind immuno-specifically to the novel NOV6 substances for use in therapeutic or diagnostic methods. These antibodies may be generated according to methods known in the art, using prediction from hydrophobicity charts, as described in the "Anti-NOVX Antibodies" section below. The disclosed NOV6 protein has multiple hydrophilic regions, each of which can be used as an immunogen. In one embodiment, a contemplated NOV6 epitope is from about amino acids 60 to 75. In another embodiment, a NOV6 epitope is from about amino acids 100 to 135. In additional embodiments, NOV6 epitopes are from about amino acids 145 to 155, from about amino acids 160 to 190, from about amino acids 200 to 220, from about amino acids 230 to 235, from about amino acids 250 to 270, from about amino acids 280 to 290, and from about amino acids 320 to 360. These novel proteins can be used in assay systems for functional analysis of various human disorders, which will help in understanding of pathology of the disease and development of new drug targets for various disorders.

NOV7

In another embodiment, the novel sequence is NOV7 (alternatively referred to herein as 24SC526), which includes the 2004 nucleotide sequence (SEQ ID NO:42) shown in Table 7A. A NOV7 ORF begins with a Kozak consensus ATG initiation codon at nucleotides 176–178 and ends with a TGA codon at nucleotides 404–406. Putative untranslated regions upstream from the initiation codon and downstream from the termination codon are underlined in Table 7A, and the start and stop codons are in bold letters.

TABLE 7A

NOV7 Nucleotide Sequence (SEQ ID NO:42)
GGGCGCGCGGCCTCGAGGCCTTCCGGTGCGGGAGAAACTACTACTCCCATAATGCCCCGCGGTCCCGCGAGCTG

CCAGTCTCGTCGCGAGAAGCAGCGGCCCGGGGCGACTGAGCGGACAAACGGAAGTGTAGGTTACGGTCTGAGAC

ATCACCGCCAAGCTGGGCATCGGGGAGATGGCCGAGACTGACCCCAAGACCGTGCAGGACCTCACCTCGGTGGT

GCAGACACTCCTGCAGCAGATGCAAGATAAATTTCAGACCATGTCTGACCAGATCATTGGGAGAATTGATGATA

TGAGTAGTCGCATTGATGATCTGGAAAAGAATATCGCGGACCTCATGACACAGGCTGGGGTGGAAGAACTGGAA

AGTGAAAACAAGATACCTGCCACGCAAAAGAGTTGAAGGTTGCTAATAATTTATACTGGAATCTGGCATTTTTC

CAAGCCAAGAGAAGATCGAATGGCTTTTTGCAGCTAACTACTATGTGTAGACAGGTTTTATATTATAAAGTATG

CATTCTTATCACCTAGTATATAGTTAGTTTGTAGAGTGATTTCCCCCCAGTTTCTTGAACATGGTATCTTCACA

TCTTGGACCTTGGTCAGTTGTGCTATTCATTATTAAACACTAAAACTTTGGCGGTTCTTGCATAACATTGTCAG

ATTTTTTAGTGTATTTCTGTGAAGTCATTTTTTTTCTTGTCATTCCTTTTGTAGTAGTTGCTGTTTGGATAAAA

GTTGATGTGTGATTTTTTATTAAACAAATAGTAAACCCTTCAATTATAGTTAGTCTTGGTGAAGTAAGATGTTT

GTAGACTTTAGAGTTCTTTAATTCTTGGCACAACGTGACTTTTGAGCTAACACCAAATAGTGTGTTGGCAATAC

TTTTCAAATGGCTGAAAACACCTAAAAATTGTTCATTCAGAAATATCTGTCACTGCTCTGTTGCCAAAACTCAG

AATAGAACTTAGACGTATGTCTGAGTCCCTGAGATCACATGCTAAAGTCGATGAAAAGTAACCACTGCCACTGT

CTTGTGTCAGAACTTTTACAGTACAGAAAATAACAGAATAGCCTTCTGTAATGAGGCGTTTGTTAGAGTTTTGC

ATGAGATTCTAATACTTCAGTAGGACCCTACCTACGTGGTTCATCTACAATGGTTACCATAAAAAATCTGGCAG

GATTTTAAAACTCAATCAGTCTTTCCTTTGAGCTAGTGACTTGAAAAGAAAGAGAGAAGAAAAAGAGACCATAT

TABLE 7A-continued

NOV7 Nucleotide Sequence

TAAGTCCATGCCAGTTGCTTGGCTAGAATATGATCAACGACTTGTAGTAGACTCAAGTTTTTAAAAAACACTAT

TTTACTTAAACTGTTTCTTATCTAAATTCTTGCAGAGTGTCAATGTTATCATTGATTATAGAAGACAGGGATAA

TACCTTTATCTCTGGCCACTCAAAAATGCAGTGCCAGGAGTGCTAAACCTAGAGGCCAATACTGATGACCTGGA

AGGTGATCCATATGATTGTCACCACAAAGTGCTTTTACACAAAAACTTGAAAATTTGAAAAACATGATTTTTTT

AAGTTTCTCATCTCACCAGTCTTGGTGTTTATATTGCAAATCTATCAAAGTAAGAAATAATTTGTGCTGTATAC

AAATTACATGGGGAACATAAAGGAGTGAGATCCTTCTGTGATAAAATGAATTCACCACTCTGGTTACCCAACTA

CAGAACCTCCTTTGATCAGGCCAGTAGGTTGTGATGCAGGCTGGAGCCCCCGAATGCCCCACACACACTGCAGC

ATTGACCAGACCATCCGAAACCTGCGTCCCTGGTGATGTTCTCAAGCCTCGGAAGTGGCAAATGGAAATGATAT

GGCCGGTTGCGGTTGTAGGAGAGTTGTGACTTAGGCAGGAGTCGACCTCCTCAAGTAATGGAACGATTTCAAAG

GCAGGCTGCCCTGACCAAAAATATCTGCCATGAATAAAGGTGCCTGAAATCCTGCTAAAAAAAAAAAAAAAAAA

AAAAAA

The NOV7 8543.5 Dalton protein (SEQ ID NO:43) encoded by SEQ ID NO:42 is 76 amino acids in length and is presented using the one-letter code in Table 7B. The Psort profile for NOV7 predicts that this sequence has no known signal peptide and is likely to be localized in the cytoplasm with a certainty of 0.6500. In alternative embodiments, a NOV7 polypeptide is located to the mitochondrial matrix space with a certainty of 0.1000, or the lysosome (lumen) with a certainty of 0.1000.

TABLE 7B

NOV7 protein sequence (SEQ ID NO:43)
MAETDPKTVQDLTSVVQTLLQQMQDKFQTMSDQIIGRIDDMSSRIDDLEKNIADLMTQAGVEELESENKIPATQKS The reverse complement for NOV7 is presented in Table 7C.

TABLE 7C

NOV7 reverse complement (SEQ ID NO:44)
TTTTTTTTTTTTTTTTTTTTTTAGCAGGATTTCAGGCACCTTTATTCATGGCAGATATTTTTGGTCAGGGCAGCCTG

CCTTTGAAATCGTTCCATTACTTGAGGAGGTCGACTCCTGCCTAAGTCACAACTCTCCTACAACCGCAACCGGCCATAT

CATTTCCATTTGCCACTTCCGAGGCTTGAGAACATCACCAGGGACGCAGGTTTCGGATGGTCTGGTCAATGCTGCAGTG

TGTGTGGGGCATTCGGGGGCTCCAGCCTGCATCACAACCTACTGGCCTGATCAAAGGAGGTTCTGTAGTTGGGTAACCA

GAGTGGTGAATTCATTTTATCACAGAAGGATCTCACTCCTTTATGTTCCCCATGTAATTTGTATACAGCACAAATTATT

TCTTACTTTGATAGATTTGCAATATAAACACCAAGACTGGTGAGATGAGAAACTTAAAAAAATCATGTTTTTCAAATTT

TCAAGTTTTTGTGTAAAAGCACTTTGTGGTGACAATCATATGGATCACCTTCCAGGTCATCAGTATTGGCCTCTAGGTT

TAGCACTCCTGGCACTGCATTTTTGAGTGGCCAGAGATAAAGGTATTATCCCTGTCTTCTATAATCAATGATAACATTG

ACACTCTGCAAGAATTTAGATAAGAAACAGTTTAAGTAAAATAGTGTTTTTTAAAAACTTGAGTCTACTACAAGTCGTT

GATCATATTCTAGCCAAGCAACTGGCATGGACTTAATATGGTCTCTTTTCCTTCTCTCTTTCTTTTCAAGTCACTAGCT

CAAAGGAAAGACTGATTGAGTTTTAAAATCCTGCCAGATTTTTTATGGTAACCATTGTAGATGAACCACGTAGGTAGGG

TABLE 7C-continued

NOV7 reverse complement

TCCTACTGAAGTATTAGAATCTCATGCAAAACTCTAACAAACGCCTCATTACAGAAGGCTATTCTGTTATTTTCTGTAC

TGTAAAAGTTCTGACACAAGACAGTGGCAGTGGTTACTTTTCATCGACTTTAGCATGTGATCTCAGGGACTCAGACATA

CGTCTAAGTTCTATTCTGAGTTTTGGCAACAGAGCAGTGACAGATATTTCTGAATGAACAATTTTTAGGTGTTTTCAGC

CATTTGAAAAGTATTGCCAACACACTATTTGGTGTTAGCTCAAAAGTCACGTTGTGCCAAGAATTAAAGAACTCTAAAG

TCTACAAACATCTTACTTCACCAAGACTAACTATAATTGAAGGGTTTACTATTTGTTTAATAAAAAATCACACATCAAC

TTTTATCCAAACAGCAACTACTACAAAAGGAATGACAAGAAAAAAAATGACTTCACAGAAATACACTAAAAAATCTGAC

AATGTTATGCAAGAACCGCCAAAGTTTTAGTGTTTAATAATGAATAGCACAACTGACCAAGGTCCAAGATGTGAAGATA

CCATGTTCAAGAAACTGGGGGGAAATCACTCTACAAACTAACTATATACTAGGTGATAAGAATGCATACTTTATAATAT

AAAACCTGTCTACACATAGTAGTTAGCTGCAAAAAGCCATTCGATCTTCTCTTGGCTTGGAAAAATGCCAGATTCCAGT

ATAAATTATTAGCAACCTTCAACTCTTTTGCGTGGCAGGTATCTGTTTTCACTTTCCAGTTCTTCCACCCCAGCCCTGT

GTCATGAGGTCCGCGATATTCTTTTCCAGATCATCAATGCGACTACTCATATCATCAATTCTCCCAATGATCTGGTCAG

ACATGGTCTGAAATTTATCTTGCATCTGCTGCAGGAGTGTCTGCACCACCGAGGTGAGGTCCTGCACGGTCTTGGGGTC

AGTCTCGGCCATCTCCCCGATGCCCAGCTTGGCGGTGATGTCTCAGACCGTAACCTACACTTCCGTTTGTCCGCTCAGT

CGCCCCGGGCCGCTGCTTCTCGCGACGAGACTGGCAGCTCGCGGGACCGCGGGGCATTATGGGAGTAGTAGTTTCTCCC

GCACCGGAAGGCCTCGAGGCCGCGCGCCC

BLASTP results for NOV7 are shown in Table 7D.

TABLE 7D

BLAST results for NOV7

| Matching Entry (in Swissprot + SpTrEMBL) | Description | aa Length | % Identity | % Positive | E Value |
|---|---|---|---|---|---|
| HBP1_HUMAN; AF068754; AAC25186.1 | HEAT SHOCK FACTOR BINDING PROTEIN 1. homo sapiens. 5/2000 | 76 | 76/76 (100%) | 76/76, (100%) | 4e−36 |
| Q9CQZ1; AK018708; BAB31359.1 | 0610007A03RIK PROTEIN (SIMILAR TO HEAT SHOCK FACTOR BINDING PROTEIN1). mus musculus. 6/2001 | 76 | 67/76 (88%) | 71/76, (93%) | 8e−32 |
| Q9VK90; AE003636; AAF53188.1 | CG5446 PROTEIN. drosophila melanogaster. 5/2000 | 86 | 44/61 (72%) | 51/61, (84%) | 1e−18 |
| Q9U3B7; Z77666; CAB01233.2 | K08E7.2 PROTEIN. caenorhabditis elegans. 3/2001 | 80 | 36/54 (67%) | 44/54, (81%) | 3e−13 |
| Q9FP22; AP003044; BAB19328.1 | P0036C05.1 PROTEIN. oryza sativa. 3/2001 | 99 | 28/56 (50%) | 42/56, (75%) | 5e−10 |

A multiple sequence alignment is given in Table 7E, with the NOV7 protein of the invention being shown on lines 1 in a ClustalW analysis comparing NOV7 with related protein sequences of Table 7D.

TABLE 7E

Information for the ClustalW protein:

1. SEQ ID NO:43, NOV7
2. SEQ ID NO:45, HBP1_HUMAN HEAT SHOCK FACTOR BINDING PROTEIN 1. 5/2000
3. SEQ ID NO:46, Q9CQZ1 0610007A03RIK PROTEIN mus musculus. 6/2001
4. SEQ ID NO:47, Q9VK90 CG5446 PROTEIN. drosophila melanogaster. 5/2000
5. SEQ ID NO:48, Q9U3B7 K08E7.2 PROTEIN. caenorhabditis elegans. 3/2001
6. SEQ ID NO:49, Q9FP22 P0038C05.1 PROTEIN. oryza sativa. 3/2001

```
NOV7        1   ------------------MAETDPKTVQDLISVVQTLLQQMQDKFQTMSDQIIGRIDDMS 42
HBP1_HUMAN  1   ------------------MAETDPKTVQDLISVVQTLLQQMQDKFQTMSDQIIGRIDDMS 42
Q9CQZ1      1   ------------------MAETDPKTVQDILLVVETLLQQMQDKFQIMSDQIIGRIDDMS 42
Q9VK90      1   MTDLRNEMDSDLDQNYSLNSNADPKNMQEELIIYVQNLLQNVQDKFQTMSDQITTRIDDMG 60
Q9U3B7      1   MSD-----EKSTTPTAQLDAPADG-NMNDRISLIQGVLQQTQDRFQHMSDQIIRRIDDMT 54
Q9FP22      1   MAAPGSG-SGGIPIKADQDSDGSAQSTADMIAFVQNLIMQMQTRFQSMSENLISKIDEMG 59

NOV7       43   SRIDDLEKNIADLMTQAGVEELESENKIPATQKS------                     76
HBP1_HUMAN 43   SRIDDLEKNIADLMTQAGVEELESENKIPATQKS------                     76
Q9CQZ1     43   SRIDDLEKNIADLMTQAGVEELDPENKIPTAQKS------                     76
Q9VK90     61   NRIDDLEKSIADLMNQAGIEGQGPEK--------------                     86
Q9U3B7     55   TRIDDLEKNINDLEQSNQVEHPPSAQ--------------                     80
Q9FP22     60   ARIDELEQEINDIKVEMGTEGITPTKPKDEESKPAGSSAE                     99
```

BLASTP domain results for NOV7 were collected from a proprietary database. The results are listed in Table 7F with the statistics and domain description.

TABLE 7F

Domain results for NOV7

ProDom Analysis

| Sequence producing High-scoring Segment Pairs: | High Score | Smallest Sum Probability P(N) |
|---|---|---|
| prdm:42125 p36 (1) STE4_SCHPO // SEXUAL DIFFERENTIATION P . . . | 78 | 0.0030 |
| prdm:56790 p36 (1) BUD6_YEAST // BUD SITE SELECTION PROTE . . . | 73 | 0.0059 |
| prdm:53072 p36 (1) GAGY_DROME // RETROVIRUS-RELATED GAG P . . . | 57 | 0.0074 |
| prdm:35747 p36 (1) RLX2_SALTY // 22 KD RELAXATION PROTEIN . . . | 69 | 0.017 |
| prdm:8937 p36 (3) YOPE(3) // OUTER MEMBRANE VIRULENCE P . . . | 64 | 0.073 | prdm:42125 p36 (1) STE4_SCHPO//SEXUAL DIFFERENTIATION PROTEIN STE4. MEIOSIS, 264 aa
Identities = 20/70 (28%), Positives = 42/70 (60%) for NOV7: 11-76, Sbjct: 62-131

>prdm.56790 p36 (1) BUD6_YEAST // BUD SITE SELECTION PROTEIN BUD6 (ACTIN INTERACTING PROTEIN 3), 788 aa.
Identities = 12/50 (24%), Positives = 32/50 (64%) for NOV7: 20-69, Sbjct: 559-608
Identities = 7/24 (29%), Positives = 14/24 (58%) for NOV7: 3-26, Sbjct: 106-129

>prdm.53072 p36 (1) GAGY_DROME // RETROVIRUS-RELATED GAG POLYPROTEIN (TRANSPOSON GYPSY). CORE PROTEIN; POLYPROTEIN; TRANSPOSABLE ELEMENT, 451 aa.
Identities = 12/38 (31%), Positives = 20/38 (52%) for NOV7: 5-41, Sbjct: 43-80
Identities = 8/19 (42%), Positives = 13/19 (68%) for NOV7: 58-76, Sbjct: 412-430

>prdm:35747 p36 (1) RLX2_SALTY // 22 KD RELAXATION PROTEIN PLASMID, 194 aa.
Identities = 20/70 (28%), Positives = 37/70 (52%) for NOV7: 7-24, Sbjct: 20-89

>prdm:8937 p36 (3) YOPE(3)//OUTER MEMBRANE VIRULENCE PROTEIN YOPE PLASMID, 219 aa.
Identities = 16/37 (43%), Positives = 22/37 (59%) for NOV7: 2-38, Sbjct: 111-147

PFAM HMM Domain Analysis

Scores for sequence family classification (score includes all domains):

| Model | Description | Score | E-value | N |
|---|---|---|---|---|
| Leptin | (InterPro) Leptin | 2.2 | 10 | 1 |

TABLE 7F-continued

Domain results for NOV7

Parsed for domains:

| Model | Domain | seq-f | seq-t | hmm-f | hmm-t | score | E-value |
|---|---|---|---|---|---|---|---|
| Leptin | 1/1 | 20 | 42 .. | 1 | 25 [. | 2.2 | 10 |

PROSITE—Protein Domain Matches for Gene ID: NOV7

Pattern-ID: PKC_PHOSPHO_SITE PS00005 (Interpro) PDOC00005
Pattern-DE: Protein kinase C phosphorylation site
Pattern: [ST]·[RK]
NOV7 Position 42-ssr; 73-tqk Pattern-ID: CK2_PHOSPHO_SITE PS00006 (Interpro) PDOC00006
Pattern-DE: Casein kinase II phosphorylation site
Pattern: [ST].{2} [DE]
NOV7 Position: 8-TVQD; 29-TMSD; 43-SRID

BLOCKS Analysis

| AC# | Description | Strength | Score |
|---|---|---|---|
| BL01291A | 0 NAD:arginine ADP-ribosyltransferases proteins | 1609 | 1027 |
| BL00058A | 0 DNA mismatch repair proteins mutL / hexB / PM | 1767 | 1001 |
| BL00902A | 0 Glutamate 5-kinase proteins. | 1549 | 994 |
| BL01213C | 0 Protozoan/cyanobacterial globins proteins. | 1420 | 994 |
| BL00579B | 0 Ribosomal protein L29 proteins. | 1361 | 991 |
| BL00487G | 0 IMP dehydrogenase / GMP reductase proteins. | 1525 | 989 |
| BL00564F | 0 Argininosuccinate synthase proteins. | 1759 | 987 |
| BL00154A | 0 E1-E2 ATPases phosphorylation site proteins. | 1268 | 983 |

The STE4_SCHPO//sexual differentiation protein STE4 is involved with meiosis. The bud6_yeast//bud site selection protein BUD6 (actin interacting protein 3) interacts with the cytoskeleton. The gagy_drome//retrovirus-related GAG polyperotein (transposon gypsy) is involved with viral core proteins; plyproteins; and transposable elements. Leptin is involved in fatty acid metabolism and body weight regulation.

Other BLAST results include sequences from the Patp database, which is a proprietary database that contains sequences published in patents and patent publications. Patp results include those listed in Table 7G.

NOV7 is expressed in at least the following tissues: Small intestine, skin, spleen, thyroid, placenta, colonl, cervix, heart, uterus, tonsil, lung, parathyroid and others, This information was derived by determining the tissue sources of the sequences that were included in the invention including but not limited to SeqCalling sources, Public EST sources, Literature sources, and/or RACE sources. Based on the tissues in which NOV7 is most highly expressed, specific uses include developing products for the diagnosis or treatment of a variety of diseases and disorders. Additional disease indications and tissue expression for NOV7 is presented in Example 2.

TABLE 7G

Patp alignments of NOV7

| Sequences producing High-scoring Segment Pairs: | % Identity | % Positive |
|---|---|---|
| patp:AAG19756 Arabidopsis thaliana protein fragment SEQ I... | 54% | 73% |
| patp:AAG19757 Arabidopsis thaliana protein fragment SEQ I . . . | 60% | 78% |
| patp:AAG19758 Arabidopsis thaliana protein fragment SEQ I . . . | 60% | 77% |
| patp:AAM60940 Streptococcus pneumoniae encoded polypeptid . . . | 32% | 51% |
| patp:AAY43986 Mouse alcohol dehydrogenase #1—Mus sp, 37 . . . | 35% | 57% |
| patp:AAY43987 Rat alcohol dehydrogenase #1—Rattus sp, 3 . . . | 35% | 57% |

The disclosed NOV7 nucleic acid encoding a novel protein includes the nucleic acid whose sequence is provided in Table 7A, or a fragment thereof. The invention also includes a mutant or variant nucleic acid any of whose bases may be changed from the corresponding base shown in Table 7A while still encoding a protein that maintains its activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 18% percent of the bases may be so changed.

The disclosed NOV7 protein of the invention includes the novel protein whose sequence is provided in Table 7B. The invention also includes a mutant or variant protein any of whose residues may be changed from the corresponding residue shown in Table 7B while still encoding a protein that maintains its activities and physiological functions, or a functional fragment thereof. In the mutant or variant protein, up to about 18% percent of the residues may be so changed.

The invention further encompasses antibodies and antibody fragments, such as $F_{ab}$ or $(F_{ab})_2$, that bind immuno-specifically to any of the proteins of the invention.

The NOV7 nucleic acids and proteins of the invention are useful in potential therapeutic applications implicated in cancer including but not limited to breast cancer, ovarian cancer, and/or other pathologies and disorders. For example, a cDNA encoding the novel protein (NOV7) may be useful in cancer therapy, and the novel protein (NOV7) may be useful when administered to a subject in need thereof. By way of nonlimiting example, the compositions of the present invention will have efficacy for treatment of patients suffering from cancer including but not limited to breast and ovarian cancer. The NOV7 nucleic acid encoding novel protein, of the invention, or fragments thereof, may further be useful in diagnostic applications, wherein the presence or amount of the nucleic acid or the protein are to be assessed.

NOV7 nucleic acids and polypeptides are further useful in the generation of antibodies that bind immuno-specifically to the novel NOV7 substances for use in therapeutic or diagnostic methods. These antibodies may be generated according to methods known in the art, using prediction from hydrophobicity charts, as described in the "Anti-NOVX Antibodies" section below. The disclosed NOV7 protein has multiple hydrophilic regions, each of which can be used as an immunogen. In one embodiment, a contemplated NOV7 epitope is from about amino acids 1 to 10. In another embodiment, a NOV7 epitope is from about amino acids 20 to 25. In additional embodiments, NOV7 epitopes are from about amino acids 35 to 55, and from about amino acids 60 to 75. These novel proteins can be used in assay systems for functional analysis of various human disorders, which will help in understanding of pathology of the disease and development of new drug targets for various disorders.

NOV8

A disclosed NOV8 nucleic acid of 4204 nucleotides (also referred to as 24SC714) encoding a novel secreted protein is shown in Table 8A. An open reading frame was identified beginning with an ATG initiation codon at nucleotides 1911–1913 and ending with a TGA codon at nucleotides 2181–2183. A putative untranslated region upstream from the initiation codon and downstream from the termination codon is underlined in Table 8A, and the start and stop codons are in bold letters.

TABLE 8A

NOV8 nucleotide sequence.

(SEQ ID NO:50)

TTTTTGGAATATAAGTAGGGGGTTTATTTGGGCCAGTCTTGAGGATTGAAACTTCAAAGCACAGATTAAAGTTATCCTGAAT

ATGTAGTCCGGTCCCACCAGCAACAGTTACAAATGGATTTTTAAAGGAAATAAAAGAAAAGGCAGTTCCTAAGTTGTTTAGC

AATAATTAACATATGAAAATAACATAAGCTATTGATCTGGCTATATGTTGTTCTTTGTTTCCTAAATTACAAGAAACGAAAG

ATAATGGGTGAGGCAGCTAGTTAGGAACTAAATGCTTTTAAACAATTCCCCCCACCCCCCACCCGTGTGGGTCCTGTGAGGG

AGTGGGAGCATGACTGAAGTCCCATACTCACGCTGGCCCTGATCAAGTTTTCATACCTCACATAGCTCAGCCTGCTCTGAGT

TGATTCTTTTTTATTGCTTTGATTCATGTGGAGTTGACACTGCATTCTGAAGCCAAGTGGAGTTTCTCATTACTTTTGCCCA

ACAAAGCAGGAGAGACTTCAAATAAGGGTCCAGAATTCTTACACTGAAGAAGAAAATTTTTCCACTGTCTCTAACCTTCCTC

TCTTCCACTCATAATCTTACCCTCATCTCTGCTTCTCTCTGCTAAATATGAACTGCCACACCCACCTAAGCTTTGCCTTCTC

CTTCATGCTATAAATGTTCCTTGTCACTCCAATGCTTTGACAGAAGGCCAGAGGACATTGGGTTCAGGACCAGAGTCTTCAC

CCTGCAGGTTTTGATGGAATTTGAGCAGAATCCAGCATGGTTCATCCCTGTCAGGTCTGGATGGCACTGAGTTATCACTACA

AGCAAATGCAAATCCAGCCATTCAGATGTCAGAAAGGCCTTCGCAAATTTGCCTTTCTATTTCAGATTCCCGGGAAGGTGAC

TGTTCTCTTCTCAAGTTAGAAGATTTCAGGTCAGAGGCCAGAATATGGGAGGAATGCCTGTCTCTGCAAACCCACATGGCTC

TGGATTAGTTGGGACGGGACCCCAAGGTCATGGTGAGGAACAAACTGTACTCTTCAGCCAAAGTGTGGCGCTCACTCTGCAG

AGGTCCCTATAAAATAATAAGCTTCCTTTTGGCATCTGGATATTTTCTGCCCCTGCTTGAGCCCATGGATTTCAGAAAGACC

TABLE 8A-continued

NOV8 nucleotide sequence.

TAACTGTTGGCTTACAACAGTCCAGCATCTGGGTCAAAAAAGGGGAACTCTAGGCTAGCGGTCCTCAATGTATGGTCTGCAG

GACAAGTTGCATCAGCATCATATGGGAACTGGTTAGAAACTCAAATTAATGAGCTCTGCCTTAGAACTACAGAACCAAAAAC

TATCAGGGTAGAGTTCAGCAATCAGTGTTTTAACATGATGCCTTAGGTGAGTCTGATGCAAGCTCAAGTTTCAGAAATACCA

CTCTTAAGTCTAAGAAGATGAAGGTTCTAGGACTTCAAAGTACTCTAATGCTTCTCCTATGGTAGAGCTAGCAGGAGTTCAT

TTATTATTCGTCCAGATGCTGATTATGCAGTTCCAGGAATTTGAGTCAATGCCAGAGCAGTTGAGGTAGAGCAAGGAGGAAT

AACAAAAATGCTAGGATATCGTGGTGTTCTGAGACAGGTGAGCTTTTCGGAGCCTCCCAACTTGTCCCCTAGTGCTTAAAAT

TTGGCACAGATGCTACCATCAGCCATGACATGGATAGAGGAGACTCTCCCCTTTATGCTGATGTATACACCAAAACGAGTCA

CAGAAAAAGCAGGCTTCCAAGATTTTTCAGCTCCCGTTGTTCCAATCATCTTCTATGATTCTGTCTCCTAGACCTGTAGCCT

TAAAGCAAGCTTATTTAAAATAAATCTGCCAGTCTGTTTCAAAGAGATTTGTTCTCCTAAATTTGTCCCAGACTGAAAACTG

CACACGTCCAAAGTTTAAGAGGTTATGTTAGGAGAAATTGAACATTATGTTTTCCTACTGCTACTTAAATTTCCAGAGGCAT

TTACAAAAATTAAACATCAATGGGAAGCCAAGTCCTTTATGAAGCTAGCAATAGACATTGATCCTGTGATAATGTTATTATT

TTTCTTATTGCTCTTGTCAGTATGCATTTCATCATCGCTGGGTTGGATGAGTATAGGGCAGCATGGGAAAACAATGTTTATT

GACTTGCAGTTTCTAGGTGCTTTAAAAAAAGTTATGCACAGGTACATATGAGCATATTAAAGCTCTTAATTTGTGTTTCTAA

TAATTTCTTCTTGAATCTCTAAAATTATGACACTACGATTAGCATTTTATTACCACATGTACAATCTATCCAGTCACCTTGA

AGTTAGATTAGATGGCATTCAAGTCACTCAGCACAGGTGAGTCAGACGGACTTTTGACCTCTCTGTAAAATAGGAAAATAAA

GACAGTGACTTTATTTATAAGAAAAATGAACTTGGCCAACAACATTAGAGAATGCTTACTCATTCTGTACCTAGACACAGAG

GAGCTTGGAACAGACCAGGAGAAATGAGACCATTATATACCCTATAATTACAACTTGTCTAATTGATCCAAGGGGAAGCAGA

GAAAGTTAACTGTAGGGCAGCAAGATGTAAACTTGGGAAGTCAGATAAGAATGGACCTTGAAAGGGACCTTGAAAGGTATGC

AGGGGGCCTGGGCACAACTGCCAAGCATAATCAGACACTGTGTGAGAAGAGGAAGTAAGTCTAGTCCCAATCACTTAATAAG

TACAGATCTCTTAGGAAGAGGCTCTGGTACAGTATCCTTCCCCCGTCTTAAAGGGACATGGAGTCTCAGCCTCCCAGCAGGA

ATGTCTAGAGAAAAAGTATCTAGCTAATTTTGTGGGCAGGGGTGAGGGAAGGAGAAATATTGTCTGGCTTAGTAAGAGTGTG

GTCTCCACAGTAACACAGATCCCTGATGTGACATTTGAGGCAGCATCCTTTCTGTGTCAAGACTGGTTCCTCCTCCTGCATT

CTGGATCCCTTCCCTGGTGTCTTTTCAGGGCATCAATTACCCCATCTCTCTCTTATCTAGTCAACCCTTTCCTCGCAATCTT

CCCCAAAACACTTAAACAGGCTCAAGCTTTCCCCACCTTAAAAATATCTTCCCTCTACCCCACACTTCCTGCAGCTACAGCA

CTCTCTCCTCCTCCTCACACCCAAAGTTTTCCAGAAAATTATCCATCCTTGCCATCTCCATATGCTCCCCTCCCACTCCTCA

ATTCACCTCGCTCTGTCTTCCACTCCTGTCACAGGCTTTAAAAAGCCACTGCAATCATTAGGTGACCTGTCTATTGCCAAAG

TCTCAGGACATTTTCAATTCTACCTTACTTGAAACCTCCGCAGTGTGAAGGTCACTCCTTCCATCTATGCTCCTTCCTGGGT

TCTTGGGGCTCCACAATCTCCTGGGCTTCCTCCTACCCACCTGCCTGCTTATTCATTTATTCTGCAGGCTCCTTCTCCCTAC

CCGACATGCCAGAGTTCCTACAAGCTTCAGGAGTCGTCCTTGACTTCTCCCTCTTCCTCACCACTCTCCAATCCAAAACATC

ACCAAATCTTGTTAATTTGGGTCCTTTGGTATTTGTTTATTCTGTCGGTTTTTTCTGTCTTCACTCCTCTCATTCTCTAAG

AGCTGCTATAGCCTCCTTCACAACAAAGAGAGAGCTGCCTAAAGTCACCCAGCTAATGAATGATGACTAGGAGTGGTTCC

CAGATATTTTATCCCTTACTGCTGTGGAGGTTCCTCATCACCCTAATAGAATCACTCTTTATTCACAAAAGTAGAAAATTAA

TTTTGGATACATCATTTATTATCAAGATGTTGTTGAGGAAAAATAGGGTCATGTAAGGTGCCTCTCAGCATCTTCCTTCAAG

TTGCAAGAATTAGAAAAACAGAGACAAGATTCTATGTGTGTCCTCAGAAGACCTTCCTGAGGACCATTCCCCTAGGAACTTA

AAAAAATTAAGCCTCCAACTCTTTCCATCTTAACTGTGTAACAGAGGAAGGTGATGACAAGAGGAAGGAGACAAGCAAGAGT

CAGACTTCGAAGGCTTGGCAGCCACTGTCAGCAAGAGGTGAGAACAGCAGACAAGACAGCAACACTCCTGAAATAATCAATC

CATACGGACTGCCATGTGAAATGTGGAGCAGACTAGTTCTAAATGGCTCCAGGAGGCAAAATAAGACTCAAGAGAAGTTACT

GGTAGATTTCAACCCAATGTGA

The NOV8 nucleic acid was identified on chromosome 3 by comparing a NOV8 nucleic acid to the human genome. Exons were predicted by homology and the intron/exon boundaries were determined using standard genetic rules. Exons were further selected and refined by means of similarity determination using multiple BLAST (for example, tBlastN, BlastX, and BlastN) searches, and, in some instances, GeneScan and Grail. Expressed sequences from both public and proprietary databases were also added when available to further define and complete the gene sequence. The DNA sequence was then manually corrected for apparent inconsistencies thereby obtaining the sequences encoding the full-length protein. The NOV8 nucleic acid was further localized to the 3p22 region, a locus associated with cancer, e.g. esophageal (OMIM 604050), hepatoblastoma (OMIM 116806), lung (OMIM 604050), and ovarian carcinoma (OMIM 116806), and psuedo-Zellweger syndrome (OMIM 604054). NOV8 is useful as a marker for these diseases.

A disclosed NOV8 polypeptide (SEQ ID NO:51) encoded by SEQ ID NO:50 has 90 amino acid residues and is presented in Table 8B using the one-letter amino acid code. SignalP, Psort and/or Hydropathy results predict that NOV8 has a signal peptide and is likely to be secreted with a certainty of 0.8200. The most likely cleavage site for a NOV8 peptide is between amino acids 61 and 62, at SLG-WM. NOV8 has a molecular weight of 10,474.6 Daltons.

transport system permease protein SAPB (prdm:35160, Expect=1.1). Table 8C lists the domain description from DOMAIN analysis results against NOV8. This indicates that the NOV8 sequence has properties similar to those of other proteins known to contain this domain.

TABLE 8C

Domain Analysis of NOV8

ProDom Protein Domain Analysis

| Sequences producing High-scoring Segment Pairs: | High Score | Smallest Sum Probability P (N) |
|---|---|---|
| prdm: 2196 p36 (12) ATCD (5) ATCE (4) ATCB (2) - CALCIUM R . . . | 52 | 0.30 |
| prdm: 57835 p36 (1) YJK9__YEAST - HYPOTHETICAL 200.0 KD PR . . . | 68 | 0.30 |
| prdm: 15250 p36 (2) G49 (1) G49B (1) - GLYCOPROTEIN MAST . . . | 50 | 0.44 |
| prdm: 47898 p36 (1) WNT1__CAEEL - WNT-1 PROTEIN PRECURSOR . . . | 50 | 0.44 |
| prdm: 35160 p36 (1) SAP3__HAEIN - PEPTIDE TRANSPORT SYSTEM . . . | 55 | 0.66 |

TABLE 8B

Encoded NOV8 protein sequence.

(SEQ ID NO:51)
MLGEIEHYVFLLLLKFPEAFTKIKHQWEAKSFMKLAIDIDPVIMLLFFLLLLSVCISSSLGWMSIGQHGKTMFIDLQFLGAL

KKVMHRYI

The presence of identifiable domains in NOV8, as well as all other NOVX proteins, was determined by searches using software algorithms such as PROSITE, DOMAIN, Blocks, Pfam, ProDomain, and Prints, and then determining the Interpro number by crossing the domain match (or numbers) using the Interpro website (maintained by the European Bioinformatics Institute, Hinxton, Cambridge, UK). DOMAIN results for NOV8 as disclosed in Tables 1E, were collected from the Conserved Domain Database (CDD) with Reverse Position Specific BLAST analyses. This BLAST analysis software samples domains found in the Smart and Pfam collections.

Prodom domain analysis of the NOV8 polypeptide indicates that the NOV8 polypeptide has 11 of 23 (47%) identical to, and 14 of 23 (60%) positive with, the 40 aa p36 (12) ATC ATCE(4) ATCB(2)—calcium reticulum calcium-transporting ATPase type hydrolase transport transmembrane endoplasmic class (prdm:2196, Expect=0.36); 28 of 84 (33%) identical to, and 38 of 84 (45%) positive with, the 1769 aa p36 (1) YJK9__YEAST—hypothetical 200.0 kD protein in GZF3-SMEI intergenic region, hypothetical protein (prdm:57835, Expect=0.36); 11 of 32 (34%) identical to, and 18 of 32 (56%) positive with, the 68 aa p36 (2) G49(1) G49B(1)—glycoprotein mast cell surface precursor signal transmembrane imminoglobulin fold GP49A (prdm:15250, Expect=0.58); 9 of 23 (39%) identical to, and 17 of 23 (73%) positive with, the 41 aa p36 (1) WNT1__CAEEL—WNT-1 protein precursor (prdm:47898, Expect= 0.58); and 15 of 46 (32%) identical to, and 26 of 46 (56%) positive with, the 89 aa p36 (1) SAPB__HAEIN—peptide TABLE 8C-continued Domain Analysis of NOV8

BLOCKS Protein Domain Analysis

| AC# | | Description | Strength | Score |
|---|---|---|---|---|
| BL00456D | 0 | Sodium: solute symporter family proteins. | 1174 | 1038 |
| BL01271B | 0 | Sodium: sulfate symporter family proteins. | 1480 | 1033 |
| BL00790A | 0 | Receptor tyrosine kinase class V proteins. | 1390 | 1031 |
| BL00284A | 0 | Serpins proteins. | 1308 | 1029 |
| BL01313A | 0 | Lipoate-protein ligase B proteins. | 1390 | 1018 |

PROSITE - Protein Domain Analysis

Protein Domain Matches for Gene ID: NOV08
No PROSITE patterns found

In a search of public sequence databases, the NOV8 amino acid sequence had no hits with the Expect value set at 1.0. Public amino acid databases include the GenBank databases, SwissProt, PDB and PIR.

Other BLAST results include sequences from the Patp database, which is a proprietary database that contains sequences published in patents and patent publications. BLASTP analysis again the NOV8 protein shows that the NOV8 protein has 18 of 28 aa residues (64%) identical to, and 18 of 28 aa residues (64%) positive with, the 78 aa Zea mays protein fragment SEQ ID NO: 30302 of patent EP1033405-A2 (patp: AAG26008, Expect=0.097);14 of 30 aa residues (46%) identical to, and 16 of 30 aa residues (53%) positive with, the 51 aa Human secreted protein sequence encoded by gene 65 SEQ ID NO: 188 (patp:AAY91515, Expect=0.50); 14 of 30 aa residues (46%) identical to, and 16 of 30 aa residues (53%) positive with, the 50 aa Human secreted protein sequence encoded by gene 65 SEQ ID NO:329 (patp:AAY91656, Expect=0.50); 21 of 64 aa residues (32%) identical to, and 32 of 64 aa residues (50%) positive with, the 997 aa Human shear stress-response protein SEQ ID NO: 28 (patp:AAB90764, Expect= 0.91); 13 of 31 aa residues (41%) identical to, and 19 of 31 aa residues (61%) positive with, the 52 aa Gene 9 human secreted protein homologous amino acid sequence #123—*Chlorella vulgaris* (patp:AAB34919, Expect=1.0); and 14 of 43 aa residues (32%) identical to, and 22 of 43 aa residues (51%) positive with, the 46 aa Human secreted protein sequence encoded by gene 4 SEQ ID NO:64 (patp:AAB34580, Expect=2.7). Patp results include those listed in Table 8D.

corresponding residue shown in Table 8B while still encoding a protein that maintains its secreted protein-like activities and physiological functions, or a functional fragment thereof.

The invention further encompasses antibodies and antibody fragments, such as $F_{ab}$ or $(F_{ab})_2$, that bind immuno-specifically to any of the proteins of the invention.

The above defined information for this invention suggests that this secreted protein-like protein (NOV8) may function as a member of a secreted protein family. Therefore, the NOV8 nucleic acids and proteins identified here may be useful in potential therapeutic applications implicated in (but not limited to) various pathologies and disorders as indicated below. The potential therapeutic applications for this invention include, but are not limited to: cancer research tools, for all tissues and cell types composing (but not limited to) those defined here, including esophagus, liver, lung and ovary.

The NOV8 nucleic acids and proteins of the invention are useful in potential therapeutic applications implicated in cancer including but not limited to esophageal, liver, lung

TABLE 8D

Patp alignments of NOV8

| Sequences producing High-scoring Segment Pairs: | High Score | Smallest Sum Prob. P(N) |
|---|---|---|
| patp:AAY91515 Human secreted protein sequence encoded by . . . | 59 | 0.39 |
| patp:AAY91656 Human secreted protein sequence encoded by . . . | 59 | 0.39 |
| patp:AAB90764 Human shear stress-response protein SEQ ID . . . | 70 | 0.60 |
| patp:AAB34919 Gene 9 human secreted protein homologous am . . . | 56 | 0.64 |
| patp:AAB34580 Human secreted protein sequence encoded by . . . | 52 | 0.93 |

The NOV8 protein domain information and chromosomal mapping suggest that NOV8 is a cancer-associated secreted protein. As such, it is useful as a diagnostic tool for the onset and or progression of cancer, such as esophageal, hepatoblastoma, lung, and ovarian carcinoma.

The disclosed NOV8 nucleic acid encoding a secreted protein includes the nucleic acid whose sequence is provided in Table 8A, or a fragment thereof. The invention also includes a mutant or variant nucleic acid any of whose bases may be changed from the corresponding base shown in Table 8A while still encoding a protein that maintains its secreted protein-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

The disclosed NOV8 protein of the invention includes the secreted protein-like protein whose sequence is provided in Table 8B. The invention also includes a mutant or variant protein any of whose residues may be changed from the and ovary and/or other pathologies and disorders. For example, a cDNA encoding the secreted protein-like protein (NOV8) may be useful in cancer therapy, and the secreted protein-like protein (NOV8) may be useful when administered to a subject in need thereof. By way of nonlimiting example, the compositions of the present invention will have efficacy for treatment of patients suffering from cancer including but not limited to esophageal, hepatic, lung and ovarian cancer. The NOV8 nucleic acid encoding secreted protein-like protein, and the secreted protein-like protein of the invention, or fragments thereof, may further be useful in diagnostic applications, wherein the presence or amount of the nucleic acid or the protein are to be assessed.

NOV8 nucleic acids and polypeptides are further useful in the generation of antibodies that bind immuno-specifically to the novel NOV8 substances for use in therapeutic or diagnostic methods. These antibodies may be generated according to methods known in the art, using prediction from hydrophobicity charts as described in the "Anti-NOVX Antibodies" section below. The disclosed NOV8 protein has multiple hydrophilic regions, each of which can be used as an immunogen. In one embodiment, a contemplated NOV8 epitope is from about amino acids 1 to 30 In another embodiment, a NOV8 epitope is from about amino acids 18 to 35. In additional embodiments, NOV8 epitopes are from about amino acids 65 to 90. These novel proteins can be used in assay systems for functional analysis of various human disorders, which will help in understanding of pathology of the disease and development of new drug targets for various disorders.

NOV9

A disclosed NOV9 nucleic acid of 3111 nucleotides (also referred to as 6CS060) encoding a novel Kelch-like protein is shown in Table 9A. An open reading frame was identified beginning with an ATG initiation codon at nucleotides 1–3 and ending with a TAA codon at nucleotides 1708–1710. A putative untranslated region downstream from the termination codon is underlined in Table 9A, and the start and stop codons are in bold letters.

TABLE 9A

NOV9 nucleotide sequence.

(SEQ ID NO:52)

ATGAATGCCACCAGATCTGAAGAGCAGTTCCATGTTATAAACCACGCAGAGCAAACTCTTCGTAAAATGGAGAACTACTTG

AAAGAGAAACAACTATGTCATGTGCTACTGATTGCAGGACACCTCCGCATCCCAGCCCATAGGTTGGTTCTCAGCGCAGTG

TCTGATTATTTTGCTGCAATGTTTACTAATGATGTGCTTGAAGCCAAACAAGAAGAGGTCAGGATGGAAGGAGTAGATCCA

AATGCACTAAATTCCTTGGTGCAGTATGCTTACACAGGAGTCCTGCAATTGAAAGAAGATACCATTGAAAGTTTGCTGGCT

GCAGCTTGTCTTCTGCAGCTGACTCAGGTCATTGATGTTTGCTCCAATTTTCTCATAAAGCAGCTCCATCCTTCAAACTGC

TTAGGGATTCGATCATTTGGAGATGCCCAAGGCTGTACAGAACTTCTGAACGTGGCACACAAATACACTATGGAACACTTC

ATTGAGGTAATAAAAAACCAAGAATTCCTCCTGCTTCCAGCTAATGAAATTTCAAAACTTCTGTGCAGTGATGACATTAAT

GTGCCTGATGAAGAGACCATTTTTCATGCTCTAATGCAGTGGGTGGGGCATGATGTGCAGAATAGGCAAGGAGAACTGGGG

ATGCTGCTTTCTTACATCAGACTGCCATTACTCCCACCACAGTTACTGGCAGATCTTGAAACCAGTTCCATGTTTACTGGT

GATCTTGAGTGTCAGAAGCTCCTGATGGAAGCTATGAAGTATCATCTTTTGCCTGAGAGAAGATCCATGATGCAAAGCCCT

CGGACAAAGCCTAGAAAATCAACTGTGGGGGCACTTTATGCTGTAGGAGGCATGGATGCTATGAAAGGTACTACTACTATT

GAAAAATATGACCTCAGGACCAACAGTTGGCTACATATTGGCACCATGAATGGCCGTAGGCTTCAATTTGGAGTCGCAGTT

ATTGATAATAAGCTCTATGTCGTGGGAGGAAGAGACGGTTTAAAAACTTTGAATACAGTGGAATGTTTTAATCCAGTTGGC

AAAATCTGGACTGTGATGCCTCCCATGTCAACACATCGGCACGGCTTAGGTGTAGCCACTCTTGAAGGACCAATGTATGCT

GTAGGTGGTCATGATGGATGGAGCTATCTAAATACTGTAGAAAGATGGGACCCTGAGGGACGACAGTGGAATTACGTAGCC

AGTATGTCAACTCCTAGAAGCACAGTTGGTGTTGTTGCATTAAACAACAAATTATATGCTATTGGTGGACGTGATGGAAGT

TCCTGCCTCAAATCAATGGAATACTTTGACCCACACACTAACAAGTGGAGTTTGTGTGCTCCAATGTCCAAAAGACGTGGA

GGTGTGGGAGTTGCCACATACAATGGATTCTTATATGTTGTAGGGGGGCATGATGCCCCTGCTTCCAACCATTGCTCCAGG

CTTTCTGACTGTGTGGAACGGTATGATCCAAAAGGTGATTCATGGTCAACTGTGGCACCTCTGAGTGTTCCTCGAGATGCT

GTTGCTGTGTGCCCTCTTGGAGACAAACTCTACGTGGTTGGAGGATATGACGGACATACTTATTTGAACACAGTTGAGTCA

TATGATGCACAGAGAAATGAATGGAAAGAGGAAGTTCCTGTTAACATTGGAAGAGCTGGTGCATGTGTTGTAGTGGTGAAG

CTACCCTAAAGCTATCTATCTTTATCAAATGGAATGAAACTAGATAATTTCAAGAAACTGAGTAGGACAAAGGGAGAAAGA

AATACATGTTCTTTTTCCTGCAATTAATAATCAGACTGGAAAATTGTTGTATCATTTTAATTTGTAGTTACAATTGCTTTC

ATTCGTGAAGCCGAAACGTTTTTAAACATGAATTACATATGAATTATTAAGCATATGTGCTTTCGCAGCTGATAATATAAA

AGGAAATCCCACAGTCTAGATATAGCCCCATTACTACAAAATGCTAAAATATTTAATGAAAATTGATGGTGGCCACAGTGT

GCAGGTTATAAAAGCATTAATACATTTCAAGGTAAGAGCCTTAAAAGTTAAAAACATTTTCAGTTTTTTTTAAAAAACGT

ACTCTTATTATCTGGAACATAGAAATATAAAAGGTAACATCTAAAGCTTAGAATAGTGTGATTTTTAGTAAGCCATTATTC

TCCTATTCAAATAATATCCCAAAGAGCTAAACAATTCCTTACATTTACCAAGAGGAAAGCTTTTACTGTGTTGAAGCTAAA

AAAATAATGGCTCTTTGACAAAACTTGTTATGTTGATCGCGGTATGTCAAAATTTTTACAGGTTTGCTCATCTGCCAGAGC

ACACATATAAATTTGGTATTTCTTAACATATTATCTTGTTAGATTTGTTACCAGTAAAATATTACTGTAATTTCATATACA

CAGTCTATACAATGAAATAATGAATATTTATCATATTGATACAAACTGTGACCTCAGCTTCAGAGTGTCAGGGCCTCACTT

GTATAGAATGTAATGTTCTCCTCAAACATTTATGTTAACTCTATAAACAAATATCGTTAAGTTAAACAAGTTTTCAAAAAC

AAAACAATTTTTAAAGTACCTTAAAATTGAGGATGTTACTCAGTGTTAACACATGGGAACACCAAAATATTCAATAAGCCT

GGTCAATTCTATAGTTATCTTTTTTGTACCAACACATGCTTTTCTGTTACTGTTATATTATCCAGTAGAAAATGTTAGGAT

ATGTGTGCTATATAAAAAAAAAAAAGACTTGTTAAGTTTTAAAATAACAAAAAATGGCTAGTTGAATAGTATTTTATGTGT

TABLE 9A-continued

NOV9 nucleotide sequence.

AATTCTTCCATTTATTCTGTTTAATTATACAACTAAGATGAAATATTGAAAAACCCTTTGTGAAAGTAACTTTTCAAGTAA

ATGCACAACTTTAGAATTTCTACAAATAAGTTCTTTTAAACAGTCTTTTTATTGTGGATTGTGAAATCAAAATCTGGAGAA

ATGCTTATAAAATATACTACTAGCTTTTAAGTTTTAAGAAAGAAGAACGTAAGTTGTACAAAGATATTTGTACTTTGACAA

ACTGAATTTAAATAAACTTTATTTCCTCTCAAA

The NOV9 nucleic acid was identified on the human X chromosome by comparing the NOV9 nucleic acid to the human genome. Exons were predicted by homology and the intron/exon boundaries were determined using standard genetic rules. Exons were further selected and refined by means of similarity determination using multiple BLAST (for example, tBlastN, BlastX, and BlastN) searches, and, in some instances, GeneScan and Grail. Expressed sequences from both public and proprietary databases were also added when available to further define and complete the gene sequence. The DNA sequence was then manually corrected for apparent inconsistencies thereby obtaining the sequences encoding the full-length protein. The NOV9 nucleic acid was further mapped to the q13 region of the X chromosome. This locus is associated with Menkes disease (OMIM 300011), myoglobinuria/hemlolysis due to PGK deficiency (OMIM 311800), Wieacker-Wolff syndrome (OMIM 314580) and/or other diseases/disorders. NOV9 is a useful marker for these and/or other diseases/disorders.

In a search of public sequence databases, the NOV9 nucleic acid sequence has 2751 of 2767 bases (99%) identical to a human Kelch-4 cDN (Accession No. XM039746). Public nucleotide databases include all GenBank databases and the GeneSeq patent database.

A disclosed NOV9 polypeptide (SEQ ID NO:53) encoded by SEQ ID NO:52 has 569 amino acid residues and is presented in Table 9B using the one-letter amino acid code. SignalP, Psort and/or Hydropathy results predict that NOV9 does not contain a known signal peptide and is likely to be localized endoplasmic reticulum (membrane with a certainty of 0.6000. In alternative embodiments, the NOV9 protein is localized to a microbody (peroxisome) with a certainty of 0.3000; the mitochondrial inner membrane with a certainty of 0.1000; or the plasma membrane with a certainty of 0.1000. NOV9 has a molecular weight of 63292.0 Daltons.

TABLE 9B

Encoded NOV9 protein sequence.

(SEQ ID NO:53)
MNATRSEEQFHVINHAEQTLRKMENYLKEKQLCDVLLIAGHLRIPAHRLVLSAVSDYFAAMFTNDVLEAKQEEVRMEGVDP

NALNSLVQYAYTGVLQLKEDTIESLLAAACLLQLTQVIDVCSNFLIKQLHPSNCLGIRSFGDAQGCTELLNVAHKYTMEHF

IEVIKNQEFLLLPANEISKLLCSDDINVPDEETIFHALMQWVGHDVQNRQGELGMLLSYIRLPLLPPQLLADLETSSMFTG

DLECQKLLMEAMKYHLLPERRSMMQSPRTKPRKSTVGALYAVGGMDAMKGTTTIEKYDLRTNSWLHIGTMNGRRLQFGVAV

IDNKLYVVGGRDGLKTLNTVECFNPVGKIWTVMPPMSTHRHGLGVATLEGPMYAVGGHDGWSYLNTVERWDPEGRQWNYVA

SMSTPRSTVGVVALNNKLYAIGGRDGSSCLKSMEYFDPHTNKWSLCAPMSKRRGGVGVATYNGFLYVVGGHDAPASNHCSR

LSDCVERYDPKGDSWSTVAPLSVPRDAVAVCPLGDKLYVVGGYDGHTYLNTVESYDAQRNEWKEEVPVNIGRAGACVVVVK

LP

The reverse complement for NOV9 is presented in Table 9C.

TABLE 9C

NOV9 reverse complement (SEQ ID NO:54)
TTTGAGAGGAAATAAAGTTTATTTAAATTCAGTTTGTCAAAGTACAAATATCTTTGTACAACTTACGTTCTTCTTTCTTAA AACTTAAAAGCTAGTAGTATATTTTATAAGCATTTCTCCAGATTTTGATTTCACAATCCACAATAAAAAGACTGTTTAAAA GAACTTATTTGTAGAAATTCTAAAGTTGTGCATTTACTTGAAAAGTTACTTTCACAAAGGGTTTTTCAATATTTCATCTTA GTTGTATAATTAAACAGAATAAATGGAAGAATTACACATAAAATACTATTCAACTAGCCATTTTTGTTATTTTAAAACTTA ACAAGTCTTTTTTTTTTTTTATATAGCACACATATCCTAACATTTTCTACTGGATAATATAACAGTAACAGAAAAGCATGT

TABLE 9C-continued

NOV9 reverse complement

```
GTTGGTACAAAAAAGATAACTATAGAATTGACCAGGCTTATTGAATATTTTGGTGTTCCCATGTGTTAACACTGAGTAACA
TCCTCAATTTTAAGGTACTTTAAAAATTGTTTTGTTTTTGAAAACTTGTTTAACTTAACGATATTTGTTTATAGAGTTAAC
ATAAATGTTTGAGGAGAACATTACATTCTATACAAGTGAGGCCCTGACACTCTGAAGCTGAGGTCACAGTTTGTATCAATA
TGATAAATATTCATTATTTCATTGTATAGACTGTGTATATGAAATTACAGTAATATTTTACTGGTAACAAATCTAACAAGA
TAATATGTTAAGAAATACCAAATTTATATGTGTGCTCTGGCAGATGAGCAAACCTGTAAAAATTTTGACATACCGCGATCA
ACATAACAAGTTTTGTCAAAGAGCCATTATTTTTTTAGCTTCAACACAGTAAAAGCTTTCCTCTTGGTAAATGTAAGGAAT
TGTTTAGCTCTTTGGGATATTATTTGAATAGGAGAATAATGGCTTACTAAAAATCACACTATTCTAAGCTTTAGATGTTAC
CTTTTATATTTCTATGTTCCAGATAATAAGAGTACGTTTTTTAAAAAAAAACTGAAAATGTTTTTAACTTTTAAGGCTCTT
ACCTTGAAATGTATTAATGCTTTTATAACCTGCACACTGTGGCCACCATCAATTTTCATTAAATATTTTAGCATTTTGTAG
TAATGGGCTATATCTAGACTGTGGGATTTCCTTTTATATTATCAGCTGCGAAAGCACATATGCTTAATAATTCATATGTA
ATTCATGTTTAAAAACGTTTCGGCTTCACGAATGAAAGCAATTGTAACTACAAATTAAAATGATACAACAATTTTCCAGTC
TGATTATTAATTGCAGGAAAAAGAACATGTATTTCTTTCTCCCTTTGTCCTACTCAGTTTCTTGAAATTATCTAGTTTCAT
TCCATTTGATAAAGATAGATAGCTTTAGGGTAGCTTCACCACTACAACACATGCACCAGCTCTTCCAATGTTAACAGGAAC
TTCCTCTTTCCATTCATTTCTCTGTGCATCATATGACTCAACTGTGTTCAAATAAGTATGTCCGTCATATCCTCCAACCAC
GTAGAGTTTGTCTCCAAGAGGGCACACAGCAACAGCATCTCGAGGAACACTCAGAGGTGCCACAGTTGACCATGAATCACC
TTTTGGATCATACCGTTCCACACAGTCAGAAAGCCTGGAGCAATGGTTGGAAGCAGGGGCATCATGCCCCCCTACAACATA
TAAGAATCCATTGTATGTGGCAACTCCCACACCTCCACGTCTTTTGGACATTGGAGCACACAAACTCCACTTGTTAGTGTG
TGGGTCAAAGTATTCCATTGATTTGAGGCAGGAACTTCCATCACGTCCACCAATAGCATATAATTTGTTGTTTAATGCAAC
AACACCAACTGTGCTTCTAGGAGTTGACATACTGGCTACGTAATTCCACTGTCGTCCCTCAGGGTCCCATCTTTCTACAGT
ATTTAGATAGCTCCATCCATCATGACCACCTACAGCATACATTGGTCCTTCAAGAGTGGCTACACCTAAGCCGTGCCGATG
TGTTGACATGGGAGGCATCACAGTCCAGATTTTGCCAACTGGATTAAAACATTCCACTGTATTCAAAGTTTTTAAACCGTC
TCTTCCTCCCACGACATAGAGCTTATTATCAATAACTGCGACTCCAAATTGAAGCCTACGGCCATTCATGGTGCCAATATG
TAGCCAACTGTTGGTCCTGAGGTCATATTTTTCAATAGTAGTAGTACCTTTCATAGCATCCATGCCTCCTACAGCATAAAG
TGCCCCCACAGTTGATTTTCTAGGCTTTGTCCGAGGGCTTTGCATCATGGATCTTCTCTCAGGCAAAAGATGATACTTCAT
AGCTTCCATCAGGAGCTTCTGACACTCAAGATCACCAGTAAACATGGAACTGGTTTCAAGATCTGCCAGTAACTGTGGTGG
GAGTAATGGCAGTCTGATGTAAGAAAGCAGCATCCCCAGTTCTCCTTGCCTATTCTGCACATCATGCCCCACCCACTGCAT
TAGAGCATGAAAAATGGTCTCTTCATCAGGCACATTAATGTCATCACTGCACAGAAGTTTTGAAATTTCATTAGCTGGAAG
CAGGAGGAATTCTTGGTTTTTTATTACCTCAATGAAGTGTTCCATAGTGTATTTGTGTGCCACGTTCAGAAGTTCTGTACA
GCCTTGGGCATCTCCAAATGATCGAATCCCTAAGCAGTTTGAAGGATGGAGCTGCTTTATGAGAAAATTGGAGCAAACATC
AATGACCTGAGTCAGCTGCAGAAGACAAGCTGCAGCCAGCAAACTTTCAATGGTATCTTCTTTCAATTGCAGGACTCCTGT
GTAAGCATACTGCACCAAGGAATTTAGTGCATTTGGATCTACTCCTTCCATCCTGACCTCTTCTTGTTTGGCTTCAAGCAC
ATCATTAGTAAACATTGCAGCAAAATAATCAGACACTGCGCTGAGAACCAACCTATGGGCTGGGATGCGGAGGTGTCCTGC
AATCAGTAGCACATCACATAGTTGTTTCTCTTTCAAGTAGTTCTCCATTTTACGAAGAGTTTGCTCTGCGTGGTTTATAAC
ATGGAACTGCTCTTCAGATCTGGTGGCATTCAT
```

In a search of public sequence databases, the NOV9 amino acid sequence has 431 of 569 amino acid residues (76%) identical to, and 500 of 569 residues (88%) positive with, the 569 amino acid residue human Kelch-like protein-1. Public amino acid databases include the GenBank databases, SwissProt, PDB and PIR.

It was also found that NOV9 had homology to the amino acid sequences shown in the BLASTP data listed in Table 9D.

TABLE 9D

BLAST results for NOV9

| Gene Index/ Identifier | Protein/Organism | Length (aa) | Identity (%) | Positives (%) | Expect |
|---|---|---|---|---|---|
| Q9C0H6; AB051474; BAB21778.1 | KIAA1687 PROTEIN (FRAGMENT). homo sapiens. 6/2001 | 728 | 569/569 (100%) | 569/569, (100%) | 0.0 |
| Q9Y3J5; AL035424; CAB39994.1 | DA22012.1. homo sapiens. 6/2001 | 569 | 569/569 (100%) | 569/569, (100%) | 0.0 |
| KHL1_HUMAN; AF252283; AAF81719.1 | KELCH-LIKE PROTEIN 1. homo sapiens. 10/2000 | 748 | 431/569 (76%) | 500/569, (88%) | 0.0 |
| KHL1_MOUSE; AF252281; AAF81717.1 | KELCE-LIKE PROTEIN 1. mus musculus. 10/2000 | 751 | 430/569 (76%) | 497/569, (87%) | 0.0 |
| Q9H955; AK023057; BAB14382.1 | CDNA FLJ12995 FIS, CLONE NT2RP3000233, weakly similar to ring canal protein. homo sapiens. 6/2001 | 411 | 411/411 (100%) | 411/411, (100%) | 0.0 |

A multiple sequence alignment is given in Table 9E, with the NOV9 protein of the invention being shown on lines 1 in a ClustalW analysis comparing NOV9 with related protein sequences of Table 9D.

TABLE 9E

Information for the ClustalW proteins:

1. SEQ ID NO:53, NOV9
2. SEQ ID NO:55, Q9C0H6 KIAA1687 PROTEIN (FRAGMENT). homo sapiens. 6/2001
3. SEQ ID NO:56, Q9Y3J5 DA22D12.1. homo sapiens. 6/2001
4. SEQ ID NO:57, KHL1_HUMAN KELCH-LIKE PROTEIN 1. homo sapiens. 10/2000
5. SEQ ID NO:58, KHL1_MOUSE KELCH-LIKE PROTEIN 1. mus musculus. 10/2000
6. SEQ ID NO:59, Q9H955 CDNA FLJ12995 FIS. homo sapiens. 6/2001

```
NOV9         1    EKAFVFPPATMSVSGKKEFDVKQILRLRWRWFSHP--FQGSRNRGSCLQQE----GYEHR 54
Q9C0H6       1    EKAFVFPPATMSVSGKKEFDVKQILRLRWRWFSHP--FQGSRNRGSCLQQE----GYEHR 54
Q9Y3J5       1    ------------------------------------------------------------ 1
KHL1_HUMAN   1    ---------MSGSGRKDFDVKHILRLRWKLFSHPSPSTGGPAGGGCLQQD-GSGSFEHW 49
KHL1_MOUSE   1    ---------MSGSGRKDFDVKHILRLRWKLFSHPSPASSSPAGGSCLQQDSGGGSFEHW 50
Q9H955       1    ------------------------------------------------------------ 1

NOV9         55   GTPVQGRLKSHSRD-------RNGLKKSNSPVHHNILAP----------VPGPAPAHQRA 97
Q9C0H6       55   GTPVQGRLKSHSRD-------RNGLKKSNSPVHHNILAP----------VPGPAPAHQRA 97
Q9Y3J5       1    ------------------------------------------------------------ 1
KHL1_HUMAN   50   GPSQSRLLKSQERSGVSTFWKKPSSSSSSSSSPSSSSSS--FNPLNGTLLPVATRLQQGA 107
KHL1_MOUSE   51   GPSQSRLLKNQEKGSVSAFWKKPSSSSSSSSSSSSASSSPFNPLNGRLLPVATRLQQGA 110
Q9H955       1    ------------------------------------------------------------ 1

NOV9         98   VQNLQQHNLIVHFQANEDTPKSVPEKNLFKEACEK--RAQDLEMMADDNIEDS----TAR 151
Q9C0H6       98   VQNLQQHNLIVHFQANEDTPKSVPEKNLFKEACEK--RAQDLEMMADDNIEDS----TAR 151
Q9Y3J5       1    ------------------------------------------------------------ 1
KHL1_HUMAN   108  PGQGTQQPARTLFYVESLEEEVVPGMD-FPGPQDKGLALKELQAEPASSIQATGWGCGHR 166
KHL1_MOUSE   111  PGQGTQQPARTLFQVESLEEEVVTGMD-FPGPQDKGLALKELQAEPASSIQATGEGCGHR 169
Q9H955       1    ------------------------------------------------------------ 1

NOV9         152  LD-RQHS----EDMNATRSEEQFHVINHAEQTLRKMENYLKEKQLCDVLIAGHLRIPAH 206
Q9C0H6       152  LD-TQHS----EDMNATRSEEQFHVINHAEQTLRKMENYLKEKQLCDVLIAGHLRIPAH 206
Q9Y3J5       1    -------------MNATRSEEQFHVINHAEQTLRKMENYLKEKQLCDVLIAGHLRIPAH 47
KHL1_HUMAN   167  LSSTGHSMTPQSDLLDSSSEEFYQAVHHAEQTFRKMESYLKQQQLCDVILVGNRKIPAH 226
KHL1_MOUSE   170  LTSTNHSLTPQSDLLSSSSEEFYQAVRHAEQSFRKMENYLKQQQLCDVILVGNRKIPAH 229
Q9H955       1    ------------------------------------------------------------ 1

NOV9         207  RLVLSAVSDYFAAMFTNDVLEAKQEEVRMEGVDPNAINSLVQYAYTGVLQLKEDTIESLL 266
Q9C0H6       207  RLVLSAVSDYFAAMFTNDVLEAKQEEVRMEGVDPNAINSLVQYAYTGVLQLKEDTIESLL 266
Q9Y3J5       48   RLVLSAVSDYFAAMFTNDVLEAKQEEVRMEGVDPNAINSLVQYAYTGVLQLKEDTIESLL 107
KHL1_HUMAN   227  RLVLSAVSDYFAAMFTSDVCEAKQEEIKMEGIDPNAIWDLVQFAYTGCLLKEDTIENLL 286
KHL1_MOUSE   230  RLVLSAVSDYFAAMFTSDVCEAKQEEIKMEGIDPNAIWDLVQFAYTGCLLKEDTIENLL 289
Q9H955       1    ------------------------------------------------------------ 1
```

TABLE 9E-continued

Information for the ClustalW proteins:

```
NOV9       267 AAACLLQLTQVTDVCSNFLIKQLHPSNCLGIRSFGDAQGCTELLNVAHKYTMBHFIEVIK 326
Q9C0H6     267 AAACLLQLTQVTDVCSNFLIKQLHPSNCLGIRSFGDAQGCTELLNVAHKYTMBHFIEVIK 326
Q9Y3J5     108 AAACLLQLTQVTDVCSNFLIKQLHPSNCLGIRSFGDAQGCTELLNVAHKYTMBHFIEVIK 167
KHL1_HUMAN 287 AAACLLQLPQVVEVCCHFLMKLLHPSNCLGIRAFADAQGCIELMKVAHSYTMBNIMEVIR 346
KHL1_MOUSE 290 AAACLLQLPQVVEVCCHFLMKLLHPSNCLGIRAFADAQGCIELMKVAHSYTMBNIMEVIR 349
Q9H955       1 ------------------------------------------------MBNIMEVIR 9

NOV9       327 NQEFLLLPANEISKLLCSDDINVPDEETIFHALMQWVGHDVQNRQGELGMLLSYIRLPLL 386
Q9C0H6     327 NQEFLLLPANEISKLLCSDDINVPDEETIFHALMQWVGHDVQNRQGELGMLLSYIRLPLL 386
Q9Y3J5     168 NQEFLLLPANEISKLLCSDDINVPDEETIFHALMQWVGHDVQNRQGELGMLLSYIRLPLL 227
KHL1_HUMAN 347 NQEFLLLPAEELHKLLASDDVNVPDEETIFHALMMVVKYDMQSRCNDLSMLLAFIRLPLL 406
KHL1_MOUSE 350 NQEFLLLPAEELHKLLASDDVNVPDEETIFHALMMWVKYDMQSRCNDLSMLLAFIRLPLL 409
Q9H955      10 NQEFLLLPANEISKLLCSDDINVPDEETIFHALMQWVGHDVQNRQGELGMLLSYIRLPLL 69

NOV9       387 PPQELADLETSSMFTGDLECQKLLMEAMKYHLLPERRSMMQSPRTKPRKSTVGALYAVGG 446
Q9C0H6     387 PPQELADLETSSMFTGDLECQKLLMEAMKYHLLPERRSMMQSPRTKPRKSTVGALYAVGG 446
Q9Y3J5     228 PPQELADLETSSMFTGDLECQKLLMEAMKYHLLPERRSMMQSPRTKPRKSTVGALYAVGG 287
KHL1_HUMAN 407 PPQILADLENHALTKNDLECQKLILEAMKYHLLPERRTLMQSPRTKPRKSTVGTLYAVGG 466
KHL1_MOUSE 410 PPQILADLENHALTKNDLECQKLILEAMKYHLLPERRTLMQSPRTKPRKSTVGTLYAVGG 469
Q9H955      70 PPQELADLETSSMFTGDLECQKLLMEAMKYHLLPERRSMMQSPRTKPRKSTVGALYAVGG 129

NOV9       447 MDAMKGTTTIEKYDLRTNSWLHIGTMNGRRLQFGVAVIDNKLYVVGGRDGLKTLNTVECF 506
Q9C0H6     447 MDAMKGTTTIEKYDLRTNSWLHIGTMNGRRLQFGVAVIDNKLYVVGGRDGLKTLNTVECF 506
Q9Y3J5     288 MDAMKGTTTIEKYDLRTNSWLHIGTMNGRRLQFGVAVIDNKLYVVGGRDGLKTLNTVECF 347
KHL1_HUMAN 467 MDNNKGATTIEKYDLRTNLWIQAGMMNGRRLQFGVAVIDDKLFVIGGRDGLKTLNTVECY 526
KHL1_MOUSE 470 MDNNKGATTIEKYDLRTNLWIQAGMMNGRRLQFGVAVIDDKLFVIGGRDGLKTLNTVECY 529
Q9H955     130 MDAMKGTTTIEKYDLRTNSWLHIGTMNGRRLQFGVAVIDNKLYVVGGRDGLKTLNTVECF 189

NOV9       507 NPVGKIWTVMPPMSTHRHGLGVATLEGPMYAVGGHDGWSYLNTVERWDPEGRQWNYVASM 566
Q9C0H6     507 NPVGKIWTVMPPMSTHRHGLGVATLEGPMYAVGGHDGWSYLNTVERWDPEGRQWNYVASM 566
Q9Y3J5     348 NPVGKIWTVMPPMSTHRHGLGVATLEGPMYAVGGHDGWSYLNTVERWDPEGRQWNYVASM 407
KHL1_HUMAN 527 NPKTKTWTVEPPMSTHRHGLGVTVLEGPIYAVGGHDGWSYLNTVERWDPQSQQWTFVASM 586
KHL1_MOUSE 530 NPKTKTWTVEPPMSTHRHGLGVTVLEGPIYAVGGHDGWSYLNTVERWDPQSQQWIYVASM 589
Q9H955     190 NPVGKIWTVMPPMSTHRHGLGVATLEGPMYAVGGHDGWSYLNTVERWDPEGRQWNYVASM 249

NOV9       567 STPRSTVGVVALNNKLYAIGGRDGSSCLKSMEYFDPHTNKWSLCAPMSKRRGGVGVATYN 626
Q9C0H6     567 STPRSTVGVVALNNKLYAIGGRDGSSCLKSMEYFDPHTNKWSLCAPMSKRRGGVGVATYN 626
Q9Y3J5     408 STPRSTVGVVALNNKLYAIGGRDGSSCLKSMEYFDPHTNKWSLCAPMSKRRGGVGVATYN 467
KHL1_HUMAN 587 SIARSTVGVAALNGKLYSVGGRDGSSCLSSMEYFDPHTNKWNMCAPMCKRRGGVGVATCD 646
KHL1_MOUSE 590 SIARSTVGVAALNGKLYSVGGRDGSSCLSSMEYFDPHTNKWSMCPPMCKKRGGVGVATCD 649
Q9H955     250 STPRSTVGVVALNNKLYAIGGRDGSSCLKSMEYFDPHTNKWSLCAPMSKRRGGVGVATYN 309

NOV9       627 GFLYVVGGHDAPASNHCSRLSDCVERYDPKGDSWSTVAPLSVPRDAVAVCPLGDKLYVVG 686
Q9C0H6     627 GFLYVVGGHDAPASNHCSRLSDCVERYDPKGDSWSTVAPLSVPRDAVAVCPLGDKLYVVG 686
Q9Y3J5     468 GFLYVVGGHDAPASNHCSRLSDCVERYDPKGDSWSTVAPLSVPRDAVAVCPLGDKLYVVG 527
KHL1_HUMAN 647 GFLYAVGGHDAPASNHCSRLLDYVERYDPKTDTWTMVAPLSMPRDAVGVCLLGDRLYAVG 706
KHL1_MOUSE 650 GFLYAVGGHDAPASNHCSRLLDYVERYEPKTDTWTMVAPLSMPRDAVGVCLLGDRLYAVG 709
Q9H955     310 GFLYVVGGHDAPASNHCSRLSDCVERYDPKGDSWSTVAPLSVPRDAVAVCPLGDKLYVVG 369

NOV9       687 GYDGHTYLNTVESYDAQRNEWKEEVPVNIGRAGACVVVVKLP                    728
Q9C0H6     687 GYDGHTYLNTVESYDAQRNEWKEEVPVNIGRAGACVVVVKLP                    728
Q9Y3J5     528 GYDGHTYLNTVESYDAQRNEWKEEVPVNIGRAGACVVVVKLP                    569
KHL1_HUMAN 707 GYDGQTYLNIMESYDPQTNEWTQMASLNIGRAGACVVVIKQP                    748
KHL1_MOUSE 710 GYDGQTYLNIMESYDPQTNEWTQMASLNIGRAGACVVVIKQP                    751
Q9H955     370 GYDGHTYLNTVESYDAQRNEWKEEVPVNIGRAGACVVVVKLP                    411
```

ProDom analysis indicates that the NOV9 polypeptide has 66 of 164 aa residues (40%) identical to, and 99 of 164 aa residues (60%) positive with, the 170 aa p36 (1) KELC_DROME—ring canal prptein (KELCH protein) repeat (prdm:36769, Expect=2.0e−27); 64 of 191 aa residues (33%) identical to, and 98 of 191 aa residues (51%) positive with, the 265 aa p36 (36) SCRB(3) YC81(2) KELC(2)—protein repeat chromosome scruin EGF-like domain intergenic region cytoskeleton precursor (prdm:569, Expect=2.9e−19); 50 of 201 aa residues (24%) identical to, and 99 of 201 aa residues (49%) positive with, the 263 aa p36 (3) VFO3(2) VC13(1)-protein F3 C13, (prdm:9161, Expect 8.5e−16); 41 of 116 aa residues (35%) identical to, and 65 of 116 aa residues (56%) positive with, the 220 aa p36 (30) BAC 1 (2) BCL6(2) Z151(5)—protein transcription nuclear DNA-binding regulation zinc-finger metal-binding zinc finger activator (prdm:716, Expect=3.1e−12); and 29 of 115 aa residues (25%) identical to, and 57 of 115 aa residues (49%) positive with, the 148 aa p36 (4) VA55(2) VC02(2)—protein early A55 C2 (prdm:6493, Expect=5.7e−07).

Pfam query for NOV9 indicates that NOV9 has high homology to two Interpro protein motifs, including the Kelch Kelch motif (Score=233.9, E-value=2.3e−66) and the BTB/POZ domain (Score=114.0, E-value=2.9e−30). PROSITE—software analysis indicates that NOV9 has one N-glycosylation site (Pattern-ID: ASN_glycosylation PS00001 (Interpro)); one cAMP- and cGMP-dependent protein kinase phosphorylation site (Pattern-ID: CAMP_PHOSPHO_SITE PS00004 (Interpro)); six Protein kinase C phosphorylation sites (Pattern-ID: PKC_PHOSPHO_SITE PS00005 (Interpro)); three Casein kinase II phosphorylation sites (Pattern-ID: CK2_PHOSPHO_SITE PS00006 (Interpro)); one Tyrosine kinase phosphorylation site (Pattern-ID: TYR_PHOSPHO_SITE PS00007 (Interpro)); eleven N-myristoylation sites (Pattern-ID: MYRISTYL PS00008 (Interpro)); and one Amidation site (Pattern-ID: AMIDATION PS00009 (Interpro)).

Table 9F lists the domain description from other domain analyses results against NOV9. This indicates that the NOV9 sequence has properties similar to those of other proteins known to contain this domain.

TABLE 9F

Domain Analysis of NOV9

Prodom

| Sequences producing High-scoring Segment Pairs: | High Score | Smallest Sum Probability P(N) |
|---|---|---|
| prdm:36769 p36 (1) KELC_DROME−RING CANAL PROTEIN (KELC . . . | 306 | 2.0e-27 |
| prdm:569 p36 (36) SCRB(3) YC81(2) KELC(2)−PROTEIN R . . . | 231 | 5.8e-20 |
| prdm:9161 p36 (3) VF03(2) VC13(1)−PROTEIN F3 C13, 26 . . . | 199 | 8.5e-16 |
| prdm:716 p36 (30) BAC1(2) BCL6(2) Z151(2)−PROTEIN T . . . | 166 | 3.1e-12 |
| prdm:6493 p36 (4) VA55(2) VC02(2)−PROTEIN EARLY A55 . . . | 117 | 5.7e-07 |

BLOCKS Protein Domain Analysis

| AC# | Description | Strength | Score |
|---|---|---|---|
| BL00913B 0 | Iron-containing alcohol denydrogenases protei | 1389 | 1043 |
| BL00115S 0 | Eukaryotic RNA polymerase II heptapeptide rep | 1762 | 1040 |
| DL00655C 0 | Glycosyl hydrolases family 6 proteins. | 1384 | 1037 |
| BL01092Q 0 | Adenylate cyclases class-I proteins. | 1997 | 1035 |
| BL01066D 0 | Uncharacterized protein fanily UPF0015 protei | 1584 | 1029 |

| BLOCKS Protein Domain Analysis | NOV9 aa position |
|---|---|
| Pattern-ID: ASN_GLYCOSYLATION PS00001 (Interpro) | 2 |
| Pattern-DE: N-glycosylation site, Pattern: N[^P] [ST] [^P] | |
| Pattern-ID: CAMP_PHOSPHO_SITE PS00004 (Interpro) | 275 |
| Pattern-DE: cAMP- and cGMP-dependent protein kinase phosphorylation site | |
| Pattern: [RK] {2}·[ST] | |
| Pattern-ID: PKC_PHOSPHO_SITE PS00005 (Interpro) | 19, 269, 362, 409, 445, 455 |
| Pattern-DE: Protein kinase C phosphorylation site | |
| Pattern: [ST] [RK] | |
| Pattern-ID: CK2_PHOSPHO_SITE PS00006 (Interpro) | 4, 140, 295 |
| Pattern-DE: Casein kinase II phosphorylation site | |
| Pattern: [ST]·{2} [DE] | |
| Pattern-ID: TYR_PHOSPHO_SITE PS00007 (Interpro) | 249 |
| Pattern-DE: Tyrosine kinase phosphorylation site | |
| Pattern: [RE]·{2,3} [DE]·{2,3}Y | |
| Pattern-ID: MYRISTYL PS00008 (Interpro) | 78, 218, 280, 288, 311, 333, |
| Pattern-DE: N-myristoylation site | 366, 380, 427, 460, 527 |
| Pattern: G[^EDRKHPFYW].{2} [STAGCN][^P] | |
| Pattern-ID: AMIDATION PS00009 (Interpro) | 314 |
| Pattern-DE: Amidation site, Pattern: .G[RK] [RK] | |

Other BLAST results include sequences from the Patp database, which is a proprietary database that contains sequences published in patents and patent publications. BLASTP analysis of the patp database shows that NOV9 has 569 of 569 aa residues (100%) identical to, and 569 of 569 aa residues (100%) positive with, the 569 aa Human protein sequence SEQ ID NO:14569 (patp:AAB94214, Expect= 2.8e–314); 411 of 411 aa residues (100%) identical to, and 411 of 411 aa residues (100%) positive with, the 411 aa Human protein sequence SEQ ID NO:14985 (patp:AAB94406, Expect=7.3e–229); 381 of 508 aa residues (75%) identical to, and 439 of 508 aa residues (86%) positive with, the 508 aa Human protein sequence SEQ ID NO:13220 (patp:AAB93678, Expect=9.8e–218); 380 of 508 aa residues (74%) identical to, and 438 of 508 aa residues (86%) positive with, the 508 aa Human protein sequence SEQ ID NO:12231 (patp:AAB93233, Expect=8.8e–217); and 242 of 554 aa residues (43%) identical to, and 349 of 554 aa residues (62%) positive with, the 609 aa Human protein sequence SEQ ID NO:11635 (patp:AAB92953, Expect=2.9e–122). Patp results include those listed in Table 9GF.

includes a mutant or variant nucleic acid any of whose bases may be changed from the corresponding base shown in Table 9A while still encoding a protein that maintains its Kelch-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

The disclosed NOV9 nucleic acid is useful as a marker for Menkes disease, myoglobinuria/hemolysis due to PGK deficiency. Wieacker-Wolff syndrome and/or other diseases/disorders.

Based on the tissues in which NOV9 is most highly expressed; including uterus, brain breast, and stomach;

TABLE 9G

Patp alignments of NOV9

| Sequences producing High-scoring Segment Pairs: | High Score | Smallest Sum Prob. P(N) |
|---|---|---|
| patp:AAB94214 Human protein sequence SEQ ID NO:14569 – Ho . . . | 3015 | 2.8e–314 |
| patp:AAH94406 Human protein sequence SEQ ID NO:14985 – Ho . . . | 2209 | 7.3e–229 |
| patp:AAB93678 Human protein sequence SEQ ID NO:13220 – Ho . . . | 2104 | 9.8e–218 |
| patp:AAB93233 Human protein sequence SEQ ID NO:12231 – Ho . . . | 2095 | 8.8e–217 |
| patp:AAB92953 Human protein senuence SEQ ID NO:11635 – Ho . . . | 1203 | 2.9e–122 |

The kelch motif was discovered as a sixfold tandem element in the sequence of the *Drosophila* kelch ORFI protein. The repeated kelch motifs predict a conserved tertiary structure, a beta-propeller. This module appears in many different polypeptide contexts and contains multiple potential protein-protein contact sites. Members of this growing superfamily are present throughout the cell and extracellularly and have diverse activities.

The *Drosophila* kelch protein is a structural component of ring canals and is required for oocyte maturation. Recently, a new human homologue of kelch, KLHL3, was cloned. At the amino acid level, KLHL3 shares 77% similarity with *Drosophila* kelch and 89% similarity with Mayven (KLHL2), another human kelch homolog. Like kelch and KLHL2, the KLHL3 protein contains a poxyirus and zinc finger domain at the N-terminus and six tandem repeats (kelch repeats) at the C-terminus. Various KLHL3 isoforms result from alternative promoter usage, alternative polyadenylation sites and alternative splicing. The KLHL3 gene is mapped to human chromosome 5, band q31, contains 17 exons, and spans approximately 120 kb of genomic DNA. KLHL3 maps within the smallest commonly deleted segment in myeloid leukemias characterized by a deletion of 5q; however, no inactivating mutations of KLHL3 were detected in malignant myeloid disorders with loss of 5q.

The disclosed NOV9 nucleic acid encoding a Kelch-like protein includes the nucleic acid whose sequence is provided in Table 9A, or a fragment thereof. The invention also specific uses include developing products for the diagnosis or treatment of a variety of diseases and disorders. Additional disease indications and tissue expression for NOV9 is presented in Example 2.

The disclosed NOV9 protein of the invention includes the Kelch-like protein whose sequence is provided in Table 9B. The invention also includes a mutant or variant protein any of whose residues may be changed from the corresponding residue shown in Table 9B while still encoding a protein that maintains its Kelch-like activities and physiological functions, or a functional fragment thereof.

The invention further encompasses antibodies and antibody fragments, such as $F_{ab}$ or $(F_{ab})_2$, that bind immunospecifically to any of the proteins of the invention.

The above defined information for this invention suggests that this Kelch-like protein (NOV9) may function as a member of a "Kelch family". Therefore, the NOV9 nucleic acids and proteins identified here may be useful in potential therapeutic applications implicated in (but not limited to) various pathologies and disorders as indicated below. The potential therapeutic applications for this invention include, but are not limited to: leukemia research tools, for all tissues and cell types composing (but not limited to) those defined here.

The NOV9 nucleic acids and proteins of the invention are useful in potential therapeutic applications implicated in cancer including but not limited to leukemias and/or other pathologies and disorders. For example, a cDNA encoding the Kelch-like protein (NOV9) may be useful in disease therapy for Menkes disease, myoglobinuria/hemolysis due to PGK deficiency, and Wieacker-Wolff syndrome, and the Kelch-like protein (NOV9) may be useful when administered to a subject in need thereof. By way of nonlimiting example, the compositions of the present invention will have efficacy for treatment of patients suffering from neurological disorders including but not limited to Menkes disease. The NOV9 nucleic acid encoding Kelch-like protein, and the Kelch-like protein of the invention, or fragments thereof, may further be useful in diagnostic applications, wherein the presence or amount of the nucleic acid or the protein are to be assessed.

NOV9 nucleic acids and polypeptides are further useful in the generation of antibodies that bind immuno-specifically to the novel NOV9 substances for use in therapeutic or diagnostic methods. These antibodies may be generated according to methods known in the art, using prediction from hydrophobicity charts, as described in the "Anti-NOVX Antibodies" section below. The disclosed NOV9 protein has multiple hydrophilic regions, each of which can be used as an immunogen. In one embodiment, a contemplated NOV9 epitope is from about amino acids 1 to 40. In another embodiment, a NOV9 epitope is from about amino acids 60–95. In additional embodiments, NOV9 epitopes are from about amino acids 130 to 220, from about amino acids 240–320, from about amino acids 330 to 370, from about amino acids 380 to 415, from about amino acids 425 to 460, from about amino acids 470 to 510 and from about amino acids 520 to 569. These novel proteins can be used in assay systems for functional analysis of various human disorders, which will help in understanding of pathology of the disease and development of new drug targets for various disorders.

NOV10

NOV10 includes three novel Type IIIb plasma membrane-like proteins disclosed below. The disclosed NOV10 proteins have been named NOV10a, NOV10b and NOV10c.

NOV10a

A disclosed NOV10a nucleic acid of 1339 nucleotides (also referred to as 100340173; 1373975; 1373976; 1373977 and 1373978) encoding a novel hypothetical Y305_SYNY3 22.2 kDa prrotein SLR0305-like protein/Type IIIb plasma membrane-like proteins is shown in Table 10A. An open reading frame was identified beginning with an ATG initiation codon at nucleotides 367–369 and ending with a TGA codon at nucleotides 925–927. A putative untranslated region upstream from the initiation codon and downstream from the termination codon is underlined in Table 10A, and the start and stop codons are in bold letters.

TABLE 10A

NOV10a nucleotide sequence.

(SEQ ID NO:60)
CACGGTCCGCCCAGAGGCTTCGGAGCTGCCGGAGCCGGGCGGGGCCTTGGCGGGCGGCCCCGGGAGTGGCGCCGGCGGCGTG

GTGGTCGGCGTGGCTGAGGTGAGAAACTGGCGCTGCGGCTGCCTCGGAGCACCTGTTGGTGCCGGAGCCTCGTGCTGGTCTG

CGTGTTGGCCGCCCTGTGCTTCGCTTCCCTGGCCCTGGTCCGCCGCTACCTTCACCACCTCCTGCTGTGGGTGGAGAGCCTT

GACTCGCTGCTGGGGGTCCTGCTCTTCGTCGTGGGCTTCATCGTGGTCTCTTTCCCCTGCGGCTGGGGCTACATCGTGCTCA

ACGTGGCCGCTGGCTACCTGTACGGCTTCGTGCTGGGCATGGGTCTGATGATGGTGGGCGTCCTCATCGGCACCTTCATCGC

CCATGTGGTCTGCAAGCGGCTCCTCACCGCCTGCGTGGCCGCCAGGATCCAGAGCAGCGAGAAGCTGAGCGCGGTTATTCGC

GTAGTGGAGGGAGGAAGCGGCCTGAAAGTGGTGGCGCTGGCCAGACTGACACCCATACCTTTTGGGCTTCAGAATGCAGTGT

TTTCGATTACTGATCTCTCATTACCCAACTAPCTGATGGCATCTTCGGTTCGACTGCTTCCTACCCAGCTTCTGAATTCTTA

CTTGGGTACCACCCTGCGGACAATGGAAGATGTCATTGCAGAACAGAGTGTTAGTGGATATTTTGTTTTTTGTTTACAGATT

ATTATAAGTATAGGCCTCATGTTTTATGTAGTTCATCGAGCTCAAGTGGAATTGAATGCAGCTATTGTAGCTTGTGAAATGG

AACTGAAATCTTCTCTGGTTAAAGGCAATCAACCAAATACCAGTGGCTCTTCATTCTACAACAAGAGGACCCTAACATTTTC

TGGAGGTGGAATCAATGTTGTATGATTCTAATGACATACGTGATTGTCAAGAGCCTAGTGTGCTATCTAAGGTCTAGCAGTC

ACTTCACTAGTGGGCAGAGACAAGTTCTAATTGTATTACAGCACAAACAAAACTGACTAGTTTTTAAATTGCACAATTTTTT

TTTTTTTAAGCAAGAATCATTTTCTGGGTATCTAAGTGTAAATGTAGATGCAAATTTGGCTGCACCTCTTTATCATGCCTGT

ATTGGCCTATAGGTCTGCACTTTAGTGTTTTTTAATTGTTTTATTTCTGTGTATTTACGAACAGAGAAATAACTCAAATATT

ATTTCTGCTTAGTGTCTTTATTTATAAAGCCCATGAGTAGTTTGTATGCATCTTTCCTACTTGTAAAGATGAGTAAAAGTAT

GCAGTTTTAAATTTAAAAAAAAAAAAA

A disclosed NOV10a polypeptide (SEQ ID NO:61) encoded by SEQ ID NO:60 has 186 amino acid residues and is presented in Table 10B using the one-letter amino acid code.

SignalP, Psort and/or Hydropathy results predict that NOV10 has a signal peptide and is likely to be localized endoplasmic reticulum (membrane) with a certainty of 0.6850. In alternative embodiments, the NOV10a protein localizes to the plasma membrane with a certainty of 0.6400; a Golgi body with a certainty of 0.4600; or the endoplasmic reticulum (lumen) with a certainty of 0.1000. The most likely cleavage site for a NOV10a peptide is between amino acids 19 and 20, at: VVC-KR. NOV10a has a molecular weight of 19946.3 Daltons.

TABLE 10B

Encoded NOV10a protein sequence.

(SEQ ID NO:61)
MGLMMVGVLIGIFIAHVVCKRLLTAWVAARIQSSEKLSAVIRVVEGGSGLKVVALARLTPIPFGLQNAVFSITDLSLPNYLM

ASSVGLLPTQLLNSYLGTTLRTMEDVIAEQSVSGYFVFCLQIIISIGLMFYVVHRAQVELNAAIVACEMELKSSLVKGNQPN

TSGSSFYNKRTLTFSGGGINVV

NOV10b

A disclosed NOV10 nucleic acid of 512 nucleotides (also referred to as CG56409-02) encoding a novel hypothetical 22.2 kDa prtotein SLR0305-like, Type IIIb Plasma Membrane-like, protein is shown in Table 10C. The sequence was derived by laboratory cloning of cDNA fragments and by in silico prediction of the sequence. An open reading frame was identified beginning with an ATG initiation codon at nucleotides 108–110 and ending with a TGA codon at nucleotides 510–512. A putative untranslated region upstream from the initiation codon is underlined in Table 10C, and the start and stop codons are in bold letters.

NOV10c

A disclosed NOV10c nucleic acid of 1339 nucleotides (also referred to as CG56409-03) encoding a novel hypothetical 22.2 kDa prtotein SLR0305-like protein is shown in Table 10E. An open reading frame was identified beginning with an ATG initiation codon at nucleotides 1–3 and ending with a TGA codon at nucleotides 649–651. A putative untranslated region downstream from the termination codon is underlined in Table 10F, and the start and stop codons are in bold letters.

TABLE 10C

NOV10b nucleotide sequence.

(SEQ ID NO:62)
GGGTCCTGCTCTTCGTCGTGGGCTTCATCGTGGTCTCTTTCCCCTGCGGCTGGGGCTACATCGTGCTCAACGTGGCCG

CTGGCTACCTGTACGGCTTCGTGCTGGGCATGGGTCTGATGATGGTGGGCGTCCTCATCGGCACCTTCATCGCCCATG

TGGTCTGCAAGCGGCTCCTCACCGCCTGGGTGGCCGCCAGGATCCAGAGCAGCGAGAAGCTGAGCGCGGTTATTCGCG

TAGTGGAGGGAGGAAGCGGCCTGAAAGTGGTGGCGCTGGCCAGACTGACACCCATACCTTTTGGGCTTCAGAATGCAG

TGTTTTCGATTATTATAAGTATAGGCCTCATGTTTTATGTAGTTCATCGAGCTCAAGTGGAATTGAATGCAGCTATTG

AGAGGACCCTAACATTTTCTGGAGGTGGAATCAATGTTGTATGA

A disclosed NOV10b polypeptide (SEQ ID NO:63) encoded by SEQ ID NO:62 has 134 amino acid residues and is presented in Table 10D using the one-letter amino acid code. SignalP, Psort and/or Hydropathy results predict that NOV10b has a signal peptide, cleavage site and localization results analogous to those listed for NOV10a and NOV10c. Additional software analysis suggests that NOV10b has an INTEGRAL likelihood of –6.74 for a predicted transmembrane region at aa3-aa19 (1–20) and an INTEGRAL likelihood of –5.47 for a predicted transmembrane region at aa68-aa84 (63–86), and that it is likely a Type IIIb membrane protein (Nexo Ccyt). NOV10b has a molecular weight of 14249.2 Daltons.

TABLE 10D

Encoded NOV10b protein sequence.

(SEQ ID NO:63)
MGLMMVGVLIGTFIAHVVCKRLLTAWVAARIQSSEKLSAVIRVVEGGSGLKVVALARLTPIPFGLQNAVFSIIISIGLMFYV

VHRAQVELNAAIVACEMELKSSLVKGNQPNTSGSSFYNKRTLTFSGCGTNVV

TABLE 10E

NOV10c nucleotide sequence.

(SEQ ID NO:64)

ATGGGCTTCATCGTGGTCTCTTTCCCCTGCGGCTGGGGCTACATCGTGCTCAACGTGGCCGCTGGCTACCTGTACGGC

TTCGTGCTGGGCATGGGTCTGATGATGGTGGGCGTCCTCATCGGCACCTTCATCCCCCATGTGGTCTGCAAGCGGCTC

CTCACCGCCTGGGTCGCCGCCAGGATCCAGAGCAGCGAGAAGCTGAGCGCGGTTATTCGCGTAGTGCAGGGAGGAAGC

GGCCTGAAAGTGGTGGCGCTGGCCAGACTGACACCCATACCTTTTGGGCTTCAGAATGCGGTGTTTTCGATTACTGAT

CTCTCATTACCCAACTATCTGATGGCATCTTCGGTTGGACTGCTTCCTACCCAGCTTCTGAATTCTTACTTGGGTACC

ACCCTGCGGACAATGGAAGATGTCATTGCAGAACAGAGTGTTAGTGGATATTTTGTTTTTTGTTTACAGATTATTATA

AGTATAGGCCTCATGTTTTATGTAGTTCATCGAGCTCAAGTGGAATTGAATGCAGCTATTGTAGCTTGTGAAATGGAA

CTGAAATCTTCTCTGGTTAAAGGCAATCAACCAAATACCAGTGGCTCTTCATTCTACAACAAGAGGACCCTAACATTT

TCTGGAGGTGGAATCAATGTTGTATGATTCTAATGAGATACGTGATTGTTAAGAGCCTAGTGTGTA

A disclosed NOV10c polypeptide (SEQ ID NO:65) encoded by SEQ ID NO:64 has 216 amino acid residues and is presented in Table 10F using the one-letter amino acid code. SignalP, Psort and/or Hydropathy results predict that NOV10c has a signal peptide, cleavage site and localization results analogous to those listed for NOV10a and NOV10b. Additional software analysis suggests that NOV10c has an INTEGRAL likelihood of –8.12 for a predicted transmembrane region at aa149-aa165 (142–167) and an INTEGRAL likelihood of –6.74 for a predicted transmembrane region at aa33-aa49 (22–50), and that it is likely a Type IIIb membrane protein (Nexo Ccyt). The most likely cleavage site for a NOV10c peptide is between amino acids 49 and 50, at: VVC-KR. NOV10c has a molecular weight of 23141 Daltons.

TABLE 10F

Encoded NOV10c protein sequence.

(SEQ ID NO:65)

MGFIVVSFPCGWGYIVLNVAAGYLYGFVLGMGLMMVGVLIGTFIAHVVCKRLLTAWVAARIQSSEKLSAVIRVVEGGSGLKV

VALARLTPIPFGLQNAVFSITDLSLPNYLMASSVGLLPTQLLNSYLGTTLRTMEDVIAEQSVSGYFVFCLQIIISIGLMFYV

VHRAQVELNAAIVACEMELKSSLVKGNQPNTSGSSFYNKRTLTFSGGGINVV

NOV10a, NOV10b and NOV10c polypeptides are related to each other as shown in the ClustalW alignment in Table 10G.

TABLE 10G

ClustalW of NOV10 Variants

```
NOV10a   ------------------------------MGLMMVGVLIGTFIAHVVCK    20
NOV10b   ------------------------------MGLMMVGVLIGTFIAHVVCK    20
NOV10c   MGFIVVSFPCGWGYIVLNVAAGYLYGFVLGMGLMMVGVLIGTFIAHVVCK    50

NOV10a   RLLTAWVAARIQSSEKLSAVIRVVEGGSGLKVVALARLTPIPFGLQNAVF    70
NOV10b   RLLTAWVAARIQSSEKLSAVIRVVEGGSGLKVVALARLTPIPFGLQNAVF    70
NOV10c   RLLTAWVAARIQSSEKLSAVIRVVEGGSGLKVVALARLTPIPFGLQNAVF   100

NOV10a   SITDLSLPNYLMASSVGLLPTQLLNSYLGTTLRTMEDVIAEQSVSGYFVF   120
NOV10b   S-------------------------------------------------   71
NOV10c   SITDLSLPNYLMASSVGLLPTQLLNSYLGTTLRTMEDVIAEQSVSGYFVF   150

NOV10a   CLQIIISIGLMFYVVHRAQVELNAAIVACEMELKSSLVKGNQPNTSGSSF   170
NOV10b   ---IIISIGLMFYVVHRAQVELNAAIVACEMELKSSLVKGNQPNTSGSSF   118
NOV10c   CLQIIISIGLMFYVVHRAQVELNAAIVACEMELKSSLVKGNQPNTSGSSF   200

NOV10a   YNKRTLTFSGGGINVV   186
NOV10b   YNKRTLTFSGGGINVV   134
NOV10c   YNKRTLTFSGGGINVV   216
```

Additional NOV10 SNP and coding variant sequences are described in Example 3.

In a search of sequence databases, it was found, for example, that the NOV10b nucleic acid sequence has 156 of 245 bases (63%) identical to a gb:GenBank-ID:MFU727441 acc:U72744.1 mRNA from *Mycobacterium fortuitum* (*Mycobacterium fortuitum* nitrite extrusion protein gene, complete cds). The full NOV10b amino acid sequence was found to have 29 of 80 amino acid residues (36%) identical to, and 45 of 80 amino acid residues (56%) similar to, the 209 amino acid residue ptnr:SwissProt-ACC:Q55909 protein from *Synechocystis* sp. (strain PCC 6803) (hypothetical 22.2 kDa protein SLR0305). In a search of sequence databases, it was found, for example, that the NOV10c nucleic acid sequence has 156 of 245 bases (63%) identical to a gb:GenBank-ID:MFU72744|acc:U72744.1 mRNA from *Mycobacterium fortuitum* (*Mycobacterium fortuitum* nitrite extrusion protein gene, complete cds). The full NOV10c amino acid sequence of the protein of the invention was found to have 52 of 170 amino acid residues (30%) identical to, and 96 of 170 amino acid residues (56%) similar to, the 209 amino acid residue ptnr: SwissProt-ACC:Q55909 protein from *Synechocystis* sp. (strain PCC 6803) (hypothetical 22.2 kDa protein SLR0305).

In an additional search of public protein databases, the NOV10a amino acid sequences have homology to the amino acid sequences shown in the BLASTP data listed in Table 10H. Public amino acid databases include the GenBank databases, SwissProt, PDB and PIR.

TABLE 10H

BLAST results for NOV10a

| Gene Index/ Identifier | Protein/Organism | Length (aa) | Identity (%) | Positives (%) | Expect |
|---|---|---|---|---|---|
| Y305_SYNY3; D64005; BAA10672.1; Q55909 | HYPOTHETICAL 22.2 KDA PROTEIN SLR0305. synechocystis sp. (strain pcc 6803). 11/1997 | 209 | 46/154 (30%) | 86/154, (56%) | 3e−12 |
| Q9VNR8; AE003598; AAF51854.2 | CG11367 PROTEIN. *drosophila melanogaster*. 3/2001 | 834 | 28/81 (35%) | 56/81, (69%) | 6e−10 |
| Q9ZVS7; AC005278; AAC72122.1 | F15K9.14. *arabidopsis thaliana*. 5/1999 | 269 | 41/153 (27%) | 82/153, (54%) | 7e−09 |
| Q9RPT3; AF148265; AAD55929.1 | HYPOTHETICAL TRANSMEMBRANE PROTEIN. uncultured bacterium ah1. 5/2000 | 225 | 40/144 (28%) | 73/144, (51%) | 2e−05 |

The homology of these and other sequences is shown graphically in the ClustalW analysis shown in Table 10I. In the ClustalW alignment of the NOV10 proteins, as well as all other ClustalW analyses herein, the black outlined amino acid residues indicate regions of conserved sequence (i.e., regions that may be required to preserve structural or functional properties), whereas non-highlighted amino acid residues are less conserved and can potentially be mutated to a much broader extent without altering protein structure or function.

TABLE 10I

ClustalW Analysis of NOV10

```
1) NOV10a  (SEQ ID NO:61)
2) NOV10b  (SEQ ID NO:63)
3) NOV10c  (SEQ ID NO:65)
4) Y305_SYNY3  (SEQ ID NO:66)
5) Q9VNR8  (partial sequence)  (SEQ ID NO:67)
6) Q9ZVS7  (SEQ ID NO:68)
7) Q9RPT3  (SEQ ID NO:69)

NOV10a      ------------------------------------------------------   1
NOV10b      ------------------------------------------------------   1
NOV10c      ------------------------------------------------------   1
Y305_SYNY3  ----------------------------------------MA-----DYLLN      7
Q9VNR8      ...HNRKRNSCWGRAHSFLTRNWYLGCLVPATILGALVFIGWATRDYARQ       150
Q9ZVS7      -------------MSFTPSTFRIAISLLLLVAIVSAVIFL-----PKLKD        32
Q9RPT3      ---------------------------------------MVS-----PWLPE       8
```

TABLE 10I-continued

ClustalW Analysis of NOV10

```
NOV10a    --------------------------------------------------MG   2
NOV10b    --------------------------------------------------MG   2
NOV10c    ----------------MGFIVVSFP-CGWGYIVLNVAAGYLYGFVLGMG  32
Y305_SYNY3 ALQWIDG-LGTWAAIAFMLLYTVATV-VFLPGSILTLGAGVVFGVILCSI  55
Q9VNR8    LLFWIEMQNAWITFAVYMGLFALVSFPVVVGYFVLLITAGYLFGCLRGWV  200
Q9ZVS7    FLLWIKEDLGPFGPLALALAYIPLTI-MAVPASVLTLGGGYLFGLPVGFV   81
Q9RPT3    FAGWVHS-LGVWAPIAFVAAYIAVVV-LMLPAFLLIMAGGAVFGVVECSL   56

NOV10a    LMMVGVLIGRFIAHVVCK----------------------RLLTAWVAA   29
NOV10b    LMMVGVLIGRFIAHVVCK----------------------RLLTAWVAA   29
NOV10c    LMMVGVLIGRFIAHVVCK----------------------RLLTAWVAA   59
Y305_SYNY3 YVFIGARLGARAAFLVGR----------------------YLARGWVAK   82
Q9VNR8    TVILGANLGIAVAHATIRSCRHRIPVQSPYITHCSVCFLYSPMLRFLRNF  250
Q9ZVS7    ADSLGATLGATAAFLLGR----------------------TIGKSYVTS  108
Q9RPT3    LALLGAVLGGTAAFLIGR----------------------HYARAAVER   83

NOV10a    RIQSSEKLSAVIRVVEGGSGLKVVALA----------RLTP---IPFGLQN   67
NOV10b    RIQSSEKLSAVIRVVEGGSGLKVVALA----------RLTP---IPFGLQN   67
NOV10c    RIQSSEKLSAVIRVVEGGSGLKVVALA----------RLTP---IPFGLQN   97
Y305_SYNY3 KIAGNQKFKAIDEAVGK-EGLKIVILT----------RLSPV-FPPNLLN  120
Q9VNR8    KYYAWQSVRRGCSVVAPPDRSDVLLVLPTVWPSELTKRIRPLSVPDLIEK  300
Q9ZVS7    KIKHYPKFQAVSVAIQK-SGFKIVLLL----------RVVPI-LPPNMLN  146
Q9RPT3    RVASNPTLSALDHVIGE-DGLKLVFLL----------RLSPA-VPFVITN  121

NOV10a    AVFSITD---LSLPNYLMASSV--G-ILPTQL------------------   93
NOV10b    AVF-------S-----------------------------------   71
NOV10c    AVFSITD---LSLPNYLMASSV--G-ILPTQL------------------  123
Y305_SYNY3 YAYGITN---VSLKDVVIGSLG----MIPGTI------------------  145
Q9VNR8    FSCDAPGGQFATMSEVLRSDPRPDGVLLPDEIDLHRKMSLDDLNSYMHAK  350
Q9ZVS7    YLLSVIP---VRIGEYMLATWL--GMMQPITF------------------  173
Q9RPT3    YALSITR---VRLRDFFIGTLG----LAPIVV------------------  146

NOV10a    ---------------------------------LNSYLGITLRT-MEDV  108
NOV10b    ---------------------------------------------- 71
NOV10c    ---------------------------------LNSYLGITLRT-MEDV  138
Y305_SYNY3 ---------------------------------MYVYIGSLAGSLATLG  161
Q9VNR8    DAFKEPHRKNRIFSHVLVVAGADSARSYPFRQRPDFLYLCDCLRPGAALV  400
Q9ZVS7    ---------------------------------ALVYVGITLKD-LSDI  188
Q9RPT3    ---------------------------------MYAAYGSASG--ATPN  160

NOV10a    IAEQSVSGYFVFCL---QILISIGLMFYVVHRAQVELNAAIVAC------  149
NOV10b    ----------------ILISIGLMFYVVHRAQVELNAAIVAC------   97
NOV10c    IAEQSVSGYFVFCL---QILISIGLMFYVVHRAQVELNAAIVAC------  179
Y305_SYNY3 TATNQANPTLQWTIRIVGFIATVAVTIYVTKIARKALNEAILT-------  204
Q9VNR8    LTRSRKRNTGALLFLSQDVDSQLSTIFSHMHYVDDVLPLAMLKKSLLWLL  450
Q9ZVS7    THGWHEVSVFRWVIMMVGVALAVILIICITRVAKSSLDKALAEN------  232
Q9RPT3    ADGSAAVTPMMFTA---GIVVTVLLGLLLAKIVQKALREAELSR------  201

NOV10a    --------------------EMELKSSLVKGNQP---NTSGSSFYNKR  174
NOV10b    --------------------EMELKSSLVKGNQP---NTSGSSFYNKR  122
NOV10c    --------------------EMELKSSLVKGNQP---NTSGSSFYNKR  204
Y305_SYNY3 ----------------------SEVDE--------------------  209
Q9VNR8    RDHSPELWHFYDPSSPVSCIVQEVANEAKIPMGNPRYILQYTRIVKTSRE  500
Q9ZVS7    --------------------GTELDGKKNDDASVLPIAEPPPDLQEPL  260
Q9RPT3    --------------------LKQLEIDATP----------ETPTVLPTPI  221

NOV10a    ILTFSGGGINVV----------------------------------  186
NOV10b    ILTFSGGGINVV----------------------------------  134
NOV10c    ILTFSGGGINVV----------------------------------  216
Y305_SYNY3 ----------------------------------------------  209
Q9VNR8    LRALRRANATAADSMAEVIAQHHQIPQELAADFDYKCRLRHARPDVT...  550
Q9ZVS7    VIRIDPSNT-------------------------------------  269
Q9RPT3    IESI------------------------------------------  225
```

The presence of identifiable domains in NOV10a, and to NOV10b and NOV10c in analogous regions, was determined. DOMAIN results for NOV10 as disclosed in Tables 10J, were collected from the Conserved Domain Database (CDD) with Reverse Position Specific BLAST analyses. This BLAST analysis software samples domains found in the Smart and Pfam collections.

ProDom analysis of NOV10a shows homology to various domains. Specifically, NOV10a has 32 of 124 aa residues (25%) identical to, and 67 of 124 aa residues (54%) positive with, the 208 aa p36 (7) protein transmembrane intergenic region CY20H10.06C SLR0305 CY277.13C XTHA-GDHA NUCB-AROD DNAI-THRS (prdm:3727, Expect=2.7e−08); 14 of 36 aa residues (38%) identical to, and 21 of 36 aa residues (58%) positive with, the 68 aa p36 (1) NU2M__HANWI—NADH-ubiquinone oxidoreductase chain 2 (EC 1.6.5.3)(prdm:21748, Expect=0.27); 13 of 30 aa residues (43%) identical to, and 18 of 30 aa residues (60%) positive with, the 41 aa p36 (1) SODE_DIRIM—extracellular superoxide dismutase precursor (CU-ZN) (EC 1.15.1.1) (EC-SOD)(prdm:27499, Expect=0.27); 15 of 54 (27%) identical to, and 23 of 54 (42%) positive with, the 69 aa p36 (1) RL37_TETTH—ribosomal protein L37 (P1 TYPE) (prdm:21871, Expect=0.74); and 14 of 31 aa residues (45%)

identical to, and 20 of 31 aa residues (64%) positive with, the 158 aa p36 (1) YIK5_YEAST—hypothetical 78.0 KD protein in MOB1-SGA1 intergenic region (prdm:55957, Expect=1.3). Table 10J lists various domain description from domain software analysis results against NOV10. This indicates that the NOV10 sequence has properties similar to those of other proteins known to contain this domain.

(patp:AAB56667, Expect=3.0e–42); 45 of 144 aa residues (31%) identical to, and 80 of 144 aa residues (55%) positive with, the 280 aa *Arabidopsis thaliana* protein fragment SEQ ID NO: 12140 (patp:AAG12863, Expect=1.6e–12); 39 of 130 aa residues (30%) identical to, and 66 of 130 aa residues (50%) positive with, the 174 aa *Arabidopsis thaliana* protein fragment SEQ ID NO:64446 (patp:AAG50824, Expect=

TABLE 10J

Domain Analysis of NOV10

PFAM HMM Domain Analysis of NOV10

| Model | Domain | seq-f | seq-t | hmm-f | hmm-t | score | E-value |
|-------|--------|-------|-------|-------|-------|-------|---------|

[no hits above thresholds]

ProDom analysis

| Sequences producing High-scoring Segment Pairs: | High Score | Smallest Sum Probability P(N) |
|---|---|---|
| prdm:3727 p36 (7)-PROTEIN TRANSMEMBRANE INTERGENIC R . . . | 129 | 2.7e-08 |
| prdm:21748 p36 (1) NU2M_HANWI-NADH-UBIQUINONE OXIDORED . . | 58 | 0.23 |
| prdm:27499 p36 (1) SODE-DIRIM-EXTRACELLULAR SUPEROXIDE . . | 58 | 0.23 |
| prdm:21871 p36 (1) RL37_TETTH-RIBOSOMAL PROTEIN L37 (P . . | 54 | 0.52 |
| prdm:55957 p36 (1) YIK5_YEAST-HYPOTHETICAL 78.0 KD PRO . . | 68 | 0.73 |

BLOCKS Protein Domain Analysis

| AC# | Description | Strength | Score |
|---|---|---|---|
| BL00495E | 0 Apple domain proteins. | 1844 | 1049 |
| BL00505C | 0 Phosphoenolpyruvate carboxykinase (GTP) prote | 1787 | 1019 |
| BL00853C | 0 Beta-eliminating lyases pyridoxal-phosphate a | 1544 | 1017 |
| BL01235B | 0 Uncharacterized protein family UPF0019 protei | 2114 | 1016 |

PROSITE Analysis

Pattern-ID: ASN_GLYCOSYLATION PS00001 (Interpro)
one N-glycosylation site

Pattern-ID: GLYCOSANINOGLYCAN PS00002 (Interpro)
one Glycosaminoglycan attachment site Pattern-ID: PKC_PHOSPHO_SITE PS00005 (Interpro)
two Protein kinase C phosphorylation sites Pattern-ID: CK2_PHOSPHO_SITE PS00006 (Inrerpro)
two Casein kinase II phosphorylation sites Pattern-ID: MYRISTYL PS00008 (Interpro)
five N-myristoylation sites Other BLAST results include sequences from the Patp database, which is a proprietary database that contains sequences published in patents and patent publications. In a BLASTP analysis of the patp database, NOV10 was found to have 93 of 102 aa residues (91%) identical to, and 95 of 102 aa residues (93%) positive with, the 111 aa Human prostate cancer antigen protein sequence SEQ ID NO:1245 3.0e–06); 39 of 130 aa residues (30%) identical to, and 66 of 130 aa residues (50%) positive with, the 204; aa *Arabidopsis thaliana* protein fragment SEQ ID NO: 37254 (patp:AAG31071, Expect=9.5e–06); and 39 of 130 aa residues (30%) identical to, and 66 of 130 aa residues (50%) positive with, the 204 aa *Arabidopsis thaliana* protein fragment SEQ ID NO: 64445 (patp:AAG50823, Expect=9.5e–06). Patp results include those listed in Table 10K.

TABLE 10K

Patp alignments of NOV10

| Sequences producing High-scoring Segment Pairs: | High Score | Smallest Sum Prob. P(N) |
|---|---|---|
| patp:AAB56667 Human prostate cancer antigen protein seque . . . | 448 | 3.0e-42 |
| patp:AAG12863 Arabidopsis thaliana protein fragment SEQ I . . . | 169 | 1.6e-12 |
| patp:AAG50824 Arabidopsis thaliana protein fragment SEQ I . . . | 118 | 3.0e-06 |
| patp:AAG31071 Arabidopsis thaliana protein fragment SEQ I . . . | 118 | 9.5e-06 |
| patp:AAG50823 Arabidopsis thaliana protein fragment SEQ I . . . | 118 | 9.5e-06 |

The Type IIIb Plasma Membrane-like NOV10 disclosed in this invention maps to chromosome 8q13 and 8q21. This assignment was made using mapping information associated with genomic clones, public genes and ESTs sharing sequence identity with the disclosed sequence and CuraGen Corporation's Electronic Northern bioinformatic tool.

The disclosed NOV10 nucleic acid encoding a novel hypothetical 22.2 kDa prtotein SLR0305-like protein includes the nucleic acid whose sequence is provided in Table 10A, or a fragment thereof. The invention also includes a mutant or variant nucleic acid any of whose bases may be changed from the corresponding base shown in Table 10A while still encoding a protein that maintains its novel hypothetical 22.2 kDa prtotein SLR0305-like protein activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 37% percent of the bases may be so changed.

The disclosed NOV10 protein of the invention includes the novel hypothetical 22.2 kDa prtotein SLR0305-like protein whose sequence is provided in Table 10B. The invention also includes a mutant or variant protein any of whose residues may be changed from the corresponding residue shown in Table 10B while still encoding a protein that maintains its novel hypothetical 22.2 kDa prtotein SLR0305-like activities and physiological functions, or a functional fragment thereof. In the mutant or variant protein, up to about 64% percent of the residues may be so changed.

The Type IIIb Plasma Membrane-like NOV10 gene disclosed in this invention is expressed in at least in peripheral blood tissues. Expression information was derived from the tissue sources of the sequences that were included in the derivation of the sequence, as provided in Example 1.

The invention further encompasses antibodies and antibody fragments, such as $F_{ab}$ or $(F_{ab})_2$, that bind immunospecifically to any of the proteins of the invention.

The above defined information for this invention suggests that this novel hypothetical 22.2 kDa prtotein SLR0305-like protein (NOV10) may function as a member of a "Type IIIb plasma membrane-like protein family". Therefore, the NOV10 nucleic acids and proteins identified here may be useful in potential therapeutic applications implicated in (but not limited to) various pathologies and disorders as indicated below. The potential therapeutic applications for this invention include, but are not limited to: Type IIIb plasma membrane-related research tools, for all tissues and cell types composing (but not limited to) those defined herein.

The NOV10 nucleic acids and proteins of the invention are useful in potential therapeutic applications implicated in cancer including but not limited to disorders such as neural, immune, muscular, reproductive, gastrointestinal, pulmonary, cardiovascular, renal, and proliferative disorders, wounds, and infectious diseases, and/or other pathologies and disorders. For example, a cDNA encoding the SLR0305-like NOV10 protein may be useful in gene and protein therapy, and the SLR0305-like protein (NOV10) may be useful when administered to a subject in need thereof. By way of nonlimiting example, the compositions of the present invention will have efficacy for treatment of patients suffering from Type IIIb plasma membrane-related disorders including but not limited to those described in the Examples. The NOV10 nucleic acid encoding the SLR0305-like protein, and the SLR0305-like protein of the invention, or fragments thereof, may further be useful in diagnostic applications, wherein the presence or amount of the nucleic acid or the protein are to be assessed.

The protein similarity information, expression pattern, cellular localization, and map location for the protein and nucleic acid disclosed herein suggest that this Type IIIb Plasma Membrane-like NOV10 protein may have important structural and/or physiological functions characteristic of the Type IIIb Plasma Membrane family.

The NOV10 nucleic acids and proteins of the invention have applications in the diagnosis and/or treatment of various diseases and disorders. For example, the NOV10 compositions of the present invention will have efficacy for the treatment of patients suffering from: ACTH deficiency; familial febrile convulsions 1; Duane syndrome; congenital Adrenal hyperplasia due to 11-beta-hydroxylase deficiency; glucocorticoid-remediable Aldosteronism; congenital Hypoaldosteronism due to CMO I deficiency; congenital Hypoaldosteronism due to CMO II deficiency; Nijmegen breakage syndrome; susceptibility to Low renin hypertension; Anemia, Ataxia-telangiectasia, Autoimmume disease, Immunodeficiencies as well as other diseases, disorders and conditions.

These materials are further useful in the Generation of antibodies that bind immunospecifically to the novel substances of the invention for use in diagnostic and/or therapeutic methods.

NOV10 nucleic acids and polypeptides are further useful in the generation of antibodies that bind immunospecifically to the novel NOV10 substances for use in therapeutic or diagnostic methods. These antibodies may be generated according to methods known in the art, using prediction from hydrophobicity charts, as described in the "Anti-NOVX Antibodies" section below. The disclosed NOV10a protein has multiple hydrophilic regions, each of which can be used as an immunogen. In one embodiment, a contemplated NOV10a epitope is from about amino acids 18 to 25. In another embodiment, a NOV10 epitope is from about amino acids 30 to 50. In additional embodiments, NOV10a epitopes are from about amino acids 100 to 120 and from about amino acids 135 to 186. In another embodiment, a contemplated NOV10b epitope is from about amino acids 25 to 45 and from about amino acids 100 to 134.

In a further embodiment, a contemplated NOV10c epitope is from about amino acids 50 to 75, from about amino acids 120 to 145 and from about amino acids 180 to 216. These novel NOV10 proteins can be used in assay systems for functional analysis of various human disorders, which will help in understanding of pathology of the disease and development of new drug targets for various disorders.

NOV11

A disclosed NOV11 nucleic acid of 6540 nucleotides (also referred to as 87938450) encoding a novel transposase-like protein is shown in Table 11A. An open reading frame was identified beginning with an ATG initiation codon at nucleotides 758–760 and ending with a TGA codon at nucleotides 1175–1177. A putative untranslated region upstream from the initiation codon and downstream from the termination codon is underlined in Table 11A, and the start and stop codons are in bold letters.

TABLE 11A

NOV11 nucleotide sequence.

(SEQ ID NO:70)

CTGGAGTTCCTTTATTCTGGGGATAGCTCAAGTCCACTGCCAATGGCTGACAGTCATTAATACACAGGCAGAAAAAGAA

ATAAGCTGCTGTGTCTGCAGTTGGGAGGGGAGCACTGGGAAGGACAGAATGGAAGTTACTGTATCCAGATACCAGCGGCC

TTTACATTTTAAACATGGAGAGGAAGGAACAGGCAGATTAAAAAGTGAAAAATGGCAGTTTACAGAGAAGGCCTAACTGT

TGGAGAATGAGTACGAGATGAAGGGAAGCAGCTTTGATAGCAAACCAGGGGAATAAGGCAGTTATCTGCCAGTATCTACT

GCTTCAAAGAGAAGCTCAAGCATCATCTAAGTAGTTTTACACAGGGAGTGAGACTGAGTTTGGTGGGGATTTCATTGAGT

AATGGGATAAAAATTCAGGCACTGCTCATTCAGTTCCAAGGTTCTCTTGCAACCCAGTTTTGAGCTGGAGGGAATTGTGT

TTTGGTACATATTTATGTTTGAATGCAAGCCAGCCCACATTCGACAGGCACGGAGCTCTTTCATGCTCAGAAAAGGGAAA

AAAAAGTTCCTGTTCTTGTATATTCTTTCATCCTAAACCTGAGACACTTAACAAGAAGCCGGTGTTGGCAAAGGTGTGTG

TGTGTGTGTGTCTGTGTGTGTGTCCTAACGAAATGCACATATTTGCTGCAGTGAAGGAGCCAGTTTTTCCATAAAT

GGCTAACAGGAATTTGATGAAGTGTTTGCAACATTAAATGTGTTGTGGGTCACGTTGTAACTTACATTGTTCCCCAGCCT

CCACTTTTCCTTGTTTCCTAACCAACCTCCATCCCGCCCCACATGCCACATTCATCCAGGCCTTCAATAGGTCTGCTGTC

AGTTCCCATAAACTGGCTCAGGTTGTAGAAATGGTTAGTGAAGTCGGGCATCTCAGCCATTCCCACCTCTTACTTCCCAA

GGTGTCTCATGTCACCAAATTACAAATCATCCACAAGCAGAAGATCAAATCCAGGCTGACTAAAGCCATGTGGAATGTGG

ACACTTGGGGGCAGTTAAATACCTTACAGGTTTCTGCTGTAAGATTTGAAGCTTTGAAGGCAGAAATCAATGGCCAGATT

TTCAAAGGAAAAGGTTACAGGTGTGTCCAGGTGAGCCCCAGACAGATGGATCTGTGAAAGCAAGTGCCTGTGCAGGTGCA

GTGACTGCTCTGGCCATATGTCCTGTACAGACATGGGCTGCAGAGGAAGGAACAAGACTGTGAGTCAAAGAAGACAGGCC

CGTGCAGCCATCCGTGCCTTACTTGTCTCCAGGTATATGGGGCAGATCTGTAAGTAGAGAATAAGAACAGCAGATGGGAT

TTTCCATGGGACTCTACTTCCTACTCCAAGGCATTCAGAAACATGGCTAAAATGAAACCAGTGAATTTGGGGCCATAGA

GCTATCTCAAAACCAAGAGAATGAACTGCCAGGATGCATGAAGAGGGATGCCGAAGGCAGGCAGTAAGGGAGGGGAAAC

TGAGTGGGCTCTGAATGTCACCTGCACGGTGTAGGCCCTCACGGCATCTTTCTGACCTCTAAATGTTGGAACACCCCAAC

AGGCCTCGGTCCTGCCTCCCCTGTCCCTCTGCCACACTCTCTCTGGGTGAGCTCACTCAGCCCCACGCCTTTACATCCC

ATTTATGCACTGATCGCTCCTAACTCTAAATCTCCACCCCGACCCTTCTCCTGAGCTCCCGATTCAAAATCTTATGCCT

GTTCATCCTCTTGGATATCTAATAGAGCTCCCAAAGTTAATGTGTCCAAACCTGAACCCCAGATTCGCCACTATGTTCCC

AAATCCCACTATGGGTTAGTCTCCCCCATCTCAGAAAAGTAACCCTCCATTACCCAAGTGGTCTGGACAAAAGTTTGGGA

TTATCCTCAATTCTTTTCTTTATCTCACATCCCGCATCTAATCCATCAGCAAGTTTCGTCAGCTCTCCCTGTAAAATGCA

TCCCATTCCTACTTTTCATTGCTTCCACCACTACCAGCCCTGTTCAAAGCAACACCCTTTCTTTCCTTGATGACTGCAAT

TABLE 11A-continued

NOV11 nucleotide sequence.

GTTGTTGAGCTGACTGCCTTGATCCCATGCCTGCCACCTTGTGTCTTGTCTCCACACGGAAACTCAAGTGACTTTTTAAA

AGTATAAATTAGATTAGCCTCCTTTCTTGCTCAAAAACTTCTGCTGGTATTTCCTACTTTTAAAATGAAGTTCAAAGTCC

TAAAATAGCCTAACCTCTATTTACCACCCCCACCCCACCTCCTTCTATCTCCCTTTTGCCATTCCACCCACACCAACCTC

CTGATCACCCTTCAAAATACATCACCTTGTTCCCTCTGTGGCATCTTGATATTTGTTCCTGTATCCACCTGGAAATCTTT

CACATTGCTCGTTCCCCTGATGCACTCAAAACTCTCTAATCCCACGTTCATCTTTGCAAAGAAGTCTTTCCTGACCACAG

ATTCTAAAGGAGACCAACCACCATCCAGCTCTTGGATCCTCCTCTTCTCTTCCCTTCTCCTGTTCCACGCATAGGGCACA

TTGATCATGGTTTTTGGCTACCCAGTGTATTTTAACATTCTTGTCCTATTTGAGAAAATTTGAGACTCCCCAAAGCAGAA

GGCAGTATAGTGAGTTTAATAGTGTTTCCCCTGATGTACATCTACCCACAGCCTCAGAATATGACCTTAATTGGAAATAG

GTTCTTTGCAGCTATAATTAGTTAAGGAGTGGAAGATGAAGTCATCCTGAATTTAGGGTGGGCCCTAATTCCAATGACTG

GCATCCTTATGACATAATGGAGAAGGAGATTTGGACACAGACATGAAGACATGCAGGAAAGAAGGCCACCTAGTAATGGA

GGCAGGGTGACTCATGGAGCCACAAGCCAACGGACATCAAGTACCACTGGCCCCATCAAAACTTTAAAAAGGCAGGGGA

AAGGTTCTTCTCTAGAGCCTCCAGAGGGAACAGGACTCTGTTAACACCTCAATCTCAGCCTTCCAGCCTCCAGACTGTGA

GAGAATAAAGCCATCAAGTTTGTGGTTATTAGTTACAGCAGGCTTAGGAAACTAATACAGCCAAACATTTCTCTAGATGC

TCAGTAACCAGGGCACAAGACAGAGACCCACACCCCCAGTCAGATGATTCTGCATGAGACTTCCATTGTACATCTGAGT

GCATTGAGGAGCTCACCCCAGCAGTTCCTATCATCCCAGCTCAGGCCTCAGACATCAAGAAGCAGGAGACAAGCCATCT

CTGTGTGTCCTGTCCAAACCCTGAGCCATAGACTTCATGGGCATAACAAAATGGTTTGTGTTTGAGCCCATAAAAGTTGG

AGTCCTTTGTTGTACAGCAATAGTAACTGCAACAAAAATCAAAATAATTCCTCTCTGATGGTGGGCATGGGGAAGATGA

AGGAAAGAGATATAGTGAATACACATCTTTGTCAGAAAGACAGTGCCTTCATTTGAGTAGTTGGATTATGTATTTCCCACA

GCCATCTCTCAGGATAAACCTAAGCTTCTTCAGGATACAAGGAAATTTCCTGGAATCCTAAACATTTAGAAAAACATTTC

AAAAAACCTCGGTGTGGTACACTTGAAAGAATCTTCAGTTTCCTTGCCACGATAACAAATTAGCCACATATATCAACACT

GCACCAGGCATCTCCATAGTCACAGTTTGATGCAAGTTTCCAAATACCTCTGCAAAGCAGGCATTACTGTTACTATTTTA

CAAATGATGCCTGGAGAATATAGAAATTTCAACTCATGCTTTGAATCCTGAAAACCACTTGAAGGCCCAAATTCGGATGG

TCCATCTCCCAGAGTTGTCTCTAATAACAACACTGTGTAGAATGAGAAGGCTGAAATGCCAAGTGATCTCAGTGACCCCC

CTTTCATGATATTTTAAGACTACTGCCAAGAACAATGTTGTCTTACAGGCAGCATAGGGTAGTTATCAATGTAAGAGAAA

ACTGCCAGGATGCCTGCAAAGCCCACAATCGGAAGTTCAGAGCGGCAGGTCATAAATTATTTTTATAAGAGAAAAGGCCA

AGCAAGGGGCCGTTCTAACAGCCGTCTGGCATCCCTATCCTGCAACCTGGGCTGAGTTTGTACCGAATTTCTGCTTTGGG

GCAGAAATTCATACCAGAAAATGTTTCGTGATGCATTTTGTTCAGTTGAATAGAGCCCAAGAATTTGTTCTAATTTAAA

TTAGATCACCTCTGAGCTGATATACTATAAAAATATTAATCAAGTAACCCCAGCAAATACTGATAGGGCTATCACCAGGG

ACTCAATGATATCACCAGGATGAAAAGAGACGGTGGCCTTTTGGCTGCTATGATCCATAATTCCCACATAATCCACGTC

TATAAGTTAGAGAGAATTCTCAAGTACAGTTCAGTGCTAACCTGGAAACAAATACCCCTTATAAGGCTGCTAATCCACTT

AAAATAATCAGTTCCAGATTATTAATTTGGCACCCTCCCAAGGATACTACGAGGATCTGTCAGATTTCATGAACATATAG

GCAACAATAGACCAATACCCTAAACCCCAGAATCTAGATATGAAAGCTATGTAGAATCATACCCTTTCTAGTCCCCCACT

GCTTCATAATACAAATGACAAAAATTCAGCTCATGAGGATTAAGGGACTTTTCAGTGGGGCATCAGCTCACGGTTGCATA

CAGCTCAGTCTTTTTTTTTTTTTGAGACAGGGTCTTACTCTGCTACCCAGGCCACAGTGCACTGGGGCCATCTTGGCTC

ACTGCAGCCTCAACCTCCTGGGCTCAAGCAATCCTCCCACCTTAGCTTCCCAAATAGCTGAGATGACAGGTGCACACAAC

CATGCCTGGCTAATTTTTTATTTTTTGAAGAGATAGGGCCTCACTATGTTGCCCAGGCTGGAGCCCAGTCTTCAGAGATG

GAAACACATGCGTCTATGTCATTTACGAGTTTCATGGCCTGTGTCAAGCTAATTCTACCCCCTGAGCCTCAGCTTGTTTC

TABLE 11A-continued

NOV11 nucleotide sequence.

TTCTTTTCAAAAATGAAGATGCCAGTGGTTCTCACCTCATATTGTTGCAGGAATGGAACAATGGGTGTGAGGGCACCTGG

TGTAGAGTAGGTGCTCAGTCACATGTAGTTGCTGTTGTTCTTCCCCAGATTATACAAACAAATTCTTGCTAAGCCAGGAT

GAAAACCCAGGTTTCAGGACTCTCAGGCTGATACTCATACCATGCCACTCCATCAAAGAGAAGGGCATTTTCCACCTCTA

GAAAACCCAGGTTTCAGGACTCTCAGGCTGATACTCATACCATGCCACTCCATCAAAGAGAAGGGCATTTTCCACCTGTA

TCCCTGGGTCTGTGTTCCAATCATTCTAAACTCTGACCAGCGCCTCATAAGTTGAATGAAATATAAACGACTTCAATAAA

TCTCTTTTTTTCCAAATAAATGAAGTTTATCAAGCTGTCCCATAACCCCGTGCTAAATCTATAAACTGTAGGCAGCTTCC

TTTGGGACCAACATTTCCTGGCTAATTAAAATGAATGTTGTATCGATGAAAGATTATTTTAAAATGGCACTGATAGTGTT

TAGACATTGTCATAACATCAGCCGGGTGGATCACTAATTTGCAAATTTTACTAAAGATCTTGCCAATTAAACCCCTTCTA

GACACTCTCAAACACACTGTCAGTGACAGCTGAGAGACCACATGGTAAAGACATGATCACATTAAATTCACACAAGACTG

TTCTCCCTGGAACGGCTGAGGGAGAGAGACGGCCGCACGTCCCCATAGCAGGTGCCACTGAGTCAACCCAGCCAGACTGT

CATAAGAGAAAAGCAAATTTTTGGGTTTTATTTTACCCTAACTGCTTTCCAAAACAAACAGTGGAAATTCTTCTAAAAAT

CTGTAGGAAATTATCCTGAAAAATTGTGTTTCTCTTTGAGAGACAAGTGAAGAGAAGTGAATCTCTGAACCAATCTGAAA

CTCGCCAAGGTACAAGTTGGCTCACCTGGGAGGTGGTGGGCTTTAGCCCAGAGTCTTCTGGGACAGTTTGTCCCTCTCCA

GGGGTTGCAGAAGCGGCAACAATAGTGATGAGTCTGTCTCTGGGAAGTCACCTCAATTAACAGCCACAGTGAATTCCTTT

AAAAGTTAACTTTACAACCTCTGCCCAGCAGTGGGTCACTGGCGGAAATTTTCCAGATTTGAAAGTCAAGGTAGCATGAC

ATGGCATGTATTTAAATGATCAGATTTCATGCAGATAACCCTAACAGCCAACACTTATTAAGGGCCTACCATGTGCATGA

TGTCATTTATTCATTACAACAATCCTATAAGATTGGTGCTATTATTATCCCCGAAGGACAGATGAGAAAATTAAGACTCA

GAGATATTGCAACTCATCCTTGTACACAGAGTTGCTATGCAATATAGCTGGAATTCTAAACCCGGTCCCACTGAGGGCCG

TGACCCTGGTGGTGAAACTCCACAGTGTGACAGGCCTTATCCCTGAGATTTGTGGTCTATCCACATACCAGTCCATGGGA

GATTATGGTCTTTTCTGATATCCATGTGTAATATTTCTCCATCCACTGAGATATTCCGGA

In a search of public sequence databases, the NOV11 nucleic acid sequence has no hits using, an Expect value of 1.0. Public nucleotide databases include all GenBank databases and the GeneSeq patent database.

A disclosed NOV11 polypeptide (SEQ ID) NO:71) encoded by SEQ ID NO:70 has 139 amino acid residues and is presented in Table 11B using, the one-letter amino acid code. SignalP, Psort and/or Hydropathy results predict that NOV11 has no known signal peptide and is likely to be localized to the mitochondrial matrix space with a certainty of 0.4344. In alternative embodiments, the NOV11 protein is localized to a microbody (peroxisome) with a certainty of 0.3191; a lysosome (lumen) with a certainty of 0.1589; or the mitochondrial inner membrane with a certainty of 0.1162. NOV11 has a molecular weight of 15546.1 Daltons.

PROSITE analysis of NOV11 predicts that the NOV11 protein has one N-glycosylation site (Pattern-ID: ASN_GLYCOSYLATION PS00001 (Interpro)); two Protein kinase C phosphorylation sites (Pattern-ID: PKC_PHOSPHO_SITE PS00005 (Interpro)); and two N-myristoylation sites (Pattern-ID: MYRISTYL PS00008 (Interpro)), Table 11C lists the domain description from DOMAIN analysis results against NOV11. This indicates that the NOV11 sequence has properties similar to those of other proteins known to contain this transposase_17 domain.

TABLE 11B

Encoded NOV11 protein sequence.

(SEQ ID NO:71)
MCCGSRCNLHCSPASTFPCFLTNLHPAPHATFTQAFNRSAVSSHKLAQVVEMVSEVGHLSHSHLLLPKVSHVTKLQIIH

KQKTKSRLTKAMWNVDTWGQLNTLQVSAVRFEALKAEINGQIFKGKGYRCVQVSPRQMDL

TABLE 11C

Domain Analysis of NOV11

PFAM HbIM Domain Analysis of NOV11

| Model | Description | Score | E-value |
|---|---|---|---|
| Transposase_17 | (InterPro) Transposase IS200 like | −42.6 | 9.5 |

PRODOM Domain Analysis of NOV11

| Sequences producing High-scoring Segment Pairs: | High Score | Smallest Sum Probability P(N) |
|---|---|---|
| prdm:29481 p36 (1) AADR_RHOPA-ANAEROBIC AROMATIC DEGRA... | 51 | 0.61 |
| prdm:20370 p36 (1) YVAU_VACCC-HYPOTHETICAL 8.8 KD PROT... | 49 | 0.80 |
| prdm:44828 p36 (1) YM91_SCHPO-HYPOTHETICAL 91 KD PROTE... | 49 | 0.80 |
| prdm:28458 p36 (1) PR1_MEDTR-PATHOGENESIS-RELATED PROT... | 47 | 0.93 |
| prdm:29156 p36 (1) POL_SMRVH-POL POLYPROTEIN (REVERSE... | 46 | 0.97 |

BLOCKS Protein Domain Analysis

| AC# | Description | Strength | Score |
|---|---|---|---|
| BL01280E | 0 Glucose inhibited division protein A family p | 1592 | 1031 |
| BL00884D | 0 Osteopontin proteins. | 1466 | 1027 |
| BL00130E | 0 Oracil-DNA glycosylase proteins. | 1320 | 1006 |
| BL00441E | 0 Chalcone and stilbene synthases proteins. | 2040 | 1000 |

Table 11D provides percent homology to the domains identified in Table 11C.

According to a BlastP analysis, NOV11 has 38 of 64 aa residues(59%) identical to, and 49 of 64 (76%) positive

TABLE 11D

ProDom BLASTP results for NOV11

| ProDom Identifier | Protein/Organism | Length (aa) | Identity (%) | Positive (%) | Expect |
|---|---|---|---|---|---|
| prdm:29481 | p36 (1) AADR_RHOPA-DNA-binding ANAEROBIC AROMATIC DEGRADATION REGULATOR | 47 | 12/31 (38%) | 13/31 (41%) | 0.95 |
| prdm:20370 | p36 (1) YVAU_VACCC HYPOTHETICAL 8.8 KO PROTEIN | 53 | 10/20 (50%) | 12/20 (60%) | 1.6 |
| prdm:44828 | p36 (1) YM91_SCHPO-HYPOTHETICAL 91 KD PROTEIN IN COB INTRON. HYPOTHETICAL PROTEIN; MITOCHONDRION | 34 | 8/20 (40%) | 13/20 (65%) | 1.6 |
| prdm:28458 | p36 (1) PR1_MEDTR-PATHOGENESIS-RELATED PROTEIN PR-1 PRECURSOR | 45 | 12/26 (46%) | 16/26 (61%) | 2.7 |
| prdm:29156 | p36 (1) POL_SMRVH-POL POLYPROTEIN (REVERSE TRANSCRIPTASE (EC 2.7.7.49); ENDONUCLEASE) | 34 | 9/28 (32%) | 14/28 (50%) | 3.5 |

NOV11 polypeptide sequence produced no hits in a BLASTP search for homology (Expect value setting=1.0) to the GenBank and EMBL public databases. Other BLAST results did find homologous sequences from the Patp database, which is a proprietary database that contains sequences published in patents and patent publications. with, the 102 aa Human protein sequence SEQ ID NO:18455 from PN=EP1074617-A2 (patp: AAB95670, Expect=4.6e−16); 35 of 58 aa residues(60%) identical to, and 42 of 58 (72%) positive with, the 101 aa an secreted protein, SEQ ID NO: 4718 from PN=EP1033401-A2 (patp: AAG00637, Expect=5.1e−15);20 of 61 aa residues(32%)

identical to, and 35 of 61 (57%) positive with, the 136 aa *Arabidopsis thaliana* protein fragment SEQ ID NO: 42276 (patp:AAG34708, Expect=0.51); 20 of 61 (32%) identical to, and 35 of 61 (57%) positive with, the 150 aa *Arabidopsis thaliana* protein fragment SEQ ID NO: 42275 (patp:AAG34707, Expect=0.71); 20 of 61 (32%) identical to, and 35 of 61 (57%) positive with, the 162 aa *Arabidopsis thaliana* protein fragment SEQ ID NO: 42274 (patp:AAG34706. Expect=0.89); 20 of 61 (32%) identical to, and 35 of 61 (57%) positive with, the 270 aa *Arabidopsis thaliana* protein fragment SEQ ID NO: 21878 (patp:AAG19901, Expect=2.5); 13 of 36 (36%) identical to, and 17 of 36 (47%) positive with, the 66 aa Human endometrium tumour EST encoded protein 343 (patp:AAY60283, Expect=4.3); 10 of 26 (38%) identical to, and 18 of 26 (69%) positive with, the 64 aa Gene 8 human secreted protein homologous amino acid sequence #113— Bos taurus (patp:AAB39364, Expect=5.6); and 10 of 26 (38%) identical to, and 18 of 26 (69%) positive with, the 64 aa Human secreted protein sequence encoded by gene 8 SEQ ID NO:114 (patp:AAB39365, Expect=5.6). Patp results include those listed in Table 11E.

protein any of whose residues may be changed from the corresponding residue shown in Table 11B while still encoding a protein that maintains its transposase-like activities and physiological functions, or a functional fragment thereof. In the mutant or variant protein, up to about 60% percent of the residues may be so changed.

The invention further encompasses antibodies and antibody fragments, such as $F_{ab}$ or $(F_{ab})_2$, that bind immunospecifically to any of the proteins of the invention.

The above defined information for this invention suggests that this transposase-like protein (NOV11) may function as a member of a "transposase family". Therefore, the NOV11 nucleic acids and proteins identified here may be useful in potential therapeutic applications implicated in (but not limited to) various pathologies and disorders as indicated below. The potential therapeutic applications for this invention include, but are not limited to: transposase related research tools, for all tissues and cell types composing (but not limited to) those defined herein.

The protein similarity information, expression pattern, cellular localization, and map location for the protein and nucleic acid disclosed herein suggest that this novel intra-

TABLE 11E

Patp alignments of NOV11

| Sequences producing High-scoring Segment Pairs: | High Score | Smallest Sum Prob. P(N) |
|---|---|---|
| patp:AAG34708 *Arabidopsis thaliana* protein fragment SEQ I . . . | 74 | 0.40 |
| patp:AA034707 *Arabidopsis thaliena* protein fragment SEQ I . . . | 74 | 0.51 |
| patp:AAG34706 *Arabidopsis thaliana* protein fragment SEQ I . . . | 74 | 0.59 |
| patp:AAG19901 *Arabidopsis thaliana* protein fragment SEQ I . . . | 74 | 0.91 |
| patp:AAY60283 Human endometrium tumour EST encoded protei . . . | 53 | 0.99 |

The disclosed NOV11 nucleic acid encoding a transposase-like protein includes the nucleic acid whose sequence is provided in Table 11A, or a fragment thereof. The invention also includes a mutant or variant nucleic acid any of whose bases may be changed from the corresponding base shown in Table 11A while still encoding a protein that maintains its transposase-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 60% percent of the bases may be so changed.

The disclosed NOV11 protein of the invention includes the transposase-like protein whose sequence is provided in Table 11B. The invention also includes a mutant or variant cellular transposase domain containing protein-like NOV11 protein may have important structural and/or physiological functions characteristic of the novel transposase domain containing protein family. Therefore, the NOV11 nucleic acids and proteins are useful in potential diagnostic and therapeutic applications and as a research tool. These include serving as a specific or selective nucleic acid or protein diagnostic and/or prognostic marker, wherein the presence or amount of the nucleic acid or the protein are to be assessed. These also include potential therapeutic applications such as the following: (i) a protein therapeutic, (ii) a small molecule drug target, (iii) an antibody target (therapeutic, diagnostic, drug targeting/cytotoxic antibody), (iv) a nucleic acid useful in gene therapy (gene delivery/ gene ablation). (v) an agent promoting tissue regeneration in vitro and in vivo, and (vi) a biological defense weapon.

The NOV11 nucleic acids and proteins of the invention are useful in potential therapeutic applications including but not limited to those provided in Example 2, and/or other pathologies and disorders. For example, a cDNA encoding the transposase-like protein (NOV11) may be useful in gene and protein therapy, and the transposase-like protein (NOV11) may be useful when administered to a subject in need thereof. The NOV11 nucleic acid encoding the transposase-like protein, and the transposase-like protein of the invention, or fragments thereof, may further be useful in diagnostic applications wherein the presence or amount of the nucleic acid or the protein are to be assessed.

NOV11 nucleic acids and polypeptides are further useful in the generation of antibodies that bind immunospecifically to the novel NOV11 substances for use in therapeutic or diagnostic methods. These antibodies may be generated according to methods known in the art, using prediction from hydrophobicity charts, as described in the "Anti-NOVX Antibodies" section below. The disclosed NOV11 protein has multiple hydrophilic regions, each of which can be used as an immunogen. In one embodiment, a contemplated NOV11 epitope is from about amino acids 25 to 45. In additional embodiments, NOV11 epitopes are from about amino acids 70 to 105 and from about amino acids 1- to 139. These novel proteins can be used in assay systems for functional analysis of various human disorders, which will help in understanding of pathology of the disease and development of new drug targets for various disorders.

NOV12

A disclosed NOV12 nucleic acid of 2760 nucleotides (also referred to as 87917235 or 13373979) encoding a novel Novel Leucine Zipper Containing Type II membrane like protein-like protein is shown in Table 12A. An open reading frame was identified beginning with an ATG initiation codon at nucleotides 1789–791 and ending with a TGA codon at nucleotides 2101–2103. A putative untranslated region upstream from the initiation codon and downstream from the termination codon is underlined in Table 12A, and the start and stop codons are in bold letters.

TABLE 12A

NOV12 Nucleotide Sequence.

(SEQ ID NO:72)

TCTGCCTCCTGGGTTGAAGCGATTCTTCTGCCTCAGCCTCCTGAGTAGCTGGGACTACAAGCAGGCGCCACTACGCCTGGC

TAATTTTTGTATTTTTAGTAGAGACAGGGTTTCACCATATTGGCCAGGATGGTTTCAAACTCCTGACCTCATGATCTGCCC

ACCTAGGCCTCCCAAAGTGCTGGGATTACAGGCGTGAGCCACCGCGCCTGGTGAGGACTCCATTTTCTACCCCTAGGCTAA

AGAGCCTGGAGGATTATAGCTTACAGAGCAGAGAAGAACTCTGATACTCATAGGTGCATAGTGCTAGCTAGTCAGTAGACA

ATACTTAGATAATTCATTTTCTGATTTCTGACATTAGTGAGAGGTTGGGGTTTTGTTTGTTTAATAACAGCCTTCATTTAG

ATCTTTGCAAACAGCCTTGAATGAGGAATGTCCTTATGTTTCAGGGAACATATCAGGCCTGGAAGCAGCTTTTTTAGGATA

AAGCTCACTCATTGAACTTCAAATGCACTGACTCCAACCATTTCCTAAAATAAGGAAAATCTGTCTGCACAGACGGCATTT

TCACTCTCCTGAATGTTTTCTGTTGGTTGGTTGGTTGGTTGGTTTTATTGGTTGGTTGGTTTTGATACAGAGTGATACAAT

ATCATGAAGAATATTAGTCAGAAATGGGCACAGGTCTCAAGCAGGTCTTGGGACCTTGGGCTATTAATCTTTCTGGGCCT

TAATTTACTTATCTATAACATAAAAGGACCTTAATATATGATTGAGAAGGCCCAAACCACCTTTAAAATTTAGATCTGTGT

CTCCCCATCAGACCTCTCTGGAGACACAGGATCTTATTCAACCTCACACAGATTCTTGGGTTTCTGCCATTCACATCTACA

TTGAAAATTCTCCCATAAACTTTATACAAGTCCTTATGGAATCATTAAAGCTTTGCAAGAAAACAACAGTACCCATTATAA

AAGCCCAAGAAACAGAGAAGAAAATCATGTTTTATAACCCAAGAAATCTGTCCAAATCCTAGAATTTTTCTTCAGAGTACA

TCACAAGAAGGAACAGTCTCTTCCTTCCTAGTGGGAAAGTCAGGGTTTCTTTCATTTCCACCTTGTTCGCTTGTAACCGCT

CTCACCAGGCAAAGTTCTGAGCAAGTGAGATGGACTCATCTCGGAACTCCAGGCTGTGTTTACATAATTGGTAAAAGAAAC

ATTCCAATCCCATTCCTTCGTCAGCTCCGACAGACCAACCAGCATCCCCCTCCCACTTGCCACTTTGATAGGGGTGACTGG

TATCTCCATCTCCTTATCTTTGTTGATCATGTTTCTGGGTTTCCAATTGCGTCAATTTAACTGGTTGCCAATAATTCTGTC

ATCTGAGGGGAAAGCAGAATCTCAACTGAACATGCAGATGTCCTATTGAGACTTTGCCCATAAGGGAGCGTCTTTGGTGCT

TAAAATTCCATCTTTTGGACCTCATATCAGTTGATGTTTTTAGTTGCATCGGAAACCAACTCTAAGTGATTTAAGCAGGAG

AGAAAGTTATTTAAGGATATTTATAGTTCACAGAATCTCTGGAGGAGCGGGGGCTAGAAAACCAGACTTGAAGACTACAC

AGAGAGACTCCGAGTCCCCCTGGGACTGACCTGAGATGACCAGGGAGCTGGTATTTTTAGCTTCCAGAGGTAAATAACAGC

CTTCACTTCCATCAAAACTCATTAGGTAGAAAACACACCAAACATGGGAAAGGCGTTCCGGAGCTGGGCTACCAAAGAGAA

TAATAAATGTTCACTATAGTTTCATCTTCTAGTTTTGTACCATCCCTGAAACATTTTCTTTTTCCTCCAGGAGCCTCAAAA

TTACAGTTAAGTCTACAGTCAGACAGAAGGAAACTGGCATTTATTAAACACCAACTTTGTGCCTGGAAGATTCACTTACAA

TATCATAATCTTTACAATAACTCTGCAATATGGATCTCATTATCAGCATTCTTTTTTTGTTTGTTTGGTTGGTTGGTTTTG

GTGGTTTTAGTGTCAGGGTCTCACTCTGTTGCTCAGGCTGGAGCATGGTGGCATGATCATAACTCACTGCAGCCTTGAACT

TABLE 12A-continued

NOV12 Nucleotide Sequence.

CCTGGAATCAAATGATCCTCCCACCTCACCTCCAAGTAGCTGGGACTACAGGCATGCACCATCATGCCCAGCTAATTTTCT

TTTTCTTTTTTTTTAAGAGGTAGGATCTTGCTATAATGCCCAGGTTGGTCTCAAACTCCTGGTATCAAGTGATCCTCCCAT

CTTGGCCTCCCAAAGTGCGGGAATTACAGGTGTGAACCACTGCACCCAACCTCATTCTCAGCATTCTTATTATGTTTTGTC

TTATTATCCTCCAAGGATAGGTTAAGTAATTGTTATGGGTTGAATTGGGTCTCCCCAAAATTCCTATGTTAAAGTCCTAAT

CCCAGTATCTCAAAATGAAGGTAAGGTCTTTATAGAGGTAATCAAGTTAAAATGATGTTATTAGGATGGGCATTAATTCAA

TATGACTAGTCTCCTTATAAAAAGCAGACATTCACACACAAGGACACATGCACACAGGGAATATGATACCTGAGATTAGGG

TGATGCGTCTGCAGGCCAAAGAATGCCAAAGACTGCCAGCACACCACCAGAAACTGGGGGAGAGGCATGGAACGGATTCTT

CTTCACAGCTCTCAGAAAGAACCATGCTGCTGACACCTTGATCTTGGAATTCTAGCCACTGGAACTGTAAAACAATAAATT

TCTATT

The NOV12 nucleic acid was identified on chromosome 17 as run against the Genomic Daily Files made available by GenBank or from files downloaded from the individual sequencing centers. Exons were predicted by homology and the intron/exon boundaries were determined using standard genetic rules. Exons were further selected and refined by means of similarity determination using multiple BLAST (for example, tBlastN, BlastX, and BlastN) searches, and, in some instances, GeneScan and Grail. Expressed sequences from both public and proprietary databases were also added when available to further define and complete the gene sequence. The DNA sequence was then manually corrected for apparent inconsistencies thereby obtaining the sequences encoding the full-length protein. The NOV12 nucleic acid was further mapped to the p11 region of chromosome 17, a locus associated with prostate cancer (OMIM 176807) and congenital slow-channel myosthenic syndrome (OMIM 601462).

A disclosed NOV12 polypeptide (SEQ ID NO:73) encoded by SEQ ID NO:72 is 104 amino acid residues and is presented using the one-letter amino acid code in Table 12B. SignalP, Psort and/or Hydropathy results predict that NOV12 does not contain a known signal peptide and in the likely to be localized in the cytoplasm with a certainty of 0.8387 predicted by PSORT. In alternative embodiments, NOV12 is likely to be localized to the mitochondrial inner membrane with a certainty of 0.8387, to a microbody (peroxisome) with a certainty of 0.7480, the plasma membrane with a certainty of 0.4400, or the mitochondrial intermembrane space with a certainty of 0.3751. The NOV12 hydropathy profile is characteristic of the 'leucine zipper' gene family. A NOV12 polypeptide has a molecular Height of 11855.7 Daltons.

In a search of sequence databases, it was found, for example, that the nucleic acid sequence of this invention has 168 of 252 bases (66%) identical to a gb:GENBANK-ID:HS435C23|acc:Z92844.1 mRNA from Homo sapiens (Human DNA sequence from PAC 435C23 on chromosome X. Contains ESTs). No sequences were found in the EMBL, PIR or GenBank databases that had homology to the NOV12 polypeptide in an unfiltered BLASTP search (expectation value=1.0 for input parameter).

Table 12C lists the domain description from DOMAIN analysis results against NOV12. This indicates that the NOV12 sequence has properties similar to those of other proteins known to contain this domain.

TABLE 12B

Encoded NOV12 protein sequence.

(SEQ ID NO:73)
MFTIVSSSSFVPSLKHFLFPPGASKLQLSLQSDRRKLAFIKHQLCAWKIHLQYHNLYNNSAIWISLSAFFFCLFGWLVLV

VLVSGSHSVAQAGAWWHDHNSLQP

TABLE 12C

Domain Analysis of NOV12

PRODOM Analysis prdm:49789 p36 (1) RED1_HUMAN//DOUBLE-STRANDED RNA-SPECIFIC EDITASE 1 (DSRNA ADENOSINE DEAMINASE) (RNA EDITING ENZYME 1). RNA EDITING; HYDROLASE; ZINC; RNA-BINDING; REPEAT; ALTERNATIVE SPLICING, 55 aa.
Expect = 0.012, Identities = 12/23 (52%), Positives = 15/23 (65%)
for aa of Query: 82 to 104, Sbjct: 1 to 23 prdm:5031 p36 (5) NU4M(5)//OXIDOREDUCTASE NADH-UBIQUINONE CHAIN NAD UBIQUINONE MITOCHONDRION, 43 aa.
Expect = 0.63, Identities = 9/22 (40%), Positives = 12/22 (54%)
for aa of Query: 56 to 77, Sbjct: 20 to 41 prdm:22836 p36 (1) NU1C_SYNY3//NADH-PLASTOQUINONE OXIDOREDUCTASE CHAIN 1 (EC 1.6.5.3). OXIDOREDUCTASE; NAD; PLASTOQUINONE; TRANSMEMBRANE, 28 aa.
Expect = 0.83, Identities = 10/19 (52%), Positives = 14/19 (73%)
for aa of Query: 8 to 26, Sbjct: 9 to 27

PROSITE Analysis

| Pattern Name | Pattern | Position of NOV12 |
|---|---|---|
| ASN_GLYCOSYLATION PS00001 (Interpro) PDOC00001 | N[^P] [ST] [^P] | 58 |
| PKC_PHOSPHO_SITE PS00005 (Interpro) PDOC00005 | [ST]. [RK] | 13, 32 |
| LEUCINE_ZIPPER PS00029 (Interpro) PDOC00029 | L.{6}L.{6}L.{6}L | 30 |

BLOCKS Analysis

| AC# | Description | Strength | Score |
|---|---|---|---|
| BL00435D | Peroxidases proximal heme-ligand proteins. | 1230 | 1101 |
| BL00604C | Synaptophysin/synaptoporin proteins. | 1917 | 1030 |
| BL00439D | Acyltransferases ChoActase/COT/CPT family | 1332 | 1029 |
| BL00177C | DNA topoisomerase II proteins. | 1219 | 1021 |
| BL00487H | IMP dehydrogenase/GMP reductase proteins. | 1405 | 1016 |

PFam Analysis

[no hits above thresholds]

Patp BLAST results for NOV12 include those listed in Table 12D.

TABLE 12D

Patp alignments of NOV12

| Sequences producing High-scoring Segment Pairs: | Score | Smallest Sum Prob. |
|---|---|---|
| patp:AAG03340 Human secreted protein, SEQ ID NO: 7421-H . . . | 68 | 0.00028 |
| patp:AAY27571 Human secreted protein encoded by gene No . . . | 92 | 0.00071 |
| patp:AAB95648 Human protein sequence SEQ ID NO:18400-Ho . . . | 85 | 0.0010 |
| patp:AAB42720 Human ORFX ORF2484 polypeptide sequence SEQ . . . | 81 | 0.0023 |
| patp:AAG00591 Human secreted protein, SEQ ID NO: 4672-H . . . | 81 | 0.0023 |

A structure, referred to as the "leucine zipper", has been proposed to explain how some eukaryotic gene regulatory proteins work. The leucine zipper consist of a periodic repetition of leucine residues at every seventh position over a distance covering eight helical turns. The segments containing these periodic arrays of leucine residues seem to exist in an alpha-helical conformation. The leucine side chains extending from one alpha-helix interact with those from a similar alpha helix of a second polypeptide, facilitating dimerization; the structure formed by cooperation of these two regions forms a coiled coil.

The leucine zipper pattern is present in many gene regulatory proteins, e.g the CCATT-box and enhancer binding protein (C/EBP), the cAMP response element (CRE) binding proteins (e.g. CREB, CRE-BPI, ATFs), the Jun/AP1 family of transcription factors, the yeast general control protein GCN4, the fos oncoene and the fos-related proteins fra-1 and fos B. the C-myc, L-myc and N-myc oncogenes, and the octamer-binding transcription factor 2 (Oct-2/OTF-2). Thus, leucine zipper-like proteins are involved in cell proliferation, migration and differentiation. Leucine zipper-like proteins may thus be implicated in the onset and/or maintenance of diseases including cancer, e.g. prostate cancer, diabetes, abnormal wound healing, congenital slow-channel myosthenic syndrome, inflammation and/or other diseases and disorders. The consensus pattern for leucine zipper-like proteins is: L-x(6)-L-x(6)-L-x(6)-L.

The above defined information for this invention suggests that these Leucine Zipper Containing Type II membrane protein-like proteins (NOV12) may function as a member of a "leucine zipper family". Therefore, the NOV12 nucleic acids and proteins identified here may be useful in potential therapeutic applications implicated in (but not limited to) various pathologies and disorders as indicated herein. The potential therapeutic applications for this invention include, but are not limited to: cancer, e.g. prostate cancer, diabetes, abnormal wound healing, congenital slow-channel myosthenic syndrome, inflammation and/or other diseases and disorders.

The novel nucleic acid encoding a Leucine Zipper Containing Type II membrane like protein-like NOV12 protein includes the nucleic acid whose sequence is provided in Table 12A, or a fragment thereof. The invention also includes a mutant or variant nucleic acid any of whose bases may be changed from the corresponding base shown in Table 12A while still encoding a protein that maintains its Leucine Zipper Containing Type II membrane like protein-like activities and physiological functions, or a fragment of such a nucleic acid. The invention further includes nucleic acids whose sequences are complementary to the Leucine Zipper Containing Type II membrane like protein-like NOV12 nucleic acid sequence, including nucleic acid fragments that are complementary to any of the nucleic acids just described. The invention additionally includes nucleic acids or nucleic acid fragments, or complements thereto, whose structures include chemical modifications. In the mutant or variant NOV12 nucleic acids, and their complements, up to about 34% of the bases may be so changed.

The novel protein of the invention includes the Leucine Zipper Containing Type II membrane like protein-like NOV12 protein whose sequence is provided in Table 12B. The invention also includes a mutant or variant protein any of whose residues may be changed from the corresponding NOV12 residue while still encoding a protein that maintains its Leucine Zipper Containing Type 11 membrane like protein-like activities and physiological functions, or a functional fragment thereof. In the mutant or variant protein, up to about 37% of the NOV12 amino acid residues may be so changed.

The NOV12 nucleic acids and proteins of the invention are useful in potential therapeutic applications implicated in cancer, e.g. prostate cancer, diabetes, abnormal wound healing, congenital slow-channel myosthenic syndrome, inflammation and/or other pathologies and disorders. For example, a cDNA encoding the leucine zipper-like NOV12 protein may be useful in detecting prostate cancer, and the leucine zipper-like protein may be useful when administered to a subject in need thereof. By way of nonlimiting example, the compositions of the present invention will have efficacy for treatment of patients suffering from prostate cancer or congenital slow-channel myosthenic syndrome. The NOV12 nucleic acid encoding leucine zipper-like protein, and the leucine zipper-like protein of the invention, or fragments thereof, may further be useful in diagnostic applications, wherein the presence or amount of the nucleic acid or the protein are to be assessed. Additional disease indications and tissue expression for NOV12 is presented in Example 2.

NOV12 nucleic acids and polypeptides are further useful in the generation of antibodies that bind immunospecifically to the novel NOV12 substances for use in therapeutic or diagnostic methods. These antibodies may be generated according to methods known in the art, using prediction from hydrophobicity charts, as described in the "Anti-NOVX Antibodies" section below. For example the disclosed NOV12 proteins have multiple hydrophilic regions, each of which can be used as an immunogen. In one embodiment, a contemplated NOV12 epitope is from about amino acids 20 to 40. In additional embodiments, NOV12 epitopes are from about amino acids 20 to 25 and from about amino acids 30 to 40. This novel protein also has value in development of powerful assay systems for functional analysis of various human disorders, which will help in understanding of pathology of the disease and development of new drug targets for various disorders.

NOV13

A disclosed NOV13 nucleic acid of 1183 nucleotides (also referred to as 87919652) encoding a novel tyrosine kinase-like protein is shown in Table 13A. An open reading, frame was identified beginning with an ATG initiation codon at nucleotides 398–400 and ending with a TAG codon at nucleotides 1181–1183. A putative untranslated region upstream from the initiation codon is underlined in Table 13A, and the start and stop codons are in bold letters.

TABLE 13A

NOV13 nucleotide sequence.

(SEQ ID NO:74)
AGCTAGAGCTCCAAGGACCCCACGCCTGTGTCTCTGTGACAGAGCTCAAAGGGCCCTGGGCCTTCCCTCCCTGGCTCGGC

TGTGCTTGGGAGGGTTCCCCAGTCCAGAATCCCTAAGGAGCATGGGGCAGCTGATCCATCCCTGGTGTACAAACTGCTGA

CTGCAGACAGATGCTGAGCTACCCAAACCAACACCTAGCCTCTCCCTGAAGATCCTCCCAGGCTGAGAGAGTTCTGGGTG

TCCTAGGACCAAGGACACTGGCAGACTTCCAGAAGGGCCCCAAAGCCCTAACCTGTCCAGCCAGAGCATGCGTCTCAGC

AGAGCTGTCTTCCCAAGCCTTTGATGACAAACCAATTTCCCTCGATGATGTGCTTCTGAGTGCTCTGCTGAGGAACAATG

GGAAGTCTGCCCAGCAGAAGAAAATCTCTGCCAAGCCCAAGCTTGAGTTCCTCTGTCCAAGGCCAGGGACCTGTGACCAT

TABLE 13A-continued

NOV13 nucleotide sequence.

GGAAGCAGAGAGAAGCAAGGCCACAGCCGTGGCCCTGGGCAGTTTCCCGGCAGGTGGCCCGGCCGAGCTGTCGCTGAGAC

TCGGGGAGCCATTGACCATCGTCTCTGAGGATGGAGACTGGTGGACGGTGCTGTCTGAAGTCTCAGGCAGAGAGTATAAC

ATCCCCAGCGTCCACGTGGGCAAAGTCTCCCATGGGTGGCTGTATGAGGGCCTGAGCAGGGAGAAAGCAGAGGAACTGCT

GTTGTTACCTGGGAACCCTGGAGGGGCCTTCCTCATCCGGGAGAGCCAGACCAGGAGAGGCTCTTACTCTCTGTCAGTCC

GCCTCAGCCGCCCTGCATCCTGGGACCGGATCAGACACTACAGGATCCACTGCCTTGACAATGGCTGGCTGTACATCTCA

CCGCGCCTCACCTTCCCCTCACTCCAGGCCCTGGTGGACCATTACTCTGAGCTGGCGGATGACATCTGCTGCCTACTCAA

GGAGCCCTGTGTCCTGCAGAGGGCTGGCCCGCTCCCTGGCAAGGATATACCCCTACCTGTGACTGTGCAGAGGACACCAC

TCAACTGGAAAGAGCTGGACAGCTCCCTCCTGTTTTCTGAAGCTGCCACAGGGGAGGAGTCTCTTCTCAGTGAGGGTCTC

CGGGAGTCCCTCAGCTTCTACATCAGCCTGAATGACGAGGCTGTCTCTTTGGATGATGCCTAG

The NOV13 nucleic acid was identified on chromosome 20 by comparing it to the human genome database. Exons were predicted by homology and the intron/exon boundaries were determined using standard genetic rules. Exons were further selected and refined by means of similarity determination using multiple BLAST (for example, tBlastN, BlastX, and BlastN) searches, and, in some instances, GeneScan and Grail. Expressed sequences from both public and proprietary databases were also added when available to further define and complete the gene sequence. The DNA sequence was then manually corrected for apparent inconsistencies thereby obtaining the sequences encoding the full-length protein.

A disclosed NOV13 polypeptide (SEQ ID NO:75) encoded by SEQ ID NO:74 has 261 amino acid residues and is presented in Table 13B using the one-letter amino acid code. SignalP, Psort and/or Hydropathy results predict that NOV13 does not have a known signal peptide and is likely to be localized in the mitochondrial matrix space with a certainty of 0.4737. In an alternative embodiment, NOV13 is likely to be localized in the cytoplasm with a certainty of 0.4500.

TABLE 13B

Encoded NOV13 protein sequence.

(SEQ ID NO:75)

MGSLPSRRKSLPSPSLSSSVQGQGPVTMEAERSKATAVALGSFPAGGPAELSLRLGEPLTIVSEDGDWWTVLSEVSGREYN

IPSVHVGKVSHGWLYEGLSREKAEELLLLPGNPGGAFLIRESQTRRGSYSLSVRLSRPASWDRIRHYRIHCLDNGWLYISP

RLTFPSLQALVDHYSELADDICCLLKEPCVLQRAGPLPGKDIPLPVTVQRTPLNWKELDSSLLFSEAATGEESLLSEGLRE

SLSFYISLNDEAVSLDDA

The reverse complement for NOV13 is presented in Table 13C.

TABLE 13C

NOV13 reverse complement.

(SEQ ID NO:76)

CTAGGCATCATCCAAAGAGACAGCCTCGTCATTCAGGCTGATGTAGAAGCTGAGGGACTCCCGGAGACCCTCACTGAGAA

GAGACTCCTCCCCTGTGGCAGCTTCAGAAAACAGGAGGGAGCTGTCCAGCTCTTTCCAGTTGAGTGGTGTCCTCTGCACA

GTCACAGGTAGGGGTATATCCTTGCCAGGGAGCGGGCCAGCCCTCTGCAGGACACAGGGCTCCTTGAGTAGGCAGCAGAT

GTCATCCGCCAGCTCAGAGTAATGGTCCACCAGGGCCTGGAGTGAGGGGAAGGTGAGGCGCGGTGAGATGTACAGCCAGC

CATTGTCAAGGCAGTGGATCCTGTAGTGTCTGATCCGGTCCCAGGATGCAGGGCGGCTGAGGCGGACTGACAGAGAGTAA

GAGCCTCTCCTGGTCTGGCTCTCCCGGATGAGGAAGGCCCCTCCAGGGTTCCCAGGTAACAACAGCAGTTCCTCTGCTTT

CTCCCTGCTCAGGCCCTCATACAGCCACCCATGGGAGACTTTGCCCACGTGGACGCTGGGGATGTTATACTCTCTGCCTG

AGACTTCAGACAGCACCGTCCACCAGTCTCCATCCTCAGAGACGATGGTCAATGGCTCCCCGAGTCTCAGCGACAGCTCG

TABLE 13C-continued

NOV13 reverse complement.

GCCGGGCCACCTGCCGGGAAACTGCCCAGGGCCACGGCTGTGGCCTTGCTTCTCTCTGCTTCCATGGTCACAGGTCCCTG

GCCTTGGACAGAGGAACTCAAGCTTGGGCTTGGCAGAGATTTTCTTCTGCTGGGCAGACTTCCCATTGTTCCTCAGCAGA

GCACTCAGAAGCACATCATCGAGGGAAATTGGTTTGTCATCAAAGGCTTGGGAAGACAGCTCTGCTGAGACGCATGCTCT

GGCTGGACAGGTTAGGGCTTTGGGGGCCCTTCTGGAAGTCTGCCAGTGTCCTTGGTCCTAGGACACCCAGAACTCTCTCA

GCCTGGGAGGATCTTCAGGGAGAGGCTAGGTGTTGGTTTGGGTAGCTCAGCATCTGTCTGCAGTCAGCAGTTTGTACACC

AGGGATGGATCAGCTGCCCCATGCTCCTTAGGGATTCTGGACTGGGGAACCCTCCCAAGCACAGCCGAGCCAGGGAGGGA

AGGCCCAGGGCCCTTTGAGCTCTGTCACAGAGACACAGGCGTGGGGTCCTTGGAGCTCTAGCT

In a search of public sequence databases, the NOV13 amino acid sequence has 175 of 197 amino acid residues (89%) identical to, and 175 residues (89%) positive with, the 197 amino acid residue human protein tyrosine kinase (Accession No. Q9H135). Public amino acid databases include the GenBank databases, SwissProt, PDB and PIR.

It was also found that NOV13 had homology to the amino acid sequences shown in the BLASTP data listed in Table 13D.

TABLE 13D

BLAST results for NOV13

| Gene Index/ Identifier | Protein/Organism | Length (aa) | Identity (%) | Positives (%) | Expect |
|---|---|---|---|---|---|
| Q9H6Q3; AK025645; BAB15201.1 | CDNA: FLJ21992 FIS, CLONE HEP06554. *homo sapiens*. 6/2001 | 261 | 260/261 (100%) | 260/261, (100%) | 1e−149 |
| Q9H135; AL050318; CAB75365.1 | DJ977B1.1 (NOVEL PROTEIN TYROSINE KINASE WITH SRC HOMOLOGY DOMAIN 2DOMAINS) (FRAGMENT). *homo sapiens*. 6/2001 | 197 | 196/197 (99%) | 196/197, (99%) | 1e−113 |
| Q9D1Z9; AK020837; BAB32223.1 | A930009E21RIK PROTEIN. *mus musculus*. 6/2001 | 179 | 148/181 (82%) | 159/181, (88%) | 8e−79 |
| Q60898; U29056; AAA82756.1 | SRC-LIKE ADAPTER PROTEIN. *mus musculus*. 6/2001 | 281 | 106/253 (42%) | 148/253, (58%) | 2e−47 |
| Q13239; U30473; AAC50357.1; AAC27662.1; BAA13758.1 | PUTATIVE SRC-LIKE ADAPTER PROTEIN (SLAP). *homo sapiens*. 6/2001 | 276 | 96/219 (44%) | 135/219, (62%) | 1e−46 |

The homology of these sequences listed in Table 13D is shown graphically in the ClustalW analysis shown in Table 13E.

TABLE 13E

Information for the ClustalW proteins

1) NOV13 (SEQ ID NO:75)
2) Q9H6Q3 (SEQ ID NO:77)
3) Q9H135 (SEQ ID NO:78)
4) Q9D1Z9 (SEQ ID NO:79)
5) Q60898 (SEQ ID NO:80)
6) Q13239 (SEQ ID NO:89)

TABLE 13E-continued

Information for the ClustalW proteins

```
NOV13    1   MGSLPSRRKSLPSPSLSSSVQGQGPVTMEAERSKATAVALGSFPAGGPAELSLRLGEPLT  60
Q9H6Q3   1   MGSLPSRRKSLPSPSLSSSVQGQGPVTMEAERSKATAVALGSFPAGGPAELSLRLGEPLT  60
Q9H135   1   ------------------------------------------------------------   1
Q9D1Z9   1   ------------------------------------------------------------   1
Q60898   1   MG---NSMKSTSPPS-------ERPLSSSEGLESDFLAVLTDYPSPDISPPIFRRGEKLR  50
Q13239   1   MR---NSMKSTPAPA-------ERPLPNPEGLDSDFLAVLSDYPSPDISPPIFRRGEKLR  50

NOV13    61  IVSEDGDWWTVLSEVSGREYNIPSVHVAKVSHGWLYEGLSREKAEELLLLPGNPGGAFLI  120
Q9H6Q3   61  IVSEDGDWWTVLSEVSGREYNIPSVHVAKVSHGWLYEGLSREKAEELLLLPGNPGGAFLI  120
Q9H135   1   ----DGDWWTVLSEVSGREYNIPSVHVAKVSHGWLYEGLSREKAEELLLLPGNPGGAFLI   56
Q9D1Z9   1   -------------------MESVYVAKVAHGWLYEGLSREKAEELLLLPGNPGGAFLI   39
Q60898   51  VISDEGGWWKAISLSTGRESYIPGICVARVYHGWLEEGLGRDKAEELLQLPDTKIGSFMI  110
Q13239   51  VISDEGGWWKAISLSTGRESYIPGICVARVYHGWLFEGLGRDKAEELLQLPDTKVGSFMI  110

NOV13    121 RESQTRRGSYSLSVRLSRPASWDRIRHYRIHCLDNGWLYISPRLTFPSLQALVDHYSELA  180
Q9H6Q3   121 RESQTRRGSYSLSVRLSRPASWDRIRHYRIHCLDNGWLYISPRLTFPSLQALVDHYSELA  180
Q9H135   57  RESQTRRGSYSLSVRLSRPASWDRIRHYRIHCLDNGWLYISPRLTFPSLQALVDHYSELA  116
Q9D1Z9   40  RESQTRRGCYSLSVRLSRPASWDRIRHYRIHCLDNGWLYISPRLTFPSLHALVEHYSELA   99
Q60898   111 RESETKKGFYSLSVR-HR-----QVKHYRIFRLPNNWYYISPRLTFQCLEDLVTHYSEVA  164
Q13239   111 RESETKKGFYSLSVR-HR-----QVKHYRIFRLPNNWYYISPRLTFQCLEDLVNHYSEVA  164

NOV13    181 DDICCLLKEPCVLQRAGPLPGEDIP-----LPVTVQRTPLNWKELDSSLLFSEA-ATG--  232
Q9H6Q3   181 DDICCLLKEPCVLQRAGPLPGEDIP-----LPVTVQRTPLNWKELDSSLLFSEA-ATG--  232
Q9H135   117 DDICCLLKEPCVLQRAGPLPGEDIP-----LPVTVQRTPLNWKELDSSLLFSEA-ATG--  168
Q9D1Z9   40  DGICCPLREPCVLQKLGPLPGKDTP-----PPVTVPTSSLNWKKLDRSLLFLEAPASG--  152
Q60898   111 DGLCCVLTTPCLAQNIPAPTSHPSPCTSPGSPVTLRQKTFDWKRVSRLQEGSEG-AENPL  223
Q13239   111 DGLCCVLTTPCETQSTAAPAVRAS-----SSPVTLRQKTVDWRRVSRLQEDPEG-TENPL  218

NOV13    232 --EESLLSEGLRESLSFYISLN-DEAVSLDDA------------------------  261
Q9H6Q3   232 --EESLLSEGLRESLSFYISLN-DEAVSLDDA------------------------  261
Q9H135   168 --EESLLSEGLRESLSFYISLN-DEAVSLDDA------------------------  197
Q9D1Z9   152 --EASLLSEGLRESLSFYISLA-EDP--LDDA------------------------  179
Q60898   224 RVDESLFSYGLRESIASYLSITGDDSSFDRKKKSLSLMYTGSKRKSSFFSAPQYFED  281
Q13239   219 GVDESLFSYGLRESIASYLSITSEDNTSFDRKKKSISLMYGGSKRKSSFFSSPPYFED  276
```

Table 13F lists the domain description from DOMAIN analysis results against NOV13. This indicates that the NOV13 sequence has properties similar to those of other proteins known to contain this domain.

TABLE 13F

Domain Analysis of NOV13

PFAM Analysis

| Model | Description | Score | E-value |
|---|---|---|---|
| SH2 (InterPro) | Src homology domain 2 | 110.5 | 4.6e−37 |
| SH3 (InterPro) | SH3 domain | 26.3 | 0.00012 |

PRODOM Analysis

| Sequences producing High-scoring Segment Pairs: | High Score | Smallest Sum Probability |
|---|---|---|
| prdm: 64 p36 (157) SRC (10) KSYK (8) YES (7) // DOMAIN KI . . . | 214 | 2.4e−18 |
| prdm: 46 p36 (181) SRC (10) YES (7) GRB2 (6) // DOMAIN SH . . . | 77 | 0.0038 |

PROSITE Analysis

| Pattern Name | Pattern | Number in NOV13 |
|---|---|---|
| CAMP_PHOSPHO_SITE PS00004 (Interpro) PDOC00004 | [RK]{2}.[ST] | 2 |
| PKC_PHOSPHO_SITE PS00005 (Interpro) PDOC00005 | [ST].[RK] | 6 |
| CK2_PHOSPHO_SITE PS00006 (Interpro) PDOC00006 | [ST].{2}[DE] | 4 |

BLOCKS Analysis

| AC# | Description | Strength | Score |
|---|---|---|---|
| BL00512B | Alpha-galactosidase proteins. | 1411 | 1054 |
| BL00439A | Acyltransferases ChoActase/COT/CPT | 1390 | 1031 |
| BL00543A | HlyD family secretion proteins. | 1402 | 1029 |
| BL00535B | Respiratory chain NADH dehydrogenase | 1555 | 1025 |
| BL00564G | Argininosuccinate synthase proteins. | 1440 | 1023 |
| BL01276C | Peptidase family U32 proteins. | 1425 | 1023 |
| BL00481F | Thiol-activated cytolysins proteins. | 1675 | 1022 |
| BL00117A | Galactose-1-phosph. uridyl transferase | 1843 | 1020 |

Other BLAST results include sequences from the Patp database, which is a proprietary database that contains sequences published in patents and patent publications. Patp results include those listed in Table 13G.

TABLE 13G

Patp alignments of NOV13

| Sequences producing High-scoring Segment Pairs: | High Score | Smallest Sum Prob. P(N) |
|---|---|---|
| patp:AAB42993 Human OREX ORF2757 polypeptide sequence SEQ . . . | 1269 | 3.0e-129 |
| patp:AAY49420 PKA substrate, Src-family protein-Homo sa . . . | 342 | 6.9e-31 |
| patp:AAB37700 Human lymphocyte kinase-Homo sapiens, 508 . . . | 334 | 5.9e-30 |
| patp:AAY29668 Human src-family kinase laloo prorein-Hom . . . | 300 | 3.8e-26 |
| patp:AAY24421 Human yes1 protein-Homo sapiens, 543 aa. | 300 | 5.8e-26 |

Receptor tyrosine kinases (RTKs) and their associated signaling pathways are critical to proper cell function, and perturbations in these pathways contribute to the onset and progression of diseases, e.g. cancer. Given the strong evidence that links signaling by certain families of RTKs to the progression of breast cancer, it is not surprising that the expression profile of key downstream signaling intermediates in this disease has also come under scrutiny, particularly because some exhibit transforming potential or amplify mitogenic signaling pathways when they are overexpressed. Reflecting the diverse cellular processes regulated by RTKs, it is now clear that altered expression of such signaling proteins in breast cancer may influence not only cellular proliferation (e.g. Grb2) but also the invasive properties of the cancer cells (e.g. EMS1/cortactin).

SH2 domains are discrete structural motifs common to a variety of critical intracellular signaling proteins. Inhibitors of specific SH2 domains have become important therapeutic targets in the treatment and/or prevention of restenosis, cancers (including small cell lung), cardiovascular disease, osteoporosis, apoptosis among others. Considering the social and economic impact of these diseases significant attention has been focused on the development of potent and selective inhibitors of specific SH2 domains. In particular, considerable research has been performed on Src, PI 3-kinase, Grb2 and Lck.

Receptor tyrosine kinases are also important in diabetes. Diabetes mellitus is commonly considered as a disease of a scant beta-cell mass that fails to respond adequately to the functional demand. Tyrosine kinases may play a role for beta-cell replication, differentiation (neoformation) and survival. Transfection of beta-cells with DNA constructs coding for tyrosine kinase receptors yields a ligand-dependent increase of DNA synthesis in beta-cells. Several tyrosine kinase receptors, such as the VEGFR-2 (vascular endothelial growth factor receptor 2) and c-Kit, are present in pancreatic duct cells. Because ducts are thought to harbor beta-cell precursor cells, these receptors may play a role for the neoformation of beta-cells. The Src-like tyrosine kinase mouse Gtk (previously named Bsk/lyk) is expressed in islet cells, inhibits cell proliferation. Furthermore, Gtk confers decreased viability in response to cytokine exposure. Shb is a Src homology 2 domain adaptor protein which participates in tyrosine kinase signaling. Transgenic mice overexpressing Shb in beta-cells exhibit an increase in the neonatal beta-cell mass, an improved glucose homeostasis, but also decreased survival in response to cytokines and streptozotocin. Thus, tyrosine kinase signaling may generate multiple responses in beta-cells, involving proliferation, survival and differentiation.

The disclosed NOV13 nucleic acid encoding a receptor tyrosine kinase-like protein includes the nucleic acid whose sequence is provided in Table 13A, or a fragment thereof. The invention also includes a mutant or variant nucleic acid any of whose bases may be changed from the corresponding base shown in Table 13A while still encoding a protein that maintains its receptor tyrosine kinase-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject The disclosed NOV13 protein of the invention includes the receptor tyrosine kinase-like protein whose sequence is provided in Table 13B. The invention also includes a mutant or variant protein any of whose residues may be changed from the corresponding residue shown in Table 13B while still encoding a protein that maintains its receptor tyrosine kinase-like activities and physiological functions, or a functional fragment thereof.

The invention further encompasses antibodies and antibody fragments, such as $F_{ab}$ or $(F_{ab})_2$, that bind immunospecifically to any of the proteins of the invention.

The above defined information for this invention suggests that this receptor tyrosine kinase-like protein (NOV13) may function as a member of a "receptor tyrosine kinase family". Therefore, the NOV13 nucleic acids and proteins identified here may be useful in potential therapeutic applications implicated in (but not limited to) various pathologies and disorders as indicated below. The potential therapeutic applications for this invention include, but are not limited to: cancer and diabetes research tools, for all tissues and cell types composing (but not limited to) those defined here, e.g. normal and cancerous tissue and pancreatic tissue.

Based on the tissues in which NOV13 is most highly expressed; including spleen and pituitary; specific uses include developing products for the diagnosis or treatment of a variety of diseases and disorders.

The NOV13 nucleic acids and proteins of the invention are useful in potential therapeutic applications implicated in cancer including but not limited to breast cancer and diabetes and/or other pathologies and disorders. For example, a cDNA encoding the receptor tyrosine kinase—like protein (NOV13) may be useful in cancer therapy, and the receptor tyrosine kinase-like protein (NOV13) may be useful when administered to a subject in need thereof. By way of nonlimiting example, the compositions of the present invention will have efficacy for treatment of patients suffering from cancer including but not limited to breast cancer. The NOV13 nucleic acid encoding receptor tyrosine kinase-like protein, and the receptor tyrosine kinase-like protein of the invention, or fragments thereof, may further be useful in diagnostic applications, wherein the presence or amount of the nucleic acid or the protein are to be assessed. Additional disease indications and tissue expression for NOV13 is presented in Example 2.

NOV13 nucleic acids and polypeptides are further useful in the generation of antibodies that bind immuno-specifically to the novel NOV13 substances for use in therapeutic or diagnostic methods. These antibodies may be generated according to methods known in the art, using prediction from hydrophobicity charts, as described in the "Anti-NOVX Antibodies" section below. The disclosed NOV13 protein has multiple hydrophilic regions, each of which can be used as an immunogen. In one embodiment, a contemplated NOV13 epitope is from about amino acids 1 to 10. In another embodiment, a NOV13 epitope is from about amino acids 25 to 40. In additional embodiments, NOV13 epitopes are from about amino acids 100 to 110 from about amino acids 120 to 130 and from about amino acids 250 to 255. These novel proteins can be used in assay systems for functional analysis of various human disorders, which will help in understanding of pathology of the disease and development of new drug targets for various disorders.

NOV14

A disclosed NOV14 nucleic acid of 5193 nucleotides (also referred to as 87919652) encoding a novel multidrug resistance-associated transporter-like protein is shown in Table 14A. An open reading frame was identified beginning with an ATG initiation codon at nucleotides 71–73 and ending with a TGA codon at nucleotides 4652–4654. A putative untranslated region upstream from the initiation codon and downstream from the termination codon is underlined in Table 14A, and the start and stop codons are in bold letters.

TABLE 1A

NOV14 nucleotide sequence.

(SEQ ID NO:82)

CTCCGGCGCCCGCTCTGCCCGCCGCTGGGTCCGACCGCGCTCGCCTTCCTTGCAGCCGCGCCTCGGCCCCATGGACGCCC

TGTGCGGTTCCGGGGAGCTCGGCTCCAAGTTCTGGGACTCCAACCTGTCTGTGCACACAGAAACCCGGACCTCGCTCCC

TGCTTCCAGAACTCCCTGCTGGCCTGGGTGCCCTGCATCTACCTGTGGGTCGCCCTGCCCTGCTACTTGCTCTACCTGCG

GCACCATTGTCGTGGCTACATCATCCTCTCCCACCTGTCCAAGCTCAAGATGGTCCTGGGTGTCCTGCTGTGGTGCGTCT

CCTGGGCGGACCTTTTTTACTCCTTCCATGGCCTGGTCCATGGCCGGGCCCTGCCCCTGTTTTCTTTGTCACCCCCTTG

GTGGTGGGGGTCACCATGCTGCTGGCCACCCTGCTGATACAGTATGAGCGGCTGCAGGGCGTACAGTCTTCGGGGGTCCT

CATTATCTTCTGGTTCCTGTGTGTGGTCTGCGCCATCGTCCCATTCCGCTCCAAGATCCTTTTAGCCAAGGCAGAGGGTG

AGATCTCAGACCCCTTCCGCTTCACCACCTTCTACATCCACTTTGCCCTGGTACTCTCTGCCCTCATCTTGGCCTCGTTC

AGGGAGAAACCTCCATTTTTCTCCGCAAAGAATGTCGACCCTAACCCCTACCCTGAGACCAGCGCTGGCTTTCTCTCCCG

CCTGTTTTTCTGGTGGTTCACAAAGATGGCCATCTATGCTACCGGCATCCCCTGGAGGAGAAGGACCTCTGGTCCCTAA

AGGAAGAGGACAGATCCCAGATGGTGGTGCAGCAGCTCCTGGAGGCATGGAGGAAGCAGGAAAAGCAGACGGCACGACAC

AAGGCTTCAGCAGCACCTGGGAAAAATGCCTCCGGCGAGGACGAGGTGCTGCTGGGTGCCCGGCCCAGGCCCCGGAAGCC

CTCCTTCCTGAAGGCCCTGCTGGCCACCTTCGGCTCCAGCTTCCTCATCAGTGCCTGCTTCAAGCTTATCCAGGACCTGC

TCTCCTTCATCAATCCACAGCTGCTCAGCATCCTGATCAGGTTTATCTCCAACCCCATGGCCCCCTCCTCGTGGGGCTTC

CTGGTGGCTGGGCTGATGTTCCTGTGCTCCATGATGCAGTCGCTGATCTTACAACACTATTACCACTACATCTTTGTGAC

TGGGGTGAAGTTTCGTACTGGGATCATGGGTGTCATCTACAGGAAGGCTCTGGTTATCACCAACTCAGTCAAACGTGCGT

CCACTGTGGGGAAATTGTCAACCTCATGTCAGTGGATGCCCAGCGCTTCATGGACCTTGCCCCCTTCCTCAATCTGCTG

TGGTCAGCACCCCTGCAGATCATCCTGGCGATCTACTTCCTCTGGCAGAACCTAGGTCCCTCTGTCCTGGCTGGAGTCGC

TTTCATGGTCTTGCTGATTCCACTCAACGGAGCTGTGGCCGTGAAGATGCGCGCCTTCCAGGTAAAGCAAATGAAATTGA

AGGACTCGCGCATCAAGCTGATGAGTGAGATCCTGAACGGCATCAAGGTGCTGAAGCTGTACGCCTGGGAGCCCAGCTTC

CTGAAGCAGGTGGAGGGCATCAGGCAGGGTGAGCTCCAGCTGCTGCGCACGGCGGCCTACCTCCACACCACAACCACCTT

CACCTGGATGTGCAGCCCCTTCCTGGTGACCCTGATCACCCTCTGGGTGTACGTGTACGTGGACCCAAACAATGTGCTGG

ACGCCGAGAAGGCCTTTGTGTCTGTGTCCTTGTTTAATATCTTAAGACTTCCCCTCAACATGCTGCCCCAGTTAATCAGC

AACCTGACTCAGGCCAGTATGTCTCTGAAACGGATCCAGCAATTCCTGAGCCAAGAGGAACTTGACCCCAGAGTGTGGA

AAGAAAGACCATCTCCCCAGGCTATGCCATCACCATACACAGTGGCACCTTCACCTGGGCCCAGGACCTGCCCCCCACTC

TGCACAGCCTAGACATCCAGGTCCCGAAAGGGCACTGGTGGCCGTGGTGGGGCCTGTGGGCTGTGGGAAGTCCTCCCTG

TABLE 1A-continued

NOV14 nucleotide sequence.

GTGTCTGCCCTGCTGGGAGAGATGGAGAAGCTAGAAGGCAAAGTGCACATGAAGGGCTCCGTGGCCTATGTGCCCCAGCA
GGCATGGATCCAGAACTGCACTCTTCAGGAAAACGTGCTTTTCGGCAAAGCCCTGAACCCCAAGCGCTACCAGCAGACTC
TGGAGGCCTGTGCCTTGCTAGCTGACCTGGAGATGCTGCCTGGTGGGGATCAGACAGAGATTGGAGAGAAGGGCATTAAC
CTGTCTGGGGGCCAGCGGCAGCGGGTCAGTCTGGCTCGAGCTGTTTACAGTGATGCCGATATTTTCTTGCTGGATGACCC
ACTGTCCGCGGTGGACTCTCATGTGGCCAAGCACATCTTTGACCACGTCATCGGGCCAGAAGGCGTGCTGGCAGGCAAGA
CGCGAGTGCTGGTGACGCACGGCATTAGCTTCCTGCCCCAGACAGACTTCATCATTGTGCTAGCTGATGGACAGGTGTCT
GAGATGGGCCCCTACCCAGCCCTGCTGCAGCGCAACGGCTCCTTTGCCAACTTTCTCTGCAACTATGCCCCCGATGAGGA
CCAAGGGCACCTGGAGGACAGCTGGACCGCGTTGGAAGGTGCAGAGGATAAGGAGGCACTGCTGATTGAAGACACACTCA
GCAACCACACGGATCTGAGACACAATGATCCAGTCACCTATGTGGTCCACAAGCACTTTATGAGACAGCTGAGTGCCCTC
TCCTCAGATGGGGAGGGACAGGGTCCCCCTGTACCCCGGAGGCACCTCGGTCCATCACAGAAGGTGCAGGTGACAGAGGC
GAAGGCAGATGGGGCACTGACCCAGGAGGAGAAAGCAGCCATTGGCACTGTGGAGCTCAGTGTGTTCTGGGATTATGCCA
AGGCCGTGGGGCTCTGTACCACGCTGGCCATCTGTCTCCTGTATGTGGGTCAAAGTGCGGCTGCCATTGGAGCCAATGTG
TGGCTCAGTGCCTGGACAAATGATGCCATGGCAGACAGTAGACAGAACAACACTTCCCTGAGGCTGGGCGTCTATGCTGC
TTTAGGAATTCTGCAAGGGTTCTTGGTGATGCTGGCAGCCATGGCCATGGCAGCGGGTGGCATCCAGGCTGCCCGTGTGT
TGCACCAGGCACTGCTGCACAACAAGATACGCTCGCCACAGTCCTTCTTTGACACCACACCATCAGGCCGCATCCTCAAC
TGCTTCTCCAAGGACATCTATGTCGTTGATGAGGTTCTGGCCCCTGTCATCCTCATGCTGCTCAATTCCTTCTTCAACGC
CATCTCCACTCTTGTGGTCATCATGGCCAGCACGCCGCTCTTCACTGTGGTCATCCTGCCCCTGGCTCTGCTCTACACCT
TAGTGCAGCGCTTCTATGCAGCCACATCACGGCAACTGAAGCGGCTGGAATCAGTCAGCCGCTCACCTATCTACTCCCAC
TTTTCGGAGACAGTGACTGGTGCCAGTGTCATCCGGGCCTACAACCGCAGCCGGGATTTTGAGATCATCAGTGATACTAA
GGTGGATGCCAATCAGAGAAGCTGCTACCCCTACATCATCTCCAACCGGTGGCTGAGCATCGGAGTCGAGTTCGTGGGGA
ACTGCGTGGTGCTCTTTGCTGCACTATTTGCCGTCATCGGGAGGAGCAGCCTGAACCCGGGGCTGGTGGGCCTTTCTGTG
TCCTACTCCTTGCAGGTGACATTTGCTCTGAACTGGATGATACGAATGATGCCAGATTTGGAATCTAACATCGTGGCTGT
GGAGAGGGTCAAGGAGTACTCCAAGACAGAGACAGAGGCGCCCTGGGTGGTGGAAGGCAGCCGCCCTCCCCAAGGTTGGC
CCCCACGTGGGGAGGTGGAGTTCCGGAATTATTCTGTGCGCTACCGGCCGGGCCTAGACCTGGTGCTGAGAGACCTGAGT
CTGCATGTGCACGGTGGCGAGAAGGTGGGGATCGTGGGCCGCACTGGGGCTCGCAAGTCTTCCATGACCCTTTGCCTGTT
CCGCATCCTGGAGGCGGCAAAGCGTGAAATCCGCATTGATGGCCTCAATGTGGCAGACATCGGCCTCCATGACCTGCGCT
CTCAGCTGACCATCATCCCGCAGGACCCCATCCTGTTCTCGGGGACCCTGCGCATGAACCTGGACCCCTTCGGCAGCTAC
TCAGAGGAGGACATTTGGTGGCTTTGGAGCTGTCCCACCTGCACACGTTTGTGAGCTCCCAGCCGGCAGGCCTGGACTT
CCACTGCTCAGAGGGCGGGGAGAATCTCAGCGTGGGCCAGAGGCAGCTCGTGTGCCTGGCCCGAGCCCTGCTCCGCAAGA
GCCGCATCCTGGTTTTAGACGAGGCCACAGCTGCCATCGACCTGGAGACTGACAACCTCATCCAGGCTACCATCCGCACC
CAGTTTGATACCTGCACTGTCCTGACCATCGCACACCGGCTTAACACTATCATGGACTACACCAGGGTCCTGGTCCTGGA
CAAAGGAGTAGTAGCTGAATTTGATTCTCCAGCCAACCTCATTGCAGCTAGAGGCATCTTCTACGGCATGGCCAGAGATG
CTGGACTTGCCTAAAATATATTCCTGAGATTTCCTCCTGGCCTTTCCTGGTTTTCATCAGGAAGGAAATGACACCAAATA
TGTCCGCAGAATCGACTTGATAGCAAACACTGGGGGCACCTTAAGATTTTGCACCTGTAAAGTGCCTTACAGCGTAACTG
TGCTGAATGCTTTAGATGAGGAAATGATCCCCAACTGGTGAATGACACGCCTAAGGTCACAGCTAGTTTGAGCCAGTTAC
ACTAGTCCCCGGTCTCCCGATTCCCAACTGAGTGTTATTTGCACACTGCACTGTTTTCAAATAACGATTTTATGAAATGA
CCTCTGTCCTCCCTCTGATTTTTCATATTTTCTAAAGTTTCGTTTCTGTTTTTTAATAAAAAGCTTTTTCCTCCTGGAAC

TABLE 1A-continued

NOV14 nucleotide sequence.

AGAAGACAGCTGCTGGGTCAGGCCACCCCTAGGAACTCAGTCCTGTACTCTCGGGTGCTGCCTGAATCCATTAAAAATGG

GAGTACTGATGAAATAAAACTACATGGTCAACAGTAAAAAAAAAAAAAAAAAAAAAAAAAAAAAAAAAAAAA

The NOV14 nucleic acid was identified on chromosome 17 by comparing it to the human genome sequence. Exons were predicted by homology and the intron/exon boundaries were determined using standard genetic rules. Exons were further selected and refined by means of similarity determination using multiple BLAST (for example, tBlastN, BlastX, and BlastN) searches, and, in some instances, GeneScan and Grail. Expressed sequences from both public and proprietary databases were also added when available to further define and complete the gene sequence. The DNA sequence was then manually corrected for apparent incon- (Accession No. XM_038002). Public nucleotide databases include all GenBank databases and the GeneSeq patent database.

A disclosed NOV14 polypeptide (SEQ ID NO:83) encoded by SEQ ID NO:82 has 1527 amino acid residues and is presented in Table 14B using the one-letter amino acid code. SignalP, Psort and/or Hydropathy results predict that NOV14 has a signal peptide and is likely to be localized to the plasma membrane with a certainty of 0.8000. The most likely cleavage site for a NOV14 peptide is between amino acids 53 and 54 of SEQ ID NO.28, i.e. at CYL-LY.

TABLE 14B

Encoded NOV14 protein sequence.

(SEQ ID NO:83)

MDALCGSGELGSKFWDSNLSVHTENPDLTFCFQNSLLAWVPCIYLWVALPCYLLYLRHHCRGYIILSHLSKLKMVLGVLLW

CVSWADLFYSFHGLVHGRAPAPVFFVTPLVVGVTMLLATLLIQYERLQGVQSSGVLIIFWFLCVVCAIVPFRSKILLAKAE

GEISDPFRFTTFYIHFALVLSALILACFREKPPFFSAKNVDPNPYPETSAGFLSRLFFWWFTKMAIYGYRHPLEEKDLWSL

KEEDRSQMVVQQLLEAWRKQEKQTARHKASAAPGKNASGEDEVLLGARPRPRKPSFLKALLATFGSSFLISACFKLIQDLL

SFINPQLLSILIRFISNPMAPSWWGFLVAGLMFLCSMMQSLILQHYYHYIFVTGVKFRTGIMGVIYRKALVITNSVKRAST

VGEIVNLMSVDAQRFMDLAPFLNLLWSAPLQIILAIYFLWQNLGPSVLAGVAFMVLLIPLNGAVAVKMRAFQVKQMKLKDS

RIKLMSEILNGIKVLKLYAWEPSFLKQVEGIRQGELQLLRTAAYLHTTTTFTWMCSPFLVTLITLWVYVYVDPNNVLDAEK

AFVSVSLFNILRLPLNMLPQLISNLTQASVSLKRIQQFLSQEELDPQSVERKTISPGYAITIHSGTFTWAQDLPPTLHSLD

IQVPKGALVAVVGPVGCGKSSLVSALLGEMEKLEGKVHMKGSVAYVPQQAWIQNCTLQENVLFGKALNPKRYQQTLEACAL

LADLEMLPGGDQTEIGEKGINLSGGQRQRVSLARAVYSDADIFLLDDPLSAVDSHVAKHIFDHVIGPEGVLAGKTRVLVTH

GISFLPQTDFIIVLADGQVSEMGPYPALLQRNGSFANFLCNYAPDEDQGHLEDSWTALEGAEDKEALLIEDTLSNHTDLTD

NDPVTYVVQKQFMRQLSALSSDGEGQGRPVPRRHLGPSEKVQVTEAKADGALTQEEKAAIGTVELSVFWDYAKAVGLCTTL

AICLLYVGQSAAAIGANVWLSAWTNDAMADSRQNNTSLRLGVYAALGILQGFLVMLAAMAMAAGGIQAARVLHQALLHNKI

RSPQSFFDTTPSGRILNCFSKDIYVVDEVLAPVILMLLNSFFNAISTLVVIMASTPLFTVVILPLAVLYTLVQRFYAATSR

QLKRLESVSRSPIYSHFSETVTGASVIRAYNRSRDFEIISDTKVDANQRSCYPYIISNRWLSIGVEFVGNCVVLFAALFAV

IGRSSLNPGLVGLSVSYSLQVTFALNWMIRMMSDLESNIVAVERVKEYSRTETEAPWVVEGSRPPEGWPPRGEVEFRNYSV

RYRPGLDLVLRDLSLHVHGGEKVGIVGRTGAGKSSMTLCLFRILEAAKGETRIDGLNVADTGLHDLRSQLTIIPQDPILFS

GTLRMNLDPFGSYSEEDIWWALELSHLHTEVSSQPAGLDFQCSEGGENLSVGQRQLVCLARALLRKSRTLVLDEATAAIDL

ETDNLTQATIRTQFDTCTVLTIAHRLNTIMDYTRVLVLDKGVVAEFDSPANLIAARGIPYGMARDAGLA sistencies thereby obtaining the sequences encoding the full-length protein. The NOV14 nucleic acid was further mapped to the 17q21 locus. This locus is associated with breast cancer (OMIM 176705, 113705), glycogen storage disease (OMIM 232200), essential hypertension (OMIM 171190) and/or other diseases/disorders.

In a search of public sequence databases, the NOV14 nucleic acid sequence has 5151 of 5155 bases (99%) identical to a human ATP-binding cassette, sub-family C In a search of public sequence databases, the NOV14 amino acid sequence has 1527 of 1527 amino acid residues (100%) identical to, and 1527 residues (100%) positive with, the 1527 amino acid residue human canicular multispecific organic anion transporter/multidrug resistance-associated protein (Accession No. 015438). Public amino acid databases include the GenBank databases, SwissProt, PDB and PIR. It was also found that NOV14 had homology to the amino acid sequences shown in the BLASTP data listed in Table 14C.

TABLE 14C

BLAST results for NOV14

| Gene Index/Identifier | Protein/Organism | Length (aa) | Identity (%) | Positives (%) | Expect |
|---|---|---|---|---|---|
| MRP3_HUMAN; 015438; BAA28146.1; CAA76658.1; CAA76658.1; AAD01430.1; | CANALICULAR MULTISPECIFIC ORGANIC ANION TRANSPORTER 2 (MULTIDRUGRESISTANCE-ASSOCIATED PROTEIN 3). homo sapiens. 5/2000 | 1527 | 1527/1527 (100%) | 1527/1527 (100%) | 0.0 |
| MRP3_RAT; 088563; AAC25416.1; BAA28955.1 | CANALICULAR MULTISPECIFIC ORGANIC ANION TRANSPORTER 2 (MULTIDRUGRESISTANCE-ASSOCIATED PROTEIN 3) (MRP-LIKE PROTEIN-2) (MLP-2). rattus norvegicus. 5/2000 | 1522 | 1194/1528 (78%) | 1334/1528 (87%) | 0.0 |
| MRP1_HUMAN; P33527; AAB46616.1; AAB83983.1 | MULTIDRUG RESISTANCE-ASSOCIATED PROTEIN 1. homo sapiens. 5/2000 | 1531 | 872/1538 (57%) | 1131/1538 (74%) | 0.0 |
| Q9UQ99; AF022853; AAB83979.1 | MULTIDRUG RESISTANCE PROTEIN (FRAGMENT). homo sapiens. 6/2001 | 1515 | 870/1529 (57%) | 1128/1529 (74%) | 0.0 |
| O35379; AF022908; AAB80938.1 | MULTIDRUG RESISTANCE PROTEIN. mus musculus. 6/2001 | 1528 | 859/1540 (56%) | 1117/1540 (73%) | 0.0 |

The alignment and homology of these sequences is shown graphically in the ClustalW analysis in Table 14D.

TABLE 14D

Information for the ClustalW proteins

1) NOV14 (SEQ ID NO:83)
2) MRP3_HUMAN (SEQ ID NO:84)
3) MRP3_RAT (SEQ ID NO:85)
4) MRP1_HUMAN (SEQ ID NO:86)
5) Q9UQ99 (SEQ ID NO:87)
6) O35379 (SEQ ID NO:88)

```
NOV14        1   -MDALCGSGELGSKFWDSNLSVETENPDLIPCFQNSLLAWVPCIYLWVALPCYLLYLRHH  59
MRP3_HUMAN   1   -MDALCGSGELGSKFWDSNLSVETENPDLIPCFQNSLLAWVPCIYLWVALPCYLLYLRHH  59
MRP3_RAT     1   -MDRLCGSGELGSKFWDSNLTVYTNTPDLIPCFQNSLLAWVPCIYLWAALPCYLFYLRHH  59
MRP1_HUMAN   1   MALRGFCSADGSDPLWDWNVTWNTSNPDFIKCFQNTVLVWVPCFYLWACFPFYFLYLSRH  60
Q9UQ99       1   ----------------DWNVTWNTSNPDFTKCFQNTVLVWVPCFYLWACFPFYFLYLSRH  44
O35379       1   MALRSFCSADGSDPLWDWNVTWHTSNPDFIKCFQNTVLTWVPCFYLWSCFPLYFFYLSRH  60

NOV14       60   CRGYIILSHLSKLKMVLGVLLWCVSWADLFYSFHGLVHGRAPAPVFFVTPLVVGVTMLLA  119
MRP3_HUMAN  60   CRGYIILSHLSKLKMVLGVLLWCVSWADLFYSFHGLVHGRAPAPVFFVTPLVVGVTMLLA  119
MRP3_RAT    60   RLGYIVLSCLSRLKTALGVLLWCTSWVDLFYSFHGLVHGSSPAPVFFTTPLLVGITMLLA  119
MRP1_HUMAN  51   DRGYIQMTPLNKTKTALGFLLWIVCWADLFYSFWERSRGIFLAPVFLVSPTLLGITTLLA  120
Q9UQ99      45   DRGYIQMTPLNKTKTALGFLLWIVCWADLFYSFWERSRGIFLAPVFLVSPTLLGITTLLA  104
O35379      61   DRGYIQMTHLNKTKTALGFFLWITCWADLFYSFWERSQGVLRAPVLLVSPTLLGITMLLA  120

NOV14      120   TLLIQYERLQGVQSSGVLIIFWFLCVVCAIVPFRSKILLAKAEGEISDPFRFTTFYIHHA  179
MRP3_HUMAN 120   TLLIQYERLQGVQSSGVLIIFWFLCVVCAIVPFRSKILLAKAEGEISDPFRFTTFYIHHA  179
MRP3_RAT   120   TLLIQYERLRGVRSSGVLIIFWLLCVICAIIPFRSKILLALAEGKILDPFRFTTFYIYFA  179
MRP1_HUMAN 121   TFLIQLERRKGVQSSGIMLTFWLVALVCALAILRSKIMTALKEDAQVDLFRDITFYVYFS  180
Q9UQ99     105   TFLIQLERRKGVQSSGIMLTFWLVALVCALAILRSKIMTALKEDAQVDLFRDITFYVYFS  164
O35379     121   TFLIQLERRKGVQSSGIMLTFWLVALLCALAILRSKIISALKKDAHVDVFRDSTFYLYFT  180

NOV14      180   LVLSAILLACEREKPPFFSAKNVDPNPYPETSAGFLSRLFFWWFIKMAIYGYRHPLEEKD  239
MRP3_HUMAN 180   LVLSAILLACEREKPPFFSAKNVDPNPYPETSAGFLSRLFFWWFIKMAIYGYRHPLEEKD  239
MRP3_RAT   180   LVLCAFILSCQEKPPLFSPENLDTNPCPEASAGFFSRLSFWWFIKLAILGYRRPLEDSD  239
MRP1_HUMAN 181   LLLIQLVLSCFSDRSPLFSETIHDPNPCPESSASFLSRITFWWIIGLIVRGYRQPLEGSD  240
Q9UQ99     165   LLLIQLVLSCFSDRSPLFSETIHDPNPCPESSASFLSRITFWWIIGLIVRGYRQPLEGSD  224
O35379     181   LVLVQLVLSCFSDCSPLFSETVHDRNPCPESSASFLSRITFWWITGMMVHGYRQPLESSD  240
```

TABLE 14D-continued

Information for the ClustalW proteins

```
NOV14       240 LWSLKEEDRSQMVVQQLLEAWRKQEKQTARHKASAAPGK--------------NASGEDEV 286
MRP3_HUMAN  240 LWSLKEEDRSQMVVQQLLEAWRKQEKQTARHKASAAPGK--------------NASGEDEV 286
MRP3_RAT    240 LWSLSEEDCSHKVVQRLLEAWQKQQTQAS-GPQTAALEP--------------KIAGEDEV 285
MRP1_HUMAN  241 LWSLNKEDTSEQVVPVLVKNWKKECAKTRKQPVKVVYSS-KDPAQPKESSKVDANEEVEA 299
Q9UQ99      225 LWSLNKEDTSEQVVPVLVKNWKKECAKTRKQPVKVVYSS-PDPAQPKESSKVDANEEVEA 283
O35379      241 LWSLNKEDTSEEVVPVLVNNWKKECDKSRKQPVRIVYAPPKDPSKPKGSSQLDVNEEVEA 300

NOV14       287 LLGARP-RPRKPSFLKALLATFGSSFLISACFKLIQDLLSFINPQLLSILIRFISNPMAP 345
MRP3_HUMAN  287 LLGARP-RPRKPSFLKALLATFGSSFLISACFKLIQDLLSFINPQLLSILIRFISNPMAP 345
MRP3_RAT    286 LLKARP-KTKKPSFLRALVRIFTSSLLMGACFKLIQDLSPSS-THSCSASSSGIFRPHGP 343
MRP1_HUMAN  300 LIVKSPQKEWNPSLFKVLYKTFGPYFLMSFFFKAIHDLMMFSGPQIILKLLIKFVNDTKAP 359
Q9UQ99      284 LIVKSPQKEWNPSLFKVLYKTFGPYFLMSFFFKAIHDLMMFSGPQIILKLLIKFVNDTKAP 343
O35379      301 LIVKSPHKDREPSLFKVLYKTFGPYFLMSFLYKALHDLMMFAGPKTIELIINFVNDREAP 360

NOV14       346 SWWGFLVAGLMFLCSMMQSLIIQHYYHYIFVTGVKFRTGIMGVIYRKALVITNSVKRAST 405
MRP3_HUMAN  346 SWWGFLVAGLMFLCSMMQSLIIQHYYHYIFVTGVKFRTGIMGVIYRKALVITNSVKRAST 405
MRP3_RAT    344 YWWGFLLAGLMFVSSTMQTLILHQHYHCIFVMAIRIRTATIGVIYRKALTITNSVKREYT 403
MRP1_HUMAN  360 DWQGYGYTVLFVTACLQTLVLHQMFHICFVSGMRIKTAVIGAVYRKALVITNSARKSST 419
Q9UQ99      344 DWQGYFYTVLFVTACLQTLVLHQMFHICFVSGMRIKTAVIGAVYRKALVITNSARKSST 403
O35379      361 DWQGYFYTALLFVSACLQTLALHQMFHICFVSGMRIKTAVVGAVYRKALLITNAARKSST 420

NOV14       406 VGEIVNLMSVDAQRFMDLAPEINLIWSAPLQIILAIYFLWQNLGPSVLAGVAFMVLLIPL 465
MRP3_HUMAN  406 VGEIVNLMSVDAQRFMDLAPEINLIWSAPLQIILAIYFLWQNLGPSVLAGVAFMVLLIPL 465
MRP3_RAT    404 VGEMVNLMSVDAQRFMDVSPFINLWSAPLQVILAIYFLWQILGPSALAGVAVRVLLIPL 463
MRP1_HUMAN  420 VGEIVNLMSVDAQRFMDLATYINMIWSAPLQVILALYLLWLNLGPSVLAGVAVMVLMVPV 479
Q9UQ99      404 VGEIVNLMSVDAQRFMDLATYINMIWSAPLQVILALYLLWNLGPSVLAGVAVMVLMVPV 463
O35379      421 VGEIVNLMSVDAQRFMDLATYINMIWSAPLQVILAIYFLWLSLGPSVLAGVAVMILMVPL 480

NOV14       466 NGAVAVKMRAFQVKQMKLKDSRIKLMSEILNGIKVLKLYAWEPSFLKQVEGIRQGELQLL 525
MRP3_HUMAN  466 NGAVAVKMRAFQVKQMKLKDSRIKLMSEILNGIKVLKLYAWEPSFLKQVEGIRQGELQLL 525
MRP3_RAT    464 NGAVSMKMKTYVQQMKFKLSRIKLMSEILNGIKVLKLYAWEPTFLEQVEGIRQGELQLL 523
MRP1_HUMAN  480 NAVMAMKTKTYQVAHMKSKDNRIKLMNEILNGIKVLKLYAWELAFKDKVLAIRQEELKVL 539
Q9UQ99      464 NAVMAMKTKTYQVAHMKSKDNRIKLMNEILNGIKVLKLYAWELAFKDKVLAIRQEELKVL 523
O35379      481 NAVMAMKTKTYQVAHMKSKDNRIKLMNEILNGIKVLKLYAWELAFQDKVMSIRQEELKVL 540

NOV14       526 RTAAYLHTTTTFTWMCSPFLVTLITLWVYVYVDPNNVLDAEKAFVSVSLFNILRLPLNML 585
MRP3_HUMAN  526 RTAAYLHTTTTFTWMCSPFLVTLITLWVYVYVDPNNVLDAEKAFVSVSLFNILRLPLNML 585
MRP3_RAT    524 RKGAYLQAISTFIWYCTPFMVTLITLGVYVCVDKNNVLDAEKAFVSLSLFNILKIPLNLL 583
MRP1_HUMAN  540 KKSAYLSAVGTFTWVCTPFLVALCITFAVYYTIDENNILDAQTAFVSLALFNILRFPLNIL 599
Q9UQ99      524 KKSAYLSAVGTFTWVCTPFLVALCITFAVYYTIDENNILDAQTAFVSLALFNILRFPLNIL 583
O35379      541 KKSAYLAAVGTFTWVCTPFLVALSTFAVFVTVDERNILDAKKAFVSLALFNILRFPLNIL 600

NOV14       586 PQLISNLTQASVSLKRIQQFLSQEELDPQSVERKTISPG---YATTIHSGTFTWAQDLPP 642
MRP3_HUMAN  586 PQLISNLTQASVSLKRIQQFLSQEELDPQSVERKTISPG---YATTIHSGTFTWAQDLPP 642
MRP3_RAT    584 PQLISGMTQTSVSLKRIQDFINQDELDPQCVERKTISPG---RAITIHNGTFSWSKDLPP 640
MRP1_HUMAN  600 PMVISSIVQASVSLKRLRIFLSHEELEPDSIERRPVKDGGGTNSITVRNATFTWARSDPP 659
Q9UQ99      584 PMVISSIVQASVSLKRLRIFLSHEELEPDSIERRPVKDGGGTNSITVRNATFTWARSDPP 643
O35379      601 PMVISSIVQASVSLKRLRIFLSHEELEPDSIERRSIKSGEG-NSITVKNATFTWARGEPP 659

NOV14       643 TLHSLDIQVPKGALVAVVGPVGCGKSSLVSALLGEMEKLEGKVHMKGSVAYVPQQAWIQN 702
MRP3_HUMAN  643 TLHSLDIQVPKGALVAVVGPVGCGKSSLVSALLGEMEKLEGKVHMKGSVAYVPQQAWIQN 702
MRP3_RAT    641 TLHSIDIQIPKGALVAVVGPVGCGKSSLVSALLEGAVSVKGSVAYVPQQAWIQN 700
MRP1_HUMAN  660 TLNGITFSIPEGALVAVVGQVGCGKSSLLSALLAEMDKVEGHVAIKGSVAYVPQQAWIQN 719
Q9UQ99      644 TLNGITFSIPEGALVAVVGQVGCGKSSLLSALLAEMDKVEGHVAIKGSVAYVPQQAWIQN 703
O35379      660 TLNGITFSIPEGALVAVVGQVGCGKSSLLSALLAEMDKVEGHVTLKGSVAYVPQQAWIQN 719

NOV14       703 CTLQENVLFGKALNPKRYQQTLEACALLADLEMLPGGDQTEIGEKGINLSGGQRQRVSLA 762
MRP3_HUMAN  703 CTLQENVLFGKALNPKRYQQTLEACALLADLEMLPGGDQTEIGEKGINLSGGQRQRVSLA 762
MRP3_RAT    701 CTLQENVLFGQPMNPKRYQQALETCALLADLEVLPGGDQTEIGEKGINLSGGQRQRVSLA 760
MRP1_HUMAN  720 DSLRENILFGCQLEEPYYRSVIQACALLPDLEILPSGDRTEIGEKGVNLSGGQKQRVSLA 779
Q9UQ99      704 DSLRENILFGCQLEEPYYRSVIQACALLPDLEILPSGDRTEIGEKGVNLSGGQKQRVSLA 763
O35379      720 DSLRENILFGHPLQENYYKAVMEACALLPDLEILPSGDRTEIGEKGVNLSGGQKQRVSLA 779

NOV14       763 RAVYSDADIFLLDDPLSAVDSHVAKHIFDHVIGPKCVLAGKTRVLVTHGISFLPQTDFII 822
MRP3_HUMAN  763 RAVYSDADIFLLDDPLSAVDSHVAKHIFDHVIGPKCVLAGKTRVLVTHGISFLPQTDFII 822
MRP3_RAT    761 RAVYSDADIFLLDDPLSAVDSHVAKHIFDQVIGPRCVLAGKTRVLVTHGISFLPQTDFII 820
MRP1_HUMAN  780 RAVYSNADIYLFDDPLSAVDAHVGKHIFENVIGPKGMLKNKTRILVTHSMSYLPQVDVII 839
Q9UQ99      764 RAVYSNADIYLFDDPLSAVDAHVGKHIFENVIGPKGMLKNKTRILVTHSMSYLPQVDVII 823
O35379      780 RAVYSNSDIYLFDDPLSAVDAHVGKHIFEKVVGPNGLLKNKTRILVTHGISYLPQVDVII 839

NOV14       823 VLADGQVSEMGPYPALLQRNGSFANFLCNYAPDEDQGHLEDSWTALEGAEDKEALLIEDT 882
MRP3_HUMAN  823 VLADGQVSEMGPYPALLQRNGSFANFLCNYAPDEDQGHLEDSWTALEGAEDKEALLIEDT 882
MRP3_RAT    821 VLADGQITEMGHYSELLQHDGSFANHLQHAN-EANEGVLQHAN-EEVLLLEDT 876
MRP1_HUMAN  840 VMSGKISEMGSYQELLARDCAFAEFLRTYASTEQE----------QDAENGVTGVSGP 889
Q9UQ99      824 VMSGKISEMGSYQELLARDCAFAEFLRTYASTEQE----------QDAENGVTGVSGP 873
O35379      840 VMSGKISEMGSYQELLDRDCAFAEFLRTYANAEQD----------LASEDD---SVSGS 886
```

TABLE 14D-continued

Information for the ClustalW proteins

```
NOV14       883  LSNHTDLTDNDPVTYVVQKQFMRQLSALSSDGEGQGRPVPRRHLGPSEK-VQVTEAKADG  941
MRP3_HUMAN  883  LSNHTDLTDNDPVTYVVQKQFMRQLSALSSDGEGQGRPVPRRHLGPSEK-VQVTEAKADG  941
MRP3_RAT    877  LSTHTDLTDTEPAIYEVTKQFMRENSSLSSEGEGQNRPVLKRYTSSLEKEVPATQTKETG  936
MRP1_HUMAN  890  GKEAKQMENGMLVTDSAGKQLQRQLSSSSS----YSGDISRHHNSTAELQKAEAKKEETW  945
Q9UQ99      874  GKEAKQMENGMLVTDSAGKQLQRQLSSSSS----YSGDISRHHNSTAELQKAEAKKEETW  929
O35379      887  GKESKPVENGMLVTDTVGKHLQRHLSNSSS----HSGDTSQQHSSIAELQKAGAK-EETW  941

NOV14       942  ALTQEEKAAIGTVELSVFWDYAKAVGLCTTLAICLLYVGQSAAAIGANVWLSAWTNDA-M 1000
MRP3_HUMAN  942  ALTQEEKAAIGTVELSVFWDYAKAVGLCTTLAICLLYVGQSAAAIGANVWLSAWTNDA-M 1000
MRP3_RAT    937  ALIKEEIAETCNVKLSVYWDYAKSVGLCTTLFICLLYAGQNAVAIGANVWLSAWTNDV-E  995
MRP1_HUMAN  946  KLMEADKAQTGQVKLSVYWDYMKAIGLFISFLSIFLFMCNHVSALASNYWLSLWTDDP-I 1004
Q9UQ99      930  KLMEADKAQTGQVKLSVYWDYMKAIGLFISFLSIFLFMCNHVSALASNYWLSLWTDDP-I  988
O35379      942  KLMEADKAQTGQVQLSVYWNYMKAIGLFITFLSIPLFLCNHVSALASNYWLSLWTDDPPY 1001

NOV14      1001  ADSRQNNTSLRLGVYAALGILQGFLVMLAAMAMAAGGIQAARVLHQALLHNKIRSPQSFF 1060
MRP3_HUMAN 1001  ADSRQNNTSLRLGVYAALGILQGFLVMLAAMAMAAGGIQAARVLHQALLHNKIRSPQSFF 1060
MRP3_RAT    996  EHGQQNNLSVRLGVYATLGILQGLLVMLSAFTMVVGAIQAARLLHTALLHNQIRAPQSFF 1055
MRP1_HUMAN 1005  VNGTQEHIKVRLSVYGALGISQGIAVFGYSMAVSIGGILASRCLHVDLLHSILRSPMSFF 1064
Q9UQ99      989  VNGTQEHLKVRLSVYGALGISQGIAVFGYSMAVSIGGILASRCLHVDLLHSILRSPMSFF 1048
O35379     1002  VNGTQANRNFRLSVYGALGILQGAAIFGYSMAVSIGGIFASRRLHLDLLVNVLRSPMSFF 1061

NOV14      1061  DTTPSGRIENCFSKDIYVVDEVLAPVILMLLNSFFNAISTLVVIMASTPLFTVVILPLAV 1120
MRP3_HUMAN 1061  DTTPSGRIENCFSKDIYVVDEVLAPVILMLLNSFFNAISTLVVIMASTPLFTVVILPLAV 1120
MRP3_RAT   1056  DTTPSGRILNRFSKDIYVIHEVLAPTILMLFNSFYTSISTIVVVASTPLFCVVVLPLAV 1115
MRP1_HUMAN 1065  ERTPSGNLVNRFSKELDTVDSMIPEVIKMFMGSNFNVIGACIVILLATPIAAIIIPPLGL 1124
Q9UQ99     1049  ERTPSGNLVNRFSKELDTVDSMIPEVIKMFMGSLFNVIGACIVLLATPIAAIIIPPLGL 1108
O35379     1062  ERTPSGNLVNRFSKELDTVDSMIPQVIKMFMGSLFSVIGAVIILLATPIAAVIIPPLGL 1121

NOV14      1121  LYTLVQRFYAATSRQLKRLESVSRSPIYSHFSETVTGASVIRAYNRSRDFEIISDTKVDA 1180
MRP3_HUMAN 1121  LYTLVQRFYAATSRQLKRLESVSRSPIYSHFSETVTGASVIRAYNRSRDFEIISDTKVDA 1180
MRP3_RAT   1116  FYGFVQRFYAATSRQLKRLESVSRSPIFSHFSETVTCTSVIRAYGRVQDFKVLSDAKVDS 1175
MRP1_HUMAN 1125  IYFFVQRFYVASSRQLKRLESVSRSPVYSHFNETLLGVSVIRAFEEQERFIHQSDLKVDE 1184
Q9UQ99     1109  IYFFVQRFYVASSRQLKRLESVSRSPVYSHFNETLLGVSVIRAFEEQERFIHQSDLKVDE 1168
O35379     1122  VYFFVQRFYVASSRQLKRLESVSRSPVYSHFNETLLGVSVIRAFEEQERFIHQSDLKVDE 1181

NOV14      1181  NQRSCYPYIISNRWLSIGVEFVGNCVVLFAALFAVIGRSSLNPGLVGLSVSYSLQVTFAL 1240
MRP3_HUMAN 1181  NQRSCYPYIISNRWLSIGVEFVGNCVVLFAALFAVIGRSSLNPGLVGLSVSYSLQVTFAL 1240
MRP3_RAT   1176  NQETTYPYIASNRWIGVHVDFVGNCVVLFSALFAVIGRNSLNPGLVGLSVSYALQVTLSL 1235
MRP1_HUMAN 1185  NQKAYYPSIVANRWIAVRLDCVGNCIVLFAALFAVISRHSLSAGLVGLSVSYSLQVTTYL 1244
Q9UQ99     1169  NQKAYYPSIVANRWIAVRLDCVGNCIVLFAALFAVISRHSLSAGLVGLSVSYSLQVTTYL 1228
O35379     1182  NQKAYYPSIVANRWIAVRLDCVGNCIVLFAALFAVISRHSLSAGLVGLSVSYSLQTTAYL 1241

NOV14      1241  NWMIRMMSDLESNIVAVERVKEYSKTETEAPWVVEGSRPPEGWPPRGEVEFRNYSVRYRP 1300
MRP3_HUMAN 1241  NWMIRMMSDLESNIVAVERVKEYSKTETEAPWVVEGSRPPEGWPPRGEVEFRNYSVRYRP 1300
MRP3_RAT   1236  NWMIRTLSDLESNIIAVERVKEYSKTETEAPWVLESNRAPEGWPRSGVVEFRNYSVRYRP 1295
MRP1_HUMAN 1245  NWLVRMSSEMETNIVAVERVKEYSETEKEAPWQIQETAPPSSWPQVGRVEFRNYCLRYRE 1304
Q9UQ99     1229  NWLVRMSSEMETNIVAVERVKEYSETEKEAPWQIQETAPPSSWPQVGRVEFRNYCLRYRE 1288
O35379     1242  NWLVRMSSEMETNIVAVERVKEYSETEKEAPWQIQETAPPSTWPHSGRVEFRDYCLRYRE 1301

NOV14      1301  GLDLVLRDLSLHVHGGEKVGIVGRTGAGKSSMTLCLFRILEAAKGEIRIDGLNVADIGLH 1360
MRP3_HUMAN 1301  GLDLVLRDLSLHVHGGEKVGIVGRTGAGKSSMTLCLFRILEAAKGEIRIDGLNVADIGLH 1360
MRP3_RAT   1296  GLELVLKNLTLHVQGGEKVGIVGRTGAGKSSMTLCLFRILEAAEGEIFIDGLNVAHIGLH 1355
MRP1_HUMAN 1305  DLDFVLRHINETINGGERVGIVGRTGAGKSSLTLGLFRINESAEGEIIIDGINIAKIGLH 1364
Q9UQ99     1289  DLDFVLRHINVTINGGERVGIVGRTGAGKSSLTLGLFRINESAEGEIIIDGINIAKIGLH 1348
O35379     1302  DLDLVLKHINVTIEGGEKVGIVGRTGAGKSSLTLGLFRINESAEGEIIIDGVNIAKIGLH 1361

NOV14      1361  DLRSQLTIIPQDPILFSGTLRMNLDPFGSYSEEDIWWALEISHLHTFVSSQPAGLDFQCG 1420
MRP3_HUMAN 1361  DLRSQLTIIPQDPILFSGTLRMNLDPFGSYSEEDIWWALEISHLHTFVSSQPAGLDFQCS 1420
MRP3_RAT   1356  DLRSQLTIIPQDPILFSGTLRMNLDPFGRYSEEDIWRTLEISHLSAFVSSQPTGLDFQCS 1415
MRP1_HUMAN 1365  DLRFKITIIPQDPVLFSGSLRMNLDPFSQYSDEEVWTSLELAHLKDFVSALPDKLDHECA 1424
Q9UQ99     1349  DLRFKITIIPQDPVLFSGSLRMNLDPFSQYSDEEVWTSLELAHLKDFVSALPDKLDHECA 1408
O35379     1362  NLRFKITIIPQDPVLFSGSLRMNLDPFSQYSDEEVWMALELAHLKGFVSALPDKLNHECA 1421

NOV14      1421  EGGENLSVGQRQLVCLARALLRKSRILVLDEATAAIDLETDNLIQATIRTQFDTCVLTI 1480
MRP3_HUMAN 1421  EGGENLSVGQRQLVCLARALLRKSRILVLDEATAAIDLETDNLIQATIRTQFDTCVLTI 1480
MRP3_RAT   1416  EGGENLSVGQRQLVCLARALLRKSGILVLDEATAAIDLETDDLIQCTIRTQFDTCVLTI 1475
MRP1_HUMAN 1425  EGGENLSVGQRQLVCLARALLRKTKILVLDEATAAVDLETDDLIQSTIRTQFEDCTVLTI 1484
Q9UQ99     1409  EGGENLSVGQRQLVCLARALLRKTKILVLDEATAAVDLETDDLIQSTIRTQFEDCTVLTI 1468
O35379     1422  EGGENLSVGQRQLVCLARALLRKTKILVLDEATAAVDLETDDLIQSTIRTQFEDCTVLTI 1481

NOV14      1481  AHRLNTIMDYTRVLVLDKGVVAEFDSPANLIAARGIFYGMARDAGLA              1527
MRP3_HUMAN 1481  AHRLNTIMDYTRVLVLDKGVVAEFDSPANLIAARGIFYGMARDAGLA              1527
MRP3_RAT   1476  AHRLNTIMDYTRVLVLDKGVVAEFDSPVNLIAAGGIFYGMARDAGIA              1522
MRP1_HUMAN 1485  AHRLNTIMDYTRVIVLDKGEIQEYGAPSDLLQQRGIFYSMAKDAGV              1531
Q9UQ99     1469  AHRLNTIMDYTRVIVLDKGEIQEYGAPSDLLQQRGIFYSMAKDAGV              1515
O35379     1482  AHRLNTIMDYTRVIVLDKGEVRECGAPSELLQQRGIFYSMAKDAGIV              1528
```

Table 14E lists the domain description from DOMAIN analysis results against NOV14. This indicates that the NOV14 sequence has properties similar to those of other proteins known to contain this domain.

TABLE 14E

Domain Analysis of NOV14

PROSITE

| Pattern Name | |
|---|---|
| LEUCINE_ZIPPER PS00029 (Interpro) PDOC00029 | 2 positions in NOV14 |
| ABC_TRANSPORTER PS00211 (Interpro) PDOC00185 | 2 sites in NOV14 |

PRODOM

| Sequences producing High-scoring Segment Pairs. | High Score | Smallest Sum Probability P (N) |
|---|---|---|
| prdm: 8775 p36 (3) MRP2 (2) MRP1 (1) - MULTIDRUG PROTEIN . . . | 384 | 7.1e−35 |
| prdm: 1070 p36 (21) CFTR (7) SUR (3) MRP2 (2) - TRANSMEMBR . . . | 305 | 1.9e−26 |
| prdm: 923 p36 (24) CFTR (7) MRP2 (4) SUR (3) - TRANSMEMBR . . . | 244 | 5.8e−20 |
| prdm: 993 p36 (22) CFTR (7) SUR (3) MRP2 (2) - TRANSMEMBR . . . | 214 | 9.0e−17 |

BLOCKS

| AC# | Description | Strength | Score |
|---|---|---|---|
| BL00211B | ABC transporters family proteins. | 1331 | 1326 |
| BL01247C | Inosine-uridine preferring nucleoside hydrola | 1351 | 1084 |
| BL00577B | Avidin/Streptavidin family proteins. | 1442 | 1067 |
| BL00853E | Beta-eliminating lyases pyridoxal-phosphate a | 1602 | 1064 |
| BL00019E | Actinin-type actin-binding domain proteins. | 1179 | 1060 |
| BL00256 | Adipokinetic hormone family proteins. | 1358 | 1057 |
| BL00545B | Aldose 1-epimerase proteins. | 1282 | 1056 |
| BL00699A | Nitrogenases component 1 alpha and beta subun | 1357 | 1056 |

Other BLAST results include sequences from the Patp database, which is a proprietary database that contains sequences published in patents and patent publications. Patp results include those listed in Table 1F.

TABLE 1F

Patp alignments of NOV14

| Sequences producing High-scoring Segment Pairs: | High Score | Smallest Sum Prob. P(N) |
|---|---|---|
| patp:AAY43543 A human MPR-related ABC transporter designa . . . | 7845 | 0.0 |
| patp:AAW33363 Human multidrug resistance-associated prote . . . | 7679 | 0.0 |
| patp:AAR54928 Multidrug resistance protein-Homo sapiens . . . | 4470 | 0.0 |
| patp:AAR93153 Multi-drug resistance protein-Homo sapien . . . | 4470 | 0.0 |
| patp:AAW57485 Human multidrug resistance-associated prote . . . | 4470 | 0.0 |

Members of the multidrug resistance-associated transporter-like protein family are critical modulators of cell physiology, and perturbations are associated with many diseases/disorders. Multidrug resistance (MDR) describes the phenomenon of simultaneous resistance to unrelated drugs. The two MDR genes identified in humans to date (the MDR-associated protein (MRP) and Pgp genes) are structurally similar and both are members of the ATP-binding cassette (ABC) transporter family. Although the physiological role of MRP is not yet understood, one Pgp gene (mdr1) plays an important role in the blood-tissue barrier and the other (mdr2/3) is involved in phospholipid transport in the liver. A variety of compounds (chemosensitizing agents) can interfere with Pgp and MRP function; such agents may improve the efficacy of conventional therapy when used in combination with such regimens. Determining the roles cellular MDR mechanisms play in patients' response to chemotherapy is a major challenge. Using Pgp and MRP as molecular markers to detect MDR tumor cells is technically demanding, and solid tumors in particular contain heterogeneous cell populations. Since MDR requires Pgp or MRP gene expression, clinically relevant gene expression thresholds need to be established; sequential samples from individual patients are valuable for correlating MDR gene expression with the clinical course of disease. Studies in leukemias, myelomnas, and some childhood cancers show that Pgp expression correlates with poor response to chemotherapy. However, in some cases, inclusion of a reversing or chemosensitizing agent such as verapamil or cyclosporin A has improved clinical efficacy. Such agents may inactivate Pgp in tumor cells or affect Pgp function in normal cells, resulting in altered pharmacokinetics. The ABC transporter superfamily in prokaryotes and eukaryotes is involved in the transport of substrates ranging from ions to large proteins. Of the 15 or more ABC transporter genes characterized in human cells, two (Pgp and MRP) cause MDR. Therefore, it would be relevant to determine the number of such genes present in the human genome; however, extrapolating from the number of ABC transporter gyenes in bacteria, the human gene probably contains a minimum of 200 ABC transporter superfamily members. Thus, tumor cells can potentially use many ABC transporters to mount resistance to known and future therapeutic agents.

Members of the multidrug resistance-associated transporter-like protein family are also important in liver disease. In several liver diseases the biliary transport is disturbed, resulting in, for example, jaundice and cholestasis. Many of these symptoms can be attributed to altered regulation of hepatic transporters. Organic anion transport, mediated by the canalicular multispecific organic anion transporter (cmoat), has been extensively studied. The regulation of intracellular vesicular sorting of CMOAT by protein kinase C and protein kinase A, and the regulation of cmoat-mediated transport in endotoxemic liver disease, have been examined. The discovery that the multidrug resistance protein (MRP), responsible for multidrug resistance in cancers, transports similar substrates as cmoat led to the cloning of a MRP homologue from rat liver, named mrp2. Mrp2 turned out to be identical to cmnoat. At present there is evidence that at least two mrp's are present in hepatocytes, the original mrp (mrp1) on the lateral membrane, and mrp2 (cmoat) on the canalicular membrane. The expression of mrp1 and mrp2 in hepatocytes appears to be cell-cycle-dependent and regulated in a reciprocal fashion. These findings show that biliary transport of organic anions and possibly other canalicular transport is influenced by the entry of hepatocytes into the cell cycle.

Further, members of the multidrug resistance-associated transporter-like protein family are involved in various leukaemias. Approximately 15–30% of acute rnyeloid leukaemia (AML) patients are primarily resistant to chemotherapy, and 60–80% of patients who achieve complete remission will inevitably relapse and succumb to their disease. The multidrug resistant (MDR) phenotype has been suspected as a major mechanism of therapy failure in AML; it is one of the best understood mechanisms of resistance to anticancer drugs. The classical MDR phenotype is characterized by the reduced ability of cells to accumulate drugs as compared to normal cells. The increased drug efflux is due to the activity of a 170 kDa glycoprotein, the P-glycoprotein (Pgp), a unidirectional drug-efflux pump which is encoded by the MDR1 gene. While studies of myeloid leukaemia and myeloma have provided the best evidence for the potential association between Pgp expression and clinical outcome, the lack of standardized methods for MDR detection and perhaps even more importantly, inconsistencies in the interpretation of MDR expression data account for divergent results in the literature. The clinicians' strong interest in MDR stems from the availability of agents capable of interfering with MDR, at least in vitro. If these laboratory results were reproducible in vivo, reversal of MDR would offer a rare opportunity to incorporate laboratory experience into the clinical management of patients.

The NOV14 nucleic acids are useful for screening a test compound for inhibition of MDR mediated transport, indicated by restoration of anticancer drug sensitivity, which in turn causes a reduction of transporter mediated cellular efflux of anticancer agents. The disclosed NOV14 nucleic acid encoding a multidrug resistance-associated transporter-like protein includes the nucleic acid whose sequence is provided in Table 14A, or a fragment thereof. The invention also includes a mutant or variant nucleic acid any of whose bases may be changed from the corresponding base shown in Table 14A while still encoding a protein that maintains its multidrug resistance-associated transporter-like activities and physiological functions, or a fragment of such a nucleic acid.

The disclosed NOV14 protein of the invention includes the multidrug resistance-associated transporter-like protein whose sequence is provided in Table 14B. The invention also includes a mutant or variant protein any of whose residues may be changed from the corresponding residue shown in Table 14B while still encoding a protein that maintains its multidrug resistance-associated transporter-like activities and physiological functions, or a functional fragment thereof.

The above defined information for this invention suggests that this multidrug resistance-associated transporter-like protein (NOV14) may function as a member of a "multidrug resistance-associated transporter family". Therefore, the NOV14 nucleic acids and proteins identified here may be useful in potential therapeutic applications implicated in (but not limited to) various pathologies and disorders as indicated below. The potential therapeutic applications for this invention include, but are not limited to: cancer and liver disease research tools, for all tissues and cell types composing (but not limited to) those defined here, e.g. cancerous and normal tissue and liver tissue. Additional disease indications and tissue expression for NOV14 is presented in Example 2.

The NOV14 nucleic acids and proteins of the invention are useful in potential therapeutic applications implicated in cancer including but not limited to cancer, liver disease and/or other pathologies and disorders. For example, a cDNA encoding the multidrug resistance-associated transporter-like protein (NOV14) may be useful in liver disease therapy, and the multidrug resistance-associated transporter-like protein (NOV14) may be useful when administered to a subject in need thereof. By way of nonlimiting example, the compositions of the present invention will have efficacy for treatment of patients suffering from liver disease and cancer including but not limited to leukemia. The NOV14 nucleic acid encoding multidrug resistance-associated transporter-like protein, and the multidrug resistance-associated transporter-like protein of the invention, or fragments thereof, may further be useful in diagnostic applications, wherein the presence or amount of the nucleic acid or the protein are to be assessed.

NOV14 nucleic acids and polypeptides are further useful in the generation of antibodies that bind immuno-specifically to the novel NOV14 substances for use in therapeutic or diagnostic methods. These antibodies may be generated according to methods known in the art, using prediction from hydrophobicity charts, as described in the "Anti-NOVX Antibodies" section below. The disclosed NOV14 protein has multiple hydrophilic regions, each of which can be used as an immunogen. In one embodiment, a contemplated NOV14 epitope is from about amino acids 200 to 300. In another embodiment, a NOV14 epitope is from about amino acids 300 to 400. In additional embodiments, NOV14 epitopes are from about amino acids 900 to 300 and from about amino acids 1400 to 1500. These novel proteins can be used in assay systems for functional analysis of various human disorders, which will help in understanding of pathology of the disease and development of new drug targets for various disorders.

NOV15

NOV15 includes two novel novel intracellular thrombospondin domain containing protein-like proteins disclosed below. The disclosed proteins have been named NOV15a and NOV15b.

NOV15a

A disclosed NOV15a nucleic acid of 1794 nucleotides (also referred to as 100399281 and 159518754) encoding a novel thrombospondin-like protein is shown in Table 15A. A partial open reading frame was identified beginning with an GGA codon at nucleotides 178–180 and ending with a TAA codon at nucleotides 1792–1794. A putative untranslated intronic region upstream from the first in-frame coding triplet is underlined in Table 15A, and the start and stop codons are in bold letters.

TABLE 15A

NOV15a Nucleotide Sequence (SEQ ID NO:89)

ACGCGTAGCCACAAGACCGGGTCCGTTTCTGGTTGCCGTTCCCGCAGGTGACGCTGCAGACAGACCAGAGACTCCAGTC
ACCCTCGCCATCTGTGGAATCATATTCTGGCTGATCTTTGGTTTCAAAAGTCCGGTGGCCTGGGGCTGTATGGTCCCAC
CCCCTGGGGGGGTTGAGGAAGTTGCTGTCGTCTGAGGTACTGCCGTACGTGTAGTCCTGAAACCAGCTTTTCTCTCTCC
AAAGAAGCACCAAGGGAGCATCTCGACCACCAGGCTGCACACCAACCCTTCCCCAGACCGCGATTCCGACAAGACACGG
GGCACCCTTCATTGCAAAGAGATTTCCCCAGATCCTTTCTCCTTGATCTACCAAACTTTCCAGATCTTTCCAAAGCTGA
TATCAATGGGCAGAATCCAAATATCCAGGTCACCATAGAGGTGGTCGACGGTCCTGACTCTGAAGCAGATAAAGATCAG
CATCCGCAGAATAAGCCCAGCTGGTCAGTCCCATCCCCCGACTGGCGGGCCTGGTGGCAGAGCTCCCTGTCCTTGGCCA
GGGCAAACAGCGGGGACCAGGACTACAAGTACGACAGTACCTCAGACGACAGCAACTTCCTCAACCCCCCCAGGGGGTG
GGACCATACAGCCCCAGGCCACCGGACTTTTGAAACCAAAGATCAGCCAGAATATGATTCCACAGATGGCGAGGGTGAC
TGGAGTCTCTGGTCTGTCTGCAGCGTCACCTGCGGGAACGGCAACCAGAAACGGACCCGGTCTTGTGGCTACGCGTGCA
CTGCAACAGAATCGAGGACCTGTGACCGTCCAAACTGCCCAGCTTGCACCGGATTCCTGATTGTAAAGGAAGCTTGGTT
AGGGGTGGTAGTTTGGCATGTCCCTGCACCTCCAACTGGCAACCCCTCTGTGCCTTTGCCTGAGGTCTTTCTCTGGACC
CGAGCCCAGCTGCGCATGAATGCACAGGGCATTCCTAGCTGGAAATCCAGGACCAGTCCCCTGTCAGTGATGAATGGGA
GCTGGTGGATAAAAACTCAGATCCCCATCAATAAAAACAAATCCGGACTCAGTAAGGAGAGGATTTATTCAAAGGATTA
TTGCAGGGAGGCAAGGGATGTTATCTCCCTATTATTGCAATGGGATGAACGCTGTGACCATAAGATCTGCAAGCATCTC
AAGGAACAGCCTGGTGTCACATGCTCCTTGAAGCACCTCCTGTGGGCCGGTTGTACACGCGGTGAGAGGGTTTCTCTTT
GGCCTTTTCCAGACACAGACAGCTGTGAGCGCTGGATGAGCTTCAAAGCGAGGTTCTTAAAGAAGTACATGCACAAGGT
GATGAATGACCTGCCCAGCTGCCCCTGCTCCTACCCCACTGAGGTGGCCTACAGCACGGCGGACATCTTCGACCGCATC
AAGCGCAAGGACTTCCGCTGGAAGGACGCCAGCGGGCCCAAGGAGAAGCTGGAGATCTACAAGCCCACTGCCCGGTACT
GCATCCGCTCCATGCTGTCCTGGAAGAGCACCACGCTGGCGGCACAGCACTGCTGCTACGGCGACAACATGCAGCTCAT
CACCAGGGGCAAGGGGCGGGCACGCCCAACCTCATCAGCACCGAGTTCTCCGCGGAGCTCCACTACAAGGTGGACGTC
CTGCCCTGGATTATCTGCAAGGGTGACTGGAGCAGGTATAACGAGGCCCGGCCTCCCAACAACGGACAGAAGTGCACAG
AGAGCCCCTCGGACGAGGACTACATCAAGCAGTTCCAAGAGGCCAGGGAATATTAA

A disclosed NOV15a polypeptide (SEQ ID NO:90) encoded by SEQ ID NO:89 is 539 amino acid residues and is presented using the one-letter amino acid code in Table 15B. SignalP, Psort and/or Hydropathy results predict that NOV15a does not contain a known signal peptide and is likely to be localized to the mitochondrial matrix space with a certainty of 0.6574. In alternative embodiments, NOV15l is localized to the mitochondrial inner membrane with a certainty of 0.3502; the mitochondrial intermembrane space with a certainty of 0.3502; or the mitochondrial outer membrane with a certainty of 0.3502. NOV15a has a molecular weight of 61683.6 Daltons.

TABLE 15B

Encoded NOV15a protein sequence.

(SEQ ID NO:90)

GSCCRLRYCRTCSPETSFSLSKEAPREHLDHQAAHQPFPRPRFRQETGHPSLQRDFPRSFLLDLPNFPDLSKADINGQNP
NIQVTIEVVDGPDSEADKDQHPENKPSWSVPSPDWRAWWQRSLSLARANSGDQDYKYDSTSDDSNFLNPPRGWDHTAPGH
RTFETKDQPEYDSTDGEGDWSLWSVCSVTCGNGNQKRTRSCGYACTATESRTCDRPNCPACTGFLIVKEAWLGVVVWHVP
APPTGNPSVPLPEVFLWTRAQLRMNAQGIPSWKSRTSPLSVMNGSWWIKTQIPINKNKSGLSKERIYSKDYCREARDVIS
LLLQWDERCDHKICKHLKEQPGVTCSLKHLLWAGCTRGERVSLWPFPDTDSCERWMSFKARFLKKYMHKVMNDLPSCPCS
YPTEVAYSTADIFDRIKRKDFRWKDASGPKEKLEIYKPTARYCIRSMLSLESTTLAAQHCCYGDNMQLITRGKGAGTPNL
ISTEFSAELHYKVDVLPWIICKGDWSRYNEARPPNNGQKCTESPSDEDYIKQFQEAREY

NOV15b

A disclosed NOV15b nucleic acid of 1238 nucleotides (also referred to as CG57356–01) encoding a novel novel intracellular thrombospondin domain containing protein-like protein is shown in Table 15C. A partial open reading flame was identified beginning with an ACG codon at nucleotides 3–5 and ending with a TAA codon at nucleotides 1236–1238. A partial codon upstream from the first in-frame coding triplet is italicized in Table 15C, and the start and stop codons are in bold letters. In further embodiments, the NOV15 coding region extends 5' to the sequence disclosed in Table 15C.

TABLE 15C

NOV15b Nucleotide Sequence (SEQ ID NO:91)

GACGTGTAGTCCTGAAACCAGCTTTTCTCTCTCCAAAGAAGCACCAAGGGAGCATCTGGACCACCAGGCTGCACACCA

ACCCTTCCCCAGACCGCGATTCCGACAAGAGACGGGGCACCCTTCATTGCAAAGAGATTTCCCCAGATCCTTTCTCCTT

GATCTACCAAACTTTCCAGATCTTTCCAAAGCTGATATCAATGGGCAGAATCCAAATATCCAGGTCACCATAGAGGTGG

TCGACGGTCCTGACTCTGAAGCAGATAAAGATCAGCATCCGGAGAATAAGCCCAGCTGGTCAGTCCCATCCCCCGACTG

GCGGGCCTGGTGGCAGAGGTCCCTGTCCTTGGCCAGGGCAAACAGCGGGGACCAGGACTACAAGTACGACAGTACCTCA

GACGACAGCAACCTTCCTCAACCCCCCAGGGGGTGGGACCATACAGCCCCAGGCCACCGGACTTTTGAAACCAAAGATC

AGCCAGAATATGATTCCACAGATGGCGAGGGTGACTGGAGTCTCTGGTCTGTCTGCAGCGTCACCTGCGGGAACGGCAA

CCAGAAACGGACCCGGTCTTGTGGCTACGCGTGCACTGCAACAGAATCGAGGACCTGTGACCGTCCAAACTGCCCAGGA

ATTGAAGACACTTTTAGGACAGCTGCCACCGAAGTGAGTCTGCTTGCGGGAAGCGAGGAGTTTAATGCCACCAAACTGT

TTGAAGTTGACACAGACAGCTGTGAGCGCTGGATGAGCTGCAAAGCGAGTTCTTAAAGAAGTACATGCACAAGGGTGAT

GAATGACCTGCCCAGCTGCCCCTGCTCCTACCCCACTGAGGTGGCCTACAGCACGGCTGACATCTTCGACCGCATCAAG

CGCAAGGACTTCCGCTGGAAGGACGCCAGCGGGCCCAAGGAGAAGCTGGAGATCTACAAGCCCACTGCCCGGTACTGCA

TCCGCTCCATGCTGTCCCTGGAGAGCACCACGCTGGCGGCACAGCACTGCTGCTACGGCGACAACATGCAGCTCATCAC

CAGGGGCAAGGGGGCGGGCACGCCCAACCTCATCGGCACCGAGTTCTCCGCGGAGCTCCACTACAAGGTGGACGTCCTG

CCCTGGATTATCTGCAAGGGTGACTGGAGCAGGTATAACGAGGCCCGGCCTCCCAACAACGGACAGGAGTGCACAGAGA

GCCCCTCGCACGAGGACTACATCAAGCAGTTCCAAGAGGCCAGGGAATATTAA

A disclosed NOV15b polypeptide (SEQ ID NO:92) encoded by SEQ ID NO:91 is 411 amino acid residues and is presented using, the one-letter amino acid code in Table 15D. NOV15b is believed to be a mature protein. SignalP, Psort and/or Hydropathy results predict if that NOV15b does not contain a known signal peptide and is likely to be localized in the cytoplasm with a certainty of 0.4500. In alternative embodiments, NOV15b is localized to a microbody (peroxisome) with a certainty of 0.1163; the mitochondrial matrix space with a certainty of 0.1000; or a lysosome (lumen) with a certainty of 0.1000. NOV15b has a molecular weight of 46743.0 Daltons.

TABLE 15D

Encoded NOV15b protein sequence.

(SEQ ID NO:92)

TCSPETSFSLSKEAPREHLDHQAAHQPFPRPRFRQETGHPSLQRDFPRSFLLDLPNFPDLSKADINGQNPNIQVTIEVVDGP

DSEADKDQHPENKPSWSVPSPDWRAWWQRSLSLARANSGDQDYKYDSTSDDSNFLNPPRGWDHTAPGHRTFETKDQPEYDST

DGEGDWSLWSVCSVTCGNGNQKRTRSCGYACTATESRTCDRPNCPGIEDTFRTAATEVSLLAGSEEFNATKLFEVDTDSCER

WMSCKSEFLKKYMHKVMNDLPSCPCSYPTEVAYSTADIFDRIKRKDFRWKDASGPKEKLEIYKPTARYCIRSMLSLESTTLA

AQHCCYGDNMQLITRGKGAGTPNLIGTEFSAELHYKVDVLPWIICKGDWSRYNEARPPNNGQECTESPSDEDYIKQFQEAREY

NOV15a and NOV15b are related to each other as shown in the alignment listed in Table 15E.

TABLE 15E

ClustalW of NOV15 Variants

```
NOV15a  GSCCRLRYCRTCSPETSFSLSKEAPREHLDHQAAHQPFPRPRFRQETGHP  50
NOV15b  ----------TCSPETSFSLSKEAPREHLDHQAAHQPFPRPRFRQETGHP  40

NOV15a  SLQRDFPRSFLLDLPNFPDLSKADINGQNPNIQVTIEVVDGPDSEADKDQ  100
NOV15b  SLQRDFPRSFLLDLPNFPDLSKADINGQNPNIQVTIEVVDGPDSEADKDQ  90

NOV15a  HPENKPSWSVPSPDWRAWWQRSLSLARANSGDQDYKYDSTSDDSNFLNPP  150
NOV15b  HPENKPSWSVPSPDWRAWWQRSLSLARANSGDQDYKYDSTSDDSNFLNPP  140

NOV15a  RGWDHTAPGHRTFETKDQPEYDSTDGEGDWSLWSVCSVTCGNGNQKRTRS  200
NOV15b  RGWDHTAPGHRTFETKDQPEYDSTDGEGDWSLWSVCSVTCGNGNQKRTRS  190

NOV15a  DGYACTATESRTCDRPNCPACTGFLIVKEAWLGVVVWHVPAPPTGNPSVP  250
NOV15b  DGYACTATESRTCDRPNCP-------------------------------  209

NOV15a  LPEVFLWTRAQLRMNAQGIPSWKSRTSPLSVMNGSWWIKTQIPINKNKSG  300
NOV15b  -----------------G--------------------------------  210

NOV15a  LSKERIYSKDYCREARDVISLLLQWDERCDHKICKHLKEQPGVTCSLKHL  350
NOV15b  -------IEDTFRTAATEVSLLAGSEEFNATKLF-E--------------  238

NOV15a  LWAGCTRGERVSLWPFPDTDSCERWMSFKARFLKKYMHKVMNDLPSCPCS  400
NOV15b  --V--------------DTDSCERWMSCKSEFLKKYMHKVMNDLPSCPCS  272

NOV15a  YPTEVAYSTADIFDRIKRKDFRWKDASGPKEKLEIYKPTARYCIRSMLSL  450
NOV15b  YPTEVAYSTADIFDRIKRKDFRWKDASGPKEKLEIYKPTARYCIRSMLSL  322

NOV15a  ESTTLAAQHCCYGDNMQLITRGKGAGTPNLISTEFSAELHYKVDVLPWII  500
NOV15b  ESTTLAAQHCCYGDNMQLITRGKGAGTPNLIGTEFSAELHYKVDVLPWII  372

NOV15a  CKGDWSRYNEARPPNNGQHCTESPSDEDYIKQFQEAREY           539
NOV15b  CKGDWSRYNEARPPNNGQHCTESPSDEDYIKQFQEAREY           411
```

The novel intracellular thrombospondin domain containing protein-like NOV15 gene maps to chromosome 7. This assignment was made using mapping information associated with genomic clones, public genes and ESTs sharing sequence identity with the disclosed sequence and CuraGen Corporation's Electronic Northern bioinformatic tool. Exons were predicted by homology and the intron/exon boundaries were determined using standard genetic rules. Exons were further selected and refined by means of similarity determination using multiple BLAST (for example, tBlastN, BlastX, and BlastN) searches, and, in some instances, GeneScan and Grail. Expressed sequences from both public and proprietary databases were also added when available to further define and complete the gene sequence. The DNA sequence was then manually corrected for apparent inconsistencies thereby obtaining the sequences encoding the full-length protein.

In a search of sequence databases, it was found, for example, that the NOV15b nucleic acid sequence of this invention has 373 of 512 bases (72%) identical to a gb:GENBANK-ID:AF111168|acc:AF111168.2 mRNA from Homo sapiens (Homo sapiens serine palmitoyl transferase, subunit II gene, complete cds; and unknown genes). The full NOV15b amino acid sequence was found to have 162 of 164 amino acid residues (98%) identical to, and 163 of 164 amino acid residues (99%) similar to the 361 amino acid residue ptnr:TREMBLNEW-ACC:CAC16127 protein from Homo sapiens (Human) (BA149118.1 (NOVEL PROTEIN).

The disclosed NOV15a was found to have homology to the amino acid sequences shown in the BLASTP data listed in Table 15F.

TABLE 15F

BLAST results for NOV15a

| Gene Index/ Identifier | Protein/Organism | Length (aa) | Identity (%) | Positives (%) | Expect |
| --- | --- | --- | --- | --- | --- |
| Q9H599; AL133463; CAC16127.2 | BA149I18.1 (NOVEL PROTEIN (FRAGMENT) *homo sapiens*. Jun. 2001 | 391 | 189/189, (100%) | 189/189, (100%) | 1e−117 |
| 095432; AF111168; | HYPOTHETICAL 72.5 | 658 | 102/172 | 138/172, | 2e−63 |

TABLE 15F-continued

BLAST results for NOV15a

| Gene Index/ Identifier | Protein/Organism | Length (aa) | Identity (%) | Positives (%) | Expect |
|---|---|---|---|---|---|
| AAD09622.1 | KDA PROTEIN. homo sapiens. Jun. 2001 | | (59%) | (80%) | |
| Q9BQL4; AL050320; CAC36074.1 | DJ107712.1 (NOVEL PROTEIN) (FRAGMENT). homo sapiens. Jun. 2001 | 60 | 49/49 (100%) | 49/49, (100%) | 3e−22 |
| Q23832; U42213; AAC48313.1 | MICRONEMAL TRAP-C1 PROTEIN HOMOLOG (FRAGMENT). cryptosporidium wrairi. Jun. 2001 | 660 | 27/61 (44%) | 33/61, (54%) | 2e−05 |
| TSP1_HUMAN; P07996; M25631; AAA36741; CAA28370; CAA32889; AAA61178; AAB59366 | THROMBOSPONDIN 1 PRECURSOR. homo sapiens. Oct. 1996 | 1170 | 24/54 (44%) | 31/54, (57%) | 3e−05 |

The disclosed NOV15b was found to have homology to the amino acid sequences shown in the BLASTP data listed in Table 15G.

TABLE 15G

BLAST results for NOV15b

| Gene Index/ Identifier | Protein/Organism | Length (aa) | Identity (%) | Positives (%) | Expect |
|---|---|---|---|---|---|
| Q9H599; AL133463; CAC16127.2 | BA149I18.1 (NOVEL PROTEIN) (FRAGMENT). homo sapiens. Jun. 2001 | 391 | 390/391, (100%) | 390/391, (100%) | 0.0 |
| O95432; AF111168; AAD09622.1 | HYPOTHETICAL 72.5 KDA PROTEIN. homo sapiens. Jun. 2001 | 658 | 183/392 (47%) | 242/392, (62%) | 2e−95 |
| Q9BQL4; AL050320; CAC36074.1 | DJ107712.1 (NOVEL PROTEIN) (FRAGMENT). homo sapiens. Jun. 2001 | 60 | 49/49 (100%) | 49/49, (100%) | 2e−22 |
| TSP1_HUMAN; P07996; M25631; AAA36741; CAA28370; CAA32889; AAA61178; AAB59366 | THROMBOSPONDIN 1 PRECURSOR. homo sapiens. Oct. 1996 | 1170 | 24/54 (44%) | 31/54, (57%) | 2e−05 |
| TSP1_MOUSE; P35441; AAA5O611; AAA40431 | THROMBOSPONDIN 1 PRECURSOR. mus musculus. Oct. 1996 | 1170 | 23/54 (43%) | 31/54, (57%) | 4e−05 |

The homology of these sequences is shown graphically in the ClustalW analysis shown in Table 15H.

TABLE 15H

Information for the ClustalW proteins

1) NOV15a (SEQ ID NO:90)
2) NOV15b (SEQ ID NO:92)
3) Q9H599 (SEQ ID NO:93)
4) O95432 (SEQ ID NO:94)
5) Q9BQL4 (SEQ ID NO:95)
6) Q23832 (SEQ ID NO:96)
7) TSP1_HUMAN N-ter fragment (SEQ ID NO:97)
8) TSP1_MOUSE N-ter fragment (SEQ ID NO:98)

TABLE 15H-continued

Information for the ClustalW proteins

```
NOV15a      ------------------------------------------------------   1
NOV15b      ------------------------------------------------------   1
Q9H599      ------------------------------------------------------   1
O95432      -MRALRDRAGLLLCVLLAALLEAALG------LPVKKPRLRGPRPGSLT         43
Q9BQL4      ------------------------------------------------------   1
Q23832      KLTHYSVGGHASTSRVKGRSSSGSSSG--------D--FKVPGLNG-YLC        39
TSP1_HUMAN  -MGLAWGLGVLFLMGVCGTNRIPESGGDNSVFDIFELTGAARKGSGRRLV        49
TSP1_MOUSE  -MELLRGLGVLFLLHMCGSNRIPESGGDNGVFDIFELIGGARRGPGRRLV        49

NOV15a      ------------------------------------------------------   1
NOV15b      ------------------------------------------------------   1
Q9H599      ------------------------------------------------------   1
O95432      RLAEVSGGGTGLRSALSVPPPQPAGSSRAGSGTGTHT-----GSDPPMER        88
Q9BQL4      ------------------------------------------------------   1
Q23832      PSYNRDPRGFGCFGLNTAYTVKKNSWQECANQCYWSKYTIYGNCQRSVYN        89
TSP1_HUMAN  KGPDPSSPAFRIEDANLIPPVPDDKFQDLVDAVRTEKGFLLLASLRQMKK        99
TSP1_MOUSE  KGPDLSSPAFRIENANLIPAVPDDKFQDLLDAVWADKGFIFLASLRQMKK        99

NOV15a      ------------------------------------------------------   1
NOV15b      ------------------------------------------------------   1
Q9H599      ------------------------------------------------------   1
O95432      GAGAGRKLPDTGRCPVTEGSTVQLIAPWNAADVHSGDKDSQTCIRVSAS         138
Q9BQL4      ------------------------------------------------------   1
Q23832      SNNQDCHIKGGDNDCMKSPDGMILTNRQSYMIGECATTCTVSSWSSWTPC        139
TSP1_HUMAN  TRGTLLALERKDHSGQVFSVVSNGKAGTLDLSLTVQGKQHVVSVEEALLA        149
TSP1_MOUSE  TRGTLLAVERKDNTGQIFSVVSNGKAGTLDLSLSLPGKQQVVSVEEALLA        149

NOV15a      ------------------------------------------------------   1
NOV15b      ------------------------------------------------------   1
Q9H599      ------------------------------------------------------   1
O95432      PDPRPLKEEEEAPLLPRTHLQAEPHQHGCWTVTEPAAMTPGNATPPRT--        186
Q9BQL4      ------------------------------------------------------   1
Q23832      SGVCGEMRSRTRSVLSFPRYDHEYCP-HLIEYSNCVVQNKCPENCPQYGV        188
TSP1_HUMAN  TGQWKSITLFVQEDRAQLYIDCEKMENAELDVPIQSVFTRDLASIARLRI        199
TSP1_MOUSE  TGQWKSITLFVQEDRAQLYIDCDKMESAELDVPIQSIFTRDLASVARLRV        199

NOV15a      ------------------------------HQAAHQPFPRPRFRQETG---       18
NOV15b      ---------TCSPETSFSLSKEAPREHLDHQAAHQPFPRPRFRQETG---        38
Q9H599      ------------------------------HQAAHQPFPRPRFRQETG---       18
O95432      --PEVTPLRLELQKLPGLANTTLSTPNPDTQASASPDPRPLREEEEARLL       234
Q9BQL4      ------------------------------------------------------   1
Q23832      SILGWGCQFESMFSFNKNLFVSYEEDWKGCMSTCKQDPFCVAWSYNATLS       238
TSP1_HUMAN  AKGGVNDNFQGVLQNVRFVFGITPEDILRNKGCSSSTSVLLTLDNNVVNG       249
TSP1_MOUSE  AKGDVNDNFQGVLQNVRFVFGITPEDILRNKGCSSSTNVLLTLDNNVVNG       249

NOV15a      ----HPSLQRDFPRS---------------------------------       29
NOV15b      ----HPSLQRDFPRS---------------------------------       49
Q9H599      ----HPSLQRDFPRS---------------------------------       29
O95432      ---PRTHLQAELHQHGCWTVTEPA--------------------ALTPGN       261
Q9BQL4      ------------------------------------------------------   1
Q23832      EGPDSVGFSREYRPCYTHRFASGCQALAPG-------------WVSGNKY       275
TSP1_HUMAN  ---SSPAIRTNYIGHKTKDLQAICGISCDELSSMVLELRGLRTIVTTLQD       296
TSP1_MOUSE  ---SSPAIRTNYIGHKTKDLQAICGLSCDELSSMVLELKGLRTIVTTLQD       296

NOV15a      -----------FLLDLPNFPDLSKADINGQNPNIQVTIEVV------DGP   62
NOV15b      -----------FLLDLPNFPDLSKADINGQNPNIQVTIEVV------DGP   82
Q9H599      -----------FLLDLPNFPDLSKADINGQNPNIQVTIEVV------DGP   62
O95432      ATPPRTQEVTPLLDLQKLPKLVHATLSTPNPDNQVTIKVV------EDP   305
Q9BQL4      -----------------------------NNLN-----V------CS     7
Q23832      TRDVDCETGTCIHNEWSSWTTCKDPCSNTETMSRNRLVKSVSQNWASTTC   325
TSP1_HUMAN  SIRKVTEENKELANEIRRPPLCYHNGVQYRN-NEEWLVDSC------TEC   339
TSP1_MOUSE  SIRKVTEENRELVSPLKRPPLCFHNGVQYKN-NEEWLVDSC------TEC   339

NOV15a      DSEADKDQHPE--------NKPS----------WSVP-----SPDWRAWW   89
NOV15b      DSEADKDQHPE--------NKPS----------WSVP-----SPDWRAWW  109
Q9H599      DSEADKDQHPE--------NKPS----------WSVP-----SPDWRAWW   89
O95432      QAEVSIDLLAEP------SNPPQDTLSWLPALWSFL-----WGDYKGEE   344
Q9BQL4      DTTSET-----------------------------------------    13
Q23832      RDESQIQLCSE---------NPQS--IETKTCLVG--------SWSEWS   356
TSP1_HUMAN  HCQNSVTICKKVSCPIMPCSNATVPDGECCPRCWPSDSADDGWSPWSEWT  389
TSP1_MOUSE  HCQNSVTICKKVSCPIMPCSNATVPDGECCPRCWPSDSADDGWSPWSEWT  389
```

TABLE 15H-continued

Information for the ClustalW proteins

```
NOV15a      QRSLSIARANSGDQDYKMDSTSDDSN---------------FLNPPRGWD   124
NOV15b      QRSLSIARANSGDQDYKMDSTSDDSN---------------FLNPPRGWD   144
Q9H599      QRSLSIARANSGDQDYKMDSTSDDSN---------------FLNPPRGWD   124
O95432      KDRAPGEKGEEKEEDEDYPSEDIEGEDQEDKEEDEEEQALWENGTTDNWD   394
Q9BQL4      --SFSISKEAPREH-----------------------------------LD    27
Q23832      DCSTSCGEGNRIRTRESTKPP--------------------LNGDES--   383
TSP1_HUMAN  SCSTSCGNGIQQRGRSCDSLNNRCEGSSVQTRTCHIQECDKRFKQDGGWS   439
TSP1_MOUSE  SCSATCGNGIQQRGRSCDSLNNRCEGSSVQTRTCHIQECDKRFKQDGGWS   439

NOV15a      H---------------------------------TAPGHRTFETKDQPEMD   142
NOV15b      H---------------------------------TAPGHRTFETKDQPEMD   162
Q9H599      H---------------------------------TAPGHRTFETKDQPEMD   142
O95432      QGW-------------------------------LAPGDWVFKDSVSYDME   414
Q9BQL4      H---------------------------------------QAA-HQPFP--    36
Q23832      T---------------------------------------CPELIAKESCNKDVEC   400
TSP1_HUMAN  HWSPWSSCSVTCGDGVITRIRLCNSPSPQMNGKPCEGEARETKACKKDAC   489
TSP1_MOUSE  HWSPWSSCSVTCGDGVITRIRLCNSPSPQMNGKPCEGEARETKACKKDAC   489

NOV15a      S-TDG-EGDWSLWSVCSVTCGNGNQKRTRSC-------GYACT--ATES   180
NOV15b      S-TDG-EGDWSLWSVCSVTCGNGNQKRTRSC-------GYACT--ATES   200
Q9H599      S-TDG-EGDWSLWSVCSVTCGNGNQKRTRSC-------GYACT--ATES   180
O95432      P-----QKEWSPWSPCSGNCSTGKQQRTRPC-------GYGCT--ATET   449
Q9BQL4      -------------------------------------------------    36
Q23832      PNIQCELGEWSSWSPCSVTCGSGTTSRNREVK-------GENCTELPTES   443
TSP1_HUMAN  P-INGGWGPWSPWDICSVTCGGGVQKRSRLCNNPTPQFGGKDCVGDVTEN   538
TSP1_MOUSE  P-INGGWGPWSPWDICSVTCGGGVQRRSRLCNNPTPQFGGKDCVGDVTEN   538

NOV15a      RTCDRPNCPGI-------EDTFRTAATEVSLLAG---SEEFNATKLFEVD   220
NOV15b      RTCDRPNCPGI-------EDTFRTAATEVSLLAG---SEEFNATKLFEVD   240
Q9H599      RTCDRPNCPGI-------EDTFRTAATEVSLLAG---SEEFNATKLFEVD   220
O95432      RTCDLPSCPGT-------EDK-DILGLPSEEWKL---LAR--NAIDMHDQD   487
Q9BQL4      ----RP-------------------------------R------FRQE    43
Q23832      KKCNLANCGDN-------SASCTAVMSVWSEWSACS-EKCDQGLVRRYRD   485
TSP1_HUMAN  QICNKQDCPIDGCLSNPCFAGVKCTSYPDGSWKCGACPPGYSGNGIQCTD   588
TSP1_MOUSE  QVCNKQDCPIDGCLSNPCFAGAKCTSYPDGSWKCGACPPGYSGNGIQCKD   588

NOV15a      TDSCERW----MSCKSEFLKKYMHKVMNDLPSCPCSY----PTEVAYSTA   262
NOV15b      TDSCERW----MSCKSEFLKKYMHKVMNDLPSCPCSY----PTEVAYSTA   282
Q9H599      TDSCERW----MSCKSEFLKKYMHKVMNDLPSCPCSY----PTEVAYSTA   262
O95432      VDSCERW----LNCKSDFLIKYLSQMLRDLPSCPCAY----PLEAMDSPV   529
Q9BQL4      TG--------------------------H----------S--    48
Q23832      FDFSKIG---VFGYVPPGKSEEQNKVREICKDTPTLE--EEPCTSGVTCT   530
TSP1_HUMAN  VDECKEVPDACFNHNGEHRCENTDPGYNCLP-CPPRFTGSQPFGQGVEHA   637
TSP1_MOUSE  VDECKEVPDACFNHNGEHRCKNTDPGYNCLP-CPPRFTGSQPFGRGVEHA   637

NOV15a      DIFDRIKRKDFRWKDASGPKEK------LEIYKP--------TARYCIRSM   299
NOV15b      DIFDRIKRKDFRWKDASGPKEK------LEIYKP--------TARYCIRSM   319
Q9H599      DIFDRIKRKDFRWKDASGPKEK------LEIYKP--------TARYCIRSM   299
O95432      SLQDEHQGRSFRWKDASGPRER------LEIYQP--------TARFCLRSM   566
Q9BQL4      -----LQR-DF--------P--------------------------RSF    57
Q23832      PGCKYTEWSAWNSSCDCSGSQTR------------------DRVVTFP-EGI   562
TSP1_HUMAN  TANKQVCKPRNPCTDGTHDCNKNAKCNYLGHYSDPMYRCECKPGYAGNGI   687
TSP1_MOUSE  MANKQVCKPRNPCTDGTHDCNKNAKCNYLGHYSDPMYRCECKPGYAGNGI   687

NOV15a      LSLESTTLA----AQHCCYGDNMQLITRGKGAGTPNLISTEFS-------   338
NOV15b      LSLESTTLA----AQHCCYGDNMQLITRGKGAGTPNLIGTEFS-------   358
Q9H599      LSLESTTLA----AQHCCYGDNMQLITRGKGAGTPNLISTEFS-------   338
O95432      LSGESSTLA----AQHCCYDEDSRLLTRGKGAGMPNLISTDFS-------   605
Q9BQL4      L-LB---------------------------------------------    60
Q23832      IDAICQSSK----DTRSCSKPEGCTETTPDSGDATLATAIGLP-------   601
TSP1_HUMAN  ICGEDTDLDGWPNENLVCVANATYHCKKDNCPNLPNSGQEDYDKDGIGDA   737
TSP1_MOUSE  ICGEDTDLDGWPNENLVCVANATYHCKKDNCPNLPNSGQEDYDKDGIGDA   737

NOV15a      --------------AELHYKVDVLPWITCKGDWSRYNEARPPNN------   368
NOV15b      --------------AELHYKVDVLPWITCKGDWSRYNEARPPNN------   388
Q9H599      --------------AELHYKVDVLPWITCKGDWSRYNEARPPNN------   368
O95432      --------------PKLHFKFDTTPWITCKGDWSRLHAVLPPNN------   635
Q9BQL4      -------------------------------------------------    60
Q23832      --------------VGILGLCIIAGSLFLIGGRSGNQEEDETSYQYFD---   635
TSP1_HUMAN  CDDDDDNDKIPDDRDNCPFHYNPAQYDYDRDDVGDRCDNCPYNHNPDQAD   787
TSP1_MOUSE  CDDDDDNDKIPDDRDNCPFHYNPAQYDYDRDDVGDRCDNCPYNHNPDQAD   787
```

TABLE 15H-continued

Information for the ClustalW proteins

| | | |
|---|---|---|
| NOV15a | ------GQKCTESPSDEEYIKQFQEAREY- | 391 |
| NOV15b | ------GQKCTESPSDEEYIKQFQEAREY- | 411 |
| Q9H599 | ------GQKCTESPSDEEYIKQFQEAREY- | 391 |
| O95432 | ------GRACTDNPLEEEYLAQLQEAKEY- | 658 |
| Q9BQL4 | | 60 |
| Q23832 | -------QPSAALDQDSRYVQEIGPESQNWAS-- | 660 |
| TSP1_HUMAN | TDNNGECDACAADIDGDGILNERDNCQYVYNVDQRDTDMDGVGD ... | 837 |
| TSP1_MOUSE | TDNNGECDACAVDIDGDGILNERDNCQYVYNVDQRDTDMDGVGD ... | 837 |

Table 15I lists the domain description from DOMAIN analysis results against NOV15a, and in the analogous regions for NOV15b. This indicates that the NOV15a sequence has properties similar to those of other proteins known to contain this domain.

instances of this repeat. It has been involved in cell-cell interraction, inhibition of angiogenesis, and apoptosis.

The intron-exon organisation of the properdin gene confirms the hypothesis that the repeat might have evolved by a process involving exon shuffling. A study of properdin

TABLE 15I

Domain Analysis of NOV15a

PFAM HMM Domain Analysis of NOV15

| Model | Description | Score | E-value |
|---|---|---|---|
| tsp_1 | (InterPro) Thrombospondin type 1 domain | 32.5 | 9.8e-06 |

Parsed for domains:

| Model | Domain | seq-f | seq-t | hmm-f | hmm-t | score | E-value |
|---|---|---|---|---|---|---|---|
| tsp_1 | 1/1 | 178 | 218 | 1 | 54 [ ] | 32.5 | 9.8e-06 |

| ProDom Sequences producing High-scoring Segment Pairs: | High Score | Smallest Sum Probability P(N) |
|---|---|---|
| prdm:1719 p36 (14) FSPO(5) TSP1(3) TSP2(2) - PRECURSOR ... | 110 | 3.0e-06 |
| prdm:873 p36 (25) TSP1(9) TSP2(4) PROP(3) - COMPLEMEN ... | 91 | 0.00033 |
| prdm:36045 p36 (1) SSP2_PLAYO - SPOROZOITE SURFACE PROTE ... | 85 | 0.0014 |
| prdm:1268 p36 (18) CSP(18) - CIRCUMSPOROZOITE PROTEIN ... | 74 | 0.022 |
| prdm:53698 p36 (1) FSPO_XENLA - F-SPONDIN PRECURSOR. GLY ... | 62 | 0.35 |

BLOCKS Protein Domain Analysis

| AC# | Description | Strength | Score |
|---|---|---|---|
| BL00612B | 0 Osteonectin domain proteins. | 1891 | 1066 |
| BL00652C | 0 TNFR/NGFR fanily cysteine-rich region protein | 1217 | 1062 |
| BL00979I | 0 C-protein coupled receptors family 3 proteins | 1459 | 1059 |
| BL00641E | 0 Respiratory-chain NADH dehydrogenase 75 Kd su | 1700 | 1039 |
| BL00512A | 0 Alpha-galactosidase proteins. | 1403 | 1035 |
| BL00096G | 0 Serine hydroxymethyltransferase pyridoxal-pho | 1543 | 1030 |

The thrombospondin repeat was first described in 1986 by Lawler & Hynes. It was found in the thrombospondin protein where it is repeated 3 times. Now a number of proteins involved in the complement pathway (properdin. C6, C7, C8A, C8B, C9) as well as extracellular matrix protein like mindin, F-spondin, SCO-spondin and even the circumsporozoite surface protein 2 and TRAP proteins of Plasmodium have been shown to contain one or more structure provides some information about the structure of the thrombospondin type I repeat.

BLASTP analysis shows that NOV15 has 24 of 55 (43%) identical to, and 27 of 55 (49%) positive with, the 57 aa p36 (14) FSPO(5) TSP1(3) TSP2(2)—precursor glycoprotein signal repeat cell adhesion EGF-like domain thrombospondin calcium binding (prdm: 1719, Expect=3.0e–06); 15 of 35 (42%) identical to, and 18 of 35 (51%) positive with, the 54 aa p36 (25) TSP1(9) TSP2(4) PROP(3)—complement precursor repeat signal glycoprotein EGF-like domain pathway thrombospondin cell (prdm:873, Expect=0.00033); 20 of 68 (29%) identical to, and 28 of 68 (41%) positive with, the 108 aa p36 (1) SSP2_PLAYO—sporozoite surface protein 2 precursor, malaria; sporozoite; repeat; signal; antigen; transmembrane (prdm:36045, Expect=0.0014); 23 of 59 (38%) identical to, and 28 of 59 (47%) positive with, the 87 aa p36 (18) CSP(18)—circumsporozoite protein precursor CS malaria sporozoite repeat signal (prdm:1268, Expect=0.022); and 10 of 21 (47%) identical to, and 13 of 21 (61%) positive with, the 59 aa p36 (1) FSPO_XENLA—90) (NOV15b has 155/290 aa (53%) identical, 205/290 aa (70%) positive). NOV15a has 24 of 54 aa residues (44%) identical to, and 31 of 54 aa residues (57%) positive with, the 57 aa Human METH1 thombospondin-like domain #3 (patp:AAY49505, Expect=3.2e–06) (NOV15b has 24/54 aa (44%) identical, 31/54 aa (57%) positive). NOV15a has 24 of 54 aa residues (44%) identical to, and 31 of 54 aa residues (57%) positive with, the 57 aa Homo sapiens TSP1 domain (patp:AAB50007, Expect=3.2e–06) (NOV15b has 24/54 aa (44%) identical, 31/54 aa (57%) positive). The Patp BLAST results for NOV15a and NOV15b are listed in Table 15J.

TABLE 15J

Patp alignments of NOV15

| Sequences producing High-scoring Segment Pairs. | High Score | Smallest P(N) NOV15a | Sum Prob. P(N) NOV15b |
|---|---|---|---|
| patp:AAB41922 Human ORFX ORF1686 polypeptide seque . . . | 1048 | 7.8e-106 | 7.8e-106 |
| patp:AAB49765 Human proliferation differentiation . . . | 616 | 1.2e-90 | 5.2e-95 |
| patp:AAB88393 Human membrane or secretory protein . . . | 616 | 1.2e-90 | 5.2e-95 |
| patp:AAY49505 Human METH1 thombospondin-like doma . . . | 118 | 3.2e-06 | 2.1e-06 |
| patp:AAB50007 TSP1 domain #3-Homo sapiens, 57 aa . . . | 118 | 3.2e-06 | 2.1e-06 |

F-spondin precursor, glycoprotein; signal; repeat; cell adhesion (prdm:53698, Expect=0.43).

PROSITE analysis of NOV15a shows that the NOV15a polypeptide has two N-glycosylation sites (Pattern-ID: ASN_glycosylation PS00001 (Interpro)); four Protein kinase C phosphorylation sites (Pattern-ID: PKC_PHOSPHO_SITE PS00005 (Interpro)); eight Casein kinase II phosphorylation sites (Pattern-ID: CK2_PHOSPHO_SITE PS00006 (Interpro)), one Tyrosine kinase phosphorylation site (Pattern-ID: TYR_PHOSPHO_SITE PS00007 (Interpro)); and fourN-myristoylation sites (Pattern-ID: MYRISTYL PS00008 (Interpro)). PROSITE analysis of NOV15b shows that the NOV15b polypeptide has one N-glycosylation site (Pattern-ID: ASN_glycosylation PS00001 (Interpro)); three Protein kinase C phosphorylation sites (Pattern-ID: PKC_PHOSPHO_SITE PS00005 (Interpro)); seven Casein kinase II phosphorylation sites (Pattern-ID: CK2_PHOSPHO_SITE PS00006 (Interpro)); one Tyrosine kinase phosphorylation site (Pattern-ID: TYR_PHOSPHO_SITE PS00007 (Interpro)); and four N-myristoylation sites (Pattern-ID: MYRISTYL PS00008 (Interpro)).

In a BlastP analysis of a public database, NOV15a was found to have 185 of 188 aa residues aa residues (98%) identical to, and 188 of 188 aa residues (100%) positive with, the 198 aa Human ORFX ORF1686 polypeptide sequence SEQ ID NO:3372 (patp:AAB41922, Expect=7.8e–106) (NOV15b has 185/188 aa (98%) identical, 188/188 aa (100%) positive). NOV15a has 102 of 172 aa residues (59%) identical to, and 138 of 172 aa residues (80%) positive with, the 571 aa Human proliferation differentiation factor amino acid sequence (patp:AAB49765, Expect=1.2e–90) (NOV15b has 155/290 aa (53%) identical, 205/290aa (70%) positive). NOV15a has 102 of 172 aa residues (59%) identical to and 138 of 172 aa residues (80%) positive with, the 571 aa Human membrane or secretory protein clone PSECO137 (patp:AAB88393, Expect=1.2e–

The homologies shown above are shared by NOV15b insofar as NOV15b is homologous to NOV15a as shown in Table 15E.

The novel intracellular thrombospondin domain containing protein-like NOV15 gene disclosed in this invention is expressed in at least the following tissues: lung, testis, b-cell. Expression information was derived from the tissue sources of the sequences that were included in the derivation of the sequence, as described in Example 1.

The above defined information for this invention suggests that these novel intracellular thrombospondin domain containing protein-like NOV15 proteins may function as a member of a "novel intracellular thrombospondin domain containing protein-like family". Therefore, the NOV15 nucleic acids and proteins identified here may be useful in potential therapeutic applications implicated in (but not limited to) various pathologies and disorders as indicated below.

The protein similarity information, expression pattern, cellular localization, and map location for the protein and nucleic acid disclosed herein suggest that this novel intracellular thrombospondin domain containing protein-like NOV15 protein may have important structural and/or physiological functions characteristic of the novel intracellular thrombospondin domain containing protein family. Therefore, the NOV15 nucleic acids and proteins are useful in potential diagnostic and therapeutic applications and as a research tool. These include serving as a specific or selective nucleic acid or protein diagnostic and/or prognostic marker, wherein the presence or amount of the nucleic acid or the protein are to be assessed. These also include potential therapeutic applications such as the following: (i) a protein therapeutic, (ii) a small molecule drug target, (iii) an antibody target (therapeutic, diagnostic, drug targeting/cytotoxic antibody), (iv) a nucleic acid useful in gene therapy (gene delivery/gene ablation), (v) an agent promoting tissue regeneration in vitro and in vivo, and (vi) a biological defense weapon.

The NOV15 nucleic acids and proteins have applications in the diagnosis and/or treatment of various diseases and disorders. For example, the compositions of the present invention will have efficacy for the treatment of patients suffering from: systemic lupus erythematosus, autoimmune disease, asthma, emphysema, scleroderma, allergy, ARDS; fertility, hypogonadism; immunological disease and disorders as well as other diseases, disorders and conditions.

Based on the tissues in which NOV15 is most highly expressed; including Thryoid, heart, uterus, mammary gland, pituitary gland, lymph node, placenta, brain, pancreas, and spleen; specific uses include developing products for the diagnosis or treatment of a variety of diseases and disorders. Additional disease indications and tissue expression for NOV15 is presented in Example 2.

NOV15 nucleic acids and polypeptides are further useful in the generation of antibodies that bind immuno-specifically to the novel NOV15 substances for use in therapeutic or diagnostic methods. These antibodies may be generated according to methods known in the art, using prediction from hydrophobicity charts, as described in the "Anti-NOVX Antibodies" section below. For example the disclosed NOV15 proteins have multiple hydrophilic regions, each of which can be used as an immunogen. In one embodiment, a contemplated NOV15a epitope is from about amino acids 1 to 70. In additional embodiments, NOV15a epitopes are from about amino acids 175 to 230 and from about amino acids 250 to 539. In another embodiment, a NOV15b epitope is from about amino acids 1 to 60. In further embodiments, NOV15b epitopes are from about amino acids 65 to 225, from about amino acids 230 to 320 and from about amino acids 325 to 411. This novel protein also has value in development of powerful assay system for functional analysis of various human disorders, which will help in understanding of pathology of the disease and development of new drug targets for various disorders.

NOV16

NOV16 includes two novel FYVE finger-containing phosphoinositide kinase-like proteins disclosed below. The disclosed proteins have been named NOV16a and NOV16b.

NOV16a

A disclosed NOV16a nucleic acid of 2760 nucleotides (also referred to as 101330077 and 100391903) encoding a novel FYVE-finger kinase/Transposase-like protein is shown in Table 16A. An open reading frame was identified beginning with an ATG initiation codon at nucleotides 898–900 to and ending with a TGA codon at nucleotides 1516–1518. A putative untranslated region upstream from the initiation codon and downstream from the termination codon is underlined in Table 16A, and the start and stop codons are in bold letters.

TABLE 16A

NOV16a Nucleotide Sequence (SEQ ID NO:99)

CCGGGGGCGCAGCCGCGGGCCCACCTCGGCCTCCCCTGAGCGGACGCCTCCCCGCGCGCACCGGGGGCCCCGGAGACCG

CCTTCCCCGCTCCGAACGCACGCGGCCCGGCCCCGGCGAGGTGCCTGAACGCTACCCGAGCTGCGGCGGGGCTCCCGGG

GTGAGTGCTGCAGCCCCAGGCCCGCCTGCTCCCACAGGCTCGGGCAATGGAGACCCGCGGCCGCCCCCGCCCCTTGACC

CTGCCTCACCCCTCACGCCCGCTGCCGCCCACGACCTCCGACCCCGCTGCCGCCCGGCTCGCAGCCCGGCTCGCAGCCC

GGCTCGGCGGGCCTCACCTCCCGCGGGTTCCGCACTCCTCTTCCCGCCGTCCTGCTCCTCTCGGCCTTCTCCTCCAATA

GGCGCCTAGCACCCTGAGTGGGCTACACCAATCAGAGACGAAGCGGCGCTAACGTGACTGACTAACTAACCAATCCAAA

GTCTCAATCTCCCTGAGAGGGGCGGAGCGTACCCGGGCCAGCCCTCGCCGCCGATTGGTGATCGACCTCAGGGTTGCAG

GGGCGGTGCCCTTACACGGATTGGAGAGGGCAGCGATGGGGCGGAGTTCAAGCTCCGATTAGTCCGCGCTCCGTGGCGG

GCTTGGCGATTGGACGCCGGCGCTGTCAGCCGCGCGCGGACCGGGGCGGGGCGGCGGTGCCCCGGGCTGGGCGAGGGG

CCGGGTGCGGGGCCGCTGGCCGAGAGGCTGAGGCGGCGTCATGTCCTCCGAGGTGTCCGCGCGCCGCGACGCCAAGAAG

CTGGTGCGCTCCCCGAGCGGCCTGCGCATGGTGCCCGAACACCGCGCCTTCGGAAGCCCGTTCGGCCTGGAGGAGCCGC

AGTGGGTCCCGGACAAGGAGGTGGGTGTATGCAGTGTGACGCCAAGTTTGACTTTCTCACCAGAAAGCACCACTGTCGC

CGCTGCGGGAAGTGCTTCTGCGACAGGTGCTGCAGCCAGAAGGTGCCGCTGCGGCGCATGTGCTTTGTGGACCCCGTGC

GGCAGTGCGCGGAGTGCGCCCTGGTGTCCCTCAAGGACGGCGAGTTCTACGACAAGCAGCTCAAAGTGCTCCTGAGCGG

AGCCACCTTCCTCGTCACGTTTGGAAACTCAGAGAAACCTGAAACTATGACTTGTCGTCTTTCCAATAACCAGAGATAC

TTGTTTCTGGATGGAGACAGCCACTATGAAATCGAAATTGTACACATTTCCACCGTGCAGATCCTCACAGAAGGCTTCC

CTCCTGGAGAAAAAGACATTCACGCTTACACCAGCCTCCGGGGAGCCAGCCTGCCTCTGAAGGAGGCAACGCACGGGC

CACAGGCATGTTCCTGCAGTATACAGTGCCGCGGACGGAGGGTGTGACCCAGCTGAAGCTGACAGTGCTGGAGGACGTG

ACTGTGGGCAGGAGGCAGGCGGTGGCGTGGCTAGTGATCTGCAGGCTGCCAAGCTCCTCTATGAATCTCGGGACCAGTA

ACTCTACGTGGGCTGAGCTTGGAGTACGTGTGGTCACCAGGACTGAGTCGCTTGGAACAGCAGAGCCTGCTCCTTGCG

TACCACAGGGATTAATCCTGCTTGTGCTGGGAAATGCAACTCACTCATGTATTTGGAGAAACAGGAGTGTTCACTTATC

TAGTGCAATATGTTCACAGTTTATTAATGCTTTAAACAGCTTCATGTTTTAGAATTTGTGTATTGTCAATACTTAATTG

TABLE 16A-continued

NOV16a Nucleotide Sequence

GGGGTGGGAGAGACTGAGCTACACTACTGCTAAACTATTTTTAGCATAATATATACCATTTTTATGAGTTCGCAGGTCT

ACTAGAAGGTTCTGGCCCATCAATATTCATTTCATTTAATTCTTCCACAGAACCAGTTTGGGCAGTAGGAACTCAGGCT

TCTGGTCTGCAGTGGAGCCTGTTCGCCTCTAATAGCCAGTTTACAGCACTTGCCTTAGCCTGTTTCACAGACTTGTCCA

CTTACCTTGTCACTAATTTGGGGCTTCTGGGCTGTGAGTGATCCTTTGATACTTCACCAAGGGGAACGTGGGGGCTTTG

TGTTTTGTACTTTTCACTCACTATTTCACTTTATTAAGATGACTGTACAGCAATTTGTATATAAAGCTTATGATTAAAA

ACTATTTTGAACATACGGACAAGGCCTCGCCTTCCTGTGTCCAGATCACCTGAACCCTCGTGCCACAGCGCAGTCTGGG

TCCAGAAAGAAGACTCACAGCCGCCGGGGTGAGACGGGTTTATTGTGCACATTTACACAGCGTCAGCAGCGTCTGGGCT

GGCAGCGGCCATGCTCCTGTGGTCGGGCTGCTCTACAAGGGCGTTCACTTTTCTTCACCACACTATGTACAGTCAGTGC

TCCAAGGTGATGGGCTACAGTGCTGCATCAGTGAGTCTGTACACACATTTTTACATAAATTACACACGACTCATACATG

AAAAATAGAGCCTAAGGGCCTGTATTTTAATGAGAAAAAAAAAATTTCCAACATAGTTCGGGTAGCTTTGAATGGTCTA

GTCAAAAAATACTTTTGGTATATAAAAAGCCTGTACGTACAATTCACACCTCAGTGAAGCGCCCTCCTTGCCTTGAGGC

TGGGCCTGGGACAAAGCTGGCCTCACAGCCAGCCCAGGCAGGGAGATCGGCAGAGAGCGGTGGCCCCTGACCCCAGCTC

CTCTGCCCCAGCTGCTGCTCCTTGGTGGCGGCCCCTCCTGACACCAGGCGTCTGCCATCCTTCAGGCACCAAAC

A disclosed NOV16a polypeptide (SEQ ID NO:100) encoded by SEQ ID NO:99 is 206 amino acid residues and is presented using the one-letter amino acid code in Table 16B. SignalP, Psort and/or Hydropathy resullts predict that NOV16b has no known signal peptide and is likely to be localized in the cytoplasm with a certainty of 0.6500. In alternative embodiments, NOV16b is localized to the mitochondrial matrix space with a certainty of 0.11000, lysosome (lumen) with a certainty of 0.11000, or perhaps the endoplasmnic reticulum (membrane) with a certainty of <0.0001. NOV16a has amolecular weight of 23030.2 Daltons.

NOV16b

A disclosed NOV16b nucleic acid of 673 nucleotides (also referred to as CG 57248-01) encoding a novel FYVE-finger kinase/Transposase-like protein is shown in Table 16C. An open reading, frame was identified beginning with an ATG initiation codon at nucleotides 44–46 and ending with a TAA codon at nucleotides 650–652. A putative untranslated region upstream from the initiation codon and downstream from the termination codon is underlined in Table 16C, and the start and stop codons are in bold letters.

TABLE 16B

Encoded NOV16a protein sequence.

(SEQ ID NO:100)

MQCDAKFDFLTRKHHCRRCGKCFCDRCCSQKVPLRRMCFVDPVRQCAECALVSLKEAEFYDKQLKVLLSGATFLV

TFGNSEKPETMTCRLSNNQRYLFLDGDSHYEIETVHISTVQILTEGFPPGEKDTHAYTSLRGSQPASEGGNARAT

GMFLQYTVPGTEGVTQLKLTVVEDVTVGRRQAVAWLVICRLPSSSMNLGTSNSTWG

TABLE 16C

NOV16b Nucleotide Sequence (SEQ ID NO:101)

GTTCCAACTATTTTGTCCGCCCACAGGAATTCGCCCTTGGTGTATGCAGTGTGACGCCAAGTTTGACTTTCTCACCA

GAAAGCACCACTGTCGCCGCTGCGGGAAGTGCTTCTGCGACAGCTGCTGCAGCCAGAAGGTGCCGCTGCGGCGCATG

TGCTTTGTGGACCCCGTGCGGCAGTGCGCGGAGTGCGCCCTGGTGTCCCTCAAGGAGGCGGAGTTCTACGACAACCA

GCTCAAAGTGCTCCTGAGCGGAGCCACCTTCCTCGTCACGTTTGGAAACTCAGAGAAACCTGAAACTATGACTTGTC

GTCTTTCCAATAACCAGAGATACTTGTTTCTGGATGGAGACAGCCACTATGAAATCGAAATTGTACACATTTCCACC

TABLE 16C-continued

NOV16b Nucleotide Sequence

GTGCAGATCCTCACAGAAGGCTTCCCTCCTGGAGAAAAAGACATTCACGCTTACACCAGCCTCCGGGGGAGCCAGCC

TGCCTCTGAAGGAGGCAACGCACAGGCCACAGGCATGTTCCTGCAGTATACAGTGCCGGGGACGGAGGGTGTGACCC

AGCTGAAGCTGACAGTGGTGGAGGACGTGACTGTGGGCAGCAGGCAGGCGGTGGCGTGGCTAGTGGCCATGCACAAG

GCTGCCAAGCTCCTCTATGAATCTCGGGACCAGTAACTCTACGTGGGGCTGAGCTTG

A disclosed NOV16b polypeptide (SEQ ID NO:102) encoded by SEQ ID NO:101 is 202 amino acid residues and is presented using the one-letter amino acid code in Table 16D. SignalP, Psort and/or Hydropathy results predict that NOV16b has no known signal peptide and is likely to be localized in the cytoplasm with a certainty of 0.4500. In alternative embodiments, NOV16b is localized to the microbody (peroxisome) with a certainty of 0.3000, a mitochondrial matrix space with a certainty of 0.1000, or a lysosome (lumen) with a certainty of 0.1000. NOV16b has a molecular weight of 22751.9 Daltons.

TABLE 16D

Encoded NOV16b protein sequence.

(SEQ ID NO:102)

MQCDAKFDFLTRKHHCRRCGKCFCDRCCSQKVPLRRMCFVDPVRQCAECALVSLKEAEFYDKQLKVLLSGATPLV

TFGNSEKPETMTCRLSNNQRYLFLDGDSHYEIEIVHISTVQILTEGFPPGEKDIHAYTSLRGSQPASEGGNAQAT

GMFLQYTVPGTEGVTQLKLTVVEDVTVGRRQAVAWLVAMHKAAKLLYESRDQ

The FYVE finger-containing phosphoinositide kinase-like gene disclosed in this invention maps to chromosome 14. This assignment was made using mapping information associated with genomic clones, public genes and ESTs sharing sequence identity with the disclosed sequence and CuraGen Corporation's Electronic Northern bioinformatic tool. NOV16a and NOV16b are related to each other as shown in the alignment listed in Table 16E.

TABLE 16E

ClustalW of NOV16 Variants

```
16    MQCDAKFDFLTRKHHCRRCGKCFCDRCCSQKVPLRRMCFVDPVRQCAECA  50
16-1  MQCDAKFDFLTRKHHCRRCGKCFCDRCCSQKVPLRRMCFVDPVRQCAECA  50

16    LVSLKEAEFYDKQLKVLLSGATFLVTFGNSEKPETMTCRLSNNQRYLFLD  100
16-1  LVSLKEAEFYDKQLKVLLSGATFLVTFGNSEKPETMTCRLSNNQRYLFLD  100

16    GDSHYEIEIVHISTVQILTEGFPPGEKDIHAYTSLRGSQPASEGGNARAT  150
16-1  GDSHYEIEIVHISTVQILTEGFPPGEKDIHAYTSLRGSQPASEGGNAQAT  150

16    GMFLQYTVPGTEGVTQLKLTVVEDVTVGRRQAVAWLVICRLPSSSMNLGT  200
16-1  GMFLQYTVPGTEGVTQLKLTVVEDVTVGRRQAVAWLVAMHKAAKLLYESR  200

16    SNSTWG                                              206
16-1  DQ----                                              202
```

The disclosed NOV16a amino acid sequence has homology to the amino acid sequences shown in the BLASTP data listed in Table 16F.

TABLE 16F

BLAST results for NOV16a

| Gene Index/ Identifier | Protein/Organism | Length (aa) | Identity (%) | Positives (%) | Expect |
|---|---|---|---|---|---|
| Q9BQ24; BC005999; AAH05999.1; AAH01130 | HYPOTHETICAL 26.5 KDA PROTEIN (UNKNOWN) (PROTEIN FOR MGC:2550). homo sapiens. Jun. 2001 | 234 | 169/187 (90%) | 169/187, (90%) | 7e−95 |
| Q9D1E2; AK003661; BAB22923.1 | 1110013H04RIK PROTEIN. mus musculus Jun. 2001 | 212 | 136/186 (73%) | 145/186, (78%) | 4e−75 |
| FYV1_MOUSE; Q9Z1T6; AF102777; AAD10191.1 | FYVE finger-containing phosphoinositide kinase (EC 2.7.1.68 (1-phosphatidylinositol-4-phosphate kinase) (PIP5K) (PTDINS(4)P-5-KINASE) (P235). mus musculus. May 2000 | 2052 | 35/113 (31%) | 56/113, (50%) | 3e−09 |
| Q9HCC9; AB046863; BAB13469.1 | KIAA1643 PROTEIN (FRAGMENT). homo sapiens. Jun. 2001 | 993 | 26/47 (55%) | 27/47, (57%) | 5e−09 |
| Q9CVQ1; AK007036 BAB24835.1 | 1700092A20RIK PROTEIN (FRAGMENT). | 173 | 23/47 (49%) | 28/47, (60%) | 8e−09 |

In a search of sequence databases, it was found, for example, that the NOV16 nucleic acid sequence of this invention has 208 of 215 bases (96%) identical to a gb:GenBank-ID:AK001921|acc:AK001921.1 mRNA from Homo sapiens (Homo sapiens cDNA FLJ11059 fis, clone PLACE1004740). The full NOV16 amino acid sequence was found to have 37 of 111 amino acid residues (33%) identical to, and 61 of 111 amino acid residues (54%) similar to, the 2052 amino acid residue ptnr:SWISSNEW-ACC:Q9Z1T6 protein from Mtis musculus (Mouse) (FYVE finger-containing phosphoinositide kinase (EC 2.7.1.68) (1-phospatidylinositol-4-phosphate kinase) (PIP5K) (PTDINS(4)P-5-KINASE) (P235)).

The disclosed NOV16b amino acid sequence has homology to the amino acid sequences shown in the BLASTP data listed in Table 16G.

TABLE 16G

BLAST results for NOV16b

| Gene Index/ Identifier | Protein/Organism | Length (aa) | Identity (%) | Positives (%) | Expect |
|---|---|---|---|---|---|
| Q9BQ24 | HYPOTHETICAL 26.5 KDA PROTEIN (UNKNOWN) (PROTEIN FOR MGC:2550). homo sapiens. Jun. 2001 | 234 | 183/202 (91%) | 184/202, (91%) | 1e−103 |
| Q9D1E2 | 1110013H04RIK PROTEIN. mus musculus. Jun. 2001 | 212 | 150/202 (74%) | 159/202, (79%) | 2e−83 |
| FYV1_MOUSE | FYVE FINGER- CONTAINING PHOSPHOINOSITIDE KINASE (EC 2.7.1.68) (1-PHOSPHATIDYLINOSITOL-4-PHOSPHATE KINASE) (PIP5K) (PTDINS (4) P-5-KINASE) (P235). mus musculus. May 2000 | 2052 | 35/113 (31%) | 56/113, (50%) | 3e−09 |
| Q9HCC9 | K1AA1643 PROTEIN (FRAGMENT). | 993 | 26/47 (55%) | 27/47, (57%) | 5e−09 |
| Q9CVQ1 | 1700092A20RIK PROTEIN (FRAGMENT). | 173 | 23/47 (49%) | 28/47, (60%) | 8e−09 |

The homology of these sequences is shown graphically in the ClustalW analysis shown in Table 16H.

TABLE 16H

Information for the ClustalW proteins

1) NOV16a (SEQ ID NO:100)
2) NOV16b (SEQ ID NO:102)
3) Q9BQ24 (SEQ ID NO:103)

TABLE 16H-continued

Information for the ClustalW proteins

4) Q9D1E2 (SEQ ID NO:104)
5) Q9HCC9N-ter fragment (SEQ ID NO:105)
6) Q9CVQ1 (SEQ ID NO:106)
7) FYV1_MOUSE N-ter fragment (SEQ ID NO:107)

```
NOV16a     --------------------------------------------------  1
NOV16b     --------------------------------------------------  1
Q9BQ24     --------------------------------------------------  1
Q9D1E2     --------------------------------------------------  1
Q9HCC9     PAERWVSVSSEEPRAPVPASVRAPERPLPGLRSARRAACRAYSGP-----  45
Q9CVQ1     -----LHHKWLNSHSGRPSTTSSPDQPS--RSHLDDDGMPVYTDT-----  38
FYV1_MOUSE MATDDKSSPTLDSANDLPRSPASPSHLTHFKPLTPDQDEPPFKSAYSSFV  50

NOV16a     ----------------MSSEVSARRDAKKLVRSPSGLRMVEEHRAFGSPF  34
NOV16b     --------------------------------------------------  1
Q9BQ24     ----------------MSSEVSARRDAKKLVRSPSGLRMVEEHRAFGSPF  34
Q9D1E2     --------------------------------------MVEEHRAFGSPF  12
Q9HCC9     ---RTCPAHLPAARSALRASLASLPATARGLRPCLRVRPAEQPGPGAALR  92
Q9CVQ1     -----IQQRLRQIESGHQQEVETLKKQVQELKSRLESQYLTSSLRFNGDE  83
FYV1_MOUSE NLFRFNKERGEGGQGEQQSPSSSWASPQIPSRTQSVRSPVEYKKQLNEEL 100

NOV16a     G---------LEEPQ-----------------------------------  40
NOV16b     --------------------------------------------------  1
Q9BQ24     G---------LEEPQ-----------------------------------  40
Q9D1E2     G---------LEEPQ-----------------------------------  18
Q9HCC9     R---------ARAAR-----------------------------------  98
Q9CVQ1     G---------DEVMTR----------------------------------  90
FYV1_MOUSE HRRSSVLENTLPHPQESTDSRRKAEPACGGHDPRTAVQLRSLSTVLKRLK 150

NOV16a     ----------------WVPDKECRRCMQCDAKFDFITRKHHCRRCGKCFCD  75
NOV16b     --------------------------MQCDAKFDFITRKHHCRRCGKCFCD  25
Q9BQ24     ----------------WVPDKECRRCMQCDAKFDFITRKHHCRRCGKCFCD  75
Q9D1E2     ----------------WVPDKECRRCMQCDAKFDFITRKHHCRRCGKCFCD  53
Q9HCC9     ----------------SPARAGAAMMNRFRKWLYKPKRSDPQLLARFYYA  132
Q9CVQ1     ----------------WLPDHLAAHCYACDSAFWLASRKHHCRNCGNVFCS 125
FYV1_MOUSE EIMEGKSQDSDLKQYWMPDSQCKECYDCSEKFTTFRRRHHCRLCGQIFCS 200

NOV16a     RCCSQKVPLRRMCFVDPVRQCAECALVSLKEAEFYD-------------- 111
NOV16b     RCCSQKVPLRRMCFVDPVRQCASCALVSLKEAEFYD--------------  61
Q9BQ24     RCCSQKVPLRRMCFVDPVRQCAECALVSLKEAEFYD-------------- 111
Q9D1E2     RCCSQKVPLRRMCFVDPVRQCADCALVSHREAEFYD--------------  89
Q9HCC9     DEELNQVAAELDSLDGR-KDPQRCTLEVSQFRSCQDN-------------- 168
Q9CVQ1     SCCNQKVPSQQLFEPSRVCKSCYSSLHPTSSSID---------------- 161
FYV1_MOUSE RCCNQEIPGKFMGYTGDLRACTYCRKIALSYAHSTDSNSIGEDLNALSDS 250

NOV16a     -------------------------------------------------- 111
NOV16b     --------------------------------------------------  61
Q9BQ24     -------------------------------------------------- 111
Q9D1E2     --------------------------------------------------  89
Q9HCC9     -------------------------------------------------- 168
Q9CVQ1     -------------------------------------------------- 161
FYV1_MOUSE TCSVSILDPSEPRTPVGSRKASRNIFLEDDLAWQSLIHPDSSNSALSTRL 300

NOV16a     ------------------KQLKVLLSGATFLVTFGNSEKPET----MTC 138
NOV16b     ------------------KQLKVLLSGATFLVTFGNSEKPET----MTC  88
Q9BQ24     ------------------KQLKVLLSGATFLVTFGNSEKPET----MTC 138
Q9D1E2     ------------------KQLKVLLSGATFLVTFGSSEKPET----MVC 116
Q9HCC9     ---------VLNIINQIMDECIPQDRAPRDECVKFPEEIRHDN----LAG 205
Q9CVQ1     ----------------LELDKP----IAATSN----------------- 173
FYV1_MOUSE VSVQEDAGKSPARNRSASITNLSLDRSGSPMVPSYETSVSEQANRNYIRT 350

NOV16a     RLSNNQRYLFLD-------------------------------------- 150
NOV16b     RLSNNQRYLFLD-------------------------------------- 100
Q9BQ24     RLSNNQRYLFLD-------------------------------------- 150
Q9D1E2     RLSNNQRCLVLD-------------------------------------- 128
Q9HCC9     QLWFGAECLAAG-------------------------------------- 217
Q9CVQ1     -------------------------------------------------- 173
FYV1_MOUSE ETTEDERKILLDSAQLKDLWKKICHHTSGMEFQDHRYWLRTHPNCIVGKE 400

NOV16a     -----GDSHYEIEIVHISTVQILTEG------------------FPPG 175
NOV16b     -----GDSHYEIEIVHISTVQILTEG------------------FPPG 125
Q9BQ24     -----GDSHYEIEIVHISTVQILTEG------------------FPPG 175
Q9D1E2     -----GDSHREIEIAHVCTVQILTEG------------------FTPG 153
Q9HCC9     -------SIIMNRELESMAMRPLAKELTR------------------S 240
Q9CVQ1     -------------------------------------------------- 173
FYV1_MOUSE LVNWLIRNGHIATRAQAIAIGQAMVDGRWLDCVSHHDQLFRDEYALYRPL 450
```

TABLE 16H-continued

Information for the ClustalW proteins

```
NOV16a      --------------------GCN--------------------ARATGMFL  186
NOV16b      EKDIHAYTSLRGSQPA-SEGCN--------------------AQATGMFL  154
Q9BQ24      --------------------GCN--------------------ARATGMFL  186
Q9D1E2      --------------------ACS--------------------TLATGMLL  164
Q9HCC9      ---------------LEDVRCALR-----------------DQALRDLN   257
Q9CVQ1      --------------------------------------------------  173
FYV1_MOUSE  QSTEFSETPSPSDSVNSVECHSEPSWFKDIKFDDSDTEQIAEEGDDNLA   500

NOV16a      QYTVPGTEG---------------------------------VTQLKLT   202
NOV16b      QYTVPGTEG---------------------------------VTQLKLT   170
Q9BQ24      QYTVPGTEG---------------------------------VTQLKLT   202
Q9D1E2      QYTVPGAEA---------------------------------AAQIRLM   180
Q9HCC9      TYTEKMREALR-----------------------HFDVLFAEFELS    280
Q9CVQ1      --------------------------------------------------  173
FYV1_MOUSE  KYLVSDTGGQQLSISDAFIKESLFNRRVEEKSKELPFTPLGWHHNNLELL  550

NOV16a      VVED---------VTVGRRQAVAWLVAMHKAAKLLYESRDQ-         234
NOV16b      VVED---------VTVGRRQAVAWLVAMHKAAKLLYESRDQ-         202
Q9BQ24      VVED---------VTVGRRQAVAWLVAMHKAAKLLYESRDQ-         234
Q9D1E2      AGED---------ASGSKRQAAAWLAAMHKATKLLYESRDQ-         212
Q9HCC9      YVSAMVPVKSPREYYVQQEVIVLPCETVERALDFGYLTQDMIDDYEP... 330
Q9CVQ1      --------------------------------------------------  173
FYV1_MOUSE  REENEEKQAMERLLSANHNHMMALLQQLLQNESLSSSWRDIIVSLVC... 600
```

Table 16I lists the domain description from DOMAIN analysis results against NOV16a. This indicates that the NOV16a sequence has properties similar to those of other proteins known to contain this domain.

A PROSITE Protein Domain Matches analysis of the NOV16a protein suggests that NOV16a has one N-glycosylation site (Pattern-ID: ASN_glycosylation PS00001 (Interpro)); six Protein kinase C phosphorylation

TABLE 16I

Domain Analysis of NOV16a

PFAM HMM Domain Analysis of NOV16

| Model | Domain | seq-f | seq-t | hmm-f | hmm-t | score | E-value |
|-------|--------|-------|-------|-------|-------|-------|---------|
| FYVE  | 1/1    | 1     | 49 [. | 13    | 66 .. | 29.1  | 8.9e-07 |

PRODOM analysis of Nov16 prdm:3303 p36 (8) FGD1(2)-PROTEIN KINASE RHO/RAC FACTOR ZINC-FINGER PUTATIVE GUANINE NUCLEOTIDE EXCHANGE GEF, 235 aa
Expect = 0.00015, identity = 20/50 (40%), positive = 24/50 (48%) for NOV16a: 1 to 49; Sbjct: 148 to 197 prdm:28902 p36 (1) YLN2_CAEEL-HYPOTHETICAL 46.2 KD TRP-ASP REPEATS CONTAINING PROTEIN D2013.2 IN CHROMOSOME II. HYPOTHETICAL PROTEIN; REPEAT; WD REPEAT, 138 aa
Expect = 0.0019, identity = 14/38 (36%), positive = 18/38 (47%) for NOV16a: 12 to 49; Sbjct: 38 to 75 prdm:4778 p38 (5)-INHIBITOR SERINE PROTEASE CHYMOTRYPSIN/ELASTASE PROTEIN TRYPSIN ISOINHIBITOR ISOINHIBITORS R10H1.1 CHROMOSOME, 67 aa
Expect = 0.053, identity = 14/38 (35%), positive = 21/38 (58%), for NOV16a: 18 to 53; Subject: 13 to 48

BLOCKS Protein Domain Analysis of NOV16a

| AC#      | Description                                 | Strength | Score |
|----------|---------------------------------------------|----------|-------|
| BL00940B | 0 Gamma-thionins family proteins.           | 1324     | 1093  |
| BL01102  | 0 Prokaryotic dksA/traR C4-type zinc finger.| 1600     | 1053  |
| BL00518  | 0 Zinc finger, C3HC4 type (RING finger), protei | 1150 | 1034  |
| BL01185D | 0 C-terminal cystine knot proteins.         | 1733     | 1026  |
| BL00478A | 0 LIM domain proteins.                      | 1037     | 1023  |
| BL00597B | 0 Plant lipid transfer proteins.            | 1514     | 1021  | sites (Pattern-ID: PKC_PHOSPHO_SITE PS00005 (Interpro)); three Casein kinase II phosphorylation sites (Pattern-ID: CK2_PHOSPHO_SITE PS00006 (Interpro)); three N-myristoylation sites (Pattern-ID: MYRISTYL PS00008 (Interpro)); and one Amidation site (Pattern-ID: AMIDATION PS00009 (Interpro)).

Table 16J lists the domain description from DOMAIN analysis results against NOV16b. This indicates that the NOV16b sequence has properties similar to those of other proteins known to contain this domain.

TABLE 16J

Domain Analysis of NOV16b

ProDom Analysis prdm:3303 p36 (8) FGD1(2) - PROTEIN KINASE RHO/RAC FACTOR ZINC-FINGER PUTATIVE GUANINE NUCLEOTIDE EXCHANGE GEF, 235 aa
Expect = 0.00014, identical = 20 of 50 (40%), positive = 24 of 50 (48%)
prdm:28902 p36 (1) YLN2_CAEEL - HYPOTHETICAL 46.2 KD TRP-ASP REPEATS CONTAINING PROTEIN D2013.2 IN CHROMOSOME II. HYPOTHETICAL PROTEIN; REPEAT; WD REPEAT, 138 aa
Expect = 0.0018, identical = 14 of 38 (36%), positive = 18 of 38 (47%)
prdm:4778 p36 (5) - INHIBITOR SERINE PROTEASE CHYMOTRYPSIN/ELASTASE PROTEIN TRYPSIN ISOINTHIBITOR ISOINHIBITORS R1OH1.1 CHROMOSOME, 67 aa
Expect = 0.051, identical = 14 of 36 (38%), positive = 21 of 36 (58%)

BLOCKS Protein Domain Analysis of NOV16b

| AC # | Description | Strength | Score |
|---|---|---|---|
| BL00940B | Gamma-thionins family proteins. | 1324 | 1093 |
| BL01102 | Prokaryotic dksA/traR C4-type zinc finger. | 1600 | 1053 |
| BL00518 | Zinc finger, C3HC4 type (RING finger), protei | 1150 | 1034 |
| BL01185D | C-terminal cystine knot proteins. | 1733 | 1028 |
| BL00478A | LIM domain proteins | 1037 | 1023 |
| BL00597B | Plant lipid transfer proteins. | 1514 | 1021 |

PROSITE - Protein Domain Matches for Gene ID: NOV16-1

Pattern-ID: PKC_PHOSPHO_SITE PS00005 (Interpro) PDOC00005
6 Protein kinase C phosphorylation site
Pattern-ID: CK2_PHOSPHO_SITE PS00006 (Interpro) PDOC00006
3 Casein kinase II phosphorylation site
Pattern-ID: MYRISTYL PS00008 (Interpro) PDOC00008
2 N-myristoylation site
Pattern-ID: AMIDATION PS00009 (Interpro) PDOC00009
1 Amidation site

PFAM HMM Domain Analysis of NOV16b

| Model | Domain | seq-f | seq-t | hmm-f | hmm-t | score | E-value |
|---|---|---|---|---|---|---|---|
| FYVE zinc finger | 1/1 | 1 | 49 [. | 13 | 66 . . . | 29.1 | 8.9e–07 |

In a BlastP analysis of a public database, NOV16a was found to have 70 of 70 (100%) identical to, and 70 of 70 (100%) positive with, the 146 aa Human ORFX ORF3149 polypeptide sequence SEQ ID NO:6298 (patp:AAB43385, Expect=1.2e–36); 37 of 111 (33%) identical to, and 61 of 111 (54%) positive with, the 2052 aa Mus sp phosphatidylinositol-4-phosphate-5-kinase, designated p235 (patp:AAB08634, Expect=6.9e–10); 21 of 47 (44%) identical to, and 25 of 47 (53%) positive with, the 195 aa Homo sapiens Polypeptide fragment encoded by gene 57 (patp:AAY01473, Expect=3.5e–07); 28 of 64 (43%) identical to, and 37 of 64 (57%) positive with, the 1235 aa *Xenopus* sp Smad Anchor for Receptor Activation protein-1 (patp:AAY44751, Expect=8.8e–07); and 18 of 47 (38%) identical to, and 24 of 47 (51%) positive with, the 138 aa *Arabidopsis thaliana* protein fragment SEQ ID NO: 28225 (patp:AAG24520, Expect=3.3e–06). The Patp BLAST results for NOV16a and NOV16b are listed in Table 16K.

TABLE 16K

Patp alignments of NOV16

| Sequences producing High-scoring Segment Pairs: | High Score | NOV16a Smallest Sum Prob. P (N) | NOV16b Smallest Sum Prob. (N) |
|---|---|---|---|
| patp: AAB43385 Human ORFX ORF3149 polypeptide sequence SEQ . . . | 395 | 1.2e–36 | 1.2e–36 |
| patp: AAB08634 A murine phosphatidylinositol-4-phosphate-5 . . . | 159 | 6.9e–10 | 6.9e–10 |
| patp: AAY01473 Polypeptide fragment encoded by gene 57 - H . . . | 129 | 3.5e–07 | 3.1e–07 |
| patp: AAY44751 Xenopus Smad Anchor for Receptor Activation . . . | 139 | 8.8e–07 | 6.7e–07 |

TABLE 16K-continued

Patp alignments of NOV16

| Sequences producing High-scoring Segment Pairs: | High Score | NOV16a Smallest Sum Prob. P (N) | NOV16b Smallest Sum Prob. (N) |
|---|---|---|---|
| patp: AAG24520 *Arabidopsis thaliana* protein fragment SEQ I . . . | 110 | 3.3e−06 | 3.0e−06 |
| patp: AAY44749 Human Smad Anchor for Receptor Activation p . . . | 134 | 4.6e−06 | 3.8e−06 |

The homologies shown above are shared by NOV16b insofar as NOV16b is homologous to NOV16a as shown in Table 16E.

Signaling by phosphorylated species of phosphatidylinositol (PI) appears to regulate diverse responses in eukaryotic cells. A differential display screen for fat- and muscle-specific transcripts led to identification and cloning of the full-length cDNA of a novel mammalian 2,052-amino-acid protein (p235) from a mouse adipocyte cDNA library. Analysis of the deduced amino acid sequence revealed that p235 contains an N-terminal zinc-binding FYVE finger, a chaperonin-like region in the middle of the molecule, and a consensus for phosphoinositide 5-kinases at the C terminus. p235 mRNA appears as a 9-kb transcript, enriched in insulin-sensitive cells and tissues, likely transcribed from a single-copy gene in at least two close-in-size splice variants. Specific antibodies against mouse p235 were raised, and both the endogenously and heterologously expressed proteins were biochemically detected in 3T3-L1 adipocytes and transfected COS cells, respectively. Immunofluorescence microscopy analysis of endogenous p235 localization in 3T3-L1 adipocytes with affinity-purified anti-p235 antibodies documented a punctate peripheral pattern. In COS cells, the expressed p235 N-terminal but not the C-terminal region displayed a vesicular pattern similar to that in 3T3-L1 adipocytes that became diffuse upon Zn2+ chelation or FYVE finger truncation. A recombinant protein comprising the N-terminal but not the C-terminal region of the molecule was found to bind 2.2 mole equivalents of Zn2+. Determination of the lipid kinase activity in the p235 immunoprecipitates derived from 3T3-L1 adipocytes or from COS cells transiently expressing p235 revealed that p235 displayed unique preferences for PI substrate over already phosphorylated PI. In conclusion, the mouse p235 protein determines an important novel class of phosphoinositide kinases that seems to be targeted to specific intracellular loci by a Zn-dependent mechanism See, PMID: 9858586

Isoforms of protein kinase B (PKB, or AKT1; 164730) are overexpressed in some ovarian, pancreatic, and breast cancer cells, and PKB has been shown to protect cells from apoptosis. Activation of PKB, which is preventable by inhibitors of phosphoinositide 3-kinase (see PIK3CG; 601232), is stimulated by insulin or growth factors after phosphorylation of PKB at thr308 and ser473. Alessi et al. (1997) biochemically purified a protein kinase, which they called PDK1, that phosphorylates PKB at thr308 in response to phosphotidylinositol 3,4,5-trisphosphate (Ptdlns(3,4,5) P3) or phosphotidylinositol 3,4-biphosphate (Ptdlns(3,4)P2) and enhances PKB activity. By microsequence analysis of the approximately 67- to 69-kD PDK1 protein, searching an EST database, and probing a breast cancer cell line cDNA library, Alessi et al. (1997) isolated a cDNA encoding PDK1, also called PDPK1. Sequence analysis predicted that the 556-amino acid PDPK1 protein contains a catalytic domain with II classic kinase subdomains and a C-terminal pleckstrin homology (PH) domain. Expression of recombinant PDPK1 resulted in the activation and phosphorylation of PKB at thr308 in a Ptdlns(3,4,5)P3- or Ptdlns(3,4)P2-dependent manner via the PH domains.

Ptdlns(3,4,5)P3 and Ptdlns(3,4)P2 bind to the PH domains of PKB and PDPK1, causing their translocation to the membrane and leading to PKB activation. See, Stephens et al., Science 279: 710–714, 1998. PDPK1 selectively phosphorylates the 70-kD ribosomal protein S6 kinase (p70-RPS6K) at thr229, which is required for its activation. See, Pullen et al., Science 279: 707–710, 1998. Thr229 of p70-RPS6K is homologous to thr308 of the PKB protein. The PDPK1 gene was mapped to 16p13.3 based on its identity to a sequence located in the same region as the PKD1 (601313) and TSC2 (191092) loci. See, Burn et al., Genome Res. 6: 525–537, 1996; Alessi et al., Curr. Biol. 7: 261–269, 1997; Alessi et al., Curr. Biol. 7: 776–789, 1997.

The FYVE zinc finger is named after four proteins that it has been found in: Fab1, YOTB/ZK632.12, Vac1, and EEA1. The FYVE finger has been shown to bind two Zn2+ ions. The FYVE finger has eight potential zinc coordinating cysteine positions. Many members of this family also include two histidines in a motif R+HHC+XCG, where + represents a charged residue and X any residue. See, IPR000306

This indicates that the NOV16 sequence has properties similar to those of other proteins known to contain this/these domain(s) and similar to the properties of these domains.

The above defined information for this invention suggests that these FYVE finger-containing phosphoinositide kinase-like NOV16 proteins may function as a member of a "FYVE finger-containing phosphoinositide kinase-like protein family". Therefore, the NOV16 nucleic acids and proteins identified here may be useful in potential therapeutic applications implicated in (but not limited to) various pathologies and disorders as indicated below.

The protein similarity information, expression pattern, cellular localization, and map location for the protein and nucleic acid disclosed herein suggest that this FYVE finger-containing phosphoinositide kinase-like protein may have important structural and/or physiological functions characteristic of the FYVE finger-containing phosphoinositide kinase family. Therefore, the nucleic acids and proteins of the invention are useful in potential diagnostic and therapeutic applications and as a research tool. These include serving as a specific or selective nucleic acid or protein diagnostic and/or prognostic marker, wherein the presence or amount of the nucleic acid or the protein are to be assessed. These also include potential therapeutic applications such as the following: (i) a protein therapeutic, (ii) a small molecule drug target, (iii) an antibody target (therapeutic, diagnostic, drug targeting/cytotoxic antibody), (iv) a nucleic acid useful in gene therapy (gene delivery/gene ablation), (v) an agent promoting tissue regeneration in vitro and in vivo, and (vi) a biological defense weapon.

The nucleic acids and proteins of the invention have applications in the diagnosis and/or treatment of various diseases and disorders. For example, the compositions of the present invention will have efficacy for the treatment of patients suffering from: diabetes, obesity, fertility, signaling as well as other diseases, disorders and conditions.

Based on the tissues in which NOV16 is most highly expressed; including placenta, spleen, prostate, kidney, pancreas, thyroid, testis, ovary, uterus, heart, lung, brain cervix, umbilical vein, adrenal gland, bone and others; specific uses include developing products for the diagnosis or treatment of a variety of diseases and disorders. Additional disease indications and tissue expression for NOV16 is presented in Example 2.

These materials are further useful in the generation of antibodies that bind immunospecifically to the novel substances of the invention for use in diagnostic and/or therapeutic methods. NOV16 nucleic acids and polypeptides are further useful in the generation of antibodies that bind immuno-specifically to the novel NOV16 substances for use in therapeutic or diagnostic methods. These antibodies may be generated according to methods known in the art, using prediction from hydrophobicity charts, as described in the "Anti-NOVX Antibodies" section below. For example the disclosed NOV16 proteins have multiple hydrophilic regions, each of which can be used as an immunogen. In one embodiment, a contemplated NOV16a epitope is from about amino acids 1 to 45. In additional embodiments, NOV16a epitopes are from about amino acids 50 to 60, from about amino acids 75 to 110, from about amino acids 120 to 160 and from about amino acids 190 to 206. In another embodiment, a NOV16b epitope is from about amino acids 1 to 45. In further embodiments, NOV16b epitopes are from about amino acids 50 to 70, from about amino acids 75 to 110, from about amino acids 120 to 160 and from about amino acids 180 to 202. This novel protein also has value in development of powerful assay system for functional analysis of various human disorders, which will help in understanding of pathology of the disease and development of new drug targets for various disorders.

NOVX Nucleic Acids and Polypeptides

One aspect of the invention pertains to isolated nucleic acid molecules that encode NOVX polypeptides or biologically active portions thereof. Also included in the invention are nucleic acid fragments sufficient for use as hybridization probes to identify NOVX-encoding nucleic acids (e.g., NOVX mRNAs) and fragments for use as PCR primers for the amplification and/or mutation of NOVX nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule may be single-stranded or double-stranded, but preferably is comprised double-stranded DNA.

An NOVX nucleic acid can encode a mature NOVX polypeptide. As used herein, a "mature" form of a polypeptide or protein disclosed in the present invention is the product of a naturally occurring polypeptide or precursor form or proprotein. The naturally occurring polypeptide, precursor or proprotein includes, by way of nonlimiting example, the full-length gene product, encoded by the corresponding gene. Alternatively, it may be defined as the polypeptide, precursor or proprotein encoded by an ORF described herein. The product "mature" form arises, again by way of nonlimiting example, as a result of one or more naturally occurring processing steps as they may take place within the cell, or host cell, in which the gene product arises. Examples of such processing steps leading to a "mature" form of a polypeptide or protein include the cleavage of the N-terminal methionine residue encoded by the initiation codon of an ORF, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

The term "probes", as utilized herein, refers to nucleic acid sequences of variable length, preferably between at least about 10 nucleotides (nt), 100 nt, or as many as approximately, e.g., 6,000 nt, depending upon the specific use. Probes are used in the detection of identical, similar, or complementary nucleic acid sequences. Longer length probes are generally obtained from a natural or recombinant source, are highly specific, and much slower to hybridize than shorter-length oligomer probes. Probes may be single- or double-stranded and designed to have specificity in PCR, membrane-based hybridization technologies, or ELISA-like technologies.

The term "isolated" nucleic acid molecule, as utilized herein, is one, which is separated from other nucleic acid molecules which are present in the natural source of the nucleic acid. Preferably, an "isolated" nucleic acid is free of sequences which naturally flank the nucleic acid (i.e., sequences located at the 5'- and 3'-termini of the nucleic acid) in the genomic DNA of the organism from which the nucleic acid is derived. For example, in various embodiments, the isolated NOVX nucleic acid molecules can contain less than about 5 kb, 4 kb, 3 kb, 2 kb, 1 kb, 0.5 kb or 0.1 kb of nucleotide sequences which naturally flank the nucleic acid molecule in genomic DNA of the cell/tissue from which the nucleic acid is derived (e.g., brain, heart, liver, spleen, etc.). Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the invention, e.g., a nucleic acid molecule having the nucleotide sequence SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101, or a complement of this aforementioned nucleotide sequence, can be isolated using standard molecular biology techniques and the sequence information provided herein, Using all or a portion of the nucleic acid sequence of SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101 as a hybridization probe, NOVX molecules can be isolated using standard hybridization and cloning techniques (e.g., as described in Samlirook, et al., (eds.), MOLECULAR CLONING: A LABORATORY MANUAL $2^{nd}$ Ed., Cold Spring Harbor Laboratory Press, Cold Spring Harbor, N.Y., 1989; and Ausubel, et al., (eds.), CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate cligonucleotide primers according to standard PCR amplification techniques. The nucleic acid so amplified can be cloned into an appropriate vector and characterized by DNA sequence analysis. Furthermore, oligonucleotides corresponding to NOVX nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or oDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment of the invention, an oligonucleotide comprising a nucleic acid molecule less than 100 nt in length would further comprise at least 6 contiguous nucleotides SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101, or a complement thereof. Oligonucleotides may be chemically synthesized and may also be used as probes.

In another embodiment, an isolated nucleic acid molecule of the invention comprises a nucleic acid molecule that is a complement of the nucleotide sequence shown in SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101, or a portion of this nucleotide sequence (e.g., a fragment that can be used as a probe or primer or a fragment encoding a biologically-active portion of an NOVX polypeptide). A nucleic acid molecule that is complementary to the nucleotide sequence shown SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101 is one that is sufficiently complementary to the nucleotide sequence shown SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101 that it can hydrogen bond with little or no mismatches to the nucleotide sequence shown SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be as ilderived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type. Homologs are nucleic acid sequences or amino acid sequences of a particular gene that are derived from different species.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, or 95% identity (with a preferred identity of 80–95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel. et al., CURRENT PROTOCOLS IN MOLECULAR BIOLOGY, John Wiley & Sons, New York, N.Y., 1993, and below.

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of NOVX polypeptides. Isoforms can be expressed in different tissues of the same organism as a result of, for example, alternative splicing of RNA. Alternatively, isoforms can be encoded by different genes. In the invention, homologous nucleotide sequences include nucleotide sequences encoding for an NOVX polypeptide of species other than humans, including, but not limited to: vertebrates, and thus can include, e.g, frog, mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the exact nucleotide sequence encoding human NOVX protein. Homologous nucleic acid sequences include those nucleic acid sequences that encode conservative amino acid substitutions (see below) in SEQ ID NOS:2, 9, 11, 19, 27, 35, 43, 51, 53, 61, 63, 65, 71, 73, 75, 83, 90, 92, 100 and 102, as well as a polypeptide possessing NOVX biological activity. Various biological activities of the NOVX proteins are described below.

An NOVX polypeptide is encoded by the open reading frame ("ORF") of an NOVX nucleic acid. An ORF corresponds to a nucleotide sequence that could potentially be translated into a polypeptide. A stretch of nucleic acids comprising an ORF is uninterrupted by a stop codon. An ORF that represents the coding sequence for a full protein begins with an ATG "start" codon and terminates with one of the three "stop" codons, namely, TAA, TAG, or TGA. For the purposes of this invention, an ORF may be any part of a coding sequence, with or without a start codon, a stop codon, or both. For an ORF to be considered as a good candidate for coding for a bonafide cellular protein, a minimum size requirement is often set, e.g., a stretch of DNA that would encode a protein of 50 amino acids or more.

The nucleotide sequences determined from the cloning of the human NOVX genes allows for the generation of probes and primers designed for use in identifying and/or cloning NOVX homologues in other cell types, e.g. from other tissues, as well as NOVX homologues from other vertebrates. The probe/primer typically comprises substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101; or an anti-sense strand nucleotide sequence of SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101; or of a naturally occurring mutant of SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101.

Probes based on the human NOVX nucleotide sequences can be used to detect transcripts or genomic sequences encoding the same or homologous proteins. In various embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissues which mis-express an NOVX protein, such as by measuring a level of an NOVX-encoding nucleic acid in a sample of cells from a subject e.g., detecting NOVX mRNA levels or determining whether a genomic NOVX gene has been mutated or deleted.

"A polypeptide having a biologically-active portion of an NOVX polypeptide" refers to polypeptides exhibiting activity similar, but not necessarily identical to, an activity of a polypeptide of the invention, including mature forms, as measured in a particular biological assay, with or without dose dependency. A nucleic acid fragment encoding a "biologically-active portion of NOVX" can be prepared by isolating a portion SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101, that encodes a polypeptide having an NOVX biological activity (the biological activities of the NOVX proteins are described below), expressing the encoded portion of NOVX protein (e.g., by recombinant expression in vitro) and assessing the activity of the encoded portion of NOVX.

NOVX Nucleic Acid and Polypeptide Variants

The invention further encompasses nucleic acid molecules that differ from the nucleotide sequences shown in SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101 due to degeneracy of the genetic code and thus encode the same NOVX proteins as that encoded by the nucleotide sequences shown in SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101. In another embodiment, an isolated nucleic acid molecule of the invention has a nucleotide sequence encoding a protein having an amino acid sequence shown in SEQ ID NOS:2, 9, 11, 19, 27, 35, 43, 51, 53, 61,63, 65, 71, 73, 75, 83, 90, 92, 100 and 102.

In addition to the human NOVX nucleotide sequences shown in SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101, it will be appreciated by those skilled in the art that DNA sequence polymorphisms that lead to changes in the amino acid sequences of the NOVX polypeptides may exist within a population (e.g., the human population). Such genetic polymorphism in the NQVX genes may exist among individuals within a population due to natural allelic variation. As used herein, the terms "gene" and "recombinant gene" refer to nucleic acid molecules comprising an open reading frame (ORF) encoding an NOVX protein, preferably a vertebrate NOVX protein. Such natural allelic variations can typically result in 1–5% variance in the nucleotide sequence of the NOVX genes. Any and all such nucleotide variations and resulting amino acid polymorphisms in the NOVX polypeptides, which are the result of natural allelic variation and that do not alter the functional activity of the NOVX polypeptides, are intended to be within the scope of the invention.

Moreover, nucleic acid molecules encoding NOVX proteins from other species, and thus that have a nucleotide sequence that differs from the human SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101 are intended to be within the scope of the invention. Nucleic acid molecules corresponding to natural allelic variants and homologues of the NOVX cDNAs of the invention can be isolated based on their homology to the human NOVX nucleic acids disclosed herein using the human cDNAs, or a portion thereof, as a hybridization probe according to standard hybridization techniques under stringent hybridization conditions.

Accordingly, in another embodiment, an isolated nucleic acid molecule of the invention is at least 6 nucleotides in length and hybridizes under stringent conditions to the nucleic acid molecule comprising the nucleotide sequence of SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101. In another embodiment, the nucleic acid is at least 10, 25, 50, 100, 250, 500, 750, 1000, 1500, or 2000 or more nucleotides in length. In yet another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding NOVX proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents such as formamide.

Stringent conditions are known to those skilled in the art and can be found in Ausubel, et al., (eds.), CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C. An isolated nucleic acid molecule of the invention that hybridizes under stringent conditions to the sequences SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101, corresponds to a naturally-occuriing nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101, or fragments, analogs or derivatives thereof, under conditions of moderate stringency is provided. A non-limiting example of moderate stringency hybridization conditions are hybridization in 6×SSC, 5× Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known within the art. See, e.g., Ausubel, et at. (eds.), 1993, CURRENT PROTOCOLS IN MOLECULAR BIOLOGY, John Wiley & Sons, NY, and Kriegler, 1990; GENE TRANSFER AND EXPRESSION, A LABORATORY MANUAL, Stockton Press, NY.

In a third embodiment, a nucleic acid that is hybridizable to the nucleic acid molecule comprising the nucleotide sequences SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel, et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981. *Proc Natl Acad Sci USA* 78: 6789–6792.

Conservative Mutations

In addition to naturally-occurring allelic variants of NOVX sequences that may exist in the population, the skilled artisan will further appreciate that changes can be introduced by mutation into the nucleotide sequences SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101, thereby leading to changes in the amino acid sequences of the encoded NOVX proteins, without altering the functional ability of said NOVX proteins. For example, nucleotide substitutions leading to amino acid substitutions at "non-essential" amino acid residues can be made in the sequence SEQ ID NOS:2, 9, 11, 19, 27, 35, 43, 51, 53, 61, 63, 65, 71, 73, 75, 83, 90, 92, 100 and 102. A "non-essential" amino acid residue is a residue that can be altered from the wild-type sequences of the NOVX proteins without altering their biological activity, whereas an "essential" amino acid residue is required for such biological activity. For example, amino acid residues that are conserved among the NOVX proteins of the invention are predicted to be particularly non-amenable to alteration. Amino acids for which conservative substitutions can be made are well-known within the art.

Another aspect of the invention pertains to nucleic acid molecules encoding NOVX proteins that contain changes in amino acid residues that are not essential for activity. Such NOVX proteins differ in amino acid sequence from SEQ ID NOS:2, 9, 11, 19, 27, 35, 43, 51, 53, 61, 63, 65, 71, 73, 75, 83, 90, 92, 100 and 102 yet retain biological activity. In one embodiment, the isolated nucleic acid molecule comprises a nucleotide sequence encoding a protein, wherein the protein comprises an amino acid sequence at least about 45% homologous to the amino acid sequences SEQ ID NOS:2, 9, 11, 19, 27, 35, 43, 51, 53, 61, 63, 65, 71, 73, 75, 83, 90, 92, 100 and 102. Preferably, the protein encoded by the nucleic acid molecule is at least about 60% homologous to SEQ ID NOS:2, 9, 11, 19, 27, 35, 43, 51, 53, 61, 63, 65, 71, 73, 75, 83, 90, 92, 100 and 102; more preferably at least about 70% homologous SEQ ID NOS:2, 9, 11, 19, 27, 35, 43, 51, 53, 61, 63, 65, 71, 73, 75, 83, 90, 92, 100 and 102; still more preferably at least about 80% homologous to SEQ ID NOS:2, 9, 11, 19, 27, 35, 43, 51, 53, 61, 63, 65, 71, 73, 75, 83, 90, 92, 100 and 102; even more preferably at least about 90% homologous to SEQ ID NOS:2, 9, 11, 19, 27, 35, 43, 51, 53, 61, 63, 65, 71 73, 75, 83, 90, 92, 100 and 102; and most preferably at least about 95% homologous to SEQ ID NOS:2, 9, 11, 19, 27, 35, 43, 51, 53, 61, 63, 65, 71, 73, 75, 83, 90, 92, 100 and 102.

An isolated nucleic acid molecule encoding an NOVX protein homologous to the protein of SEQ ID NOS:2, 9, 11, 19, 27, 35, 43, 51, 53, 61, 63, 65, 71, 73, 75, 83, 90, 92, 100 and 102 can be created by introducing one or more nucleotide substitutions, additions or deletions into the nucleotide sequence of SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101, such that one or more amino acid substitutions, additions or deletions are introduced into the encoded protein.

Mutations can be introduced into SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101 by standard techniques, such as site-directed mutagenesis and PCR-mediated mutagenesis. Preferably, conservative amino acid substitutions are made at one or more predicted, non-essential amino acid residues. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine). nonpolar side chains (e.g., alanine, valine, leucine, isoleucine, proline. phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in the NOVX protein is replaced with another amino acid residue from the same side chain family. Alternatively, in another embodiment, mutations can be introduced randomly along all or part of an NOVX coding sequence, such as by saturation mutagenesis, and the resultant mutants can be screened for NOVX biological activity to identify mutants that retain activity. Following mutagenesis of SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101, the encoded protein can be expressed by any recombinam technology known in the art and the activity of the protein can be determined.

The relatedness of amino acid families may also be determined based on side chain interactions. Substituted amino acids may be fully conserved "strong" residues or fully conserved "weak" residues. The "strong" group of conserved amino acid residues may be any one of the following groups: STA, NEQK, NHQK, NDEQ, QHRK, MILV, MILF, HY, FYW, wherein the single letter amino acid codes are grouped by those amino acids that may be substituted for each other. Likewise, the "weak" group of conserved residues may be any one of the following: CSA, ATV, SAG, STNK, STPA, SGND, SNDEQK, NDEQHK, NEQHRK, VLIM, HFY, wherein the letters within each group represent the single letter amino acid code.

In one embodiment, a mutant NOVX protein can be assayed for (i) the ability to form protein:protein interactions with other NOVX proteins, other cell-surface proteins, or biologically-active portions thereof (ii) complex formation between a mutant NOVX protein and an NOVX ligand; or (iii) the ability of a mutant NOVX protein to bind to an intracellular target protein or biologically-active portion thereof, (e.g. avidin proteins).

In yet another embodiment, a mutant NOVX protein can be assayed for the ability to regulate a specific biological function (e.g., regulation of insulin release).

Antisense Nucleic Acids

Another aspect of the invention pertains to isolated antisense nucleic acid molecules that are hybridizable to or complementary to the nucleic acid molecule comprising the nucleotide sequence of SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101, or fragments, analogs or derivatives thereof, An "antisense" nucleic acid comprises a nucleotide sequence that is complementary to a "sense" nucleic acid encoding a protein (e.g., complementary to the coding strand of a double-stranded cDNA molecule or complementary to an mRNA sequence). In specific aspects, antisense nucleic acid molecules are provided that comprise a sequence complementary to at least about 10, 25, 50, 100, 250 or 500 nucleotides or an entire NOVX coding strand, or to only a portion thereof. Nucleic acid molecules encoding fragments, homologs, derivatives and analogs of an NOVX protein of SEQ ID NOS:2, 9, 11, 19, 27, 35, 43, 51, 53, 61, 63, 65, 71, 73, 75, 83, 90, 92, 100 and 102, or antisense nucleic acids complementary to an NOVX nucleic acid sequence of SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101, are additionally provided.

In one embodiment, an antisense nucleic acid molecule is antisense to a "coding region" of the coding strand of a nucleotide sequence encoding an NOVX protein. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding the NOVX protein. The term "noncoding region" refers to 5' and 3' sequences which flank the coding region that are not translated into amino acids (i.e., also referred to as 5' and 3' uIntranslated regions).

Given the coding strand sequences encoding the NOVX protein disclosed herein, antisense nucleic acids of the invention can be designed according to the rules of Watson and Crick or Hoogsteen base pairing. The antisense nucleic acid molecule can be complementary to the entire coding region of NOVX mRNA, but more preferably is an oligonucleotide that is antisense to only a portion of the coding or noncoding region of NOVX mRNA. For example, the antisense oligonucleotide can be complementary to the region surrounding the translation start site of NOVX mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally-occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

Examples of modified nucleotides that can be used to generate the antisense nucleic acid include: 5-fluorouracil, 5-bromouracil, 5-chlorouracil, 5-iodouracit, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methyl cytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (ie., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an NOVX protein to thereby inhibit expression of the protein (e.g., by inhibiting transcription and/or translation). The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface (e.g., by linking the antisense nucleic acid molecules to peptides or antibodies that bind to cell surface receptors or antigens). The antisense nucleic acid molecules can also be delivered to cells using the vectors described herein. To achieve sufficient nucleic acid molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other. See, e.g. Gaultier, et al., 1987. *Nucl. Acids Res.* 15: 6625–6641. The antisense nucleic acid molecule can also comprise a 2'-o-methylribonucleotide (See, e.g., Inoue, et al. 1987. *Nucl. Acids Res.* 15: 6131–6148) or a chimeric RNA-DNA analogue (See, e.g., Inoue, et al., 1987. *FEBS Lett.* 215: 327–330.

Ribozymes and PNA Moieties

Nucleic acid modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

In one embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes as described in Haselhoff and Gerlach 1988. *Nature* 334: 585–59 1) can be used to catalytically cleave NOVX mRNA transcripts to thereby inhibit translation of NOVX mRNA. A ribozyme having specificity for an NOVX-encoding nucleic acid can be designed based upon the nucleotide sequence of an NOVX cDNA disclosed herein (i.e., SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101). For example, a derivative of a Tetrahymena L-19 IVS RNA can be constructed in which the nucleotide sequence of the active site is complementary to the nucleotide sequence to be cleaved in an NOVX-encoding mRNA. See, e.g., U.S. Pat. No. 4,987,071 to Cech, et al. and U.S. Pat. No. 5,116,742 to Cech, et al. NOVX mRNA can also be used to select a catalytic RNA having a specific ribonuclease activity from a pool of RNA molecules. See, e.g., Bartel et al., (1993) *Science* 261:1411–1418.

Alternatively, NOVX gene expression can be inhibited by targeting nucleotide sequences complementary to the regulatory region of the NOVX nucleic acid (e.g., the NOVX promoter and/or enhancers) to form triple helical structures that prevent transcription of the NOVX gene in target cells. See, e.g., Helene, 1991. *Anticancer Drug Des.* 6: 569–84; Helene, el al. 1992. *Ann. N.Y. Acad. Sci.* 660: 27–36; Maher, 1992. *Bioassays* 14: 807–15.

In various embodiments, the NOVX nucleic acids can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids. See, e.g., Hyrup, et al., 1996. *Bioorg Med Chem* 4: 5–23. As used herein, the terms "peptide nucleic acids" or "PNAs" refer to nucleic acid mimics (e.g., DNA mimics) in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup, et al., 1996. supra; Perry-O'Keefe, et al., 1996. *Proc. Natl. Acad. Sci. USA* 93: 14670–14675.

PNAs of NOVX can be used in therapeutic and diagnostic applications. For example, PNAs can be used as antisense or antigene agents for sequence-specific modulation of gene expression by, e.g., inducing transcription or translation arrest or inhibiting replication. PNAs of NOVX can also be used, for example, in the analysis of single base pair mutations in a gene (e.g., PNA directed PCR clamping; as artificial restriction enzymes when used in combination with other enzymes, e.g., $S_1$ nucleases (See, Hyrup, et al., 1996. supra); or as probes or primers for DNA sequence and hybridization (See, Hyrup, et al., 1996, supra; Perry-O'Keefe, et al., 1996. supra).

In another embodiment, PNAs of NOVX can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of NOVX can be generated that may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (see, Hyrup, et al., 1996. supra). The synthesis of PNA-DNA chimeras can be performed as described in Hyrup, et al., 1996. supra and Finn, et al., 1996. *Nucl Acids Res* 24: 3357–3363. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA. See, e.g., Mag, et al., 1989. *Nucl Acid Res* 17: 5973–5988. PNA monomers are then coupled in a stepwise manner to produce a chimeric molecule with a 5' PNA segment and a 3' DNA segment. See, e.g., Finn, et al., 1996. supra. Alternatively, chimeric molecules can be synthesized with a 5' DNA segment and a 3' PNA segment. See, e.g, Petersen, et al., 1975. *Bioorg. Med Chem. Lett* 5: 1119–11124.

In other embodiments, the oligonucleotide may include other appended groups such as peptides (e.g., for targeting host cell receptors in vivo), or agents facilitating transport across the cell membrane (see, e g., Letsinger, et al., 1989. *Proc. Natl. Acad. Sci. U.S.A.* 86: 6553–6556; Lemaitre, et al., 1987. *Proc. Natl. Acad. Sci.* 84: 648–652; PCT Publication No. WO88/09810) or the blood-brain barrier (see.e.g., PCT Publication No. WO 89/10134). In addition, oligonucleotides can be modified with hybridization triggered cleavage agents (see, e.g., Krol, et al., 1988. *BioTechniques* 6:958–976) or intercalating agents (see, e.g., Zon, 1988. *Pharm. Res.* 5: 539–549). To this end, the oligonucleotide may be conjugated to another molecule, e.g., a peptide, a hybridization triggered cross-linking agent, a transport agent, a hybridization-triggered cleavage agent, and the like.

NOVX Polypeptides

A polypeptide according to the invention includes a polypeptide including the amino acid sequence of NOVX polypeptides whose sequences are provided in SEQ ID NOS:2, 9, 11, 19, 27, 35, 43, 51, 53, 61, 63, 65, 71, 73, 75, 83, 90, 92, 100 and 102. The invention also includes a mutant or variant protein any of whose residues may be changed from the corresponding residues shown in SEQ ID NOS:2, 9, 11, 19, 27, 35, 43, 51, 53, 61, 63, 65, 71, 73, 75, 83, 90, 92, 100 and 102 while still encoding a protein that maintains its NOVX activities and physiological functions, or a functional fragment thereof.

In general, an NOVX variant that preserves NOVX-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated NOVX proteins, and biologically-active portions thereof, or derivatives, fragments, analogs or homologs thereof. Also provided are polypeptide fragments suitable for use as immunogens to raise anti-NOVX antibodies. In one embodiment, native NOVX proteins can be isolated from cells or tissue sources by an appropriate purification scheme using standard protein purification techniques. In another embodiment, NOVX proteins are produced by recombinant DNA techniques. Alternative to recombinant expression, an NOVX protein or polypeptide can be synthesized chemically using standard peptide synthesis techniques.

An "isolated" or "purified" polypeptide or protein or biologically-active portion thereof is substantially free of cellular material or other contaminating proteins from the cell or tissue source from which the NOVX protein is derived, or substantially free from chemical precursors or other chemicals when chemically synthesized. The language "substantially free of cellular material" includes preparations of NOVX proteins in which the protein is separated from cellular components of the cells from which it is isolated or recombinantly-produced. In one embodiment, the language "substantially free of cellular material" includes preparations of NOVX proteins having less than about 30% (by dry weight) of non-NOVX proteins (also referred to herein as a "contaminating protein"), more preferably less than about 20% of non-NOVX proteins, still more preferably less than about 10% of non-NOVX proteins, and most preferably less than about 5% of non-NOVX proteins. When the NOVX protein or biologically-active portion thereof is recombinantly-produced, it is also preferably substantially free of culture medium, i.e., culture medium represents less than about 20%, more preferably less than about 10%, and most preferably less than about 5% of the volume of the NOVX protein preparation.

The language "substantially free of chemical precursors or other chemicals" includes preparations of NOVX proteins in which the protein is separated from chemical precursors or other chemicals that are involved in the synthesis of the protein. In one embodiment, the language "substantially free of chemical precursors or other chemicals" includes preparations of NOVX proteins having less than about 30% (by dry weight) of chemical precursors or non-NOVX chemicals, more preferably less than about 20% chemical precursors or non-NOVX chemicals, still more preferably less than about 10% chemical precursors or non-NOVX chemicals, and most preferably less than about 5% chemical precursors or non-NOVX chemicals.

Biologically-active portions cf NOVX proteins include peptides comprising amino acid sequences sufficiently homologous to or derived from the amino acid sequences of the NOVX proteins (e.g., the amino acid sequence shown in SEQ ID NOS:2, 9, 11, 19, 27, 35, 43, 51, 53, 61, 63, 65, 71, 73, 75, 83, 90, 92, 100 and 102) that include fewer amino acids than the full-length NOVX proteins, and exhibit at least one activity of an NOVX protein. Typically, biologically-active portions comprise a domain or motif with at least one activity of the NOVX protein. A biologically-active portion of an NOVX protein can be a polypeptide which is, for example, 10, 25, 50, 100 or more amino acid residues in length.

Moreover, other biologically-active portions, in which other regions of the protein are deleted, can be prepared by recombinant techniques and evaluated for one or more of the functional activities of a native NOVX protein.

In an embodiment, the NOVX protein has an amino acid sequence shown SEQ ID NOS:2, 9, 11, 19, 27, 35, 43, 51, 53, 61, 63, 65, 71, 73, 75, 83, 90, 92, 100 and 102. In other embodiments, the NOVX protein is substantially homologous to SEQ ID NOS:2, 9, 11, 19, 27, 35, 43, 51, 53, 61, 63, 65, 71, 73, 75, 83, 90, 92, 100 and 102, and retains the functional activity of the protein of SEQ ID NOS:2, 9, 11, 19, 27, 35, 43, 51, 53, 61, 63, 65, 71, 73, 75, 83, 90, 92, 100 and 102, yet differs in amino acid sequence due to natural allelic variation or mutagenesis, as described in detail, below. Accordingly, in another embodiment, the NOVX protein is a protein that comprises an amino acid sequence at least about 45% homologous to the amino acid sequence SEQ ID NOS:2, 9, 11, 19, 27, 35, 43, 51, 53, 61, 63, 65, 71, 73, 75, 83, 90, 92, 100 and 102, and retains the functional activity of the NOVX proteins of SEQ ID NOS:2, 9, 11, 19, 27, 35, 43, 51, 53, 61, 63, 65, 71, 73, 75, 83, 90, 92, 100 and 102.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be dettermined using computer programs known in the art, such as GAP software provided in the GCG program package. See, Needleman and Wunsch, 1970. *J. Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identitv. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides NOVX chimeric or fusion proteins. As used herein, an NOVX "chimeric protein" or "fusion protein" comprises an NOVX polypeptide operatively-linked to a non-NOVX polypeptide. An "NOVX polypeptide" refers to a polypeptide having an amino acid sequence corresponding to an NOVX protein SEQ ID NOS:2, 9, 11, 19, 27, 35, 43, 51, 53, 61, 63, 65, 71, 73, 75, 83, 90, 92, 100 and 102), whereas a "non-NOVX polypeptide" refers to a polypeptide having an amino acid sequence corresponding to a protein that is not substantially homologous to the NOVX protein. e.g., a protein that is different from the NOVX protein and that is derived from the same or a different organism. Within an NOVX fusion protein the NOVX polypeptide can correspond to all or a portion of an NOVX protein. In one embodiment, an NOVX fusion protein comprises at least one biologically-active portion of an NOVX protein. In another embodiment, an NOVX fusion protein comprises at least two biologically-active portions of an NOVX protein. In yet another embodiment, an NOVX fusion protein comprises at least three biologically-active portions of an NOVX protein. Within the fusion protein, the term "operatively-linked" is intended to indicate that the NOVX polypeptide and the non-NOVX polypeptide are fused in-frame with one another. The non-NOVX polypeptide can be fused to the N-terminus or C-terminus of the NOVX polypeptide.

In one embodiment, the fusion protein is a GST-NOVX fusion protein in which the NOVX sequences are fused to the C-terminus of the GST (glutathione S-transferase) sequences. Such fusion proteins can facilitate the purification of recombinant NOVX polypeptides.

In another embodiment, the fusion protein is an NOVX protein containing a heterologous signal sequence at its N-terminus. In certain host cells (e.g., mammalian host cells), expression and/or secretion of NOVX can be increased through use of a heterologous signal sequence.

In yet another embodiment, the fusion protein is an NOVX-immunoglobulin fusion protein in which the NOVX sequences are fused to sequences derived from a member of the immunoglobulin protein family. The NOVX-immunoglobulin fusion proteins of the invention can be incorporated into pharmaceutical compositions and administered to a subject to inhibit an interaction between an NOVX ligand and an NOVX protein on the surface of a cell, to thereby suppress NOVX-mediated signal transduction in vivo. The NOVX-immunoglobulin fusion proteins can be used to affect the bioavailability of an NOVX cognate ligand. Inhibition of the NOVX ligand/NOVX interaction may be useful therapeutically for both the treatment of proliferative and differentiative disorders, as well as modulating (e.g. promoting or inhibiting) cell survival. Moreover, the NOVX-immunoglobulin fusion proteins of the invention can be used as immunogens to produce anti-NOVX antibodies in a subject, to purify NOVX ligands, and in screening assays to identify molecules that inhibit the interaction of NOVX with an NOVX ligand.

An NOVX chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). An NOVX-encoding nucleic acid can be cloned into such an expression vector such that the fusion moiety is linked in-frame to the NOVX protein.

NOVX Agonists and Antagonists

The invention also pertains to variants of the NOVX proteins that function as either NOVX agonists (i.e., mimetics) or as NOVX antagonists. Variants of the NOVX protein can be generated by mutagenesis (e.g., discrete point mutation or truncation of the NOVX protein). An agonist of the NOVX protein can retain substantially the same, or a subset of, the biological activities of the naturally occurring form of the NOVX protein. An antagonist of the NOVX protein can inhibit one or more of the activities of the naturally occurring form of the NOVX protein by, for example, competitively binding to a downstream or upstream member of a cellular signaling cascade which includes the NOVX protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the NOVX proteins.

Variants of the NOVX proteins that function as either NOVX agonists (i.e., mimetics) or as NOVX antagonists can be identified by screening combinatorial libraries of mutants (e.g., truncation mutants) of the NOVX proteins for NOVX protein agonist or antagonist activity. In one embodiment, a variegated library of NOVX variants is generated by combinatorial mutagenesis at the nucleic acid level and is encoded by a variegated gene library. A variegated library of NOVX variants can be produced by, for example, enzymatically ligating a mixture of synthetic oligonucleotides into gene sequences such that a degenerate set of potential NOVX sequences is expressible as individual polypeptides, or alternatively, as a set of larger fusion proteins (e.g., for phage display) containing the set of NOVX sequences therein. There are a variety of methods which can be used to produce libraries of potential NOVX variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential NOVX sequences. Methods for synthesizing degenerate oligonucleotides are well-known within the art. See, e.g., Narang, 1983. *Tetrahedron* 39: 3; Itakura, et al., 1984. *Annu. Rev. Biochem.* 53: 323; Itakura, et al., 1984. *Science* 198: 1056; Ike, et al., 1983. *Nucl. Acids Res.* 11: 477.

Polypeptide Libraries

In addition, libraries of fragments of the NOVX protein coding sequences can be used to generate a variegated population of NOVX fragments for screening and subsequent selection of variants of an NOVX protein. In one embodiment, a library of coding sequence fragments can be generated by treating a double stranded PCR fragment of an NOVX coding sequence with a nuclease under conditions wherein nicking occurs only about once per molecule, denaturing the double stranded DNA, renaturing the DNA to form double-stranded DNA that can include sense/antisense pairs from different nicked products, removing single stranded portions from reformed duplexes by treatment with $S_1$ nuclease, and ligating the resulting fragment library into an expression vector. By this method, expression libraries can be derived which encodes N-terminal and internal fragments of various sizes of the NOVX proteins.

Various techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of NOVX proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify NOVX variants. See, e.g., Arkin and Yourvan, 1992. *Proc. Natl. Acad. Sci. USA* 89: 7811–7815; Delgrave, et al., 1993. *Protein Engineering* 6:327–331.

Anti-NOVX Antibodies

Also included in the invention are antibodies to NOVX proteins, or fragments of NOVX proteins. The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, an antibody molecule obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated NOVX-related protein of the invention may be intended to serve as an antigen, or a portion or fragment thereof, and additionally can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of NOVX-related protein that is located on the surface of the protein, e.g., a hydrophilic region. A hydrophobicity analysis of the human NOVX-related protein sequence will indicate which regions of a NOVX-related protein are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each of which is incorporated herein by reference in its entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow and Lane, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, MONOCLONAL ANTIBODIES: PRINCIPLES AND PRACTICE, Academic Press, (1986) pp. 59–103). Iminortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, *J. Immunol.,* 133:3001 (1984); Brodeur et al., MONOCLONAL ANTIBODY PRODUCTION TECHNIQUES AND APPLICATIONS, Marcel Dekker, Inc., New York, (1987) pp. 51–63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980). Preferably, antibodies having a high degree of specificity and a high binding affinity for the target antigen are isolated.

After the desired hybridoma cells are identified, the clones can be subcloned by limiting dilution procedures and grown by standard methods. Suitable culture media for this purpose include, for example. Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature,* 321:522–525 (1986); Riechmann et al., *Nature,* 332:323–327 (1988); Verhoeyen et al., *Science,* 239:1534–1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, Curr. Op. Struct. Biol., 2:593–596 (1992)).

Human Antibodies

Fully human antibodies relate to antibody molecules in which essentially the entire sequences of both the light chain and the heavy chain, including the CDRs, arise from human genes. Such antibodies are termed "human antibodies", or ",fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al. 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. Proc Natt Acad Sci USA 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

In addition, human antibodies can also be produced using additional techniques, including phage display libraries (Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in Marks et al. (Bio/Technology 10, 779–783 (1992)); Lonberg et al. (Nature 368 856–859 (1994)); Morrison (Nature 368, 812–13 (1994)); Fishwild et al, (Nature Biotechnology 14, 845–51 (1996)); Neuberger (Nature Biotechnology 14, 826 (1996)); and Lonberg and Huszar (Intern. Rev. Immunol. 1365–93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, el al., 1989 Science 246: 1275–1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature,* 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., 1991 *EMBO J.,* 10:3655–3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology,* 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (eg. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. $F_{(ab')2}$ bispecific antibodies). Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., *J. Exp. Med.* 175:217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med., 176: 1191–1195 (1992) and Shopes, J. Immunol., 148: 2918–2922 (1992). Homodimeric antibodies with enhanced anti-tumor activity can also be prepared using heterobifunctional cross-linkers as described in Wolff et al. Cancer Research, 53: 2560–2565 (1993). Alternatively, an antibody can be engineered that has dual Fc regions and can thereby have enhanced complement lysis and ADCC capabilities. See Stevenson et al., Anti-Cancer Drug Design, 3: 219–230 (1989).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of an NOVX protein is facilitated by generation of hybridomas that bind to the fragment of an NOVX protein possessing such a domain. Thus, antibodies that are specific for a desired domain within an NOVX protein, or derivatives, fragments, analogs or homologs thereof, are also provided herein.

Anti-NOVX antibodies may be used in methods known within the art relating to the localization and/or quantitation of an NOVX protein (e.g., for use in measuring levels of the NOVX protein within appropriate physiological samples, for use in diagnostic methods, for use in imaging the protein, and the like). In a given embodiment, antibodies for NOVX proteins, or derivatives, fragments, analogs or homologs thereof, that contain the antibody derived binding domain, are utilized as pharmacologically-active compounds (hereinafter "Therapeutics").

An anti-NOVX antibody (e.g., monoclonal antibody) can be used to isolate an NOVX polypeptide by standard techniques, such as affinity chromatography or iminunoprecipitation. An anti-NOVX antibody can facilitate the purification of natural NOVX polypeptide from cells and of recombinantly-produced NOVX polypeptide expressed in host cells. Moreover, an anti-NOVX antibody can be used to detect NOVX protein (e.g., in a cellular lysate or cell supernatant) in order to evaluate the abundance and pattern of expression of the NOVX protein. Anti-NOVX antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetyleholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

NOVX Recombinant Expression Vectors and Host Cells

Another aspect of the invention pertains to vectors, preferably expression vectors, containing a nucleic acid encoding an NOVX protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., NOVX proteins, mutant forms of NOVX proteins, fusion proteins, etc.).

The recombinant expression vectors of the invention can be designed for expression of NOVX proteins in prokaryotic or eukaryotic cells. For example, NOVX proteins can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111–2118). Such alteration of nucleic acid sequences of the invention can be carried out by standard DNA synthesis techniques.

In another embodiment, the NOVX expression vector is a yeast expression vector. Examples of vectors for expression in yeast *Soccharomyces cerivisae* include pYepSecl (Baldari, et al., 1987. *EMBO J.* 6: 229–234), pMFa (Kurjan and Herskowitz, 1982. *Cell* 30: 933–943), pJRY88 (Schultz et al., 1987. *Gene* 54: 113–123), pYES2 (Invitrogen Corporation, San Diego, Calif.), and picZ (InVitrogen Corp, San Diego, Calif.).

Alternatively, NOVX can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3:2156–2165) and the pVL series (Lucklow and Summers. 1989. *Virology* 170: 31–39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187–195). When used in mammalian cells, the expression vector's control functions are often provided by viral regulatory elements. For example, commonly used promoters are derived from polyoma, adenovirus 2, cytomegaloviruls, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press. Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268–277), lymphoid-specific promoters (Calame and Eaton, 1988. *Adv. Immunol.* 43: 235–275), in particular promoters of T cell receptors (Winoto and Baltimore, 1989. *EMBO J.* 8: 729–733) and immunoglobulins (Banerji, et al., 1983. *Cell* 33: 729–740; Queen and Baltimore, 1983. *Cell* 33: 741–748), neuron-specific promoters (e.g., the neurofilament promoter; Byrne and Ruddle, 1989. *Proc. Natl. Acad. Sci. USA* 86: 5473–5477), pancreas-specific promoters (Edlund, et al., 1985. *Science* 230: 912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374–379) and the O-fetoprotein promoter (Campes and Tilghman, 1989. *Genes Dev.* 3: 537–546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to NOVX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," *Reviews-Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, NOVX protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding NOVX or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) NOVX protein. Accordingly, the invention further provides methods for producing NOVX protein using the host cells of the invention. In one embodiment, the method comprises culturing the host cell of invention (into which a recombinant expression vector encoding NOVX protein has been introduced) in a suitable medium such that NOVX protein is produced. In another embodiment, the method further comprises isolating NOVX protein from the medium or the host cell.

Transgenic NOVX Animals

The host cells of the invention can also be used to produce non-human transgenic animals. For example, in one embodiment, a host cell of the invention is a fertilized oocyte or an embryonic stem cell into which NOVX protein-coding sequences have been introduced. Such host cells can then be used to create non-human transgenic animals in which exogenous NOVX sequences have been introduced into their genome or homologous recombinant animals in which endogenous NOVX sequences have been altered. Such animals are useful for studying the function and/or activity of NOVX protein and for identifying and/or evaluating modulators of NOVX protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous NOVX gene has been altered by homologous recombination between the endogenous gene and an exogenous DNA molecule introduced into a cell of the animal, e.g., an embryonic cell of the animal, prior to development of the animal.

A transgenic animal of the invention can be created by introducing NOVX-encoding nucleic acid into the male pronuclei of a fertilized oocyte (e.g., by microinjection, retroviral infection) and allowing the oocyte to develop in a pseudopregnant female foster animal. The human NOVX cDNA sequences SEQ ID NOS:1, 8, 10, 12 18, 20, 26, 28, 34, 36, 42, 44, 50, 52, 54, 60, 62, 64, 70, 72, 74, 76, 82, 89, 91, 99 and 101 can be introduced as a transgene into the genome of a non-human animal. Alternatively, a non-human homologue of the human NOVX gene, such as a mouse NOVX gene, can be isolated based on hybridization to the human NOVX cDNA (described further supra) and used as a transgene. Intronic sequences and polyadenylation signals can also be included in the transgene to increase the efficiency of expression of the transgene. A tissue-specific regulatory sequence(s) can be operably-linked to the NOVX transgene to direct expression of NOYX protein to particular cells. Methods for generating transgenic animals via embryo manipulation and microinjection, particularly animals such as mice, have become conventional in the art and are described, for example, in U.S. Pat. Nos. 4,736,866; 4,870, 009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the NOVX transgene in its genome and/or expression of NOVX mRNA in tissues or cells of the animals. A trausgenic founder animal can then be used to breed additional animals carrying the transgene. Moreover, transgenic animals carrying a transgene-encoding NOVX protein can further be bred to other transgenic animals carrying other transgenes.

To create a homologous recombinant animal, a vector is prepared which contains at least a portion of an NOVX gene into which a deletion, addition or substitution has been introduced to thereby alter, e.g., functionally disrupt, the NOVX gene. The NOVX gene can be a human gene (e.g., the cDNA of SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101), but more preferably, is a non-human homologue of a human NOVX gene. For example, a mouse homologue of human NOVX gene of SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101 can be used to construct a homologous recombination vector suitable for altering an endogenous NOVX gene in the mouse genome. In one embodiment, the vector is designed such that, upon homologous recombination, the endogenous NOVX gene is functionally disrupted (i.e., no longer encodes a functional protein; also referred to as a "knock out" vector).

Alternatively, the vector can be designed such that, upon homologous recombination, the endogenous NOVX gene is mutated or otherwise altered but still encodes functional protein (e.g., the upstream regulatory region can be altered to thereby alter the expression of the endogenous NOVX protein). In the homologous recombination vector, the altered portion of the NOVX gene is flanked at its 5'- and 3'-termini by additional nucleic acid of the NOVX gene to allow for homologous recombination to occur between the exogenous NOVX gene carried by the vector and an endogenous NOVX gene in an embryonic stem cell. The additional flanking NOVX nucleic acid is of sufficient length for successful homologous recombination with the endogenous gene. Typically, several kilobases of flanking DNA (both at the 5'- and 3'-termini) are included in the vector. See, e.g., Thomas, et al., 1987. *Cell* 51: 503 for a description of homologous recombination vectors. The vector is ten introduced into an embryonic stem cell line (e.g., by electroporation) and cells in which the introduced NOVX gene has homologously-recombined with the endogenous NOVX gene are selected. See, e.g., Li, et al., 1992. *Cell* 69: 915.

The selected cells are then injected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. *Curr. Opin. Biotechnol.* 2: 823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, See, e.g. Lakso, et al., 1992. *Proc. Natl. Acad. Sci. USA* 89: 6232–6236. Another example of a recombinase system is the FLP recombinase system of *Saccharomyces cerevisiae*. See, O'Gorman, et al., 1991. *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, et al., 1997. *Nature* 385: 810–813. In brief, a cell (e.g., a somatic cell) from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

Pharmaceutical Compositions

The NOVX nucleic acid molecules, NOVX proteins, and anti-NOVX antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an NOVX protein or anti-NOVX antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transderrnal means. For transmucosal or transdermal administration, penetrants appropriate to the barrier to be permeated are used in the formulation. Such penetrants are generally known in the art, and include, for example, for transmucosal administration, detergents, bile salts, and flisidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054–3057). The pharmaceutical preparation of the gene therapy vector can include the gene therapy vector in an acceptable diluent, or can comprise a slow release matrix in which the gene delivery vehicle is imbedded. Alternatively, where the comnplete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Screening and Detection Methods

The isolated nucleic acid molecules of the invention can be used to express NOVX protein (e.g., via a recombinant expression vector in a host cell in gene therapy applications), to detect NOVX mRNA (e.g., in a biological sample) or a genetic lesion in an NOVX gene, and to modulate NOVX activity, as described further, below. In addition, the NOVX proteins can be used to screen drugs or compounds that modulate the NOVX protein activity or expression as well as to treat disorders characterized by insufficient or excessive production of NOVX protein or production of NOVX protein forms that have decreased or aberrant activity compared to NOVX wild-type protein (e.g.; diabetes (regulates insulin release); obesity (binds and transport lipids); metabolic disturbances associated with obesity, the metabolic syndrome X as well as anorexia and wasting disorders associated with chronic diseases and various cancers, and infectious disease(possesses anti-microbial activity) and the various dyslipidemias. In addition, the anti-NOVX antibodies of the invention can be used to detect and isolate NOVX proteins and modulate NOVX activity. In yet a further aspect, the invention can be used in methods to influence appetite, absorption of nutrients and the disposition of metabolic substrates in both a positive and negative fashion.

The invention further pertains to novel agents identified by the screening assays described herein and uses thereof for treatments as described, supra.

Screening Assays

The invention provides a method (also referred to herein as a "screening assay") for identifying modulators, i.e candidate or test compounds or agents (e.g., peptides, peptidomimetics, small molecules or other drugs) that bind to NOVX proteins or have a stimulatory or inhibitory effect on, e.g., NOVX protein expression or NOVX protein activity. The invention also includes compounds identified in the screening assays described herein.

In one embodiment, the invention provides assays for screening candidate or test compounds which bind to or modulate the activity of the membrane-bound form of an NOVX protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. *Anticancer Drug Design* 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad. Sci. U.S.A.* 90: 6909; Erb, et al., 1994. *Proc. Natl. Acad. Sci. U.S.A.* 91: 11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37: 1233.

Libraries of compounds may be presented in solution (e.g., Houghten, 1992. *Biotechniques* 13: 412–421), or on beads (Lam, 1991. *Nature* 354: 82–84), on chips (Fodor, 1993. *Nature* 364: 555–556), bacteria (Ladner, U.S. Pat. No. 5,223,409), spores (Ladner, U.S. Pat. No. 5,233,409), plasmids (Cull, et al., 1992. *Proc. Natl. Acad. Sci. USA* 89: 1865–1869) or on phage (Scott and Smith, 1990. *Science* 249: 386–390; Devlin, 1990. *Science* 249: 404–406; Cwirla, et al., 1990. *Proc. Natl Acad. Sci. U.S.A.* 87:66378–6382; Felici, 1991. *J. Mol. Biol.* 222:301–310; Ladner, U.S. Pat. No. 5,233,409.).

In one embodiment, an assay is a cell-based assay in which a cell which expresses a membrane-bound form of NOVX protein, or a biologically-active portion thereof, on the cell surface is contacted with a test compound and the ability of the test compound to bind to an NOVX protein determined. The cell, for example, can of mammalian origin or a yeast cell. Determining the ability of the test compound to bind to the NOVX protein can be accomplished, for example, by coupling the test compound with a radioisotope or enzymatic label such that binding of the test compound to the NOVX protein or biologically-active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of NOVX protein, or a biologically-active portion thereof, on the cell surface with a known compound which binds NOVX to form an assay mixture, contacting the assay mixture with a test compound, and determining the ability of the test compound to interact with an NOVX protein, wherein determining the ability of the test compound to interact with an NOVX protein comprises determining the ability of the test compound to preferentially bind to NOVX protein or a biologically-active portion thereof as compared to the knowvn compound.

In another embodiment, an assay is a cell-based assay comprising contacting a cell expressing a membrane-bound form of NOVX protein, or a biologically-active portion thereof, on the cell surface with a test compound and determining the ability of the test compound to modulate (e.g., stimulate or inhibit) the activity of the NOVX protein or biologically-active portion thereof. Determining the ability of the test compound to modulate the activity of NOVX or a biologically-active portion thereof can be accomplished, for example, by determining the ability of the NOVX protein to bind to or interact with an NOVX target molecule. As used herein, a "target molecule" is a molecule with which an NOVX protein binds or interacts in nature, for example, a molecule on the surface of a cell which expresses an NOVX interacting protein, a molecule on the surface of a second cell, a molecule in the extracellular milieu, a molecule associated with the internal surface of a cell membrane or a cytoplasmic molecule. An NOVX target molecule can be a non-NOVX molecule or an NOVX protein or polypeptide of the invention. In one embodiment, an NOVX target molecule is a component of a signal transduction pathway that facilitates transduction of an extracellular signal (e.g. a signal generated by binding of a compound to a membrane-bound NOVX molecule) through the cell membrane and into the cell. The targets for example, can be a second intercellular protein that has catalytic activity or a protein that facilitates the association of downstream signalinig molecules with NOVX.

Determining the ability of the NOVX protein to bind to or interact with an NOVX target molecule can be accomplished by one of the methods described above for determining direct binding. In one embodiment, determining the ability of the NOVX protein to bind to or interact with an NOVX target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising an NOVX-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting an NOVX protein or biologically-active portion thereof with a test compound and determining the ability of the test compound to bind to the NOVX protein or biologically-active portion thereof. Binding of the test compound to the NOVX protein can be determined either directly or indirectly as described above. In one such embodiment, the assay comprises contacting the NOVX protein or biologically-active portion thereof with a known compound which binds NOVX to form an assay mixture, contacting the assay mixture with a test compound, and determining the ability of the test compound to interact with an NOVX protein, wherein determining the ability of the test compound to interact with an NOVX protein comprises determining the ability of the test compound to preferentially bind to NOVX or biologically-active portion thereof as compared to the known compound.

In still another embodiment, an assay is a cell-free assay comprising contacting NOVX protein or biologically-active portion thereof with a test compound and determining the ability of the test compound to modulate (e.g. stimulate or inhibit) the activity of the NOVX protein or biologically-active portion thereof. Determining the ability of the test compound to modulate the activity of NOVX can be accomplished, for example, by determining the ability of the NOVX protein to bind to an NOVX target molecule by one of the methods described above for determining direct binding. In an alternative embodiment, determining the ability of the test compound to modulate the activity of NOVX protein can be accomplished by determining the ability of the NOVX protein further modulate an NOVX target molecule. For example, the catalytic/enzymatic activity of the target molecule on an appropriate substrate can be determined as described, sipra.

In yet another embodiment, the cell-free assay comprises contacting the NOVX protein or biologically-active portion thereof with a known compound which binds NOVX protein to form an assay mixture, contacting the assay mixture with a test compound, and determining the ability of the test compound to interact with an NOVX protein, wherein determining the ability of the test compound to interact with an NOVX protein comprises determining the ability of the NOVX protein to preferentially bind to or modulate the activity of an NOVX target molecule.

The cell-free assays of the invention are amenable to use of both the soluble form or the membrane-bound form of NOVX protein. In the case of cell-free assays comprising the membrane-bound form of NOVX protein, it may be desirable to utilize a solubilizing agent such that the membrane-bound form of NOVX protein is maintained in solution. Examples of such solubilizing agents include non-ionic detergents such as n-octylglucoside, n-dodecylglIucoside, n-dodecylmaltoside, octanoyl-N-methylglucamide, decanoyl-N-methylglucamiide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl) dimethylamminiol-2-hydoxy-1-propane sulfonate (CHAPSO).

In more than one embodiment of the above assay methods of the invention, it may be desirable to immobilize either NOVX protein or its target molecule to facilitate separation of complexed from uncomplexed forms of one or both of the proteins, as well as to accommodate automation of the assay. Binding of a test compound to NOVX protein, or interaction of NOVX protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-NOVX fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or NOVX protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of NOVX protein binding or activity determined using standard techniques.

Other techniques for immobilizing proteins on matrices can also be used in the screening assays of the invention. For example, either the NOVX protein or its target molecule can be immobilized utilizing conjugation of biotin and streptavidin. Biotinylated NOVX protein or target molecules can be prepared from biotin-NHS(N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with NOVX protein or target molecules, but which do not interfere with binding of the NOVX protein to its target molecule, can be derivatized to the wells of the plate, and unbound target or NOVX protein trapped in the wells by antibody conjugation. Methods for detecting such complexes, in addition to those described above for the GST-immobilized complexes, include immunodetection of complexes using antibodies reactive with the NOVX protein or target molecule, as well as enzyme-linked assays that rely on detecting an enzymatic activity associated with the NOVX protein or target molecule.

In another embodiment, modulators of NOVX protein expression are identified in a method wherein a cell is contacted with a candidate compound and the expression of NOVX mRNA or protein in the cell is determined. The level of expression of NOVX mRNA or protein in the presence of the candidate compound is compared to the level of expression of NOVX mRNA or protein in the absence of the candidate compound. The candidate compound can then be identified as a modulator of NOVX mRNA or protein expression based upon this comparison. For example, when expression of NOVX mRNA or protein is greater (i.e., statistically significantly greater) in the presence of the candidate compound than in its absence, the candidate compound is identified as a stimulator of NOVX mRNA or protein expression. Alternatively, when expression of NOVX mRNA or protein is less (statistically significantly less) in the presence of the candidate compound than in its absence, the candidate compound is identified as an inhibitor of NOVX mRNA or protein expression. The level of NOVX mRNA or protein expression in the cells can be determined by methods described herein for detecting NOVX mRNA or protein.

In yet another aspect of the invention, the NOVX proteins can be used as "bait proteins" in a two-hybrid assay or three hybrid assay (see, e.g., U.S. Pat. No. 5,283,317; Zervos, el al., 1993. *Cell* 72: 223–232; Madura, et al., 1993. *J. Biol. Chem.* 268: 12046–12054; Bartel, et al., 1993. *Biotechniqies* 14: 920–924; twabuchi, et al., 1993. *Oncogene* 8: 1693–1696; and Brent WO 94/10300), to identify other proteins that bind to or interact with NOVX ("NOVX-binding proteins" or "NOVX-bp") and modulate NOVX activity. Such NOVX-binding proteins are also likely to be involved in the propagation of signals by the NOVX proteins as, for example, upstream or downstream elements of the NOVX pathway.

The two-hybrid system is based on the modular nature of most transcription factors, which consist of separable DNA-binding and activation domains. Briefly, the assay utilizes two different DNA constructs. In one construct, the gene that codes for NOVX is fused to a gene encoding the DNA binding domain of a known transcription factor (e g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an NOVX-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with NOVX.

The invention further pertains to novel agents identified by the aforementioned screening assays and uses thereof for treatments as described herein.

Detection Assays

Portions or fragments of the cDNA sequences identified herein (and the corresponding complete gene sequences) can be used in numerous ways as polynucleotide reagents. By way of example, and not of limitation, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. Some of these applications are described in the subsections, below.

Chromosome Mapping

Once the sequence (or a portion of the sequence) of a gene has been isolated, this sequence can be used to map the location of the gene on a chromosome. This process is called chromosome mapping. Accordingly, portions or fragments of the NOVX sequences, SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101, or fragments or derivatives thereof, can be used to map the location of the NOVX genes, respectively, on a chromosome. The mapping of the NOVX sequences to chromosomes is an important first step in correlating these sequences with genes associated with disease.

Briefly, NOVX genes can be mapped to chromosomes by preparing PCR primers (preferably 15–25 bp in length) from the NOVX sequences. Computer analysis of the NOVX, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the NOVX sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. See, e.g., D'Eustachio, et al., 1983. *Science* 220: 919–924. Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the NOVX sequences to design oligonucleotide primers, sub-localization can be achieved with panels of fragments from specific chromosomes.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see, Verma, et al., HUMAN CHROMOSOMES: A MANUAL OF BASIC TECHNIQUES (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. Such data are found, e.g., in McKusick, MENDELIAN INHERITANCE IN MAN, available on-line through Johns Hopkins University Welch Medical Library). The relationship between genes and disease, mapped to the same chromosomal region, can then be identified through linkage analysis (co-inheritance of physically adjacent genes), described in, e.g., Egeland, et al., 1987. Nature, 325: 783–787.

Moreover, differences in the DNA sequences between individuals affected and unaffected with a disease associated with the NOVX gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The NOVX sequences of the invention can also be used to identify individuals from minute biological samples. In this technique, an individual's genomic DNA is digested with one or more restriction enzymes, and probed on a Southern blot to yield unique bands for identification. The sequences of the invention are useful as additional DNA markers for RFLP ("restriction fragment length polymorphisms," described in U.S. Pat. No. 5,272,057).

Furthermore, the sequences of the invention can be used to provide an alternative technique that determines the actual base-by-base DNA sequence of selected portions of an individual's genome. Thus, the NOVX sequences described herein can be used to prepare two PCR primers from the 5'- and 3'-termini of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the invention can be used to obtain such identification sequences from individuals and from tissue. The NOVX sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncodirig regions, fewer sequences are necessary to differentiate individuals. The noncoding sequences can comfortably provide positive individual identification with a panel of perhaps 10 to 1,000 primers that each yield a noncoding amplified sequence of 100 bases. If predicted coding sequences, such as those in SEQ ID NOS:1, 8, 10, 12, 18, 20, 26, 28, 34, 36, 42, 44, 50, 52, 54, 60, 62, 64, 70, 72, 74, 76, 82, 89, 91, 99 and 101 are used, a more appropriate number of primers for positive individual identification would be 500–2,000.

Predictive Medicine

The invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the invention relates to diagnostic assays for determining NOVX protein and/or nucleic acid expression as well as NOVX activity, in the context of a biological sample (e.g., blood, serum, cells, tissue) to thereby determine whether an individual is afflicted with a disease or disorder, or is at risk of developing a disorder, associated with aberrant NOVX expression or activity. The disorders include metabolic disorders, diabetes, obesity, infectious disease, anorexia, cancer-associated cachexia, cancer, neurodegenerative disorders, Alzheimer's Disease, Parkinson's Disorder, immune disorders, and hematopoietic disorders, and the various dyslipidemias, metabolic disturbances associated with obesity, the metabolic syndrome X and wasting disorders associated with chronic diseases and various cancers. The invention also provides for prognostic (or predictive) assays for determining whether an individual is at risk of developing a disorder associated with NOVX protein, nucleic acid expression or activity. For example, mutations in an NOVX gene can be assayed in a biological sample. Such assays can be used for prognostic or predictive purpose to thereby prophylactically treat an individual prior to the onset of a disorder characterized by or associated with NOVX protein, nucleic acid expression, or biological activity.

Another aspect of the invention provides methods for determining NOVX protein, nucleic acid expression or activity in an individual to thereby select appropriate therapeutic or prophylactic agents for that individual (referred to herein as "pharmacogenomics"). Pharmacogenomics allows for the selection of agents (e g, drugs) for therapeutic or prophylactic treatment of an individual based on the genotype of the individual (e.g, the genotype of the individual examined to determine the ability of the individual to respond to a particular agent.)

Yet another aspect of the invention pertains to monitoring the influence of agents (e.g., drugs, compounds) on the expression or activity of NOVX in clinical trials.

These and other agents are described in further detail in the following sections.

Diagnostic Assays

An exemplary method for detecting the presence or absence of NOVX in a biological sample involves obtaining a biological sample from a test subject and contacting the biological sample with a compound or an agent capable of detecting NOVX protein or nucleic acid (e.g., mRNA, genomic DNA) that encodes NOVX protein such that the presence of NOVX is detected in the biological sample. An agent for detecting NOVX mRNA or genomic DNA is a labeled nucleic acid probe capable of hybridizing to NOVX mRNA or genomic DNA. The nucleic acid probe can be, for example, a full-length NOVX nucleic acid, such as the nucleic acid of SEQ ID NOS:1, 8, 10, 12, 18, 20, 26, 28, 34, 36, 42,44, 50, 52, 54, 60, 62, 64, 70, 72, 74, 76, 82, 89, 91, 99 and 101, or a portion thereof, such as an oligonucleotide of at least 15, 30, 50, 100, 250 or 500 nucleotides in length and sufficient to specifically hybridize under stringent conditions to NOVX mRNA or genomic DNA. Other suitable probes for use in the diagnostic assays of the invention are described herein.

An agent for detecting NOVX protein is an antibody capable of binding to NOVX protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect NOVX mRNA, protein, or genomic DNA in a biological sample in vitro as well as in vivo. For example, in vitro techniques for detection of NOVX mRNA include Northern hybridizations and in situ hybridizations. In vitro techniques for detection of NOVX protein include enzyme linked immunosorbent assays (ELISAs), Western blots, immunoprecipitations, and immunofluorescence. In vitro techniques for detection of NOVX genomic DNA include Southern hybridizations. Furthermore, in vivo techniques for detection of NOVX protein include introducing into a subject a labeled anti-NOVX antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting NOVX protein, mRNA, or genomic DNA, such that the presence of NOVX protein, mRNA or genomic DNA is detected in the biological sample, and comparing the presence of NOVX protein, mRNA or genomic DNA in the control sample with the presence of NOVX protein, mRNA or genomic DNA in the test sample.

The invention also encompasses kits for detecting the presence of NOVX in a biological sample. For example, the kit can comprise: a labeled compound or agent capable of detecting NOVX protein or mRNA in a biological sample; means for determining the amount of NOVX in the sample; and means for comparing the amount of NOVX in the sample with a standard. The, compound or agent can be packaged in a suitable container. The kit can further comprise instructions for using the kit to detect NOVX protein or nucleic acid.

Prognostic Assays

The diagnostic methods described herein can furthermore be utilized to identify subjects having or at risk of developing a disease or disorder associated with aberrant NOVX expression or activity. For example, the assays described herein, such as the preceding diagnostic assays or the following assays, can be utilized to identify a subject having or at risk of developing a disorder associated with NOVX protein, nucleic acid expression or activity. Alternatively, the prognostic assays can be utilized to identify a subject having or at risk for developing a disease or disorder. Thus, the invention provides a method for identifying a disease or disorder associated with aberrant NOVX expression or activity in which a test sample is obtained from a subject and NOVX protein or nucleic acid (e.g., mRNA, genomic DNA) is detected, wherein the presence of NOVX protein or nucleic acid is diagnostic for a subject having or at risk of developing a disease or disorder associated with aberrant NOVX expression or activity. As used herein, a "test sample" refers to a biological sample obtained from a subject of interest. For example, a test sample can be a biological fluid (e.g, serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant NOVX expression or activity. For example, such methods can be used to determine whether a subject can be effectively treated with an agent for a disorder. Thus, the invention provides methods for determining whether a subject can be effectively treated with an agent for a disorder associated with aberrant NOVX expression or activity in which a test sample is obtained and NOVX protein or nucleic acid is detected (e.g., wherein the presence of NOVX protein or nucleic acid is diagnostic for a subject that can be administered the agent to treat a disorder associated with aberrant NOVX expression or activity).

The methods of the invention can also be used to detect genetic lesions in an NOVX gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding an NOVX-protein, or the misexpression of the NOVX gene. For example, such genetic lesions can be detected by ascertaining the existence of at least one of: (i) a deletion of one or more nucleotides from an NOVX gene; (ii) an addition of one or more nucleotides to an NOVX gene; (iii) a substitution of one or more nucleotides of an NOVX gene, (iv) a chromosomal rearrangement of an NOVX gene; (v) an alteration in the level of a messenger RNA transcript of an NOVX gene, (vi) aberrant modification of an NOVX gene, such as of the methylation pattern of the genomic DNA, (vii) the presence of a non-wild-type splicing pattern of a messenger RNA transcript of an NOVX gene, (viii) a non-wild-type level of an NOVX protein, (ix) allelic loss of an NOVX gene, and (x) inappropriate post-translational modification of an NOVX protein. As described herein, there are a large number of assay techniques known in the art which can be used for detecting lesions in an NOVX gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran, et al., 1988. *Science* 241: 1077–1080; and Nakazawa, et al., 1994. *Proc. Natl. Acad. Sci. USA* 91: 360–364), the latter of which can be particularly useful for detecting point mutations in the NOVX-gene (see, Abravaya, et al., 1995. *Nucl. Acids Res.* 23: 675–682). This method can include the steps of collecting a sample of cells from a patient, isolating nucleic acid (e.g., genomic, mRNA or both) from the cells of the sample, contacting the nucleic acid sample with one or more primers that specifically hybridize to an NOVX gene under conditions such that hybridization and amplification of the NOVX gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (see, Guatelli, et al., 1990. *Proc. Natl. Acad. Sci. USA* 87: 1874–1878), transcriptional amplification system (see, Kwoh, et al., 1989. *Proc. Natl. Acad. Sci. USA* 86: 1173–1177); Qβ Replicase (see, Lizardi, et al, 1988. *BioTechnology* 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an NOVX gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,493,531) can be used to score for the presence of specific mutations by development or loss of a ribozyme cleavage site.

In other embodiments, genetic mutations in NOVX can be identified by hybridizing a sample and control nucleic acids, e.g., DNA or RNA, to high-density arrays containing hundreds or thousands of oligonucleotides probes. See, e.g., Cronin, et al., 1996. *Human Mutation* 7: 244–255; Kozal, et al., 1996. *Nat. Med.* 2: 753–759. For example, genetic mutations in NOVX can be identified in two dimensional arrays containing light-generated DNA probes as described in Cronin, et al., supra. Briefly, a first hybridization array of probes can be used to scan through long stretches of DNA in a sample and control to identify base changes between the sequences by making linear arrays of sequential overlapping probes. This step allows the identification of point mutations. This is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the NOVX gene and detect mutations by comparing the sequence of the sample NOVX with the corresponding wild-type (control) sequence. Examples of sequencing reactions include those based on techniques developed by Maxim and Gilbert, 1977. *Proc. Natl. Acad. Sci USA* 74: 560 or Sanger, 1977. *Proc. Natl. Acad. Sci. USA* 74: 5463. It is also contemplated that any of a variety of automated sequencing procedures can be utilized when performing the diagnostic assays (see.e.g., Naeve, et al., 1995. *Biotechniques* 19: 448), including sequencing by mass spectrometry (see, e.g., PCT International Publication No. WO 94/16101; Cohen, et al., 1996. *Adv. Chromatography* 36: 127–162; and Griffin, et al., 1993. *Appl. Biochem. Biotechnol.* 38: 147–159).

Other methods for detecting mutations in the NOVX gene include methods in which protection from cleavage agents is used to detect mismatched bases in RNA/RNA or RNA/DNA heteroduplexes. See, e.g., Myers, el al., 1985. *Science* 230: 1242. In general, the art technique of "mismatch cleavage" starts by providing heteroduplexes of formed by hybridizing (labeled) RNA or DNA containing the wild-type NOVX sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with $S_1$ nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton, et al., 1988. *Proc. Natl. Acad. Sci. USA* 85: 4397; Saleeba, et al., 1992. *Methods Enzymol.* 217: 286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in NOVX cDNAs obtained from samples of cells. For example, the mutY enzyme of *E. coli* cleaves A at G/A mismatches and the thymidine DNA glycosylase fiom HeLa cells cleaves T at G/T mismatches. See, e.g., Hsu, et al., 1994. *Carcinogenesis* 15: 1657–1662. According to an exemplary embodiment, a probe based on an NOVX sequence, e.g., a wild-type NOVX sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in NOVX genes. For example, single strand conformation polymorphism (SSCP) may be used to detect differences in electrophoretic mobility between mutant and wild type nucleic acids. See, e.g., Orita, et al., 1989. *Proc. Natl. Acad. Sci. USA:* 86: 2766;

Cotton, 1993. *Mutat. Res.* 285: 125–144; Hayashi, 1992. *Genet. Anal. Tech. Appl.* 9: 73–79. Single-stranded DNA fragments of sample and control NOVX nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility. See, e.g., Keen, et al., 1991. Trends Genet. 7:5.

In yet another embodiment, the movement of mutant or wild-type fragments in polyacrylamide gels containing a gradient of denaturant is assayed using denaturing gradient gel electrophoresis (DGGE). See, e.g., Myers, et al., 1985. *Nature* 313: 495. When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA. See, e.g., Rosenbaum and Reissner, 1987. *Biophys. Chem.* 265: 12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. See, e.g., Saiki, et al., 1986. *Nature* 324:163; Saiki, et al., 1989. *Proc. Natl. Acad. Sci. USA* 86: 6230. Such allele specific oligonucleotides are hybridized to PCR amplified target DNA or a number of different mutations when the oligonuLcleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization; see, e.g., Gibbs. et al., 1989. *Nucl. Acids Res.* 17: 2437–2448) or at the extreme 3'-terminus of one primer where, under appropriate conditions, mismatch can prevent, or reduce polymerase extension (see, e.g., Prossner, 1993. *Tibtech.* 11: 238). In addition it maw be desirable to introduce a novel restriction site in the region of the mutation to create cleavage-based detection. See, e.g., Gasparini, et al., 1992. *Mol. Cell Probes* 6: 1. It is anticipated that in certain embodiments amplification may also be performed using Taq ligase for amplification. See, e.g., Barany, 1991. *Proc. Natl. Acad. Sci. USA* 88: 189. In such cases, ligation will occur only if there is a perfect match at the 3'-terminus of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an NOVX gene.

Furthermore, any cell type or tissue, preferably peripheral blood leukocytes, in which NOVX is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on NOVX activity (e.g., NOVX gene expression), as identified by a screening assay described herein can be administered to individuals to treat (prophylactically or therapeutically) disorders (The disorders include metabolic disorders, diabetes, obesity, infectious disease, anorexia, cancer-associated cachexia, cancer, neurodegenerative disorders, Alzheimer's Disease, Parkinson's Disorder, immune disorders, and hematopoietic disorders, and the various dyslipidemias, metabolic disturbances associated with obesity, the metabolic syndrome X and wasting disorders associated with chronic diseases and various cancers.) In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of NOVX protein, expression of NOVX nucleic acid, or mutation content of NOVX genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, 1996. *Clin. Exp. Pharmacol. Physiol.,* 23: 983–985; Linder, 1997. *Clin. Chem.,* 43: 254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, the activity of NOVX protein, expression of NOVX nucleic acid, or mutation content of NOVX genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an NOVX modulator, such as a modulator identified by one of the exemplary screening assays described herein.

Monitoring of Effects During Clinical Trials

Monitoring the influence of agents (e.g., drugs, compounds) on the expression or activity of NOVX (e.g., the ability to modulate aberrant cell proliferation and/or differentiation) can be applied not only in basic drug screening, but also in clinical trials. For example, the effectiveness of an agent determined by a screening assay as described herein to increase NOVX gene expression, protein levels, or upregulate NOVX activity, can be monitored in clinical trails of subjects exhibiting decreased NOVX gene expression, protein levels, or downregulated NOVX activity. Alternatively, the effectiveness of an agent determined by a screening assay to decrease NOVX gene expression, protein levels, or downregulate NOVX activity, can be monitored in clinical trails of subjects exhibiting increased NOVX gene expression, protein levels, or upregulated NOVX activity. In such clinical trials, the expression or activity of NOVX and, preferably, other genes that have been implicated in, for example, a cellular proliferation or immune disorder can be used as a "read out" or markers of the immune responsiveness of a particular cell.

By way of example, and not of limitation genes, including NOVX, that are modulated in cells by treatment with an agent (e.g., compound, drug or small molecule) that modulates NOVX activity (e.g., identified in a screening assay as described herein) can be identified. Thus, to study the effect of agents on cellular proliferation disorders, for example, in a clinical trial, cells can be isolated and RNA prepared and analyzed for the levels of expression of NOVX and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of NOVX or other genes. In this manner, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of an NOVX protein, mRNA, or genomic DNA in the preadministration sample; (iii) obtaining one or more post-administration samples from the subject; (iv) detecting the level of expression or activity of the NOVX protein, mRNA, or genomic DNA in the post-administration samples; (v) comparing the level of expression or activity of the NOVX protein, mRNA, or genomic DNA in the pre-administration sample with the NOVX protein, mRNA, or genomic DNA in the post administration sample or samples; and (vi) altering the administration of the agent to the subject accordingly. For example, increased administration of the agent may be desirable to increase the expression or activity of NOVX to higher levels than detected, i.e. to increase the effectiveness of the agent. Alternatively, decreased administration of the agent may be desirable to decrease expression or activity of NOVX to lower levels than detected, i.e., to decrease the effectiveness of the agent.

Methods of Treatment

The invention provides for both prophylactic and therapeutic methods of treating a subject at risk of (or susceptible to) a disorder or having a disorder associated with aberrant NOVX expression or activity. The disorders include cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, scleroderma, obesity, transplantation, adrenoleukodystrophy, congenital adrenal hyperplasia, prostate cancer, neoplasm; adenocarcinoma, lymphoma, uterus cancer, fertility, hemophilia, hypercoagulation, idiopathic thrombocytopenic purpura, immunodeficiencies, graft versus host disease, AIDS, bronchial asthma, Crohn's disease; multiple sclerosis, treatment of Albright Hereditary Osteoedystrophy, and other diseases, disorders and conditions of the like.

These methods of treatment will be discussed more fully, below.

Disease and Disorders

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to: (i) an aforementioned peptide, or analogs, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endogenous function of an aforementioned peptide by homologous recombination (see, e.g., Capecchi, 1989. *Science* 244: 1288–1292); or (v) modulators (i.e, inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity may be treated with Therapeutics that increase (i.e., are agonists to) activity.

Therapeutics that upregulate activity may be administered in a therapeutic or prophylactic manner. Therapeutics that may be utilized include, but are not limited to, an aforementioned peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Prophylactic Methods

In one aspect, the invention provides a method for preventing, in a subject, a disease or condition associated with an aberrant NOVX expression or activity, by administering to the subject an agent that modulates NOVX expression or at least one NOVX activity. Subjects at risk for a disease that is caused or contributed to by aberrant NOVX expression or activity can be identified by, for example, any or a combination of diagnostic or prognostic assays as described herein. Administration of a prophylactic agent can occur prior to the manifestation of symptoms characteristic of the NOVX aberrancy, such that a disease or disorder is prevented or, alternatively, delayed in its progression. Depending upon the type of NOVX aberrancy, for example, an NOVX agonist or NOVX antagonist agent can be used for treating the subject. The appropriate agent can be determined based on screening assays described herein. The prophylactic methods of the invention are further discussed in the following subsections.

Therapeutic Methods

Another aspect of the invention pertains to methods of modulating NOVX expression or activity for therapeutic purposes. The modulatory method of the invention involves contacting a cell with an agent that modulates one or more of the activities of NOVX protein activity associated with the cell. An agent that modulates NOVX protein activity can be an agent as described herein, such as a nucleic acid or a protein, a naturally-occurring cognate ligand of an NOVX protein, a peptide, an NOVX peptidomimetic, or other small molecule. In one embodiment, the agent stimulates one or more NOVX protein activity. Examples of such stimulatory agents include active NOVX protein and a nucleic acid molecule encoding NOVX that has been introduced into the cell. In another embodiment, the agent inhibits one or more NOVX protein activity. Examples of such inhibitory agents include antisense NOVX nucleic acid molecules and anti-NOVX antibodies. These modulatory methods can be performed in vitro (e.g., by culturing the cell with the agent) or, alternatively, in vivo (e.g., by administering the agent to a subject). As such, the invention provides methods of treating an individual afflicted with a disease or disorder characterized by aberrant expression or activity of an NOVX protein or nucleic acid molecule. In one embodiment, the method involves administering an agent (e.g., an agent identified by a screening assay described herein), or combination of agents that modulates (e.g., up-regulates or down-regulates) NOVX expression or activity. In another embodiment, the method involves administering an NOVX protein or nucleic acid molecule as therapy to compensate for reduced or aberrant NOVX expression or activity.

Stimulation of NOVX activity is desirable in situations in which NOVX is abnormally downregulated and/or in which increased NOVX activity is likely to have a beneficial effect. One example of such a situation is where a subject has a disorder characterized by aberrant cell proliferation and/or differentiation (e.g., cancer or immune associated disorders). Another example of such a situation is where the subject has a gestational disease (e.g., preclampsia).

Determination of the Biological Effect of the Therapeutic

In various embodiments of the invention, suitable in vitro or in vivo assays are performed to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Prophylactic and Therapeutic Uses of the Compositions of the Invention

The NOVX nucleic acids and proteins of the invention are useful in potential prophylactic and therapeutic applications implicated in a variety of disorders including, but not limited to: metabolic disorders, diabetes, obesity, infectious disease, anorexia, cancer-associated cancer, neurodegenerative disorders, Alzheimer's Disease, Parkinson's Disorder, immune disorders, hematopoietic disorders, and the various dyslipidemias, metabolic disturbances associated with obesity, the metabolic syndrome X and wasting disorders associated with chronic diseases and various cancers.

As an example, a cDNA encoding the NOVX protein of the invention may be useful in gene therapy, and the protein may be useful when administered to a subject in need thereof. By way of non-limiting example, the compositions of the invention will have efficacy for treatment of patients suffering from: metabolic disorders, diabetes, obesity, infectious disease, anorexia, cancer-associated cachexia, cancer, neurodegenerative disorders, Alzheimer's Disease. Parkinson's Disorder, immune disorders, hematopoietic disorders, and the various dyslipidemias.

Both the novel nucleic acid encoding the NOVX protein, and the NOVX protein of the invention, or fragments thereof, may also be useful in diagnostic applications, wherein the presence or amount of the nucleic acid or the protein are to be assessed. A further use could be as an anti-bacterial molecule (i.e., some peptides have been found to possess anti-bacterial properties). These materials are further useful in the generation of antibodies, which immunospecifically-bind to the novel substances of the invention for use in therapeutic or diagnostic methods.

The invention will be further described in the following examples, which do not limit the scope of the invention described in the claims.

EXAMPLES

Example 1

Identification of NOVX Clones

The novel NOVX target sequences identified in the present invention were subjected to the exon linking process to confirm the sequence. PCR primers were designed by starting at the most upstream sequence available, for the forward primer, and at the most downstream sequence available for the reverse primer. Table 17A shows the sequences of the PCR primers used for obtaining different clones. In each case, the sequence was examined, walking inward from the respective termini toward the coding, sequence, until a suitable sequence that is either unique or highly selective was encountered, or, in the case of the reverse primer, until the stop codon was reached. Such primers were designed based on in silico predictions for the full length cDNA, part (one or more exons) of the DNA or protein sequence of the target sequence, or by translated homology of the predicted exons to closely related human sequences from other species. These primers were then employed in PCR amplification based on the following pool of human cDNAs: adrenal gland, bone marrow, brain—amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea, uterus. Usually the resulting amplicons were gel purified, cloned and sequenced to high redundancy. The PCR product derived from exon linking was cloned into the pCR2.1 vector from Invitrogen. The resulting bacterial clone has an insert covering the entire open reading frame cloned into the pCR2.1 vector. Table 17B shows a list of these bacterial clones. The resulting sequences from all clones were assembled with themselves, with other fragments in CuraGen Corporation's database and with public ESTs. Fragments and ESTs were included as components for an assembly when the extent of their identity with another component of the assembly was at least 95% over 50 bp. In addition, sequence traces were evaluated manually and edited for corrections if appropriate. These procedures provide the sequence reported herein.

sequence. The DNA sequence was then manually corrected for apparent inconsistencies thereby obtaining the sequences encoding the full-length protein.

TABLE 17B

Physical Clones for PCR products

| NOVX Clone | Bacterial Clone |
|---|---|
| NOV2 | Physicel clone: 110021::COR24CS059.698230.G1 |
| NOV3 | Physical clone: 104046::COR24SC113.698230.C13 |
| NOV4 | Physical clone: 110189::COR24SC128.698230.M23 |
| NOV10b | Physical clone: 112812::COR100340173.698230.J3 |
| NOV10c | Physical clone: 128970::80083680.698655.M23 |
| NOV12 | Physical clone: 112818::COR87917235.698230.N1 |
| NOV15 | Physical clone: 112824::COR100399281.698230.B6 |
| NOV16 | Physical clone: 112826::COR101330077.698230.F18 |

Example 2

Quantitative Expression Analysis of Clones in Various Cells and Tissues

The quantitative expression of various clones was assessed using microtiter plates containing RNA samples from a variety of normal and pathology-derived cells, cell lines and tissues using real time quantitative PCR (RTQ

TABLE 17A

PCR Primers for Exon Linking

| NOVX Clone | Primer 1 (5'-3') | SEQ ID NO | Primer 2 (5'-3') | SEQ ID NO |
|---|---|---|---|---|
| NOV2 | TGGCTTGATGATATGTGCCTGTAG | 108 | TTATAGTACGAGCAAGAACTTTGG | 109 |
| NOV3 | TTATTGACAGTTTATCCTGCCGCACCT | 110 | AACTACTCGTGAGGCTGAGGCAGGAG | 111 |
| NOV4-1 | CAATCCTTGCGTGTCCTTGCACTC | 112 | AGCAAGCAAAATCAGGATGTTTTCCTC | 113 |
| NOV4-2 | CAATCCTTGCGTGTCCTTGCAGTC | 114 | AGCAAGCAAAATCAGGATGTTTTCCTC | 115 |
| NOV10b | GCTACCTTCACCACCTCCTGCTGT | 116 | AAGTGCAGACCTATAGGCCAATACAGG | 117 |
| NOV10c | AGAACCCAAGGCTCCCTGGATT | 118 | CATGGAATTATTCAAATTTGCTCTG | 119 |
| NOV15 | GTAGCCACAAGACCGGGTCCG | 120 | CCCTGGCCTCTTGGAACTGCTTGAT | 121 |
| NOV16 | CCGCTGGCCGAGAGGCTGA | 122 | TGTTTAAAGCATTAATAAA | 123 |

Physical clone: Exons were predicted by homology and the intron/exon boundaries were determined using standard genetic rules. Exons were further selected and refined by means of similarity determination using multiple BLAST (for example, tBlastN, BlastX, and BlastN) searches, and, in some instances, GeneScan and Grail. Expressed sequences from both public and proprietary databases were also added when available to further define and complete the gene PCR). RTQ PCR was performed on a Perkin-Elmer Biosystems ABI PRISM® 7700 Sequence Detection System. Various collections of samples are assembled on the plates, and referred to as Panel I (containing cells and cell lines from normal and cancer sources), Panel 2 (containing samples derived from tissues, in particular from surgical samples, from normal and cancer sources), Panel 3 (containing samples derived from a wide variety of cancer sources), Panel 4 (containing cells and cell lines from normal cells and cells related to inflammatory conditions) and Panel CNSD.01 (containing samples from normal and diseased brains).

First, the RNA samples were normalized to reference nucleic acids such as constitutively expressed genes (for example, β-actin and GAPDH). Normalized RNA (5 ul) was converted to cDNA and analyzed by RTQ-PCR using One Step RT-PCR Master Mix Reagents (PE Biosystems; Catalog No. 4309169) and gene-specific primers according to the manufacturer's instructions. Probes and primers were designed for each assay according to Perkin Elmer Biosystem's Primer Express Software package (version I for Apple Computer's Macintosh Power PC) or a similar algorithm using the target sequence as input. Default settings were used for reaction conditions and the following parameters were set before selecting primers: primer concentration=250 nM, primer melting temperature ($T_m$) range=58°–60° C., primer optimal Tm=59° C., maximum primer difference=2° C., probe does not have 5' G, probe $T_m$ must be 10° C. greater than primer $T_m$, amplicon size 75 bp to 100 bp. The probes and primers selected (see below) were synthesized by Synthegen (Houston, Tex., USA). Probes were double purified by HPLC to remove uncoupled dye and evaluated by mass spectroscopy to verify coupling of reporter and quencher dyes to the 5 and 3' ends of the probe, respectively. Their final concentrations were: forward and reverse primers, 900 nM each, and probe, 200 nM.

PCR conditions: Normalized RNA from each tissue and each cell line was spotted in each well of a 96 well PCR plate (Perkin Elmer Biosystems). PCR cocktails including two probes (a probe specific for the target clone and another gene-specific probe multiplexed with the target probe) were set up using 1×TaqMan™ PCR Master Mix for the PE Biosystems 7700, with 5 mM MgCl2, dNTPs (dA, G, C. U at 1:1:1:2 ratios). 0.25 U/ml AmpliTaq Gold™ (PE Biosystems), and 0.4 U/µl RNase inhibitor, and 0.25 U/µl reverse transcriptase. Reverse transcription was performed at 48° C. for 30 minutes followed by amplification/PCR cycles as follows: 95° C. 10 min, then 40 cycles of 95° C. for 15 seconds, 60° C. for 1 minute. Results were recorded as CT values (cycle at which a given sample crosses a threshold level of fluorescence) using a log scale, with the difference in RNA concentration between a given sample and the sample with the lowest CT value being represented as 2 to the power of delta CT. The percent relative expression is then obtained by taking the reciprocal of this RNA difference and multiplying by 100.

In the results for Panel 1, the following abbreviations are used:

ca.=carcinoma,
*=established from metastasis,
met=metastasis,
s cell var=small cell variant,
non-s=non-sm=non-small,
squam=squamous,
pl. eff=p1 effusion=pleural effusion,
glio=glioma,
astro=astrocytoma, and
neuro=neuroblastoma.

Panel 2

The plates for Panel 2 generally include 2 control wells and 94 test samples composed of RNA or cDNA isolated from human tissue procured by surgeons working in close cooperation with the National Cancer Institute's Cooperative Human Tissue Network (CHTN) or the National Disease Research Initiative (NDRI). The tissues are derived from human malignancies and in cases where indicated many malignant tissues have "matched margins" obtained from noncancerous tissue just adjacent to the tumor. These are termed normal adjacent tissues and are denoted "NAT" in the results below. The tumor tissue and the "matched margins" are evaluated by two independent pathologists (the surgical pathologists and again by a pathologists at NDRI or CHTN). This analysis provides a gross histopathological assessment of tumor differentiation grade. Moreover, most samples include the original surgical pathology report that provides information regarding the clinical stage of the patient. These matched margins are taken from the tissue surrounding (i.e. immediately proximal) to the zone of surgery (designated "NAT", for normal adjacent tissue, in Table RR). In addition, RNA and cDNA samples were obtained from various human tissues derived from autopsies performed on elderly people or sudden death victims (accidents, etc.). These tissues were ascertained to be free of disease and were purchased from various commercial sources such as Clontech (Palo Alto, Calif.), Research Genetics, and Invitrogen.

RNA integrity from all samples is controlled for quality by visual assessment of agarose gel electropherograms using 28S and 18S ribosomal RNA staining intensity ratio as a guide (2:1 to 2.5:1 28s:18s) and the absence of low molecular weight RNAs that would be indicative of degradation products. Samples are controlled against genomic DNA contamination by RTQ PCR reactions run in the absence of reverse transcriptase using probe and primer sets designed to amplify across the span of a single exon.

Panel 3D

The plates of Panel 3D are comprised of 94 cDNA samples and two control samples. Specifically, 92 of these samples are derived from cultured human cancer cell lines, 2 samples of human primary cerebellar tissue and 2 controls. The human cell lines are generally obtained from ATCC (American Type Culture Collection), NCI or the German tumor cell bank and fall into the following tissue groups: Squamous cell carcinoma of the tongue, breast cancer, prostate cancer, melanoma, epidermoid carcinoma, sarcomas, bladder carcinomas, pancreatic cancers, kidney cancers, leukemias/lymphomas, ovarian/uterine/cervical, gastric, colon, lung and CNS cancer cell lines. In addition, there are two independent samples of cerebellum. These cells are all cultured under standard recommended conditions and RNA extracted using the standard procedures. The cell lines in panel 3D and 10.3D are of the most common cell lines used in the scientific literature.

RNA integrity from all samples is controlled for quality by visual assessment of agarose gel electropherograms using 28S and 18S ribosomal RNA staining intensity ratio as a guide (2:1 to 2.5:1 28s:18s) and the absence of low molecular weight RNAs that would be indicative of degradation products. Samples are controlled against genomic DNA contamination by RTQ PCR reactions run in the absence of reverse transcriptase using probe and primer sets designed to amplify across the span of a single exon.

Panel 4

Panel 4 includes samples on a 96 well plate (2 control wells, 94 test samples) composed of RNA (Panel 4r) or cDNA (Panel 4d) isolated from various human cell lines or tissues related to inflammatory conditions. Total RNA from control normal tissues such as colon and lung (Stratagene, La Jolla, Calif.) and thymus and kidney (Clontech) were employed. Total RNA from liver tissue from cirrhosis patients and kidney from lupus patients was obtained from BioChain (Biochain Institute, Inc., Hayward. Calif.). Intestinal tissue for RNA preparation from patients diagnosed as having Crohn's disease and ulcerative colitis was obtained from the National Disease Research Interchange (NDRI) (Philadelphia, Pa.).

Astrocytes, lung fibroblasts, dermal fibroblasts, coronary artery smooth muscle cells, small airway epithelium, bronchial epithelium, microvascular dermal endothelial cells, microvascular lung endothelial cells, human pulmonary aortic endothelial cells, human umbilical vein endothelial cells were all purchased from Clonetics (Walkersville, Md.) and grown in the media supplied for these cell types by Clonetics. These primary cell types were activated with various cytokines or combinations of cytokines for 6 and/or 12–14 hours, as indicated. The following cytokines were used; IL-1 beta at approximately 1–5 ng/ml, TNF alpha at approximately 5–10 ng/ml, IFN gamma at approximately 20–50 ng/ml, IL-4 at approximately 5–10 ng/ml, 1L-9 at approximately 5–10 ng/ml, IL-13 at approximately 5–10 ng/ml. Endothelial cells were sometimes starved for various times by culture in the basal media from Clonetics with 0.1% serum.

Mononuclear cells were prepared from blood of employees at CuraGen Corporation, using Ficoll. LAK cells were prepared from these cells by culture in DMEM 5% FCS (Hyclone), 100 $\mu$M non essential amino acids (Gibco/Life Technologies, Rockville, Md.), 1 mM sodium pyruvate (Gibco), mercaptoethanol $5.5 \times 10^{-5}$ M (Gibco), and 10 mM Hepes (Gibco) and Interleukin 2 for 4–6 days. Cells were then either activated with 10–20 ng/ml PMA and 1–2 $\mu$g/ml ionomycin, IL-12 at 5–10 ng/ml, IFN gamma at 20–50 ng/ml and IL-18 at 5–10 ng/ml for 6 hours. In some cases, mononuclear cells were cultured for 4–5 days in DMEM 5% FCS (Hyclone), 100 $\mu$M non essential amino acids (Gibco), 1 mM sodium pyruvate (Gibco), mercaptoethanol $5.5 \times 10^{-5}$ M (Gibco). and 10 mM Hepes (Gibco) with PHA (phytohemagglutinin) or PWM (pokeweed mitogen) at approximately 5 $\mu$g/ml. Samples were taken at 24, 48 and 72 hours for RNA preparation. MLR (mixed lymphocyte reaction) samples were obtained by taking blood from two donors, isolating the mononuclear cells Lusing Ficoll and mixing the isolated mononuclear cells 1:1 at a final concentration of approximately $2 \times 10^6$ cells/ml in DMEM 5% FCS (Hyclone), 100 $\mu$M non essential amino acids (Gibco), 1 mM sodium pyruvate (Gibco), mercaptoethanol $(5.5 \times 10^{-5}$ M) (Gibco), and 10 mM Hepes (Gibco). The MLR was cultured and samples taken at various time points ranging from 1–7 days for RNA preparation.

Monocytes were isolated from mononuclear cells using CD14 Miltenyi Beads, +ve VS selection columns and a Vario Magnet according to the manufacturer's instructions. Monocytes were differentiated into dendritic cells by culture in DMEM 5% fetal calf serum (FCS) (Hyclone, Logan, Utah), 100 $\mu$M non essential amino acids (Gibco), 1 mM sodium pyruvate (Gibco), mercaptoethanol $5.5 \times 10^{-5}$ M (Gibco), and 10 mM Hepes (Gibco), 50 ng/ml GMCSF and 5 ng/ml IL-4 for 5–7 days. Macrophages were prepared by culture of monocytes for 5–7 days in DMEM 5% FCS (Hyclone), 100 $\mu$M non essential amino acids (Gibco), 1 mM sodium pyruvate (Gibco), mercaptoethanol $5.5 \times 10^{-5}$ M (Gibco), 10 mM Hepes (Gibco) and 10% AB Human Serum or MCSF at approximately 50 ng/ml. Monocytes, macrophages and dendritic cells were stimulated for 6 and 12–14 hours with lipopolysaccharide (LPS) at 100 ng/ml. Dendritic cells were also stimulated with anti-CD40 monoclonal antibody (Pharmingen) at 10 $\mu$g/ml for 6 and 12–14 hours.

CD4 lymphocytes, CD8 lymphocytes and NK cells were also isolated from mononuclear cells using CD4, CD8 and CD56 Miltenyi beads, positive VS selection columns and a Vario Magnet according to the manufacturer's instructions. CD45RA and CD45RO CD4 lymphocytes were isolated by depleting mononuclear cells of CD8, CD56, CD14 and CD19 cells using CD8, CD56, CD14 and CD19 Miltenyi beads and positive selection. Then CD45RO beads were used to isolate the CD45RO CD4 lymphocytes with the remaining cells being CD45RA CD4 lymphocytes. CD45RA CD4, CD45RO CD4 and CD8 lymphocytes were placed in DMEM 5% FCS (Hyclone), 100 $\mu$M non essential amino acids (Gibco), 1 mM sodium pyruvate (Gibco), mercaptoethanol $5.5 \times 10^{-5}$ M (Gibco). and 10 mM Hepes (Gibco) and plated at $10^6$ cells/ml onto Falcon 6 well tissue culture plates that had been coated overnight with 0.5 $\mu$g/ml anti-CD28 (Pharmingen) and 3 ug/ml anti-CD3 (OKT3, ATCC) in PBS. After 6 and 24 hours, the cells were harvested for RNA preparation. To prepare chronically activated CD8 lymphocytes, we activated the isolated CD8 lymphocytes for 4 days on anti-CD28 and anti-CD3 coated plates and then harvested the cells and expanded them in DMEM 5% FCS (Hyclone), 100 $\mu$M non essential amino acids (Gibco), 1 mM sodium pyruvate (Gibco), mercaptoethanol $5.5 \times 10^{-5}$ M (Gibco), and 10 mM Hepes (Gibco) and IL-2. The expanded CD8 cells were then activated again with plate bound anti-CD3 and anti-CD28 for 4 days and expanded as before. RNA was isolated 6 and 24 hours after the second activation and after 4 days of the second expansion culture. The isolated NK cells were cultured in DMEM 5% FCS (Hyclone), 100 $\mu$M non essential amino acids (Gibco), 1 mM sodium pyruvate (Gibco), mercaptoethanol $5.5 \times 10^{-5}$ M (Gibco), and 10 mM Hepes (Gibco) and IL-2 for 4–6 days before RNA was prepared.

To obtain B cells, tonsils were procured from NDRI. The tonsil was cut up with sterile dissecting scissors and then passed through a sieve. Tonsil cells were then spun down and resupended at $10^6$ cells/ml in DMEM 5% FCS (Hyclone), 100 $\mu$M non essential amino acids (Gibco), 1 mM sodium pyruvate (Gibco), mercaptoethanol $5.5 \times 10^{-5}$ M (Gibco), and 10 mM Hepes (Gibco). To activate the cells, we used PWM at 5 $\mu$g/ml or anti-CD40 (Pharmingen) at approximately 10 $\mu$g/ml and IL-4 at 5–10 ng/ml. Cells were harvested for RNA preparation at 24, 48 and 72 hours.

To prepare the primary and secondary Th1/Th2 and Tr1 cells, six-well Falcon plates were coated overnight with 10 $\mu$g/ml anti-CD28 (Pharmingen) and 2 $\mu$g/ml OKT3 (ATCC), and then washed twice with PBS. Umbilical cord blood CD4 lymphocytes (Poietic Systems, German Town, Md.) were cultured at $10^5$–$10^6$ cells/ml in DMEM 5% FCS (Hyclone), 100 $\mu$M non essential amino acids (Gibco), 1 ml/sodium pyruvate (Gibco), mercaptoethanol $5.5 \times 10^{-5}$ M (Gibco), 10 mM Hepes (Gibco) and IL-2 (4 ng/ml). IL-12 (5 ng/ml) and anti-IL4 (1 □g/ml) were used to direct to Th1, while IL-4 (5 ng/ml) and anti-IFN gamma (1 □g/ml) were used to direct to Th2 and IL-10 at 5 ng/ml was used to direct to Tr1. After 4–5 days, the activated Th1, Th2 and Tr1 lymphocytes were washed once in DMEM and expanded for 4–7 days in DMEM 5% FCS (Hyclone), 100 $\mu$M non essential amino acids (Gibco), 1 mM sodium pyruvate (Gibco), mercaptoethanol $5.5 \times 10^{-5}$ M (Gibco), 10 mM Hepes (Gibco) and IL-2 (1 ng/ml). Following this, the activated Th1, Th2 and Tr1 lymphocytes ere re-stimulated for 5 days with anti-CD28/OKT3 and cytokines as described above, but with the addition of anti-CD95L (1 □g/ml) to prevent apoptosis. After 4–5 days, the Th1, Th2 and Tr1 lymphocytes were washed and then expanded again with IL-2 for 4–7 days.

Activated Th1 and Th2 lymphocytes were maintained in this way for a maximum of three cycles. RNA was prepared from primary and secondary Th1, Th2 and Tr1 after 6 and 24 hours following the second and third activations with plate bound anti-CD3 and anti-CD28 mAbs and 4 days into the second and third expansion cultures in Interleukin 2.

The following leukocyte cells lines were obtained from the ATCC: Ramos, EOL-1, KU-812. EOL cells were further differentiated by culture in 0.1 mM dbcAMP at $5\times10^5$ cells/ml for 8 days, changing the media every 3 days and adjusting the cell concentration to $5\times10^5$ cells/ml. For the culture of these cells, we used DMEM or RPMI (as recommended by the ATCC), with the addition of 5% FCS (Hyclone), 100 μM non essential amino acids (Gibco), 1 mM sodium pyruvate (Gibco), mercaptoethanol $5.5\times10^{-5}$ M (Gibco), 10 mM Hepes (Gibco). RNA was either prepared from resting cells or cells activated with PMA at 10 ng/ml and ionomycin at 1 μg/ml for 6 and 14 hours. Keratinocyte line CCD106 and an airway epithelial tumor line NCI-H292 were also obtained from the ATCC. Both were cultured in DMEM 5% FCS (Hyclone), 100 μM non essential amino acids (Gibco), 1 mM sodium pyruvate (Gibco), mercaptoethanol $5.5\times10^{-5}$ M (Gibco), and 10 mM Hepes (Gibco). CCD1106 cells were activated for 6 and 14 hours with approximately 5 ng/ml TNF alpha and 1 ng/ml IL-1 beta, while NCI-H292 cells were activated for 6 and 14 hours with the following cytokines: 5 ng/ml IL-4, 5 ng/ml IL-9, 5 ng/ml IL-13 and 25 ng/ml IFN gamma.

For these cell lines and blood cells, RNA was prepared by lysing approximately $10^7$ cells/ml using Trizol (Gibco BRL). Briefly, 1/10 volume of bromochloropropane (Molecular Research Corporation) was added to the RNA sample, vortexed and after 10 minutes at room temperature, the tubes were spun at 14,000 rpm in a Sorvall SS34 rotor. The aqueous phase was removed and placed in a 15 ml Falcon Tube. An equal volume of isopropanol was added and left at −20 degrees C. overnight. The precipitated RNA was spun down at 9,000 rpm for 15 min in a Sorvall SS34 rotor and washed in 70% ethanol. The pellet was redissolved in 300 μl of RNAse-free water and 35 μl buffer (Promega) 5 μl DTT, 7 μl RNAsin and 8 μl DNAse were added. The tube was incubated at 37 degrees C. for 30 minutes to remove contaminating genomic DNA, extracted once with phenol chloroform and re-precipitated with 1/10 volume of 3 M sodium acetate and 2 volumes of 100% ethanol. The RNA was spun down and placed in RNAse free water. RNA was stored at −80 degrees C.

Panel CNSD.01

The plates for Panel CNSD.01 include two control wells and 94 test samples comprised of cDNA isolated from postmortem human brain tissue obtained from the Harvard Brain Tissue Resource Center. Brains are removed from calvaria of donors between 4 and 24 hours after death, sectioned by neuroanatomists, and frozen at −80° C. in liquid nitrogen vapor. All brains are sectioned and examined by neuropathologists to confirm diagnoses with clear associated neuropathology.

Disease diagnoses are taken from patient records. The panel contains two brains from each of the following diagnoses: Alzheimer's disease, Parkinson's disease, Huntington's disease, Progressive Supernuclear Palsy, Depression, and "Normal controls". Within each of these brains, the following regions are represented: cingulate gyrus, temporal pole, globus palladus, substantia nigra, Brodman Area 4 (primary motor strip), Brodman Area 7 (parietal cortex), Brodman Area 9 (prefrontal cortex), and Brodman area 17 (occipital cortex). Not all brain regions are represented in all cases; e.g., Huntington's disease is characterized in part by neurodegeneration in the globus palladus, thus this region is impossible to obtain from confirmed Huntington's cases. Likewise Parkinson's disease is characterized by degeneration of the substantia nigra making this region more difficult to obtain. Normal control brains were examined for neuropathology and found to be free of any pathology consistent with neurodegeneration.

RNA integrity from all samples is controlled for quality by visual assessment of agarose gel electropherograms using 28S and 18S ribosomal RNA staining intensity ratio as a guide (2:1 to 2.5:1 28s: 18s) and the absence of low molecular weight RNAs that would be indicative of degradation products. Samples are controlled against genomic DA contamination by RTQ PCR reactions run in the absence of reverse transcriptase using probe and primer sets designed to amplify across the span of a single exon.

In the labels employed to identify tissues in the CNS panel, the following abbreviations are used:

PSP=Progressive supranuclear palsy

Sub Nigra=Substantia nigra

Glob Palladus=Globus palladus

Temp Pole=Temporal pole

Cing Gyr=Cingulate gyrus

BA 4=Brodman Area 4

The AC068339_A gene encodes a G protein-coupled receptor (GPCR), a type of cell surface receptor involved in signal transduction. The AC068339_A gene product is most similar to members of the odorant receptor subfamily of GPCRs. Based on analogy to other odorant receptor genes, we predict that expression of the AC068339_A gene may be highest in nasal epithelium, a sample not represented on these panels.

NOV1-24CS059

Expression of the NOV1 gene, referred to as 24CS059, was assessed using the primer-probe set Ag3975, described in Table 18A. Results from RTQ-PCR runs are shown in Tables 18B and 18C.

TABLE 18A

Probe Name Ag3975

| Primers | Sequences | TM | Length | Start Position | SEQ ID NO |
|---|---|---|---|---|---|
| Forward | 5'-CTGAACTCAGTTGGCAAAGG-3' | 58.5 | 20 | 5598 | 124 |
| Probe | FAM-5'-TCTGTGGGTAAATCCTCTTTCACATG-3'-TAMRA | 64.5 | 26 | 5622 | 125 |
| Reverse | 5'-AGGGCCACATCATGTATGTTAG-3' | 58.9 | 22 | 5672 | 126 |

TABLE 18B

Panel 2.1

| Tissue Name | Relative Expression (%) 2.1x4tm6080f_ag3975_a1 | Tissue Name | Relative Expression (%) 2.1x4tm6080f_ag3975_a1 |
|---|---|---|---|
| Normal Colon GENPAK 061003 | 41.7 | Kidney Cancer Clontech 9010320 | 0.0 |
| 97759 Colon cancer (OD06064) | 7.2 | Kidney NAT Clontech 9010321 | 52.9 |
| 97760 Colon cancer NAT (OD06064) | 0.0 | Kidney Cancer Clontech 8120607 | 3.3 |
| 97778 Colon cancer (OD06159) | 0.0 | Kidney NAT Clontech 8120608 | 0.0 |
| 97779 Colon cancer NAT (OD06159) | 10.2 | Normal Uterus GENPAK 061018 | 33.6 |
| 98859 Colon cancer (OD06298-08) | 5.3 | Uterus Cancer GENPAK 064011 | 10.8 |
| 98860 Colon cancer NAT (OD06298-018) | 0.0 | Normal Thyroid Clontech A+ 6570-1 (7080817) | 8.3 |
| 83237 CC Gr.2 ascend colon (ODO3921) | 41.1 | Thyroid Cancer GENPAK 064010 | 22.6 |
| 83238 CC NAT (ODO3921) | 30.9 | Thyroid Cancer INVITROGEN A302152 | 44.3 |
| 97766 Colon cancer metastasis (OD06104) | 17.0 | Thyroid NAT INVITROGEN A302153 | 82.8 |
| 97767 Lung NAT (OD06104) | 0.0 | Normal Breast GENPAK 061019 | 88.8 |
| 87472 Colon mets to lung (OD04451-01) | 23.5 | 84877 Breast Cancer (OD04566) | 40.5 |
| 87473 Lung NAT (OD04451-02) | 12.0 | Breast Cancer Res. Gen. 1024 | 18.7 |
| Normal Prostate Clontech A+ 6546-1 (8090438) | 2.5 | 85975 Breast Cancer (OD04590-01) | 0.0 |
| 84140 Prostate Cancer (OD04410) | 4.5 | 85976 Breast Cancer Mets (OD04590-03) | 17.9 |
| 84141 Prostate NAT (OD04410) | 8.1 | 87070 Breast Cancer Metastasis (OD04655-05) | 10.8 |
| Normal Lung GENPAK 061010 | 28.0 | GENPAK Breast Cancer 064006 | 10.2 |
| 92337 Invasive poor diff. lung adeno (ODO4945-01 | 26.1 | Breast Cancer Clontech 9100266 | 13.6 |
| 92338 Lung NAT (ODO4945-03) | 99.1 | Breast NAT Clontech 9100265 | 34.7 |
| 84136 Lung Malignant Cancer (OD03126) | 4.3 | Breast Cancer INVITROGEN A209073 | 0.0 |
| 84137 Lung NAT (OD03126) | 30.4 | Breast NAT INVITROGEN A2090734 | 79.2 |
| 90372 Lung Cancer (OD05014A) | 19.9 | Normal Liver GENPAK 061009 | 44.5 |
| 90373 Lung NAT (OD05014B) | 30.8 | Liver Cancer Research Genetics RNA 1026 | 0.0 |
| 85950 Lung Cancer (OD04237-01) | 18.1 | Liver Cancer Research Genetics RNA 1025 | 8.3 |
| 85970 Lung NAT (OD04237-02) | 42.7 | Paired Liver Cancer Tissue Research Genetics RNA 6004-T | 4.2 |
| 83255 Ocular Mel Met to Liver (ODO4310) | 18.6 | Paired Liver Tissue Research Genetics RNA 6004-N | 0.0 |
| 83256 Liver NAT (ODO4310) | 11.2 | Paired Liver Cancer Tissue Research Genetics RNA 6005-T | 3.7 |
| 84139 Melanoma Mets to Lung (OD04321) | 32.4 | Paired Liver Tissue Research Genetics RNA 6005-N | 0.0 |
| 84138 Lung NAT (OD04321) | 13.8 | Liver Cancer GENPAK 064003 | 0.0 |
| Normal Kidney GENPAK 061008 | 44.0 | Normal Bladder GENPAK 061001 | 35.0 |
| 83786 Kidney Ca, Nuclear grade 2 (OD04338) | 41.7 | Bladder Cancer Research Genetics RNA 1023 | 0.0 |
| 83787 Kidney NAT (OD04338) | 51.4 | Bladder Cancer INVITROGEN A302173 | 36.6 |
| 83788 Kidney Ca Nuclear grade 1/2 (OD04339) | 22.1 | Normal Ovary Res. Gen. | 0.0 |
| 83789 Kidney NAT (OD04339) | 10.5 | Ovarian Cancer GENPAK 064008 | 2.9 |

TABLE 18B-continued

Panel 2.1

| Tissue Name | Relative Expression (%) 2.1x4tm6080f_ ag3975_a1 | Tissue Name | Relative Expression (%) 2.1x4tm6080f_ ag3975_a1 |
|---|---|---|---|
| 83790 Kidney Ca, Clear cell type (OD04340) | 20.1 | 97773 Ovarian cancer (OD06145) | 0.0 |
| 83791 Kidney NAT (OD04340) | 34.2 | 97775 Ovarian cancer NAT (OD06145) | 9.9 |
| 83792 Kidney Ca, Nuclear grade 3 (OD04348) | 4.6 | Normal Stomach GENPAK 061017 | 14.6 |
| 83793 Kidney NAT (OD04348) | 17.4 | Gastric Cancer Clontech 9060397 | 0.0 |
| 85973 Kidney Cancer (OD04450-01) | 100.0 | NAT Stomach Clontech 9060396 | 6.3 |
| 85974 Kidney NAT (OD04450-03) | 55.5 | Gastric Cancer Clontech 9060395 | 39.4 |
| Kidney Cancer Clontech 8120613 | 0.0 | NAT Stomach Clontech 9060394 | 16.6 |
| Kidney NAT Clontech 8120614 | 0.0 | Gastric Cancer GENPAK 064005 | 55.3 |

TABLE 18C

Panel 4.1D

| Tissue Name | Relative Expression (%) 4.1dx4tm6081f_ ag3975_a1 | Tissue Name | Relative Expression (%) 4.1dx4tm6081f_ ag3975_a1 |
|---|---|---|---|
| 93768_Secondary Th1_anti-CD28/anti-CD3 | 3.2 | 93100_HUVEC (Endothelial)_IL-1b | 0.6 |
| 93769_Secondary Th2_anti-CD28/anti-CD3 | 4.3 | 93799_HUVEC (Endothelial)_IFN gamma | 0.3 |
| 93770_Secondary Tr1_anti-CD28/anti-CD3 | 2.0 | 93102_HUVEC (Endothelial)_TNF alpha + IFN gamma | 1.7 |
| 93573_Secondary Th1_resting day 4–6 in IL-2 | 0.0 | 93101_HUVEC (Endothelial)_TNF alpha + IL4 | 1.3 |
| 93572_Secondary Th2_resting day 4–6 in IL-2 | 0.8 | 93781_HUVEC (Endothelial)_IL-11 | 0.5 |
| 93571_Secondary Tr1_resting day 4–6 in IL-2 | 0.0 | 93583_Lung Microvascular Endothelial Cells_none | 3.2 |
| 93568_primary Th1_anti-CD28/anti-CD3 | 4.3 | 93584_Lung Microvascular Endothelial Cells_TNFa (4 ng/ml) and IL1b (1 ng/ml) | 4.2 |
| 93569_primary Th2_anti-CD28/anti-CD3 | 6.0 | 92662_Microvascular Dermal endothelium_none | 1.1 |
| 93570_primary Tr1_anti-CD28/anti-CD3 | 2.8 | 92663_Microvasular Dermal endothelium_TNFa (4 ng/ml) and IL1b (1 ng/ml) | 1.4 |
| 93565_primary Th1_resting dy 4–6 in IL-2 | 0.0 | 93773_Bronchial epithelium_TNFa (4 ng/ml) and IL1b (1 ng/ml)** | 5.8 |
| 93566_primary Th2_resting dy 4–6 in IL-2 | 0.4 | 93347_Small Airway Epithelium_none | 0.0 |
| 93567_primary Tr1_resting dy 4–6 in IL-2 | 0.3 | 93348_Small Airway Epithelium_TNFa (4 ng/ml) and IL1b (1 ng/ml) | 6.3 |
| 93351_CD45RA CD4 lymphocyte_anti-CD28/anti-CD3 | 3.0 | 92668_Coronery Artery SMC_resting | 1.4 |
| 93352_CD45RO CD4 lymphocyte_anti-CD28/anti-CD3 | 3.2 | 92669_Coronery Artery SMC_TNFa (4 ng/ml) and IL1b (1 ng/ml) | 0.2 |
| 93251_CD8 Lymphocytes_anti-CD28/anti-CD3 | 0.9 | 93107_astrocytes_resting | 1.0 |
| 93353_chronic CD8 Lymphocytes 2ry_resting dy 4–6 in IL-2 | 4.9 | 93108_astrocytes_TNFa (4 ng/ml) and IL1b (1 ng/ml) | 1.8 |

TABLE 18C-continued

Panel 4.1D

| Tissue Name | Relative Expression (%) 4.1dx4tm6081f_ag3975_a1 | Tissue Name | Relative Expression (%) 4.1dx4tm6081f_ag3975_a1 |
|---|---|---|---|
| 93574_chronic CD8 Lymphocytes 2ry_activated CD3/CD28 | 0.6 | 92666_KU-812 (Basophil)_resting | 3.3 |
| 93354_CD4_none | 0.4 | 92667_KU-812 (Basophil)_PMA/ionoycin | 3.9 |
| 93252_Secondary Th1/Th2/Tr1_anti-CD95 CH11 | 0.8 | 93579_CCD1106 (Keratinocytes)_none | 6.1 |
| 93103_LAK cells_resting | 1.2 | 93580_CCD1106 (Keratinocytes)_TNFa and IFNg** | 10.2 |
| 93788_LAK cells_IL-2 | 1.2 | 93791_Liver Cirrhosis | 4.2 |
| 93787_LAK cells_IL-2 + IL-12 | 100.0 | 93577_NCI-H292 | 17.7 |
| 93789_LAK cells_IL-2 + IFN gamma | 1.8 | 93358_NCI-H292_IL-4 | 18.5 |
| 93790_LAK cells_IL-2 + IL-18 | 3.8 | 93360_NCI-H292_IL-9 | 19.4 |
| 93104_LAK cells_PMA/ionomycin and IL-18 | 3.1 | 93359_NCI-H292_IL-13 | 13.3 |
| 93578_NK Cells IL-2_resting | 1.1 | 93357_NCI-H292_IFN gamma | 14.2 |
| 93109_Mixed Lymphocyte Reaction_Two Way MLR | 3.9 | 93777_HPAEC_- | 0.0 |
| 93110_Mixed Lymphocyte Reaction_Two Way MLR | 2.2 | 93778_HPAEC_IL-1 beta/TNA alpha | 2.9 |
| 93111_Mixed Lymphocyte Reaction_Two Way MLR | 0.7 | 93254_Normal Human Lung Fibroblast_none | 1.0 |
| 93112_Mononuclear Cells (PBMCs)_resting | 0.3 | 93253_Normal Human Lung Fibroblast_TNFa (4 ng/ml) and IL-1b (1 ng/ml) | 0.5 |
| 93113_Mononuclear Cells (PBMCs)_PWM | 6.8 | 93257_Normal Human Lung Fibroblast_IL-4 | 0.4 |
| 93114_Mononuclear Cells (PBMCs)_PHA-L | 2.0 | 93256_Normal Human Lung Fibroblast_IL-9 | 1.2 |
| 93249_Ramos (B cell)_none | 31.1 | 93255_Normal Human Lung Fibroblast_IL-13 | 0.7 |
| 93250_Ramos (B cell)_ionomycin | 34.8 | 93258_Normal Human Lung Fibroblast_IFN gamma | 1.4 |
| 93349_B lymphocytes_PWM | 5.9 | 93106_Dermal Fibroblasts CCD1070_resting | 0.8 |
| 93350_B lymphoytes_CD40L and IL-4 | 11.2 | 93361_Dermal Fibroblasts CCD1070_TNF alpha 4 ng/ml | 1.9 |
| 92665_EOL-1 (Eosinophil)_dbcAMP differentiated | 13.0 | 93105_Dermal Fibroblasts CCD1070_IL-1 beta 1 ng/ml | 0.0 |
| 93248_EOL-1 (Eosinophil)_dbcAMP/PMAionomycin | 3.6 | 93772_dermal fibroblast_IFN gamma | 0.3 |
| 93356_Dendritic Cells_none | 4.0 | 93771_dermal fibroblast_IL-4 | 1.0 |
| 93355_Dendritic Cells_LPS 100 ng/ml | 2.2 | 93892_Dermal fibroblasts_none | 0.7 |
| 93775_Dendritic Cells_anti-CD40 | 4.1 | 99202_Neutrophils_TNFa + LPS | 7.3 |
| 93774_Monocytes_resting | 7.4 | 99203_Neutrophils_none | 8.3 |
| 93776_Monocytes_LPS 50 ng/ml | 11.4 | 735010_Colon_normal | 3.0 |
| 93581_Macrophages_resting | 0.8 | 735019_Lung_none | 4.8 |
| 93582_Macrophages_LPS 100 ng/ml | 0.0 | 64028-1_Thymus_none | 19.9 |
| 93098_HUVEC (Endothelial)_none | 0.9 | 64030-1_Kidney_none | 50.8 |
| 93099_HUVEC (Endothelial)_starved | 0.4 | | |

Panel 2.1 Summary: Ag3975 The level of expression of the NOV1-24CS059 gene is low in the samples used for Panel 2.1, with highest expression in a kidney cancer sample (CT=33.9). However, expression of this gene shows a moderate association with samples derived from gastric cancer when compared to their associated normal adjacent tissue as well as with a single sample of renal cancer compared A ith normal adjacent tissue. Thus, based upon its profile, the expression of the 24CS059 gene could be of use as a marker for gastric cancer. In addition, therapeutic inhibition of the activity of this gene product, through the use of antibodies or small molecule drugs, may be useful in the therapy of gastric cancer.

Panel 4.1D Summary: Ag3975 The NOV1-24CS059 gene is most highly expressed in LAK cells activated by treatment with IL-2 and IL-12 (CT=29.5). This expression appears to be induced by IL-12 treatment since LAK treated with only IL-2 shows is expressed at much lower levels (CT=35.9). IL-12 has been shown to synergize with IL-2 to augment NK- and induce LAK-mediated cytotoxicity; this synergistic increase is associated with enhanced transcription of perforin and granzyme genes (ref. 1). Activated LAK cells are able to lyse a wide range of targets including fresh tumor cells and virally infected cells. Therefore, the NOV1 protein encoded by the 24CS059 gene could be used as a protein therapeutic in the treatment of many cancerous tumors and also in infectious disease, (viral disease in particular). Additional low but significant expression of the 24CS059 gene is seen in activated B cells, in a mucoepiderinoid carcinoma cell line and in monocytes but not on macrophages, suggesting that this protein is down regulated during macrophage differentiation.

References (1). DeBlaker-Hohe D. F., Yamauchi A., Yu C. R., Horvath-Arcidiacono J. A., Bloom E. T. (1995) IL-12 synergizes with IL-2 to induce lymphokine-activated cytotoxicity and perforin and granzyme gene expression in fresh human NK cells. Cell. Immunol. 165: 33–43.

NK-mediated cytotoxicity is regulated by a variety of cytokines and is thought to involve perforin and granzymes. The effects of IL-2 and IL-12 on the expression and activation of cytolysis were examined in freshly isolated human NK cells. A dose-dependent increase in cytolysis of the NK-sensitive target cell, K562, and the NK-insensitive but lymphokine-activated killer (LAK) cell-sensitive target, UCLA-SO-M14, was observed after short term culture of purified human NK cells in either IL-2 or IL-12. Moreover, the two cytokines often synergized to produce augmented lytic activity. A suboptimal dose of IL-2 (60 IU/ml) combined with IL-12 (2 U/ml) could induce lytic activity equal to twice the additive effect of each cytokine alone. Northern analyses revealed time-dependent increases in mRNAs encoding for perforin and granzymes A and B following treatment with IL-2 alone or IL-2 plus IL-12. IL-2 and IL-12 also synergized for the induction of granzyme mRNAs, in that treatment with both cytokines increased mRNA levels approximately 50% above the sum of each cytokine alone, as quantitated by phosphorimage analysis and normalized to GAPDH gene expression. However, the synergy between IL-2 and IL-12 for the induction of mRNA was less dramatic than for lytic activity. Results of experiments in which cytokine-treated cells were pulsed with actinomycin D indicated that the increased granzyme and perforin gene mRNA levels in response to IL-2, IL-12, or the combination were not due to increased transcript stability. The data suggest that low doses of IL-2 and IL-12 synergize to augment NK- and induce LAK-mediated cytotoxicity and that this increase is associated with enhanced transcription of perforin and granzyme genes in a synergistic fashion. PMID: 7671323

NOV3-24SC113

Expression of gene 24SC113 was assessed using the primer-probe set Ag1460, described in Table 19A. Results from RTQ-PCR runs are shown in Tables 19B and 19C.

TABLE 19A

Probe Name Ag1460

| Primers | Sequences | TM | Length | Start Position | SEQ ID NO |
|---|---|---|---|---|---|
| Forward | 5'-CCCTGAAATACACAGAGGACAT-3' | 58.1 | 22 | 860 | 158 |
| Probe | FAM-5'-ATGGAATCCCTGGCCCTGTCTAATG-3'-TAMRA | 68.9 | 25 | 913 | 159 |
| Reverse | 5'-GGTGAACAGAACCTACCTGTTG-3' | 58.6 | 22 | 938 | 127 |

TABLE 19B

Panel 2.1

| Tissue Name | Relative Expression (%) 2.1tm6078f_ ag1460 | Tissue Name | Relative Expression (%) 2.1tm6078f_ ag1460 |
|---|---|---|---|
| Normal Colon GENPAK 061003 | 8.0 | Kidney Cancer Clontech 9010320 | 3.2 |
| 97759 Colon cancer (OD06064) | 8.7 | Kidney NAT Clontech 9010321 | 55.5 |
| 97760 Colon cancer NAT (OD06064) | 0.0 | Kidney Cancer Clontech 8120607 | 2.3 |
| 97778 Colon cancer (OD06159) | 0.0 | Kidney NAT Clontech 8120608 | 7.3 |
| 97779 Colon cancer NAT (OD06159) | 6.7 | Normal Uterus GENPAK 061018 | 100.0 |
| 98859 Colon cancer (OD06298-08) | 6.9 | Uterus Cancer GENPAK 064011 | 23.0 |
| 98860 Colon cancer NAT (OD06298-018) | 3.6 | Normal Thyroid Clontech A+ 6570-1 (7080817) | 3.7 |
| 83237 CC Gr.2 ascend colon (ODO3921) | 2.8 | Thyroid Cancer GENPAK 064010 | 0.0 |
| 83238 CC NAT (ODO3921) | 12.0 | Thyroid Cancer INVITROGEN A302152 | 6.7 |

TABLE 19B-continued

Panel 2.1

| Tissue Name | Relative Expression (%) 2.1tm6078f_ag1460 | Tissue Name | Relative Expression (%) 2.1tm6078f_ag1460 |
|---|---|---|---|
| 97766 Colon cancer metastasis (OD06104) | 4.1 | Thyroid NAT INVITROGEN A302153 | 29.1 |
| 97767 Lung NAT (OD06104) | 3.6 | Normal Breast GENPAK 061019 | 20.0 |
| 87472 Colon mets to lung (OD04451-01) | 0.0 | 84877 Breast Cancer (OD04566) | 12.2 |
| 87473 Lung NAT (OD04451-02) | 28.3 | Breast Cancer Res. Gen. 1024 | 30.8 |
| Normal Prostate Clontech A+ 6546-1 (8090438) | 0.0 | 85975 Breast Cancer (OD04590-01) | 4.1 |
| 84140 Prostate Cancer (OD04410) | 0.0 | 85976 Breast Cancer Mets (OD04590-03) | 16.3 |
| 84141 Prostate NAT (OD04410) | 0.0 | 87070 Breast Cancer Metastasis (OD04655-05) | 26.8 |
| Normal Lung GENPAK 061010 | 53.6 | GENPAK Breast Cancer 064006 | 3.2 |
| 92337 Invasive poor diff. lung adeno (ODO4945-01) | 4.5 | Breast Cancer Clontech 9100266 | 2.0 |
| 92338 Lung NAT (ODO4945-03) | 71.2 | Breast NAT Clontech 9100265 | 8.7 |
| 84136 Lung Malignant Cancer (OD03126) | 5.6 | Breast Cancer INVITROGEN A209073 | 8.8 |
| 84137 Lung NAT (OD03126) | 10.4 | Breast NAT INVITROGEN A2090734 | 32.3 |
| 90372 Lung Cancer (OD05014A) | 7.3 | Normal Liver GENPAK 061009 | 5.6 |
| 90373 Lung NAT (OD05014B) | 19.5 | Liver Cancer Research Genetics RNA 1026 | 0.0 |
| 85950 Lung Cancer (OD04237-01) | 11.0 | Liver Cancer Research Genetics RNA 1025 | 5.0 |
| 85970 Lung NAT (OD04237-02) | 19.6 | Paired Liver Cancer Tissue Research Genetics RNA 6004-T | 18.2 |
| 83255 Ocular Mel Met to Liver (ODO4310) | 0.0 | Paired Liver Tissue Research Genetics RNA 6004-N | 0.0 |
| 83256 Liver NAT (ODO4310) | 10.2 | Paired Liver Cancer Tissue Research Genetics RNA 6005-T | 3.7 |
| 84139 Melanoma Mets to Lung (OD04321) | 7.9 | Paired Liver Tissue Research Genetics RNA 6005-N | 7.5 |
| 84138 Lung NAT (OD04321) | 11.6 | Liver Cancer GENPAK 064003 | 0.0 |
| Normal Kidney GENPAK 061008 | 15.0 | Normal Bladder GENPAK 061001 | 3.0 |
| 83786 Kidney Ca, Nuclear grade 2 (OD04338) | 15.4 | Bladder Cancer Research Genetics RNA 1023 | 2.7 |
| 83787 Kidney NAT (OD04338) | 12.9 | Bladder Cancer INVITROGEN A302173 | 4.3 |
| 83788 Kidney Ca Nuclear grade 1/2 (OD04339) | 12.5 | Normal Ovary Res. Gen. | 2.9 |
| 83789 Kidney NAT (OD04339) | 8.5 | Ovarian Cancer GENPAK 064008 | 22.5 |
| 83790 Kidney Ca, Clear cell type (OD04340) | 3.4 | 97773 Ovarian cancer (OD06145) | 0.0 |
| 83791 Kidney NAT (OD04340) | 9.2 | 97775 Ovarian cancer NAT (OD06145) | 33.2 |
| 83792 Kidney Ca, Nuclear grade 3 (OD04348) | 0.0 | Normal Stomach GENPAK 061017 | 65.5 |
| 83793 Kidney NAT (OD04348) | 10.5 | Gastric Cancer Clontech 9060397 | 3.6 |
| 85973 Kidney Cancer (OD04450-01) | 29.9 | NAT Stomach Clontech 9060396 | 0.0 |
| 85974 Kidney NAT (OD04450-03) | 11.6 | Gastric Cancer Clontech 9060395 | 17.3 |
| Kidney Cancer Clontech 8120613 | 0.0 | NAT Stomach Clontech 9060394 | 7.4 |
| Kidney NAT Clontech 8120614 | 2.8 | Gastric Cancer GENPAK 064005 | 2.5 |

TABLE 19C

Panel 4.1D

| Tissue Name | Relative Expression (%) 4.1dx4tm5965f_ag1460_a1 | Tissue Name | Relative Expression (%) 4.1dx4tm5965f_ag1460_a1 |
|---|---|---|---|
| 93768_Secondary Th1_anti-CD28/anti-CD3 | 0.0 | 93100_HUVEC (Endothelial)_IL-1b | 4.7 |
| 93769_Secondary Th2_anti-CD28/anti-CD3 | 0.0 | 93779_HUVEC (Endothelial)_IFN gamma | 9.3 |
| 93770_Secondary Tr1_anti-CD28/anti-CD3 | 1.3 | 93102_HUVEC (Endothelial)_TNF alpha + IFN gamma | 4.1 |
| 93573_Secondary Th1_resting day 4–6 in IL-2 | 0.0 | 93101_HUVEC (Endothelial)_TNF alpha + IL4 | 3.0 |
| 93572_Secondary Th2_resting day 4–6 in IL-2 | 0.0 | 93781_HUVEC (Endothelial)_IL-11 | 9.0 |
| 93571_Secondary Tr1_resting day 4–6 in IL-2 | 0.0 | 93583_Lung Microvascular Endothelial Cells none | 2.5 |
| 93568_primary Th1_anti-CD28/anti-CD3 | 0.0 | 93584_Lung Microvascular Endothelial Cells_TNFa (4 ng/ml) and IL1b (1 ng/ml) | 4.9 |
| 93569_primary Th2_anti-CD28/anti-CD3 | 0.0 | 92662_Microvascular Dermal endothelium_none | 3.4 |
| 93570_primary Tr1_anti-CD28/anti-CD3 | 0.0 | 92663_Microsvascular Dermal endothelium_TNFa (4 ng/ml) and IL1b (1 ng/ml) | 1.3 |
| 93565_primary Th1_resting dy 4–6 in IL-2 | 0.0 | 93773_Bronchial epithelium_TNFa (4 ng/ml) and IL1b (1 ng/ml)** | 10.7 |
| 93566_primary Th2_resting dy 4–6 in IL-2 | 0.0 | 93347_Small Airway Epithelium_none | 5.5 |
| 93567_primary Tr1_resting dy 4–6 in IL-2 | 0.0 | 93348_Small Airway Epithelium_TNFa (4 ng/ml) and IL1b (1 ng/ml) | 22.2 |
| 93351_CD45RA CD4 lymphocyte_anti-CD28/anti-CD3 | 5.8 | 92668_Coronery Artery SMC_resting | 12.3 |
| 93352_CD45RO CD4 lymphocyte_anti-CD28/anti-CD3 | 0.0 | 92669_Coronery Artery SMC_TNFa (4 ng/ml) and IL1b (1 ng/ml) | 12.4 |
| 93251_CD8 Lymphocytes_anti-CD28/anti-CD3 | 0.0 | 93107_astrocytes_resting | 100.0 |
| 93353_chronic CD8 Lymphocytes 2ry_resting dy 4–6 in IL-2 | 0.0 | 93108_astrocytes_TNFa (4 ng/ml) and IL1b (1 ng/ml) | 15.4 |
| 93574_chronic CD8 Lymphocytes 2ry_activated CD3/CD28 | 0.0 | 92666_KU-812 (Basophil)_resting | 0.0 |
| 93354_CD4_none | 0.0 | 92667_KU-812 (Basophil)_PMA/ionoycin | 0.0 |
| 93252_Secondary Th1/Th2/Tr1_anti-CD95 CH11 | 0.0 | 93579_CCD1106 (Keratinocytes)_none | 16.5 |
| 93103_LAK cells_resting | 0.0 | 93580_CCD1106 (Keratinocytes)_TNFa and IFNg** | 16.8 |
| 93788_LAK cells_IL-2 | 0.0 | 93791_Liver Cirrhosis | 4.7 |
| 93787_LAK cells_IL-2 + IL-12 | 0.0 | 93577_NCI-H292 | 3.8 |
| 93789_LAK cells_IL-2 + IFN gamma | 0.0 | 93358_NCI-H292_IL-4 | 1.1 |
| 93790_LAK cells_IL-2 + IL-18 | 0.0 | 93360_NCI-H292_IL-9 | 5.7 |
| 93104_LAK cells_PMA/ionomycin and IL-18 | 0.0 | 93359_NCI-H292_IL-13 | 3.5 |
| 93578_NK Cells IL-2_resting | 1.1 | 93357_NCI-H292_IFN gamma | 1.5 |
| 93109_Mixed Lymphocyte Reaction_Two Way MLR | 0.0 | 93777_HPAEC_- | 10.6 |
| 93110_Mixed Lymphocyte Reaction_Two Way MLR | 0.0 | 93778_HPAEC_IL-1 beta/TNA alpha | 16.8 |
| 93111_Mixed Lymphocyte Reaction_Two Way MLR | 0.0 | 93254_Normal Human Lung Fibroblast_none | 12.7 |
| 93112_Mononuclear Cells | 0.0 | 93253_Normal Human Lung | 8.7 |

TABLE 19C-continued

Panel 4.1D

| Tissue Name | Relative Expression (%) 4.1dx4tm5965f_ag1460_a1 | Tissue Name | Relative Expression (%) 4.1dx4tm5965f_ag1460_a1 |
|---|---|---|---|
| (PBMCs)_resting | | Fibroblast_TNFa (4 ng/ml) and IL-1b (1 ng/ml) | |
| 93113_Mononuclear Cells (PBMCs)_PWM | 0.0 | 93257_Normal Human Lung Fibroblast_IL-4 | 11.2 |
| 93114_Mononuclear Cells (PBMCs)_PHA-L | 0.0 | 93256_Normal Human Lung Fibroblast_IL-9 | 23.6 |
| 93249_Ramos (B cell)_none | 0.0 | 93255_Normal Human Lung Fibroblast_IL-13 | 27.2 |
| 93250_Ramos (B cell)_ionomycin | 0.0 | 93258_Normal Human Lung Fibroblast_IFN gamma | 13.3 |
| 93349_B lymphocytes_PWM | 0.0 | 93106_Dermal Fibroblasts CCD1070_resting | 27.1 |
| 93350_B lymphoytes_CD40L and IL-4 | 1.4 | 93361_Dermal Fibroblasts CCD1070_TNF alpha 4 ng/ml | 1.2 |
| 92665_EOL-1 (Eosinophil)_dbcAMP differentiated | 0.0 | 93105_Dermal Fibroblasts CCD1070_IL-1 beta 1 ng/ml | 15.6 |
| 93248_EOL-1 (Eosinophil)_dbcAMP/PMAionomycin | 0.0 | 93772_dermal fibroblast_IFN gamma | 24.9 |
| 93356_Dendritic Cells_none | 0.0 | 93771_dermal fibroblast_IL-4 | 34.5 |
| 93355_Dendritic Cells_LPS 100 ng/ml | 0.0 | 93892_Dermal fibroblasts_none | 5.1 |
| 93775_Dendritic Cells_anti-CD40 | 0.0 | 99202_Neutrophils_TNFa + LPS | 0.0 |
| 93774_Monocytes_resting | 0.0 | 99203_Neutrophils_none | 0.0 |
| 93776_Monocytes_LPS 50 ng/ml | 0.0 | 735010_Colon_normal | 1.9 |
| 93581_Macrophages_resting | 0.0 | 735019_Lung_none | 10.4 |
| 93582_Macrophages_LPS 100 ng/ml | 0.0 | 64028-1_Thymus_none | 2.8 |
| 93098_HUVEC (Endothelial)_none | 0.0 | 64030-1_Kidney_none | 10.2 |
| 93099_HUVEC (Endothelial)_starved | 2.3 | | |

Panel 2.1 Summary: Ag1460 The level of expression of the NOV3-24SC113 gene is low in the samples used for Panel 2.1, with highest expression in normal uterus (CT= 32.5). However, this gene appears to be more highly expressed in some samples derived from normal uterus, stomach, kidney and lung when compared to the associated cancer tissue. Thus, based upon its profile, the expression of the 24SC113 gene could be of use as a marker for these normal tissues or as a protein therapeutic for the treatment of gastric, uterine, lung and kidney cancer. In addition, therapeutic activity of the 24SC113 gene product, through the use of peptides, chimeric molecules or small molecule drugs, may be useful in the therapy of gastric cancer.

Panel 4.1D Summary: Agf1460 Expression of the NOV3-24SC113 gene is highest in resting astrocytes (CT=30.9), suggesting that this gene would be an effective marker for astrocytes. Strikingly, expression of this gene in astrocytes is down regulated after treatment with the inflammatory cytokines TNFa and IL-1. Considering the deleterious effect of these cytokines on astrocytes we may propose that the protein encoded by the 24SC113 gene may be a trophic factor for astrocytes and thus, that the protein encoded by this gene could be beneficial as a protein therapeutic in the treatment of neurodegenerative diseases associated with inflammation, such as Alzheimer's disease, multiple sclerosis, and stroke. In addition, lowv but significant expression of the 24SC113 gene is seen in activated and non-activated fibroblasts (dermal and lung).

NOV4-24SC128

Expression of gene 24SC128 was assessed using the pimer-probe set Ag3976, described in Table 20A. Results from RTQ-PCR runs are shown in Tables 20B and 20C.

TABLE 20A

Probe Name Ag3976

| Primers | Sequences | TM | Length | Start Position | SEQ ID NO |
|---|---|---|---|---|---|
| Forward | 5'-GCTCTCGAAAGTGGGCTATATT-3' | 58.9 | 22 | 453 | 128 |
| Probe | FAM-5'-CACTTTTGTTTTATCTTCTCCAACCACCA-3'-TAMRA | 66.9 | 29 | 493 | 129 |
| Reverse | 5'-TCTCCTATTCAGGTGACTTTCG-3' | 58.5 | 22 | 524 | 130 |

TABLE 20B

Panel 2.1

| Tissue Name | Relative Expression (%) 2.1x4tm6080f_ag3976_a2 | Tissue Name | Relative Expression (%) 2.1x4tm6080f_ag3976_a2 |
|---|---|---|---|
| Normal Colon GENPAK 061003 | 15.0 | Kidney Cancer Clontech 9010320 | 3.5 |
| 97759 Colon cancer (OD06064) | 8.9 | Kidney NAT Clontech 9010321 | 34.6 |
| 97760 Colon cancer NAT (OD06064) | 4.0 | Kidney Cancer Clontech 8120607 | 12.7 |
| 97778 Colon cancer (OD06159) | 4.2 | Kidney NAT Clontech 8120608 | 4.1 |
| 97779 Colon cancer NAT (OD06159) | 8.1 | Normal Uterus GENPAK 061018 | 47.1 |
| 98859 Colon cancer (OD06298-08) | 36.8 | Uterus Cancer GENPAK 064011 | 31.1 |
| 98860 Colon cancer NAT (OD06298-018) | 32.2 | Normal Thyroid Clontech A+ 6570-1 (7080817) | 2.4 |
| 83237 CC Gr 2 ascend colon (ODO3921) | 19.4 | Thyroid Cancer GENPAK 064010 | 9.5 |
| 83238 CC NAT (ODO3921) | 20.4 | Thyroid Cancer INVITROGEN A302152 | 13.9 |
| 97766 Colon cancer metastasis (OD06104) | 22.5 | Thyroid NAT INVITROGEN A302153 | 89.5 |
| 97767 Lung NAT (OD06104) | 37.7 | Normal Breast GENPAK 061019 | 72.8 |
| 87472 Colon mets to lung (OD04451-01) | 16.6 | 84877 Breast Cancer (OD04566) | 10.0 |
| 87473 Lung NAT (OD04451-02) | 13.6 | Breast Cancer Res. Gen. 1024 | 27.7 |
| Normal Prostate Clontech A+ 6546-1 (8090438) | 9.4 | 85975 Breast Cancer (OD04590-01) | 12.5 |
| 84140 Prostate Cancer (OD04410) | 3.0 | 85976 Breast Cancer Mets (OD04590-03) | 32.8 |
| 84141 Prostate NAT (OD04410) | 9.1 | 87070 Breast Cancer Metastasis (OD04655-05) | 95.4 |
| Normal Lung GENPAK 061010 | 38.5 | GENPAK Breast Cancer 064006 | 4.5 |
| 92337 Invasive poor diff. lung adeno (ODO4945-01 | 25.0 | Breast Cancer Clontech 9100266 | 19.4 |
| 92338 Lung NAT (ODO4945-03) | 30.5 | Breast NAT Clontech 9100265 | 35.0 |
| 84136 Lung Malignant Cancer (OD03126) | 20.6 | Breast Cancer INVITROGEN A209073 | 9.2 |
| 84137 Lung NAT (OD03126) | 16.6 | Breast NAT INVITROGEN A2090734 | 36.4 |
| 90372 Lung Cancer (OD05014A) | 14.7 | Normal Liver GENPAK 061009 | 13.3 |
| 90373 Lung NAT (OD05014B) | 8.2 | Liver Cancer Research Genetics RNA 1026 | 7.9 |
| 85950 Lung Cancer (OD04237-01) | 18.6 | Liver Cancer Research Genetics RNA 1025 | 23.7 |
| 85970 Lung NAT (OD04237-02) | 14.9 | Paired Liver Cancer Tissue Research Genetics RNA 6004-T | 13.6 |
| 83255 Ocular Mel Met to Liver (ODO4310) | 18.8 | Paired Liver Tissue Research Genetics RNA 6004-N | 8.3 |
| 83256 Liver NAT (ODO4310) | 9.3 | Paired Liver Cancer Tissue Research Genetics RNA 6005-T | 32.2 |
| 84139 Melanoma Mets to Lung (OD04321) | 22.5 | Paired Liver Tissue Research Genetics RNA 6005-N | 8.7 |
| 84138 Lung NAT (OD04321) | 26.3 | Liver Cancer GENPAK 064003 | 9.4 |
| Normal Kidney GENPAK 061008 | 23.6 | Normal Bladder GENPAK 061001 | 16.8 |
| 83786 Kidney Ca, Nuclear grade 2 (OD04338) | 33.0 | Bladder Cancer Research Genetics RNA 1023 | 19.8 |
| 83787 Kidney NAT (OD04338) | 18.3 | Bladder Cancer INVITROGEN A302173 | 17.5 |
| 83788 Kidney Ca Nuclear grade 1/2 (OD04339) | 12.6 | Normal Ovary Res. Gen. | 27.1 |
| 83789 Kidney NAT (OD04339) | 13.4 | Ovarian Cancer GENPAK 064008 | 4.9 |

TABLE 20B-continued

Panel 2.1

| Tissue Name | Relative Expression (%) 2.1x4tm6080f_ag3976_a2 | Tissue Name | Relative Expression (%) 2.1x4tm6080f_ag3976_a2 |
|---|---|---|---|
| 83790 Kidney Ca, Clear cell type (OD04340) | 10.0 | 97773 Ovarian cancer (OD06145) | 2.2 |
| 83791 Kidney NAT (OD04340) | 27.0 | 97775 Ovarian cancer NAT (OD06145) | 37.8 |
| 83792 Kidney Ca, Nuclear grade 3 (OD04348) | 9.0 | Normal Stomach GENPAK 061017 | 39.1 |
| 83793 Kidney NAT (OD04348) | 18.6 | Gastric Cancer Clontech 9060397 | 8.4 |
| 85973 Kidney Cancer (OD04450-01) | 100.0 | NAT Stomach Clontech 9060396 | 8.1 |
| 85974 Kidney NAT (OD04450-03) | 18.1 | Gastric Cancer Clontech 9060395 | 40.5 |
| Kidney Cancer Clontech 8120613 | 3.9 | NAT Stomach Clontech 9060394 | 26.5 |
| Kidney NAT Clontech 8120614 | 6.5 | Gastric Cancer GENPAK 064005 | 18.9 |

TABLE 20C

Panel 4.1D

| Tissue Name | Relative Expression (%) 4.1dx4tm6081_ag3976_a2 | Tissue Name | Relative Expression (%) 4.1dx4tm6081_ag3976_a2 |
|---|---|---|---|
| 93768_Secondary Th1_anti-CD28/anti-CD3 | 86.4 | 93100_HUVEC (Endothelial)_IL-1b | 55.1 |
| 93769_Secondary Th2_anti-CD28/anti-CD3 | 70.2 | 93779_HUVEC (Endothelial)_IFN gamma | 67.6 |
| 93770_Secondary Tr1_anti-CD28/anti-CD3 | 57.3 | 93102_HUVEC (Endothelial)_TNF alpha + IFN gamma | 32.8 |
| 93573_Secondary Th1_resting day 4–6 in IL-2 | 16.6 | 93101_HUVEC (Endothelial)_TNF alpha + IL4 | 51.5 |
| 93572_Secondary Th2_resting day 4–6 in IL-2 | 28.4 | 93781_HUVEC (Endothelial)_IL-11 | 50.1 |
| 93571_Secondary Tr1_resting day 4–6 in IL-2 | 24.6 | 93583_Lung Microvascular Endothelial Cells_none | 94.1 |
| 93568_primary Th1_anti-CD28/anti-CD3 | 58.7 | 93584_Lung Microvascular Endothelial Cells_TNFa (4 ng/ml) and IL1b (1 ng/ml) | 59.7 |
| 93569_primary Th2_anti-CD28/anti-CD3 | 100.0 | 92662_Microvascular Dermal endothelium_none | 14.3 |
| 93570_primary Tr1_anti-CD28/anti-CD3 | 70.4 | 92663_Microvasular Dermal endothelium_TNFa (4 ng/ml) and IL1b (1 ng/ml) | 24.0 |
| 93565_primary Th1_resting dy 4–6 in IL-2 | 27.5 | 93773_Bronchial epithelium_TNFa (4 ng/ml) and IL1b (1 ng/ml)** | 54.5 |
| 93566_primary Th2_resting dy 4–6 in IL-2 | 13.8 | 93347_Small Airway Epithelium_none | 32.1 |
| 93567_primary Tr1_resting dy 4–6 in IL-2 | 48.9 | 93348_Small Airway Epithelium_TNFa (4 ng/ml) and IL1b (1 ng/ml) | 65.8 |
| 93351_CD45RA CD4 lymphocyte_anti-CD28/anti-CD3 | 57.4 | 92668_Coronery Artery SMC_resting | 32.0 |
| 93352_CD45RO CD4 lymphocyte_anti-CD28/anti-CD3 | 68.7 | 92669_Coronery Artery SMC_TNFa (4 ng/ml) and IL1b (1 ng/ml) | 25.5 |
| 93251_CD8 Lymphocytes_anti-CD28/anti-CD3 | 91.9 | 93107_astrocytes_resting | 30.9 |
| 93353_chronic CD8 Lymphocytes 2ry_resting dy 4–6 in IL-2 | 76.2 | 93108_astrocytes_TNFa (4 ng/ml) and IL1b (1 ng/ml) | 18.4 |

TABLE 20C-continued

Panel 4.1D

| Tissue Name | Relative Expression (%) 4.1dx4tm6081_ag3976_a2 | Tissue Name | Relative Expression (%) 4.1dx4tm6081_ag3976_a2 |
|---|---|---|---|
| 93574_chronic CD8 Lymphocytes 2ry_activated CD3/CD28 | 42.0 | 92666_KU-812 (Basophil)_resting | 32.3 |
| 93354_CD4_none | 25.1 | 92667_KU-812 (Basophil)_PMA/ionoycin | 36.0 |
| 93252_Secondary Th1/Th2/Tr1_anti-CD95 CH11 | 37.9 | 93579_CCD1106 (Keratinocytes)_none | 82.5 |
| 93103 LAK cells resting | 45.0 | 93580_CCD1106 (Keratinocytes) TNFa and IFNg** | 56.6 |
| 93788_LAK cells_IL-2 | 58.1 | 93791_Liver Cirrhosis | 7.8 |
| 93787_LAK cells_IL-2 + IL-12 | 48.5 | 93577_NCI-H292 | 31.2 |
| 93789_LAK cells_IL-2 + IFN gamma | 44.6 | 93358_NCI-H292_IL-4 | 53.9 |
| 93790_LAK cells_IL-2 + IL-18 | 70.0 | 93360_NCI-H292_IL-9 | 56.7 |
| 93104_LAK cells_PMA/ionomycin and IL-18 | 19.9 | 93359_NCI-H292_IL-13 | 52.6 |
| 93578_NK Cells IL-2_resting | 51.3 | 93357_NCI-H292_IFN gamma | 38.8 |
| 93109_Mixed Lymphocyte Reaction_Two Way MLR | 68.7 | 93777_HPAEC_- | 23.4 |
| 93110_Mixed Lymphocyte Reaction_Two Way MLR | 57.2 | 93778_HPAEC_IL-1 beta/TNA alpha | 28.2 |
| 93111_Mixed Lymphocyte Reaction_Two Way MLR | 49.9 | 93254_Normal Human Lung Fibroblast_none | 27.7 |
| 93112_Mononuclear Cells (PBMCs)_resting | 16.1 | 93253_Normal Human Lung Fibroblast_TNFa (4 ng/ml) and IL-1b (1 ng/ml) | 17.2 |
| 93113_Mononuclear Cells (PBMCs)_PWM | 49.7 | 93257_Normal Human Lung Fibroblast_IL-4 | 32.8 |
| 93114_Mononuclear Cells (PBMCs)_PHA-L | 57.0 | 93256_Normal Human Lung Fibroblast_IL-9 | 52.1 |
| 93249_Ramos (B cell)_none | 59.6 | 93255_Normal Human Lung Fibroblast_IL-13 | 49.4 |
| 93250_Ramos (B cell)_ionomycin | 79.4 | 93258_Normal Human Lung Fibroblast_IFN gamma | 40.9 |
| 93349_B lymphocytes_PWM | 67.0 | 93106_Dermal Fibroblasts CCD1070_resting | 49.9 |
| 93350_B lymphoytes_CD40L and IL-4 | 64.2 | 93361_Dermal Fibroblasts CCD1070_TNF alpha 4 ng/ml | 61.9 |
| 92665_EOL-1 (Eosinophil)_dbcAMP differentiated | 66.9 | 93105_Dermal Fibroblasts CCD1070_IL-1 beta 1 ng/ml | 31.4 |
| 93248_EOL-1 (Eosinophil)_dbcAMP/PMAionomycin | 43.9 | 93772_dermal fibroblast_IFN gamma | 23.0 |
| 93356_Dendritic Cells_none | 26.0 | 93771_dermal fibroblast_IL-4 | 30.4 |
| 93355_Dendritic Cells_LPS 100 ng/ml | 20.9 | 93892_Dermal fibroblasts_none | 19.0 |
| 93775_Dendritic Cells_anti-CD40 | 30.1 | 99202_Neutrophils_TNFa + LPS | 1.5 |
| 93774_Monocytes_resting | 16.0 | 99203_Neutrophils_none | 1.0 |
| 93776_Monocytes_LPS 50 ng/ml | 11.7 | 735010_Colon_normal | 12.3 |
| 93581_Macrophages_resting | 33.9 | 735019_Lung_none | 17.7 |
| 93582_Macrophages_LPS 100 ng/ml | 10.9 | 64028-1_Thymus_none | 35.8 |
| 93098_HUVEC (Endothelial)_none | 37.4 | 64030-1_Kidney_none | 30.3 |
| 93099_HUVEC (Endothelial)_starved | 38.3 | | |

Panel 2.1 Summary: Ag3976 The NOV4-24SC128 gene is fairly ubiquitously expressed at moderate levels in the cancer tissues as well as the normal adjacent tissues used for Panel 2.1. However, a high level of expression is seen in a kidney cancer sample (CT=29.7) when compared to its associated normal adjacent tissue (CT=32.2), as well as in a single sample of metastatic breast cancer (CT=29.7). Thus, based upon this profile, expression of the 24SC128 gene could be of use as a marker for a form of renal or breast cancer. In addition, therapeutic inhibition of the activity of this gene product, through the use of antibodies or small molecule drugs, may be useful in the treatment of renal or breast cancer.

Panel 4.1D Summary: Ag3976 The NOV4-24SC128 gene is ubiquitously expressed at a moderate levels in activated T cells (CD4 and CD8), B cells, eosinophils, endothelial cells (HUVEC and lung microvasculature endothelial cells) and fibroblasts. Inter-estingly, 24SC128 gene expression appears to be up-regulated in TH1 and TH2 cells upon activation, suggesting a role for this gene in T cell-mediated diseases such as asthma, delayed type hypersensitivity, infectious disease, and autoimmune disease (rheumatoid arthritis, inflammatory bowel disease, and psoriasis).

NOV8-24SC714

Expression of gene 24SC714 was assessed using the primer-probe set Ag4002, described in Table 21A. Results from RTQ-PCR runs are shown in Tables 21B and 21C.

TABLE 21A

Probe Name Ag4002

| Primers | Sequences | TM | Length | Start Position | SEQ ID NO |
|---|---|---|---|---|---|
| Forward | 5'-GCCCTGATCAAGTTTTCATACC-3' | 59.8 | 22 | 364 | 131 |
| Probe | FAM-5'-CACATAGCTCAGCCTGCTCTGAGTTGA-3'-TAMRA | 69 | 27 | 387 | 132 |
| Reverse | 5'-TGTCAACTCCACATGAATCAAA-3' | 59 | 22 | 428 | 133 |

TABLE 21B

Panel 2.1

| Tissue Name | Relative Expression (%) 2.1x4tm6143f__ag4002_b1 | Tissue Name | Relative Expression (%) 2.1x4tm6143f__ag4002_b1 |
|---|---|---|---|
| Normal Colon GENPAK 061003 | 2.8 | Kidney Cancer Clontech 9010320 | 0.0 |
| 97759 Colon cancer (OD06064) | 0.0 | Kidney NAT Clontech 9010321 | 7.5 |
| 97760 Colon cancer NAT (OD06064) | 0.0 | Kidney Cancer Clontech 8120607 | 0.0 |
| 97778 Colon cancer (OD06159) | 0.0 | Kidney NAT Clontech 8120608 | 0.0 |
| 97779 Colon cancer NAT (OD06159) | 0.0 | Normal Uterus GENPAK 061018 | 2.7 |
| 98859 Colon cancer (OD06298-08) | 28.5 | Uterus Cancer GENPAK 064011 | 0.0 |
| 98860 Colon cancer NAT (OD06298-018) | 2.1 | Normal Thyroid Clontech A+ 6570-1 (7080817) | 0.0 |
| 83237 CC Gr.2 ascend colon (ODO3921) | 5.1 | Thyroid Cancer GENPAK 064010 | 0.0 |
| 83238 CC NAT (ODO3921) | 3.6 | Thyroid Cancer INVITROGEN A302152 | 0.0 |
| 97766 Colon cancer metastasis (OD06104) | 20.4 | Thyroid NAT INVITROGEN A302153 | 0.0 |
| 97767 Lung NAT (OD06104) | 2.6 | Normal Breast GENPAK 061019 | 5.4 |
| 87472 Colon mets to lung (OD04451-01) | 76.7 | 84877 Breast Cancer (OD04566) | 0.0 |
| 87473 Lung NAT (OD04451-02) | 1.3 | Breast Cancer Res. Gen. 1024 | 2.5 |
| Normal Prostate Clontech A+ 6546-1 (8090438) | 0.0 | 85975 Breast Cancer (OD04590-01) | 0.0 |
| 84140 Prostate Cancer (OD04410) | 0.0 | 85976 Breast Cancer Mets (OD04590-03) | 10.5 |
| 84141 Prostate NAT (OD04410) | 0.0 | 87070 Breast Cancer Metastasis (OD04655-05) | 3.0 |
| Normal Lung GENPAK 061010 | 16.2 | GENPAK Breast Cancer 064006 | 0.0 |
| 92337 Invasive poor diff. lung adeno (ODO4945-01) | 24.4 | Breast Cancer Clontech 9100266 | 0.0 |
| 92338 Lung NAT (ODO4945-03) | 32.7 | Breast NAT Clontech 9100265 | 0.0 |
| 84136 Lung Malignant Cancer (OD03126) | 3.4 | Breast Cancer INVITROGEN A209073 | 0.0 |
| 84137 Lung NAT (OD03126) | 12.6 | Breast NAT INVITROGEN A2090734 | 3.3 |
| 90372 Lung Cancer (OD05014A) | 8.2 | Normal Liver GENPAK 061009 | 0.0 |
| 90373 Lung NAT (OD05014B) | 100.0 | Liver Cancer Research Genetics RNA 1026 | 0.0 |

TABLE 21B-continued

Panel 2.1

| Tissue Name | Relative Expression (%) 2.1x4tm6143f__ag4002_b1 | Tissue Name | Relative Expression (%) 2.1x4tm6143f__ag4002_b1 |
|---|---|---|---|
| 85950 Lung Cancer (OD04237-01) | 5.4 | Liver Cancer Research Genetics RNA 1025 | 0.0 |
| 85970 Lung NAT (OD04237-02) | 32.8 | Paired Liver Cancer Tissue Research Genetics RNA 6004-T | 0.0 |
| 83255 Ocular Mel Met to Liver (ODO4310) | 3.3 | Paired Liver Tissue Research Genetics RNA 6004-N | 0.0 |
| 83256 Liver NAT (ODO4310) | 0.0 | Paired Liver Cancer Tissue Research Genetics RNA 6005-T | 0.0 |
| 84139 Melanoma Mets to Lung (OD04321) | 0.0 | Paired Liver Tissue Research Genetics RNA 6005-N | 0.0 |
| 84138 Lung NAT (OD04321) | 0.0 | Liver Cancer GENPAK 064003 | 0.0 |
| Normal Kidney GENPAK 061008 | 6.1 | Normal Bladder GENPAK 061001 | 0.0 |
| 83786 Kidney Ca, Nuclear grade 2 (OD04338) | 0.0 | Bladder Cancer Research Genetics RNA 1023 | 6.9 |
| 83787 Kidney NAT (OD04338) | 2.6 | Bladder Cancer INVITROGEN A302173 | 9.9 |
| 83788 Kidney Ca Nuclear grade 1/2 (OD04339) | 0.0 | Normal Ovary Res. Gen. | 0.0 |
| 83789 Kidney NAT (OD04339) | 0.0 | Ovarian Cancer GENPAK 064008 | 0.0 |
| 83790 Kidney Ca, Clear cell type (OD04340) | 0.0 | 97773 Ovarian cancer (OD06145) | 0.0 |
| 83791 Kidney NAT (OD04340) | 1.5 | 97775 Ovarian cancer NAT (OD06145) | 0.0 |
| 83792 Kidney Ca, Nuclear grade 3 (OD04348) | 2.8 | Normal Stomach GENPAK 061017 | 5.0 |
| 83793 Kidney NAT (OD04348) | 0.0 | Gastric Cancer Clontech 9060397 | 9.9 |
| 85973 Kidney Cancer (OD04450-01) | 0.0 | NAT Stomach Clontech 9060396 | 2.2 |
| 85974 Kidney NAT (OD04450-03) | 0.0 | Gastric Cancer Clontech 9060395 | 0.0 |
| Kidney Cancer Clontech 8120613 | 0.0 | NAT Stomach Clontech 9060394 | 0.0 |
| Kidney NAT Clontech 8120614 | 0.0 | Gastric Cancer GENPAK 064005 | 0.0 |

TABLE 21C

Panel 4.1D

| Tissue Name | Relative Expression (%) 4.1dtm6147f__ag4002 | Tissue Name | Relative Expression (%) 4.1dtm6147f__ag4002 |
|---|---|---|---|
| 93768_Secondary Th1_anti-CD28/anti-CD3 | 0.0 | 93100_HUVEC (Endothelial)_IL-1b | 3.9 |
| 93769_Secondary Th2_anti-CD28/anti-CD3 | 0.0 | 93779_HUVEC (Endothelial)_IFN gamma | 15.7 |
| 93770_Secondary Tr1_anti-CD28/anti-CD3 | 0.0 | 93102_HUVEC (Endothelial)_TNF alpha + IFN gamma | 20.6 |
| 93573_Secondary Th1_resting day 4–6 in IL-2 | 0.0 | 93101_HUVEC (Endothelial)_TNF alpha + IL4 | 26.1 |
| 93572_Secondary Th2_resting day 4–6 in IL-2 | 0.0 | 93781_HUVEC (Endothelial)_IL-11 | 0.0 |
| 93571_Secondary Tr1_resting day 4–6 in IL-2 | 0.0 | 93583_Lung Microvascular Endothelial Cells_none | 3.7 |
| 93568_primary Th1_anti-CD28/anti-CD3 | 0.0 | 93584_Lung Microvascular Endothelial Cells_TNFa (4 ng/ml) and IL1b (1 ng/ml) | 2.4 |
| 93569_primary Th2_anti-CD28/anti-CD3 | 0.0 | 92662_Microvascular Dermal endothelium_none | 5.3 |

TABLE 21C-continued

Panel 4.1D

| Tissue Name | Relative Expression (%) 4.1dtm6147f_ag4002 | Tissue Name | Relative Expression (%) 4.1dtm6147f_ag4002 |
|---|---|---|---|
| 93570_primary Tr1_anti-CD28/anti-CD3 | 0.0 | 92663_Microvasular Dermal endothelium_TNFa (4 ng/ml) and IL1b (1 ng/ml) | 1.9 |
| 93565_primary Th1_resting dy 4–6 in IL-2 | 0.0 | 93773_Bronchial epithelium_TNFa (4 ng/ml) and IL1b (1 ng/ml)** | 0.0 |
| 93566_primary Th2_resting dy 4–6 in IL-2 | 0.0 | 93347_Small Airway Epithelium_none | 1.2 |
| 93567_primary Tr1_resting dy 4–6 in IL-2 | 0.0 | 93348_Small Airway Epithelium_TNFa (4 ng/ml) and IL1b (1 ng/ml) | 0.0 |
| 93351_CD45RA CD4 lymphocyte_anti-CD28/anti-CD3 | 0.0 | 92668_Coronery Artery SMC_resting | 0.0 |
| 93352_CD45RO CD4 lymphocyte_anti-CD28/anti-CD3 | 0.0 | 92669_Coronery Artery SMC_TNFa (4 ng/ml) and IL1b (1 ng/ml) | 3.1 |
| 93251_CD8 Lymphocytes_anti-CD28/anti-CD3 | 0.0 | 93107_astrocytes_resting | 1.0 |
| 93353_chronic CD8 Lymphocytes 2ry_resting dy 4–6 in IL-2 | 0.0 | 93108_astrocytes_TNFa (4 ng/ml) and IL1b (1 ng/ml) | 0.0 |
| 93574_chronic CD8 Lymphocytes 2ry_activated CD3/CD28 | 0.0 | 92666_KU-812 (Basophil)_resting | 0.0 |
| 93354_CD4_none | 0.0 | 92667_KU-812 (Basophil)_PMA/ionoycin | 0.0 |
| 93252_Secondary Th1/Th2/Tr1_anti-CD95 CH11 | 1.0 | 93579_CCD1106 (Keratinocytes)_none | 0.0 |
| 93103_LAK cells_resting | 0.0 | 93580_CCD1106 (Keratinocytes)_TNFa and IFNg** | 0.0 |
| 93788_LAK cells_IL-2 | 0.0 | 93791_Liver Cirrhosis | 0.0 |
| 93787_LAK cells_IL-2 + IL-12 | 0.0 | 93577_HCT-H292 | 0.0 |
| 93789_LAK cells_IL-2 + IFN gamma | 0.0 | 93358_NCI-H292_IL-4 | 0.0 |
| 93790_LAK cells_IL-2 + IL-18 | 0.0 | 93360_NCI-H292_IL-9 | 0.0 |
| 93104_LAK cells_PMA/ionomycin and IL-18 | 0.0 | 93359_NCI-H292_IL-13 | 0.0 |
| 93578_NK Cells IL-2_resting | 0.0 | 93357_NCI-H292_IFN gamma | 0.0 |
| 93109_Mixed Lymphocyte Reaction_Two Way MLR | 1.7 | 93777_HPAEC_- | 1.4 |
| 93110_Mixed Lymphocyte Reaction_Two Way MLR | 0.0 | 93778_HPAEC_IL-1 beta/TNA alpha | 0.0 |
| 93111_Mixed Lymphocyte Reaction_Two Way MLR | 0.0 | 93254_Normal Human Lung Fibroblast_none | 0.0 |
| 93112_Mononuclear Cells (PBMCs)_resting | 0.9 | 93253_Normal Human Lung Fibroblast_TNFa (4 ng/ml) and IL-1b (1 ng/ml) | 0.0 |
| 93113_Mononuclear Cells (PBMCs)_PWM | 0.0 | 93257_Normal Human Lung Fibroblast_IL-4 | 0.9 |
| 93114_Mononuclear Cells (PBMCs)_PHA-L | 0.0 | 93256_Normal Human Lung Fibroblast_IL-9 | 0.9 |
| 93249_Ramos (B cell)_none | 0.0 | 93255_Normal Human Lung Fibroblast_IL-13 | 4.0 |
| 93250_Ramos (B cell)_ionomycin | 0.0 | 93258_Normal Human Lung Fibroblast_IFN gamma | 2.5 |
| 93349_B lymphocytes_PWM | 0.0 | 93106_Dermal Fibroblasts CCD1070_resting | 6.8 |
| 93350_B lymphoytes_CD40L and IL-4 | 1.5 | 93361_Dermal Fibroblasts CCD1070_TNF alpha 4 ng/ml | 6.9 |
| 92665_EOL-1 (Eosinophil)_dbcAMP differentiated | 0.0 | 93105_Dermal Fibroblasts CCD1070_IL-1 beta 1 ng/ml | 0.0 |
| 93248_EOL-1 (Eosinophil)_dbcAMP/PMAionomycin | 0.0 | 93772_dermal fibroblast_IFN gamma | 0.0 |
| 93356_Dendritic Cells_none | 1.0 | 93771_dermal fibroblast_IL-4 | 0.0 |

TABLE 21C-continued

Panel 4.1D

| Tissue Name | Relative Expression (%) 4.1dtm6147f_ag4002 | Tissue Name | Relative Expression (%) 4.1dtm6147f_ag4002 |
|---|---|---|---|
| 93355_Dendritic Cells_LPS 100 ng/ml | 0.0 | 93892_Dermal fibroblasts_none | 0.8 |
| 93775_Dendritic Cells_anti-CD40 | 0.0 | 99202_Neutrophils_TNFa + LPS | 0.9 |
| 93774_Monocytes_resting | 0.0 | 99203_Neutrophils_none | 0.0 |
| 93776_Monocytes_LPS 50 ng/ml | 0.0 | 735010_Colon_normal | 6.7 |
| 93581_Macrophages_resting | 2.1 | 735019_Lung_none | 12.5 |
| 93582_Macrophages_LPS 100 ng/ml | 0.0 | 64028-1_Thymus_none | 32.8 |
| 93098_HUVEC (Endothelial)_none | 7.8 | 64030-1 Kidney_none | 100.0 |
| 93099_HUVEC (Endothelial)_starved | 11.0 | | |

Panel 2.1 Summary: Ag4002 The NOV8-24SC714 gene is expressed at low levels in normal lung tissues but to a lesser degree in the associated lung tumor tissues in Panel 2.1. Low but significant expression of this gene is also seen in a metastatic colon cancer sample (CT=33.8) when compared to its associated normal adjacent tissue. Thus, based upon this profile, the expression of the 24SC714 gene could be of use as a marker for nornal lung or colon cancer. In addition, therapeutic inhibition of the activity of this gene product, through the use of antibodies or small molecule drugs, may be useful in the treatment of colon cancer. Furthermore, peptides, chimeric molecules and small molecule drugs might be useful in the therapy of lung cancer.

Panel 4.1D Summary: Ag4002 Expression of this NOV8 gene is highest in normal kidney (CT=31.2). In addition, the NOV8-24SC714 gene is expressed at low levels in HUVECs independent of treatment with cytokines (CT values=33 to 35). Consistent with these data, this gene is also expressed in endothelial cells from lung and dermis, independent of activation status. Therefore, antibody or protein therapeutic against the protein encoded by the 24SC714 gene could be useful in the treatment of inflammation.

NOV10a-100340173

Expression of gene 100340173 (NOV10a) was assessed using, the primer-probe set Ag4001, described in Table 22A. Results from RTQ-PCR runs are shown in Tables 22B and 22C.

TABLE 22A

Probe Name Ag4001

| Primers | Sequences | TM | Length | Start Position | SEQ ID NO |
|---|---|---|---|---|---|
| Forward | 5'-TCCTACCCAGCTTCTGAATTCT-3' | 59.4 | 22 | 633 | 134 |
| Probe | FAM-5'-TACTTGGGTACCACCCTGCGGACAAT-3'-TAMRA | 70.8 | 26 | 655 | 135 |
| Reverse | 5'-AACACTCTGTTCTGCAATGACA-3' | 58.4 | 22 | 687 | 136 |

TABLE 22B

Panel 2.1

| Tissue Name | Relative Expression (%) 2.1dx4tm6143f_ag4001_a2 | Tissue Name | Relative Expression (%) 2.1dx4tm6143f_ag4001_a2 |
|---|---|---|---|
| Normal Colon GENPAK 061003 | 19.3 | Kidney Cancer Clontech 9010320 | 14.8 |
| 97759 Colon cancer (OD06064) | 30.9 | Kidney NAT Clontech 9010321 | 79.9 |
| 97760 Colon cancer NAT (OD06064) | 10.4 | Kidney Cancer Clontech 8120607 | 28.2 |
| 97778 Colon cancer (OD06159) | 11.3 | Kidney NAT Clontech 8120608 | 8.6 |
| 97779 Colon cancer NAT (OD06159) | 8.6 | Normal Uterus GENPAK 061018 | 78.1 |
| 98859 Colon cancer (OD06298-08) | 32.3 | Uterus Cancer GENPAK 064011 | 10.6 |
| 98860 Colon cancer NAT (OD06298-018) | 17.4 | Normal Thyroid Clontech A+ 6570-1 (7080817) | 5.0 |

TABLE 22B-continued

Panel 2.1

| Tissue Name | Relative Expression (%) 2.1dx4tm6143f_ag4001_a2 | Tissue Name | Relative Expression (%) 2.1dx4tm6143f_ag4001_a2 |
|---|---|---|---|
| 83237 CC Gr.2 ascend colon (ODO3921) | 13.3 | Thyroid Cancer GENPAK 064010 | 28.4 |
| 83238 CC NAT (ODO3921) | 14.1 | Thyroid Cancer INVITROGEN A302152 | 7.7 |
| 97766 Colon cancer metastasis (OD06104) | 8.7 | Thyroid NAT INVITROGEN A302153 | 31.8 |
| 97767 Lung NAT (OD06104) | 96.0 | Normal Breast GENPAK 061019 | 31.0 |
| 87472 Colon mets to lung (OD04451-01) | 9.7 | 84877 Breast Cancer (OD04566) | 1.4 |
| 87473 Lung NAT (OD04451-02) | 42.3 | Breast Cancer Res. Gen. 1024 | 11.2 |
| Normal Prostate Clontech A+ 6546-1 (8090438) | 4.5 | 85975 Breast Cancer (OD04590-01) | 3.7 |
| 84140 Prostate Cancer (OD04410) | 3.8 | 85976 Breast Cancer Mets (OD04590-03) | 0.0 |
| 84141 Prostate NAT (OD04410) | 26.6 | 87070 Breast Cancer Metastasis (OD04655-05) | 13.7 |
| Normal Lung GENPAK 061010 | 38.0 | GENPAK Breast Cancer 064006 | 1.9 |
| 92337 Invasive poor diff. lung adeno (ODO4945-01) | 6.9 | Breast Cancer Clontech 9100266 | 6.5 |
| 92338 Lung NAT (ODO4945-03) | 47.4 | Breast NAT Clontech 9100265 | 25.4 |
| 84136 Lung Malignant Cancer (OD03126) | 7.9 | Breast Cancer INVITROGEN A209073 | 16.8 |
| 84137 Lung NAT (OD03126) | 24.4 | Breast NAT INVITROGEN A2090734 | 28.2 |
| 90372 Lung Cancer (OD05014A) | 17.8 | Normal Liver GENPAK 061009 | 40.8 |
| 90373 Lung NAT (OD05014B) | 45.2 | Liver Cancer Research Genetics RNA 1026 | 6.1 |
| 85950 Lung Cancer (OD04237-01) | 3.3 | Liver Cancer Research Genetics RNA 1025 | 32.8 |
| 85970 Lung NAT (OD04237-02) | 26.6 | Paired Liver Cancer Tissue Research Genetics RNA 6004-T | 22.1 |
| 83255 Ocular Mel Met to Liver (ODO4310) | 20.7 | Paired Liver Tissue Research Genetics RNA 6004-N | 7.9 |
| 83256 Liver NAT (ODO4310) | 16.0 | Paired Liver Cancer Tissue Research Genetics RNA 6005-T | 27.8 |
| 84139 Melanoma Mets to Lung (OD04321) | 43.8 | Paired Liver Tissue Research Genetics RNA 6005-N | 28.1 |
| 84138 Lung NAT (OD04321) | 46.2 | Liver Cancer GENPAK 064003 | 12.6 |
| Normal Kidney GENPAK 061008 | 21.6 | Normal Bladder GENPAK 061001 | 12.8 |
| 83786 Kidney Ca, Nuclear grade 2 (OD04338) | 36.7 | Bladder Cancer Research Genetics RNA 1023 | 3.1 |
| 83787 Kidney NAT (OD04338) | 35.1 | Bladder Cancer INVITROGEN A302173 | 12.8 |
| 83788 Kidney Ca Nuclear grade 1/2 (OD04339) | 14.3 | Normal Ovary Res. Gen. | 8.9 |
| 83789 Kidney NAT (OD04339) | 13.0 | Ovarian Cancer GENPAK 064008 | 6.8 |
| 83790 Kidney Ca, Clear cell type (OD04340) | 21.5 | 97773 Ovarian cancer (OD06145) | 3.2 |
| 83791 Kidney NAT (OD04340) | 23.2 | 97775 Ovarian cancer NAT (OD06145) | 18.8 |
| 83792 Kidney Ca, Nuclear grade 3 (OD04348) | 7.2 | Normal Stomach GENPAK 061017 | 22.4 |
| 83793 Kidney NAT (OD04348) | 19.5 | Gastric Cancer Clontech 9060397 | 9.1 |
| 85973 Kidney Cancer (OD04450-01) | 100.0 | NAT Stomach Clontech 9060396 | 6.8 |
| 85974 Kidney NAT (OD04450-03) | 29.7 | Gastric Cancer Clontech 9060395 | 24.3 |

TABLE 22B-continued

Panel 2.1

| Tissue Name | Relative Expression (%) 2.1dx4tm6143f_ ag4001_a2 | Tissue Name | Relative Expression (%) 2.1dx4tm6143f_ ag4001_a2 |
|---|---|---|---|
| Kidney Cancer Clontech 8120613 | 0.5 | NAT Stomach Clontech 9060394 | 17.8 |
| Kidney NAT Clontech 8120614 | 7.0 | Gastric Cancer GENPAK 064005 | 9.9 |

TABLE 22C

Panel 4.1D

| Tissue Name | Relative Expression (%) 4.1dtm6146f_ ag4001 | Tissue Name | Relative Expression (%) 4.1dtm6146f_ ag4001 |
|---|---|---|---|
| 93768_Secondary Th1_anti-CD28/anti-CD3 | 20.0 | 93100_HUVEC (Endothelial)_IL-1b | 20.3 |
| 93769_Secondary Th2_anti-CD28/anti-CD3 | 28.5 | 93779_HUVEC (Endothelial)_IFN gamma | 25.5 |
| 93770_Secondary Tr1_anti-CD28/anti-CD3 | 23.7 | 93102_HUVEC (Endothelial)_TNF alpha + IFN gamma | 9.2 |
| 93573_Secondary Th1_resting day 4–6 in IL-2 | 4.6 | 93101_HUVEC (Endothelial)_TNF alpha + IL4 | 11.9 |
| 93572_Secondary Th2_resting day 4–6 in IL-2 | 5.5 | 93781_HUVEC (Endothelial)_IL-11 | 8.6 |
| 93571_Secondary Tr1_resting day 4–6 in IL-2 | 4.3 | 93583_Lung Microvascular Endothelial Cells_none | 32.1 |
| 93568_primary Th1_anti-CD28/anti-CD3 | 15.9 | 93584_Lung Microvascular Endothelial Cells_TNFa (4 ng/ml) and IL1b (1 ng/ml) | 14.8 |
| 93569_primary Th2_anti-CD28/anti-CD3 | 18.4 | 92662_Microvascular Dermal endothelium_none | 17.1 |
| 93570_primary Tr1_anti-CD28/anti-CD3 | 20.2 | 92663_Microvsaular Dermal endothelium_TNFa (4 ng/ml) and IL1b (1 ng/ml) | 10.5 |
| 93565_primary Th1_resting dy 4–6 in IL-2 | 3.4 | 93773_Bronchial epithelium_TNFa (4 ng/ml) and IL1b (1 ng/ml)** | 14.4 |
| 93566_primary Th2_resting dy 4–6 in IL-2 | 1.8 | 93347_Small Airway Epithelium_none | 6.9 |
| 93567_primary Tr1_resting dy 4–6 in IL-2 | 3.2 | 93348_Small Airway Epithelium_TNFa (4 ng/ml) and IL1b (1 ng/ml) | 14.3 |
| 93351_CD45RA CD4 lymphocyte_anti-CD28/anti-CD3 | 18.2 | 92668_Coronery Artery SMC_resting | 15.2 |
| 93352_CD45RO CD4 lymphocyte_anti-CD28/anti-CD3 | 28.9 | 92669_Coronery Artery SMC_TNFa (4 ng/ml) and IL1b (1 ng/ml) | 14.5 |
| 93251_CD8 Lymphocytes_anti-CD28/anti-CD3 | 30.1 | 93107_astrocytes_resting | 24.1 |
| 93353_chronic CD8 Lymphocytes 2ry_resting dy 4–6 in IL-2 | 20.4 | 93108_astrocytes_TNFa (4 ng/ml) and IL1b (1 ng/ml) | 15.0 |
| 93574_chronic CD8 Lymphocytes 2ry_activated CD3/CD28 | 10.6 | 92666_KU-812 (Basophil)_resting | 42.3 |
| 93354_CD4_none | 3.8 | 92667_KU-812 (Basophil)_PMA/ionoycin | 100.0 |
| 93252_Secondary Th1/Th2/Tr1_anti-CD95 CH11 | 4.0 | 93579_CCD1106 (Keratinocytes)_none | 17.1 |
| 93103_LAK cells_resting | 12.7 | 93580_CCD1106 (Keratinocytes)_TNFa and IFNg** | 10.9 |

TABLE 22C-continued

Panel 4.1D

| Tissue Name | Relative Expression (%) 4.1dtm6146f__ ag4001 | Tissue Name | Relative Expression (%) 4.1dtm6146f__ ag4001 |
|---|---|---|---|
| 93788__LAK cells__IL-2 | 21.0 | 93791__Liver Cirrhosis | 7.1 |
| 93787__LAK cells__IL-2 + IL-12 | 15.0 | 93577__NCI-H292 | 6.7 |
| 93789__LAK cells__IL-2 + IFN gamma | 16.4 | 93358__NCI-H292__IL-4 | 10.2 |
| 93790__LAK cells__IL-2 + IL-18 | 19.8 | 93360__NCI-H292__IL-9 | 16.5 |
| 93104__LAK cells__PMA/ionomycin and IL-18 | 22.5 | 93359__NCI-H292__IL-13 | 20.7 |
| 93578__NK Cells IL-2__resting | 42.9 | 93357__NCI-H292__IFN gamma | 12.9 |
| 93109__Mixed Lymphocyte Reaction__Two Way MLR | 20.7 | 93777__HPAEC__- | 14.9 |
| 93110__Mixed Lymphocyte Reaction__Two Way MLR | 16.0 | 93778__HPAEC__IL-1 beta/TNA alpha | 16.8 |
| 93111__Mixed Lymphocyte Reaction__Two Way MLR | 16.3 | 93254__Normal Human Lung Fibroblast__none | 16.3 |
| 93112__Mononuclear Cells (PBMCs)__resting | 4.0 | 93253__Normal Human Lung Fibroblast__TNFa (4 ng/ml) and IL-1b (1 ng/ml) | 8.2 |
| 93113__Mononuclear Cells (PBMCs)__PWM | 15.8 | 93257__Normal Human Lung Fibroblast__IL-4 | 21.8 |
| 93114__Mononuclear Cells (PBMCs)__PHA-L | 12.3 | 93256__Normal Human Lung Fibroblast__IL-9 | 22.7 |
| 93249__Ramos (B cell)__none | 24.8 | 93255__Normal Human Lung Fibroblast__IL-13 | 20.2 |
| 93250__Ramos (B cell)__ionomycin | 28.3 | 93258__Normal Human Lung Fibroblast__IFN gamma | 22.2 |
| 93349__B lymphocytes__PWM | 16.6 | 93106__Dermal Fibroblasts CCD1070__resting | 14.6 |
| 93350__B lymphoytes__CD40L and IL-4 | 11.9 | 93361__Dermal Fibroblasts CCD1070__TNF alpha 4 ng/ml | 17.6 |
| 92665__EOL-1 (Eosinophil)__dbcAMP differentiated | 10.2 | 93105__Dermal Fibroblasts CCD1070__IL-1 beta 1 ng/ml | 13.9 |
| 93248__EOL-1 (Eosinophil)__dbcAMP/PMAionomycin | 4.1 | 93772__dermal fibroblast__IFN gamma | 11.9 |
| 93356__Dendritic Cells__none | 9.7 | 93771__dermal fibroblast__IL-4 | 17.6 |
| 93355__Dendritic Cells__LPS 100 ng/ml | 5.6 | 93892__Dermal fibroblasts__none | 7.4 |
| 93775__Dendritic Cells__anti-CD40 | 11.4 | 99202__Neutrophils__TNFa + LPS | 1.4 |
| 93774__Monocytes__resting | 3.8 | 99203__Neutrophils__none | 0.8 |
| 93776__Monocytes__LPS 50 ng/ml | 7.4 | 735010__Colon__normal | 7.9 |
| 93581__Macrophages__resting | 7.3 | 735019__Lung__none | 17.7 |
| 93582__Macrophages__LPS 100 ng/ml | 4.5 | 64028-1__Thymus__none | 12.9 |
| 93098__HUVEC (Endothelial)__none | 9.2 | 64030-1__Kidney__none | 18.8 |
| 93099__HUVEC (Endothelial)__starved | 13.7 | | |

Panel 2.1 Summary: Ag4001 The NOV10-100340173 gene is expressed at low to moderate levels across the majority of samples on this panel, with highest expression detected in a kidney cancer sample (CT=29.2). Thus, this gene is likely to be involved in proliferation and survival of many different cell types. Specific therapeutic inhibition of the activity of this gene product, through the use of antibodies or small molecule drugs, may therefore be useful in the treatment of many different forms of cancer.

Panel 4.1D Summary: Ag4001 The NOV10-100340173 gene is ubiquitously expressed at low to moderate levels in the majority of samples on this panel (CT values=30–33). Interestingly, this gene is highly expressed in basophils after activation by treatment with PMA/ionomycin (CT=27.4). Therefore, the protein encoded for by the 100340173 gene could play a role in the development of allergies. Antibodies against this protein could thus be used to reduce or inhibit inflammation observed in allergy, asthma, and psoriasis. In addition, 100340173 gene expression is up-regulated in activated TH1 and TH2 cells, further suggesting that modulation of the protein encoded by this gene might be important in immune-mediated disease.

NOV12-87917235

Expression of gene 87917235 was assessed using the primer-probe set Ag4003, described in Table 23A.

TABLE 23A

Probe Name Ag4003

| Primers | Sequences | TM | Length | Start Position | SEQ ID NO |
|---|---|---|---|---|---|
| Forward | 5'-ATATGATTGAGAAGGCCCAAAC-3' | 59.3 | 22 | 765 | 137 |
| Probe | FAM-5'-CCTTTAAAATTTAGATCTGTGTCTCCCCA-3'-TAMRA | 65.3 | 29 | 789 | 138 |
| Reverse | 5'-CTGTGTCTCCAGAGAGGTCTGA-3' | 59.6 | 22 | 818 | 139 |

Expression of this NOV12 gene is low/undetectable (CT values>35) across all of the samples on Panel 4.1D (data not shown).

NOV13-87919652

Expression of gene NOV13-87919652 was assessed using the primer-probe set Ag4004, described in Table 24A. Results from RTQ-PCR runs are shown in Tables 24B and 24C.

TABLE 24A

Probe Name Ag4004

| Primers | Sequences | TM | Length | Start Position | SEQ ID NO |
|---|---|---|---|---|---|
| Forward | 5'-CTGGACAGGTTAGGGCTTTG-3' | 59.7 | 20 | 883 | 140 |
| Probe | FAM-5'-CCTTCTGGAAGTCTGCCAGTGTCCTT-3'-TAMRA | 68.9 | 26 | 908 | 141 |
| Reverse | 5'-TGAGAGAGTTCTGGGTGTCCTA-3' | 58.9 | 22 | 939 | 142 |

TABLE 24B

Panel 2.1

| Tissue Name | Relative Expression (%) 2.1dx4tm6143f_ ag4004_b2 | Tissue Name | Relative Expression (%) 2.1dx4tm6143f_ ag4004_b2 |
|---|---|---|---|
| Normal Colon GENPAK 061003 | 1.1 | Kidney Cancer Clontech 9010320 | 1.6 |
| 97759 Colon cancer (OD06064) | 1.6 | Kidney NAT Clontech 9010321 | 6.1 |
| 97760 Colon cancer NAT (OD06064) | 2.1 | Kidney Cancer Clontech 8120607 | 1.6 |
| 97778 Colon cancer (OD06159) | 1.5 | Kidney NAT Clontech 8120608 | 0.2 |
| 97779 Colon cancer NAT (OD06159) | 2.0 | Normal Uterus GENPAK 061018 | 1.7 |
| 98859 Colon cancer (OD06298-08) | 5.9 | Uterus Cancer GENPAK 064011 | 1.1 |
| 98860 Colon cancer NAT (OD06298-018) | 3.5 | Normal Thyroid Clontech A+ 6570-1 (7080817) | 0.0 |
| 83237 CC Gr.2 ascend colon (ODO3921) | 0.6 | Thyroid Cancer GENPAK 064010 | 1.4 |
| 83238 CC NAT (ODO3921) | 2.0 | Thyroid Cancer INVITROGEN A302152 | 0.6 |
| 97766 Colon cancer metastasis (OD06104) | 2.1 | Thyroid NAT INVITROGEN A302153 | 1.5 |
| 97767 Lung NAT (OD06104) | 100.0 | Normal Breast GENPAK 061019 | 2.8 |
| 87472 Colon mets to lung (OD04451-01) | 1.0 | 84877 Breast Cancer (OD04566) | 0.7 |
| 87473 Lung NAT (OD04451-02) | 4.4 | Breast Cancer Res. Gen. 1024 | 2.1 |
| Normal Prostate Clontech A+ 6546-1 (8090438) | 0.6 | 85975 Breast Cancer (OD04590-01) | 0.6 |
| 84140 Prostate Cancer (OD04410) | 0.5 | 85976 Breast Cancer Mets (OD04590-03) | 3.4 |

TABLE 24B-continued

Panel 2.1

| Tissue Name | Relative Expression (%) 2.1dx4tm6143f_ag4004_b2 | Tissue Name | Relative Expression (%) 2.1dx4tm6143f_ag4004_b2 |
|---|---|---|---|
| 84141 Prostate NAT (OD04410) | 1.1 | 87070 Breast Cancer Metastasis (OD04655-05) | 4.2 |
| Normal Lung GENPAK 061010 | 14.5 | GENPAK Breast Cancer 064006 | 1.0 |
| 92337 Invasive poor diff. lung adeno (ODO4945-01 | 3.4 | Breast Cancer Clontech 9100266 | 0.5 |
| 92338 Lung NAT (ODO4945-03) | 10.9 | Breast NAT Clontech 9100265 | 0.9 |
| 84136 Lung Malignant Cancer (OD03126) | 1.1 | Breast Cancer INVITROGEN A209073 | 1.1 |
| 84137 Lung NAT (OD03126) | 2.7 | Breast NAT INVITROGEN A2090734 | 2.4 |
| 90372 Lung Cancer (OD05014A) | 3.9 | Normal Liver GENPAK 061009 | 2.5 |
| 90373 Lung NAT (OD05014B) | 1.5 | Liver Cancer Research Genetics RNA 1026 | 0.5 |
| 85950 Lung Cancer (OD04237-01) | 3.1 | Liver Cancer Research Genetics RNA 1025 | 3.6 |
| 85970 Lung NAT (OD04237-02) | 5.9 | Paired Liver Cancer Tissue Research Genetics RNA 6004-T | 2.4 |
| 83255 Ocular Mel Met to Liver (ODO4310) | 0.0 | Paired Liver Tissue Research Genetics RNA 6004-N | 1.6 |
| 83256 Liver NAT (ODO4310) | 1.4 | Paired Liver Cancer Tissue Research Genetics RNA 6005-T | 2.7 |
| 84139 Melanoma Mets to Lung (OD04321) | 1.1 | Paired Liver Tissue Research Genetics RNA 6005-N | 2.8 |
| 84138 Lung NAT (OD04321) | 3.9 | Liver Cancer GENPAK 064003 | 2.0 |
| Normal Kidney GENPAK 061008 | 0.5 | Normal Bladder GENPAK 061001 | 2.1 |
| 83786 Kidney Ca, Nuclear grade 2 (OD04338) | 2.8 | Bladder Cancer Research Genetics RNA 1023 | 1.8 |
| 83787 Kidney NAT (OD04338) | 0.7 | Bladder Cancer INVITROGEN A302173 | 3.5 |
| 83788 Kidney Ca Nuclear grade 1/2 (OD04339) | 1.1 | Normal Ovary Res. Gen. | 1.4 |
| 83789 Kidney NAT (OD04339) | 0.3 | Ovarian Cancer GENPAK 064008 | 0.5 |
| 83790 Kidney Ca, Clear cell type (OD04340) | 0.7 | 97773 Ovarian cancer (OD06145) | 0.0 |
| 83791 Kidney NAT (OD04340) | 0.8 | 97775 Ovarian cancer NAT (OD06145) | 0.9 |
| 83792 Kidney Ca, Nuclear grade 3 (OD04348) | 1.2 | Normal Stomach GENPAK 061017 | 13.1 |
| 83793 Kidney NAT (OD04348) | 1.9 | Gastric Cancer Clontech 9060397 | 0.9 |
| 85973 Kidney Cancer (OD04450-01) | 0.7 | NAT Stomach Clontech 9060396 | 6.5 |
| 85974 Kidney NAT (OD04450-03) | 0.2 | Gastric Cancer Clontech 9060395 | 7.8 |
| Kidney Cancer Clontech 8120613 | 0.2 | NAT Stomach Clontech 9060394 | 8.3 |
| Kidney NAT Clontech 8120614 | 0.0 | Gastric Cancer GENPAK 064005 | 4.6 |

TABLE 24C

Panel 4.1D

| Tissue Name | Relative Expression (%) 4.1dtm6148f_ag4004 | Tissue Name | Relative Expression (%) 4.1dtm6148f_ag4004 |
|---|---|---|---|
| 93768_Secondary Th1_anti-CD28/anti-CD3 | 52.5 | 93100_HUVEC (Endothelial)_IL-1b | 0.0 |

TABLE 24C-continued

Panel 4.1D

| Tissue Name | Relative Expression (%) 4.1dtm6148f_ag4004 | Tissue Name | Relative Expression (%) 4.1dtm6148f_ag4004 |
|---|---|---|---|
| 93769_Secondary Th2_anti-CD28/anti-CD3 | 55.5 | 93799_HUVEC (Endothelial)_IFN gamma | 0.0 |
| 93770_Secondary Tr1_anti-CD28/anti-CD3 | 44.4 | 93102_HUVEC (Endothelial)_TNF alpha + IFN gamma | 0.0 |
| 93573_Secondary Th1_resting day 4–6 in IL-2 | 31.9 | 93101_HUVEC (Endothelial)_TNF alpha + IL4 | 0.0 |
| 93572_Secondary Th2_resting day 4–6 in IL-2 | 33.9 | 93781_HUVEC (Endothelial)_IL-11 | 0.2 |
| 93571_Secondary Tr1_resting day 4–6 in IL-2 | 40.1 | 93583_Lung Microvascular Endothelial Cells_none | 0.1 |
| 93568_primary Th1_anti-CD28/anti-CD3 | 16.6 | 93584_Lung Microvascular Endothelial Cells_TNFa (4 ng/ml) and IL1b (1 ng/ml) | 0.3 |
| 93569_primary Th2_anti-CD28/anti-CD3 | 48.3 | 92662_Microvascular Dermal endothelium_none | 0.0 |
| 93570_primary Tr1_anti-CD28/anti-CD3 | 43.8 | 92663_Microsvasular Dermal endothelium_TNFa (4 ng/ml) and IL1b (1 ng/ml) | 0.1 |
| 93565_primary Th1_resting dy 4–6 in IL-2 | 29.7 | 93773_Bronchial epithelium_TNFa (4 ng/ml) and IL1b (1 ng/ml)** | 0.1 |
| 93566_primary Th2_resting dy 4–6 in IL-2 | 23.0 | 93347_Small Airway Epithelium_none | 0.0 |
| 93567_primary Tr1_resting dy 4–6 in IL-2 | 79.0 | 93348_Small Airway Epithelium_TNFa (4 ng/ml) and IL1b (1 ng/ml) | 0.2 |
| 93351_CD45RA CD4 lymphocyte_anti-CD28/anti-CD3 | 23.2 | 92668_Coronery Artery SMC_resting | 0.0 |
| 93352_CD45RO CD4 lymphocyte_anti-CD28/anti-CD3 | 62.0 | 92669_Coronery Artery SMC_TNFa (4 ng/ml) and IL1b (1 ng/ml) | 0.0 |
| 93251_CD8 Lymphocytes_anti-CD28/anti-CD3 | 37.4 | 93107_astrocytes_resting | 0.0 |
| 93353_chronic CD8 Lymphocytes 2ry_resting dy 4–6 in IL-2 | 43.8 | 93108_astrocytes_TNFa (4 ng/ml) and IL1b (1 ng/ml) | 0.0 |
| 93574_chronic CD8 Lymphocytes 2ry_activated CD3/CD28 | 29.3 | 92666_KU-812 (Basophil)_resting | 0.9 |
| 93354_CD4_none | 14.2 | 92667_KU-812 (Basophil)_PMA/ionoycin | 0.9 |
| 93252_Secondary Th1/Th2/Tr1_anti-CD95 CH11 | 40.9 | 93579_CCD1106 (Keratinocytes)_none | 0.1 |
| 93103_LAK cells_resting | 15.2 | 93580_CCD1106 (Keratinocytes)_TNFa and IFNg** | 0.1 |
| 93788_LAK cells_IL-2 | 52.1 | 93791_Liver Cirrhosis | 3.4 |
| 93787_LAK cells_IL-2 + IL-12 | 23.5 | 93577_NCI-H292 | 0.3 |
| 93789_LAK cells_IL-2 + IFN gamma | 29.7 | 93358_NCI-H292_IL-4 | 0.0 |
| 93790_LAK cells_IL-2 + IL-18 | 37.1 | 93360_NCI-H292_IL-9 | 0.1 |
| 93104_LAK cells_PMA/ionomycin and IL-18 | 15.8 | 93359_NCI-H292_IL-13 | 0.1 |
| 93578_NK Cells IL-2_resting | 100.0 | 93357_NCI-H292_IFN gamma | 0.1 |
| 93109_Mixed Lymphocyte Reaction_Two Way MLR | 27.5 | 93777_HPAEC_- | 0.1 |
| 93110_Mixed Lymphocyte Reaction_Two Way MLR | 27.4 | 93778_HPAEC_IL-1beta/TNA alpha | 0.0 |
| 93111_Mixed Lymphocyte Reaction_Two Way MLR | 36.3 | 93254_Normal Human Lung Fibroblast_none | 0.1 |
| 93112_Mononuclear Cells (PBMCs)_resting | 20.6 | 93253_Normal Human Lung Fibroblast_TNFa (4 ng/ml) and IL-1b (1 ng/ml) | 0.0 |

TABLE 24C-continued

Panel 4.1D

| Tissue Name | Relative Expression (%) 4.1dtm6148f_ ag4004 | Tissue Name | Relative Expression (%) 4.1dtm6148f_ ag4004 |
|---|---|---|---|
| 93113_Mononuclear Cells (PBMCs)_PWM | 34.9 | 93257_Normal Human Lung Fibroblast_IL-4 | 0.0 |
| 93114_Mononuclear Cells (PBMCs)_PHA-L | 40.3 | 93256_Normal Human Lung Fibroblast_IL-9 | 0.0 |
| 93249_Ramos (B cell)_none | 2.6 | 93255_Normal Human Lung Fibroblast_IL-13 | 0.4 |
| 93250_Ramos (B cell)_ionomycin | 3.0 | 93258_Normal Human Lung Fibroblast_IFN gamma | 0.5 |
| 93349_B lymphocytes_PWM | 27.0 | 93106_Dermal Fibroblasts CCD1070_resting | 1.6 |
| 93350_B lymphoytes_CD40L and IL-4 | 6.8 | 93361_Dermal Fibroblasts CCD1070_TNF alpha 4 ng/ml | 52.8 |
| 92665_EOL-1 (Eosinophil)_dbcAMP differentiated | 11.0 | 93105_Dermal Fibroblasts CCD1070_IL-1beta 1 ng/ml | 0.2 |
| 93248_EOL-1 (Eosinophil)_dbcAMP/PMAionomycin | 2.1 | 93772_dermal fibroblast_IFN gamma | 0.3 |
| 93356_Dendritic Cells_none | 2.3 | 93771_dermal fibroblast_IL-4 | 0.4 |
| 93355_Dendritic Cells_LPS 100 ng/ml | 0.3 | 93892_Dermal fibroblasts_none | 0.2 |
| 93775_Dendritic Cells_anti-CD40 | 0.2 | 99202_Neutrophils_TNFa + LPS | 0.8 |
| 93774_Monocytes_resting | 0.9 | 99203_Neutrophils_none | 2.0 |
| 93776_Monocytes_LPS 50 ng/ml | 1.9 | 735010_Colon_normal | 2.8 |
| 93581_Macrophages_resting | 1.1 | 735019_Lung_none | 2.5 |
| 93582_Macrophages_LPS 100 ng/ml | 0.9 | 64028-1_Thymus_none | 19.3 |
| 93098_HUVEC (Endothelial)_none | 0.0 | 64030-1_Kidney_none | 9.5 |
| 93099_HUVEC (Endothelial)_starved | 0.3 | | |

Panel 2.1 Summary: Ag4004 The NOV13-87919652 gene is strongly expressed in normal lung tissues when compared to the associated lung tumor tissue in Panel 2.1, with highest expression in a normal lung tissue sample (CT=29.6). Thus, based Upon this profile, expression of this gene could be used as a marker to differentiate normal lung tissues from lung tumors. Furthermore, the 87919652 gene product may be useful as a protein therapeutic in the treatment of lung cancer, through the use of peptides, chimeric molecules and small molecule drugs.

Panel 4.1D Summary: Ag4004 The highest expression of the NOV13-87919652 gene is seen in NK cells (CT=28.2 vs 29.1 to 33.1 in other activated T cells). Moderate expression of ihis gene is seen in other T cells irrespective of treatment. Besides lmphoid cells, the 87919652 gene is also highly expressed in dermal fibroblasts treated with TNFa. Therefore, modulation of the protein encoded for by the 87919652 gene could be important in immune-mediated diseases such as asthma, IBD, contact hypersensitivity, infection disease, allorejection and autoimmunity.

NOV14-87935554

Expression of gene 87935554 was assessed using the primer-probe set Ag3998, described in Table 25A. Results from RTQ-PCR runs are shown in Table 25B.

TABLE 25A

Probe Name Ag3998

| Primers | Sequences | TM | Length | Start Position | SEQ ID NO |
|---|---|---|---|---|---|
| Forward | 5'-CTGCCCTGCTACTTGCTCTAC-3' | 59.3 | 21 | 215 | 143 |
| Probe | FAM-5'-CACCATTGTCGTGGCTACATCATCCT-3'-TAMRA | 69 | 26 | 242 | 144 |
| Reverse | 5'-AGGACCATCTTGAGCTTGGA-3' | 59.8 | 20 | 278 | 145 |

TABLE 25B

Panel 4.1D

| Tissue Name | Relative Expression (%) 4.1dx4tm6155f_ag3998_a2 | Tissue Name | Relative Expression (%) 4.1dx4tm6155f_ag3998_a2 |
|---|---|---|---|
| 93768_Secondary Th1_anti-CD28/anti-CD3 | 0.2 | 93100_HUVEC (Endothelial)_IL-1b | 0.7 |
| 93769_Secondary Th2_anti-CD28/anti-CD3 | 0.0 | 93779_HUVEC (Endothelial)_IFN gamma | 0.7 |
| 93770_Secondary Tr1_anti-CD28/anti-CD3 | 0.2 | 93102_HUVEC (Endothelial)_TNF alpha + IFN gamma | 0.4 |
| 93573_Secondary Th1_resting day 4–6 in IL-2 | 0.2 | 93101_HUVEC (Endothelial)_TNF alpha + IL4 | 0.3 |
| 93572_Secondary Th2_resting day 4–6 in IL-2 | 0.0 | 93781_HUVEC (Endothelial)_IL-11 | 1.5 |
| 93571_Secondary Tr1_resting day 4–6 in IL-2 | 0.0 | 93583_Lung Microvascular Endothelial Cells_none | 27.4 |
| 93568_primary Th1_anti-CD28/anti-CD3 | 0.0 | 93584_Lung Microvascular Endothelial Cells_TNFa (4 ng/ml) and IL1b (1 ng/ml) | 16.6 |
| 93569_primary Th2_anti-CD28/anti-CD3 | 0.1 | 92662_Microvascular Dermal endothelium_none | 29.5 |
| 93570_primary Tr1_anti-CD28/anti-CD3 | 0.0 | 92663_Microvasular Dermal endothelium_TNFa (4 ng/ml) and IL1b (1 ng/ml) | 7.0 |
| 93565_primary Th1_resting dy 4–6 in IL-2 | 0.0 | 93773_Bronchial epithelium_TNFa (4 ng/ml) and IL1b (1 ng/ml)** | 8.5 |
| 93566_primary Th2_resting dy 4–6 in IL-2 | 0.0 | 93347_Small Airway Epithelium_none | 3.3 |
| 93567_primary Tr1_resting dy 4–6 in IL-2 | 0.0 | 93348_Small Airway Epithelium_TNFa (4 ng/ml) and IL1b (1 ng/ml) | 16.2 |
| 93351_CD45RA CD4 lymphocyte_anti-CD28/anti-CD3 | 16.6 | 92668_Coronery Artery SMC_resting | 0.5 |
| 93352_CD45RO CD4 lymphocyte_anti-CD28/anti-CD3 | 0.0 | 92669_Coronery Artery SMC_TNFa (4 ng/ml) and IL1b (1 ng/ml) | 1.0 |
| 93251_CD8 Lymphocytes_anti-CD28/anti-CD3 | 0.0 | 93107_astrocytes_resting | 16.9 |
| 93353_chronic CD8 Lymphocytes 2ry_resting dy 4–6 in IL-2 | 0.2 | 93108_astrocytes_TNFa (4 ng/ml) and IL1b (1 ng/ml) | 12.7 |
| 93574_chronic CD8 Lymphocytes 2ry_activated CD3/CD28 | 0.0 | 92666_KU-812 (Basophil)_resting | 0.0 |
| 93354_CD4_none | 0.2 | 92667_KU-812 (Basophil)_PMA/ionoycin | 0.1 |
| 93252_Secondary Th1/Th2/Tr1_anti-CD95 CH11 | 0.0 | 93579_CCD1106 (Keratinocytes)_none | 10.8 |
| 93103_LAK cells_resting | 18.0 | 93580_CCD1106 (Keratinocytes)_TNFa and IFNg** | 7.9 |
| 93788_LAK cells_IL-2 | 0.1 | 93791_Liver Cirrhosis | 17.7 |
| 93787_LAK cells_IL-2 + IL-12 | 0.5 | 93577_NCI-H292 | 5.1 |
| 93789_LAK cells_IL-2 + IFN gamma | 0.7 | 93358_NCI-H292_IL-4 | 7.7 |
| 93790_LAK cells_IL-2 + IL-18 | 0.4 | 93360_NCI-H292_IL-9 | 8.0 |
| 93104_LAK cells_PMA/ionomycin and IL-18 | 10.5 | 93359_NCI-H292_IL-13 | 8.9 |
| 93578_NK Cells IL-2_resting | 0.0 | 93357_NCI-H292_IFN gamma | 4.3 |
| 93109_Mixed Lymphocyte Reaction_Two Way MLR | 6.6 | 93777_HPAEC_- | 1.3 |
| 93110_Mixed Lymphocyte Reaction_Two Way MLR | 4.6 | 93778_HPAEC_IL-1beta/TNA alpha | 0.9 |

TABLE 25B-continued

Panel 4.1D

| Tissue Name | Relative Expression (%) 4.1dx4tm6155f_ag3998_a2 | Tissue Name | Relative Expression (%) 4.1dx4tm6155f_ag3998_a2 |
|---|---|---|---|
| 93111_Mixed Lymphocyte Reaction_Two Way MLR | 1.7 | 93254_Normal Human Lung Fibroblast_none | 11.1 |
| 93112_Mononuclear Cells (PBMCs)_resting | 1.3 | 93253_Normal Human Lung Fibroblast_TNFa (4 ng/ml) and IL-1b (1 ng/ml) | 6.7 |
| 93113_Mononuclear Cells (PBMCs)_PWM | 0.7 | 93257_Normal Human Lung Fibroblast_IL-4 | 7.2 |
| 93114_Mononuclear Cells (PBMCs)_PHA-L | 1.8 | 93256_Normal Human Lung Fibroblast_IL-9 | 13.3 |
| 93249_Ramos (B cell)_none | 0.0 | 93255_Normal Human Lung Fibroblast_IL-13 | 7.6 |
| 93250_Ramos (B cell)_ionomycin | 0.0 | 93258_Normal Human Lung Fibroblast_IFN gamma | 7.6 |
| 93349_B lymphocytes_PWM | 0.0 | 93106_Dermal Fibroblasts CCD1070_resting | 26.2 |
| 93350_B lymphoytes_CD40L and IL-4 | 0.4 | 93361_Dermal Fibroblasts CCD1070_TNF alpha 4 ng/ml | 25.1 |
| 92665_EOL-1 (Eosinophil)_dbcAMP differentiated | 0.0 | 93105_Dermal Fibroblasts CCD1070_IL-1beta 1 ng/ml | 25.3 |
| 93248_EOL-1 (Eosinophil)_dbcAMP/PMAionomycin | 0.0 | 93772_dermal fibroblast_IFN gamma | 1.2 |
| 93356_Dendritic Cells_none | 44.9 | 93771_dermal fibroblast_IL-4 | 0.9 |
| 93355_Dendritic Cells_LPS 100 ng/ml | 55.4 | 93892_Dermal fibroblasts_none | 2.4 |
| 93775_Dendritic Cells_anti-CD40 | 100.0 | 99202_Neutrophils_TNFa + LPS | 0.4 |
| 93774_Monocytes_resting | 5.3 | 99203_Neutrophils_none | 0.4 |
| 93776_Monocytes_LPS 50 ng/ml | 24.2 | 735010_Colon_normal | 4.5 |
| 93581_Macrophages_resting | 45.1 | 735019_Lung_none | 7.5 |
| 93582_Macrophages_LPS 100 ng/ml | 16.6 | 64028-1_Thymus_none | 2.3 |
| 93098_HUVEC (Endothelial)_none | 0.4 | 64030-1_Kidney_none | 13.5 |
| 93099_HUVEC (Endothelial)_starved | 0.9 | | |

Panel 4.1D Summary: Ag3998 In lymphoid cells, the NOV14-87935554 gene is highly expressed in dendritic cells and in mature dendritic cells treated with anti-CD40 (CT=26.3). Moderate to high expression of this gene is also found in monocytes and macrophages (independently of their activation), untreated LAK cells, activated naive T cells (but not memory T cells), fibroblasts (dermis and lung), and endothelial cells. This gene encodes a putative canalicular multispecific organic anion transporter, a member of the multidrug resistance-associated protein family; proteins in this family have been reported to play a widespread role in detoxification, drug resistance, and, due to their role in the export of glutathione disulfide by MRP1 and MRP2, in the defense against oxidative stress. See, Wijnholds el al., Nat. Med. 3: 1275–1279, 1997. Therefore, regulation of the 87935554 gene product by small molecule therapeutics could be important in the treatment of inflammatory diseases and cancer.

The multidrug resistance-associated protein (MRP) mediates the cellular excretion of many drugs, glutathione S-conjugates (GS-X) of lipophilic xenobiotics and endogenous cysteinyl leukotrienes. Increased MRP levels in tumor cells can cause multidrug resistance (MDR) by decreasing the intracellular drug concentration. The physiological role or roles of MRP remain ill-defined, however. MRP-deficient mice have been generated by using embryonic stem cell technology. Mice homozygous for the mrp mutant allele, mrp-/-, are viable and fertile, but their response to an inflammatory stimulus is impaired. This defect is attribute to a decreased secretion of leukotriene C4 (LTC4) from leukotriene-synthesizing cells. Moreover, the mrp-/- mice are hypersensitive to the anticancer drug etoposide. The phenotype of mrp-/- mice is consistent with a role for MRP as the main LTC4-exporter in leukotriene-synthesizing cells, and as an important drug exporter in drug-sensitive cells. Results suggest that this ubiquitous GS-X pump is dispensable in mice, making treatment of MDR with MRP-specific reversal agents potentially feasible. PMID: 9359705

NOV15a-100399281

Expression of gene NOV15a-100399281 was assessed using the primer-probe sets Ag391, Ag672, and Ag3999, described in Tables 26A, 26B, and 26C. Results from RTQ-PCR runs are shown in Table 26D and 26E.

TABLE 26A

Probe Name Ag391

| Primers | Sequences | TM | Length | Start Position | SEQ ID NO |
|---|---|---|---|---|---|
| Forward | 5'-GACGGTCACAGGTCCTCGAT-3' | | 20 | 629 | 146 |
| Probe | TET-5'-TGCACGCGTAGCCACAAGACCG-3' TAMRA | | 22 | 597 | 147 |
| Reverse | 5'-GGGAACGGCAACCAGAAAC-3' | | 19 | 573 | 148 |

TABLE 26B

Probe Name Ag672

| Primers | Sequences | TM | Length | Start Position | SEQ ID NO |
|---|---|---|---|---|---|
| Forward | 5'-CCAGATCCTTTCTCCTTGATCT-3' | 58.8 | 22 | 172 | 149 |
| Probe | TET-5'-CCAAACTTTCCAGATCTTTCCAAAGCTG-3'-TAMRA | 68.5 | 28 | 195 | 150 |
| Reverse | 5'-TGACCTGGATATTTGGATTCTG-3' | 58.9 | 22 | 234 | 151 |

TABLE 26C

Probe Name Ag3999

| Primers | Sequences | TM | Length | Start Position | SEQ ID NO |
|---|---|---|---|---|---|
| Forward | 5'-AACAGAATCGAGGACCTGTGA-3' | 59.7 | 21 | 795 | 152 |
| Probe | FAM-5'-CCAGCTTGCACCGGATTCCTGAT-3'-TAMRA | 70.5 | 23 | 829 | 153 |
| Reverse | 5'-CCCTAACCAAGCTTCCTTTACA-3' | 59.7 | 22 | 852 | 154 |

TABLE 26D

Panel 1

| Tissue Name | Relative Expression (%) 1tm408f | Tissue Name | Relative Expression (%) 1tm408f |
|---|---|---|---|
| Endothelial cells | 0.1 | Kidney (fetal) | 9.5 |
| Endothelial cells (treated) | 0.0 | Renal ca. 786-0 | 3.9 |
| Pancreas | 12.1 | Renal ca. A498 | 7.2 |
| Pancreatic ca. CAPAN 2 | 1.6 | Renal ca. RXF 393 | 16.0 |
| Adipose | 24.8 | Renal ca. ACHN | 1.0 |
| Adrenal gland | 4.2 | Renal ca. UO-31 | 0.8 |
| Thyroid | 96.6 | Renal ca. TK-10 | 20.2 |
| Salavary gland | 17.1 | Liver | 22.5 |
| Pituitary gland | 3.4 | Liver (fetal) | 0.4 |
| Brain (fetal) | 3.6 | Liver ca. (hepatoblast) HepG2 | 2.2 |
| Brain (whole) | 6.7 | Lung | 6.2 |
| Brain (amygdala) | 5.0 | Lung (fetal) | 45.4 |
| Brain (cerebellum) | 17.7 | Lung ca. (small cell) LX-1 | 4.8 |
| Brain (hippocampus) | 5.7 | Lung ca. (small cell) NCI-H69 | 14.6 |
| Brain (substantia nigra) | 8.0 | Lung ca. (s.cell var) SHP-77 | 5.7 |
| Brain (thalamus) | 14.4 | Lung ca. (large cell)NCI-H460 | 3.6 |
| Brain (hypothalamus) | 9.5 | Lung ca. (non-sm. cell) A549 | 3.1 |

TABLE 26D-continued

Panel 1

| Tissue Name | Relative Expression (%) 1tm408f | Tissue Name | Relative Expression (%) 1tm408f |
|---|---|---|---|
| Spinal cord | 11.9 | Lung ca. (non-s.cell) NCI-H23 | 1.4 |
| CNS ca. (glio/astro) U87-MG | 2.8 | Lung ca (non-s.cell) HOP-62 | 0.6 |
| CNS ca (glio/astro) U-118-MG | 9.3 | Lung ca. (non-s.cl) NCI-H522 | 0.4 |
| CNS ca. (astro) SW1783 | 0.7 | Lung ca. (squam.) SW 900 | 34.6 |
| CNS ca.* (neuro; met) SK-N-AS | 0.9 | Lung ca. (squam.) NCI-H596 | 35.4 |
| CNS ca. (astro) SF-539 | 1.1 | Mammary gland | 100.0 |
| CNS ca. (astro) SNB-75 | 3.7 | Breast ca.* (pl. effusion) MCF-7 | 4.3 |
| CNS ca. (glio) SNB-19 | 1.8 | Breast ca.* (pl.ef) MDA-MB-231 | 1.5 |
| CNS ca. (glio) U251 | 1.4 | Breast ca.* (pl. effusion) T47D | 8.3 |
| CNS ca. (glio) SF-295 | 0.6 | Breast ca. BT-549 | 3.7 |
| Heart | 5.8 | Breast ca. MDA-N | 0.6 |
| Skeletal muscle | 4.1 | Ovary | 2.8 |
| Bone marrow | 3.3 | Ovarian ca. OVCAR-3 | 2.3 |
| Thymus | 11.0 | Ovarian ca. OVCAR-4 | 0.9 |
| Spleen | 15.1 | Ovarian ca. OVCAR-5 | 4.4 |
| Lymph node | 5.7 | Ovarian ca. OVCAR-8 | 3.1 |
| Colon (ascending) | 5.4 | Ovarian ca. IGROV-1 | 1.6 |
| Stomach | 13.7 | Ovarian ca.* (ascites) SK-OV-3 | 2.2 |
| Small intestine | 9.4 | Uterus | 11.7 |
| Colon ca. SW480 | 7.0 | Placenta | 95.9 |
| Colon ca* (SW480 met) SW620 | 1.1 | Prostate | 6.2 |
| Colon ca. HT29 | 1.6 | Prostate ca.* (bone met) PC-3 | 0.3 |
| Colon ca. HCT-116 | 3.3 | Testis | 5.7 |
| Colon ca. CaCo-2 | 2.9 | Melanoma Hs688(A).T | 0.6 |
| Colon ca. HCT-15 | 2.7 | Melamoma* (met) Hs688(B).T | 0.3 |
| Colon ca. HCC-2998 | 2.3 | Melanoma UACC-62 | 1.4 |
| Gastric ca.* (liver met) NCI-N87 | 5.7 | Melanoma M14 | 1.4 |
| Bladder | 10.4 | Melanoma LOX IMVI | 1.6 |
| Trachea | 8.8 | Melanoma* (met) SK-MEL-5 | 23.2 |
| Kidney | 13.7 | Melanoma SK-MEL-28 | 18.8 |

TABLE 26E

Panel 1.1

| Tissue Name | Relative Expression (%) 1.1tm798t_ag672 | Tissue Name | Relative Expression (%) 1.1tm798t_ag672 |
|---|---|---|---|
| Adipose | 3.2 | Renal ca. TK-10 | 36.1 |
| Adrenal gland | 3.8 | Renal ca. UO-31 | 0.1 |
| Bladder | 24.3 | Renal ca. RXF 393 | 11.6 |
| Brain (amygdala) | 0.2 | Liver | 5.0 |
| Brain (cerebellum) | 3.7 | Liver (fetal) | 0.0 |
| Brain (hiopocampus) | 3.1 | Liver ca. (hepatoblast) HepG2 | 0.6 |
| Brain (substantia nigra) | 14.4 | Lung | 6.5 |
| Brain (thalamus) | 10.4 | Lung (fetal) | 57.4 |
| Cerebral Cortex | 3.2 | Lung ca (non-s.cell) HOP-62 | 0.6 |
| Brain (fetal) | 1.3 | Lung ca. (large cell) NCI-H460 | 4.9 |
| Brain (whole) | 1.5 | Lung ca. (non-s.cell) NCI-H23 | 0.1 |
| CNS ca (glio/astro) U-118-MG | 15.3 | Lung ca. (non-s.cl) NCI-H522 | 0.0 |
| CNS ca. (astro) SF-539 | 0.0 | Lung ca. (non-sm. cell) A549 | 2.5 |

TABLE 26E-continued

Panel 1.1

| Tissue Name | Relative Expression (%) 1.1tm798t_ag672 | Tissue Name | Relative Expression (%) 1.1tm798t_ag672 |
|---|---|---|---|
| CNS ca. (astro) SNB-75 | 0.6 | Lung ca. (s.cell var.) SHP-77 | 0.0 |
| CNS ca. (astro) SW1783 | 0.0 | Lung ca. (small cell) LX-1 | 11.6 |
| CNS ca. (glio) U251 | 1.0 | Lung ca. (small cell) NCI-H69 | 17.7 |
| CNS ca. (glio) SF-295 | 0.0 | Lung ca. (squam.) SW 900 | 29.3 |
| CNS ca. (glio) SNB-19 | 0.8 | Lung ca. (squam.) NCI-H596 | 63.3 |
| CNS ca. (glio/astro) U87-MG | 3.7 | Lymph node | 3.4 |
| CNS ca.* (neuro; met) SK-N-AS | 0.0 | Spleen | 3.8 |
| Mammary gland | 43.5 | Thymus | 2.5 |
| Breast ca. BT-549 | 0.8 | Ovary | 0.8 |
| Breast ca. MDA-N | 0.1 | Ovarian ca. IGROV-1 | 5.0 |
| Breast ca.* (pl. effusion) T47D | 9.6 | Ovarian ca. OVCAR-3 | 6.3 |
| Breast ca.* (pl. effusion) MCF-7 | 2.7 | Ovarian ca. OVCAR-4 | 0.0 |
| Breast ca.* (pl.ef) MDA-MB-231 | 1.2 | Ovarian ca. OVCAR-5 | 6.2 |
| Small intestine | 6.2 | Ovarian ca. OVCAR-8 | 1.8 |
| Colorectal | 0.1 | Ovarian ca.* (ascites) SK-OV-3 | 2.7 |
| Colon ca. HT29 | 0.0 | Pancreas | 54.0 |
| Colon ca. CaCo-2 | 2.1 | Pancreatic ca. CAPAN 2 | 0.1 |
| Colon ca. HCT-15 | 1.7 | Pituitary gland | 14.0 |
| Colon ca. HCT-116 | 1.7 | Placenta | 100.0 |
| Colon ca. HCC-2998 | 2.2 | Prostate | 1.0 |
| Colon ca. SW480 | 19.1 | Prostate ca.* (bone met) PC-3 | 0.0 |
| Colon ca.* (SW480 met) SW620 | 0.8 | Salavary gland | 42.3 |
| Stomach | 6.7 | Trachea | 23.8 |
| Gastric ca.* (liver met) NCI-N87 | 9.5 | Spinal cord | 6.7 |
| Heart | 23.0 | Testis | 0.0 |
| Fetal Skeletal | 1.6 | Thyroid | 78.5 |
| Skeletal muscle | 13.1 | Uterus | 1.6 |
| Endothelial cells | 0.2 | Melanoma M14 | 0.0 |
| Heart (fetal) | 4.2 | Melanoma LOX IMVI | 0.0 |
| Kidney | 6.4 | Melanoma UACC-62 | 0.0 |
| Kidney (fetal) | 5.0 | Melanoma SK-MEL-28 | 65.5 |
| Renal ca. 786-0 | 2.0 | Melanoma* (met) SK-MEL-5 | 37.1 |
| Renal ca. A498 | 13.2 | Melanoma Hs688(A).T | 0.0 |
| Renal ca. ACHN | 0.1 | Melanoma* (met) Hs688(B).T | 0.0 |

Panel 1 Summary: Ag391 Two experiments were performed using the same probe/primer set; results from one of the replicate runs were discarded because the results were artifactual (data not shown). The NOV15a-100399281 gene is moderately to highly expressed across the majority of samples on this panel. However, expression is highest in mammary gland (CT=26), placenta (CT=26.1), and thyroid (CT=26.1). Therefore, the 100399281 gene might be useful as a marker to distinguish these tissues. In addition, the observed expression in mammary gland and placenta suggests a potential role for the 100399281 gene product in pregnancy. Interestingly, expression of this gene is much lower in 5/5 breast cancer cell lines when compared to normal breast. This suggests that replacement of the 100399281 gene product using protein therapeutics, peptides or gene therapy would be valuable in the treatment of breast cancer.

In addition, the NOV15a-100399281 gene is expressed throughout the CNS with moderate expression detected in amygdala, cerebellum, hippocampus, substantia nigra, thalamus, hypothalamus and spinal cord. Expression of this gene is decreased in CNS cancer cell lines relative to normal brain tissues. The secreted protein encoded for by the 100399281 gene contains homology to thrombospondin, suggesting it may play a role in inhibiting angiogenesis. Therefore, treatment with the 100399281 protein, or in vivo modulation of the gene or the protein product may therefore be of use in slowing the growth/inhibiting CNS tumors. Selective removal of this protein via synthetic antibodies may help to increase vascularization in CNS tissue undergoing repair/regeneration.

Among the metabolically relevant tissues, the NOV15a-100399281 gene is expressed at high levels in thyroid and at more moderate levels in pancreas, adrenal gland, pituitary gland, heart, and skeletal muscle. Therefore, this gene product may have utility as a drug treatment for any or all diseases of the thyroid gland as well as other metabolic and neuroendocrine diseases. Interestingly, this gene is more highly expressed in adult liver (CT=28.2) than in fetal liver (CT=33.8), suggesting that the 100399281 gene would be a useful marker for differentiating between the adult and fetal liver. Please note that the adipose sample on this panel is contaminated with genomic DNA and, therefore, expression in this tissue cannot be analyzed.

Panel 1.1 Summary: Ag672 The results obtained in this experiment are comparable to what is observed in Panel 1. Expression of the NOV15a-100399281 gene is primarily associated with normal tissues on this panel. Highest expression is seen in placenta (CT=25), thyroid (CT=25.2), pancreas (CT=25.7), and mammary gland (CT=26). Therefore, the 100399281 gene might be useful as a marker to distinguish these tissues. In addition, the observed expression in mammary gland and placenta suggests a potential role for the 100399281 gene product in pregnancy. Interestingly, expression of this gene is much lower in 5/5 breast cancer cell lines when compared to normal breast. This suggests that replacement of the 100399281 gene product using protein therapeutics, peptides or gene therapy would be valuable in the treatment of breast cancer.

In addition, the 100399281 gene is expressed throughout the CNS with low to moderate expression detected in amygdala, cerebellum, hippocampus, substantia nigra, thalamus and cerebral cortex. Expression of this gene is decreased in CNS cancer cell lines relative to normal brain tissues. The secreted protein encoded for by the 100399281 gene contains homology to thrombospondin, suggesting it may play a role in inhibiting angiogenesis. Therefore, treatment with the 100399281 protein, or in vivo modulation of the gene or the protein product may therefore be of use in slowing the growth/inhibiting CNS tumors. Selective removal of this protein via synthetic antibodies may help to increase vascularization in CNS tissue undergoing repair/regeneration.

Among the metabolically relevant tissues, the 100399281 gene is expressed at high levels in thyroid and pancreas and at more moderate levels in adrenal gland, pituitary gland, heart, and skeletal muscle. Therefore, this gene product may have utility as a drug treatment for any or all diseases of the thyroid gland and pancreas as well as other metabolic and neuroendocrine diseases. Interestingly, this gene is more highly expressed in adult liver (CT=29) than in fetal liver (CT=40), suggesting that the 100399281 gene would be a useful marker for differentiating between the adult and fetal liver. Please note that the adipose sample on this panel is contaminated with genomic DNA and, therefore, expression in this tissue cannot be analyzed.

Panel 2.1 Summary: Ag3999 Expression of the NOV15a-100399281 gene is low/undetectable (CT values>35) across the samples on this panel (data not shown).

Panel 4.1D Summary: Ag3999 Expression of the NOV15a-100399281 gene is low/undetectable (CT values>35) across the samples on this panel (data not shown).

NOV16a-101330077

Expression of gene NOV16a-1101330077 was assessed using the primer-probe set Ag3996, described in Table 27A. Results from RTQ-PCR run are shown in Table 27B.

TABLE 27A

Probe Name Ag3996

| Primers | Sequences | TM | Length | Start Position | SEQ ID NO |
|---|---|---|---|---|---|
| Forward | 5'-GAGTGGGCTACACCAATCAG-3' | 58.2 | 20 | 411 | 155 |
| Probe | FAM-5'-AGCGGCGCTAACGTGACTGACTAACT-3'-TAMRA | 69 | 26 | 437 | 156 |
| Reverse | 5'-CCCTCTCAGGGAGATTGAGA-3' | 59.3 | 20 | 476 | 157 |

TABLE 27B

Panel 4.1D

| | Relative Expression (%) | |
|---|---|---|
| Tissue Name | 4.1dtm6144f_ ag3996 | 4.1dx4tm6155f_ ag3996_a1 |
| 93768_Secondary Th1_anti-CD28/anti-CD3 | 1.3 | 0.0 |
| 93769_Secondary Th2_anti-CD28/anti-CD3 | 1.9 | 2.7 |
| 93770_Secondary Tr1_anti-CD28/anti-CD3 | 0.0 | 0.0 |
| 93573_Secondary Th1_resting day 4–6 in IL-2 | 0.0 | 0.0 |
| 93572_Secondary Th2_resting day 4–6 in IL-2 | 0.7 | 0.0 |
| 93571_Secondary Tr1_resting day 4–6 in IL-2 | 0.0 | 1.1 |
| 93568_primary Th1_anti-CD28/anti-CD3 | 0.0 | 0.0 |
| 93569_primary Th2_anti-CD28/anti-CD3 | 0.0 | 0.0 |
| 93570_primary Tr1_anti-CD28/anti-CD3 | 0.8 | 0.0 |
| 93565_primary Th1_resting dy 4–6 in IL-2 | 0.4 | 0.0 |
| 93566_primary Th2_resting dy 4–6 in IL-2 | 0.0 | 0.0 |
| 93567_primary Tr1_resting dy 4–6 in IL-2 | 0.4 | 0.0 |
| 93351_CD45RA CD4 lymphocyte_anti-CD28/anti-CD3 | 0.0 | 0.0 |
| 93352_CD45RO CD4 lymphocyte_anti-CD28/anti-CD3 | 0.6 | 0.0 |
| 93251_CD8 Lymphocytes_anti-CD28/anti-CD3 | 0.0 | 0.0 |
| 93353_chronic CD8 Lymphocytes 2ry_resting dy 4–6 in | 0.0 | 0.0 |

TABLE 27B-continued

Panel 4.1D

| Tissue Name | Relative Expression (%) | |
|---|---|---|
| | 4.1dtm6144f__ag3996 | 4.1dx4tm6155f__ag3996_a1 |
| IL-2 | | |
| 93574_chronic CD8 Lymphocytes 2ry_activated CD3/CD28 | 0.0 | 0.0 |
| 93354_CD4_none | 0.0 | 0.0 |
| 93252_Secondary Th1/Th2/Tr1_anti-CD95 CH11 | 0.8 | 1.3 |
| 93103_LAK cells_resting | 0.0 | 0.0 |
| 93788_LAK cells_IL-2 | 0.0 | 0.0 |
| 93787_LAK cells_IL-2 + IL-12 | 0.0 | 0.0 |
| 93789_LAK cells_IL-2 + IFN gamma | 0.0 | 0.0 |
| 93790_LAK cells_IL-2 + IL-18 | 0.5 | 0.0 |
| 93104_LAK cells_PMA/ionomycin and IL-18 | 0.0 | 0.0 |
| 93578_NK Cells IL-2_resting | 0.5 | 1.6 |
| 93109_Mixed Lymphocyte Reaction_Two Way MLR | 0.0 | 0.0 |
| 93110_Mixed Lymphocyte Reaction_Two Way MLR | 0.0 | 0.0 |
| 93111_Mixed Lymphocyte Reaction_Two Way MLR | 0.0 | 0.0 |
| 93112_Mononuclear Cells (PBMCs)_resting | 0.0 | 1.2 |
| 93113_Mononuclear Cells (PBMCs)_PWM | 0.4 | 1.2 |
| 93114_Mononuclear Cells (PBMCs)_PHA-L | 0.0 | 0.0 |
| 93249_Ramos (B cell)_none | 0.0 | 0.0 |
| 93250_Ramos (B cell)_ionomycin | 0.0 | 0.0 |
| 93349_B lymphocytes_PWM | 1.4 | 0.0 |
| 93350_B lymphocytes_CD40L and IL-4 | 0.0 | 0.0 |
| 92665_EOL-1 (Eosinophil)_dbcAMP differentiated | 0.0 | 0.0 |
| 93248_EOL-1 (Eosinophil)_dbcAMP/PMAionomycin | 0.0 | 0.0 |
| 93356_Dendritic Cells_none | 0.0 | 0.0 |
| 93355_Dendritic Cells_LPS 100 ng/ml | 0.0 | 0.0 |
| 93775_Dendritic Cells_anti-CD40 | 0.0 | 0.0 |
| 93774_Monocytes_resting | 0.0 | 0.0 |
| 93776_Monocytes_LPS 50 ng/ml | 0.0 | 0.0 |
| 93581_Macrophages_resting | 0.0 | 0.0 |
| 93582_Macrophages_LPS 100 ng/ml | 1.8 | 2.2 |
| 93098_HUVEC (Endothelial)_none | 0.0 | 0.0 |
| 93099_HUVEC (Endothelial)_starved | 0.0 | 0.0 |
| 93100_HUVEC (Endothelial)_IL-1b | 0.6 | 0.0 |
| 93779_HUVEC (Endothelial)_IFN gamma | 0.0 | 0.0 |
| 93102_HUVEC (Endothelial)_TNF alpha + IFN gamma | 0.0 | 0.0 |
| 93101_HUVEC (Endothelial)_TNF alpha + IL4 | 0.0 | 0.0 |
| 93781_HUVEC (Endothelial)_IL-11 | 0.0 | 0.0 |
| 93583_Lung Microvascular Endothelial Cells_none | 0.7 | 3.1 |
| 93584_Lung Microvascular Endothelial Cells_TNFa (4 ng/ml) and IL1b (1 ng/ml) | 0.0 | 0.0 |
| 92662_Microvascular Dermal endothelium_none | 0.0 | 0.0 |
| 92663_Microsvascular Dermal endothelium_TNFa (4 ng/ml) and IL1b (1 ng/ml) | 0.0 | 0.0 |
| 93773_Bronchial epithelium_TNFa (4 ng/ml) and IL1b (1 ng/ml)** | 0.0 | 0.0 |
| 93347_Small Airway Epithelium_none | 0.0 | 0.0 |
| 93348_Small Airway Epithelium_TNFa (4 ng/ml) and IL1b (1 ng/ml) | 0.0 | 0.0 |
| 92668_Coronery Artery SMC_resting | 0.4 | 1.1 |
| 92669_Coronery Artery SMC_TNFa (4 ng/ml) and IL1b (1 ng/ml) | 0.0 | 0.0 |
| 93107_astrocytes_resting | 0.0 | 0.4 |
| 93108_astrocytes_TNFa (4 ng/ml) and IL1b (1 ng/ml) | 0.2 | 0.0 |
| 92666_KU-812 (Basophil)_resting | 0.0 | 0.0 |
| 92667_KU-812 (Basophil)_PMA/ionoycin | 0.0 | 0.0 |
| 93579_CCD1106 (Keratinocytes)_none | 0.3 | 0.0 |
| 93580_CCD1106 (Keratinocytes)_TNFa and IFNg** | 0.0 | 5.0 |
| 93791_Liver Cirrhosis | 0.0 | 0.0 |
| 93577_NCI-H292 | 0.0 | 0.0 |
| 93358_NCI-H292_IL-4 | 0.0 | 0.7 |
| 93360_NCI-H292_IL-9 | 1.0 | 0.8 |
| 93359_NCI-H292_IL-13 | 0.0 | 0.0 |
| 93357_NCI-H292_IFN gamma | 0.0 | 0.0 |
| 93777_HPAEC_- | 0.0 | 0.0 |
| 93778_HPAEC IL-1beta/TNA alpha | 0.0 | 0.0 |
| 93254_Normal Human Lung Fibroblast_none | 0.0 | 0.0 |
| 93253_Normal Human Lung Fibroblast_TNFa (4 ng/ml) and IL-1b (1 ng/ml) | 0.0 | 0.0 |
| 93257_Normal Human Lung Fibroblast_IL-4 | 0.0 | 0.0 |
| 93256_Normal Human Lung Fibroblast_IL-9 | 0.0 | 0.0 |
| 93255_Normal Human Lung Fibroblast_IL-13 | 2.3 | 0.0 |
| 93258_Normal Human Lung Fibroblast_IFN gamma | 2.9 | 0.0 |
| 93106_Dermal Fibroblasts CCD1070_resting | 0.0 | 2.4 |
| 93361_Dermal Fibroblasts CCD1070_TNF alpha 4 ng/ml | 3.4 | 0.0 |

TABLE 27B-continued

Panel 4.1D

| Tissue Name | Relative Expression (%) | |
| --- | --- | --- |
| | 4.1dtm6144f__ag3996 | 4.1dx4tm6155f__ag3996_a1 |
| 93105__Dermal Fibroblasts CCD1070__IL-1beta 1 ng/ml | 1.7 | 0.0 |
| 93772__dermal fibroblast__IFN gamma | 0.0 | 2.2 |
| 93771__dermal fibroblast__IL-4 | 0.9 | 0.0 |
| 93892__Dermal fibroblasts__none | 1.9 | 0.0 |
| 99202__Neutrophils__TNFa + LPS | 0.7 | 7.0 |
| 99203__Neutrophils__none | 0.0 | 6.9 |
| 735010__Colon__normal | 2.6 | 0.0 |
| 735019__Lung__none | 11.8 | 6.0 |
| 64028-1__Thymus__none | 27.5 | 19.6 |
| 64030-1__Kidney__none | 100.0 | 100.0 |

Panel 2.1 Summary: Ag3996 Expression of the NOV16a-101330077 gene is low/undetectable (CT values>35) across the samples on this panel (data not shown).

Panel 4.1D Summary: Ag3996 Results from two experiments usillg the same probe/priner set are in fair agreement. Low but significant expression of the NOV16a-1101330077 gene is detected only in kidney and thymus. Therefore, the 101330077 transcript, the protein encoded for by this gene or antibodies designed against this gene product could be used o identify kidney and thymus tissue.

Example 3

SNP Analysis of NOVX Clones

SeqCalling™ Technology: cDNA was derived from various human samples representing multiple tissue types, normal and diseased states, physiological states, and developmental states from different donors. Samples were obtained as whole tissue, cell lines, primary cells or tissue cultured primary cells and cell lines. Cells and cell lines may have been treated with biological or chemical agents that regulate gene expression for example, growth factors, chemokines, steroids. The cDNA thus derived was then sequenced using CuraGen's proprietary SeqCalling technology. Sequence traces were evaluated manually and edited for corrections if appropriate. cDNA sequences from all samples were assembled with themselves and with public ESTs using bioinformatics programs to generate CuraGen's human Seq-Calling database of SeqCalling assemblies. Each assembly contains one or more overlapping cDNA sequences derived from one or more human samples. Fragments and ESTs were included as components for an assembly when the extent of identity with another component of the assembly was at least 95% over 50 bp. Each assembly can represent a gene and/or its variants such as splice forms and/or single nucleotide polymorphisms (SNPs) and their combinations.

Variant sequences are included in this application. A variant sequence can include a single nucleotide polymorphism (SNP). A SNP can, in some instances, be referred to as a "cSNP" to denote that the nucleotide sequence containing the SNP originates as a cDNA. A SNP can arise in several ways. For example, a SNP may be due to a substitution of one nucleotide for another at the polymorphic site. Such a substitution can be either a transition or a transversion. A SNP can also arise from a deletion of a nucleotide or an insertion of a nucleotide, relative to a reference allele. In this case, the polymorphic site is a site at which one allele bears a gap with respect to a particular nucleotide in another allele. SNPs occurring within genes may result in an alteration of the amino acid encoded by the gene at the position of the SNP. Intragenic SNPs may also be silent, however, in the case that a codon including a SNP encodes the same amino acid as a result of the redundancy of the genetic code. SNPs occurring outside the region of a gene, or in an intron within a gene, do not result in changes in any amino acid sequence of a protein but may result in altered regulation of the expression pattern for example, alteration in temporal expression, physiological response regulation, cell type expression regulation, intensity of expression, stability of transcribed message.

Method of novel SNP Identification: SNPs are identified by analyzing sequence assemblies using CuraGen's proprietary SNPTool algorithm. SNPTool identifies variation in assemblies with the following criteria: SNPs are not analyzed within 10 base pairs on both ends of an alignment; Window size (number of bases in a view) is 10; The allowed number of mismatches in a window is 2; Minimum SNP base quality (PHRED score) is 23; Minimum number of changes to score an SNP is 2/assembly position. SNPTool analyzes the assembly and displays SNP positions, associated individual variant sequences in the assembly, the depth of the assembly at that given position, the putative assembly allele frequency, and the SNP sequence variation. Sequence traces are then selected and brought into view for manual validation. The consensus assembly sequence is imported into CuraTools along with variant sequence changes to identify potential amino acid changes resulting from the SNP sequence variation. Comprehensive SNP data analysis is then exported into the SNPCalling database.

Method of novel SNP Confirmation: SNPs are confirmed employing a validated method know as Pyrosequencing (Pyrosequencing, Westborough, Mass.). Detailed protocols for Pyrosequencing can be found in: Alderborn et al. Determination of Single Nucleotide Polymorphisms by Real-time Pyrophosphate DNA Sequencing. (2000). *Genome Research*. 10, Issue 8, August. 1249–1265. In brief, Pyrosequencing is a real time primer extension process of genotyping. This protocol takes double-stranded, biotinylated PCR products from genomic DNA samples and binds them to streptavidin beads. These beads are then denatured producing single stranded bound DNA. SNPs are characterized utilizing a technique based on an indirect bioluminometric assay of pyrophosphate (PPi) that is released from each dNTP upon DNA chain elongation. Following Klenow polymerase-mediated base incorporation, PPi is released and used as a substrate, together with adenosine 5'-phosphosul fate (APS), for ATP sulfurylase, which results in the formation of ATP. Subsequently, the ATP accomplishes the conversion of luciferin to its oxi-derivative by the action of luciferase. The ensuing light output becomes proportional to the number of added bases, up to about four bases. To allow processivity of the method dNTP excess is degraded by apyrase, which is also present in the starting reaction mixture, so that only dNTPs are added to the template during the sequencing. The process has been fully automated and adapted to a 96-well format, which allows rapid screening of large SNP panels. The DNA and protein sequences for the novel single nucleotide polymorphic variants are reported. Variants are reported individually but any combination of all or a select subset of variants are also included. In addition, the positions of the variant bases and the variant amino acid residues are underlined.

Results

Variants are reported individually but any combination of all or a select subset of variants are also included as contemplated NOVX embodiments of the invention.

NOV2 SNP Data:

In the following positions os SEQ ID NO:9, one or more consensus positions (Cons. Pos.) of the nucleotide sequence have been identified as SNPs. "Depth" rerepresents the number of clones covering the region of the SNP. The Putative Allele Frequency (Putative Allele Freq.) is the fraction of all the clones containing the SNP. A dash ("-"), when shown, means that a base is not present. The sign ">" means "is changed to".

Cons.Pos.: 7216 Depth: 31 Change: C>T; Cons.Pos.: 7118 Depth: 31 Change: C>T;
Cons.Pos.: 7266 Depth: 31 Change: T>A; Cons.Pos.: 7328 Depth: 31 Change: C>T;
Cons.Pos.: 7355 Depth: 35 Change: C>T; Cons.Pos.: 7365 Depth: 38 Change: C>T;
Cons.Pos.: 7368 Depth: 38 Change: C>T; Cons.Pos.: 7451 Depth: 27 Change: G>A.

NOV3 SNP Data:

A NOV3 variant cDNA, CG56383-01, was cloned that extended from nucleotide 1938 to 3129 of SEQ ID NO:5. SNP variants found in CG56383-01 are shown in Table 28. Two of the SNPs are in the coding sequence of NOV3, with one change from T to C at nucleotide position 2089, and the other change from T to A at nucleotid position 2630. Two additional SNPs are in the 3' non-coding region, with two nucleotides (both Ts) at nucleotide position 3019-3020 deleted when compared to SEQ ID NO:10. The NOV3 sense strand (SEQ ID NO:10) and encoded polypeptide (SEQ ID NO:611) are used in Table 28 as the reference sequences to determine the base positions of the cSNPs and coding variants.

TABLE 28 cSNP and Coding Variants for NOV3

| NT Position of cSNP | Wild Type NT | Variant NT | Amino Acid position | Amino Acid Change |
|---|---|---|---|---|
| 2089 | T | C | N/A | None |
| 2630 | T | A | 214 | Ser > Thr |
| 3019 | T | deletion | N/A | N/A |
| 3020 | T | deletion | N/A | N/A |

NOV4 SNP Data:

One or more consensus positions (Cons. Pos.) of the nucleotide sequence have been identified as SNPs as shown in Table 29. "Depth" represents the number of clones covering Cons.Pos.: 75 Depth: 18 Change: T>C; Cons.Pos.: 517 Depth: 20 Change: T>C; the region of the SNP. The Putative Allele Frequency (Putative Allele Freq.) is the fraction of all the clones containing the SNP. A dash ("-"), when shown, means that a base is not present. The sign ">" means "is changed to". Cons.Pos.: 75 Depth: 18 Change: T>C; Cons.Pos.: 517 Depth: 20 Change: T>C.

NOV4 has two SNP variants, whose variant positions for their nucleotide and amino acid sequences are numbered according to SEQ ID NOs:18 and 19, respectively. The nucleotide sequences of these NOV4 variants differ as shown in Table 29.

TABLE 29 cSNP and Coding Variants for NOV4

| NT Position of cSNP | Wild Type NT | Variant NT | Amino Acid position | Amino Acid Change |
|---|---|---|---|---|
| 718 | A | G | 179 | I > V |
| 1134 | A | G | N/A | None |

NOV5 SNP Data:

NOV5 has ten SNP variants, whose variant positions for their nucleotide and amino acid sequences are numbered according to SEQ ID NOs:26 and 27, respectively. The nucleotide sequences of these NOV5 variants differ as shown in Table 30.

TABLE 30 cSNP and Coding Variants for NOV5

| NT Position of cSNP | Wild Type NT | Variant NT | Amino Acid position | Amino Acid Change |
|---|---|---|---|---|
| 172 | A | G | 36 | E > K |
| 203 | T | C | N/A | None |
| 273 | T | C | 70 | S > P |
| 283 | G | A | 73 | G > E |
| 287 | C | T | N/A | None |
| 381 | G | T | 106 | D > Y |
| 424 | C | T | 120 | A > V |
| 460 | A | G | 132 | Q > R |
| 504 | G | A | 147 | E > K |
| 559 | C | T | 165 | S > F |

NOV7 SNP Data:

NOV7 has four SNP variants, whose variant positions for their nucleotide and amino acid sequences are numbered according to SEQ ID NOs: 43 and 43, respectively. The nucleotide sequences of these NOV7 variants d iffer as shown in Table 31.

TABLE 31 cSNP and Coding Variants for NOV7

| NT Position of cSNP | Wild Type NT | Variant NT | Amino Acid position | Amino Acid Change |
|---|---|---|---|---|
| 187 | T | C | N/A | None |
| 222 | T | C | 16 | V > A |
| 229 | A | G | N/A | None |
| 377 | A | G | 68 | N > D |

NOV8 SNP Data:

NOV8 has two SNP variants, whose variant positions for their nucleotide and amino acid sequences are numbered according to SEQ ID NOs:50 and 51, respectively. The nucleotide sequences of these NOV8 variants differ as shown in Table 32.

TABLE 32 cSNP and Coding Variants for NOV8

| NT Position of cSNP | Wild Type NT | Variant NT | Amino Acid position | Amino Acid Change |
|---|---|---|---|---|
| 2060 | G | A | N/A | None |
| 2127 | T | C | 73 | F > L |

NOV9 SNP Data:

NOV9 has three SNP variants, whose variant positions for their nucleotide and amino acid sequences are numbered according to SEQ ID NOs:52 and 53. respectively. The nucleotide sequences of these NOV9 variants differ as shown in Table 33.

TABLE 33 cSNP and Coding Variants for NOV9

| NT Position of cSNP | Wild Type NT | Variant NT | Amino Acid position | Amino Acid Change |
|---|---|---|---|---|
| 206 | C | T | 69 | A > V |
| 615 | G | T | N/A | None |
| 649 | A | G | 217 | M > V |

NOV10 SNP Data:

The novel variants for the DNA and protein sequence for the novel hypothetical 22.2 kDa protein SLR0305-like/Type IIIb plasma membrane-like gene are reported here as variant Acc. No. 100340173. Variants are reported individually but any combination of all or a select subset of variants are also included.

NOV10 has four SNP variants, whose variant positions for their nucleotide and amino acid sequences are numbered according to SEQ ID NOs:60 and 61, respectively. The nucleotide sequences of these NOV10 variants differ as shown in Table 34.

TABLE 34 cSNP and Coding Variants for NOV10

| NT Position of cSNP | Wild Type NT | Variant NT | Amino Acid position | Amino Acid Change |
|---|---|---|---|---|
| 542 | C | T | 59 | T > I |
| 643 | C | T | 93 | L > F |
| 645 | T | C | N/A | None |
| 667 | A | G | 101 | T > A |

NOV12 SNP Data:

NOV12 has one SNP variant, whose variant position for its nucleotide and amino acid sequences is numbered according to SEQ ID NOs:72 and 73, respectively. The nucleotide sequences of the the NOV12 variant differs as shown in Table 35.

TABLE 35 cSNP and Coding Variants for NOV12

| NT Position of cSNP | Wild Type NT | Variant NT | Amino Acid position | Amino Acid Change |
|---|---|---|---|---|
| 2048 | A | G | 87 | H > R |

NOV15 SNPs and cSNPs:

One or more consensus positions (Cons. Pos.) of the nucleotide sequence have been identified as SNPs. "Depth" represents the number of clones covering the region of the SNP. The Putative Allele Frequency (Putative Allele Freq.) is the fraction of all the clones containing the SNP. A dash ("-"), when shown, means that a base is not present. The sign ">" means "is changed to".

Cons.Pos.: 648 Depth: 6 Change:->A Putative Allele Freq.: 0.333 AA translation view (alpha) Fragment Listing:->146913812(+,i,1 19650936) Fpos: 137->147572388 (+,i, 119650936) Fpos: 172 Multi-Trace View

Other Embodiments

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. The choice of nucleic acid starting material, clone of interest, or library type is believed to be a matter of routine for a person of ordinary skill in the art with knowledge of the embodiments described herein. Other aspects, advantages, and modifications considered to be within the scope of the following claims.

What is claimed is:

1. An isolated nucleic acid molecule comprising a nucleic acid sequence encoding a polypeptide comprising the amino acid sequence of SEQ ID NO:75; or a nucleic acid molecule comprising the complement of the nucleic acid molecule encoding the polypeptide of SEQ ID NO:75.

2. The nucleic acid molecule of claim 1, wherein the nucleic acid molecule differs by a single nucleotide from a nucleic acid sequence selected from the group consisting of SEQ ID NOS: 74 and 76.

3. The nucleic acid molecule of claim 1, wherein said nucleic acid molecule comprises a nucleotide sequence selected from the group consisting of:
   (a) a nucleotide sequence selected from the group consisting of SEQ ID NOS: 74 and 76;
   (b) a nucleotide sequence differing by one or more nucleotides from a nucleotide sequence selected from the group consisting of SEQ ID NOS: 74 and 76, provided that no more than 5% of the nucleotides differ from said nucleotide sequence; and
   (c) the ORF of SEQ ID NO:74.

4. The nucleic acid molecule of claim 1, wherein said nucleic acid molecule hybridizes under stringent conditions to a nucleotide sequence chosen from the group consisting of SEQ ID NOS:74 and 76, or a complement of said nucleotide sequence.

5. The nucleic acid molecule of claim 1, wherein the nucleic acid molecule comprises a nucleotide sequence selected from the group consisting of:
   (a) a first nucleotide sequence comprising a coding sequence differing by one or more nucleotide sequences from a coding sequence encoding said amino acid sequence, provided that no more than 5% of the nucleotides in the coding sequence in said first nucleotide sequence differ from said coding sequence; and
   (b) an isolated second polynucleotide that is a complement of the first polynucleotide.

6. A vector comprising the nucleic acid molecule of claim 5.

7. The vector of claim 6, further comprising a promoter operably-linked to said nucleic acid molecule.

8. A transformed host cell in culture comprising the vector of claim 6.

9. A method for determining the presence or amount of the nucleic acid molecule of claim 1 in a sample, the method comprising:

(a) providing the sample;
(b) contacting the sample with a probe that binds to said nucleic acid molecule; and
(c) determining the presence or amount of the probe bound to, said nucleic acid molecule,
thereby determining the presence or amount of the nucleic acid molecule in said sample.

10. The method of claim 9, wherein the probe is a nucleic acid molecule consisting of the nucleotide sequence of SEQ ID NO:74, SEQ ID NO:76, or a complement thereof.

11. The method of claim 9 wherein presence or amount of the nucleic acid molecule is used as a marker for cell or tissue type.

12. The method of claim 11 wherein the cell or tissue type is cancerous.

13. The method of claim 11 wherein the cell or tissue type is from an immune-mediated disease.

14. A pharmaceutical composition comprising the nucleic acid molecule of claim 1 and a pharmaceutically-acceptable carrier.

15. A kit comprising in one or more containers, the pharmaceutical composition of claim 14.

16. A method for determining the presence of or predisposition to a disease associated with altered levels of the nucleic acid molecule of claim 1 in a first mammalian subject, the method comprising:
   (a) measuring the amount of the nucleic acid in a sample from the first mammalian subject; and
   (b) comparing the amount of said nucleic acid in the sample of step (a) to the amount of the nucleic acid present in a control sample from a second mammalian subject known not to have or not be predisposed to, the disease;
wherein an alteration in the level of the nucleic acid in the first subject as compared to the control sample indicates the presence of or predisposition to the disease.

17. The method of claim 16 wherein the predisposition is to a cancer.

18. The method of claim 16 wherein the predisposition is to an immune-mediated disease.

19. A vector comprising the nucleic acid molecule of claim 1.

20. The vector of claim 19, further comprising a promoter operably-linked to said nucleic acid molecule.

21. A transformed host cell in culture comprising the vector of claim 19.

22. A transformed host cell in culture which expresses the nucleic acid molecule of claim 1.

23. An isolated nucleic acid molecule comprising a nucleotide sequence selected from the group consisting of:
   a) SEQ ID NO:74;
   b) SEQ ID NO:76;
   c) the ORF of SEQ ID NO:74; and
   d) the complement of a), b), or c).

24. A method for determining the presence or amount of the nucleic acid molecule of claim 23 in a sample, the method comprising:
   (a) providing the sample;
   (b) contacting the sample with a probe that binds to said nucleic acid molecule; and
   (c) determining the presence or amount of the probe bound to said nucleic acid molecule,
thereby determining the presence or amount of the nucleic acid molecule in said sample.

25. The method of claim 24, wherein the probe is selected from the group consisting of:
   a) SEQ ID NO:140;
   b) SEQ ID NO:141;
   c) SEQ ID NO:142; and
   d) the ORF of SEQ ID NO:74, or a complement thereof.

26. A method for determining the presence of or predisposition to a disease associated with altered levels of the nucleic acid molecule of claim 23 in a first mammalian subject, the method comprising:
   (a) measuring the amount of the nucleic acid in a sample from the first mammalian subject; and
   (b) comparing the amount of said nucleic acid in the sample of step (a) to the amount of the nucleic acid present in a control sample from a second mammalian subject known not to have or not be predisposed to, the disease;
wherein an alteration in the level of the nucleic acid in the first subject as compared to the control sample indicates the presence of or predisposition to the disease.

27. The method of claim 26 wherein the predisposition is to a cancer.

28. The method of claim 26 wherein the predisposition is to an immune-mediated disease.

29. A vector comprising the nucleic acid molecule of claim 23.

30. The vector of claim 29, further comprising a promoter operably-linked to said nucleic acid molecule.

31. A transformed host cell in culture comprising the vector of claim 29.

32. A transformed host cell in culture which expresses the nucleic acid molecule of claim 23.

33. A method for determining the presence or amount of a nucleic acid molecule selected from the group consisting of:
   a) SEQ ID NO:74;
   b) SEQ ID NO:76;
   c) the ORF of SEQ ID NO:74; and
   d) the complement of a), b), or c);
in a sample, the method comprising:
   (i) providing the sample;
   (ii) contacting the sample with a probe that binds to said nucleic acid molecule; and
   (iii) determining the presence or amount of the probe bound to said nucleic acid molecule;
thereby determining the presence or amount of the nucleic acid molecule in said sample, wherein presence or amount of the nucleic acid molecule is used as a marker for a cell or tissue type.

34. The method of claim 33 wherein the cell or tissue type is cancerous.

35. The method of claim 33 wherein the cell or tissue type is from an immune-mediated disease.

36. A pharmaceutical composition comprising a nucleic acid molecule selected from the group consisting of:
   a) SEQ ID NO:74;
   b) SEQ ID NO:76;
   c) the ORF of SEQ ID NO:74; and
   d) the complement of a), b), or c);
and a pharmaceutically-acceptable carrier.

37. A kit comprising in one or more containers, the pharmaceutical composition of claim 36.

38. A nucleic acid molecule consisting of a nucleotide sequence selected from the group consisting of:
   a) SEQ ID NO:74;
   b) SEQ ID NO:76;
   c) the ORF of SEQ ID NO:74;
   d) SEQ ID NO:140;
   e) SEQ ID NO:141; and
   f) SEQ ID NO:142.

* * * * *

SEQUENCE LISTING

<160> NUMBER OF SEQ ID NOS: 159

<210> SEQ ID NO 1
<211> LENGTH: 1065
<212> TYPE: DNA
<213> ORGANISM: Homo sapiens

<400> SEQUENCE: 1

```
atgacggggc tgctcctcct cagcctccag tcaggctgtg tggcagcgat cacctccatg      60
tcgatggagt gtctgtgcag tttgggagcg aggctctgcc tctctcggtc taccctiggg     120
```

-continued

```
agtgaaatag tgaccgtccc tttgagcccg agagctgggg agaaggccgt gcctgttaac    180
agctgcctgg accctctctg gagagcagca gagagaggcg gggctggagg agatgttgcc    240
aagaacctaa gggtgaaagt catgcttcgc atctgttcca ccttggctcg agatacttca    300
gaatccagct ctttcttaaa ggtggaccca cggaagaagc agatcacctt gtacgatccc    360
ctgacttgtg gaggtcaaaa tgccttccaa aagagaggca accaggttcc tccaaagatg    420
tttgccttcg atgcagtttt tccacaagac gcttctcagg ctgaagtgtg tgcaggcacc    480
gtggcagagg tgatccagtc tgtggtcaac ggggcagatg gctgcgtgtt ctgtttcggc    540
cacgccaaac tgggaaaatc ctacaccatg atcggaaagg atgattccat gcagaacctg    600
ggcatcattc cctgtgccat ctcttggctc ttcaagctca taaacgaacg caaggaaaag    660
accggcgccc gtttctcagt ccgggtttcc gccgtggaag tgtgggggaa ggaggagaac    720
ctgcgggacc tgctgtcgga ggtggccacg ggcagcctgc aggacggcca gtccccgggc    780
gtgtacctct gtgaggaccc catctgcggc acgcagctgc agaaccagag cgagctgcgg    840 gccccccaccg cagagaaggc tgccttttc ctggatgccg ccattgcctc ccgcaggagc    900
caccaacagg actgtgatga ggacgaccac cgcaactcac acgtgttctt cacactgcac    960
atctaccagt accggatgga gaagagcggg aaaggggggaa ttctgctttc gatttggaat   1020
ctgaaagtag ggagaaatct tgaaaacaag gaaacagttc attaa                   1065
```

<210> SEQ ID NO 2
<211> LENGTH: 354
<212> TYPE: PRT
<213> ORGANISM: Homo sapiens

<400> SEQUENCE: 2

```
Met Thr Gly Leu Leu Leu Ser Leu Gln Ser Gly Cys Val Ala Ala
  1               5                  10                  15

Ile Thr Ser Met Ser Met Glu Cys Leu Cys Ser Leu Gly Ala Arg Leu
             20                  25                  30

Cys Leu Ser Arg Ser Thr Leu Gly Ser Glu Ile Val Thr Val Pro Leu
         35                  40                  45

Ser Pro Arg Ala Gly Glu Lys Ala Val Pro Val Asn Ser Cys Leu Asp
     50                  55                  60

Pro Leu Trp Arg Ala Glu Arg Gly Gly Ala Gly Gly Asp Val Ala
 65                  70                  75                  80

Lys Asn Leu Arg Val Lys Val Met Leu Arg Ile Cys Ser Thr Leu Ala
                 85                  90                  95

Arg Asp Thr Ser Glu Ser Ser Phe Leu Lys Val Asp Pro Arg Lys
                100                 105                 110

Lys Gln Ile Thr Leu Tyr Asp Pro Leu Thr Cys Gly Gly Gln Asn Ala
            115                 120                 125

Phe Gln Lys Arg Gly Asn Gln Val Pro Pro Lys Met Phe Ala Phe Asp
        130                 135                 140

Ala Val Phe Pro Gln Asp Ala Ser Gln Ala Glu Val Cys Ala Gly Thr
145                 150                 155                 160

Val Ala Glu Val Ile Gln Ser Val Val Asn Gly Ala Asp Gly Cys Val
                165                 170                 175

Phe Cys Phe Gly His Ala Lys Leu Gly Lys Ser Tyr Thr Met Ile Gly
            180                 185                 190

Lys Asp Asp Ser Met Gln Asn Leu Gly Ile Ile Pro Cys Ala Ile Ser
        195                 200                 205
```

```
Trp Leu Phe Lys Leu Ile Asn Glu Arg Lys Glu Lys Thr Gly Ala Arg
    210                 215                 220

Phe Ser Val Arg Val Ser Ala Val Glu Val Trp Gly Lys Glu Glu Asn
225                 230                 235                 240

Leu Arg Asp Leu Leu Ser Glu Val Ala Thr Gly Ser Leu Gln Asp Gly
                245                 250                 255

Gln Ser Pro Gly Val Tyr Leu Cys Glu Asp Pro Ile Cys Gly Thr Gln
            260                 265                 270

Leu Gln Asn Gln Ser Glu Leu Arg Ala Pro Thr Ala Glu Lys Ala Ala
        275                 280                 285

Phe Phe Leu Asp Ala Ala Ile Ala Ser Arg Arg Ser His Gln Gln Asp
    290                 295                 300

Cys Asp Glu Asp Asp His Arg Asn Ser His Val Phe Phe Thr Leu His
305                 310                 315                 320

Ile Tyr Gln Tyr Arg Met Glu Lys Ser Gly Lys Gly Ile Leu Leu
                325                 330                 335

Ser Ile Trp Asn Leu Lys Val Gly Arg Asn Leu Glu Asn Lys Glu Thr
                340                 345                 350

Val His

<210> SEQ ID NO 3
<211> LENGTH: 366
<212> TYPE: PRT
<213> ORGANISM: Homo sapiens

<400> SEQUENCE: 3

Gln Val Ile Leu Tyr Asp Pro Ala Ala Gly Pro Pro Gly Ser Ala Gly
  1               5                  10                  15

Pro Arg Arg Ala Ala Thr Ala Ala Val Pro Lys Met Phe Ala Phe Asp
                 20                  25                  30

Ala Val Phe Pro Gln Asp Ser Glu Gln Ala Glu Val Cys Ser Gly Thr
             35                  40                  45

Val Ala Asp Val Leu Gln Ser Val Val Ser Gly Ala Asp Gly Cys Ile
     50                  55                  60

Phe Ser Phe Gly His Met Ser Leu Gly Lys Ser Tyr Thr Met Ile Gly
 65                  70                  75                  80

Lys Asp Ser Ser Pro Gln Ser Leu Gly Ile Val Pro Cys Ala Ile Ser
                 85                  90                  95

Trp Leu Phe Arg Leu Ile Glu Glu Arg Glu Arg Thr Gly Thr Arg
                100                 105                 110

Phe Ser Val Arg Val Ser Ala Val Glu Val Cys Gly Arg Asp Gln Ser
            115                 120                 125

Leu Arg Asp Leu Leu Ala Glu Val Ala Pro Gly Ser Leu Gln Asp Thr
        130                 135                 140

Gln Ser Pro Gly Val Tyr Leu Arg Glu Asp Pro Val Cys Gly Ala Gln
145                 150                 155                 160

Leu Gln Asn Gln Ser Glu Leu Arg Ala Pro Thr Ala Glu Lys Ala Ala
                165                 170                 175

Phe Tyr Leu Asp Ala Ala Leu Ala Ala Arg Ser Thr Ser Arg Ala Gly
            180                 185                 190

Cys Gly Glu Asp Ala Arg Arg Ser Ser His Met Leu Phe Thr Leu His
        195                 200                 205

Val Tyr Gln Tyr Arg Met Glu Lys Cys Gly Arg Gly Gly Met Ser Gly
    210                 215                 220
```

```
Gly Arg Ser Arg Leu His Leu Ile Asp Leu Gly Ser Cys Glu Ala Ala
225                 230                 235                 240

Ala Gly Arg Ala Gly Glu Ala Ala Gly Gly Pro Leu Cys Leu Ser Leu
            245                 250                 255

Ser Ala Leu Gly Ser Val Ile Leu Ala Leu Val Asn Gly Ala Lys His
            260                 265                 270

Val Pro Tyr Arg Asp His Arg Leu Thr Met Leu Leu Arg Glu Ser Leu
            275                 280                 285

Ala Thr Ala Gly Cys Arg Thr Thr Met Ile Ala His Val Ser Asp Ala
            290                 295                 300

Pro Ala Gln His Ala Glu Thr Leu Ser Thr Val Gln Leu Ala Ala Arg
305                 310                 315                 320

Ile His Arg Leu Arg Arg Lys Lys Ala Lys Tyr Ala Ser Ser Ser Ser
                325                 330                 335

Gly Gly Glu Ser Ser Cys Glu Glu Gly Arg Ala Arg Arg Pro Pro His
            340                 345                 350

Leu Arg Pro Phe His Pro Arg Thr Val Ala Leu Asp Pro Asp
            355                 360                 365

<210> SEQ ID NO 4
<211> LENGTH: 130
<212> TYPE: PRT
<213> ORGANISM: Mus musculus

<400> SEQUENCE: 4

Pro Ala Pro Thr Gly Lys Ser Tyr Thr Met Ile Gly Arg Asp Asp Ser
1               5                   10                  15

Met Gln Asn Leu Gly Ile Ile Pro Cys Ala Ile Ser Trp Leu Phe Lys
            20                  25                  30

Leu Ile Asn Glu Arg Lys Glu Lys Thr Gly Ala Arg Phe Ser Val Arg
        35                  40                  45

Ile Ser Ala Val Glu Val Trp Gly Lys Glu Glu Asn Leu Arg Asp Leu
    50                  55                  60

Leu Ser Glu Val Ala Thr Gly Ser Leu Gln Asp Gly Gln Ser Pro Gly
65                  70                  75                  80

Val Tyr Leu Cys Glu Asp Pro Ala Glu Lys Ala Ala Phe Phe Leu Asp
                85                  90                  95

Ala Ala Ile Ala Ser Arg Arg Ser Asn Gln Gln Asp Cys Asp Glu Asp
            100                 105                 110

Asp His Arg Asn Ser His Met Leu Phe Thr Leu His Ile Tyr Gln Tyr
            115                 120                 125

Arg Met
    130

<210> SEQ ID NO 5
<211> LENGTH: 147
<212> TYPE: PRT
<213> ORGANISM: Mus musculus

<400> SEQUENCE: 5

Gly Lys Ser Tyr Thr Met Ile Gly Lys Asp Ser Ser Pro Gln Ser Leu
1               5                   10                  15

Gly Ile Val Pro Cys Ala Ile Ser Trp Leu Phe Arg Leu Ile Asp Glu
            20                  25                  30

Arg Lys Glu Arg Leu Gly Thr Arg Phe Ser Ile Arg Val Ser Ala Val
        35                  40                  45
```

-continued

Glu Val Cys Gly His Asp Gln Ser Leu Arg Asp Leu Ala Glu Val
 50                  55                  60

Ala Ser Gly Ser Leu Gln Asp Thr Gln Ser Pro Gly Val Tyr Leu Arg
 65                  70                  75                  80

Glu Asp Pro Val Cys Gly Thr Gln Leu Gln Asn Gln Asn Glu Leu Arg
                 85                  90                  95

Ala Pro Thr Ala Glu Lys Ala Ala Phe Tyr Leu Asp Ala Ala Leu Ala
            100                 105                 110

Ala Arg Ser Thr Ser Arg Ala Gly Cys Gly Glu Glu Ala Arg Arg Ser
        115                 120                 125

Ser His Met Leu Phe Thr Leu His Val Tyr Gln Tyr Arg Val Glu Lys
    130                 135                 140

Cys Gly Gln
145

<210> SEQ ID NO 6
<211> LENGTH: 302
<212> TYPE: PRT
<213> ORGANISM: Drosophila melanogaster

<400> SEQUENCE: 6

Met Ala Thr Thr Ser Thr Ser Asn Met Ser Arg Asn Gly Gly Phe Cys
 1               5                  10                  15

Gly Ala Leu Gln Arg Ala Pro Pro Met Pro Pro Thr Leu Ile Arg
             20                  25                  30

Arg Leu Ser Ser Arg Glu Cys Tyr Gly Val Gly Lys Val Lys Val Met
         35                  40                  45

Leu Arg Val Ala Asp Arg Asp Arg Asn Ser Gly Thr Glu Pro Asp
 50                  55                  60

Phe Met Ala Leu Asp Lys Lys Arg Gln Val Thr Leu Thr Asp Pro
 65                  70                  75              80

Arg Thr Ala Cys Pro Pro Gln Ala Ala Gln Glu Arg Ala Pro Met
                 85                  90                  95

Val Ala Ala Pro Lys Met Phe Ala Phe Asp Asn Leu Phe Thr Gly Glu
            100                 105                 110

Asp Lys Gln Ser Asp Val Cys Ala Ser Ala Leu Ser Glu Val Ile Pro
        115                 120                 125

Ala Val Leu Glu Gly Ser Asp Gly Cys Leu Leu Ala Met Gly Tyr Pro
    130                 135                 140

Ala Thr Gly Gln Ala Gln Thr Val Leu Gly Glu Leu Gly Gly Ser
145                 150                 155                 160

Gly Ser Gly Ser Ala Ser Gly Ser Gly Val Ala Cys Ser Leu Gly Ala
                165                 170                 175

Ala Pro Cys Ala Ile Ala Trp Leu Tyr Lys Gly Ile Gln Glu Arg Arg
            180                 185                 190

Gln Lys Ser Gly Ala Arg Phe Ser Val Arg Val Ser Ala Val Gly Val
        195                 200                 205

Ser Ala Thr Lys Pro Asp Ala Leu Ser Gln Asp Leu Leu Ile Ser His
    210                 215                 220

Ala Ala Glu Tyr Gly Val Tyr Ser His Ile Lys Pro Asn Ala Leu Phe
225                 230                 235                 240

Ile His Ser Pro Leu Leu Phe Phe Trp Ser Gln Tyr Trp Asn Ser Gly
                245                 250                 255

Ser Asp Tyr Gly Tyr Thr Glu Ser Asp Asp Ser Pro Gly Ile Tyr Leu
            260                 265                 270

```
Arg Asp Asp Phe Leu Ala Val Gln Arg Asn Tyr Val His Pro Pro Pro
            275                 280                 285

Ser Val Arg Pro Phe Ser Ser Thr Gln Arg Ser Pro Asp Ala
    290                 295                 300

<210> SEQ ID NO 7
<211> LENGTH: 359
<212> TYPE: PRT
<213> ORGANISM: Caenorhabditis elegans

<400> SEQUENCE: 7

Met Glu Ala Cys Ser Ser Lys Thr Ser Leu Leu His Ser Pro Leu
  1               5                  10                  15

Arg Thr Ile Pro Lys Leu Arg Leu Cys Ala Ser Ile Ser Ser Glu Asp
             20                  25                  30

Val Ala His Gly Arg Cys Ser Leu Thr Asp Gln His Leu Gln Ile Glu
         35                  40                  45

Gly Lys Asn Tyr Ser Lys Thr Thr Phe Asp His Ile Phe Arg Thr Asp
     50                  55                  60

Ala Thr Gln Asp Asp Met Tyr Thr Ala Phe Leu Ser Asp Thr Ile Asn
 65                  70                  75                  80

Ser Val Phe Ala Gly Asn Asp Ala Thr Val Leu Ala Met Gly Ala Lys
                 85                  90                  95

Thr Asn Gly Lys Asp Glu Arg Leu Tyr Gly Asn Ser Val Ser Arg Asn
            100                 105                 110

Gly Leu Val Gln Met Ala Ile Thr Gln Leu Met Asn Ala Leu Asp Asp
        115                 120                 125

Asn Lys Asp Ser Glu Glu Arg Ile Gln Val Arg Met Ser Ala Ile Met
    130                 135                 140

Val Ser Gln Asn Glu Ser Ser Ile Val Asp Leu Leu Ser Pro Phe Asn
145                 150                 155                 160

Pro Asp Pro Arg His Arg Val Val Lys Ile Val Asp Asp Ala Arg Thr
                165                 170                 175

Gly Val Phe Ile Asp Asn Glu Ser Glu Ile Arg Val Glu Thr Ile Asp
            180                 185                 190

Gln Ala Leu Phe Tyr Leu Asn Thr Ala Val Asp His Arg Met Ile Gln
        195                 200                 205

Asp Glu His Thr His Arg Thr Ser His Val Phe Ile Ser Leu Ser Leu
    210                 215                 220

Tyr Ser Tyr Lys Met Gly Asp Lys Met Gln Gly Gly Arg Arg Arg Leu
225                 230                 235                 240

Cys Phe Leu Asp Met Gly Ile Gly Glu Arg Asn Ser Thr Asn Gly Gly
                245                 250                 255

Met Thr Met Pro Ala Leu Gly Ser Ile Leu Leu Ala Met Val Gln Arg
            260                 265                 270

Asn Lys His Ile Pro Ser Arg Asp Ser Ser Val Cys Gln Leu Ile Arg
        275                 280                 285

Cys Ala Leu Ser Thr Ser Arg Phe Thr Thr Phe Val Phe Ser Phe Gly
    290                 295                 300

Ala Lys Ser Asp Asp Asn Glu Asn Ile Ala His Leu Ala Cys Lys Ile
305                 310                 315                 320

Ala Arg Thr Arg Ala Lys Ser Met Val Gly His Gly Arg Lys Ser Ser
                325                 330                 335

Gly Thr Met Ser Thr Gly Thr Met Glu Ser Asn Ser Ser Ser Cys Gly
```

```
                340             345             350
Thr Thr Thr Ile Thr Pro Gly
        355

<210> SEQ ID NO 8
<211> LENGTH: 7560
<212> TYPE: DNA
<213> ORGANISM: Homo sapiens

<400> SEQUENCE: 8
gtattctcag agctgccagg agtgcatcga gcctgtaatt tcctgttctc tgaatccccc      60
atctttctgc agctccaagc tttgtgtccc acagcctgtg actctgtgct aacaaatcgc     120
tattgtccag tggggcgaat ggtggctgga actaaagaat tgctgtctgg tttctattca     180
aatccaggta gcgagatata tgaatggact tttcgaatcg tcatgtgaat aacgtctgct     240
cggcatgaag gctcagagcc atgctaggaa ggattaactc gtaggctgac cactaacatc     300
ctttgtggta cgagggagaa acattcccaa gtatcatttt attcacactt aattttctat     360
cccataccCc caaaataagg ctagctattt aattagttgg ctgcttttct cttaattttt     420
agtgtttctg ttgataatgt gtaagtttgg gaaaatgcta agtagctttt cacttagaac     480
actgttattt tctcttttaaa gttttctacc ttacatttat tatagcatag ttatctttat     540
agcatagatg cagaaagtaa gagagagctt gttttttcaa gaaaacaacc ctttaaaata     600
ctttccaacc catgaaggga aaatcctcc tttttttcccc caagtgcatt ctacttatta     660
ctttgcattt ttctcccaaa gtccaaattt atgcaaagaa atagaaaaca gttcaaatg      720 caatgcatta accaaataaa acaagtctgc ttcaaattag gaaccaacct aagcatttgt     780
aaagtgtagc agaatcagaa ttctttttaaa aattagattt ggaacctgaa ctatataatt     840
cataattctc attttctgt ggaaaattat tttatctttc tcctgtatac ctgaaaaaat     900
gtccataggc ttaaagggtc atgcttttac attccttcca tatcacaggt actatgaagt     960
aaggagactt ttaggtttct ttttgtctta aactcagaca gctttgtaag cagtagtgtg    1020
tagattacaa gagttagaca aaagcaggcg cgactgagaa gagttggtgg gggagaagct    1080
tggggcactt cctgtcactc aacacattcc agatcactaa aaaatttcca caccctctgc    1140
attccccctt gcccactcca gttcccggta ttttctgatt ccatatgttg tggtatttac    1200
catacttctc tccctcacta ggctctggca agactgcttc agaggggatg cattcctta    1260 gattgcacaa agcggagctg ggaaaatggc tggcagtttc agaatctagt cacgatcgca    1320
cgcatgagca cctcacacat ccatgtccct acccgccccc ccgctcccgc ccctgcagct    1380
ggctgacctg tctcacccac tgctggccta tcgaacggcc aggactgtct ggttttggct    1440
cgtgcctttg tccatgtctg cttagttcc tctctgtcta tgcttgcctc tacccccacc    1500
gccccaggcg gcacaagtgt ttggccacac aaaactagag atagaaaagg tggtaaaaac    1560
ttcaaacttt tctaaattct ccaacagttt atttcttgtg aatttcttcc ttctttaaat    1620
actccatttt aagaaaacaa aaaaattaat tatctaaagg caaagaatgg aaagcaacct    1680
ttgtgttcct tataataact gacttcataa ctctctccag ctgcgttatg ggatgtgtat    1740
aaaaagcttc tgttctgaga acaaaggagc acgtgcagaa atgagacgaa aaaatccact    1800
gacagtattc cattacacaa attacttaaa agatttagt caagcccctc aacagattca    1860
attttaaaat ggcttttagt taaaaaaaaa aaattgaaag tgcttaccca gtaaaagaac    1920
cgaagtagtc ctgaactgtt acgtaagact ttttacagtt ggatctttgt caaagggga    1980
```

```
tgggggtgat gggagaaagc agcaacgaca atcaaaaaag ttcgagctgc tgtggctaga    2040
ggacaacttc tgtgtttcca gataggattc ttgctgtaga aatggaactt ccagccagca    2100
cagcatcctg tcccagtaga gaaatgagtt tgtcagttaa acaaaaaaaa aaattagata    2160
ctggaaccca ggctagacga ggtattgaac cgcgccagat ttccttgcag ccctgtctgc    2220
tcagctcgca ttgaactata tatgacccag atgatggaca gaagcacatt tagtcatgtg    2280
cacactggaa gaaagcggat tgctggtcc ctggcagtgc aggggtttgt cttctgattg    2340
ggctgtgccc tgatcggtga aatgtgaagc cctcaccatt cagaggccgt aattcaggac    2400
tggcagtttg agtgtctggc tgcctctagt cactgagaga ctttgaaggt gttgcttttg    2460
tttggtggca ttacccaccc agaggttgct tacacctctc tacttgtgtc agaagaaata    2520
ctagtctttc tgaaatacaa ataggcagcc gattttcct gaatcctaaa tcaccctatt     2580
gttgataaac ttggctctaa ctgaaaccaa ttatttgatt tgaaaattta ttgtgatcct    2640
aaccaagctt catatccaga ccaacccttg gtcttgattt tataggtttg ataaggtaaa    2700
aataaaagtg gcatatttga cttgaagcc tctatatgat ataaattgct cttaatgaaa     2760
attggataga tggacaacag agaagtgaag ttttagattc tggagtgttt ggatgtatga    2820
ggaagaagct ttatgtcttt ttatcccctt tgtgagactg tcactcttgt cccagtccta    2880
gtcacattag gggttgctgg gggggggaag ctatgaaagc atggacccta ctgagctgtg    2940
acatagcctt taatcatgca agacagccac ggtctgctct cttcagtctg tctgaactag    3000
ggtccttggg gtttattttc catctttctg agccactggg aaaccaggtc attatacagg    3060
actgtcattt gtgacatttt tgtttagtac atggcagttg ctttgtttat ttaatgcaag    3120
ttgacacttc tttaaagttt caaaacagta agttgtttt gtgagacctt gactctgata     3180
tatgaaatct actctacatg gaccaatcat tttttttccgt ggactttctt gtctctttag   3240
aaattagctt atagagtcct aaattgatac ttaaacatac caatagttct gtttatttct    3300
tgcctttctc acagttgttg aaataattcc atctgtctct tttgctgtaa attttgggtt    3360
tggatgtttg tacttggaat ttttagatg ttgactatat tatgcagcac cttccatatg     3420
aggactaccc cagaattatt ctcttgtctt aacccgagaa aagctgtttt gatgcactat    3480
tagatataag aatgttcgaa agaagaggag atgagcactc tcttgctttt tgtaagccac    3540
aagacaatct tttttttttc taagttgtgg taaggtatat gtaacataaa attgactgtt    3600
gtaataattt ttaagtgtat agttctgtgg tgttaagtgc attcacgttg ttttgcagcc    3660
ttcaccacca tccatccacc acagaactct tctcctcttg caaaactgaa attctctacc    3720
tacctgttaa acactaactt gccattcttc cctcccccag gccctgggga caaccatcat    3780
tctactttct ctttgatttt ttgttttttg ttttttggaga cggaattta ctcttgttgc     3840 ccaagctggg atgcaatggc actgtcttgg ctcactgcaa cttccgcctc ctgggttcaa    3900
gcaattctcc ttcctcagcc tcctgagtag ctgggactac aggtgcccac caccacgcct    3960
ggctagtttt tgtatttta gtagacacgg ggtttcacca tgttggccag gctggtctcg     4020
aactcgtgat ctcaagtgat ccacccacct tggcctccca aaatcctaga attacaggca    4080
tgagcccacc gtgcctagcc tctgtctgtt tgcttttga ctactctaga tacctcatat     4140
aagtggaata atacaagatg tgttcccttt tgacaggctt atttcactta gcatggtgtc    4200
ctcaaggttc atgcatgttg tcgcatgtca gaatttcctt acgttttaag gctgaataat    4260
ataccattgc atgtgtatac tactgtctta gtccctttag tgttgctgta aaggaatacc    4320
tgaggctggg taatttataa agaaaagagg tttatttggc tcatggttct gcaagctgta    4380
```

-continued

```
caagaagcat ggcaccagct tctggtgagg gcctcaagct gcctccattc atggcacaag    4440
gtgaaaggga gctggtgtgt gcagagatca catggtagga gaggaggagg caagagagag    4500
aagaaggagg tgccagacta ctttaaaacc atcagctttt gcagggagtt atagagccag    4560
cactcactga ctactgcaag aatggcacca agacattcat gagggatctg ccttcatgac    4620
ccagacacct cccaccaggc cccaccacca acataagggg ttagatttca gcatgagact    4680
caatgagggg ggagcaaaca aattacatcc aaactgtagc aaccacattt tgtttatcca    4740
ttcatctgtc aatggacact taagtagctt ccactttttt gctatcaaga cagttttcct    4800
tgactattct taaaatcatg tgagggcttc tttacagagc tgttctgacc catctcagaa    4860
gctcttttca ctttataagt tgtaagggtt ttgatgggcc ttttaactct agagaccagc    4920
tagtccctaa catcaggttt gctagagaag ggaagattct ttccagcctt cctggatgac    4980
acctaataca tactatattc ctagtaattc tgttatactt aagatttatg ggttcatctt    5040
tcctgttaca ctgtgagccc ttcctgggct gggacgatgg ccagtttctc ttgagttgtg    5100
ccttgtgcct ctgtataggc acagggccta ttatgaagta gatatcaata aatattagtt    5160
ggaaaaaatg tgaattagta aataataatt tgtattgggt ttttatgtgc cagatgtttt    5220
gaatacattt agctaattta atcttcaaaa cagtcctttc agatacatat tgttatcttc    5280
atttaataga tgagggaact tgtcaaaggc ctcagagatg taaaatgtat aactgggatt    5340
tgaacctttg ttcaaattgc ttgttctcgc ttgactcaag agccattatg ttagaggcag    5400
acttcatagt cagttgatga tcagtggggtt tggaaacatg aaatttagct caggcatcgg    5460
ctccaaatta aatactcttt cattgggcat taggaactat acccttctga tatggctcat    5520
gaatggatgc tcagaggaaa gcttggctcg ttagttactt ggacctttta tagggacttt    5580
agctgaacaa ctaattgctg aactcagttg gcaaaggctc ttctgtgggt aaatcctctt    5640
tcacatgtta ttttgaaagt gcagttaaat tctaacatac atgatgtggc cctgaatgg     5700
atgcatcagt tttctttatt ctgtttgttt ggcaggtgtg tgtgtgtgtg tgtgtgtgtg    5760
tgtgtgtgtg tgtacaaaaa aaaaaaatgt atgtataaaa gcaaccagta tctaggtatc    5820
aggaacaaaa caaggttttt tatggagctt acattctaat ggggagacag aaaaatgaat    5880
tctcaaagta ctatgaagtg aaacatgaag ctacactgtg aagaaaatag ggtagtgtgg    5940
tgatggagaa tgactgactg gtgggatgtg gtggattggg agacatcttg aatgaggaag    6000
tatcgggcta tgcctctctg aggaaccaaa gtatgcaagc tgagagccaa gtcatgacat    6060
gaagaacctc agcctacaaa gagccagaag aatgaactgg gtagtggcaa caagaaatgc    6120
aagagctctc atgtgggatt gagcttagtg tgcttgagga gccaaaaggg tagtatggct    6180
aaaatggagt gaatgcaagt agggggtgatg ttggagaggt gggatggggc cctatcacat    6240
aggaccttgt aagctatagt aagaaatttg ggtttttttcc aagtgtattt tttcccaaat    6300
ttgttttttt ccccccaaat agtaggacat tggaaggttt taagcagaat ggtaacttgt    6360
tctgcaggcc gaagaagtcc ttgtgtgcag ttccttgtcta tgtttagtcc tctgaggccc    6420
ccttgacact atctttaact ggggttcctc ccaagctgag aatcttgcca aggttctcac    6480
atgtcagtgg ccacctttga gtgtcctaga agaatcatat ttctttata accattttgg    6540
ggctaacatt ggtttcattg ccctttccac aacagagagg gtttgttcaa cgagagcttc    6600
ttccagcatt tcatacatc actgttgcct gggtagggtt ttgcagcctg attctctgta    6660
ttaatttagg ataaaattca gttattaatt agacctgatc tttcttgtc aataatttag     6720
```

```
aagcatatgt cctcggcaca taatgttggc tgactgtttg gttaataata tgttcttgaa   6780
gacatacttc tggaaatctg aaattgataa gtgaagagga actttcttac tattcataaa   6840
taaggttgta ttcagctatt ctgactctag tagggttaat tgctaacatt tgacctacat   6900
tattttattt tttcaatttc tcaaaaactc tgaaaagtat aggccagggg ccttggctca   6960
tgcctgtaat gccagtgctt tgggacgcca tggtggaagg attgcttgag gccaggagtt   7020
cgagaccagc cttagcaaca tagtaagacc cccatatcta caaaaaataa atttgcctgg   7080
cttgatgata tgtgcctgta gttctagtta cttgtgaggg tgaggagaga gggtcacttg   7140
agtgcaggag ttcaaggctg cagtgagcta tgatgatgcc accatactcc aggatggtga   7200
cagagactct gtctcttaaa aaacaacaac aaaacaaacc tctgacaaat acagaaaata   7260
acagcataca cctgatagtc ccattttata ggcaagtgac atctagtatt ttcatagtaa   7320
aatatcatgt agtgtcatct gatactttct tcttttact aaaaaaaaaa aaaagttact   7380
tgcaagctac tcagttgatt tcacagctta ctgaaggggc agccagaact ttggaaagca   7440
caaaaggtga gaaaactgag gctctggtgg ttaaatgact tgtccagtgt cacatagcaa   7500
ggaagaggca gagctgagac ttgaaccaga gcttgattcc aaagttcttg ctcgtactat   7560
```

<210> SEQ ID NO 9
<211> LENGTH: 102
<212> TYPE: PRT
<213> ORGANISM: Homo sapiens

<400> SEQUENCE: 9

```
Met Met Met Pro Pro Tyr Ser Arg Met Val Thr Glu Thr Leu Ser Leu
 1               5                  10                  15

Lys Lys Gln Gln Gln Asn Lys Pro Leu Thr Asn Thr Glu Asn Asn Ser
            20                  25                  30

Ile His Leu Ile Val Pro Phe Tyr Arg Gln Val Thr Ser Ser Ile Phe
        35                  40                  45

Ile Val Lys Tyr His Val Val Ser Ser Asp Thr Phe Phe Phe Leu Leu
    50                  55                  60

Lys Lys Lys Lys Ser Tyr Leu Gln Ala Thr Gln Leu Ile Ser Gln Leu
65                  70                  75                  80

Thr Glu Gly Ala Ala Arg Thr Leu Glu Ser Thr Lys Gly Glu Lys Thr
                85                  90                  95

Glu Ala Leu Val Val Lys
            100
```

<210> SEQ ID NO 10
<211> LENGTH: 7380
<212> TYPE: DNA
<213> ORGANISM: Homo sapiens

<400> SEQUENCE: 10

```
gtgagtcagg gaggagaaag gtaggctgct tgggccggtg gccttttgtt cttgcaattc     60
tcttcttctc cctaatttct ggttcattgc ctctttagac aagtctccag aagttcttcc    120
ttgaaagtcc aggctcagga actctcagcc actgaagata aaggccacat tagtcccttt    180
ttctgggaag ccgtgtatca ttacgcatca ggagaatgca ggggtcctgg tccaccctac    240
agtcatagct tgaggctata ttcccagcag gctctcccca cgggaagggg ccccagcagc    300
tcccagtttc cattctgcca gttttactgc tgctataaaa agagcctgct gtgtgactgc    360
cttagcaaaa gtcctgcctt agaaaaagca atgagaggtg ttggcttagt gcaggtcact    420
```

-continued

```
tgcccacccc tgaatcagtc cctgggtgcc aggagagcag atttttttg ctggcctatg      480 ttgggcccca gatcagcttt tgccccaccc aaagctcacg gcctgaagat ggcagggaaa      540
tggtgtccca caggagagg aagtcctata accagaagag gcagagatg atgagaaggc       600 agaaccctg gggctgtggg aggctcccct agtacgcagt gtggccaggc tatataaacc      660
tggcgcaggc ctgtcacagg gaggaatcgt acctcttcct tccctgatga aattaagcaa      720
agggtactta cgctcccaga ggggcagtag ctttggcaat accgtgtcta ggttttttctt    780 taccgaaagc agattttttcc ttaacaagag ttgaaatcca cattttttatt tcccactaag    840 tctgttgaga ctgctttaac ggaatagcac agactgggtg gcctctgagt aacagaaatg      900
tattgctgac agttctgaaa gctgggaagt tcaaactcaa ggcaccagca aatgcagtgt      960
ctgctgaggg cctgtttttt gtttcctgga tgatactttc tggcagagtc atcatatagt     1020
ggaaggagca aacaggctcc cttgggcctc tgttataagg gcactaatct cattcatgag     1080
gtatccactc tcatgaccta gtcacctccc aaaaagctcc atctcctaat gccatcactt     1140
taggatttag gtgttaaact taggagttct gaagaaaaca ttcaccatag catccactga     1200
gttgctgctg tgacttaccc attggaatag catatgctag taatgggatt cactcgatct     1260
atctacacac aaagagccct gtcatacacc aggccatgtt ccaggtcctg gagatgctgt     1320
agaaactcaa tgagtctgtc ctcatagagc ttcacttttta gcgggggaga gaaataataa    1380
acagatgcat gtatatactg ttgtaatgta aagcggtatt aatgctatca agaaaactcc     1440
agcaggtaag ggtggagagt aatggagaat cactatttag tgtggatagg aagacttctc     1500
agaggagttg gcttttgagc agatgcctaa ctagagtgaa ggagatagtg tcaatgtcat     1560
ggttgagaat aagacttcct gggtacagat ctcgtctctg gttcctagtt atgttaccct     1620
gccaagttac ttagcctcat ctgcctctac tttctcatgt gaaaactgca ataatatta      1680 gaaagctagc tcaaggagct gagtgattaa atgagtttac atatataaag ctcttaaagc     1740
agtacatgat catacgttaa tattactatt gctatttgtc agggggaaat gtgtcccagg     1800
cagaaggatt catagacaag ccatttttaac ctagagtctt tgtgcttgga gcaaatgagt    1860
taaggcgcat actggtacaa caaggacttc tcgtaatagg acgtgaatac catttacata    1920
agggtctgat tgttgattta ttgacagttt atcctgccgc acctggaatc ctgagacaaa     1980
ccaaggtgct atgtgtttca cgtcccagtg cagagctctg agcagctcat cagcctctcc     2040
aatgtctctc atttttttttag gtatcgacca aggtcaaatg acctatgatg ccaacactg    2100 gcatgccact gagacctgtt tctgctgtgc tcactgcaag aaatccctcc tggggcggcc     2160
attcctcccg aagcagggcc agatattctg ctcacgggcc tgcagtgctg gggaagaccc     2220
caatggttct gactcctctg attccgcctt ccagaacgcc agggcaagg agtcccggcg      2280 cagtgccaaa attggcaaga acaagggcaa gacggaggag cccatgctga accagcacag     2340
ccagctgcaa gtgagttcta accggctgtc agccgacgta gaccccctgt cactgcagat     2400
ggacatgctc agcctgtcca gccagacacc cagcctcaac cgggacccca tctggaggag     2460
ccgggaagag ccctaccatt atgggaacaa gatggagcag aaccagaccc agagccctct     2520
gcagctcctc agccagtgca acatcagaac ttcctacagt ccaggagggc aagggctgg     2580 ggcccagccc gaaatgtggg gcaagcactt cagcaacccc aaaaggagct cgtcactggc     2640
catgacagga catgctggca gcttcatcaa ggaatgccga aagactatt acccggggag      2700 gctgagatct caggagagct acagtgatat gtctagtcag agtttcagtg agacccgagg    2760
cagcatccaa gtccccaaaat atgaggagga agaggaagag aagggggct tgtccactca    2820
```

```
gcagtgtcgg acccgtcatc ccatcagttc cctgaaatac acagaggaca tgacgcccac    2880
agagcagacc cctcggggct ccatggaatc cctggccctg tctaatgcaa caggtaggtt    2940
ctgttcacct tgaaaacaga tagaaagggg gtagtctctg ggtgactgga tgctggtccc    3000
caggaatttt tttttttttt gaaatggagt ctcgctctgt cccccaggct ggagtgcagt    3060
ggcacgatct ccgctcactg caagctccac ctcccgggtt cacgccattc tcctgcctca    3120
gcctcacgag tagttgggac tacaggtgcc cgccaccatg cctggctaat ttttttgtat    3180
ttttagtaca cacgtgtttc accgtgttag ccgggatgtt ctcgatctcc tgacctcgtg    3240
atccacctgc ctcggcctcc caaagtggta ggattacagg cgtgagccac cgtgcccagc    3300
ctggtcctcc ggattttaat gttgtttctg ccacgtgccc tcttctaata ggctgctgag    3360
gaaggtaaac ccaagtttga gatggcttct atctttgatg ggcttccctg taaacaaagc    3420
ctgagacagg tccagatgcc tgtgatgtac tgagggagtg ctctcaggag aaggggagtg    3480
agagaaagag gacagagcat ggggaggagc caagtgagga atggtgtctt cactggggtc    3540
tggcttctgc ctgatcccac aggggactct gatggatgag ttgcactata gaatcaattg    3600
cttcttgtga cgaaggggct gatgttttgt accatcgtgt tagttggtca tcagctttgg    3660
gctgctgagg agtgacaaag ggatgagata gtggatgtgg gcttggggca aggcagctcc    3720
tgttggccaa aggcagcatt aaagaaagaa aatactatgg tctgaatgtt ttccccaaaa    3780
ttcttaaatt aagatcctaa atcccaaggt gatggcatta ggagaagggg ccttttggga    3840
ggtgattaag tcatgagagt ggagacctca tgaatgggat taatgccctt ataaaagagg    3900
tccaagggaa cttgtttgcc ccttgtacca tatgaaggtg gagaaggtgt agctgtgagc    3960
tgatggcagt actcacagca cctggagccc agttgcccca gcgtggtgct gcctggggca    4020
ccaaagcatc catgacagct tctgagactg ttctgaacct gtttctcacc agggaactgg    4080
cttcaaagtg cagataaaga cataagaaat gtttggctag acaaggagaa gacaggcagg    4140
ctgaaaagaa cagaagtaga gagagagaga taatggcatg cttctctctc cagtgaagtt    4200
gtccagctgg ttttgtgtgc gtgggaagac tgatgttggc caggcatggt ggctcatgcc    4260
tgtaatttca gcactttggg gaggccaagg caggaggatc acttgaggcc aggagttgga    4320
gaccagcctg gcaaccata gtgagactct gtctctacaa acatatatgt gtgtgtatat    4380
atataaaata tatagcgtgt gtatatatat atcatatata atatatattg tgtgtatata    4440
taatatataa atatatatga tataaatatat acaaatgtgt tatatatata tatataaatt    4500
agctggactt ggtggcacat gctcatagtc ccagctactt aggagactaa agcaggagga    4560
tcacttgagc ccaggaagtt gaggctgaac taagcaatga tcccacctct gcactccagc    4620
ctgggcagca gagtgacaac ctgtctctag aaaaaaaaaa aaaaaattt aatattattg    4680 atttaatatt ttaaacatta tttaaaaaat atttttaaat gtgggaaaaa atagagtaac    4740
gtagattttc tctgtgatag tgctacttaa agcagaatct gaggataaca ctggctgaga    4800
actatcaccc atcagcagtg agattagtac ttaacaccta tcagcagcga gattagtact    4860
gaaactggaa gtgttagaaa cttatagcag ttcgatgttg cggtgccatc caagtgcgtt    4920
ttcagcaggc ttgtcttatt gatcaggtta tagacccatc agggtgttat agaactcaca    4980
tactgagctc tttgtgctttt gtgctgtgtc tcagacatgc tcagcagggc catatgtcgg    5040
tccacaaggg attgaaaatg aaaacaaact ggtccttcac cactgatagc ttgagaagag    5100
tagcgctcta agatgtgcta agtatatctg ccccttttgtg ggcaaggtac cagaggaggg    5160
```

-continued

```
agatatacgt ctgcccctta cagcaaggat tccatagccg atggtgtctg gatagagact    5220
gtgataatgt tagccccatt tgaaggggac ggccactgct cagctccagc tgcttgttgc    5280
catgtgctgg gatatttatg tatccaccta acctttatat agctcttgca atgtgtcaaa    5340
cattgttctg agcacgtcat aaatattagc ttgcttaatt acattgtcat aacactgtga    5400
gggaggaata ttgttatgat tctcatttca gagttgaaga acagaaatg gagaggttga    5460 gggactcacc caaagtcact cagctttcag agtggtagag cagggatttg aacctgtgca    5520
tatgatttca gaaccttgct cttaatcaca ccaggctgcc agtctaatac aagccccatc    5580
ctgtcagatc ttccagtttt tccagagaag ttaaaaatgt ggatttttaa aaatatgaaa    5640
tctatttcaa cactgctaga caaacaaaat gaggctctga gttgtagctt gtccatgcag    5700
tgggttttac tttctatcct cctcaaatac atccacatct gtgttcccat ttgtccaaga    5760
acaaagagta gatatcctca tccccatgtt tcagatggaa aaaaaaaaa aaaatgaggc    5820 cttggtgact aagcgccttg cctgatgtct tagaagggag caattagtgc agagtgatga    5880
ctgcctgctt ccagcccagg ttatgttatt ctcgaaagat ttatgtgcta taattattta    5940
agaggacagc agataaatat atacttcagc ctctgaagaa gagtttctca aagctagacc    6000
acctgcatta gaatcatggg tgtgcttgat tcaaacatag gctcctgggc ctcccctaa    6060 cccttgcat cagaactcta cagaggtggg gcccaggaat ctgcatgtta agcagatctc    6120
tgctgaggct gatgtgcacc attgtctgag gggagatgtg cctgggtttg tctgctctga    6180
ctgtatcatc ctcacgttgt ggctcatgag gaaatcagaa gggctagagg ttgaggaatg    6240
ctggaaaggg caagtgagga agacactcaa tttccattcc taaggaggga gtggacgcgg    6300
tttccattcc taaagaagac atcatgggag atttactctc atgattttct aggatccttg    6360
ggcaaagcaa ctaatgcccc tttgcctcag attttttggga agcaaccctg gccatgcctg    6420
ataaaactga gggaaaaaaa ctcctgagat cagcactgtc taatatgcag gccatatggg    6480
gctgtggaaa tttaaacgaa ttaaaattaa atgaaattaa aatttcaggc cattagttgc    6540
actagacaca ttttaagtac tcaacagcaa tggcctgaag tttaaatttt atttaatttt    6600
aattctttta aatttcaata gcctcctgtg gctagaggtg accctgctag aaggtgcaga    6660
tgacagagtg aactgataag atgggcacga tattaagcca tcattagtct ctgaagttct    6720
tacatgagcc ctaatttttt gtctttctaa ttaattaata gttaggatta ctggttctgg    6780
agtcacactt gctgggatga gatcaagcct tcatcattta ggagttgtgt ggccttgaac    6840
aagtcactta aactctgcaa aactcaattt cctcatccat ggaattttgt gaataagtgg    6900 ataaggtgt tcctgtagta cttcctttgt atagctttgg tgaggttaa atgataattg    6960 cgtttaaaat cattaatata gtctttgaca catatgacct tctataatgg ttacctgcga    7020
ctttttatta ttattaattc tttctcctcc caaacacact gattcaagtt ttgacctgtt    7080
gtggctacta acttctccca ccatccacca gctgtgcagg tttgcatttt agatttgaaa    7140
atactcctgc atgggccagg cgtggtggct cacacctgta atctcaacac tttgggaggc    7200
caaggcaggt ggatcacttg aggccagaag ttcaagacca gccttgccaa cgtggcaaaa    7260
ccccgtctct actaaaaata cagaaattag ccaggcatgg tggtgcatga ctgtagttcc    7320
agctttttgg gaggctgagg cacaagaatc acttgaaccc aggaggcgga ggtttcagtg    7380
```

<210> SEQ ID NO 11
<211> LENGTH: 320
<212> TYPE: PRT
<213> ORGANISM: Homo sapiens -continued

<400> SEQUENCE: 11

```
Met Cys Phe Thr Ser Gln Cys Arg Ala Leu Ser Ser Ser Ala Ser
 1               5                  10                  15

Pro Met Ser Leu Ile Phe Leu Gly Ile Asp Gln Gly Gln Met Thr Tyr
                20                  25                  30

Asp Gly Gln His Trp His Ala Thr Glu Thr Cys Phe Cys Ala His
            35                  40                  45

Cys Lys Lys Ser Leu Leu Gly Arg Pro Phe Leu Pro Lys Gln Gly Gln
     50                  55                  60

Ile Phe Cys Ser Arg Ala Cys Ser Ala Gly Glu Asp Pro Asn Gly Ser
 65                  70                  75                  80

Asp Ser Ser Asp Ser Ala Phe Gln Asn Ala Arg Ala Lys Glu Ser Arg
                85                  90                  95

Arg Ser Ala Lys Ile Gly Lys Asn Lys Gly Lys Thr Glu Glu Pro Met
                100                 105                 110

Leu Asn Gln His Ser Gln Leu Gln Val Ser Ser Asn Arg Leu Ser Ala
            115                 120                 125

Asp Val Asp Pro Leu Ser Leu Gln Met Asp Met Leu Ser Leu Ser Ser
130                 135                 140

Gln Thr Pro Ser Leu Asn Arg Asp Pro Ile Trp Arg Ser Arg Glu Glu
145                 150                 155                 160

Pro Tyr His Tyr Gly Asn Lys Met Glu Gln Asn Gln Thr Gln Ser Pro
                165                 170                 175

Leu Gln Leu Leu Ser Gln Cys Asn Ile Arg Thr Ser Tyr Ser Pro Gly
            180                 185                 190

Gly Gln Gly Ala Gly Ala Gln Pro Glu Met Trp Gly Lys His Phe Ser
        195                 200                 205

Asn Pro Lys Arg Ser Ser Leu Ala Met Thr Gly His Ala Gly Ser
210                 215                 220

Phe Ile Lys Glu Cys Arg Glu Asp Tyr Tyr Pro Gly Arg Leu Arg Ser
225                 230                 235                 240

Gln Glu Ser Tyr Ser Asp Met Ser Ser Gln Ser Phe Ser Glu Thr Arg
                245                 250                 255

Gly Ser Ile Gln Val Pro Lys Tyr Glu Glu Glu Glu Glu Glu Gly
            260                 265                 270

Gly Leu Ser Thr Gln Gln Cys Arg Thr Arg His Pro Ile Ser Ser Leu
        275                 280                 285

Lys Tyr Thr Glu Asp Met Thr Pro Thr Glu Gln Thr Pro Arg Gly Ser
    290                 295                 300

Met Glu Ser Leu Ala Leu Ser Asn Ala Thr Gly Arg Phe Cys Ser Pro
305                 310                 315                 320
```

<210> SEQ ID NO 12
<211> LENGTH: 7380
<212> TYPE: DNA
<213> ORGANISM: Homo sapiens

<400> SEQUENCE: 12

```
cactgaaacc tccgcctcct gggttcaagt gattcttgtg cctcagcctc ccaaaaagct      60
ggaactacag tcatgcacca ccatgcctgg ctaatttctg tattttagt agagacgggg     120 ttttgccacg ttggcaaggc tggtcttgaa cttctggcct caagtgatcc acctgccttg    180
gcctcccaaa gtgttgagat tacaggtgtg agccaccacg cctggcccat gcaggagtat    240
```

-continued

```
tttcaaatct aaaatgcaaa cctgcacagc tggtggatgg tgggagaagt tagtagccac      300
aacaggtcaa aacttgaatc agtgtgtttg ggaggagaaa gaattaataa taataaaaag      360
tcgcaggtaa ccattataga aggtcatatg tgtcaaagac tatattaatg attttaaacg      420
caattatcat ttaaccctca ccaaagctat acaaaggaag tactacagga acacctttat      480
ccacttattc acaaaattcc atggatgagg aaattgagtt ttgcagagtt taagtgactt      540
gttcaaggcc acacaactcc taaatgatga aggcttgatc tcatcccagc aagtgtgact      600
ccagaaccag taatcctaac tattaattaa ttagaaagac aaaaaattag ggctcatgta      660
agaacttcag agactaatga tggcttaata tcgtgcccat cttatcagtt cactctgtca      720
tctgcacctt ctagcagggt cacctctagc cacaggaggc tattgaaatt taaaagaatt      780
aaaattaaat aaaatttaaa cttcaggcca ttgctgttga gtacttaaaa tgtgtctagt      840
gcaactaatg gcctgaaatt ttaatttcat ttaattttaa ttcgtttaaa tttccacagc      900
cccatatggc tgccatatta gacagtgctg atctcaggga ttttttttccc tcagttttat      960
caggcatggc cagggttgct tcccaaaaat ctgaggcaaa ggggcattag ttgctttgcc     1020
caaggatcct agaaaatcat gagagtaaat ctcccatgat gtcttcttta ggaatggaaa     1080
ccgcgtccac tccctcctta ggaatggaaa ttgagtgtct tcctcacttg ccctttccag     1140
cattcctcaa cctctagccc ttctgatttc ctcatgagcc acaacgtgag gatgatacag     1200
tcagagcaga caaacccagg cacatctccc ctcagacaat ggtgcacatc agcctcagca     1260
gagatctgct taacatgcag attcctgggc cccacctctg tagagttctg atgcaagggg     1320
ttaggggag gcccaggagc ctatgtttga atcaagcaca cccatgattc taatgcaggt      1380
ggtctagctt tgagaaactc ttcttcagag gctgaagtat atatttatct gctgtcctct     1440
taaataatta tagcacataa atctttcgag aataacataa cctgggctgg aagcaggcag     1500
tcatcactct gcactaattg ctcccttcta agacatcagg caaggcgctt agtcaccaag     1560
gcctcatttt tttttttttt ttccatctga acatgggga tgaggatatc tactctttgt       1620
tcttggacaa atgggaacac agatgtggat gtatttgagg aggatagaaa gtaaaaccca     1680
ctgcatggac aagctacaac tcagagcctc attttgtttg tctagcagtg ttgaaataga     1740
tttcatattt ttaaaaatcc acatttttaa cttctctgga aaaactggaa gatctgacag     1800
gatgggctt gtattagact ggcagcctgg tgtgattaag agcaaggttc tgaaatcata      1860
tgcacaggtt caaatccctg ctctaccact ctgaaagctg agtgactttg ggtgagtccc     1920
tcaacctctc catttctgtt tcttcaactc tgaaatgaga atcataacaa tattcctccc     1980
tcacagtgtt atgacaatgt aattaagcaa gctaatattt atgacgtgct cagaacaatg     2040
tttgacacat tgcaagagct atataaaggt taggtggata cataaatatc ccagcacatg     2100
gcaacaagca gctggagctg agcagtggcc gtccccttca aatggggcta acattatcac     2160
agtctctatc cagacaccat cggctatgga atccttgctg taaggggcag acgtatatct     2220
ccctcctctg gtaccttgcc cacaaggggg cagatatact tagcacatct tagagcgcta     2280
ctcttctcaa gctatcagtg gtgaaggacc agtttgtttt cattttcaat cccttgtgga     2340
ccgacatatg gccctgctga gcatgtctga gacacagcac aaagcacaaa gagctcagta     2400
tgtgagttct ataacaccct gatgggtcta aacctgatc aataagacaa gcctgctgaa      2460
aacgcacttg gatggcaccg caacatcgaa ctgctataag tttctaacac ttccagtttc     2520
agtactaatc tcgctgctga taggtgttaa gtactaatct cactgctgat gggtgatagt     2580
tctcagccag tgttatcctc agattctgct ttaagtagca ctatcacaga gaaaatctac     2640
```

```
gttactctat ttttcccac atttaaaaat attttttaaa taatgtttaa aatattaaat      2700
caataatatt aaattttttt tttttttttt ctagagacag gttgtcactc tgctgcccag      2760
gctggagtgc agaggtggga tcattgctta gttcagcctc aacttcctgg gctcaagtga      2820
tcctcctgct ttagtctcct aagtagctgg gactatgagc atgtgccacc aagtccagct      2880
aatttatata tatatatata acacatttgt atatattata tcatatatat ttatatatta      2940
tatatacaca caatatatat tatatatgat atatatatac acacgctata tattttatat      3000
atatacacac acatatatgt ttgtagagac agagtctcac tatggttgcc caggctggtc      3060
tccaactcct ggcctcaagt gatcctcctg ccttggcctc ccaaagtgc tgaaattaca       3120
ggcatgagcc accatgcctg gccaacatca gtcttccac gcacacaaaa ccagctggac       3180
aacttcactg gagagagaag catgccatta tctctctctc tctacttctg ttcttttcag      3240
cctgcctgtc ttctccttgt ctagccaaac atttcttatg tctttatctg cactttgaag      3300
ccagttccct ggtgagaaac aggttcagaa cagtctcaga agctgtcatg gatgctttgg      3360
tgccccaggc agcaccacgc tggggcaact gggctccagg tgctgtgagt actgccatca      3420
gctcacagct acaccttctc caccttcata tggtacaagg ggcaaacaag ttcccttgga      3480
cctctttat aagggcatta atcccattca tgaggtctcc actctcatga cttaatcacc       3540
tcccaaaagg ccccttctcc taatgccatc accttgggat ttaggatctt aatttaagaa      3600
ttttggggaa aacattcaga ccatagtatt ttctttcttt aatgctgcct ttggccaaca      3660
ggagctgcct tgccccaagc ccacatccac tatctcatcc ctttgtcact cctcagcagc      3720
ccaaagctga tgaccaacta acacgatggt acaaaacatc agccccttcg tcacaagaag      3780
caattgattc tatagtgcaa ctcatccatc agagtcccct gtgggatcag gcagaagcca      3840
gaccccagtg aagacaccat tcctcacttg gctcctcccc atgctctgtc ctctttctct      3900
cactccccctt ctcctgagag cactccctca gtacatcaca ggcatctgga cctgtctcag      3960
gctttgttta cagggaagcc catcaaagat agaagccatc tcaaacttgg gtttaccttc      4020
ctcagcagcc tattgaagaa gggcacgtgg cagaaacaac attaaaatcc ggaggaccag      4080
gctgggcacg gtggctcacg cctgtaatcc taccactttg ggaggccgag gcaggtggat      4140
cacgaggtca ggagatcgag aacatcccgg ctaacacggt gaaacacgtg tgtactaaaa      4200
atacaaaaaa attagccagg catggtggcg ggcacctgta gtcccaacta ctcgtgaggc      4260
tgaggcagga gaatggcgtg aacccgggag gtggagcttg cagtgagcgg agatcgtgcc      4320
actgcactcc agcctggggg acagagcgag actccatttc aaaaaaaaaa aaaattcctg      4380
gggaccagca tccagtcacc cagagactac cccctttcta tctgttttca aggtgaacag      4440
aacctacctg ttgcattaga cagggccagg gattccatgg agccccgagg ggtctgctct      4500
gtgggcgtca tgtcctctgt gtatttcagg gaactgatgg gatgacgggt ccgacactgc      4560
tgagtggaca agcccccttc ctcttcctct tcctcctcat atttggggac ttggatgctg      4620
cctcgggtct cactgaaact ctgactagac atatcactgt agctctcctg agatctcagc      4680
ctccccgggt aatagtcttc tcggcattcc ttgatgaagc tgccagcatg tcctgtcatg      4740
gccagtgacg agctccttttt ggggttgctg aagtgcttgc cccacatttc gggctgggcc      4800
ccagcccctt gccctcctgg actgtaggaa gttctgatgt tgcactggct gaggagctgc      4860
agagggctct gggtctggtt ctgctccatc ttgttcccat aatggtaggg ctcttcccgg      4920
ctcctccaga tggggtcccg gttgaggctg ggtgtctggc tggacaggct gagcatgtcc      4980
```

```
atctgcagtg acaggggtc tacgtcggct gacagccggt tagaactcac ttgcagctgg      5040
ctgtgctggt tcagcatggg ctcctccgtc ttgcccttgt tcttgccaat tttggcactg      5100
cgccgggact ccttggccct ggcgttctgg aaggcggaat cagaggagtc agaaccattg      5160
gggtcttccc cagcactgca ggcccgtgag cagaatatct ggccctgctt cgggaggaat      5220
ggccgcccca ggagggattt cttgcagtga gcacagcaga aacaggtctc agtggcatgc      5280
cagtgttggc catcataggt catttgacct tggtcgatac ctaaaaaaat gagagacatt      5340
ggagaggctg atgagctgct cagagctctg cactgggacg tgaaacacat agcaccttgg      5400
tttgtctcag gattccaggt gcggcaggat aaactgtcaa taaatcaaca atcagaccct      5460
tatgtaaatg gtattcacgt cctattacga gaagtccttg ttgtaccagt atgcgcctta      5520
actcatttgc tccaagcaca aagactctag gttaaaatgg cttgtctatg aatccttctg      5580
cctgggacac atttccccct gacaaatagc aatagtaata ttaacgtatg atcatgtact      5640
gctttaagag ctttatatat gtaaactcat ttaatcactc agctccttga gctagctttc      5700
taatattatt tgcagttttc acatgagaaa gtagaggcag atgaggctaa gtaacttggc      5760
agggtaacat aactaggaac cagagacgag atctgtaccc aggaagtctt attctcaacc      5820
atgacattga cactatctcc ttcactctag ttaggcatct gctcaaaagc caactcctct      5880
gagaagtctt cctatccaca ctaaatagtg attctccatt actctccacc cttacctgct      5940
ggagttttct tgatagcatt aataccgctt tacattacaa cagtatatac atgcatctgt      6000
ttattatttc tctcccccgc taaaagtgaa gctctatgag gacagactca ttgagtttct      6060
acagcatctc caggacctgg aacatggcct ggtgtatgac agggctcttt gtgtgtagat      6120
agatcgagtg aatcccatta ctagcatatg ctattccaat gggtaagtca cagcagcaac      6180
tcagtggatg ctatggtgaa tgttttcttc agaactccta agtttaacac ctaaatccta      6240
aagtgatggc attaggagat ggagcttttt gggaggtgac taggtcatga gagtggatac      6300
ctcatgaatg agattagtgc ccttataaca gaggcccaag ggagcctgtt tgctccttcc      6360
actatatgat gactctgcca gaaagtatca tccaggaaac aaaaaacagg ccctcagcag      6420
acactgcatt tgctggtgcc ttgagtttga acttcccagc tttcagaact gtcagcaata      6480
catttctgtt actcagaggc cacccagtct gtgctattcc gttaaagcag tctcaacaga      6540
cttagtggga aataaaaatg tggatttcaa ctcttgttaa ggaaaaatct gctttcggta      6600
aagaaaaacc tagacacggt attgccaaag ctactgcccc tctgggagcg taagtaccct      6660
ttgcttaatt tcatcaggga aggaagaggt acgattcctc cctgtgacag gctgcgcca      6720
ggtttatata gcctggccac actgcgtact aagggagcct cccacagccc caggggttct      6780
gccttctcat catctctgcc ctcttctggt tataggactt cctctccctg tgggacacca      6840
tttccctgcc atcttcaggc cgtgagcttt gggtggggca aaagctgatc tggggcccaa      6900
cataggccag caaaaaaaat ctgctctcct ggcacccagg gactgattca ggggtgggca      6960
agtgacctgc actaagccaa cacctctcat tgctttttct aaggcaggac ttttgctaag      7020
gcagtcacac agcaggctct tttttatagca gcagtaaaac tggcagaatg gaaactggga      7080
gctgctgggg cccccttcccg tggggagagc ctgctgggaa tatagcctca agctatgact      7140
gtagggtgga ccaggacccc tgcattctcc tgatgcgtaa tgatacacgg cttcccagaa      7200
aaagggacta atgtggcctt tatcttcagt ggctgagagt tcctgagcct ggactttcaa      7260
ggaagaactt ctggagactt gtctaaagag gcaatgaacc agaaattagg gagaagaaga      7320
gaattgcaag aacaaaaggc caccggccca agcagcctac cttttctcctc cctgactcac      7380
```

-continued

<210> SEQ ID NO 13
<211> LENGTH: 1011
<212> TYPE: PRT
<213> ORGANISM: Ciona intestinalis

<400> SEQUENCE: 13

Met Thr Met Pro Ala Ala Thr Glu Gln Thr Arg Gly Thr Met Pro
  1               5                  10                  15

Ser Asn Ile Asp Pro Lys Ser Ala Gly Leu Asp Gln Asp Ile Val Ile
             20                  25                  30

Arg Gly Pro Thr Glu Asn Arg Val Arg Arg Gln Ser Arg Arg Gln
             35                  40                  45

Ala Ser Val Arg His Asn Arg Asn Ser Ala Ser Asp Glu Glu Asn Asp
     50                  55                  60

Gly Asp Ser Gly Cys Ala Leu Glu Glu Tyr Ala Trp Val Pro Pro Asn
 65                  70                  75                  80

Leu Thr Pro Asp Gln Val Arg Tyr Tyr Phe Thr Ser Leu Pro Glu Asp
                 85                  90                  95

Lys Val Pro Leu Val Asp Ser Ile Gly Asp Lys Tyr Arg Val Arg Gln
                100                 105                 110

Leu Leu His Gln Leu Pro Pro His Asp Asp Lys Val Cys Tyr Cys Asn
            115                 120                 125

Asp Leu Ser Asp Glu Glu Lys Arg Glu Leu Arg Leu Phe Ser Glu Gln
    130                 135                 140

Arg Lys Lys Asp Tyr Leu Gly Cys Gly Lys Ile Arg Ile Leu Pro Leu
145                 150                 155                 160

Asn Thr Pro Gly Thr Pro Cys Ser Glu Cys Gly Ile Leu Val Lys Gly
                165                 170                 175

Gly Asp Ile Val Ala Val Ala Ser Arg Ala Glu Pro Gly Met Cys Trp
            180                 185                 190

His Pro Ala Cys Phe Val Cys Ser Val Cys Arg Glu Leu Leu Val Asp
        195                 200                 205

Leu Phe Tyr Phe Tyr Gln Asp Gly Arg Leu Tyr Cys Gly Arg His His
    210                 215                 220

Ala Glu Thr Leu Lys Pro Arg Cys Ser Ala Cys Asp Glu Ile Ile Phe
225                 230                 235                 240

Ser Asp Glu Cys Thr Glu Ala Glu Gly Arg His Trp His Met Asp His
                245                 250                 255

Phe Cys Cys Phe Glu Cys Asp Gln Val Leu Gly Gly Gln Arg Tyr Ile
            260                 265                 270

Met Arg Asp Gly Lys Pro Asn Cys Thr Gln Cys Phe Glu Ala Leu Tyr
        275                 280                 285

Ala Glu Tyr Cys Asp Met Cys Gly Asp Leu Ile Gly Leu Asp Ala Gly
    290                 295                 300

Gln Met Gln Tyr Glu Gly Gln His Trp His Ala Thr Asp Asn Cys Phe
305                 310                 315                 320

Cys Cys Asn Arg Cys Arg Lys Ser Leu Leu Gly Arg Pro Phe Leu Pro
                325                 330                 335

Lys His Gly Arg Ile Phe Cys Ser Lys Ala Cys Ser Leu Gly Glu Asp
            340                 345                 350

Pro Gly His Ser Glu Ser Asp Ser Gln His Ser Ser Gln Tyr Glu
        355                 360                 365

Asn Pro Gln Leu Pro Thr Ser His Asn Val Arg Arg Ser Leu Asn Leu

```
            370                 375                 380
Asp Asn Leu Ser Ile His Asp Lys Pro Trp Glu Asp Lys Gly Glu Leu
385                 390                 395                 400

Ser Pro Ala Ser Asn Asn Val Phe Ile Asp Ala Ala Asp Met Tyr Pro
                405                 410                 415

Thr Ser Ala Ala Val Ala Ala Ser Thr Arg Tyr Ser Lys Gly His Thr
                420                 425                 430

Arg Pro Ser His Pro Tyr Leu Asp Gly Met Asp Pro Val Asn Ala Glu
                435                 440                 445

Met Val Thr Glu Asn Asp Ala Gly Phe Lys Gly Ala Ala Thr Ser Arg
450                 455                 460

Lys Thr Val Thr Asp Ser Val Thr Ser Pro Thr Ser Thr Val Ser Ser
465                 470                 475                 480

Arg Thr Thr Ser Lys Asn Gly Val Gln Phe Pro Gln Asn Thr Tyr Asn
                485                 490                 495

Ser Thr Asp Ser Ser Gly Tyr Asn Ser Ser Thr Leu Asp Ala Ile
                500                 505                 510

Glu His Gln Gln Asn Ala Ala Leu Lys Ala Ala Met Gly Ser Asn Tyr
                515                 520                 525

Ser Tyr Gly Lys Ser Lys Gln Thr Pro Cys Ser Lys Arg Pro Gln Asn
                530                 535                 540

Gly Glu Asp Gly His Val Ser Ala Thr Glu Phe Thr Pro Phe His Pro
545                 550                 555                 560

Ala Ala Pro Arg Ala Ser Pro Thr Ile Ile Gly Ser Arg Lys Leu
                565                 570                 575

Ala Pro Glu Ile Lys Lys Thr Ile Asp Ser Leu Thr Lys Ala Thr Glu
                580                 585                 590

Ile Asp Asn Lys Ser Pro Pro Val Asn Val Ala Ser Met Leu Pro Lys
                595                 600                 605

Ser Ala Val Pro Ile Pro Ala Pro Arg Ala Arg Tyr Ala Pro Ser Leu
                610                 615                 620

Thr Pro Ser Pro Pro Ser Thr Ala Ala Ser Glu Leu Thr Ser Pro Trp
625                 630                 635                 640

Met His Lys Ser His Ala Arg Thr Asp Ser Pro Pro Asp Ser Arg Glu
                645                 650                 655

Phe Pro Ser Pro Pro Val Pro Val Arg Ser Pro Pro Thr Glu Ser Lys
                660                 665                 670

Glu His Ser Ser Pro Leu Gln Arg Ser Val Ser Glu Arg Leu Ala Asn
                675                 680                 685

Lys Arg Arg Ser Arg Glu Pro Ile Ser Leu Pro Glu Gln Thr Ile Ser
                690                 695                 700

Glu His Pro Arg Leu Arg Ser Asp Asp Lys His Val Ser Val Glu Asn
705                 710                 715                 720

Asp Lys Thr Ser Pro Glu Leu Lys Ser Ile Leu Lys Lys Ser Arg Asn
                725                 730                 735

Pro Ser Lys Ser Phe Arg Asn Arg Glu Arg Gly Ser Leu Ser Gly Ser
                740                 745                 750

Leu Asp Arg Leu Glu Glu Phe His Arg Lys Ser Asp Val Met Lys Tyr
                755                 760                 765

Ala Ser Asp Asp Glu Asp Gly Ala Gly Phe Gly Asp Ala Gln Gly Asp
                770                 775                 780

Phe Ser Ser Phe Gln Arg Gly Gln Arg Leu Tyr Ser Ser Ala Arg Phe
785                 790                 795                 800
```

-continued

```
Pro Glu Glu Val Thr Glu Lys Pro Arg Ser Gln Asn Gln Gly Gly Arg
                805                 810                 815

Pro Arg Ser Gln His Arg Thr Arg Phe Lys Asp Asn Ser Ala Leu Asp
            820                 825                 830

Arg Thr His Ser Ala Leu Asn Leu Asp Glu Leu Asp Cys Ala Ile Ala
        835                 840                 845

Arg Arg Asn Pro Lys Pro Gly Lys Thr Cys Ser Lys Leu Ser Gly Lys
    850                 855                 860

Ser Thr Cys Ser Lys Lys Leu Lys Arg Thr Arg Ser Thr Asp Phe Ala
865                 870                 875                 880

Phe Glu Arg Ser Ala Ala Thr Pro Thr Ser Ser Arg Lys Asn Arg Arg
                885                 890                 895

Thr Lys Arg Phe Val Glu Asp Glu Glu Asp Gly Trp Cys Ser Thr
            900                 905                 910

Cys Thr Ser Ser Asn Asp Asp Ser Asp Tyr Glu Arg Trp Asp Gly Leu
        915                 920                 925

Gly Thr Ser Pro Pro Thr Ser Pro Leu Ser Ala Met Arg Arg Gly Ser
    930                 935                 940

Ala Pro Val Gly Val Arg Val Asn Met Thr Arg Arg Gln Pro Pro His
945                 950                 955                 960

Pro Phe Leu Ala Asn Ala Asp Ser Ala Leu Ala Ala Ser Ala Ala Gly
                965                 970                 975

Phe Asn Ser Asn Gly Val Tyr Arg Pro Ser Met Pro Arg Asn Phe Ser
            980                 985                 990

Thr Thr Ser His Met Arg Tyr Arg Arg Gln Gln Lys Lys His Cys
        995                1000                1005

Ile Val Met
   1010

<210> SEQ ID NO 14
<211> LENGTH: 1066
<212> TYPE: PRT
<213> ORGANISM: Ciona intestinalis

<400> SEQUENCE: 14

Met Thr Met Pro Ala Ala Thr Glu Gln Thr Arg Gly Thr Met Pro
  1               5                  10                  15

Ser Asn Ile Asp Pro Lys Ser Ala Gly Leu Asp Gln Asp Ile Val Ile
             20                  25                  30

Arg Gly Pro Thr Glu Asn Arg Val Arg Arg Gln Ser Arg Arg Gln
         35                  40                  45

Ala Ser Val Arg His Asn Arg Asn Ser Ala Ser Asp Glu Glu Asn Asp
     50                  55                  60

Gly Asp Ser Gly Cys Ala Leu Glu Glu Tyr Ala Trp Val Pro Pro Asn
 65                  70                  75                  80

Leu Thr Pro Asp Gln Val Arg Tyr Tyr Phe Thr Ser Leu Pro Glu Asp
                 85                  90                  95

Lys Val Pro Leu Val Asp Ser Ile Gly Asp Lys Tyr Arg Val Arg Gln
            100                 105                 110

Leu Leu His Gln Leu Pro Pro His Asp Lys Val Cys Tyr Cys Asn
        115                 120                 125

Asp Leu Ser Asp Glu Glu Lys Arg Glu Leu Arg Leu Phe Ser Glu Gln
    130                 135                 140

Arg Lys Lys Asp Tyr Leu Gly Cys Gly Lys Ile Arg Ile Leu Pro Leu
```

-continued

```
            145                 150                 155                 160
      Asn Thr Pro Gly Thr Pro Cys Ser Glu Cys Gly Ile Leu Val Lys Gly
                      165                 170                 175
      Gly Asp Ile Val Ala Val Ala Ser Arg Ala Glu Pro Gly Met Cys Trp
                  180                 185                 190
      His Pro Ala Cys Phe Val Cys Ser Val Cys Arg Glu Leu Leu Val Asp
                  195                 200                 205
      Leu Phe Tyr Phe Tyr Gln Asp Gly Arg Leu Tyr Cys Gly Arg His His
              210                 215                 220
      Ala Glu Thr Leu Lys Pro Arg Cys Ser Ala Cys Asp Glu Ile Ile Phe
      225                 230                 235                 240
      Ser Asp Glu Cys Thr Glu Ala Glu Gly Arg His Trp His Met Asp His
                          245                 250                 255
      Phe Cys Cys Phe Glu Cys Asp Gln Val Leu Gly Gly Gln Arg Tyr Ile
                      260                 265                 270
      Met Arg Asp Gly Lys Pro Asn Cys Thr Gln Cys Phe Glu Ala Leu Tyr
                  275                 280                 285
      Ala Glu Tyr Cys Asp Met Cys Gly Asp Leu Ile Gly Leu Asp Ala Gly
                  290                 295                 300
      Gln Met Gln Tyr Glu Gly Gln His Trp His Ala Thr Asp Asn Cys Phe
      305                 310                 315                 320
      Cys Cys Asn Arg Cys Arg Lys Ser Leu Leu Gly Arg Pro Phe Leu Pro
                      325                 330                 335
      Lys His Gly Arg Ile Arg Cys Ser Lys Ala Cys Ser Leu Gly Glu Asp
                  340                 345                 350
      Pro Gly His Ser Glu Ser Asp Ser Gln His Ser Ser Gln Tyr Glu
                  355                 360                 365
      Asn Pro Gln Leu Pro Thr Ser His Asn Val Arg Arg Ser Leu Asn Leu
              370                 375                 380
      Asp Asn Leu Ser Ile His Asp Lys Pro Trp Glu Asp Lys Gly Glu Leu
      385                 390                 395                 400
      Ser Pro Ala Ser Asn Asn Val Phe Ile Asp Ala Ala Asp Met Tyr Pro
                      405                 410                 415
      Thr Ser Ala Ala Val Ala Ala Ser Thr Arg Tyr Ser Lys Gly His Thr
                      420                 425                 430
      Arg Pro Ser His Pro Tyr Leu Asp Gly Met Asp Pro Val Asn Ala Glu
                  435                 440                 445
      Met Val Thr Glu Asn Asp Ala Gly Phe Lys Gly Ala Ala Thr Ser Arg
      450                 455                 460
      Lys Thr Val Thr Asn Ser Val Thr Ser Pro Thr Ser Thr Val Ser Ser
      465                 470                 475                 480
      Arg Thr Thr Ser Lys Asn Gly Val Gln Phe Pro Gln Asn Thr Tyr Asn
                      485                 490                 495
      Ser Thr Asp Ser Ser Gly Tyr Asn Ser Ser Thr Leu Asp Ala Ile
                  500                 505                 510
      Glu His Gln Gln Asn Ala Ala Leu Lys Ala Ala Met Gly Ser Asn Tyr
                  515                 520                 525
      Ser Tyr Gly Lys Ser Lys Gln Thr Ser Cys Ser Lys Arg Pro Gln Asn
                  530                 535                 540
      Gly Glu Asp Gly His Val Ser Ala Thr Glu Phe Thr Pro Phe His Pro
      545                 550                 555                 560
      Ala Ala Pro Arg Ala Ser Pro Thr Ile Ile Gly Ser Arg Lys Leu
                  565                 570                 575
```

```
Ala Pro Glu Ile Lys Lys Thr Ile Asp Ser Leu Thr Lys Ala Thr Glu
            580                 585                 590
Ile Asp Asn Lys Ser Pro Pro Val Asn Val Ala Ser Met Leu Pro Lys
        595                 600                 605
Ser Ala Val Pro Ile Pro Ala Pro Arg Ala Arg Tyr Ala Pro Ser Leu
    610                 615                 620
Thr Pro Ser Pro Pro Ser Thr Ala Ala Ser Glu Leu Pro Ser Pro Trp
625                 630                 635                 640
Met His Lys Ser His Ala Arg Thr Asp Ser Pro Pro Asp Ser Arg Glu
                645                 650                 655
Phe Pro Ser Pro Pro Val Pro Val Pro Ser Pro Pro Thr Glu Ser Lys
            660                 665                 670
Glu His Ser Ser Pro Leu Gln Arg Ser Val Ser Glu Arg Leu Ala Asn
        675                 680                 685
Lys Arg Arg Ser Arg Glu Pro Ile Ser Leu Pro Glu Gln Thr Ile Ser
    690                 695                 700
Glu His Pro Arg Leu Arg Ser Asp Asp Lys His Val Ser Val Glu Asn
705                 710                 715                 720
Asp Lys Thr Ser Pro Glu Leu Lys Ser Ile Leu Lys Lys Ser Arg Asn
                725                 730                 735
Pro Ser Lys Ser Phe Arg Asn Arg Glu Arg Gly Ser Leu Ser Gly Ser
            740                 745                 750
Leu Asp Arg Leu Glu Glu Phe His Arg Lys Ser Asp Val Met Lys Tyr
        755                 760                 765
Ala Ser Asp Asp Glu Asp Gly Ala Gly Phe Gly Asp Ala Gln Gly Asp
    770                 775                 780
Phe Ser Phe Gln Arg Gly Gln Arg Leu Tyr Ser Ser Ala Arg Phe
785                 790                 795                 800
Pro Glu Glu Val Thr Glu Lys Pro Arg Ser Gln Asn Gln Gly Gly Arg
                805                 810                 815
Pro Arg Ser Gln His Arg Thr Arg Phe Lys Asp Asn Ser Ala Leu Arg
            820                 825                 830
Pro Asn Ala Gln Arg Ser Gln Phe Arg Glu Gln Lys Leu Glu Leu Asp
        835                 840                 845
Cys Ala Ile Ala Arg Arg Asn Pro Lys Pro Gly Lys Thr Cys Ser Lys
    850                 855                 860
Leu Ser Gly Lys Ser Thr Cys Ser Lys Lys Leu Lys Arg Thr Arg Ser
865                 870                 875                 880
Thr Asp Phe Ala Phe Glu Arg Ser Ala Ala Thr Pro Thr Ser Ser Arg
                885                 890                 895
Lys Asn Arg Arg Thr Lys Arg Phe Val Glu Asp Glu Glu Asp Gly
            900                 905                 910
Trp Cys Ser Thr Cys Thr Ser Ser Ser Asp Asp Ser Asp Tyr Glu Arg
            915                 920                 925
Trp Asp Gly Leu Gly Thr Ser Pro Pro Thr Ser Pro Leu Ser Ala Met
        930                 935                 940
Arg Arg Gly Ser Ala Pro Val Gly Val Arg Val Asn Met Thr Arg Arg
945                 950                 955                 960
Gln Pro Pro His Pro Phe Leu Ala Asn Ala Asp Ser Ala Leu Ala Ala
                965                 970                 975
Ser Ala Ala Gly Phe Asn Ser Asn Gly Val Tyr Arg Pro Ser Met Pro
            980                 985                 990
```

```
Arg Asn Phe Phe His His Val Ala Tyr Ala Leu Gln Ala Glu Thr
    995                 1000                1005

Ala Glu Lys Ala Leu Tyr Arg His Val Thr Thr Asn Ala Val Thr Lys
1010                1015                1020

Thr Ser Glu Ile Asp Arg Lys Ser Ser Glu Thr Lys Ser Trp Arg Ser
1025                1030                1035                1040

Gln Asp Ala Ser Tyr Leu Pro Arg Gly Gly Ser Lys Ala Arg Glu Ser
                1045                1050                1055

Ala Pro Ile Val Asp Thr Asn Thr Ser Ala
            1060                1065

<210> SEQ ID NO 15
<211> LENGTH: 785
<212> TYPE: PRT
<213> ORGANISM: Drosophila melanogaster

<400> SEQUENCE: 15

Met Gln Gln Ala Pro Gln Gln Gln His Pro His Pro Pro Ser Ser
  1               5                  10                 15

Ser Tyr Tyr Thr Gln Thr Glu Ser Glu Leu Leu Gln Ile Glu Ala Gly
                 20                  25                 30

Gly Thr Gly Leu Thr Phe Ala Ser His Ser Gln Arg Pro Glu Ser Ala
             35                  40                 45

Ile Ser Gln Val Ala Ser Thr Ala His Leu Asp Val Pro Ser Ala Ala
         50                  55                 60

Ser Ser Gly Ser Gly Gly Ser Ala Val Ser Gly Gly Ser Gly Gly Ala
 65                  70                  75                 80

Pro Glu Ser Ala Gly Arg Phe Val Ser Pro Leu Gln Arg Arg His Cys
                 85                  90                 95

Gln Pro Pro Ser His Leu Pro Leu Asn Ser Val Ala Ser Pro Leu Arg
            100                 105                110

Thr Ala Ser Tyr Lys Ser Ala Ala Val Ala Gly His Gly Phe His
            115                 120                125

His Ser His His Gln Gln Leu Asp Phe Gln Arg Asn Ser Gln Ser Asp
130                 135                 140

Asp Asp Ser Gly Cys Ala Leu Glu Glu Tyr Thr Trp Val Pro Pro Gly
145                 150                 155                160

Leu Arg Pro Asp Gln Val Arg Leu Tyr Phe Ser Gln Leu Pro Asp Asp
                165                 170                 175

Lys Val Pro Tyr Val Asn Ser Pro Gly Glu Lys Tyr Arg Val Lys Gln
            180                 185                 190

Leu Leu His Gln Leu Pro Pro Gln Asp Asn Glu Val Arg Tyr Cys His
            195                 200                 205

Ser Leu Ser Asp Glu Glu Arg Lys Glu Leu Arg Ile Phe Ser Ala Gln
210                 215                 220

Arg Lys Arg Glu Ala Leu Gly Arg Gly Ala Val Arg Leu Leu Ser Asp
225                 230                 235                 240

Glu Arg Pro Cys Lys Gly Cys Glu Glu Pro Leu Ser Gly Gly Asp Ile
                245                 250                 255

Val Val Phe Ala Gln Arg Leu Gly Ala Gln Leu Cys Trp His Pro Gly
            260                 265                 270

Cys Phe Val Cys Ser Val Cys Lys Glu Leu Leu Val Asp Leu Ile Tyr
            275                 280                 285

Phe Gln Arg Asp Gly Asn Leu Tyr Cys Gly Arg His His Ala Glu Thr
            290                 295                 300
```

```
Gln Lys Pro Arg Cys Ser Ala Cys Asp Glu Ile Ile Phe Ser Asp Glu
305                 310                 315                 320

Cys Thr Glu Ala Glu Gly Arg Thr Trp His Met Lys His Phe Ala Cys
            325                 330                 335

Gln Glu Cys Glu His Gln Leu Gly Gly Gln Arg Tyr Ile Met Arg Glu
        340                 345                 350

Gly Lys Pro Tyr Cys Leu Ala Cys Phe Asp Thr Met Phe Ala Glu Tyr
    355                 360                 365

Cys Asp Tyr Cys Gly Glu Val Ile Gly Val Asp Gln Gly Gln Met Ser
370                 375                 380

His Asp Gly Gln His Trp His Ala Thr Asp Gln Cys Phe Ser Cys Cys
385                 390                 395                 400

Thr Cys Arg Cys Ser Leu Leu Gly Arg Pro Phe Leu Pro Arg Arg Gly
            405                 410                 415

Thr Ile Tyr Cys Ser Ile Ala Cys Ser Lys Gly Glu Pro Pro Thr Pro
        420                 425                 430

Ser Asp Thr Ser Ser Gly Pro Gln Leu Arg Pro Thr His Arg Ala Ser
    435                 440                 445

Thr Ser Ser Gln Ile Ala Lys Ser Pro Arg Arg Gly Gly Glu Arg Glu
450                 455                 460

Arg Asp Pro Gly Arg Lys Ala His His Gly His Pro Lys Ala Thr Gly
465                 470                 475                 480

Ser Ala Gly Asp Leu Leu Glu Arg Gln Glu Arg Gln Arg Met Glu Ala
            485                 490                 495

Ala Gly Val Ala Asp Leu Leu Gly Gly Val Pro Gly Met Pro
        500                 505                 510

Arg Pro Ala His Pro Pro Ile Asp Leu Thr Glu Leu Gly Ile Ser
    515                 520                 525

Leu Asp Asn Ile Cys Ala Gly Asp Lys Ser Ile Phe Gly Asp Thr Gln
530                 535                 540

Thr Leu Thr Asn Ser Met Pro Asp Met Leu Ser Lys Ala Asp Asp
545                 550                 555                 560

Ser His Ser Tyr Gln Ser Ile Asp Lys Ile Asn Leu Asn Ser Pro Ser
            565                 570                 575

Asn Ser Asp Leu Thr Gln Ser Thr Gln Glu Leu Ala Asn Glu Leu Glu
        580                 585                 590

Leu Asp Asn Glu Pro Val Arg Glu Leu Pro His Asp Gly Tyr Glu Gln
    595                 600                 605

Leu Phe Ala Asn Asn Arg Asn Gln Glu His Pro Ala Glu Gln Tyr Asp
610                 615                 620

Asp Glu Gln Leu Asp Asn Arg Pro Met Lys Glu Val Arg Phe His Ser
625                 630                 635                 640

Val Gln Asp Thr Met Ser Arg Ser Lys Ser Tyr Thr Asp Asn Ser Asn
            645                 650                 655

Ala Arg Arg Arg Arg Arg Arg Asn Gln Ser Arg Ser Ser Ser Glu
        660                 665                 670

Met Gln Ile Asn Gln Thr Asn Leu Arg Leu His Asn Ala Gln Thr Gln
    675                 680                 685

Val Gly Thr Thr Pro Leu Asn Leu Leu Asn Asn Leu Asn Cys Asp
690                 695                 700

Val Ala Ser Ile Cys Ser Thr Cys Ser Ser Ser Ser Ser Asp Met
705                 710                 715                 720
```

```
Asp Asp Tyr Val Tyr Arg Leu Pro Ala Arg Lys His Tyr Gly Gly Val
            725             730             735

Arg Val Ala Tyr Val Pro Asn Asp Ala Leu Ala Tyr Glu Arg Lys Lys
            740             745             750

Lys Met Ala Gln Asp Ser Ser Leu Ala Pro Gly Ala Gly Asn Ala Ser
            755             760             765

Val Gly Gly Ala Pro Ala Ile Met His Glu Ser Lys Asn Cys Thr Ile
770             775             780

Ser
785

<210> SEQ ID NO 16
<211> LENGTH: 615
<212> TYPE: PRT
<213> ORGANISM: Homo sapiens

<400> SEQUENCE: 16

Met Phe Ala Arg Gly Ser Arg Arg Arg Ser Gly Arg Ala Pro Pro
 1               5                  10                  15

Glu Ala Glu Asp Pro Asp Arg Gly Gln Pro Cys Asn Ser Cys Arg Glu
            20                  25                  30

Gln Cys Pro Gly Phe Leu Leu His Gly Trp Arg Lys Ile Cys Gln His
        35                  40                  45

Cys Lys Cys Pro Arg Glu Glu His Ala Val His Ala Val Pro Val Asp
    50                  55                  60

Leu Glu Arg Ile Met Cys Arg Leu Ile Ser Asp Phe Gln Arg His Ser
65                  70                  75                  80

Ile Ser Asp Asp Ser Gly Cys Ala Ser Glu Glu Tyr Ala Trp Val
                85                  90                  95

Pro Pro Gly Leu Lys Pro Glu Gln Val Tyr Gln Phe Ser Cys Leu
            100                 105                 110

Pro Glu Asp Lys Val Pro Tyr Val Asn Ser Pro Gly Glu Lys Tyr Arg
            115                 120                 125

Ile Lys Gln Leu Leu His Gln Leu Pro Pro His Asp Ser Glu Ala Gln
    130                 135                 140

Tyr Cys Thr Ala Leu Glu Glu Glu Lys Lys Glu Leu Arg Ala Phe
145                 150                 155                 160

Ser Gln Gln Arg Lys Arg Glu Asn Leu Gly Arg Gly Ile Val Arg Ile
                165                 170                 175

Phe Pro Val Thr Ile Thr Gly Ala Ile Cys Glu Glu Cys Gly Lys Gln
            180                 185                 190

Ile Gly Gly Gly Asp Ile Ala Val Phe Ala Ser Arg Ala Gly Leu Gly
            195                 200                 205

Ala Cys Trp His Pro Gln Cys Phe Val Cys Thr Thr Cys Gln Glu Leu
    210                 215                 220

Leu Val Asp Leu Ile Tyr Phe Tyr His Val Gly Lys Val Tyr Cys Gly
225                 230                 235                 240

Arg His His Ala Glu Cys Leu Arg Pro Arg Cys Gln Ala Cys Asp Glu
                245                 250                 255

Ile Ile Phe Ser Pro Glu Cys Thr Glu Ala Glu Gly Arg His Trp His
            260                 265                 270

Met Asp His Phe Cys Cys Phe Glu Cys Glu Ala Ser Leu Gly Gly Gln
            275                 280                 285

Arg Tyr Val Met Arg Gln Ser Arg Pro His Cys Cys Ala Cys Tyr Glu
    290                 295                 300
```

-continued

```
Ala Arg His Ala Glu Tyr Cys Asp Gly Cys Gly Glu His Ile Gly Leu
305                 310                 315                 320

Asp Gln Gly Gln Met Ala Tyr Glu Gly Gln His Trp His Ala Ser Asp
            325                 330                 335

Arg Cys Phe Cys Cys Ser Arg Cys Gly Arg Ala Leu Leu Gly Arg Pro
            340                 345                 350

Phe Leu Pro Arg Arg Gly Leu Ile Phe Cys Ser Arg Ala Cys Ser Leu
        355                 360                 365

Gly Ser Glu Pro Thr Ala Pro Gly Pro Ser Arg Arg Ser Trp Ser Ala
370                 375                 380

Gly Pro Val Thr Ala Pro Leu Ala Ala Ser Thr Ala Ser Phe Ser Ala
385                 390                 395                 400

Val Lys Gly Ala Ser Glu Thr Thr Thr Lys Gly Thr Ser Thr Glu Leu
                405                 410                 415

Ala Pro Ala Thr Gly Pro Glu Glu Pro Ser Arg Phe Leu Arg Gly Ala
            420                 425                 430

Pro His Arg His Ser Met Pro Glu Leu Gly Leu Arg Ser Val Pro Glu
        435                 440                 445

Pro Pro Pro Glu Ser Pro Gly Gln Pro Asn Leu Arg Pro Asp Asp Ser
    450                 455                 460

Ala Phe Gly Arg Gln Ser Thr Pro Arg Val Ser Phe Arg Asp Pro Leu
465                 470                 475                 480

Val Ser Glu Gly Gly Pro Arg Arg Thr Leu Ser Ala Pro Pro Ala Gln
                485                 490                 495

Arg Arg Arg Pro Arg Ser Pro Pro Arg Ala Pro Ser Arg Arg Arg
            500                 505                 510

His His His His Asn His His His Asn Arg His Pro Ser Arg
        515                 520                 525

Arg Arg His Tyr Gln Cys Asp Ala Gly Ser Gly Ser Asp Ser Glu Ser
        530                 535                 540

Cys Ser Ser Ser Pro Ser Ser Ser Ser Glu Ser Ser Glu Asp Asp
545                 550                 555                 560

Gly Phe Phe Leu Gly Glu Arg Ile Pro Leu Pro Pro His Leu Cys Arg
                565                 570                 575

Pro Met Pro Ala Gln Asp Thr Ala Met Glu Thr Phe Asn Ser Pro Ser
            580                 585                 590

Leu Ser Leu Pro Arg Asp Ser Arg Ala Gly Met Pro Arg Gln Ala Arg
        595                 600                 605

Asp Lys Asn Cys Ile Val Ala
610                 615

<210> SEQ ID NO 17
<211> LENGTH: 1028
<212> TYPE: PRT
<213> ORGANISM: Drosophila melanogaster

<400> SEQUENCE: 17

Glu Glu Glu Ser Pro Glu Gln Glu Ala Pro Lys Pro Ala Leu Pro Pro
 1               5                  10                  15

Lys Gln Lys Gln Gln Arg Pro Val Pro Pro Leu Pro Pro Pro Pro Ala
            20                  25                  30

Asn Arg Val Thr Gln Asp Gln Gly Thr Gln Pro Ala Ala Pro Gln Val
        35                  40                  45

Pro Leu Gln Pro Leu Thr Ala Gly Asp Leu Gln Phe Leu Asn Leu Ser
```

-continued

```
                50                  55                  60
Leu Arg Gln Arg Ser Leu Pro Arg Ser Met Lys Pro Phe Lys Asp Ala
 65                  70                  75                  80

His Asp Ile Ser Phe Thr Phe Asn Glu Leu Asp Thr Ser Ala Glu Pro
                 85                  90                  95

Glu Val Ala Thr Gly Ala Ala Gln Gln Glu Ser Asn Glu Cys Arg Thr
                100                 105                 110

Pro Leu Thr Gln Ile Ser Tyr Leu Gln Lys Ile Pro Thr Leu Pro Arg
                115                 120                 125

His Phe Ser Pro Ser Gly Gln Gly Leu Ala Thr Pro Ala Leu Gly
    130                 135                 140

Ser Gly Gly Met Gly Leu Pro Ser Ser Ser Ala Ser Ala Leu Tyr
145                 150                 155                 160

Ala Ala Gln Ala Ala Ala Gly Ile Leu Pro Thr Ser Pro Leu Pro Leu
                165                 170                 175

Gln Arg His Gln Gln Tyr Leu Pro Pro His His Gln Gln His Pro Gly
                180                 185                 190

Ala Gly Met Gly Pro Gly Pro Gly Ser Gly Ala Ala Ala Gly Pro Pro
                195                 200                 205

Leu Gly Pro Gln Tyr Ser Pro Gly Cys Ser Ala Asn Pro Lys Tyr Ser
                210                 215                 220

Asn Ala Gln Leu Pro Pro Pro Pro His His His Gln Leu Ser Pro
225                 230                 235                 240

Ala Leu Ser Thr Pro Ser Pro Pro Ser Leu Leu His His Pro Ala Gly
                245                 250                 255

Gly Thr Ser Ser Ala Ser Ala His Ala Pro Phe Leu Gly Gly Pro His
                260                 265                 270

Met Asp Met Gln Arg Gln Ser His Ser Asp Asp Ser Gly Cys Ala
                275                 280                 285

Leu Glu Glu Tyr Thr Trp Val Pro Pro Gly Leu Arg Pro Asp Gln Val
                290                 295                 300

Arg Leu Tyr Phe Ser Gln Ile Pro Asp Lys Val Pro Tyr Val Asn
305                 310                 315                 320

Ser Pro Gly Glu Gln Tyr Arg Val Arg Gln Leu Leu His Gln Leu Pro
                325                 330                 335

Pro His Asp Asn Glu Val Arg Tyr Cys His Ser Leu Thr Asp Glu Glu
                340                 345                 350

Arg Lys Glu Leu Arg Leu Phe Ser Thr Gln Arg Lys Arg Asp Ala Leu
                355                 360                 365

Gly Arg Gly Asn Val Arg Gln Leu Met Ser Ala Arg Pro Cys Asp Gly
    370                 375                 380

Cys Asp Asp Leu Ile Ser Thr Gly Asp Ile Ala Val Phe Ala Thr Arg
385                 390                 395                 400

Leu Gly Pro Asn Ala Ser Trp His Pro Ala Cys Phe Ala Cys Ser Val
                405                 410                 415

Cys Arg Glu Leu Leu Val Asp Leu Ile Tyr Phe His Arg Asp Gly Arg
                420                 425                 430

Met Tyr Cys Gly Arg His His Ala Glu Thr Leu Lys Pro Arg Cys Ser
                435                 440                 445

Ala Cys Asp Glu Ile Ile Leu Ala Asp Glu Cys Thr Glu Ala Glu Gly
    450                 455                 460

Arg Ala Trp His Met Asn His Phe Ala Cys His Glu Cys Asp Lys Gln
465                 470                 475                 480
```

```
Leu Gly Gly Gln Arg Tyr Ile Met Arg Glu Gly Lys Pro Tyr Cys Leu
                485                 490                 495
His Cys Phe Asp Ala Met Phe Ala Glu Tyr Cys Asp Tyr Cys Gly Glu
            500                 505                 510
Ala Ile Gly Val Asp Gln Gly Gln Met Ser His Asp Gly Gln His Trp
        515                 520                 525
His Ala Thr Asp Glu Cys Phe Ser Cys Asn Thr Cys Arg Cys Ser Leu
    530                 535                 540
Leu Gly Arg Ala Phe Leu Pro Arg Arg Gly Ala Ile Tyr Cys Ser Ile
545                 550                 555                 560
Ala Cys Ser Lys Gly Glu Pro Thr Pro Ser Asp Ser Ser Gly Thr
                565                 570                 575
Gly Met Tyr Thr Thr Pro Thr Pro Thr Gln Arg Val Arg Pro His
            580                 585                 590
Pro Gln Ala Pro Leu Pro Ala Arg Ile Pro Ser Ser His Ala Ser Ser
        595                 600                 605
Ser Pro Pro Met Ser Pro Gln Gln Gln Gln His Gln Ala Thr Phe
    610                 615                 620
Asn Gln Ala Met Tyr Gln Met Gln Ser Gln Gln Met Glu Ala Ala Gly
625                 630                 635                 640
Gly Leu Val Asp Gln Ser Lys Ser Tyr Ala Ala Ser Asp Ser Asp Ala
                645                 650                 655
Gly Val Val Lys Asp Leu Glu His Gly Gly His Met Gly Gly Asp
            660                 665                 670
Leu Thr Asp Phe Ser Gly Gly Arg Ala Ser Ser Thr Ser Gln Asn Leu
        675                 680                 685
Ser Pro Leu Asn Ser Pro Gly Asp Phe Gln Pro His Phe Leu Pro Lys
    690                 695                 700
Pro Met Glu Leu Gln Arg Gln Leu Leu Glu Asn Pro His Thr Ala Ser
705                 710                 715                 720
Met Pro Glu Leu Ala Gly Lys Leu Val Ala Pro Ala His Met Gln
                725                 730                 735
His Leu Ser Gln Leu His Ala Val Ser Ser His Gln Phe Gln Gln His
            740                 745                 750
Glu Tyr Ala Asp Ile Leu His Pro Pro Pro Pro Gly Glu Ile
        755                 760                 765
Pro Glu Leu Pro Thr Pro Asn Leu Ser Val Ala Ser Thr Ala Leu Pro
    770                 775                 780
Pro Glu Leu Met Gly Ser Pro Thr His Ser Ala Gly Asp Arg Ser Leu
785                 790                 795                 800
Asn Thr Pro Met Ser Thr Gln Ser Ala Ser His Ala Pro Pro His Pro
                805                 810                 815
Val Ser Ile Leu Ser Gly Ala Ser Ser Ser Pro Met Ser Gly Glu
            820                 825                 830
Pro Ala Lys Lys Lys Gly Val Arg Phe Glu Gly Ile Pro Asp Thr Leu
        835                 840                 845
Pro Arg Ser Arg Ser Tyr Ser Gly Asn Gly Ala Gly Thr Ser Gly Gly
    850                 855                 860
Gly Glu Arg Glu Arg Asp Arg Asp Lys Asp Lys Glu Gly Gly Gly Arg
865                 870                 875                 880
His Gly His Gly His Ser Ser Arg Arg Arg Arg Arg Lys Ser Ser
                885                 890                 895
```

-continued

```
Ser Ser Ser Ser His His Arg Ser Gly Ser Gly His Arg Ser His Ser
            900               905               910

Thr Thr Arg Ala Asp Thr Tyr Ala Pro Ala Gln Pro Leu Ser Ser Ser
            915               920               925

Tyr Gln Gly Pro Pro Ser Val Leu Gln Ala Ala Asn Leu Val His Glu
        930               935               940

Ser Pro Ser Arg Gln Gln Arg Glu Arg Glu Arg Glu Arg Glu
945             950               955               960

Glu Ser Glu Glu Ser Asp Val Cys Ser Thr Cys Ser Ser Ser Ser
                965               970               975

Ser Ser Glu Asp Tyr Met Met Met Tyr Gln Leu Pro Gln Arg Arg His
            980               985               990

Tyr Gly Val Arg Val Ser Tyr Val Pro Asn Asp Ala Leu Ala Tyr
        995              1000              1005

Asp Arg Lys Arg Lys Pro Ser Glu Leu Gly Gly Asp Lys Asp Lys Asn
    1010              1015              1020

Cys Ile Ile Ser
1025

<210> SEQ ID NO 18
<211> LENGTH: 1278
<212> TYPE: DNA
<213> ORGANISM: Homo sapiens

<400> SEQUENCE: 18
ctcttcgtgg cccaacgccc caatccttgc gtgtccttgc agtcccaccc cacactcagc      60
cttgtgtccc tcgatccagt ctccgacttc catttcccac cctaaaccgc ctacccggtg     120
tctgttcccc gcccggttgt cctcgccctg ctgcgctgag tgtcccctgt tagcctcgac     180
cccatggcgc tgcagacgct gcagagctcg tgggtgacct tccgcaagat cctgtctcac     240
ttccccgagg agctgagtct ggctttcgtc tacggctccg gggtgtaccg ccaggcaggg     300
cccagttcag accagaagaa tgctatgctg gactttgtgt tcacagtaga tgaccctgtc     360
gcatggcatt caaagaacct gaagaaaaat tggagtcact actctttcct aaaagtttta     420
gggcccaaga ttatcacgtc catccagaat aactatggcg ctggagttta ctacaattca     480
ttgatcatgt gtaatggtag gcttatcaaa tatggagtta ttagcactaa cgttctgatt     540
gaagatctcc tcaactggaa taacttatac attgctggac gactccaaaa accggtgaaa     600
attatctcag tgaacgagga tgtcactctt agatcagccc tcgatagaaa tctgaagagt     660
gctgtgaccg ctgctttcct catgctcccc gaaagctttt ctgaagaaga cctcttcata     720
gagattgccg gtctctccta ttcaggtgac tttcggatgg tggttggaga agataaaaca     780
aaagtgttga atattgtgaa gcccaatata gcccactttc gagagctcta tggcagcata     840
ctacaggaaa atcctcaagt ggtgtataaa agccagcaag ctggctggga gatagataaa     900
agcccagaag gacagttcac tcagctgatg acattgccca aaaccttaca gcaacagata     960
aatcatatta tggaccctcc tggaaaaaac agagatgtgg aagaaacttt attccaagtg    1020
gctcatgatc ccgactgtgg agatgtggtg cgactagggc tttcagcaat cgtgagaccg    1080
tctagtataa gacagagcac gaaaggcatt tttactgctg gcctgaagaa gtcagtgatt    1140
tatagttcac taaaactgca caaaatgtgg aaagggtggc tgaggaaaac atcctgattt    1200
tgcttgcttt tatatatgtt atgtgtagat gaataaagtg tttgatcctt tttgacaaaa    1260
aaaaaaaaaa aaaaaaaa                                                  1278
```

```
<210> SEQ ID NO 19
<211> LENGTH: 337
<212> TYPE: PRT
<213> ORGANISM: Homo sapiens

<400> SEQUENCE: 19

Met Ala Leu Gln Thr Leu Gln Ser Ser Trp Val Thr Phe Arg Lys Ile
  1               5                  10                  15

Leu Ser His Phe Pro Glu Glu Leu Ser Leu Ala Phe Val Tyr Gly Ser
             20                  25                  30

Gly Val Tyr Arg Gln Ala Gly Pro Ser Ser Asp Gln Lys Asn Ala Met
         35                  40                  45

Leu Asp Phe Val Phe Thr Val Asp Asp Pro Val Ala Trp His Ser Lys
     50                  55                  60

Asn Leu Lys Lys Asn Trp Ser His Tyr Ser Phe Leu Lys Val Leu Gly
 65                  70                  75                  80

Pro Lys Ile Ile Thr Ser Ile Gln Asn Asn Tyr Gly Ala Gly Val Tyr
                 85                  90                  95

Tyr Asn Ser Leu Ile Met Cys Asn Gly Arg Leu Ile Lys Tyr Gly Val
            100                 105                 110

Ile Ser Thr Asn Val Leu Ile Glu Asp Leu Leu Asn Trp Asn Asn Leu
        115                 120                 125

Tyr Ile Ala Gly Arg Leu Gln Lys Pro Val Lys Ile Ile Ser Val Asn
    130                 135                 140

Glu Asp Val Thr Leu Arg Ser Ala Leu Asp Arg Asn Leu Lys Ser Ala
145                 150                 155                 160

Val Thr Ala Ala Phe Leu Met Leu Pro Glu Ser Phe Ser Glu Glu Asp
                165                 170                 175

Leu Phe Ile Glu Ile Ala Gly Leu Ser Tyr Ser Gly Asp Phe Arg Met
            180                 185                 190

Val Val Gly Glu Asp Lys Thr Lys Val Leu Asn Ile Val Lys Pro Asn
        195                 200                 205

Ile Ala His Phe Arg Glu Leu Tyr Gly Ser Ile Leu Gln Glu Asn Pro
    210                 215                 220

Gln Val Val Tyr Lys Ser Gln Gln Gly Trp Leu Glu Ile Asp Lys Ser
225                 230                 235                 240

Pro Glu Gly Gln Phe Thr Gln Leu Met Thr Leu Pro Lys Thr Leu Gln
                245                 250                 255

Gln Gln Ile Asn His Ile Met Asp Pro Pro Gly Lys Asn Arg Asp Val
            260                 265                 270

Glu Glu Thr Leu Phe Gln Val Ala His Asp Pro Asp Cys Gly Asp Val
        275                 280                 285

Val Arg Leu Gly Leu Ser Ala Ile Val Arg Pro Ser Ser Ile Arg Gln
    290                 295                 300

Ser Thr Lys Gly Ile Phe Thr Ala Gly Leu Lys Lys Ser Val Ile Tyr
305                 310                 315                 320

Ser Ser Leu Lys Leu His Lys Met Trp Lys Gly Trp Leu Arg Lys Thr
                325                 330                 335

Ser

<210> SEQ ID NO 20
<211> LENGTH: 1278
<212> TYPE: DNA
<213> ORGANISM: Homo sapiens
```

-continued

```
<400> SEQUENCE: 20
tttttttttt tttttttttt ttgtcaaaaa ggatcaaaca ctttattcat ctacacataa      60
catatataaa agcaagcaaa atcaggatgt tttcctcagc cacccttttcc acattttgtg     120 cagtttagt gaactataaa tcactgactt cttcaggcca gcagtaaaaa tgcctttcgt      180
gctctgtctt atactagacg gtctcacgat tgctgaaagc cctagtcgca ccacatctcc     240
acagtcggga tcatgagcca cttggaataa agtttcttcc acatctctgt tttttccagg    300
agggtccata atatgattta tctgttgctg taaggttttg ggcaatgtca tcagctgagt     360
gaactgtcct tctgggcttt tatctatctc cagccagcct tgctggcttt tatacaccac    420
ttgaggattt tcctgtagta tgctgccata gagctctcga agtgggcta tattgggctt     480 cacaatattc aacactttg ttttatcttc tccaaccacc atccgaaagt cacctgaata    540
ggagagaccg gcaatctcta tgaagaggtc ttcttcagaa aagctttcgg ggagcatgag    600
gaaagcagcg gtcacagcac tcttcagatt tctatcgagg gctgatctaa gagtgacatc    660
ctcgttcact gagataattt tcaccggttt ttggagtcgt ccagcaatgt ataagttatt    720
ccagttgagg agatcttcaa tcagaacgtt agtgctaata actccatatt tgataagcct    780
accattacac atgatcaatg aattgtagta aactccagcg ccatagttat tctggatgga    840
cgtgataatc ttgggcccta aaactttag gaaagagtag tgactccaat tttcttcag    900 gttctttgaa tgccatgcga cagggtcatc tactgtgaac acaaagtcca gcatagcatt    960
cttctggtct gaactgggcc ctgcctggcg gtacaccccg gagccgtaga cgaaagccag   1020
actcagctcc tcggggaagt gagacaggat cttgcggaag gtcacccacg agctctgcag   1080
cgtctgcagc gccatggggt cgaggctaac aggggacact cagcgcagca gggcgaggac   1140
aaccgggcgg ggaacagaca ccgggtaggc ggtttagggt gggaaatgga agtcggagac   1200
tggatcgagg gacacaaggc tgagtgtggg gtgggactgc aaggacacgc aaggattggg   1260
gcgttgggcc acgaagag                                                 1278

<210> SEQ ID NO 21
<211> LENGTH: 367
<212> TYPE: PRT
<213> ORGANISM: Mus musculus

<400> SEQUENCE: 21

Gly Thr Gly Arg Lys Arg Gly Pro His Asp Arg Glu Leu Arg Ala Gln
  1               5                  10                  15

Gly Arg His Ser Thr Val Cys Pro Thr Gly Gly Pro Pro Ala His Gly
                 20                  25                  30

Ala Ala Gly Leu His Ser Ser Gly Val Gly Leu Arg Arg Ile Leu Ala
             35                  40                  45

His Phe Pro Glu Asp Leu Ser Leu Ala Phe Ala Tyr Gly Ser Ala Val
         50                  55                  60

Tyr Arg Gln Ala Gly Pro Ser Ala His Gln Glu Asn Pro Met Leu Asp
     65                  70                  75                  80

Leu Val Phe Thr Val Asp Asp Pro Val Ala Trp His Ala Met Asn Leu
                 85                  90                  95

Lys Lys Asn Trp Ser His Tyr Ser Phe Leu Lys Leu Leu Gly Pro Arg
                100                 105                 110

Ile Ile Ser Ser Ile Gln Asn Asn Tyr Gly Ala Gly Val Tyr Phe Asn
            115                 120                 125

Pro Leu Ile Arg Cys Asp Gly Lys Leu Ile Lys Tyr Gly Val Ile Ser
```

```
              130                 135                 140
Thr Gly Thr Leu Ile Glu Asp Leu Leu Asn Trp Asn Asn Leu Tyr Ile
145                 150                 155                 160

Ala Gly Arg Leu Gln Lys Pro Val Lys Ile Val Ser Met Asn Glu Asn
                165                 170                 175

Met Ala Leu Arg Ala Ala Leu Asp Lys Asn Leu Arg Ser Ala Val Thr
                180                 185                 190

Thr Ala Cys Leu Met Leu Pro Glu Ser Phe Ser Glu Asp Leu Phe
                195                 200                 205

Ile Glu Ile Ala Gly Leu Ser Tyr Ser Gly Asp Phe Arg Met Val Ile
    210                 215                 220

Gly Glu Glu Lys Ser Lys Val Leu Asn Ile Val Lys Pro Asn Val Gly
225                 230                 235                 240

His Phe Arg Glu Leu Tyr Glu Ser Ile Leu Gln Lys Asp Pro Gln Val
                245                 250                 255

Val Tyr Lys Met His Gln Gly Gln Leu Glu Ile Asp Lys Ser Pro Glu
                260                 265                 270

Gly Gln Phe Thr Gln Leu Met Thr Leu Pro Arg Thr Leu Gln Gln Gln
                275                 280                 285

Ile Asn His Ile Met Asp Pro Pro Gly Arg Asn Arg Asp Val Glu Glu
    290                 295                 300

Thr Leu Leu Gln Val Ala Gln Asp Pro Asp Cys Gly Asp Val Val Arg
305                 310                 315                 320

Leu Ala Ile Ser Ser Ile Val Arg Pro Ser Ser Ile Arg Gln Ser Thr
                325                 330                 335

Lys Gly Leu Phe Thr Ala Gly Met Lys Lys Ser Val Ile Tyr Ser Ser
                340                 345                 350

Arg Lys Leu Asn Lys Met Trp Lys Gly Trp Met Ser Lys Ala Ser
                355                 360                 365

<210> SEQ ID NO 22
<211> LENGTH: 383
<212> TYPE: PRT
<213> ORGANISM: Schizosaccharomyces pombe

<400> SEQUENCE: 22

Met Ile Phe Gly Lys Thr His Phe Leu Ser Tyr Asn Ile Leu Arg Tyr
  1               5                  10                  15

Ser Thr Lys Arg Trp Met Asn Arg His Ser Tyr Ser His His Ala Lys
                20                  25                  30

Cys Thr Val Ala Gln Leu Leu Lys Gln Asn Leu Leu Thr Phe Glu Asn
                35                  40                  45

Gln Arg Ile Gln Pro Glu Glu Glu Leu Lys Glu Asn Leu Thr Lys Val
    50                  55                  60

Val Asn Tyr Phe Gln Ala Pro Ile Asp Val Ala Val Gly Tyr Gly Ser
65                  70                  75                  80

Gly Val Phe Arg Gln Ala Gly Tyr Ser Gln Lys Glu Asn Pro Met Ile
                85                  90                  95

Asp Phe Ile Phe Gln Val Glu Asp Pro Val Lys Trp His Lys Ile Asn
                100                 105                 110

Leu Gln Gln Asn Pro Ser His Tyr Ser Phe Val Lys Asn Phe Gly Pro
                115                 120                 125

Gly Phe Val Ser Thr Leu Gln Glu Ser Phe Gly Thr Gly Val Tyr Tyr
                130                 135                 140
```

```
Asn Thr His Val Glu Val Gly Asn Ile Ile Lys Tyr Gly Val Thr
145                 150                 155                 160

Ser Lys Lys Asp Val Tyr Glu Asp Leu Lys Asn Trp Asn Thr Met Tyr
            165                 170                 175

Leu Ala Gly Arg Phe Gln Lys Pro Val Val Ile Leu Lys Gly Glu Asp
            180                 185                 190

Glu Phe Tyr Lys Glu Asn Ser Tyr Asn Leu Ser Ser Ala Leu His Val
            195                 200                 205

Gly Leu Leu Met Leu Ala Asp Arg Phe Thr Glu Phe Asp Leu Tyr Lys
210                 215                 220

Thr Ile Val Ser Leu Ser Tyr Leu Gly Asp Ile Arg Met Ser Phe Phe
225                 230                 235                 240

Ala Glu Asn Pro Arg Lys Val Glu Asn Ile Val Ser Lys Gln Ile Ala
            245                 250                 255

Phe Phe Arg Lys Leu Tyr Leu Pro Leu Leu Tyr Ala Glu Pro Gly Val
            260                 265                 270

His Phe Ile Glu Ser Ser Glu Val Leu Lys Ser Met Asp Pro Ser Asp
            275                 280                 285

Asn Ser Arg Tyr Leu Ser Phe His Gln Asn Ile Thr Lys Asp Ser Ile
290                 295                 300

Ser Arg Leu Leu Asn Gly Leu Pro Leu Asn Leu Val Lys Ile Leu Gly
305                 310                 315                 320

Leu Lys Pro Asp Thr Ser Ser Phe Glu Lys Cys Ala Glu Leu Met Leu
            325                 330                 335

Thr Asn Gln Ile Ser Thr Arg Ser Leu Leu Ile Ser Lys Ser Ile Lys
            340                 345                 350

Lys Leu Thr Ser Phe Ser Ile Leu Thr Gln Ser Ile Lys Gly Ile Phe
            355                 360                 365

Thr Ala Arg Cys His Ser Phe Arg Trp Tyr Met Ser Met Arg Ser
            370                 375                 380

<210> SEQ ID NO 23
<211> LENGTH: 274
<212> TYPE: PRT
<213> ORGANISM: Caenorhabditis elegans

<400> SEQUENCE: 23

Met Asp Glu Tyr Arg Glu Leu Ile Ser Val Leu Pro Leu Glu Thr Val
1               5                   10                  15

Glu Tyr Ala Phe Ala Tyr Gly Ser Gly Ala Ile Gln Gln Gln Asn Glu
            20                  25                  30

Asp Lys Ser Glu Lys Met Val Asp Phe Val Ile Val Thr Lys Asn Ala
        35                  40                  45

Gln Glu Phe His Arg Asp Asn Ile Leu Lys Asn Pro Gln His Tyr Ser
    50                  55                  60

Leu Leu Arg Leu Met Gly Pro Lys Met Ile Glu Lys Ile Gln Cys Asn
65                  70                  75                  80

Phe Ala Ala Arg Val Tyr Tyr Asn Thr His Val Lys Val Gly Lys Arg
                85                  90                  95

Lys Ile Lys Tyr Gly Val Ile Ser Tyr Glu Asn Val Lys Gln Asp Leu
            100                 105                 110

Leu Asp Trp Arg Trp Ile Tyr Ile Ser Gly Arg Leu His Lys Pro Val
            115                 120                 125

Leu Glu Val Ile Lys Pro Arg Gln Asp Met Cys Asp Leu Val Thr Glu
130                 135                 140
```

```
Asn Arg Arg Ser Ala Leu His Ser Ser Leu Leu Leu Pro Glu Ser
145                 150                 155                 160

Phe Thr Leu Lys Gln Leu Phe His Lys Ile Val Gly Leu Ser Tyr Thr
                165                 170                 175

Gly Asp Phe Arg Met Val Val Gly Glu Asp Lys Asn Lys Ile Asn Lys
            180                 185                 190

Ile Val Glu Gly Asn Tyr Glu Glu Leu Leu Arg Val Tyr Glu Pro Leu
            195                 200                 205

Met Asn Asp Asp Ala Arg Leu Ser Val Ile Phe Ser Leu Ala His Arg
    210                 215                 220

His Asp Val Ala Ala Thr Val Glu Thr Ala Ile Gly Gly Ile Ile Arg
225                 230                 235                 240

Pro Val Ser Leu Ser Gln Thr Ala Lys Asn Ala Phe Ser Ala Gly Val
                245                 250                 255

Thr Arg Ser Ile Ile Tyr Ser Met Ala Lys Met Ser Lys Phe Leu Lys
            260                 265                 270

Ser Lys

<210> SEQ ID NO 24
<211> LENGTH: 647
<212> TYPE: PRT
<213> ORGANISM: Drosophila melanogaster

<400> SEQUENCE: 24

Met Leu Asp Leu Tyr Arg Arg Thr Val Ala Arg Phe Pro Leu Gly Ser
1               5                   10                  15

Val Ser Tyr Met Phe Ala Tyr Gly Ser Gly Val Lys Gln Gln Glu Gly
                20                  25                  30

Tyr Gly Lys Val Gly Asn Gly Asn Asn Leu Arg Pro Pro Gly Thr
            35                  40                  45

Val Val Asp Leu Val Phe Cys Val Arg Asp Ala Arg Gly Phe His Ala
        50                  55                  60

Glu Asn Leu His Arg His Pro Asp His Tyr Ser Ala Leu Arg His Leu
65                  70                  75                  80

Gly Pro Asn Phe Val Ala Lys Tyr Gln Glu Arg Leu Gly Ala Gly Val
                85                  90                  95

Tyr Cys Asn Thr Leu Val Pro Leu Pro Asp Val Gly Ile Thr Ile Lys
            100                 105                 110

Tyr Gly Val Val Ser Gln Glu Glu Leu Leu Glu Asp Leu Leu Asp Trp
        115                 120                 125

Arg His Leu Tyr Leu Ala Gly Arg Leu His Lys Pro Val Thr Asn Leu
    130                 135                 140

Val Asn Pro Ser Asp Asn Pro Pro Leu Lys Ala Ala Leu Glu Arg Asn
145                 150                 155                 160

Leu Val Ser Ala Leu Gln Val Ala Leu Leu Leu Pro Glu Lys Phe
                165                 170                 175

Thr Ala Tyr Gly Leu Phe His Thr Ile Ala Gly Leu Ser Tyr Lys Gly
            180                 185                 190

Asp Phe Arg Met Ile Phe Gly Glu Asn Lys Gln Lys Val His Asn Ile
        195                 200                 205

Val Ser Pro Gln Ile Asn Asp Phe Ala Leu Tyr Gln Pro Ser Leu
    210                 215                 220

Gly Gln Leu Ser Asp Tyr Val Ala Val Asn Met Lys Gly Gln Glu Pro
225                 230                 235                 240
```

-continued

```
Gly Ser Arg Lys Pro Ala Ile Ile Phe Glu Gln Asp Lys Ser Ser Ser
            245                 250                 255

Ala Thr Cys Gln His Leu Arg Gln Leu Pro Arg Glu Leu Gln Lys Arg
            260                 265                 270

Leu Gln Arg Asn Ala Ala Cys Arg Gly Asp Tyr Thr Gln Val Val Asn
            275                 280                 285

His Leu Ser Met Ala Ser Gln Leu Pro Glu Val Leu Gln Ala Ser Val
            290                 295                 300

Asn Asp Ile Ile Met Ser Ser Asp Asn Ser Ser Asp Ser Asn Ser
305                 310                 315                 320

Ser Ser Asp Glu Arg Gln Arg Lys Arg Lys Leu Lys His Ser Lys
            325                 330                 335

Asp Val Asp Lys Ser Lys Lys Lys Ser Lys Lys His Lys Lys Glu
            340                 345                 350

Lys Arg Arg His Lys Glu Lys Lys Arg Ser Lys His Glu Glu Pro
            355                 360                 365

Pro Val Pro Tyr Thr Gln Pro His Leu Ile Asn Ala Ser Pro Pro
            370                 375                 380

Asp Val Ala Thr Asn Asn Glu Asp Ser Phe Gly Pro Ala Leu Pro Pro
385                 390                 395                 400

His Leu Arg Lys Thr Gln Gln Pro Glu Leu Pro Glu Gln Ser Gln Pro
            405                 410                 415

Ala Pro Gln Pro Gln Ala Met Ile Gly Pro Val Leu Pro Ser Asn Leu
            420                 425                 430

Thr Arg Glu Lys Ser Pro Thr Lys Glu Ala Glu Ala Glu Asp Asp Asp
            435                 440                 445

Asp Leu Ala Gly Thr Phe Gly Pro Leu Pro Asn Ala Ser Gln Val Ala
            450                 455                 460

Leu Glu Glu Arg Ala Leu Ala Leu Lys Leu Ala Ala Leu Glu Gly Gly
465                 470                 475                 480

Gly Leu Gly Thr Ser Thr Asp Gln Asp Val Arg Glu Glu Trp Met Leu
            485                 490                 495

Glu Leu Pro Asp Val Gly Leu Lys Ser Gly Leu Ala Ala Leu Ser Asn
            500                 505                 510

Met Lys Arg Thr Phe Tyr Gln Gly Lys Glu Arg Pro Asp Phe Ser Asp
            515                 520                 525

Arg Ser Ser Trp Thr Lys Thr Pro Gln Ser Glu Ala Asp Ala Ala Ala
            530                 535                 540

Ser Gly Pro Lys Ser Leu Ser Ser Lys Glu Leu Glu Gln Met Ala Gln
545                 550                 555                 560

Val Lys Tyr Glu Gln Gln Arg Asp Asp Glu Gln Ser Met Ala Lys
            565                 570                 575

Arg His Lys Lys His Lys Arg Glu Glu Ser Leu Val Glu Leu His
            580                 585                 590

Gln Lys Lys Leu Arg Lys Glu Gln Arg Glu Lys Pro Glu Arg Arg Pro
            595                 600                 605

Phe Ser Arg Asp Val Asp Leu Lys Leu Asn Lys Ile Asp Lys Asn Gln
            610                 615                 620

Thr Lys Gln Ile Val Asp Lys Ala Lys Ile Leu Asn Thr Lys Phe Ser
625                 630                 635                 640

Arg Gly Gln Ala Lys Tyr Leu
            645
```

<210> SEQ ID NO 25
<211> LENGTH: 332
<212> TYPE: PRT
<213> ORGANISM: Arabidopsis thaliana

<400> SEQUENCE: 25

```
Met Glu Thr Thr Gln Lys Asp Glu Leu Ser Ser Phe Leu Ser Val Leu
  1               5                  10                  15

Pro Pro Val Asp Phe Cys Cys Val Tyr Gly Ser Thr Leu His Pro Asn
             20                  25                  30

Asn Gln Asp Lys Ser Lys Met Val Asp Tyr Ile Leu Gly Val Ser Asp
         35                  40                  45

Pro Ile Lys Trp His Ser Ala Asn Leu Lys Met Asn Ser Asp His Tyr
     50                  55                  60

Ala Ser Trp Met Val His Leu Gly Gly Ala Arg Leu Ile Thr Asn Val
 65                  70                  75                  80

Ala Asp Lys Val Gly Val Gly Val His Phe Asn Pro Phe Val Asn Trp
                 85                  90                  95

Asn Asp Arg Lys Leu Lys Tyr Gly Val Val Arg Met His Asp Leu Val
            100                 105                 110

Gln Asp Ile Leu Asp Trp Lys Arg Phe Tyr Leu Ser Gly Arg Leu Gln
        115                 120                 125

Lys Pro Val His Met Leu Val Asp Asn Leu Asp Ile Glu Asp Val Asn
    130                 135                 140

Ser Val Asn Lys Arg Ala Ala Ile Ser Ala Ala Leu Leu Leu Leu Pro
145                 150                 155                 160

Ser Lys Phe Thr Glu Glu Asp Leu Tyr Ala Lys Ile Cys Ser Leu Ser
                165                 170                 175

Tyr Met Gly Asp Leu Arg Met Phe Phe Ala Glu Asp Thr Asn Lys Val
            180                 185                 190

Asn Lys Ile Val Lys Gly Gln Phe Asp Leu Phe Gln Ser Met Tyr Lys
        195                 200                 205

Pro Phe Leu Glu Glu Cys Glu Thr Lys Asn Leu Leu Arg Phe Ser Ser
    210                 215                 220

Ala Glu Ala Ser His Thr Lys Leu Val Gln Asp Ser Ser Leu Ser Ala
225                 230                 235                 240

Thr Arg Ser Leu Val Ser Ser Leu Pro Ala Ser Val Arg Ser Gln Met
                245                 250                 255

Gly Lys Ser Leu Gly Lys Lys Phe Val Ser Glu Thr Gly Arg Val
            260                 265                 270

Met Gly Glu Val Cys Ile Ser Ser Arg Glu Glu Ala Ala Lys Cys Met
        275                 280                 285

Glu Lys Val Met Arg Arg Val Met Val Ser Ser Gly Arg Gln Ala
    290                 295                 300

Val Ser Gly Phe Leu Ala Ala Gly Ala Ile Asn Ala Thr Met Tyr Leu
305                 310                 315                 320

Ser Gln Lys Met Arg Lys Ala Trp Asn Ser Arg Ala
                325                 330
```

<210> SEQ ID NO 26
<211> LENGTH: 983
<212> TYPE: DNA
<213> ORGANISM: Homo sapiens

<400> SEQUENCE: 26

-continued

```
ccgcggctgt gtcgtcatac ttgcgcgccg acgccgccgc tcgcttgtga aactggaagg    60
ctgccatggc tagcccagcc gcctcctcgg tgcgaccacc gaggcccaag aaagagccgc   120
agacgctcgt catccccaag aatgcggcgg aggagcagaa gctcaagctg gagcggctca   180
tgaagaaccc ggacaaagca gttccaattc cagagaaaat gagtgaatgg gcacctcgac   240
ctcccccaga atttgtccga gatgtcatgg gttcaagtgc tggggccggc agtggagagt   300
tccacgtgta cagacatctg cgccggagag aatatcagcg acaggactac atggatgcca   360
tggctgagaa gcaaaaattg gatgcagagt ttcagaaaag actggaaaag aataaaattg   420
ctgcagagga gcagaccgca aagcgccgga gaagcgccca aagttaaaa gagaagaaat    480
tactggcaaa gaagatgaaa cttgaacaga gaaacaaga aggacccggt cagcccaagg    540
agcaggggtc cagcagctct gcggaggcat ctggaacaga ggaggaggag gaagtgccca   600
gtttcaccat ggggcgatga caatgtttgc cacagcctct gcctggaacc tggctcgtgc   660
tgtgaccaga agggaaaggc ggctgttttgg ctctttctcc cccgcaagga cccgctgacc   720
cgctggatgg agagcaaagg agacccctcc cgagccgctc acagtcctgt atttggcagg   780
tttgggagcc tgaggggcca tctccctgac actcagaggc actgccttgc agacaccatc   840
cgtgctcctg gtaaaggggg acagagagcc tcaccttgcc acatatttga acagtgatga   900
gtttgggget ggtttctggg aagggaacgt ttatttagta aagagcagaa caccttaaa    960
aaaaaaaaaa aaaaaaaaaa aaa                                           983
```

```
<210> SEQ ID NO 27
<211> LENGTH: 184
<212> TYPE: PRT
<213> ORGANISM: Homo sapiens

<400> SEQUENCE: 27

Met Ala Ser Pro Ala Ala Ser Ser Val Arg Pro Pro Arg Pro Lys Lys
  1               5                  10                  15

Glu Pro Gln Thr Leu Val Ile Pro Lys Asn Ala Ala Glu Glu Gln Lys
             20                  25                  30

Leu Lys Leu Glu Arg Leu Met Lys Asn Pro Asp Lys Ala Val Pro Ile
         35                  40                  45

Pro Glu Lys Met Ser Glu Trp Ala Pro Arg Pro Pro Glu Phe Val
     50                  55                  60

Arg Asp Val Met Gly Ser Ser Ala Gly Ala Gly Ser Gly Glu Phe His
 65                  70                  75                  80

Val Tyr Arg His Leu Arg Arg Arg Glu Tyr Gln Arg Gln Asp Tyr Met
                 85                  90                  95

Asp Ala Met Ala Glu Lys Gln Lys Leu Asp Ala Glu Phe Gln Lys Arg
            100                 105                 110

Leu Glu Lys Asn Lys Ile Ala Ala Glu Glu Gln Thr Ala Lys Arg Arg
        115                 120                 125

Lys Lys Arg Gln Lys Leu Lys Glu Lys Leu Leu Ala Lys Lys Met
    130                 135                 140

Lys Leu Glu Gln Lys Lys Gln Glu Gly Pro Gly Gln Pro Lys Glu Gln
145                 150                 155                 160

Gly Ser Ser Ser Ser Ala Glu Ala Ser Gly Thr Glu Glu Glu Glu
                165                 170                 175

Val Pro Ser Phe Thr Met Gly Arg
            180
```

<210> SEQ ID NO 28
<211> LENGTH: 983
<212> TYPE: DNA
<213> ORGANISM: Homo sapiens

<400> SEQUENCE: 28

```
ttttttttt ttttttttt ttttttaagg gtgttctgct ctttactaaa taaacgttcc      60
cttcccagaa accagcccca aactcatcac tgttcaaata tgtggcaagg tgaggctctc    120
tgtccccctt taccaggagc acggatggtg tctgcaaggc agtgcctctg agtgtcaggg    180
agatggcccc tcaggctccc aaacctgcca aatacaggac tgtgagcggc tcggaggggg    240
tctcctttgc tctccatcca gcgggtcagc gggtccttgc gggggagaaa gagccaaaca    300
gccgcctttc ccttctggtc acagcacgag ccaggttcca ggcagaggct gtggcaaaca    360
ttgtcatcgc cccatggtga aactgggcac ttcctcctcc tcctctgttc cagatgcctc    420
cgcagagctg ctggaccccct gctccttggg ctgaccgggt ccttcttgtt tcttctgttc    480
aagtttcatc ttctttgcca gtaatttctt ctcttttaac ttctggcgct tcttccggcg    540
ctttgcggtc tgctcctctg cagcaatttt attcttttcc agtctttttct gaaactctgc    600
atccaatttt tgcttctcag ccatggcatc catgtagtcc tgtcgctgat attctctccg    660
gcgcagatgt ctgtacacgt ggaactctcc actgccggcc ccagcacttg aacccatgac    720
atctcggaca aattctgggg gaggtcgagg tgcccattca ctcatttttct ctggaattgg    780
aactgctttg tccgggttct tcatgagccg ctccagcttg agcttctgct cctccgccgc    840
attcttgggg atgacgagcg tctgcggctc tttcttgggc ctcggtggtc gcaccgagga    900
ggcggctggg ctagccatgg cagccttcca gtttcacaag cgagcggcgg cgtcggcgcg    960
caagtatgac gacacagccg cgg                                           983
```

<210> SEQ ID NO 29
<211> LENGTH: 184
<212> TYPE: PRT
<213> ORGANISM: Homo sapiens

<400> SEQUENCE: 29

```
Met Ala Ser Pro Ala Ala Ser Ser Val Arg Pro Pro Arg Pro Lys Lys
  1               5                  10                  15

Glu Pro Gln Thr Leu Val Ile Pro Lys Asn Ala Ala Glu Glu Gln Lys
             20                  25                  30

Leu Lys Leu Glu Arg Leu Met Lys Asn Pro Asp Lys Ala Val Pro Ile
         35                  40                  45

Pro Glu Lys Met Ser Glu Trp Ala Pro Arg Pro Pro Glu Phe Val
     50                  55                  60

Arg Asp Val Met Gly Ser Ser Ala Gly Ala Gly Ser Gly Glu Phe His
 65                  70                  75                  80

Val Tyr Arg His Leu Arg Arg Glu Tyr Gln Arg Gln Asp Tyr Met
                 85                  90                  95

Asp Ala Met Ala Glu Lys Gln Lys Leu Asp Ala Glu Phe Gln Lys Arg
            100                 105                 110

Leu Glu Lys Asn Lys Ile Ala Ala Glu Glu Gln Thr Ala Lys Arg Arg
        115                 120                 125

Lys Lys Arg Gln Lys Leu Lys Glu Lys Leu Ala Lys Lys Met
        130                 135                 140

Lys Leu Glu Gln Lys Lys Gln Glu Gly Pro Gly Gln Pro Lys Glu Gln
145                 150                 155                 160
```

```
Gly Ser Ser Ser Ala Glu Ala Ser Gly Thr Glu Glu Glu Glu
            165                 170                 175

Val Pro Ser Phe Thr Met Gly Arg
            180

<210> SEQ ID NO 30
<211> LENGTH: 186
<212> TYPE: PRT
<213> ORGANISM: Mus musculus

<400> SEQUENCE: 30

Met Ala Ser Pro Ala Ala Ser Val Arg Pro Pro Arg Pro Lys Lys
  1               5                  10                  15

Glu Pro Gln Thr Leu Val Ile Pro Lys Asn Ala Ala Glu Gln Lys
             20                  25                  30

Leu Lys Leu Glu Arg Leu Met Lys Asn Pro Asp Lys Ala Val Pro Ile
             35                  40                  45

Pro Glu Lys Met Asn Glu Trp Ala Pro Arg Ala Pro Pro Glu Phe Val
     50                  55                  60

Arg Asp Val Met Gly Ser Ser Ala Gly Ala Gly Ser Gly Glu Phe His
 65                  70                  75                  80

Val Tyr Arg His Leu Arg Arg Arg Glu Tyr Gln Arg Gln Asp Tyr Met
                 85                  90                  95

Asp Ala Met Ala Glu Lys Gln Lys Leu Asp Ala Glu Phe Gln Lys Arg
            100                 105                 110

Leu Glu Lys Asn Lys Ile Ala Ala Glu Glu Gln Thr Ala Lys Arg Arg
            115                 120                 125

Lys Lys Arg Gln Lys Leu Lys Glu Lys Leu Leu Ala Lys Lys Met
130                 135                 140

Lys Leu Glu Gln Lys Lys Gln Lys Glu Glu Pro Ser Gln Cys Gln Glu
145                 150                 155                 160

Gln His Ala Ser Ser Ser Asp Glu Ala Ser Glu Thr Glu Glu Glu
            165                 170                 175

Glu Glu Pro Ser Val Leu Ile Met Gly Arg
            180                 185

<210> SEQ ID NO 31
<211> LENGTH: 186
<212> TYPE: PRT
<213> ORGANISM: Mus musculus

<400> SEQUENCE: 31

Met Ala Ser Pro Ala Ala Ser Val Arg Pro Pro Arg Pro Lys Lys
  1               5                  10                  15

Glu Pro Gln Thr Leu Val Ile Pro Lys Asn Ala Ala Glu Gln Lys
             20                  25                  30

Leu Lys Leu Glu Arg Leu Met Lys Asn Pro Asp Lys Ala Val Pro Ile
             35                  40                  45

Pro Glu Lys Met Asn Glu Trp Ala Pro Arg Ala Pro Pro Glu Phe Val
     50                  55                  60

Arg Asp Val Met Gly Ser Ser Ala Gly Ala Gly Ser Gly Glu Phe His
 65                  70                  75                  80

Val Tyr Arg His Leu Arg Arg Arg Glu Tyr Gln Arg Gln Asp Tyr Met
                 85                  90                  95

Asp Ala Met Ala Glu Lys Gln Lys Leu Asp Ala Glu Phe Gln Lys Arg
            100                 105                 110
```

-continued

```
Leu Glu Lys Asn Lys Ile Ala Ala Glu Glu Gln Thr Ala Lys Arg Arg
        115                 120                 125
Lys Lys Arg Gln Lys Leu Lys Glu Lys Leu Leu Ala Lys Lys Met
130                 135                 140
Lys Leu Glu Gln Lys Lys Gln Lys Glu Glu Pro Ser Gln Cys Gln Glu
145                 150                 155                 160
Gln His Ala Ser Ser Ser Asp Glu Ala Ser Glu Thr Glu Glu Glu Glu
                165                 170                 175
Glu Glu Pro Ser Val Val Ile Met Gly Arg
            180                 185

<210> SEQ ID NO 32
<211> LENGTH: 148
<212> TYPE: PRT
<213> ORGANISM: Mus musculus

<400> SEQUENCE: 32

Met Lys Asn Pro Asp Lys Ala Val Pro Ile Pro Glu Lys Met Asn Glu
1               5                   10                  15
Trp Ala Pro Arg Ala Pro Pro Glu Phe Val Arg Asp Val Met Gly Ser
            20                  25                  30
Ser Ala Gly Ala Gly Ser Gly Glu Phe His Val Tyr Arg His Leu Arg
        35                  40                  45
Arg Arg Glu Tyr Gln Arg Gln Asp Tyr Met Asp Ala Met Ala Glu Lys
    50                  55                  60
Gln Lys Leu Asp Ala Glu Phe Gln Lys Arg Leu Glu Lys Asn Lys Ile
65                  70                  75                  80
Ala Ala Glu Glu Gln Thr Ala Lys Arg Arg Lys Lys Arg Gln Lys Leu
                85                  90                  95
Lys Glu Lys Lys Leu Leu Ala Lys Lys Met Lys Leu Glu Gln Lys Lys
            100                 105                 110
Gln Lys Glu Glu Pro Ser Gln Cys Gln Glu Gln His Ala Ser Ser Ser
        115                 120                 125
Asp Glu Ala Ser Glu Thr Glu Glu Glu Glu Glu Glu Pro Ser Val Val
    130                 135                 140
Ile Met Gly Arg
145

<210> SEQ ID NO 33
<211> LENGTH: 253
<212> TYPE: PRT
<213> ORGANISM: Drosophila melanogaster

<400> SEQUENCE: 33

Met Ser Leu Ile Lys Asn Leu Val Lys Glu Pro Glu Gln Lys Ala Lys
1               5                   10                  15
Lys Lys Lys Lys Asn Ala Gly Ser Gly Glu Ser Asp Ser Asp Glu Lys
            20                  25                  30
Asp Lys Pro Leu Arg Pro Phe Ile Lys Thr Ala Thr Asp Leu Gln Arg
        35                  40                  45
Leu Lys Leu Glu Lys Leu Met Lys Asn Pro Asp Lys Pro Val Val Ile
    50                  55                  60
Pro Glu Gln Arg Arg Glu Arg Asp Phe Met Ser Ser Val Pro Thr Phe
65                  70                  75                  80
Val Arg Asn Val Met Gly Ser Ser Ala Gly Ala Gly Ser Gly Glu Phe
                85                  90                  95
```

His Val Tyr Arg His Leu Arg Arg Lys Glu Tyr Ala Arg Gln Lys Asn
                100                 105                 110

Ile Gln Asn Gln Ser Ala Arg Glu Ala Ala Asp Glu Ala Tyr Gln Gln
        115                 120                 125

Lys Leu Asp Asp Asn Arg Arg Ala Ala Glu Glu Lys Thr Ala Lys Lys
    130                 135                 140

Arg Ala Lys Arg Leu Lys Arg Lys Gln Arg Ala Lys Lys Pro Arg Glu
145                 150                 155                 160

Asp Lys Lys Pro Leu Ala Lys Glu Ala Ser Glu Asp Ser Asn Thr Asp
                165                 170                 175

Ser Glu Glu Glu Pro Thr Glu Glu Lys Ala Glu Ser Ser Pro Glu Glu
            180                 185                 190

Gly Gln Gln Val Ala Ser Lys Glu Ser Asp Asp Asn Thr Gln Glu
        195                 200                 205

Thr Ser Asn Glu Glu Ala Val Asn Ser Asn Thr Glu Ala Lys Ser Ala
    210                 215                 220

Glu Asp Thr Asn Ala Val Glu Leu Asp Ser Thr Glu Ala Thr Lys Glu
225                 230                 235                 240

Ser Gln Asn Val Asp Gln Glu Gln Asp Lys Pro Val Pro
                245                 250

<210> SEQ ID NO 34
<211> LENGTH: 2456
<212> TYPE: DNA
<213> ORGANISM: Homo sapiens

<400> SEQUENCE: 34

| | | | | | |
|---|---|---|---|---|---|
| gaattcctga | ctgccacagg | tgtacaggaa | acatttgtct | tttgttgctg | gaaagctgct | 60 |
| caaatcaaag | aacatttact | gaagtcaaag | tggtgccgcc | ctacatctct | caatgtggtt | 120 |
| cgaataatta | catcagagct | ctatcgatca | ctgggagatg | tcctccgtga | tgttgatgcc | 180 |
| aaggctttgg | tgcgctctga | ctttcttctg | gtgtatgggg | atgtcatctc | aaacatcaat | 240 |
| atcaccagag | cccttgagga | acacaggttg | agacggaagc | tagaaaaaaa | tgtttctgtg | 300 |
| atgacgatga | tcttcaagga | gtcatccccc | agccacccaa | ctcgttgcca | cgaagacaat | 360 |
| gtggtagtgg | ctgtggatag | taccacaaac | agggttctcc | attttcagaa | gacccagggt | 420 |
| ctccggcgtt | ttgcatttcc | tctgagcctg | tttcagggca | gtagtgatgg | agtggaggtt | 480 |
| cgatatgatt | tactggattg | tcatatcagc | atctgttctc | ctcaggtggc | acaactcttt | 540 |
| acagacaact | ttgactacca | aactcgagat | gactttgtgc | gaggtctctt | agtgaatgag | 600 |
| gagatcctag | ggaaccagat | ccacatgcac | gtaacagcta | aggaatatgg | tgcccgtgtc | 660 |
| tccaacctac | acatgtactc | agctgtctgt | gctgacgtca | tccgccgatg | ggtctaccct | 720 |
| ctcacccccag | aggcgaactt | cactgacagc | accacccaga | gctgcactca | ttcccggcac | 780 |
| aacatctacc | gagggcctga | ggtcagcctg | gccatggca | gcatcctaga | ggaaaatgtg | 840 |
| ctcctgggct | ctggcactgt | cattggcagc | aattgcttta | tcaccaacag | tgtcattggc | 900 |
| cccggctgcc | acattggtga | gcacaggtga | taacgtggtg | ctggaccaga | cctacctgtg | 960 |
| gcagggtgtt | cgagtggcgg | ctggagcaca | gatccatcag | tctctgcttt | gtgacaatgc | 1020 |
| tgaggtcaag | gaacgagtga | cactgaaacc | acgctctgtc | ctcacttccc | aggtggtcgt | 1080 |
| gggcccaaat | atcacgctgc | ctgagggctc | ggtgatctct | ttgcaccctc | cagatgcaga | 1140 |
| ggaagatgaa | gatgatggcg | agttcagtga | tgattctggg | gctgaccaag | aaaaggacaa | 1200 |

-continued

```
agtgaagatg aaaggttaca atccagcaga agtaggagct gctggcaagg gctacctctg   1260
gaaagctgca ggcatgaaca tggaggaaga ggaggaactg cagcagaatc tgtggggact   1320
caagatcaac atggaagaag agagtgaaag tgaaagtgag caaagtatgg attctgagga   1380
gccggacagc cggggaggct cccctcagat ggatgacatc aaagtgttcc agaatgaagt   1440
tttaggaaca ctacagcggg gcaaagagga gaacatttct tgtgacaatc tcgtcctgga   1500
aatcaactct ctcaagtatg cctataacat aagtctaaag gaggtgatgc aggtactgag   1560
ccacgtggtc ctggagttcc ccctgcaaca gatggattcc ccgcttgact caagccgcta   1620
ctgtgccctg ctgcttcctc tgctaaaggc ctggagccct gtttttagga actacataaa   1680
gcgcgcagcc gaccatttgg aagcgttagc agccattgag gacttcttcc tagagcatga   1740
agctcttggt atttccatgg ccaaggtact gatggctttc taccagctgg agatcctggc   1800
tgaggaaaca attctgagct ggttcagcca agagataca actgacaagg ccagcagtt    1860 gcgcaagaat caacagctgc agaggttcat ccagtggcta aaagaggcag aagaggagtc   1920
atctgaagat gactgaagtc acactgcctg ctcctttggg tgtgattgag tgccctcctg   1980
gctcctgggc tgggacaagt gaggaactag ctgcagaggg atgagtgacc accatccagg   2040
ctgagactga aggagcaga ggctggaact acagtattct ttcccctgct agcaaccatg     2100
tgcctcccat cctgactgtg gagttgggat gtggaagtgg ggctggaaca aagcttctgc   2160
ctagggagga gctaagcagg cccggcagtt ggaggaaggc cagaggaaca gctttgtgct   2220
ccggctttcc ctcagggaac agcagagagc agttggctct ttctgctgct tgtatatgtt   2280
aatattaaaa gagagagtgg tgtatttggt ttgtctccat ccccgactaa tcagccagtg   2340
aagtatgtga ccagaatcac atgatagcct ttccttaaca cctgggggag agggaggacg   2400
ggtgtgccag ccactaggtg gtactgtggt accttgctaa ttaaccttc ccatgg        2456
```

```
<210> SEQ ID NO 35
<211> LENGTH: 366
<212> TYPE: PRT
<213> ORGANISM: Homo sapiens

<400> SEQUENCE: 35
```

```
Met Cys Ser Trp Ala Leu Ala Leu Ser Leu Ala Ala Ile Ala Leu Ser
  1               5                  10                  15

Pro Thr Val Ser Leu Ala Pro Ala Ala Thr Leu Val Ser Thr Gly Asp
             20                  25                  30

Asn Val Val Leu Asp Gln Thr Tyr Leu Trp Gln Gly Val Arg Val Ala
         35                  40                  45

Ala Gly Ala Gln Ile His Gln Ser Leu Leu Cys Asp Asn Ala Glu Val
     50                  55                  60

Lys Glu Arg Val Thr Leu Lys Pro Arg Ser Val Leu Thr Ser Gln Val
 65                  70                  75                  80

Val Val Gly Pro Asn Ile Thr Leu Pro Glu Gly Ser Val Ile Ser Leu
                 85                  90                  95

His Pro Pro Asp Ala Glu Glu Asp Glu Asp Gly Glu Phe Ser Asp
            100                 105                 110

Asp Ser Gly Ala Asp Gln Glu Lys Asp Lys Val Lys Met Lys Gly Tyr
        115                 120                 125

Asn Pro Ala Glu Val Gly Ala Ala Gly Lys Gly Tyr Leu Trp Lys Ala
    130                 135                 140

Ala Gly Met Asn Met Glu Glu Glu Glu Leu Gln Gln Asn Leu Trp
145                 150                 155                 160
```

-continued

```
Gly Leu Lys Ile Asn Met Glu Glu Ser Glu Ser Glu Gln
            165                 170                 175

Ser Met Asp Ser Glu Glu Pro Asp Ser Arg Gly Gly Ser Pro Gln Met
            180                 185                 190

Asp Asp Ile Lys Val Phe Gln Asn Glu Val Leu Gly Thr Leu Gln Arg
            195                 200                 205

Gly Lys Glu Glu Asn Ile Ser Cys Asp Asn Leu Val Leu Glu Ile Asn
        210                 215                 220

Ser Leu Lys Tyr Ala Tyr Asn Ile Ser Leu Lys Glu Val Met Gln Val
225                 230                 235                 240

Leu Ser His Val Val Leu Glu Phe Pro Leu Gln Gln Met Asp Ser Pro
                245                 250                 255

Leu Asp Ser Ser Arg Tyr Cys Ala Leu Leu Pro Leu Leu Lys Ala
            260                 265                 270

Trp Ser Pro Val Phe Arg Asn Tyr Ile Lys Arg Ala Ala Asp His Leu
        275                 280                 285

Glu Ala Leu Ala Ala Ile Glu Asp Phe Phe Leu Glu His Glu Ala Leu
    290                 295                 300

Gly Ile Ser Met Ala Lys Val Leu Met Ala Phe Tyr Gln Leu Glu Ile
305                 310                 315                 320

Leu Ala Glu Glu Thr Ile Leu Ser Trp Phe Ser Gln Arg Asp Thr Thr
                325                 330                 335

Asp Lys Gly Gln Gln Leu Arg Lys Asn Gln Gln Leu Gly Arg Phe Ile
            340                 345                 350

Gln Trp Leu Lys Glu Ala Glu Glu Ser Ser Glu Asp Asp
        355                 360                 365

<210> SEQ ID NO 36
<211> LENGTH: 2456
<212> TYPE: DNA
<213> ORGANISM: Homo sapiens

<400> SEQUENCE: 36
ccatgggaaa ggttaattag caaggtacca cagtaccacc tagtggctgg cacacccgtc      60
ctccctctcc cccaggtgtt aaggaaaggc tatcatgtga ttctggtcac atacttcact    120
ggctgattag tcggggatgg agacaaacca aatacaccac tctctctttt aatattaaca    180
tatacaagca gcagaaagag ccaactgctc tctgctgttc cctgagggaa agccggagca    240
caaagctgtt cctctggcct tcctccaact gccgggcctg cttagctcct ccctaggcag    300
aagctttgtt ccagccccac ttccacatcc caactccaca gtcaggatgg gaggcacatg    360
gttgctagca ggggaaagaa tactgtagtt ccagcctctg ctcctttcag tctcagcctg    420
gatggtggtc actcatccct ctgcagctag ttcctcactt gtcccagccc aggagccagg    480
agggcactca atcacaccca aggagcagg cagtgtgact tcagtcatct tcagatgact    540
cctcttctgc ctcttttagc cactggatga acctctgcag ctgttgattc ttgcgcaact    600
gctggccctt gtcagttgta tctctttggc tgaaccagct cagaattgtt tcctcagcca    660
ggatctccag ctggtagaaa gccatcagta ccttggccat ggaaatacca agagcttcat    720
gctctaggaa gaagtcctca atggctgcta acgttccaa atggtcggct gcgcgcttta     780
tgtagttcct aaaaacaggg ctccaggcct ttagcagagg aagcagcagg gcacagtagc    840
ggcttgagtc aagcggggaa tccatctgtt gcaggggaa ctccaggacc acgtggctca    900
gtacctgcat caccctcctt tagacttatgt tataggcata cttgagagag ttgatttcca    960
```

-continued

```
ggacgagatt gtcacaagaa atgttctcct ctttgccccg ctgtagtgtt cctaaaactt    1020
cattctggaa cactttgatg tcatccatct gaggggagcc tccccggctg tccggctcct    1080
cagaatccat actttgctca ctttcacttt cactctcttc ttccatgttg atcttgagtc    1140
cccacagatt ctgctgcagt tcctcctctt cctccatgtt catgcctgca gctttccaga    1200
ggtagccctt gccagcagct cctacttctg ctggattgta acctttcatc ttcactttgt    1260
ccttttcttg gtcagcccca gaatcatcac tgaactcgcc atcatcttca tcttcctctg    1320
catctggagg gtgcaaagag atcaccgagc cctcaggcag cgtgatattt gggcccacga    1380
ccacctggga agtgaggaca gagcgtggtt tcagtgtcac tcgttccttg acctcagcat    1440
tgtcacaaag cagagactga tggatctgtg ctccagccgc cactcgaaca ccctgccaca    1500
ggtaggtctg gtccagcacc acgttatcac ctgtgctcac caatgtggca gccggggcca    1560
atgacactgt tggtgataaa gcaattgctg ccaatgacag tgccagagcc aggagcaca    1620 ttttcctcta ggatgctgcc atggcccagg ctgacctcag gccctcggta gatgttgtgc    1680
cgggaatgag tgcagctctg gtggtgctgt tcagtgaagt tcgcctctgg ggtgagaggg    1740
tagacccatc ggcggatgac gtcagcacag acagctgagt acatgtgtag gttggagaca    1800
cgggcaccat attccttagc tgttacgtgc atgtggatct ggttccctag gatctcctca    1860
ttcactaaga gacctcgcac aaagtcatct cgagtttggt agtcaaagtt gtctgtaaag    1920
agttgtgcca cctgaggaga acagatgcta atatgacaat ccagtaaatc atatcgaacc    1980
tccactccat cactactgcc ctgaaacagg ctcagaggaa atgcaaaacg ccggagaccc    2040
tgggtcttct gaaaatggag aaccctgttt gtggtactat ccacagccac taccacattg    2100
tcttcgtggc aacgagttgg gtggctgggg atgactcct tgaagatcat cgtcatcaca    2160
gaaacatttt tttctagctt ccgtctcaac ctgtgttcct caagggctct ggtgatattg    2220
atgtttgaga tgcatcccc atacaccaga agaaagtcag agcgcaccaa agccttggca    2280
tcaacatcac ggaggacatc tcccagtgat cgatagagct ctgatgtaat tattcgaacc    2340
acattgagag atgtagggcg gcaccacttt gacttcagta aatgttcttt gatttgagca    2400
gctttccagc aacaaaagac aaatgtttcc tgtacacctg tggcagtcag gaattc       2456
```

<210> SEQ ID NO 37
<211> LENGTH: 641
<212> TYPE: PRT
<213> ORGANISM: Homo sapiens

<400> SEQUENCE: 37

```
Glu Phe Leu Thr Ala Thr Gly Val Gln Glu Thr Phe Val Phe Cys Cys
  1               5                  10                  15

Trp Lys Ala Ala Gln Ile Lys Glu His Leu Leu Lys Ser Lys Trp Cys
             20                  25                  30

Arg Pro Thr Ser Leu Asn Val Arg Ile Ile Thr Ser Glu Leu Tyr
         35                  40                  45

Arg Ser Leu Gly Asp Val Leu Arg Asp Val Asp Ala Lys Ala Leu Val
     50                  55                  60

Arg Ser Asp Phe Leu Leu Val Tyr Gly Asp Val Ile Ser Asn Ile Asn
 65                  70                  75                  80

Ile Thr Arg Ala Leu Glu Glu His Arg Leu Arg Arg Lys Leu Glu Lys
                 85                  90                  95

Asn Val Ser Val Met Thr Met Ile Phe Lys Glu Ser Ser Pro Ser His
            100                 105                 110
```

-continued

```
Pro Thr Arg Cys His Glu Asp Asn Val Val Ala Val Asp Ser Thr
        115                 120                 125
Thr Asn Arg Val Leu His Phe Gln Lys Thr Gln Gly Leu Arg Arg Phe
    130                 135                 140
Ala Phe Pro Leu Ser Leu Phe Gln Gly Ser Ser Asp Gly Val Glu Val
145                 150                 155                 160
Arg Tyr Asp Leu Leu Asp Cys His Ile Ser Ile Cys Ser Pro Gln Val
                165                 170                 175
Ala Gln Leu Phe Thr Asp Asn Phe Asp Tyr Gln Thr Arg Asp Asp Phe
            180                 185                 190
Val Arg Gly Leu Leu Val Asn Glu Glu Ile Leu Gly Asn Gln Ile His
        195                 200                 205
Met His Val Thr Ala Lys Glu Tyr Gly Ala Arg Val Ser Asn Leu His
    210                 215                 220
Met Tyr Ser Ala Val Cys Ala Asp Val Ile Arg Arg Trp Val Tyr Pro
225                 230                 235                 240
Leu Thr Pro Glu Ala Asn Phe Thr Asp Ser Thr Thr Gln Ser Cys Thr
                245                 250                 255
His Ser Arg His Asn Ile Tyr Arg Gly Pro Glu Val Ser Leu Gly His
            260                 265                 270
Gly Ser Ile Leu Glu Glu Asn Val Leu Leu Gly Ser Gly Thr Val Ile
        275                 280                 285
Gly Ser Asn Cys Phe Ile Thr Asn Ser Val Ile Gly Pro Gly Cys His
    290                 295                 300
Ile Gly Asp Asn Val Val Leu Asp Gln Thr Tyr Leu Trp Gln Gly Val
305                 310                 315                 320
Arg Val Ala Ala Gly Ala Gln Ile His Gln Ser Leu Leu Cys Asp Asn
                325                 330                 335
Ala Glu Val Lys Glu Arg Val Thr Leu Lys Pro Arg Ser Val Leu Thr
            340                 345                 350
Ser Gln Val Val Val Gly Pro Asn Ile Thr Leu Pro Glu Gly Ser Val
        355                 360                 365
Ile Ser Leu His Pro Pro Asp Ala Glu Glu Asp Glu Asp Gly Glu
    370                 375                 380
Phe Ser Asp Asp Ser Gly Ala Asp Gln Glu Lys Asp Lys Val Lys Met
385                 390                 395                 400
Lys Gly Tyr Asn Pro Ala Glu Val Gly Ala Ala Gly Lys Gly Tyr Leu
                405                 410                 415
Trp Lys Ala Ala Gly Met Asn Met Glu Glu Glu Glu Leu Gln Gln
            420                 425                 430
Asn Leu Trp Gly Leu Lys Ile Asn Met Glu Glu Glu Ser Glu Ser Glu
        435                 440                 445
Ser Glu Gln Ser Met Asp Ser Glu Glu Pro Asp Ser Arg Gly Gly Ser
    450                 455                 460
Pro Gln Met Asp Asp Ile Lys Val Phe Gln Asn Glu Val Leu Gly Thr
465                 470                 475                 480
Leu Gln Arg Gly Lys Glu Glu Asn Ile Ser Cys Asp Asn Leu Val Leu
                485                 490                 495
Glu Ile Asn Ser Leu Lys Tyr Ala Tyr Asn Val Ser Leu Lys Glu Val
            500                 505                 510
Met Gln Val Leu Ser His Val Val Leu Glu Phe Pro Leu Gln Gln Met
        515                 520                 525
```

```
Asp Ser Pro Leu Asp Ser Ser Arg Tyr Cys Ala Leu Leu Pro Leu
        530                 535                 540

Leu Lys Ala Trp Ser Pro Val Phe Arg Asn Tyr Ile Lys Arg Ala Ala
545                 550                 555                 560

Asp His Leu Glu Ala Leu Ala Ala Ile Glu Asp Phe Phe Leu Glu His
                565                 570                 575

Glu Ala Leu Gly Ile Ser Met Ala Lys Val Leu Met Ala Phe Tyr Gln
            580                 585                 590

Leu Glu Ile Leu Ala Glu Thr Ile Leu Ser Trp Phe Ser Gln Arg
                595                 600                 605

Asp Thr Thr Asp Lys Gly Gln Gln Leu Arg Lys Asn Gln Gln Leu Gln
        610                 615                 620

Arg Phe Ile Gln Trp Leu Lys Glu Ala Glu Glu Ser Ser Glu Asp
625                 630                 635                 640

Asp

<210> SEQ ID NO 38
<211> LENGTH: 721
<212> TYPE: PRT
<213> ORGANISM: Oryctolagus cuniculus

<400> SEQUENCE: 38

Met Ala Thr Thr Val Val Ala Pro Pro Gly Ala Val Ser Asp Arg Ala
 1               5                  10                  15

Asn Lys Arg Gly Gly Pro Gly Gly Gly Gly Gly Gly Gly Ala
                20                  25                  30

Arg Gly Ala Glu Glu Glu Ser Pro Pro Leu Gln Ala Val Leu Val
            35                  40                  45

Ala Asp Ser Phe Asn Arg Arg Phe Phe Pro Ile Ser Lys Asp Gln Pro
 50                  55                  60

Arg Val Leu Leu Pro Leu Ala Asn Val Ala Leu Ile Asp Tyr Thr Leu
 65                  70                  75                  80

Glu Phe Leu Thr Ala Thr Gly Val Gln Glu Thr Phe Val Phe Cys Cys
                 85                  90                  95

Trp Lys Ala Ala Gln Ile Lys Glu His Leu Gln Lys Ser Lys Trp Cys
                100                 105                 110

Arg Pro Thr Ser Leu Asn Val Val Arg Ile Ile Thr Ser Glu Leu Tyr
            115                 120                 125

Arg Ser Leu Gly Asp Val Leu Arg Asp Val Asp Ala Lys Ala Leu Val
        130                 135                 140

Arg Ser Asp Phe Leu Leu Val Tyr Gly Asp Val Val Ser Asn Ile Asn
145                 150                 155                 160

Val Thr Arg Ala Leu Glu Glu His Arg Leu Arg Arg Lys Leu Glu Lys
                165                 170                 175

Asn Val Ser Val Met Thr Met Ile Phe Lys Glu Ser Ser Pro Ser His
                180                 185                 190

Pro Thr Arg Cys His Glu Asp Asn Val Val Ala Val Asp Ser Ala
            195                 200                 205

Thr Asn Arg Ile Leu His Phe Gln Lys Thr Gln Gly Leu Arg Arg Phe
        210                 215                 220

Ser Phe Pro Leu Ser Leu Phe Gln Gly Ser Gly Ala Gly Val Glu Ile
225                 230                 235                 240

Arg Tyr Asp Leu Leu Asp Cys His Ile Ser Ile Cys Ser Pro Gln Val
                245                 250                 255
```

-continued

```
Ala Gln Leu Phe Thr Asp Asn Phe Asp Tyr Gln Thr Arg Asp Asp Phe
                260                 265                 270

Val Arg Gly Leu Leu Val Asn Glu Glu Ile Leu Gly Asn Gln Ile His
            275                 280                 285

Met His Val Thr Thr Arg Glu Tyr Gly Ala Arg Val Ser Asn Leu His
    290                 295                 300

Met Tyr Ser Ala Val Cys Ala Asp Val Ile Arg Arg Trp Val Tyr Pro
305                 310                 315                 320

Leu Thr Pro Glu Ala Asn Phe Thr Asp Ser Thr Ala Gln Ser Cys Thr
                325                 330                 335

His Ser Arg His Asn Ile Tyr Arg Gly Pro Glu Val Ser Leu Gly His
            340                 345                 350

Gly Ser Ile Leu Glu Glu Asn Val Leu Leu Gly Ser Gly Thr Val Ile
        355                 360                 365

Gly Ser Asn Cys Ser Ile Thr Asn Ser Val Ile Gly Pro Gly Cys Cys
    370                 375                 380

Ile Gly Asp Asn Val Val Leu Asp Arg Ala Tyr Leu Trp Lys Gly Val
385                 390                 395                 400

Gln Val Ala Ser Gly Ala Gln Ile His Gln Ser Leu Leu Cys Asp His
                405                 410                 415

Ala Glu Val Lys Glu Gln Val Thr Leu Lys Pro His Cys Val Leu Thr
            420                 425                 430

Ser Gln Val Val Val Gly Pro Asn Ile Thr Leu Pro Glu Gly Ser Val
        435                 440                 445

Ile Ser Leu His Pro Pro Asp Ala Glu Glu Asp Glu Asp Asp Gly Gln
    450                 455                 460

Phe Ser Asp Asp Ser Gly Val Asn Gln Ala Lys Glu Lys Ala Lys Leu
465                 470                 475                 480

Lys Gly Tyr Asn Pro Ala Glu Val Gly Val Ala Gly Lys Gly Tyr Leu
                485                 490                 495

Trp Lys Ala Ala Asp Met Asn Thr Glu Lys Glu Glu Glu Leu Arg Gln
            500                 505                 510

Ser Leu Trp Gly Leu Thr Ile Asn Glu Glu Glu Glu Ser Glu Thr Glu
        515                 520                 525

Ser Glu Arg Ser Met Asp Ser Glu Glu Leu Asp Ser Arg Ala Gly Ser
    530                 535                 540

Pro Gln Leu Asp Asp Ile Lys Val Phe Gln Asn Glu Val Leu Gly Thr
545                 550                 555                 560

Leu Gln Arg Gly Lys Glu Ser Ile Ser Cys Asp Asn Leu Ile Leu
                565                 570                 575

Glu Ile Asn Ser Leu Lys Tyr Ala Tyr Asn Ile Ser Leu Lys Glu Val
            580                 585                 590

Met Gln Val Leu Ser His Val Val Leu Glu Phe Pro Leu Gln Gln Met
        595                 600                 605

Asp Ser Pro Leu Glu Ala Asn Arg Tyr Cys Ala Leu Leu Leu Pro Leu
    610                 615                 620

Leu Lys Ala Trp Ser Pro Val Phe Arg Asn Tyr Ile Lys Arg Ala Ala
625                 630                 635                 640

Asp His Leu Glu Ala Leu Ala Ala Ile Glu Glu Phe Phe Leu Glu His
                645                 650                 655

Glu Ala Leu Gly Thr Cys Ile Ala Lys Val Leu Met Gly Phe Tyr Gln
            660                 665                 670

Leu Glu Ile Leu Ala Glu Glu Thr Ile Leu Ser Trp Phe Gly Gln Arg
```

```
            675                 680                 685
Asp Val Thr Asp Lys Gly Arg Gln Leu Arg Lys Asn Gln Gln Leu Gln
        690                 695                 700

Arg Phe Ile Gln Trp Leu Lys Glu Ala Glu Glu Ser Ser Glu Asp
705                 710                 715                 720

Asp

<210> SEQ ID NO 39
<211> LENGTH: 716
<212> TYPE: PRT
<213> ORGANISM: Rattus norvegicus

<400> SEQUENCE: 39

Met Ala Thr Ala Ala Val Pro Ser Ala Val Gly Gly Arg Ala Asn
 1               5                  10                  15

Lys Arg Gly Gly Gly Ser Gly Gly Gly Thr Gln Gly Ala Glu Glu
                20                  25                  30

Glu Pro Pro Pro Leu Gln Ala Val Leu Ala Asp Ser Phe Asp
            35                  40                  45

Arg Arg Phe Phe Pro Ile Ser Lys Asp Gln Pro Arg Val Leu Leu Pro
 50                  55                  60

Leu Ala Asn Val Ala Leu Ile Asp Tyr Thr Leu Glu Phe Leu Thr Ala
 65                  70                  75                  80

Thr Gly Val Gln Glu Thr Phe Val Phe Cys Cys Trp Lys Ala Ala Gln
                85                  90                  95

Ile Lys Glu His Leu Gln Lys Ser Lys Trp Cys His Pro Thr Ser Leu
                100                 105                 110

Asn Val Val Arg Ile Thr Thr Ser Asp Leu Tyr Arg Ser Leu Gly Asp
                115                 120                 125

Val Leu Arg Asp Val Asp Ala Lys Ala Leu Val Arg Ser Asp Phe Leu
130                 135                 140

Leu Ile Tyr Gly Asp Val Val Ser Asn Ile Asn Ile Ser Lys Ala Leu
145                 150                 155                 160

Glu Glu His Arg Leu Arg Arg Lys Leu Glu Lys Asn Val Ser Val Met
                165                 170                 175

Thr Met Val Phe Lys Glu Ser Ser Pro Ser His Pro Thr Arg Cys His
                180                 185                 190

Glu Asp Asn Val Val Leu Ala Val Asp Ser Thr Thr Asn Arg Ile Leu
                195                 200                 205

His Phe Gln Lys Thr Gln Gly Leu Arg His Phe Ser Phe Pro Leu Gly
                210                 215                 220

Leu Phe Gln Gly Ser Leu Asp Gly Val Glu Ile Arg Tyr Asp Leu Leu
225                 230                 235                 240

Asp Cys His Ile Ser Ile Cys Ser Pro Gln Val Ala Gln Leu Phe Thr
                245                 250                 255

Asp Asn Phe Asp Tyr Gln Thr Arg Asp Asp Phe Val Arg Gly Leu Leu
                260                 265                 270

Val Asn Glu Glu Ile Leu Gly Asn Gln Ile His Leu His Val Thr Ser
                275                 280                 285

Arg Glu Tyr Gly Ser Arg Val Ser Asn Leu His Met Tyr Ser Ala Val
                290                 295                 300

Cys Thr Asp Val Ile Arg Arg Trp Val Tyr Pro Leu Thr Pro Glu Val
305                 310                 315                 320

Asn Phe Thr Asp Ser Ser Thr Gln Ser Tyr Thr His Ser Arg His Asn
```

```
                    325                 330                 335
Ile Tyr Arg Gly Pro Glu Val Ser Leu Gly His Gly Ser Val Leu Glu
            340                 345                 350
Glu Asn Val Leu Leu Gly Ala Gly Thr Val Val Gly Ser Asn Cys Ser
        355                 360                 365
Ile Thr Asn Ser Val Ile Gly Pro Asn Cys His Ile Gly Asp Asn Val
    370                 375                 380
Val Leu Asp Gln Ala Tyr Leu Trp Gln Gly Val Arg Val Ala Ala Gly
385                 390                 395                 400
Ala Gln Ile His Gln Ser Leu Leu Cys Asp Arg Ala Glu Val Lys Glu
            405                 410                 415
Arg Val Ile Leu Lys Pro His Cys Val Leu Thr Ser Gln Val Val
        420                 425                 430
Gly Pro Asp Ile Ile Leu Pro Glu Gly Ser Val Ile Ser Leu His Pro
    435                 440                 445
Pro Asp Ala Glu Glu Asp Glu Asp Asp Gly Gln Phe Ser Asp Asp Ser
    450                 455                 460
Gly Ala Asp Gln Glu Lys Glu Lys Val Lys Leu Lys Gly Tyr Asn Pro
465                 470                 475                 480
Ala Glu Val Gly Pro Glu Gly Gln Gly Tyr Leu Trp Lys Ala Glu Asp
            485                 490                 495
Val Asp Glu Lys Glu Asp Glu Glu Leu Arg Gln Ser Leu Trp Gly Leu
        500                 505                 510
Met Ile Asn Met Glu Glu Glu Ser Glu Thr Glu Ser Glu Arg Ser Val
    515                 520                 525
Asp Pro Glu Glu Leu Asp Ser Arg Ala Gly Ser Pro Gln Leu Asp Asp
    530                 535                 540
Ile Arg Val Phe Gln Asn Glu Val Leu Gly Thr Leu Gln Arg Gly Arg
545                 550                 555                 560
Glu Glu Asn Ile Ser Cys Asp Asn Leu Val Leu Glu Ile Asn Ser Leu
            565                 570                 575
Lys Tyr Ala Tyr Asn Ile Ser Leu Lys Glu Val Met Gln Val Leu Ser
        580                 585                 590
His Val Val Leu Glu Phe Pro Leu Gln Gln Val Asp Gly Val Leu Asp
    595                 600                 605
Pro Asn Arg Tyr Cys Ala Leu Leu Leu Pro Leu Leu Lys Ala Trp Ser
    610                 615                 620
Pro Val Phe Arg Asn Tyr Ile Lys Arg Ala Ala Asp His Leu Glu Ala
625                 630                 635                 640
Leu Ala Ala Ile Glu Asp Phe Phe Leu Glu His Glu Thr Leu Val Pro
            645                 650                 655
Ser Leu Ala Lys Val Leu Met Ala Phe Tyr Gln Leu Glu Ile Leu Ala
        660                 665                 670
Glu Glu Thr Ile Leu Ser Trp Phe Ser Gln Arg Asp Ile Thr Asp Lys
    675                 680                 685
Gly Gln Gln Leu Arg Lys Asn Gln Gln Leu Gln Arg Phe Ile Gln Trp
    690                 695                 700
Leu Arg Glu Ala Glu Glu Glu Ser Ser Asp Asp Asp
705                 710                 715

<210> SEQ ID NO 40
<211> LENGTH: 730
<212> TYPE: PRT
<213> ORGANISM: Arabidopsis thaliana
```

<400> SEQUENCE: 40

```
Met Gly Ala Gln Lys Lys Gly Gly Ala Ala Arg Val Ser Glu Asp
  1               5                  10                  15

Ala Glu Val Gln Ser Arg His Arg Leu Gln Ala Ile Leu Leu Ala Asp
             20                  25                  30

Ser Phe Ala Thr Lys Phe Arg Pro Val Thr Leu Glu Arg Pro Lys Val
         35                  40                  45

Leu Leu Pro Ile Val Asn Val Pro Met Ile Asp Tyr Thr Leu Ala Trp
 50                  55                  60

Leu Glu Ser Ala Gly Ile Glu Glu Val Phe Val Phe Cys Cys Ala His
 65                  70                  75                  80

Ser Met Gln Val Ile Glu Tyr Leu Glu Lys Ser Glu Trp Tyr Ser His
             85                  90                  95

Pro Asn Leu Leu Val Arg Thr Ile Glu Ser His Lys Ser Ile Ser Ala
         100                 105                 110

Gly Asp Ala Leu Arg Tyr Met Tyr Glu Gln Gln Thr Glu Thr Ser Gln
         115                 120                 125

Ile Gln Gly Asp Phe Val Leu Val Ser Gly Asp Thr Val Ser Asn Met
130                 135                 140

Pro Leu Ala Asp Leu Ile Gln Glu His Arg Glu Arg Lys Lys Lys Asp
145                 150                 155                 160

Glu Lys Ala Ile Met Thr Met Val Ile Lys Gln Ser Lys Ser Ser Pro
                 165                 170                 175

Leu Thr His Gln Ser Arg Leu Gly Thr Asp Gln Leu Phe Ile Ala Val
             180                 185                 190

Asp Pro Leu Thr Lys Gln Leu Leu His Tyr Glu Glu Asp Lys Ile Asp
         195                 200                 205

His Pro Ser Gly Ser Val Cys Leu Glu Lys Ser Leu Leu Asp Thr Asn
     210                 215                 220

Pro Ser Val Leu Val Cys Asn Asp Met Gln Asp Cys Tyr Ile Asp Ile
225                 230                 235                 240

Cys Ser Pro Glu Val Leu Ser Leu Phe Glu Asp Asn Phe Asp Tyr Gln
                 245                 250                 255

His Leu Arg Arg His Phe Val Lys Gly Val Leu Val Asp Asp Ile Met
             260                 265                 270

Gly Tyr Lys Ile Phe Thr His Glu Ile His Ser Ser Tyr Ala Gly Arg
         275                 280                 285

Ile Asp Asn Phe Arg Ser Tyr Asp Thr Val Ser Lys Asp Ile Ile Gln
290                 295                 300

Arg Trp Thr Tyr Pro Tyr Val Pro Asp Ile Asn Phe Ser Gly Asn Arg
305                 310                 315                 320

Pro Leu Lys Leu Gly Arg Gln Gly Ile Tyr Lys Ala Ser Asp Val Val
                 325                 330                 335

Gln Ser Arg Ser Ala Asp Val Gly Ala Ser Thr Val Ile Gly Tyr Gly
             340                 345                 350

Thr Lys Ile Gly His Gly Asp Lys Ile Met Asn Ser Val Ile Gly Asn
         355                 360                 365

Gly Cys Ser Ile Gly Ser Asn Val Val Ile Glu Gly Ser Tyr Ile Trp
     370                 375                 380

Asn Asn Val Thr Ile Glu Asp Gly Cys Glu Ile Arg Asn Ala Ile Val
385                 390                 395                 400

Cys Asp Gly Val Lys Ile Arg Ala Gly Ala Val Leu Gln Pro Gly Val
```

```
                405                 410                 415
Val Leu Ser Phe Asn Val Val Gly Arg Asp Phe Val Val Pro Ala
            420                 425                 430
Tyr Ser Lys Val Ser Leu Leu Gln Gln Pro Thr Thr Glu Asp Ser Asp
            435                 440                 445
Glu Glu Leu Glu Tyr Ala Asp Ser Ser Ser Gly Thr Ala Asp His Leu
    450                 455                 460
Ser Gly Leu Asn Leu Gln Met Glu Ser Lys Ala Ser Glu Leu Gly Pro
465                 470                 475                 480
Asp Gly Ala Gly Tyr Ile Trp Glu Val Cys Glu Gly Ala His Asp Glu
                485                 490                 495
Glu Trp Lys His Ser Val Ala Pro Ile Pro Lys Asp Lys Leu Ser Glu
            500                 505                 510
Ile Thr Gln Ala Ile Asp Asp Asp Thr Asp Asp Glu Ser Val Val
            515                 520                 525
Pro Thr Ser Gly Glu Leu Lys Ser Asp Ala Asp Ser Ile Asn Thr Asp
    530                 535                 540
Val Asn Asp Pro Asn Asp Asp Tyr Tyr Tyr Phe Glu Lys Val Glu
545                 550                 555                 560
Gly Thr Val Leu Arg Ala Val Glu Glu Asn Ile Lys Val Asp Leu Val
                565                 570                 575
Thr Met Glu Ile Asn Gly Leu Arg Leu Ser Phe Asn Met Glu Ser Ala
            580                 585                 590
Asp Cys Ala Gly Ala Thr Phe Phe Ser Met Ile Lys Leu Ala Leu Asp
            595                 600                 605
Thr Pro His Asn Ser Gly Ser Glu Leu Tyr Lys Asn Ala Ala Ser Ile
    610                 615                 620
Ile Thr Lys Trp Lys Asp Leu Leu Gly Phe Tyr Ala Lys Lys Ile Asp
625                 630                 635                 640
Glu Gln Ile Glu Val Ile Met Lys Phe Glu Met Cys Gln Glu Ser
                645                 650                 655
His Lys Glu Leu Gly Pro Leu Phe Thr Gln Ile Leu His Leu Leu Tyr
            660                 665                 670
Asp Lys Asp Val Leu Gln Glu Asp Ala Ile Leu Arg Trp Glu Glu Glu
            675                 680                 685
Lys Ala Gly Ala Asp Glu Ala Asp Lys Val Tyr Leu Lys Gln Cys Asp
    690                 695                 700
Thr Phe Ile Gln Trp Leu Lys Glu Ala Ser Glu Glu Asp Glu Asp
705                 710                 715                 720
Asp Glu Asp Glu Glu Glu Glu Asp Asn
                725                 730

<210> SEQ ID NO 41
<211> LENGTH: 676
<212> TYPE: PRT
<213> ORGANISM: Arabidopsis thaliana

<400> SEQUENCE: 41

Met Ala Ser Arg Lys Lys Arg Ala Ala Lys Ile Ser Glu Asp Ser Glu
1               5                   10                  15
Glu Glu Gln Ser Arg Arg Gln Arg Leu Gln Ala Ile Leu Leu Ala Asp
            20                  25                  30
Ser Phe Ala Thr Lys Leu Leu Pro Leu Thr Leu Glu Arg Pro Asn Val
        35                  40                  45
```

```
Leu Leu Pro Leu Val Asn Ile Pro Met Ile Asp Tyr Thr Leu Ala Trp
     50                      55                      60

Leu Glu Ser Ala Gly Ile Glu Glu Val Phe Val Phe Cys Ser Met Gln
 65                      70                      75                  80

Val Ile Asp Tyr Leu Asn Asn Ser Asp Trp Tyr Ser His Lys Asp Phe
                     85                      90                      95

Thr Val Lys Thr Ile Glu Ser Pro Gln Asn Ser Thr Ser Ala Gly Asp
                100                     105                     110

Ala Leu Arg Tyr Ile Tyr Glu Gln Gln Ile Glu Thr Ser Gln Ile Gln
            115                     120                     125

Gly Asp Phe Val Leu Val Asn Gly Cys Ile Val Ser Asn Met Pro Leu
    130                     135                     140

Thr Gln Leu Ile Gln Glu His Arg Asp Arg Lys Lys Lys Asp Glu Lys
145                     150                     155                     160

Ala Ile Met Thr Met Val Ile Arg Gln Ser Leu Ile Thr Asp His Gln
                165                     170                     175

Leu Phe Ile Ala Val Asn Pro Leu Thr Lys Gln Leu Leu Tyr Tyr Asp
            180                     185                     190

Glu Asp Asn Ile Cys Phe Asp Lys Ser Leu Leu Asp Arg Asn Pro Ser
        195                     200                     205

Val Leu Leu Cys Ser Asp Met Gln Asp Cys Tyr Ile Asp Ile Cys Ser
    210                     215                     220

Leu Glu Val Leu Ser Leu Phe Val Asp Asn Phe Asp Tyr Gln His Met
225                     230                     235                     240

Arg Cys Asp Phe Val Glu Gly Val Leu Ala Asp Asp Ile Ile Gly Tyr
                245                     250                     255

Lys Ile Phe Thr His Glu Ile Ser Ser Cys Tyr Ala Ser Arg Ile Glu
            260                     265                     270

Asn Phe Arg Ser Tyr Asp Met Val Ser Lys Asp Ile Ile Gln Arg Arg
        275                     280                     285

Thr Phe Pro Tyr Val Pro Asp Met Lys Phe Ser Gly Asn Arg Thr Leu
    290                     295                     300

Lys Leu Glu Arg Gln Gly Ile Tyr Lys Ala Ser Asp Ala Thr Gln Leu
305                     310                     315                     320

Pro Ser Ala His Val Gly Ala Ser Tyr Val Ile Gly His Ala Thr Asn
                325                     330                     335

Ile Gly Ser Gly Thr Lys Ile Leu Asn Ser Val Ile Gly Asn Gly Cys
            340                     345                     350

Ser Ile Gly Ser Asn Val Val Ile Gln Gly Ser Tyr Ile Trp Asn Asn
        355                     360                     365

Val Thr Val Glu Asp Gly Cys Glu Ile Arg Asn Ala Ile Val Cys Asp
    370                     375                     380

Glu Val Lys Val Cys Ala Gly Ala Ile Val Lys Pro Gly Val Val Leu
385                     390                     395                     400

Ser Phe Lys Val Val Gly Arg Asp Phe Val Pro Ala Tyr Ser
                405                     410                     415

Gln Val Ser Leu Leu Arg Gln Pro Met Glu Glu Asp Ser Asp Glu Glu
            420                     425                     430

Asn Leu Leu Ser Gly Val Asp Leu Gln Met Glu Ser Lys Leu Gly Leu
        435                     440                     445

Asp Gly Ala Gly Tyr Ile Trp Arg Gln Ala Cys Glu Asp Glu Trp Lys
    450                     455                     460

His Ser Val Pro Pro Ile Pro Lys Asp Lys Leu Ala Glu Ile Ile Lys
```

```
                465                 470                 475                 480
Ala Ile Asp Asp Asp Thr Asp Asp Glu Ser Val Val Thr Thr Ser
                    485                 490                 495
Gly Asp Ala Asn Thr Ser Ile Asn Asn Asp Leu Phe Asp Phe Glu Arg
                500                 505                 510
Glu Val Asp Gly Thr Phe Leu Arg Ala Val Glu Glu Asn Ile Val Ala
            515                 520                 525
Asp Leu Ala Val Leu Glu Ile Asn Ser Leu Arg Leu Ser Tyr Asn Met
        530                 535                 540
Glu Ser Ala His Cys Ala Gly Ala Ile Phe Tyr Ser Met Met Lys Leu
545                 550                 555                 560
Ala Val Ser Thr Pro His Ser Ser Ile Asn Asp Leu Tyr Arg Asn Ala
                565                 570                 575
Ser Ser Ile Ile Thr Arg Trp Lys Gly Leu Leu Gly Phe Tyr Val Lys
                580                 585                 590
Lys Ser Asp Glu Gln Ile Glu Val Ile Ser Arg Leu Glu Glu Met Cys
            595                 600                 605
Glu Glu Ser Ala His Glu Leu Gly Thr Leu Phe Ala His Ile Leu Arg
        610                 615                 620
Tyr Met Tyr Glu Glu Glu Asn Asp Leu Leu Gln Glu Val Ala Ile Leu
625                 630                 635                 640
Arg Trp Ser Asp Glu Lys Ala Gly Ala Asp Glu Ser Asp Lys Val Tyr
                645                 650                 655
Leu Lys Gln Cys Glu Pro Phe Ile Thr Trp Leu Lys Gly Thr Ser Asp
                660                 665                 670
Asp Glu Asp Gly
        675

<210> SEQ ID NO 42
<211> LENGTH: 2004
<212> TYPE: DNA
<213> ORGANISM: Homo sapiens

<400> SEQUENCE: 42
gggcgcgcgg cctcgaggcc ttccggtgcg ggagaaacta ctactcccat aatgccccgc      60
ggtcccgcga gctgccagtc tcgtcgcgag aagcagcggc ccggggcgac tgagcggaca     120
aacggaagtg taggttacgg tctgagacat caccgccaag ctgggcatcg ggagatggc     180
cgagactgac cccaagaccg tgcaggacct cacctcggtg gtgcagacac tcctgcagca     240
gatgcaagat aaatttcaga ccatgtctga ccagatcatt gggagaattg atgatatgag     300
tagtcgcatt gatgatctgg aaaagaatat cgcggacctc atgacacagg ctggggtgga     360
agaactggaa agtgaaaaca agatacctgc cacgcaaaag agttgaaggt tgctaataat     420
ttatactgga atctggcatt tttccaagcc aagagaagat cgaatggctt tttgcagcta     480
actactatgt gtagacaggt tttatattat aaagtatgca ttcttatcac ctagtatata     540
gttagtttgt agagtgattt cccccccagtt tcttgaacat ggtatcttca catcttggac     600
cttggtcagt tgtgctattc attattaaac actaaaactt tggcggttct tgcataacat     660
tgtcagattt tttagtgtat ttctgtgaag tcatttttttt tcttgtcatt ccttttgtag     720
tagttgctgt ttggataaaa gttgatgtgt gatttttttat taaacaaata gtaaaccctt     780
caattatagt tagtcttggt gaagtaagat gtttgtagac tttagagttc tttaattctt     840
ggcacaacgt gacttttgag ctaacaccaa atagtgtgtt ggcaatactt ttcaaatggc     900
```

-continued

```
tgaaaacacc taaaaattgt tcattcagaa atatctgtca ctgctctgtt gccaaaactc      960
agaatagaac ttagacgtat gtctgagtcc ctgagatcac atgctaaagt cgatgaaaag     1020
taaccactgc cactgtcttg tgtcagaact tttacagtac agaaaataac agaatagcct     1080
tctgtaatga ggcgtttgtt agagttttgc atgagattct aatacttcag taggacccta     1140
cctacgtggt tcatctacaa tggttaccat aaaaaatctg gcaggatttt aaaactcaat     1200 cagtcttttcc tttgagctag tgacttgaaa agaaagagag aaggaaaaga gaccatatta     1260
agtccatgcc agttgcttgg ctagaatatg atcaacgact tgtagtagac tcaagttttt     1320
aaaaaacact attttactta aactgtttct tatctaaatt cttgcagagt gtcaatgtta     1380
tcattgatta tagaagacag ggataatacc tttatctctg ccactcaaa aatgcagtgc      1440 caggagtgct aaacctagag gccaatactg atgacctgga aggtgatcca tatgattgtc     1500
accacaaagt gcttttacac aaaaacttga aaatttgaaa aacatgattt ttttaagttt     1560
ctcatctcac cagtcttggt gtttatattg caaatctatc aaagtaagaa ataatttgtg     1620
ctgtatacaa attacatggg gaacataaag gagtgagatc cttctgtgat aaaatgaatt     1680
caccactctg gttacccaac tacagaacct cctttgatca ggccagtagg ttgtgatgca     1740
ggctggagcc cccgaatgcc ccacacacac tgcagcattg accagaccat ccgaaacctg     1800
cgtccctggt gatgttctca agcctcggaa gtggcaaatg gaaatgatat ggccggttgc     1860
ggttgtagga gagttgtgac ttaggcagga gtcgacctcc tcaagtaatg gaacgatttc     1920
aaaggcaggc tgccctgacc aaaaatatct gccatgaata aggtgcctg aaatcctgct      1980 aaaaaaaaaa aaaaaaaaaa aaaa                                            2004
```

<210> SEQ ID NO 43
<211> LENGTH: 76
<212> TYPE: PRT
<213> ORGANISM: Homo sapiens

<400> SEQUENCE: 43

```
Met Ala Glu Thr Asp Pro Lys Thr Val Gln Asp Leu Thr Ser Val Val
 1               5                  10                  15

Gln Thr Leu Leu Gln Gln Met Gln Asp Lys Phe Gln Thr Met Ser Asp
                20                  25                  30

Gln Ile Ile Gly Arg Ile Asp Asp Met Ser Ser Arg Ile Asp Asp Leu
            35                  40                  45

Glu Lys Asn Ile Ala Asp Leu Met Thr Gln Ala Gly Val Glu Glu Leu
        50                  55                  60

Glu Ser Glu Asn Lys Ile Pro Ala Thr Gln Lys Ser
65                  70                  75
```

<210> SEQ ID NO 44
<211> LENGTH: 2004
<212> TYPE: DNA
<213> ORGANISM: Homo sapiens

<400> SEQUENCE: 44

```
tttttttttt tttttttttt tttagcagg atttcaggca cctttattca tggcagatat        60
ttttggtcag ggcagcctgc ctttgaaatc gttccattac ttgaggaggt cgactcctgc      120
ctaagtcaca actctcctac aaccgcaacc ggccatatca tttccatttg ccacttccga      180
ggcttgagaa catcaccagg gacgcaggtt tcggatggtc tggtcaatgc tgcagtgtgt      240
gtggggcatt cggggggctcc agcctgcatc acaacctact ggcctgatca aaggaggttc      300
```

-continued

```
tgtagttggg taaccagagt ggtgaattca ttttatcaca gaaggatctc actcctttat      360
gttccccatg taatttgtat acagcacaaa ttatttctta ctttgataga tttgcaatat      420
aaacaccaag actggtgaga tgagaaactt aaaaaaatca tgttttcaa attttcaagt       480
ttttgtgtaa aagcactttg tggtgacaat catatggatc accttccagg tcatcagtat      540
tggcctctag gtttagcact cctggcactg cattttgag tggccagaga taaaggtatt       600
atccctgtct tctataatca atgataacat tgacactctg caagaattta gataagaaac      660
agtttaagta aaatagtgtt ttttaaaaac ttgagtctac tacaagtcgt tgatcatatt      720
ctagccaagc aactggcatg gacttaatat ggtctctttt ccttctctct ttcttttcaa      780
gtcactagct caaaggaaag actgattgag ttttaaaatc ctgccagatt ttttatggta      840
accattgtag atgaaccacg taggtagggt cctactgaag tattagaatc tcatgcaaaa      900
ctctaacaaa cgcctcatta cagaaggcta ttctgttatt ttctgtactg taaaagttct      960
gacacaagac agtggcagtg gttacttttc atcgacttta gcatgtgatc tcagggactc     1020
agacatacgt ctaagttcta ttctgagttt tggcaacaga gcagtgacag atatttctga     1080
atgaacaatt tttaggtgtt ttcagccatt tgaaaagtat tgccaacaca ctatttggtg     1140
ttagctcaaa agtcacgttg tgccaagaat taagaactc taaagtctac aaacatctta     1200
cttccaccaag actaactata attgaagggt ttactatttg tttaataaaa aatcacacat    1260
caacttttat ccaaacagca actactacaa aaggaatgac aagaaaaaaa atgacttcac     1320
agaaatacac taaaaaatct gacaatgtta tgcaagaacc gccaaagttt tagtgtttaa     1380
taatgaatag cacaactgac caaggtccaa gatgtgaaga taccatgttc aagaaactgg     1440
ggggaaatca ctctacaaac taactatata ctaggtgata agaatgcata ctttataata     1500
taaaacctgt ctacacatag tagttagctg caaaaagcca ttcgatcttc tcttggcttg     1560
gaaaaatgcc agattccagt ataaattatt agcaaccttc aactcttttg cgtggcaggt     1620
atcttgtttt cactttccag ttcttccacc ccagcctgtg tcatgaggtc cgcgatattc     1680
ttttccagat catcaatgcg actactcata tcatcaattc tcccaatgat ctggtcagac     1740
atggtctgaa atttatcttg catctgctgc aggagtgtct gcaccaccga ggtgaggtcc     1800
tgcacggtct tggggtcagt ctcggccatc tccccgatgc ccagcttggc ggtgatgtct     1860
cagaccgtaa cctacacttc cgtttgtccg ctcagtcgcc ccgggccgct gcttctcgcg     1920
acgagactgg cagctcgcgg gaccgcgggg cattatggga gtagtagttt ctcccgcacc     1980
ggaaggcctc gaggccgcgc gccc                                            2004
```

<210> SEQ ID NO 45
<211> LENGTH: 76
<212> TYPE: PRT
<213> ORGANISM: Homo sapiens

<400> SEQUENCE: 45

```
Met Ala Glu Thr Asp Pro Lys Thr Val Gln Asp Leu Thr Ser Val Val
  1               5                  10                  15
Gln Thr Leu Leu Gln Gln Met Gln Asp Lys Phe Gln Thr Met Ser Asp
                 20                  25                  30
Gln Ile Ile Gly Arg Ile Asp Asp Met Ser Ser Arg Ile Asp Asp Leu
             35                  40                  45
Glu Lys Asn Ile Ala Asp Leu Met Thr Gln Ala Gly Val Glu Glu Leu
         50                  55                  60
Glu Ser Glu Asn Lys Ile Pro Ala Thr Gln Lys Ser
```

```
65                  70                  75

<210> SEQ ID NO 46
<211> LENGTH: 76
<212> TYPE: PRT
<213> ORGANISM: Mus musculus

<400> SEQUENCE: 46

Met Ala Glu Thr Asp Pro Lys Thr Met Gln Asp Ile Thr Leu Val Val
 1               5                  10                  15

Glu Thr Leu Leu Gln Gln Met Gln Asp Lys Phe Gln Ile Met Ser Asp
            20                  25                  30

Gln Ile Ile Gly Arg Ile Asp Asp Met Ser Ser Arg Ile Asp Asp Leu
        35                  40                  45

Glu Lys Asn Ile Ala Asp Leu Met Thr Gln Ala Gly Val Glu Glu Leu
    50                  55                  60

Asp Pro Glu Asn Lys Ile Pro Thr Ala Gln Lys Ser
65                  70                  75

<210> SEQ ID NO 47
<211> LENGTH: 86
<212> TYPE: PRT
<213> ORGANISM: Drosophila melanogaster

<400> SEQUENCE: 47

Met Thr Asp Leu Arg Asn Glu Met Asp Ser Asp Leu Asp Gln Asn Tyr
 1               5                  10                  15

Ser Leu Asn Ser Asn Ala Asp Pro Lys Asn Met Gln Glu Leu Thr Ile
            20                  25                  30

Tyr Val Gln Asn Leu Leu Gln Asn Val Gln Asp Lys Phe Gln Thr Met
        35                  40                  45

Ser Asp Gln Ile Ile Thr Arg Ile Asp Met Gly Asn Arg Ile Asp
    50                  55                  60

Asp Leu Glu Lys Ser Ile Ala Asp Leu Met Asn Gln Ala Gly Ile Glu
65                  70                  75                  80

Gly Gln Gly Pro Glu Lys
                85

<210> SEQ ID NO 48
<211> LENGTH: 80
<212> TYPE: PRT
<213> ORGANISM: Caenorhabditis elegans

<400> SEQUENCE: 48

Met Ser Asp Glu Lys Ser Thr Thr Pro Thr Ala Gln Leu Asp Ala Pro
 1               5                  10                  15

Ala Asp Gly Asn Met Asn Asp Leu Thr Ser Leu Ile Gln Gly Val Leu
            20                  25                  30

Gln Gln Thr Gln Asp Arg Phe Gln His Met Ser Asp Gln Ile Ile Arg
        35                  40                  45

Arg Ile Asp Asp Met Thr Thr Arg Ile Asp Asp Leu Glu Lys Asn Ile
    50                  55                  60

Asn Asp Leu Leu Gln Ser Asn Gln Val Glu His Pro Pro Ser Ala Gln
65                  70                  75                  80

<210> SEQ ID NO 49
<211> LENGTH: 99
<212> TYPE: PRT
<213> ORGANISM: Oryza sativa
```

-continued

<400> SEQUENCE: 49

Met Ala Ala Pro Gly Ser Gly Ser Gly Gly Ile Pro Ile Lys Ala Asp
1               5                   10                  15
Gln Asp Ser Asp Gly Ser Ala Gln Ser Thr Ala Asp Met Thr Ala Phe
            20                  25                  30
Val Gln Asn Leu Leu Met Gln Met Gln Thr Arg Phe Gln Ser Met Ser
        35                  40                  45
Glu Asn Ile Ile Ser Lys Ile Asp Glu Met Gly Ala Arg Ile Asp Glu
50                  55                  60
Leu Glu Gln Ser Ile Asn Asp Leu Lys Val Glu Met Gly Thr Glu Gly
65                  70                  75                  80
Ile Thr Pro Thr Lys Pro Lys Asp Glu Glu Ser Lys Pro Ala Gly Ser
                85                  90                  95
Ser Ala Glu

<210> SEQ ID NO 50
<211> LENGTH: 4204
<212> TYPE: DNA
<213> ORGANISM: Homo sapiens

<400> SEQUENCE: 50

| | |
|---|---|
| tttttggaat ataagtaggg ggtttatttg ggccagtctt gaggattgaa acttcaaagc | 60 |
| acagattaaa gttatcctga atatgtagtc cggtcccacc agcaacagtt acaaatggat | 120 |
| ttttaaagga aataaaagaa aaggcagttc ctaagttgtt tagcaataat taacatatga | 180 |
| aaataacata agctattgat ctggctatat gttgttcttt gtttcctaaa ttacaagaaa | 240 |
| cgaaagataa tgggtgaggc agctagttag gaactaaatg cttttaaaca attcccccca | 300 |
| cccccaccc gtgtgggtcc tgtgagggag tgggagcatg actgaagtcc catactcacg | 360 |
| ctggccctga tcaagttttc atacctcaca tagctcagcc tgctctgagt tgattctttt | 420 |
| ttattgcttt gattcatgtg gagttgacac tgcattctga agccaagtgg agtttctcat | 480 |
| tacttttgcc caacaaagca ggagagactt caaataaggg tccagaattc ttacactgaa | 540 |
| gaagaaaatt tttccactgt ctctaacctt cctctcttcc actcataatc ttaccctcat | 600 |
| ctctgcttct ctctgctaaa tatgaactgc cacacccacc taagctttgc cttctccttc | 660 |
| atgctataaa tgttccttgt cactccaatg ctttgacaga aggccagagg acattgggtt | 720 |
| caggaccaga gtcttcaccc tgcaggtttt gatggaattt gagcagaatc cagcatggtt | 780 |
| catccctgtc aggtctggat ggcactgagt tatcactaca agcaaatgca aatccagcca | 840 |
| ttcagatgtc agaaaggcct tcgcaaattt gcctttctat ttcagattcc cgggaaggtg | 900 |
| actgttctct tctcaagtta gaagatttca ggtcagaggc cagaatatgg gaggaatgcc | 960 |
| tgtctctgca aacccacatg gctctggatt agttgggacg ggaccccaag gtcatggtga | 1020 |
| ggaacaaact gtactcttca gccaaagtgt ggcgctcact ctgcagaggt ccctataaaa | 1080 |
| taataagctt ccttttggca tctggatatt ttctgcccct gcttgagccc atggatttca | 1140 |
| gaaagaccta actgttggct tacaacagtc cagcatctgg gtcaaaaaag gggaactcta | 1200 |
| ggctagcggt cctcaatgta tggtctgcag gacaagttgc atcagcatca tatgggaact | 1260 |
| ggttagaaac tcaaattaat gagctctgcc ttagaactac agaaccaaaa actatcaggg | 1320 |
| tagagttcag caatcagtgt tttaacatga tgccttaggt gagtctgatg caagctcaag | 1380 |
| tttcagaaat accactctta agtctaagaa gatgaaggtt ctaggacttc aaagtactct | 1440 |

```
aatgcttctc ctatggtaga gctagcagga gttcatttat tattcgtcca gatgctgatt    1500
atgcagttcc aggaatttga gtcaatgcca gagcagttga ggtagagcaa ggaggaataa    1560
caaaaatgct aggatatcgt ggtgttctga gacaggtgag cttttcggag cctcccaact    1620
tgtcccctag tgcttaaaat ttggcacaga tgctaccatc agccatgaca tggatagagg    1680
agactctccc ctttatgctg atgtatacac caaaacgagt cacagaaaaa gcaggcttcc    1740
aagatttttc agctcccgtt gttccaatca tcttctatga ttctgtctcc tagacctgta    1800
gccttaaagc aagcttattt aaaataaatc tgccagtctg tttcaaagag atttgttctc    1860
ctaaatttgt cccagactga aaactgcaca cgtccaaagt ttaagaggtt atgttaggag    1920
aaattgaaca ttatgttttc ctactgctac ttaaatttcc agaggcattt acaaaaatta    1980
aacatcaatg ggaagccaag tcctttatga agctagcaat agacattgat cctgtgataa    2040
tgttattatt tttcttattg ctcttgtcag tatgcatttc atcatcgctg ggttggatga    2100
gtatagggca gcatgggaaa acaatgttta ttgacttgca gtttctaggt gctttaaaaa    2160
aagttatgca caggtacata tgagcatatt aaagctctta atttgtgttt ctaataattt    2220
cttcttgaat ctctaaaatt atgacactac gattagcatt ttattaccac atgtacaatc    2280
tatccagtca ccttgaagtt agattagatg gcattcaagt cactcagcac aggtgagtca    2340
gacggacttt tgacctctct gtaaaatagg aaaataaaga cagtgacttt atttataaga    2400
aaaatgaact tggccaacaa cattagagaa tgcttactca ttctgtacct agacacagag    2460
gagcttggaa cagaccagga gaaatgagac cattatatac cctataatta caacttgtct    2520
aattgatcca aggggaagca gagaaagtta actgtagggc agcaagatgt aaacttggga    2580
agtcagataa gaatggacct tgaaagggac cttgaaaggt atgcaggggg cctgggcaca    2640
actgccaagc ataatcagac actgtgtgag aagaggaagt aagtctagtc ccaatcactt    2700
aataagtaca gatctcttag gaagaggctc tggtacagta tccttccccc gtcttaaagg    2760
gacatggagt ctcagcctcc cagcaggaat gtctagagaa aaagtatcta gctaattttg    2820
tgggcagggg tgagggaagg agaaatattg tctggcttag taagagtgtg gtctccacag    2880
taacacagat ccctgatgtg acatttgagg cagcatcctt tctgtgtcaa gactggttcc    2940
tcctcctgca ttctggatcc cttccctggt gtcttttcag ggcatcaatt accccatctc    3000
tctcttatct agtcaaccct ttcctcgcaa tcttccccaa aacacttaaa caggctcaag    3060
ctttccccac cttaaaaata tcttccctct accccacact tcctgcagct acagcactct    3120
ctcctcctcc tcacacccaa agttttccag aaaattatcc atccttgcca tctccatatg    3180
ctcccctccc actcctcaat tcacctcgct ctgtcttcca ctcctgtcac aggctttaaa    3240
aagccactgc aatcattagg tgacctgtct attgccaaag tctcaggaca ttttcaattc    3300
taccttactt gaaacctccg cagtgtgaag gtcactcctt ccatctatgc tccttcctgg    3360
gttcttgggg ctcacaaatc tcctgggctt cctcctaccc acctgcctgc ttattcatt    3420 attctgcagg ctccttctcc ctacccgaca tgccagagtt cctacaagct tcaggagtcg    3480
tccttgactt ctccctcttc ctcaccactc tccaatccaa aacatcacca atcttgtta    3540 atttgggtcc tttggtattt gtttattctg tcggttttt tctgtcttca ctcctctcat    3600
tctctaagag ctgctatagc ctccttcaca acaaagagag agagctgcct aaagtcaccc    3660
agctaatgaa tgatgactag gagtggttcc cagatatttt atcccttact gctgtggagg    3720
ttcctcatca ccctaataga atcactcttt attcacaaaa gtagaaaatt aattttggat    3780
acatcattta ttatcaagat gttgttgagg aaaaatagg tcatgtaagg tgcctctcag    3840
```

```
catcttcctt caagttgcaa gaattagaaa aacagagaca agattctatg tgtgtcctca    3900
gaagaccttc ctgaggacca ttcccctagg aacttaaaaa aattaagcct ccaactcttt    3960
ccatcttaac tgtgtaacag aggaaggtga tgacaagagg aaggagacaa gcaagagtca    4020
gacttcgaag gcttggcagc cactgtcagc aagaggtgag aacagcagac aagacagcaa    4080
cactcctgaa ataatcaatc catacggact gccatgtgaa atgtggagca gactagttct    4140
aaatggctcc aggaggcaaa ataagactca agagaagtta ctggtagatt tcaacccaat    4200
gtga                                                                 4204
```

<210> SEQ ID NO 51
<211> LENGTH: 90
<212> TYPE: PRT
<213> ORGANISM: Homo sapiens

<400> SEQUENCE: 51

```
Met Leu Gly Glu Ile Glu His Tyr Val Phe Leu Leu Leu Lys Phe
 1               5                  10                  15

Pro Glu Ala Phe Thr Lys Ile Lys His Gln Trp Glu Ala Lys Ser Phe
                20                  25                  30

Met Lys Leu Ala Ile Asp Ile Asp Pro Val Ile Met Leu Leu Phe Phe
            35                  40                  45

Leu Leu Leu Leu Ser Val Cys Ile Ser Ser Ser Leu Gly Trp Met Ser
        50                  55                  60

Ile Gly Gln His Gly Lys Thr Met Phe Ile Asp Leu Gln Phe Leu Gly
    65                  70                  75                  80

Ala Leu Lys Lys Val Met His Arg Tyr Ile
                85                  90
```

<210> SEQ ID NO 52
<211> LENGTH: 3111
<212> TYPE: DNA
<213> ORGANISM: Homo sapiens

<400> SEQUENCE: 52

```
atgaatgcca ccagatctga agagcagttc catgttataa accacgcaga gcaaactctt     60
cgtaaaatgg agaactactt gaaagagaaa caactatgtg atgtgctact gattgcagga    120
cacctccgca tcccagccca taggttggtt ctcagcgcag tgtctgatta ttttgctgca    180
atgtttacta tgatgtgct tgaagccaaa caagaagagg tcaggatgga aggagtagat    240
ccaaatgcac taaattcctt ggtgcagtat gcttacacag gagtcctgca attgaaagaa    300
gataccattg aaagtttgct ggctgcagct tgtcttctgc agctgactca ggtcattgat    360
gtttgctcca attttctcat aaagcagctc catccttcaa actgcttagg gattcgatca    420
tttggagatg cccaaggctg tacagaactt ctgaacgtgg cacacaaata cactatggaa    480
cacttcattg aggtaataaa aaaccaagaa ttcctcctgc ttccagctaa tgaaatttca    540
aaacttctgt gcagtgatga cattaatgtg cctgatgaag agaccatttt tcatgctcta    600
atgcagtggg tggggcatga tgtgcagaat aggcaaggag aactggggat gctgctttct    660
tacatcagac tgccattact cccaccacag ttactggcag atcttgaaac cagttccatg    720
tttactggtg atcttgagtg tcagaagctc ctgatgaag ctatgaagta tcatcttttg    780
cctgagagaa gatccatgat gcaaagccct cggacaaagc ctagaaaatc aactgtgggg    840
gcactttatg ctgtaggagg catggatgct atgaaaggta ctactactat tgaaaaatat    900
```

-continued

```
gacctcagga ccaacagttg gctacatatt ggcaccatga atggccgtag gcttcaattt      960
ggagtcgcag ttattgataa taagctctat gtcgtgggag aagagacgg tttaaaaact     1020
ttgaatacag tggaatgttt taatccagtt ggcaaaatct ggactgtgat gcctcccatg    1080
tcaacacatc ggcacggctt aggtgtagcc actcttgaag gaccaatgta tgctgtaggt    1140
ggtcatgatg gatggagcta tctaaatact gtagaaagat gggaccctga gggacgacag    1200
tggaattacg tagccagtat gtcaactcct agaagcacag ttggtgttgt tgcattaaac    1260
aacaaattat atgctattgg tggacgtgat ggaagttcct gcctcaaatc aatggaatac    1320
tttgacccac acactaacaa gtggagtttg tgtgctccaa tgtccaaaag acgtggaggt    1380
gtgggagttg ccacatacaa tggattctta tatgttgtag ggggcatga tgcccctgct    1440
tccaaccatt gctccaggct ttctgactgt gtggaacggt atgatccaaa aggtgattca    1500
tggtcaactg tggcacctct gagtgttcct cgagatgctg ttgctgtgtg ccctcttgga    1560
gacaaactct acgtggttgg aggatatgac ggacatactt atttgaacac agttgagtca    1620
tatgatgcac agagaaatga atggaaagag gaagttcctg ttaacattgg aagagctggt    1680
gcatgtgttg tagtggtgaa gctaccctaa agctatctat ctttatcaaa tggaatgaaa    1740
ctagataatt tcaagaaact gagtaggaca aagggagaaa gaaatacatg ttctttttcc    1800
tgcaattaat aatcagactg gaaaattgtt gtatcatttt aatttgtagt tacaattgct    1860
ttcattcgtg aagccgaaac gttttttaaac atgaattaca tatgaattat taagcatatg  1920
tgctttcgca gctgataata taaaggaaa tcccacagtc tagatatagc cccattacta    1980
caaaatgcta aaatatttaa tgaaaattga tggtggccac agtgtgcagg ttataaaagc   2040
attaatacat ttcaaggtaa gagccttaaa agttaaaaac attttcagtt tttttttaaa   2100
aaacgtactc ttattatctg gaacatagaa atataaaagg taacatctaa agcttagaat   2160
agtgtgattt ttagtaagcc attattctcc tattcaaata atatcccaaa gagctaaaca   2220
attccttaca tttaccaaga ggaaagcttt tactgtgttg aagctaaaaa ataatggct     2280
ctttgacaaa acttgttatg ttgatcgcgg tatgtcaaaa tttttacagg tttgctcatc    2340
tgccagagca cacatataaa tttggtattt cttaacatat tatcttgtta gatttgttac   2400
cagtaaaata ttactgtaat ttcatataca cagtctatac aatgaaataa tgaatattta   2460
tcatattgat acaaactgtg acctcagctt cagagtgtca gggcctcact tgtatagaat   2520
gtaatgttct cctcaaacat ttatgttaac tctataaaca aatatcgtta agttaaacaa   2580
gttttcaaaa acaaaacaat ttttaaagta ccttaaaatt gaggatgtta ctcagtgtta   2640
acacatggga acaccaaaat attcaataag cctggtcaat tctatagtta tcttttttgt   2700
accaacacat gcttttctgt tactgttata ttatccagta gaaaatgtta ggatatgtgt   2760
gctatataaa aaaaaaaaaa gacttgttaa gttttaaaat aacaaaaatg gctagttgaa   2820
tagtatttta tgtgtaattc ttccatttat tctgtttaat tatacaacta agatgaaata   2880
ttgaaaaacc ctttgtgaaa gtaacttttc aagtaaatgc acaactttag aatttctaca   2940
aataagttct tttaaacagt cttttttattg tggattgtga aatcaaaatc tggagaaatg  3000
cttataaaat atactactag cttttaagtt ttaagaaga agaacgtaag ttgtacaaag    3060
atatttgtac tttgacaaac tgaatttaaa taaactttat ttcctctcaa a            3111
```

<210> SEQ ID NO 53
<211> LENGTH: 569
<212> TYPE: PRT
<213> ORGANISM: Homo sapiens

<400> SEQUENCE: 53

```
Met Asn Ala Thr Arg Ser Glu Glu Gln Phe His Val Ile Asn His Ala
  1               5                  10                  15
Glu Gln Thr Leu Arg Lys Met Glu Asn Tyr Leu Lys Glu Lys Gln Leu
                 20                  25                  30
Cys Asp Val Leu Leu Ile Ala Gly His Leu Arg Ile Pro Ala His Arg
             35                  40                  45
Leu Val Leu Ser Ala Val Ser Asp Tyr Phe Ala Ala Met Phe Thr Asn
         50                  55                  60
Asp Val Leu Glu Ala Lys Gln Glu Glu Val Arg Met Glu Gly Val Asp
 65                  70                  75                  80
Pro Asn Ala Leu Asn Ser Leu Val Gln Tyr Ala Tyr Thr Gly Val Leu
                 85                  90                  95
Gln Leu Lys Glu Asp Thr Ile Glu Ser Leu Leu Ala Ala Ala Cys Leu
            100                 105                 110
Leu Gln Leu Thr Gln Val Ile Asp Val Cys Ser Asn Phe Leu Ile Lys
            115                 120                 125
Gln Leu His Pro Ser Asn Cys Leu Gly Ile Arg Ser Phe Gly Asp Ala
        130                 135                 140
Gln Gly Cys Thr Glu Leu Leu Asn Val Ala His Lys Tyr Thr Met Glu
145                 150                 155                 160
His Phe Ile Glu Val Ile Lys Asn Gln Glu Phe Leu Leu Leu Pro Ala
                165                 170                 175
Asn Glu Ile Ser Lys Leu Leu Cys Ser Asp Asp Ile Asn Val Pro Asp
                180                 185                 190
Glu Glu Thr Ile Phe His Ala Leu Met Gln Trp Val Gly His Asp Val
            195                 200                 205
Gln Asn Arg Gln Gly Glu Leu Gly Met Leu Leu Ser Tyr Ile Arg Leu
        210                 215                 220
Pro Leu Leu Pro Pro Gln Leu Ala Asp Leu Glu Thr Ser Ser Met
225                 230                 235                 240
Phe Thr Gly Asp Leu Glu Cys Gln Lys Leu Leu Met Glu Ala Met Lys
                245                 250                 255
Tyr His Leu Leu Pro Glu Arg Arg Ser Met Met Gln Ser Pro Arg Thr
                260                 265                 270
Lys Pro Arg Lys Ser Thr Val Gly Ala Leu Tyr Ala Val Gly Gly Met
            275                 280                 285
Asp Ala Met Lys Gly Thr Thr Thr Ile Glu Lys Tyr Asp Leu Arg Thr
290                 295                 300
Asn Ser Trp Leu His Ile Gly Thr Met Asn Gly Arg Arg Leu Gln Phe
305                 310                 315                 320
Gly Val Ala Val Ile Asp Asn Lys Leu Tyr Val Val Gly Gly Arg Asp
                325                 330                 335
Gly Leu Lys Thr Leu Asn Thr Val Glu Cys Phe Asn Pro Val Gly Lys
            340                 345                 350
Ile Trp Thr Val Met Pro Pro Met Ser Thr His Arg His Gly Leu Gly
            355                 360                 365
Val Ala Thr Leu Glu Gly Pro Met Tyr Ala Val Gly Gly His Asp Gly
        370                 375                 380
Trp Ser Tyr Leu Asn Thr Val Glu Arg Trp Asp Pro Glu Gly Arg Gln
385                 390                 395                 400
Trp Asn Tyr Val Ala Ser Met Ser Thr Pro Arg Ser Thr Val Gly Val
```

-continued

```
                405                 410                 415
Val Ala Leu Asn Asn Lys Leu Tyr Ala Ile Gly Gly Arg Asp Gly Ser
            420                 425                 430

Ser Cys Leu Lys Ser Met Glu Tyr Phe Asp Pro His Thr Asn Lys Trp
            435                 440                 445

Ser Leu Cys Ala Pro Met Ser Lys Arg Arg Gly Gly Val Gly Val Ala
            450                 455                 460

Thr Tyr Asn Gly Phe Leu Tyr Val Val Gly Gly His Asp Ala Pro Ala
465                 470                 475                 480

Ser Asn His Cys Ser Arg Leu Ser Asp Cys Val Glu Arg Tyr Asp Pro
                485                 490                 495

Lys Gly Asp Ser Trp Ser Thr Val Ala Pro Leu Ser Val Pro Arg Asp
            500                 505                 510

Ala Val Ala Val Cys Pro Leu Gly Asp Lys Leu Tyr Val Val Gly Gly
            515                 520                 525

Tyr Asp Gly His Thr Tyr Leu Asn Thr Val Glu Ser Tyr Asp Ala Gln
            530                 535                 540

Arg Asn Glu Trp Lys Glu Val Pro Val Asn Ile Gly Arg Ala Gly
545                 550                 555                 560

Ala Cys Val Val Val Lys Leu Pro
            565
```

<210> SEQ ID NO 54
<211> LENGTH: 3111
<212> TYPE: DNA
<213> ORGANISM: Homo sapiens

<400> SEQUENCE: 54

| | | | | | |
|---|---|---|---|---|---|
| tttgagagga | aataaagttt | atttaaattc | agtttgtcaa | agtacaaata | tctttgtaca | 60 |
| acttacgttc | ttctttctta | aaacttaaaa | gctagtagta | tattttataa | gcatttctcc | 120 |
| agattttgat | ttcacaatcc | acaataaaaa | gactgtttaa | aagaacttat | ttgtagaaat | 180 |
| tctaaagttg | tgcatttact | tgaaaagtta | ctttcacaaa | gggttttca | atatttcatc | 240 |
| ttagttgtat | aattaaacag | aataaatgga | agaattacac | ataaaatact | attcaactag | 300 |
| ccatttttgt | tattttaaaa | cttaacaagt | cttttttttt | ttttatatag | cacacatatc | 360 |
| ctaacatttt | ctactggata | atataacagt | aacagaaaag | catgtgttgg | tacaaaaaag | 420 |
| ataactatag | aattgaccag | gcttattgaa | tattttggtg | ttcccatgtg | ttaacactga | 480 |
| gtaacatcct | caatttaag | gtactttaaa | aattgttttg | ttttgaaaa | cttgtttaac | 540 |
| ttaacgatat | ttgtttatag | agttaacata | aatgtttgag | gagaacatta | cattctatac | 600 |
| aagtgaggcc | ctgacactct | gaagctgagg | tcacagtttg | tatcaatatg | ataaatattc | 660 |
| attatttcat | tgtatagact | gtgtatatga | aattacagta | atattttact | ggtaacaaat | 720 |
| ctaacaagat | aaatatgttaa | gaaataccaa | atttatatgt | gtgctctggc | agatgagcaa | 780 |
| acctgtaaaa | atttgacat | accgcgatca | acataacaag | ttttgtcaaa | gagccattat | 840 |
| tttttagct | tcaacacagt | aaaagctttc | ctcttggtaa | atgtaaggaa | ttgtttagct | 900 |
| ctttgggata | ttatttgaat | aggagaataa | tggcttacta | aaaatcacac | tattctaagc | 960 |
| tttagatgtt | acctttata | tttctatgtt | ccagataata | agagtacgtt | ttttaaaaaa | 1020 |
| aaactgaaaa | tgtttttaac | ttttaaggct | cttaccttga | aatgtattaa | tgcttttata | 1080 |
| acctgcacac | tgtggccacc | atcaattttc | attaaatatt | ttagcatttt | gtagtaatgg | 1140 |
| ggctatatct | agactgtggg | atttcctttt | atattatcag | ctgcgaaagc | acatatgctt | 1200 |

-continued

```
aataattcat atgtaattca tgtttaaaaa cgtttcggct tcacgaatga aagcaattgt   1260
aactacaaat taaaatgata caacaatttt ccagtctgat tattaattgc aggaaaaaga   1320
acatgtattt ctttctccct tgtcctact  cagtttcttg aaattatcta gtttcattcc   1380
atttgataaa gatagatagc tttagggtag cttcaccact acaacacatg caccagctct   1440
tccaatgtta acaggaactt cctctttcca ttcatttctc tgtgcatcat atgactcaac   1500
tgtgttcaaa taagtatgtc cgtcatatcc tccaaccacg tagagtttgt ctccaagagg   1560
gcacacagca acagcatctc gaggaacact cagaggtgcc acagttgacc atgaatcacc   1620
ttttggatca taccgttcca cacagtcaga aagcctggag caatggttgg aagcaggggc   1680
atcatgcccc cctacaacat ataagaatcc attgtatgtg caactccca  cacctccacg   1740 tcttttggac attggagcac acaaactcca cttgttagtg tgtgggtcaa agtattccat   1800
tgatttgagg caggaacttc catcacgtcc accaatagca tataatttgt tgtttaatgc   1860
aacaacacca actgtgcttc taggagttga catactggct acgtaattcc actgtcgtcc   1920
ctcagggtcc catctttcta cagtatttag atagctccat ccatcatgac cacctacagc   1980
atacattggt ccttcaagag tggctacacc taagccgtgc cgatgtgttg acatgggagg   2040
catcacagtc cagattttgc caactggatt aaaacattcc actgtattca agttttttaa   2100
accgtctctt cctcccacga catagagctt attatcaata actgcgactc caaattgaag   2160
cctacggcca ttcatggtgc caatatgtag ccaactgttg gtcctgaggt catatttttc   2220
aatagtagta gtacctttca tagcatccat gcctcctaca gcataaagtg cccccacagt   2280
tgattttcta ggctttgtcc gagggctttg catcatggat cttctctcag gcaaaagatg   2340
atacttcata gcttccatca ggagcttctg acactcaaga tcaccagtaa acatggaact   2400
ggtttcaaga tctgccagta actgtggtgg gagtaatggc agtctgatgt aagaaagcag   2460
catccccagt tctccttgcc tattctgcac atcatgcccc acccactgca ttagagcatg   2520
aaaaatggtc tcttcatcag gcacattaat gtcatcactg cacagaagtt ttgaaatttc   2580
attagctgga agcaggagga attcttggtt ttttattacc tcaatgaagt gttccatagt   2640
gtatttgtgt gccacgttca gaagttctgt acagccttgg gcatctccaa atgatcgaat   2700
ccctaagcag tttgaaggat ggagctgctt tatgagaaaa ttggagcaaa catcaatgac   2760
ctgagtcagc tgcagaagac aagctgcagc cagcaaactt tcaatggtat cttctttcaa   2820
ttgcaggact cctgtgtaag catactgcac caaggaattt agtgcatttg gatctactcc   2880
ttccatcctg acctcttctt gtttggcttc aagcacatca ttagtaaaca ttgcagcaaa   2940
ataatcagac actgcgctga gaaccaacct atgggctggg atgcggaggt gtcctgcaat   3000
cagtagcaca tcacatagtt gtttctcttt caagtagttc tccattttac gaagagtttg   3060
ctctgcgtgg tttataacat ggaactgctc ttcagatctg gtggcattca t            3111
```

<210> SEQ ID NO 55
<211> LENGTH: 728
<212> TYPE: PRT
<213> ORGANISM: Homo sapiens

<400> SEQUENCE: 55

```
Glu Lys Ala Phe Val Phe Pro Pro Ala Thr Met Ser Val Ser Gly Lys
 1               5                  10                  15

Lys Glu Phe Asp Val Lys Gln Ile Leu Arg Leu Arg Trp Arg Trp Phe
            20                  25                  30
```

```
Ser His Pro Phe Gln Gly Ser Thr Asn Thr Gly Ser Cys Leu Gln Gln
         35                  40                  45

Glu Gly Tyr Glu His Arg Gly Thr Pro Val Gln Gly Arg Leu Lys Ser
     50                  55                  60

His Ser Arg Asp Arg Asn Gly Leu Lys Lys Ser Asn Ser Pro Val His
 65                  70                  75                  80

His Asn Ile Leu Ala Pro Val Pro Gly Pro Ala Pro His Gln Arg
                 85                  90                  95

Ala Val Gln Asn Leu Gln Gln His Asn Leu Ile Val His Phe Gln Ala
                100                 105                 110

Asn Glu Asp Thr Pro Lys Ser Val Pro Glu Lys Asn Leu Phe Lys Glu
            115                 120                 125

Ala Cys Glu Lys Arg Ala Gln Asp Leu Glu Met Met Ala Asp Asp Asn
        130                 135                 140

Ile Glu Asp Ser Thr Ala Arg Leu Asp Thr Gln His Ser Glu Asp Met
145                 150                 155                 160

Asn Ala Thr Arg Ser Glu Glu Gln Phe His Val Ile Asn His Ala Glu
                165                 170                 175

Gln Thr Leu Arg Lys Met Glu Asn Tyr Leu Lys Glu Lys Gln Leu Cys
            180                 185                 190

Asp Val Leu Leu Ile Ala Gly His Leu Arg Ile Pro Ala His Arg Leu
        195                 200                 205

Val Leu Ser Ala Val Ser Asp Tyr Phe Ala Ala Met Phe Thr Asn Asp
    210                 215                 220

Val Leu Glu Ala Lys Gln Glu Val Arg Met Glu Gly Val Asp Pro
225                 230                 235                 240

Asn Ala Leu Asn Ser Leu Val Gln Tyr Ala Tyr Thr Gly Val Leu Gln
                245                 250                 255

Leu Lys Glu Asp Thr Ile Glu Ser Leu Leu Ala Ala Ala Cys Leu Leu
            260                 265                 270

Gln Leu Thr Gln Val Ile Asp Val Cys Ser Asn Phe Leu Ile Lys Gln
        275                 280                 285

Leu His Pro Ser Asn Cys Leu Gly Ile Arg Ser Phe Gly Asp Ala Gln
    290                 295                 300

Gly Cys Thr Glu Leu Leu Asn Val Ala His Lys Tyr Thr Met Glu His
305                 310                 315                 320

Phe Ile Glu Val Ile Lys Asn Gln Glu Phe Leu Leu Leu Pro Ala Asn
                325                 330                 335

Glu Ile Ser Lys Leu Leu Cys Ser Asp Asp Ile Asn Val Pro Asp Glu
            340                 345                 350

Glu Thr Ile Phe His Ala Leu Met Gln Trp Val Gly His Asp Val Gln
        355                 360                 365

Asn Arg Gln Gly Glu Leu Gly Met Leu Leu Ser Tyr Ile Arg Leu Pro
    370                 375                 380

Leu Leu Pro Pro Gln Leu Leu Ala Asp Leu Glu Thr Ser Ser Met Phe
385                 390                 395                 400

Thr Gly Asp Leu Glu Cys Gln Lys Leu Leu Met Glu Ala Met Lys Tyr
                405                 410                 415

His Leu Leu Pro Glu Arg Arg Ser Met Met Gln Ser Pro Arg Thr Lys
            420                 425                 430

Pro Arg Lys Ser Thr Val Gly Ala Leu Tyr Ala Val Gly Gly Met Asp
        435                 440                 445

Ala Met Lys Gly Thr Thr Thr Ile Glu Lys Tyr Asp Leu Arg Thr Asn
```

-continued

```
              450                 455                 460
Ser Trp Leu His Ile Gly Thr Met Asn Gly Arg Arg Leu Gln Phe Gly
465                 470                 475                 480

Val Ala Val Ile Asp Asn Lys Leu Tyr Val Val Gly Gly Arg Asp Gly
                485                 490                 495

Leu Lys Thr Leu Asn Thr Val Glu Cys Phe Asn Pro Val Gly Lys Ile
                500                 505                 510

Trp Thr Val Met Pro Pro Met Ser Thr His Arg His Gly Leu Gly Val
                515                 520                 525

Ala Thr Leu Glu Gly Pro Met Tyr Ala Val Gly His Asp Gly Trp
530                 535                 540

Ser Tyr Leu Asn Thr Val Glu Arg Trp Asp Pro Glu Gly Arg Gln Trp
545                 550                 555                 560

Asn Tyr Val Ala Ser Met Ser Thr Pro Arg Ser Thr Val Gly Val Val
                565                 570                 575

Ala Leu Asn Asn Lys Leu Tyr Ala Ile Gly Gly Arg Asp Gly Ser Ser
                580                 585                 590

Cys Leu Lys Ser Met Glu Tyr Phe Asp Pro His Thr Asn Lys Trp Ser
                595                 600                 605

Leu Cys Ala Pro Met Ser Lys Arg Arg Gly Gly Val Gly Val Ala Thr
610                 615                 620

Tyr Asn Gly Phe Leu Tyr Val Val Gly Gly His Asp Ala Pro Ala Ser
625                 630                 635                 640

Asn His Cys Ser Arg Leu Ser Asp Cys Val Glu Arg Tyr Asp Pro Lys
                645                 650                 655

Gly Asp Ser Trp Ser Thr Val Ala Pro Leu Ser Val Pro Arg Asp Ala
                660                 665                 670

Val Ala Val Cys Pro Leu Gly Asp Lys Leu Tyr Val Gly Gly Tyr
                675                 680                 685

Asp Gly His Thr Tyr Leu Asn Thr Val Glu Ser Tyr Asp Ala Gln Arg
                690                 695                 700

Asn Glu Trp Lys Glu Val Pro Val Asn Ile Gly Arg Ala Gly Ala
705                 710                 715                 720

Cys Val Val Val Lys Leu Pro
                725

<210> SEQ ID NO 56
<211> LENGTH: 569
<212> TYPE: PRT
<213> ORGANISM: Homo sapiens

<400> SEQUENCE: 56

Met Asn Ala Thr Arg Ser Glu Glu Gln Phe His Val Ile Asn His Ala
1               5                   10                  15

Glu Gln Thr Leu Arg Lys Met Glu Asn Tyr Leu Lys Glu Lys Gln Leu
                20                  25                  30

Cys Asp Val Leu Leu Ile Ala Gly His Leu Arg Ile Pro Ala His Arg
            35                  40                  45

Leu Val Leu Ser Ala Val Ser Asp Tyr Phe Ala Ala Met Phe Thr Asn
        50                  55                  60

Asp Val Leu Glu Ala Lys Gln Glu Glu Val Arg Met Glu Gly Val Asp
65                  70                  75                  80

Pro Asn Ala Leu Asn Ser Leu Val Gln Tyr Ala Tyr Thr Gly Val Leu
                85                  90                  95
```

```
Gln Leu Lys Glu Asp Thr Ile Glu Ser Leu Ala Ala Ala Cys Leu
            100                 105                 110
Leu Gln Leu Thr Gln Val Ile Asp Val Cys Ser Asn Phe Leu Ile Lys
        115                 120                 125
Gln Leu His Pro Ser Asn Cys Leu Gly Ile Arg Ser Phe Gly Asp Ala
    130                 135                 140
Gln Gly Cys Thr Glu Leu Leu Asn Val Ala His Lys Tyr Thr Met Glu
145                 150                 155                 160
His Phe Ile Glu Val Ile Lys Asn Gln Glu Phe Leu Leu Pro Ala
                165                 170                 175
Asn Glu Ile Ser Lys Leu Leu Cys Ser Asp Asp Ile Asn Val Pro Asp
            180                 185                 190
Glu Glu Thr Ile Phe His Ala Leu Met Gln Trp Val Gly His Asp Val
        195                 200                 205
Gln Asn Arg Gln Gly Glu Leu Gly Met Leu Leu Ser Tyr Ile Arg Leu
    210                 215                 220
Pro Leu Leu Pro Pro Gln Leu Leu Ala Asp Leu Glu Thr Ser Ser Met
225                 230                 235                 240
Phe Thr Gly Asp Leu Glu Cys Gln Lys Leu Leu Met Glu Ala Met Lys
                245                 250                 255
Tyr His Leu Leu Pro Glu Arg Arg Ser Met Met Gln Ser Pro Arg Thr
            260                 265                 270
Lys Pro Arg Lys Ser Thr Val Gly Ala Leu Tyr Ala Val Gly Gly Met
        275                 280                 285
Asp Ala Met Lys Gly Thr Thr Thr Ile Glu Lys Tyr Asp Leu Arg Thr
    290                 295                 300
Asn Ser Trp Leu His Ile Gly Thr Met Asn Gly Arg Arg Leu Gln Phe
305                 310                 315                 320
Gly Val Ala Val Ile Asp Asn Lys Leu Tyr Val Val Gly Gly Arg Asp
                325                 330                 335
Gly Leu Lys Thr Leu Asn Thr Val Glu Cys Phe Asn Pro Val Gly Lys
            340                 345                 350
Ile Trp Thr Val Met Pro Pro Met Ser Thr His Arg His Gly Leu Gly
        355                 360                 365
Val Ala Thr Leu Glu Gly Pro Met Tyr Ala Val Gly Gly His Asp Gly
    370                 375                 380
Trp Ser Tyr Leu Asn Thr Val Glu Arg Trp Asp Pro Glu Gly Arg Gln
385                 390                 395                 400
Trp Asn Tyr Val Ala Ser Met Ser Thr Pro Arg Ser Thr Val Gly Val
                405                 410                 415
Val Ala Leu Asn Asn Lys Leu Tyr Ala Ile Gly Gly Arg Asp Gly Ser
            420                 425                 430
Ser Cys Leu Lys Ser Met Glu Tyr Phe Asp Pro His Thr Asn Lys Trp
        435                 440                 445
Ser Leu Cys Ala Pro Met Ser Lys Arg Arg Gly Gly Val Gly Val Ala
    450                 455                 460
Thr Tyr Asn Gly Phe Leu Tyr Val Val Gly Gly His Asp Ala Pro Ala
465                 470                 475                 480
Ser Asn His Cys Ser Arg Leu Ser Asp Cys Val Glu Arg Tyr Asp Pro
                485                 490                 495
Lys Gly Asp Ser Trp Ser Thr Val Ala Pro Leu Ser Val Pro Arg Asp
            500                 505                 510
Ala Val Ala Val Cys Pro Leu Gly Asp Lys Leu Tyr Val Val Gly Gly
```

```
                515                 520                 525
Tyr Asp Gly His Thr Tyr Leu Asn Thr Val Glu Ser Tyr Asp Ala Gln
    530                 535                 540

Arg Asn Glu Trp Lys Glu Val Pro Val Asn Ile Gly Arg Ala Gly
545                 550                 555                 560

Ala Cys Val Val Val Lys Leu Pro
                565

<210> SEQ ID NO 57
<211> LENGTH: 748
<212> TYPE: PRT
<213> ORGANISM: Homo sapiens

<400> SEQUENCE: 57

Met Ser Gly Ser Gly Arg Lys Asp Phe Asp Val Lys His Ile Leu Arg
  1               5                  10                  15

Leu Arg Trp Lys Leu Phe Ser His Pro Ser Pro Ser Thr Gly Gly Pro
                 20                  25                  30

Ala Gly Gly Gly Cys Leu Gln Gln Asp Gly Ser Gly Ser Phe Glu His
             35                  40                  45

Trp Gly Pro Ser Gln Ser Arg Leu Leu Lys Ser Gln Glu Arg Ser Gly
         50                  55                  60

Val Ser Thr Phe Trp Lys Lys Pro Ser Ser Ser Ser Ser Ser Ser Ser
 65                  70                  75                  80

Ser Pro Ser Ser Ser Ser Ser Phe Asn Pro Leu Asn Gly Thr Leu
                 85                  90                  95

Leu Pro Val Ala Thr Arg Leu Gln Gln Gly Ala Pro Gly Gln Gly Thr
                100                 105                 110

Gln Gln Pro Ala Arg Thr Leu Phe Tyr Val Glu Ser Leu Glu Glu Glu
            115                 120                 125

Val Val Pro Gly Met Asp Phe Pro Gly Pro His Glu Lys Gly Leu Val
        130                 135                 140

Leu Gln Glu Leu Lys Val Glu Pro Asp Asn Ser Ser Gln Ala Thr Gly
145                 150                 155                 160

Glu Gly Cys Gly His Arg Leu Ser Ser Thr Gly His Ser Met Thr Pro
                165                 170                 175

Gln Ser Asp Leu Asp Ser Ser Ser Glu Glu Phe Tyr Gln Ala Val
            180                 185                 190

His His Ala Glu Gln Thr Phe Arg Lys Met Glu Ser Tyr Leu Lys Gln
        195                 200                 205

Gln Gln Leu Cys Asp Val Ile Leu Ile Val Gly Asn Arg Lys Ile Pro
    210                 215                 220

Ala His Arg Leu Val Leu Ser Ser Val Ser Asp Tyr Phe Ala Ala Met
225                 230                 235                 240

Phe Thr Ser Asp Val Cys Glu Ala Lys Gln Glu Glu Ile Lys Met Glu
                245                 250                 255

Gly Ile Asp Pro Asn Ala Leu Trp Asp Leu Val Gln Phe Ala Tyr Thr
            260                 265                 270

Gly Cys Leu Glu Leu Lys Glu Asp Thr Ile Glu Asn Leu Leu Ala Ala
        275                 280                 285

Ala Cys Leu Leu Gln Leu Pro Gln Val Val Glu Val Cys Cys His Phe
    290                 295                 300

Leu Met Lys Leu Leu His Pro Ser Asn Cys Leu Gly Ile Arg Ala Phe
305                 310                 315                 320
```

-continued

```
Ala Asp Ala Gln Gly Cys Ile Glu Leu Met Lys Val Ala His Ser Tyr
            325                 330                 335

Thr Met Glu Asn Ile Met Glu Val Ile Arg Asn Gln Glu Phe Leu Leu
            340                 345                 350

Leu Pro Ala Glu Glu Leu His Lys Leu Leu Ala Ser Asp Asp Val Asn
            355                 360                 365

Val Pro Asp Glu Glu Thr Ile Phe His Ala Leu Met Met Trp Val Lys
370                 375                 380

Tyr Asp Met Gln Ser Arg Cys Asn Asp Leu Ser Met Leu Leu Ala Phe
385                 390                 395                 400

Ile Arg Leu Pro Leu Leu Pro Pro Gln Ile Leu Ala Asp Leu Glu Asn
                405                 410                 415

His Ala Leu Phe Lys Asn Asp Leu Glu Cys Gln Lys Leu Ile Leu Glu
            420                 425                 430

Ala Met Lys Tyr His Leu Leu Pro Glu Arg Arg Thr Leu Met Gln Ser
            435                 440                 445

Pro Arg Thr Lys Pro Arg Lys Ser Thr Val Gly Thr Leu Tyr Ala Val
            450                 455                 460

Gly Gly Met Asp Asn Asn Lys Gly Ala Thr Thr Ile Glu Lys Tyr Asp
465                 470                 475                 480

Leu Arg Thr Asn Leu Trp Ile Gln Ala Gly Met Met Asn Gly Arg Arg
                485                 490                 495

Leu Gln Phe Gly Val Ala Val Ile Asp Asp Lys Leu Phe Val Ile Gly
                500                 505                 510

Gly Arg Asp Gly Leu Lys Thr Leu Asn Thr Val Glu Cys Tyr Asn Pro
            515                 520                 525

Lys Thr Lys Thr Trp Thr Val Leu Pro Pro Met Ser Thr His Arg His
530                 535                 540

Gly Leu Gly Val Thr Val Leu Glu Gly Pro Ile Tyr Ala Val Gly Gly
545                 550                 555                 560

His Asp Gly Trp Ser Tyr Leu Asn Thr Val Glu Arg Trp Asp Pro Gln
                565                 570                 575

Ser Gln Gln Trp Thr Phe Val Ala Ser Met Ser Ile Ala Arg Ser Thr
                580                 585                 590

Val Gly Val Ala Ala Leu Asn Gly Lys Leu Tyr Ser Val Gly Gly Arg
            595                 600                 605

Asp Gly Ser Ser Cys Leu Ser Ser Met Glu Tyr Tyr Asp Pro His Thr
            610                 615                 620

Asn Lys Trp Asn Met Cys Ala Pro Met Cys Lys Arg Arg Gly Gly Val
625                 630                 635                 640

Gly Val Ala Thr Cys Asp Gly Phe Leu Tyr Ala Val Gly Gly His Asp
                645                 650                 655

Ala Pro Ala Ser Asn His Cys Ser Arg Leu Leu Asp Tyr Val Glu Arg
                660                 665                 670

Tyr Asp Pro Lys Thr Asp Thr Trp Thr Met Val Ala Pro Leu Ser Met
            675                 680                 685

Pro Arg Asp Ala Val Gly Val Cys Leu Leu Gly Asp Arg Leu Tyr Ala
            690                 695                 700

Val Gly Gly Tyr Asp Gly Gln Thr Tyr Leu Asn Thr Met Glu Ser Tyr
705                 710                 715                 720

Asp Pro Gln Thr Asn Glu Trp Thr Gln Met Ala Ser Leu Asn Ile Gly
                725                 730                 735

Arg Ala Gly Ala Cys Val Val Val Ile Lys Gln Pro
```

```
                          740                 745

<210> SEQ ID NO 58
<211> LENGTH: 751
<212> TYPE: PRT
<213> ORGANISM: Mus musculus

<400> SEQUENCE: 58

Met Ser Gly Ser Gly Arg Lys Asp Phe Asp Val Lys His Ile Leu Arg
  1               5                  10                  15

Leu Arg Trp Lys Leu Phe Ser His Pro Ser Pro Ala Ser Ser Ser Pro
                 20                  25                  30

Ala Gly Gly Ser Cys Leu Gln Gln Asp Ser Gly Gly Ser Phe Glu
             35                  40                  45

His Trp Gly Pro Ser Gln Ser Arg Leu Leu Lys Asn Gln Glu Lys Gly
 50                  55                  60

Ser Val Ser Ala Phe Trp Lys Lys Pro Ser Ser Ser Ser Ser Ser Ser
 65                  70                  75                  80

Ser Ser Ser Ser Ser Ala Ser Ser Ser Pro Phe Asn Pro Leu Asn
                 85                  90                  95

Gly Thr Leu Leu Pro Val Ala Thr Arg Leu Gln Gln Gly Ala Pro Gly
                100                 105                 110

Gln Gly Thr Gln Gln Pro Ala Arg Thr Leu Phe Tyr Val Glu Ser Leu
                115                 120                 125

Glu Glu Glu Val Val Thr Gly Met Asp Phe Pro Gly Pro Gln Asp Lys
            130                 135                 140

Gly Leu Ala Leu Lys Glu Leu Gln Ala Glu Pro Ala Ser Ser Ile Gln
145                 150                 155                 160

Ala Thr Gly Glu Gly Cys Gly His Arg Leu Thr Ser Thr Asn His Ser
                165                 170                 175

Leu Thr Pro Gln Ser Asp Leu Asp Ser Ser Ser Glu Glu Phe Tyr
                180                 185                 190

Gln Ala Val Arg His Ala Glu Gln Ser Phe Arg Lys Met Glu Asn Tyr
            195                 200                 205

Leu Lys Gln Gln Gln Leu Cys Asp Val Ile Leu Ile Val Gly Asn Arg
210                 215                 220

Lys Ile Pro Ala His Arg Leu Val Leu Ser Ser Val Ser Asp Tyr Phe
225                 230                 235                 240

Ala Ala Met Phe Thr Ser Asp Val Cys Glu Ala Lys Gln Glu Glu Ile
                245                 250                 255

Lys Met Glu Gly Ile Asp Pro Asn Ala Leu Trp Asp Leu Val Gln Phe
                260                 265                 270

Ala Tyr Thr Gly Cys Leu Glu Leu Lys Glu Asp Thr Ile Glu Asn Leu
            275                 280                 285

Leu Ala Ala Cys Leu Leu Gln Leu Pro Gln Val Val Glu Val Cys
                290                 295                 300

Cys His Phe Leu Met Lys Leu Leu His Pro Ser Asn Cys Leu Gly Ile
305                 310                 315                 320

Arg Ala Phe Ala Asp Ala Gln Gly Cys Ile Glu Leu Met Lys Val Ala
                325                 330                 335

His Ser Tyr Thr Met Glu Asn Ile Met Glu Val Ile Arg Asn Gln Glu
            340                 345                 350

Phe Leu Leu Leu Pro Ala Glu Glu Leu His Lys Leu Leu Ala Ser Asp
            355                 360                 365
```

```
Asp Val Asn Val Pro Asp Glu Glu Thr Ile Phe His Ala Leu Met Met
    370                 375                 380

Trp Val Lys Tyr Asp Met Gln Arg Arg Cys Ser Asp Leu Ser Met Leu
385                 390                 395                 400

Leu Ala Phe Ile Arg Leu Pro Leu Pro Pro Gln Ile Leu Ala Asp
                405                 410                 415

Leu Glu Asn His Ala Leu Phe Lys Asn Asp Leu Glu Cys Gln Lys Leu
            420                 425                 430

Ile Leu Glu Ala Met Lys Tyr His Leu Leu Pro Glu Arg Arg Thr Leu
            435                 440                 445

Met Gln Ser Pro Arg Thr Lys Pro Arg Lys Ser Thr Val Gly Thr Leu
    450                 455                 460

Tyr Ala Val Gly Gly Met Asp Asn Asn Lys Gly Ala Thr Thr Ile Glu
465                 470                 475                 480

Lys Tyr Asp Leu Arg Thr Asn Leu Trp Ile Gln Ala Gly Met Met Asn
                485                 490                 495

Gly Arg Arg Leu Gln Phe Gly Val Ala Val Ile Asp Asp Lys Leu Phe
                500                 505                 510

Val Ile Gly Gly Arg Asp Gly Leu Lys Thr Leu Asn Thr Val Glu Cys
            515                 520                 525

Tyr Asn Pro Lys Thr Lys Thr Trp Thr Val Leu Pro Pro Met Ser Thr
            530                 535                 540

His Arg His Gly Leu Gly Val Thr Val Leu Glu Gly Pro Ile Tyr Ala
545                 550                 555                 560

Val Gly Gly His Asp Gly Trp Ser Tyr Leu Asn Thr Val Glu Arg Trp
                565                 570                 575

Asp Pro Gln Ser Gln Trp Thr Tyr Val Ala Ser Met Ser Ile Ala
                580                 585                 590

Arg Ser Thr Val Gly Val Ala Ala Leu Asn Gly Lys Leu Tyr Ser Val
            595                 600                 605

Gly Gly Arg Asp Gly Ser Ser Cys Leu Ser Ser Met Glu Tyr Tyr Asp
            610                 615                 620

Pro His Thr Asn Lys Trp Ser Met Cys Pro Pro Met Cys Lys Lys Arg
625                 630                 635                 640

Gly Gly Val Gly Val Ala Thr Cys Asp Gly Phe Leu Tyr Ala Val Gly
                645                 650                 655

Gly His Asp Ala Pro Ala Ser Asn His Cys Ser Arg Leu Leu Asp Tyr
            660                 665                 670

Val Glu Arg Tyr Glu Pro Lys Thr Asp Thr Trp Thr Met Val Ala Pro
            675                 680                 685

Leu Ser Met Pro Arg Asp Ala Val Gly Val Cys Leu Leu Gly Asp Arg
    690                 695                 700

Leu Tyr Ala Val Gly Gly Tyr Asp Gly Gln Thr Tyr Leu Asn Thr Met
705                 710                 715                 720

Glu Ser Tyr Asp Pro Gln Thr Asn Glu Trp Thr Gln Met Ala Ser Leu
                725                 730                 735

Asn Ile Gly Arg Ala Gly Ala Cys Val Val Ile Lys Gln Pro
            740                 745                 750

<210> SEQ ID NO 59
<211> LENGTH: 411
<212> TYPE: PRT
<213> ORGANISM: Homo sapiens

<400> SEQUENCE: 59
```

```
Met Glu His Phe Ile Glu Val Ile Lys Asn Gln Glu Phe Leu Leu Leu
 1               5                  10                  15

Pro Ala Asn Glu Ile Ser Lys Leu Leu Cys Ser Asp Asp Ile Asn Val
             20                  25                  30

Pro Asp Glu Glu Thr Ile Phe His Ala Leu Met Gln Trp Val Gly His
         35                  40                  45

Asp Val Gln Asn Arg Gln Gly Glu Leu Gly Met Leu Leu Ser Tyr Ile
     50                  55                  60

Arg Leu Pro Leu Leu Pro Pro Gln Leu Leu Ala Asp Leu Glu Thr Ser
 65              70                  75                  80

Ser Met Phe Thr Gly Asp Leu Glu Cys Gln Lys Leu Leu Met Glu Ala
                 85                  90                  95

Met Lys Tyr His Leu Leu Pro Glu Arg Arg Ser Met Met Gln Ser Pro
             100                 105                 110

Arg Thr Lys Pro Arg Lys Ser Thr Val Gly Ala Leu Tyr Ala Val Gly
         115                 120                 125

Gly Met Asp Ala Met Lys Gly Thr Thr Thr Ile Glu Lys Tyr Asp Leu
 130                 135                 140

Arg Thr Asn Ser Trp Leu His Ile Gly Thr Met Asn Gly Arg Arg Leu
145                 150                 155                 160

Gln Phe Gly Val Ala Val Ile Asp Asn Lys Leu Tyr Val Val Gly Gly
                 165                 170                 175

Arg Asp Gly Leu Lys Thr Leu Asn Thr Val Glu Cys Phe Asn Pro Val
                 180                 185                 190

Gly Lys Ile Trp Thr Val Met Pro Pro Met Ser Thr His Arg His Gly
             195                 200                 205

Leu Gly Val Ala Thr Leu Glu Gly Pro Met Tyr Ala Val Gly Gly His
     210                 215                 220

Asp Gly Trp Ser Tyr Leu Asn Thr Val Glu Arg Trp Asp Pro Glu Gly
225                 230                 235                 240

Arg Gln Trp Asn Tyr Val Ala Ser Met Ser Thr Pro Arg Ser Thr Val
                 245                 250                 255

Gly Val Val Ala Leu Asn Asn Lys Leu Tyr Ala Ile Gly Gly Arg Asp
                 260                 265                 270

Gly Ser Ser Cys Leu Lys Ser Met Glu Tyr Phe Asp Pro His Thr Asn
                 275                 280                 285

Lys Trp Ser Leu Cys Ala Pro Met Ser Lys Arg Arg Gly Gly Val Gly
             290                 295                 300

Val Ala Thr Tyr Asn Gly Phe Leu Tyr Val Val Gly Gly His Asp Ala
305                 310                 315                 320

Pro Ala Ser Asn His Cys Ser Arg Leu Ser Asp Cys Val Glu Arg Tyr
                 325                 330                 335

Asp Pro Lys Gly Asp Ser Trp Ser Thr Val Ala Pro Leu Ser Val Pro
             340                 345                 350

Arg Asp Ala Val Ala Val Cys Pro Leu Gly Asp Lys Leu Tyr Val Val
             355                 360                 365

Gly Gly Tyr Asp Gly His Thr Tyr Leu Asn Thr Val Glu Ser Tyr Asp
             370                 375                 380

Ala Gln Arg Asn Glu Trp Lys Glu Val Pro Val Asn Ile Gly Arg
385                 390                 395                 400

Ala Gly Ala Cys Val Val Val Lys Leu Pro
                 405                 410
```

<210> SEQ ID NO 60
<211> LENGTH: 1339
<212> TYPE: DNA
<213> ORGANISM: Homo sapiens

<400> SEQUENCE: 60

```
cacggtccgc ccagaggctt cggagctgcc ggagccgggc ggggccttgg cgggcggccc      60
cgggagtggc ggcggcggcg tggtggtcgg cgtggctgag gtgagaaact ggcgctgcgg     120
ctgcctcgga gcacctgttg gtgccggagc ctcgtgctgg tctgcgtgtt ggccgccctg     180
tgcttcgctt ccctggccct ggtccgccgc taccttcacc acctcctgct gtgggtggag     240
agccttgact cgctgctggg ggtcctgctc ttcgtcgtgg gcttcatcgt ggtctctttc     300
ccctgcggct ggggctacat cgtgctcaac gtggccgctg ctacctgta cggcttcgtg      360
ctgggcatgg gtctgatgat ggtgggcgtc ctcatcggca ccttcatcgc ccatgtggtc     420
tgcaagcggc tcctcaccgc ctgggtggcc gccaggatcc agagcagcga gaagctgagc     480
gcggttattc gcgtagtgga gggaggaagc ggcctgaaag tggtggcgct ggccagactg     540
acacccatac cttttgggct tcagaatgca gtgttttcga ttactgatct ctcattaccc     600
aactatctga tggcatcttc ggttggactg cttcctaccc agcttctgaa ttcttacttg     660
ggtaccaccc tgcggacaat ggaagatgtc attgcagaac agagtgttag tggatatttt     720
gttttttgtt tacagattat tataagtata ggcctcatgt tttatgtagt tcatcgagct     780
caagtggaat tgaatgcagc tattgtagct tgtgaaatgg aactgaaatc ttctctggtt     840
aaaggcaatc aaccaaatac cagtggctct tcattctaca caagaggac cctaacattt      900
tctggaggtg gaatcaatgt tgtatgattc taatgagata cgtgattgtc aagagcctag     960
tgtgctatct aaggtctagc agtcacttca ctagtgggca gagacaagtt ctaattgtat    1020
tacagcacaa acaaaactga ctagttttta aattgcacaa ttttttttttt tttaagcaag    1080
aatcattttc tgggtatgta agtgtaaatg tagatgcaaa tttggctgca cctctttatc    1140
atgcctgtat tggcctatag gtctgcactt tagtgttttt taattgtttt atttctgtgt    1200
atttacgaac agagaaataa ctcaaatatt atttctgctt agtgtctttta tttataaagc    1260
ccatgagtag tttgtatgca tctttcctac ttgtaaagat gagtaaaagt atgcagtttt    1320
aaatttaaaa aaaaaaaa                                                  1339
```

<210> SEQ ID NO 61
<211> LENGTH: 186
<212> TYPE: PRT
<213> ORGANISM: Homo sapiens

<400> SEQUENCE: 61

```
Met Gly Leu Met Met Val Gly Val Leu Ile Gly Thr Phe Ile Ala His
  1               5                  10                  15

Val Val Cys Lys Arg Leu Leu Thr Ala Trp Val Ala Arg Ile Gln
             20                  25                  30

Ser Ser Glu Lys Leu Ser Ala Val Ile Arg Val Glu Gly Gly Ser
         35                  40                  45

Gly Leu Lys Val Val Ala Leu Ala Arg Leu Thr Pro Ile Pro Phe Gly
     50                  55                  60

Leu Gln Asn Ala Val Phe Ser Ile Thr Asp Leu Ser Leu Pro Asn Tyr
 65                  70                  75                  80

Leu Met Ala Ser Ser Val Gly Leu Leu Pro Thr Gln Leu Leu Asn Ser
                 85                  90                  95
```

-continued

Tyr Leu Gly Thr Thr Leu Arg Thr Met Glu Asp Val Ile Ala Glu Gln
                100                 105                 110

Ser Val Ser Gly Tyr Phe Val Phe Cys Leu Gln Ile Ile Ile Ser Ile
            115                 120                 125

Gly Leu Met Phe Tyr Val Val His Arg Ala Gln Val Glu Leu Asn Ala
        130                 135                 140

Ala Ile Val Ala Cys Glu Met Glu Leu Lys Ser Ser Leu Val Lys Gly
145                 150                 155                 160

Asn Gln Pro Asn Thr Ser Gly Ser Ser Phe Tyr Asn Lys Arg Thr Leu
                165                 170                 175

Thr Phe Ser Gly Gly Gly Ile Asn Val Val
            180                 185

<210> SEQ ID NO 62
<211> LENGTH: 512
<212> TYPE: DNA
<213> ORGANISM: Homo sapiens

<400> SEQUENCE: 62
gggtcctgct cttcgtcgtg ggcttcatcg tggtctcttt ccctgcggc tggggctaca      60
tcgtgctcaa cgtggccgct ggctacctgt acggcttcgt gctgggcatg ggtctgatga    120
tggtgggcgt cctcatcggc accttcatcg cccatgtggt ctgcaagcgg ctcctcaccg    180
cctgggtggc cgccaggatc cagagcagcg agaagctgag cgcggttatt cgcgtagtgg    240
agggaggaag cggcctgaaa gtggtggcgc tggccagact gacacccata ccttttgggc    300
ttcagaatgc agtgttttcg attattataa gtataggcct catgttttat gtagttcatc    360
gagctcaagt ggaattgaat gcagctattg tagcttgtga atggaactg aaatcttctc     420
tggttaaagg caatcaacca aataccagtg gctcttcatt ctacaacaag aggaccctaa    480
catttctgg aggtggaatc aatgttgtat ga                                   512

<210> SEQ ID NO 63
<211> LENGTH: 134
<212> TYPE: PRT
<213> ORGANISM: Homo sapiens

<400> SEQUENCE: 63

Met Gly Leu Met Met Val Gly Val Leu Ile Gly Thr Phe Ile Ala His
1               5                   10                  15

Val Val Cys Lys Arg Leu Leu Thr Ala Trp Val Ala Ala Arg Ile Gln
            20                  25                  30

Ser Ser Glu Lys Leu Ser Ala Val Ile Arg Val Val Glu Gly Gly Ser
        35                  40                  45

Gly Leu Lys Val Val Ala Leu Ala Arg Leu Thr Pro Ile Pro Phe Gly
    50                  55                  60

Leu Gln Asn Ala Val Phe Ser Ile Ile Ile Ser Ile Gly Leu Met Phe
65                  70                  75                  80

Tyr Val Val His Arg Ala Gln Val Glu Leu Asn Ala Ala Ile Val Ala
                85                  90                  95

Cys Glu Met Glu Leu Lys Ser Ser Leu Val Lys Gly Asn Gln Pro Asn
            100                 105                 110

Thr Ser Gly Ser Ser Phe Tyr Asn Lys Arg Thr Leu Thr Phe Ser Gly
        115                 120                 125

Gly Gly Ile Asn Val Val
    130

-continued

<210> SEQ ID NO 64
<211> LENGTH: 690
<212> TYPE: DNA
<213> ORGANISM: Homo sapiens

<400> SEQUENCE: 64

| | | | | | |
|---|---|---|---|---|---|
| atgggcttca | tcgtggtctc | tttccctgc | ggctggggct | acatcgtgct | caacgtggcc | 60 |
| gctggctacc | tgtacggctt | cgtgctgggc | atgggtctga | tgatggtggg | cgtcctcatc | 120 |
| ggcaccttca | tcgcccatgt | ggtctgcaag | cggctcctca | ccgcctgggt | ggccgccagg | 180 |
| atccagagca | gcgagaagct | gagcgcggtt | attcgcgtag | tggagggagg | aagcggcctg | 240 |
| aaagtggtgg | cgctggccag | actgacaccc | atacctttg | ggcttcagaa | tgcggtgttt | 300 |
| tcgattactg | atctctcatt | acccaactat | ctgatggcat | cttcggttgg | actgcttcct | 360 |
| acccagcttc | tgaattctta | cttgggtacc | accctgcgga | caatggaaga | tgtcattgca | 420 |
| gaacagagtg | ttagtggata | ttttgttttt | tgtttacaga | ttattataag | tataggcctc | 480 |
| atgttttatg | tagttcatcg | agctcaagtg | gaattgaatg | cagctattgt | agcttgtgaa | 540 |
| atggaactga | atcttctct | ggttaaaggc | aatcaaccaa | ataccagtgg | ctcttcattc | 600 |
| tacaacaaga | ggaccctaac | attttctgga | ggtggaatca | atgttgtatg | attctaatga | 660 |
| gatacgtgat | tgttaagagc | ctagtgtgta | | | | 690 |

<210> SEQ ID NO 65
<211> LENGTH: 216
<212> TYPE: PRT
<213> ORGANISM: Homo sapiens

<400> SEQUENCE: 65

Met Gly Phe Ile Val Val Ser Phe Pro Cys Gly Trp Gly Tyr Ile Val
1               5                   10                  15

Leu Asn Val Ala Ala Gly Tyr Leu Tyr Gly Phe Val Leu Gly Met Gly
            20                  25                  30

Leu Met Met Val Gly Val Leu Ile Gly Thr Phe Ile Ala His Val Val
        35                  40                  45

Cys Lys Arg Leu Leu Thr Ala Trp Val Ala Ala Arg Ile Gln Ser Ser
    50                  55                  60

Glu Lys Leu Ser Ala Val Ile Arg Val Val Glu Gly Gly Ser Gly Leu
65                  70                  75                  80

Lys Val Val Ala Leu Ala Arg Leu Thr Pro Ile Pro Phe Gly Leu Gln
                85                  90                  95

Asn Ala Val Phe Ser Ile Thr Asp Leu Ser Leu Pro Asn Tyr Leu Met
            100                 105                 110

Ala Ser Ser Val Gly Leu Leu Pro Thr Gln Leu Leu Asn Ser Tyr Leu
        115                 120                 125

Gly Thr Thr Leu Arg Thr Met Glu Asp Val Ile Ala Glu Gln Ser Val
    130                 135                 140

Ser Gly Tyr Phe Val Phe Cys Leu Gln Ile Ile Ile Ser Ile Gly Leu
145                 150                 155                 160

Met Phe Tyr Val Val His Arg Ala Gln Val Glu Leu Asn Ala Ala Ile
                165                 170                 175

Val Ala Cys Glu Met Glu Leu Lys Ser Ser Leu Val Lys Gly Asn Gln
            180                 185                 190

Pro Asn Thr Ser Gly Ser Ser Phe Tyr Asn Lys Arg Thr Leu Thr Phe
        195                 200                 205

```
Ser Gly Gly Gly Ile Asn Val Val
    210             215

<210> SEQ ID NO 66
<211> LENGTH: 209
<212> TYPE: PRT
<213> ORGANISM: Synechococcus sp.

<400> SEQUENCE: 66

Met Ala Asp Tyr Leu Leu Asn Ala Leu Gln Trp Ile Asp Gly Leu Gly
  1               5                  10                  15

Thr Trp Ala Ala Ile Ala Phe Met Leu Leu Tyr Thr Val Ala Thr Val
                 20                  25                  30

Val Phe Leu Pro Gly Ser Ile Leu Thr Leu Gly Ala Gly Val Val Phe
             35                  40                  45

Gly Val Ile Leu Gly Ser Ile Tyr Val Phe Ile Gly Ala Thr Leu Gly
     50                  55                  60

Ala Thr Ala Ala Phe Leu Val Gly Arg Tyr Leu Ala Arg Gly Trp Val
 65                  70                  75                  80

Ala Lys Lys Ile Ala Gly Asn Gln Lys Phe Lys Ala Ile Asp Glu Ala
                 85                  90                  95

Val Gly Lys Glu Gly Leu Lys Ile Val Ile Leu Thr Arg Leu Ser Pro
            100                 105                 110

Val Phe Pro Phe Asn Leu Leu Asn Tyr Ala Tyr Gly Ile Thr Asn Val
            115                 120                 125

Ser Leu Lys Asp Tyr Val Ile Gly Ser Leu Gly Met Ile Pro Gly Thr
    130                 135                 140

Ile Met Tyr Val Tyr Ile Gly Ser Leu Ala Gly Ser Leu Ala Thr Leu
145                 150                 155                 160

Gly Thr Ala Thr Asn Gln Ala Asn Pro Thr Leu Gln Trp Thr Ile Arg
                165                 170                 175

Ile Val Gly Phe Ile Ala Thr Val Ala Val Thr Ile Tyr Val Thr Lys
            180                 185                 190

Ile Ala Arg Lys Ala Leu Asn Glu Ala Ile Leu Thr Ser Glu Val Asp
        195                 200                 205

Glu

<210> SEQ ID NO 67
<211> LENGTH: 444
<212> TYPE: PRT
<213> ORGANISM: Drosophila melanogaster

<400> SEQUENCE: 67

His Asn Arg Lys Arg Asn Ser Cys Trp Gly Arg Ala His Ser Phe Leu
  1               5                  10                  15

Thr Arg Asn Trp Tyr Leu Gly Cys Leu Val Pro Ala Thr Ile Leu Gly
                 20                  25                  30

Ala Leu Val Phe Ile Gly Trp Ala Thr Arg Asp Tyr Ala Arg Gln Leu
             35                  40                  45

Leu Phe Trp Ile Glu Met Gln Asn Ala Trp Ile Thr Phe Ala Val Tyr
     50                  55                  60

Met Gly Leu Phe Ala Leu Val Ser Phe Pro Val Val Gly Tyr Phe
 65                  70                  75                  80

Val Leu Leu Ile Thr Ala Gly Tyr Leu Phe Gly Cys Leu Arg Gly Trp
                 85                  90                  95
```

```
Val Thr Val Ile Leu Gly Ala Asn Ile Gly Ile Ala Val Ala His Ala
                100                 105                 110

Thr Ile Arg Ser Cys Arg His Arg Ile Pro Val Gln Ser Pro Tyr Ile
            115                 120                 125

Thr His Cys Ser Val Cys Phe Leu Tyr Ser Pro Met Leu Arg Phe Leu
        130                 135                 140

Arg Asn Phe Lys Tyr Tyr Ala Trp Gln Glu Val Arg Arg Gly Cys Ser
145                 150                 155                 160

Val Val Ala Pro Pro Asp Arg Ser Asp Val Leu Leu Val Leu Pro Thr
                165                 170                 175

Val Trp Pro Ser Glu Leu Thr Lys Arg Ile Arg Pro Leu Ser Val Pro
            180                 185                 190

Asp Leu Ile Glu Lys Phe Ser Cys Asp Ala Pro Gly Gly Gln Phe Ala
        195                 200                 205

Thr Met Ser Glu Tyr Leu Arg Ser Asp Pro Arg Pro Asp Gly Val Leu
    210                 215                 220

Leu Pro Asp Glu Ile Asp Leu His Arg Lys Met Ser Leu Asp Asp Leu
225                 230                 235                 240

Asn Ser Tyr Met His Ala Lys Asp Ala Phe Lys Glu Pro His Arg Lys
                245                 250                 255

Asn Arg Ile Phe Ser His Val Leu Val Val Ala Gly Ala Asp Ser Ala
            260                 265                 270

Arg Ser Tyr Pro Phe Arg Gln Arg Pro Asp Phe Leu Tyr Leu Cys Asp
        275                 280                 285

Cys Leu Arg Pro Gly Ala Ala Leu Val Leu Thr Arg Ser Arg Lys Arg
    290                 295                 300

Asn Thr Gly Ala Leu Leu Phe Leu Ser Gln Asp Val Asp Ser Gln Leu
305                 310                 315                 320

Ser Thr Ile Phe Ser His Met His Tyr Val Asp Asp Val Leu Pro Leu
                325                 330                 335

Ala Met Leu Lys Lys Ser Leu Leu Trp Leu Leu Arg Asp His Ser Pro
            340                 345                 350

Glu Leu Trp His Phe Tyr Asp Pro Ser Ser Pro Val Ser Cys Ile Val
        355                 360                 365

Gln Glu Val Ala Asn Glu Ala Lys Ile Pro Met Gly Asn Pro Arg Tyr
    370                 375                 380

Ile Leu Gln Tyr Thr Arg Thr Val Lys Thr Ser Arg Glu Leu Arg Ala
385                 390                 395                 400

Leu Arg Arg Ala Asn Ala Thr Ala Ala Asp Ser Met Ala Glu Val Ile
                405                 410                 415

Ala Gln His His Gln Ile Pro Gln Glu Leu Ala Ala Ser Phe Asp Tyr
            420                 425                 430

Lys Cys Arg Leu Arg His Ala Arg Pro Asp Val Thr
        435                 440

<210> SEQ ID NO 68
<211> LENGTH: 269
<212> TYPE: PRT
<213> ORGANISM: Arabidopsis thaliana

<400> SEQUENCE: 68

Met Ser Phe Thr Pro Ser Thr Phe Arg Ile Ala Ile Ser Leu Leu Leu
  1               5                  10                  15

Leu Val Ala Ile Val Ser Ala Val Ile Phe Leu Pro Lys Leu Lys Asp
                20                  25                  30
```

```
Phe Leu Leu Trp Ile Lys Glu Asp Leu Gly Pro Phe Gly Pro Leu Ala
            35                  40                  45

Leu Ala Leu Ala Tyr Ile Pro Leu Thr Ile Val Ala Val Pro Ala Ser
    50                  55                  60

Val Leu Thr Leu Gly Gly Gly Tyr Leu Phe Gly Leu Pro Val Gly Phe
65                  70                  75                  80

Val Ala Asp Ser Leu Gly Ala Thr Leu Gly Ala Thr Ala Ala Phe Leu
                85                  90                  95

Leu Gly Arg Thr Ile Gly Lys Ser Tyr Val Thr Ser Lys Ile Lys His
            100                 105                 110

Tyr Pro Lys Phe Gln Ala Val Ser Val Ala Ile Gln Lys Ser Gly Phe
            115                 120                 125

Lys Ile Val Leu Leu Arg Val Val Pro Ile Leu Pro Phe Asn Met
            130                 135                 140

Leu Asn Tyr Leu Leu Ser Val Thr Pro Val Arg Leu Gly Glu Tyr Met
145                 150                 155                 160

Leu Ala Thr Trp Leu Gly Met Met Gln Pro Ile Thr Phe Ala Leu Val
                165                 170                 175

Tyr Val Gly Thr Thr Leu Lys Asp Leu Ser Asp Ile Thr His Gly Trp
                180                 185                 190

His Glu Val Ser Val Phe Arg Trp Val Ile Met Val Gly Val Ala
            195                 200                 205

Leu Ala Val Ile Leu Ile Ile Cys Ile Thr Arg Val Ala Lys Ser Ser
        210                 215                 220

Leu Asp Lys Ala Leu Ala Glu Asn Gly Thr Glu Leu Asp Gly Lys Lys
225                 230                 235                 240

Asn Asp Asp Ala Ser Val Leu Pro Ile Ala Glu Pro Pro Pro Asp Leu
                245                 250                 255

Gln Glu Pro Leu Val Ile Arg Ile Asp Pro Ser Asn Thr
            260                 265

<210> SEQ ID NO 69
<211> LENGTH: 225
<212> TYPE: PRT
<213> ORGANISM: unidentified bacterium

<400> SEQUENCE: 69

Met Val Ser Pro Trp Leu Pro Glu Phe Ala Gly Trp Val His Ser Leu
1               5                   10                  15

Gly Val Trp Ala Pro Ile Ala Phe Val Ala Ala Tyr Ile Ala Val Val
                20                  25                  30

Val Leu Met Leu Pro Ala Phe Leu Leu Ile Met Ala Gly Gly Ala Val
            35                  40                  45

Phe Gly Val Val Glu Gly Ser Leu Leu Ala Leu Leu Gly Ala Val Leu
    50                  55                  60

Gly Gly Thr Ala Ala Phe Leu Ile Gly Arg His Tyr Ala Arg Ala Ala
65                  70                  75                  80

Val Glu Arg Arg Val Ala Ser Asn Pro Thr Leu Ser Ala Leu Asp His
                85                  90                  95

Val Ile Gly Glu Asp Gly Leu Lys Leu Val Phe Leu Arg Leu Ser
            100                 105                 110

Pro Ala Val Pro Phe Val Leu Thr Asn Tyr Ala Leu Ser Ile Thr Arg
            115                 120                 125

Val Arg Leu Arg Asp Phe Phe Ile Gly Thr Leu Gly Leu Ala Pro Ile
```

|   |   |   |   |   | 130 |   |   |   | 135 |   |   |   | 140 |   |   |
|---|---|---|---|---|-----|---|---|---|-----|---|---|---|-----|---|---|

Val Val Met Tyr Ala Ala Tyr Gly Ser Ala Ser Gly Ala Thr Pro Asn
145                 150                 155                 160

Ala Asp Gly Ser Ala Ala Val Thr Pro Met Met Phe Thr Ala Gly Ile
                165                 170                 175

Val Val Thr Val Leu Leu Gly Leu Leu Leu Ala Lys Ile Val Gln Lys
            180                 185                 190

Ala Leu Arg Glu Ala Glu Leu Ser Arg Leu Lys Gln Leu Glu Ile Asp
        195                 200                 205

Ala Thr Pro Glu Thr Pro Thr Val Leu Pro Thr Pro Ile Thr Glu Ser
    210                 215                 220

Ile
225

<210> SEQ ID NO 70
<211> LENGTH: 6540
<212> TYPE: DNA
<213> ORGANISM: Homo sapiens

<400> SEQUENCE: 70

```
ctggagttcc tttattctgg ggatagctca agtccactgc caatggctga cagtcattaa      60
tacacaggca gaaaaagaa ataagctgct gtgtctgcag ttgggagggg agcactggga     120
aggacagaat ggaagttact gtatccagat accagcggcc tttacatttt aaacatggag     180
aggaaggaac aggcagatta aaaagtgaaa atggcagtt tacagagaag gcctaactgt     240
tggagaatga gtacgagatg aagggaagca gctttgatag caaaccaggg gaataaggca     300
gttatctgcc agtatctact gcttcaaaga gaagctcaag catcatctaa gtagttttac     360
acagggagtg agactgagtt tggtggggat ttcattgagt aatgggataa aaattcaggc     420
actgctcatt cagttccaag gttctcttgc aacccagttt tgagctggag ggaattgtgt     480
tttggtacat atttatgttt gaatgcaagc cagcccacat tcgacaggca cggagctctt     540
tcatgctcag aaaagggaaa aaaagttcc tgttcttgta tattctttca tcctaaacct     600
gagacactta acaagaagcc ggtgttggca aaggtgtgtg tgtgtgtgtg tgtctgtgtg     660
tgtgtgtcct aacgaaatgc acatatttgc tgcagtgaag gagccagttt ttccataaat     720
ggctaacagg aatttgatga agtgtttgca acattaaatg tgttgtgggt cacgttgtaa     780
cttacattgt tccccagcct ccacttttcc ttgtttccta accaacctcc atcccgcccc     840
acatgccaca ttcatccagg ccttcaatag gtctgctgtc agttcccata aactggctca     900
ggttgtagaa atggttagtg aagtcgggca tctcagccat tcccacctct tacttcccaa     960
ggtgtctcat gtcaccaaat tacaaatcat ccacaagcag aagatcaaat ccaggctgac    1020
taaagccatg tggaatgtgg acacttgggg gcagttaaat accttacagg tttctgctgt    1080
aagatttgaa gctttgaagg cagaaatcaa tggccagatt tcaaaggaa aaggttacag    1140
gtgtgtccag gtgagcccca gacagatgga tctgtgaaag caagtgcctg tgcaggtgca    1200
gtgactgctc tggccatatg tcctgtacag acatgggctg cagaggaagg aacaagactg    1260
tgagtcaaag aagacaggcc cgtgcagcca tccgtgcctt acttgtctcc aggtatatgg    1320
ggcagatctg taagtagaga ataagaacag cagatgggat tttccatggg gactctactt    1380
cctactccaa ggcattcaga acatggctaa aaatgaaacc agtgaatttg ggccataga    1440
gctaatctca aaaccaagag aatgaaactg ccaggatgca tgaagaggga tggcgaaggc    1500
aggcagtaag gagggaaac tgagtgggct ctgaatgtca cctgcacggt gtaggccctc    1560
```

```
acggcatctt tctgacctct aaatgttgga acaccccaac aggcctgggt cctgcctccc    1620
ctgtcccctc tgccacactc tctctgggtg agctcactca gccccacgcc tttacatccc    1680
atttatgcac tgatggctcc taactctaaa tctccacccc gacccttctc ctgagctccc    1740
gattcaaaat cttatggcct gttcatcctc ttggatatct aatagagctc ccaaagttaa    1800
tgtgtccaaa cctgaacccc agattcgcca ctatgttccc aaatcccact atgggttagt    1860
ctcccccatc tcagaaagta accctccatt tacccaagtg gtctggacaa aagtttggga    1920
ttatcctcaa ttcttttctt tatctcacat cccgcatcta atccatcagc aagtttcgtc    1980
agctctccct gtaaaatgca tcccattcct acttttcatt gcttccacca ctaccagccc    2040
tgttcaaagc aacacccttt ctttccttga tgactgcaat gttgttgagc tgactgcctt    2100
gatcccatgc ctgccacctt gtgtcttgtc tccacacgga aactcaagtg acttttaaa     2160
agtataaatt agattagcct gctttcttgc tcaaaaactt ctgctggtat ttcctacttt    2220
taaaatgaag ttcaaagtcc taaaatagcc taacctctat ttaccacccc caccccacct    2280
ccttctatct ccctttttgcc attccagcca caccaacctc ctgatcaccc ttcaaaatac    2340
atcaccttgt tccctctgtg gcatcttgat atttgttgct gtatccacct ggaaatcttt    2400
cacattgctc gttcccctga tgcactcaaa actctctaat cccacgttca tctttgcaaa    2460
gaagtctttc ctgaccacag attctaaagg agaccaacca ccatccagct cttggatcct    2520
cctcttctct tcccttctcc tgttccacgc ataggggcaca ttgatcatgg ttttggcta    2580
cccagtgtat tttaacattc ttgtcctatt tgagaaaatt tgagactccc caaagcagaa    2640
ggcagtatag tgagtttaat agtgtttccc ctgatgtaca tctacccaga gcctcagaat    2700
atgaccttaa ttggaaatag gttctttgca gctataatta gttaaggagt ggaagatgaa    2760
gtcatcctga atttagggtg ggccctaatt ccaatgactg gcatccttat gagataatgg    2820
agaaggagat ttggacacag acatgaagac atgcaggaaa aaggccacc tagtaatgga     2880
ggcagggtga ctcatggagc cacaagccaa cggacatcaa gtaccactgg cccccatcaa    2940
aaactttaaa aaggcaggga aaggttcttc tctagagcct ccagagggaa caggactctg    3000
ttaacacctc aatctcagcc ttccagcctc cagactgtga gagaataaag ccatcaagtt    3060
tgtggttatt agttacagca ggcttaggaa actaatacag ccaaacattt ctctagatgc    3120
tcagtaacca gggcacaaga cagagaccca cacccccag tcagatgatt ctgcatgaga     3180
cttccattgt agatctgagt gcattgagga gctcaccccc agcagttcct atcatcccag    3240
ctcaggcctc agacatcaag aagcaggaga caagccatct ctgtgtgtcc tgtccaaaac    3300
cctgagccat agacttcatg ggcataacaa aatggtttgt gtttgagccc ataaagttgg    3360
agtgctttgt tgtacagcaa tagtaactgc aacaaaaatc aaaataattc ctctctgatg    3420
gtggggcatg gggaagatga aggaaagaga tatagtgaat cacatctttg tcagaaagac    3480
agtgggttca tttgagtagt tggattatgt atttcccaga gccatctctc aggataaacc    3540
taagcttctt caggatacaa ggaaatttcc tggaatccta aacatttaga aaacatttc     3600
aaaaaacctc ggtgtggtac acttgaaaga atcttcagtt tccttgccac gataacaaat    3660
tagccacata tatcaacact gcaccaggca tctccatagt cacagtttga tgcaagtttc    3720
caaatacctc tgcaaagcag gcattactgt tactatttta caaatgatgc ctggagaata    3780
tagaaatttc aactcatgct ttgaatcctg aaaaccactt gaaggcccaa attcggatgg    3840
tccatctccc agagttgtct ctaaataaca acactgtgta gaatgagaag gctgaaatgc    3900
```

```
caagtgatct cagtgacccc ctttcatgat attttaagac tactgccaag aacaatgttg    3960
tcttacaggc agcatagggt agttatcaat gtaagagaaa actgccagga tgcctgcaaa    4020
gcccacaatc ggaagttcag agcggcaggt cataaattat ttttataaga gaaaaggcca    4080 agcaagggc cgttctaaca gccgtctggc atccctatcc tgcaacctgg gctgagtttg     4140
taccgaattt ctgctttggg gcagaaattc ataccagaaa aatgtttcgt gatgcatttt    4200
tgttcagttg aatagagcca agaatttgtt ctaatttaaa ttagatgacc tctgagctga    4260
tatactataa aaatattaa tcaagtaacc ccagcaaata ctgatagggt atcaccaggg     4320
actcaatgat atcaccagga tgaaagaaa cggtggcctt tttggctggt atgatccata    4380
attcccacat aatccacgtc tataagttag agagaattgt caagtacagt tcagtgctaa    4440
cctggaaaca aatagccctt ataaggctgc taatccactt aaaataatca gttccagatt    4500
attaatttgg caccctccca aggatactac gaggatctgt cagatttcat gaacatatag    4560
gcaacaatag aaccaatacc ctaaaccccca gaaatctaga tatgaaagct atgtagaatc    4620 atacccttc tagtcccact gcttcataat acaaatgaca aaaattcagc tcatgaggat    4680
taagggactt ttcagtgggg catcagctca cggttgcata cagctcagtc ttttttttt    4740 ttttgagaca gggtcttact ctgctaccca ggccacagtg cagtggggcc atcttggctc    4800
actgcagcct caacctcctg ggctcaagca atcctcccac cttagcttcc caaatagctg    4860
agatgacagg tgcacacaac catgcctggc taatttttta ttttttgaag atatagggcc    4920
tcactatgtt gcccaggctg gagcccagtc ttcagagatg gaaagacatg cgtctatgtc    4980
atttacgagt ttcatggcct gtgtcaagct aattctaccc cctgagcctc agcttgtttc    5040
ttcttttcaa aaatgaagat gccagtggtt ctcacctcat attgttgcaa ggaatggaac    5100
aatgggtgta gggcacctgg tgtagagtag gtgctcagtc acatgtagtt gctgttgttc    5160
ttccccagat tatacaaaca aattcttgct aagccaggat gaaaacccag gtttcaggac    5220
tctcaggctg atactcatac catgccactc catcaaagag aagggcattt tccacctgta    5280
tccctgggtc tgtgttccaa tcattctaaa ctctgaccag cgcctcataa gttgaatgaa    5340
atataaacga cttcaataaa tctcttttt ccaaataaat gaagtttatc aagctgtccc     5400
ataaccccgt gctaaatcta taaaactgta ggcagcttcc tttgggacca acatttcctg    5460
gctaattaaa atgaatgttg tatcgatgaa agattatttt aaaatggcac tgatagtgtt    5520
tagacattgt cataacatca gccggtggat cactaatttg caaattttac taaagatctt    5580
gccaattaaa accccttcta gacactctca aacacactgt cagtgacagc tgagagacca    5640
catggtaaag acatgatcac attaaattca cacaagactg ttctccctgg aagggctgag    5700
ggagagagac gggggcacgt ccccatagca ggtgccactg agtcaaccca gccagactgt    5760
cataagagaa aagcaaattt ttgggttta ttttacccta actgctttcc aaaacaaaca     5820
gtggaaattc ttctaaaaat ctgtaggaaa ttatcctgaa aaattgtgtt ctctcttgag    5880
agacaagtga agagaagtga atctctgaac caatctgaaa ctcgccaagg tacaagttgg    5940
ctcacctggg aggtggtggg ctttagccca gagtcttctg ggacagtttg tccctctcca    6000
ggggttgcag aagcggcaac aatagtgatg agtctgtctc tgggaagtca cctcaattaa    6060
cagccacagt gaattccttt aaaagttaac tttacaagct ctgcccagca gtgggtcact    6120
gggggaaatt ttccagattt gaaagtcaag gtagcatgac atggcatgta tttaaatgat    6180
cagatttcat gcagataacc ctaacagcca acacttatta agggcctacc atgtgcatga    6240
tgtcatttat tcattacaac aatcctataa gattggtgct attattatcc ccgaaggaca    6300
```

```
gatgagaaaa ttaagactca gagatattgc aactcatcct tgtacacaga gttgctatgc      6360
aatatagctg gaattctaaa cccggtccca ctgagggccg tgaccctggt ggtgaaactc      6420
cacagtgtga caggccttat ccctgagatt tgtggtctat ccacatacca gtccatggga      6480
gattatggtc ttttctgata tccatgtgta atatttctcc atccactgag atattcggga      6540

<210> SEQ ID NO 71
<211> LENGTH: 139
<212> TYPE: PRT
<213> ORGANISM: Homo sapiens

<400> SEQUENCE: 71

Met Cys Cys Gly Ser Arg Cys Asn Leu His Cys Ser Pro Ala Ser Thr
  1               5                  10                  15

Phe Pro Cys Phe Leu Thr Asn Leu His Pro Ala Pro His Ala Thr Phe
                 20                  25                  30

Ile Gln Ala Phe Asn Arg Ser Ala Val Ser Ser His Lys Leu Ala Gln
             35                  40                  45

Val Val Glu Met Val Ser Glu Val Gly His Leu Ser His Ser His Leu
         50                  55                  60

Leu Leu Pro Lys Val Ser His Val Thr Lys Leu Gln Ile Ile His Lys
 65                  70                  75                  80

Gln Lys Ile Lys Ser Arg Leu Thr Lys Ala Met Trp Asn Val Asp Thr
                 85                  90                  95

Trp Gly Gln Leu Asn Thr Leu Gln Val Ser Ala Val Arg Phe Glu Ala
                100                 105                 110

Leu Lys Ala Glu Ile Asn Gly Gln Ile Phe Lys Gly Lys Gly Tyr Arg
            115                 120                 125

Cys Val Gln Val Ser Pro Arg Gln Met Asp Leu
        130                 135

<210> SEQ ID NO 72
<211> LENGTH: 2760
<212> TYPE: DNA
<213> ORGANISM: Homo sapiens

<400> SEQUENCE: 72
tctgcctcct gggttgaagc gattcttctg cctcagcctc ctgagtagct gggactacaa        60
gcaggcgcca ctacgcctgg ctaattttg tatttttagt agagacaggg tttcaccata       120
ttggccagga tggtttcaaa ctcctgacct catgatctgc ccaccaggc ctcccaaagt        180 gctgggatta caggcgtgag ccaccgcgcc tggtgaggac tccatttct accccctaggc      240 taaagagcct ggaggattat agcttacaga gcagagaaga actctgatac tcatacctgc      300
atagtgctag ctagtcagta gacaatactt agataattca ttttctgatt tctgacatta      360
gtgagaggtt gggttttgt ttgtttaata acagccttca tttagatctt tgcaaacagc       420
cttgaatgag gaatgtcctt atgtttcagg gaacatatca ggcctggaag cagcttttt       480 aggataaagc tcactcattg aacttcaaat gcactgactc caaccatttc ctaaaataag      540
gaaaatctgt ctgcacagac ggcattttca ctctcctgaa tgttttctgt tggttggttg      600
gttggttggt tttattggtt ggttggtttt gatacagagt gatacaatat catgaagaat      660
attagtcaga aatggggcac aggtctcaag caggtcttgg gaccttgggc tattaatctt      720
tctgggcctt aatttactta tctataacat aaaaggacct taatatatga ttgagaaggc      780
ccaaaccacc tttaaaattt agatctgtgt ctccccatca gacctctctg gagacacagg      840
```

-continued

```
atcttattca acctcacaca gattcttggg tttctgccat tcacatctac attgaaaatt    900
ctcccataaa ctttatacaa gtccttatgg aatcattaaa gctttgcaag aaaacaacag    960
tacccattat aaaagcccaa gaaacagaga agaaaatcat gttttataac ccaagaaatc   1020
tgtccaaatc ctagaatttt tcttcagagt acatcacaag aaggaacagt ctcttccttc   1080
ctagtgggaa agtcagggtt tcttttcattt ccaccttgtt cgcttgtaac cgctctcacc   1140
aggcaaagtt ctgagcaagt gagatggact catctcggaa ctccaggctg tgtttacata   1200
attggtaaaa gaaacattcc aatcccattc cttcgtcagc tccgacagac caaccagcat   1260
cccccctccca cttgccactt tgatagggt gactggtatc tccatctcct tatctttgtt   1320
gatcatgttt ctgggtttcc aattgcgtca atttaactgg ttgccaataa ttctgtcatc   1380
tgagggaaa gcagaatctc aactgaacat gcagatgtcc tattgagact ttgcccataa    1440
gggagcgtct ttggtgctta aaattccatc ttttggacct catatcagtt gatgttttta   1500
gttgcatcgg aaaccaactc taagtgattt aagcaggaga gaaagttatt taaggatatt   1560
tatagttcac agaatctctg gaggagcggg gggctagaaa accagacttg aagactacac   1620
agagagactc cgagtccccc tgggactgac ctgagatgac cagggagctg gtattttag    1680
cttccagagg taaataacag ccttcacttc catcaaaact cattaggtag aaaacacacc   1740
aaacatggga aaggcgttcc ggagctgggc taccaaagag aataataaat gttcactata   1800
gtttcatctt ctagttttgt accatccctg aaacattttc ttttcctcc aggagcctca    1860
aaattacagt taagtctaca gtcagacaga aggaaactgg catttattaa acaccaactt   1920
tgtgcctgga agattcactt acaatatcat aatctttaca ataactctgc aatatggatc   1980
tcattatcag cattctttttt ttgtttgttt ggttggttgg ttttggtggt tttagtgtca   2040
gggtctcact ctgttgctca ggctggagca tggtggcatg atcataactc actgcagcct   2100
tgaactcctg gaatcaaatg atcctcccac ctcacctcca agtagctggg actacaggca   2160
tgcaccatca tgcccagcta atttttcttttt tctttttttt taagaggtag gatcttgcta   2220
taatgcccag gttggtctca aactcctggt atcaagtgat cctcccatct ggcctccca    2280
aagtgcggga attacaggtg tgaaccactg cacccaacct cattctcagc attcttatta   2340
tgttttgtct tattatcctc caaggatagg ttaagtaatt gttatgggtt gaattgggtc   2400
tccccaaaat tcctatgtta aagtcctaat cccagtatct caaaatgaag gtaaggtctt   2460
tatagaggta atcaagttaa aatgatgtta ttaggatggg cattaattca atatgactag   2520
tctccttata aaaagcagac attcacacac aaggacacat gcacacaggg aatatgatac   2580
ctgagattag ggtgatgcgt ctgcaggcca aagaatgcca aagactgcca gcacaccacc   2640
agaaactggg ggagaggcat ggaacggatt cttcttcaca gctctcagaa agaaccatgc   2700
tgctgacacc ttgatcttgg aattctagcc actggaactg taaaacaata aatttctatt   2760
```

<210> SEQ ID NO 73
<211> LENGTH: 104
<212> TYPE: PRT
<213> ORGANISM: Homo sapiens

<400> SEQUENCE: 73

Met Phe Thr Ile Val Ser Ser Ser Ser Phe Val Pro Ser Leu Lys His
 1               5                  10                  15

Phe Leu Phe Pro Pro Gly Ala Ser Lys Leu Gln Leu Ser Leu Gln Ser
            20                  25                  30

Asp Arg Arg Lys Leu Ala Phe Ile Lys His Gln Leu Cys Ala Trp Lys
         35                  40                  45

Ile His Leu Gln Tyr His Asn Leu Tyr Asn Asn Ser Ala Ile Trp Ile
     50                  55                  60

Ser Leu Ser Ala Phe Phe Phe Cys Leu Phe Gly Trp Leu Val Leu Val
 65                  70                  75                  80

Val Leu Val Ser Gly Ser His Ser Val Ala Gln Ala Gly Ala Trp Trp
                 85                  90                  95

His Asp His Asn Ser Leu Gln Pro
            100

<210> SEQ ID NO 74
<211> LENGTH: 1183
<212> TYPE: DNA
<213> ORGANISM: Homo sapiens

<400> SEQUENCE: 74
agctagagct ccaaggaccc cacgcctgtg tctctgtgac agagctcaaa gggccctggg      60
ccttccctcc ctggctcggc tgtgcttggg agggttcccc agtccagaat ccctaaggag     120
catggggcag ctgatccatc cctggtgtac aaactgctga ctgcagacag atgctgagct     180
acccaaacca acacctagcc tctccctgaa gatcctccca ggctgagaga gttctgggtg     240
tcctaggacc aaggacactg gcagacttcc agaagggccc caaagcccct aacctgtcca     300
gccagagcat gcgtctcagc agagctgtct cccaagcct tgatgacaa accaatttcc       360
ctcgatgatg tgcttctgag tgctctgctg aggaacaatg ggaagtctgc ccagcagaag     420
aaaatctctg ccaagcccaa gcttgagttc ctctgtccaa ggccagggac ctgtgaccat     480
ggaagcagag agaagcaagg ccacagccgt ggccctgggc agtttcccgg caggtggccc     540
ggccgagctg tcgctgagac tcggggagcc attgaccatc gtctctgagg atggagactg     600
gtggacggtg ctgtctgaag tctcaggcag agagtataac atccccagcg tccacgtggg     660
caaagtctcc catgggtggc tgtatgaggg cctgagcagg gagaaagcag aggaactgct     720
gttgttacct gggaaccctg aggggccttc cctcatccgg gagagccaga ccaggagagg     780
ctcttactct ctgtcagtcc gcctcagccg ccctgcatcc tgggaccgga tcagacacta     840
caggatccac tgccttgaca atggctggct gtacatctca ccgcgcctca ccttcccctc     900
actccaggcc ctggtggacc attactctga gctggcggat gacatctgct gcctactcaa     960
ggagccctgt gtcctgcaga gggctggccc gctccctggc aaggatatac ccctacctgt    1020
gactgtgcag aggacaccac tcaactggaa agagctggac agctccctcc tgttttctga    1080
agctgccaca ggggaggagt ctcttctcag tgagggtctc cgggagtccc tcagcttcta    1140
catcagcctg aatgacgagg ctgtctcttt ggatgatgcc tag                      1183

<210> SEQ ID NO 75
<211> LENGTH: 261
<212> TYPE: PRT
<213> ORGANISM: Homo sapiens

<400> SEQUENCE: 75

Met Gly Ser Leu Pro Ser Arg Arg Lys Ser Leu Pro Ser Pro Ser Leu
  1               5                  10                  15

Ser Ser Ser Val Gln Gly Gln Gly Pro Val Thr Met Glu Ala Glu Arg
                 20                  25                  30

Ser Lys Ala Thr Ala Val Ala Leu Gly Ser Phe Pro Ala Gly Gly Pro
         35                  40                  45

```
Ala Glu Leu Ser Leu Arg Leu Gly Glu Pro Leu Thr Ile Val Ser Glu
 50                  55                  60
Asp Gly Asp Trp Trp Thr Val Leu Ser Glu Val Ser Gly Arg Glu Tyr
 65                  70                  75                  80
Asn Ile Pro Ser Val His Val Gly Lys Val Ser His Gly Trp Leu Tyr
                 85                  90                  95
Glu Gly Leu Ser Arg Glu Lys Ala Glu Glu Leu Leu Leu Pro Gly
                100                 105                 110
Asn Pro Gly Gly Ala Phe Leu Ile Arg Glu Ser Gln Thr Arg Arg Gly
                115                 120                 125
Ser Tyr Ser Leu Ser Val Arg Leu Ser Arg Pro Ala Ser Trp Asp Arg
    130                 135                 140
Ile Arg His Tyr Arg Ile His Cys Leu Asp Asn Gly Trp Leu Tyr Ile
145                 150                 155                 160
Ser Pro Arg Leu Thr Phe Pro Ser Leu Gln Ala Leu Val Asp His Tyr
                165                 170                 175
Ser Glu Leu Ala Asp Asp Ile Cys Cys Leu Leu Lys Glu Pro Cys Val
                180                 185                 190
Leu Gln Arg Ala Gly Pro Leu Pro Gly Lys Asp Ile Pro Leu Pro Val
            195                 200                 205
Thr Val Gln Arg Thr Pro Leu Asn Trp Lys Glu Leu Asp Ser Ser Leu
    210                 215                 220
Leu Phe Ser Glu Ala Ala Thr Gly Glu Glu Ser Leu Leu Ser Glu Gly
225                 230                 235                 240
Leu Arg Glu Ser Leu Ser Phe Tyr Ile Ser Leu Asn Asp Glu Ala Val
                245                 250                 255
Ser Leu Asp Asp Ala
            260

<210> SEQ ID NO 76
<211> LENGTH: 1183
<212> TYPE: DNA
<213> ORGANISM: Homo sapiens

<400> SEQUENCE: 76
ctaggcatca tccaaagaga cagcctcgtc attcaggctg atgtagaagc tgagggactc      60
ccggagaccc tcactgagaa gagactcctc ccctgtggca gcttcagaaa acaggaggga     120
gctgtccagc tctttccagt tgagtggtgt cctctgcaca gtcacaggta ggggtatatc     180
cttgccaggg agcgggccag ccctctgcag gacacagggc tccttgagta ggcagcagat     240
gtcatccgcc agctcagagt aatggtccac cagggcctgg agtgagggga aggtgaggcg     300
cggtgagatg tacagccagc cattgtcaag gcagtggatc ctgtagtgtc tgatccggtc     360
ccaggatgca gggcggctga ggcggactga cagagagtaa gagcctctcc tggtctggct     420
ctcccggatg aggaaggccc ctccagggtt cccaggtaac aacagcagtt cctctgcttt     480
ctccctgctc aggccctcat acagccaccc atgggagact tgcccacgt ggacgctggg      540
gatgttatac tctctgcctg agacttcaga cagcaccgtc caccagtctc catcctcaga     600
gacgatggtc aatggctccc cgagtctcag cgacagctcg gccgggccac ctgccgggaa     660
actgcccagg gccacggctg tggccttgct tctctctgct ccatggtca caggtccctg      720
gccttggaca gaggaactca agcttgggct tggcagagat tttcttctgc tgggcagact     780
tcccattgtt cctcagcaga gcactcagaa gcacatcatc gagggaaatt ggtttgtcat     840
```

| | | | | |
|---|---|---|---|---|
| caaaggcttg | ggaagacagc | tctgctgaga | cgcatgctct | ggctggacag gttagggctt | 900 |
| tgggggccct | tctggaagtc | tgccagtgtc | cttggtccta | ggacacccag aactctctca | 960 |
| gcctgggagg | atcttcaggg | agaggctagg | tgttggtttg | ggtagctcag catctgtctg | 1020 |
| cagtcagcag | tttgtacacc | agggatggat | cagctgcccc | atgctcctta gggattctgg | 1080 |
| actggggaac | cctcccaagc | acagccgagc | cagggaggga | aggcccaggg ccctttgagc | 1140 |
| tctgtcacag | agacacaggc | gtggggtcct | tggagctcta | gct | 1183 |

<210> SEQ ID NO 77
<211> LENGTH: 261
<212> TYPE: PRT
<213> ORGANISM: Homo sapiens

<400> SEQUENCE: 77

Met Gly Ser Leu Pro Ser Arg Arg Lys Ser Leu Pro Ser Pro Ser Leu
1               5                   10                  15

Ser Ser Ser Val Gln Gly Gln Gly Pro Val Thr Met Glu Ala Glu Arg
            20                  25                  30

Ser Lys Ala Thr Ala Val Ala Leu Gly Ser Phe Pro Ala Gly Gly Pro
        35                  40                  45

Ala Glu Leu Ser Leu Arg Leu Gly Glu Pro Leu Thr Ile Val Ser Glu
    50                  55                  60

Asp Gly Asp Trp Trp Thr Val Leu Ser Glu Val Ser Gly Arg Glu Tyr
65                  70                  75                  80

Asn Ile Pro Ser Val His Val Ala Lys Val Ser His Gly Trp Leu Tyr
                85                  90                  95

Glu Gly Leu Ser Arg Glu Lys Ala Glu Glu Leu Leu Leu Leu Pro Gly
            100                 105                 110

Asn Pro Gly Gly Ala Phe Leu Ile Arg Glu Ser Gln Thr Arg Arg Gly
        115                 120                 125

Ser Tyr Ser Leu Ser Val Arg Leu Ser Arg Pro Ala Ser Trp Asp Arg
    130                 135                 140

Ile Arg His Tyr Arg Ile His Cys Leu Asp Asn Gly Trp Leu Tyr Ile
145                 150                 155                 160

Ser Pro Arg Leu Thr Phe Pro Ser Leu Gln Ala Leu Val Asp His Tyr
                165                 170                 175

Ser Glu Leu Ala Asp Asp Ile Cys Cys Leu Leu Lys Glu Pro Cys Val
            180                 185                 190

Leu Gln Arg Ala Gly Pro Leu Pro Gly Lys Asp Ile Pro Leu Pro Val
        195                 200                 205

Thr Val Gln Arg Thr Pro Leu Asn Trp Lys Glu Leu Asp Ser Ser Leu
    210                 215                 220

Leu Phe Ser Glu Ala Ala Thr Gly Glu Glu Ser Leu Leu Ser Glu Gly
225                 230                 235                 240

Leu Arg Glu Ser Leu Ser Phe Tyr Ile Ser Leu Asn Asp Glu Ala Val
                245                 250                 255

Ser Leu Asp Asp Ala
            260

<210> SEQ ID NO 78
<211> LENGTH: 197
<212> TYPE: PRT
<213> ORGANISM: Homo sapiens

<400> SEQUENCE: 78

```
Asp Gly Asp Trp Trp Thr Val Leu Ser Glu Val Ser Gly Arg Glu Tyr
 1               5                  10                  15

Asn Ile Pro Ser Val His Val Ala Lys Val Ser His Gly Trp Leu Tyr
            20                  25                  30

Glu Gly Leu Ser Arg Glu Lys Ala Glu Leu Leu Leu Pro Gly
        35                  40                  45

Asn Pro Gly Gly Ala Phe Leu Ile Arg Glu Ser Gln Thr Arg Arg Gly
    50                  55                  60

Ser Tyr Ser Leu Ser Val Arg Leu Ser Arg Pro Ala Ser Trp Asp Arg
65                  70                  75                  80

Ile Arg His Tyr Arg Ile His Cys Leu Asp Asn Gly Trp Leu Tyr Ile
                85                  90                  95

Ser Pro Arg Leu Thr Phe Pro Ser Leu Gln Ala Leu Val Asp His Tyr
            100                 105                 110

Ser Glu Leu Ala Asp Asp Ile Cys Cys Leu Leu Lys Glu Pro Cys Val
            115                 120                 125

Leu Gln Arg Ala Gly Pro Leu Pro Gly Lys Asp Ile Pro Leu Pro Val
        130                 135                 140

Thr Val Gln Arg Thr Pro Leu Asn Trp Lys Glu Leu Asp Ser Ser Leu
145                 150                 155                 160

Leu Phe Ser Glu Ala Ala Thr Gly Glu Glu Ser Leu Leu Ser Glu Gly
                165                 170                 175

Leu Arg Glu Ser Leu Ser Phe Tyr Ile Ser Leu Asn Asp Glu Ala Val
            180                 185                 190

Ser Leu Asp Asp Ala
        195

<210> SEQ ID NO 79
<211> LENGTH: 179
<212> TYPE: PRT
<213> ORGANISM: Mus musculus

<400> SEQUENCE: 79

Met Pro Ser Val Tyr Val Ala Lys Val Ala His Gly Trp Leu Tyr Glu
 1               5                  10                  15

Gly Leu Ser Arg Glu Lys Ala Glu Leu Leu Leu Leu Pro Gly Asn
            20                  25                  30

Pro Gly Gly Ala Phe Leu Ile Arg Glu Ser Gln Thr Arg Arg Gly Cys
        35                  40                  45

Tyr Ser Leu Ser Val Arg Leu Ser Arg Pro Ala Ser Trp Asp Arg Ile
    50                  55                  60

Arg His Tyr Arg Ile Gln Arg Leu Asp Asn Gly Trp Leu Tyr Ile Ser
65                  70                  75                  80

Pro Arg Leu Thr Phe Pro Ser Leu His Ala Leu Val Glu His Tyr Ser
                85                  90                  95

Glu Leu Ala Asp Gly Ile Cys Cys Pro Leu Arg Glu Pro Cys Val Leu
            100                 105                 110

Gln Lys Leu Gly Pro Leu Pro Gly Lys Asp Thr Pro Pro Val Thr
        115                 120                 125

Val Pro Thr Ser Ser Leu Asn Trp Lys Lys Leu Asp Arg Ser Leu Leu
    130                 135                 140

Phe Leu Glu Ala Pro Ala Ser Gly Glu Ala Leu Leu Ser Glu Gly
145                 150                 155                 160

Leu Arg Glu Ser Leu Ser Ser Tyr Ile Ser Leu Ala Glu Asp Pro Leu
                165                 170                 175
```

Asp Asp Ala

<210> SEQ ID NO 80
<211> LENGTH: 281
<212> TYPE: PRT
<213> ORGANISM: Mus musculus

<400> SEQUENCE: 80

Met Gly Asn Ser Met Lys Ser Thr Ser Pro Ser Glu Arg Pro Leu
1               5                   10                  15

Ser Ser Ser Glu Gly Leu Glu Ser Asp Phe Leu Ala Val Leu Thr Asp
            20                  25                  30

Tyr Pro Ser Pro Asp Ile Ser Pro Ile Phe Arg Arg Gly Glu Lys
        35                  40                  45

Leu Arg Val Ile Ser Asp Glu Gly Trp Trp Lys Ala Ile Ser Leu
    50                  55                  60

Ser Thr Gly Arg Glu Ser Tyr Ile Pro Gly Ile Cys Val Ala Arg Val
65                  70                  75                  80

Tyr His Gly Trp Leu Phe Glu Gly Leu Gly Arg Asp Lys Ala Glu Glu
                85                  90                  95

Leu Leu Gln Leu Pro Asp Thr Lys Ile Gly Ser Phe Met Ile Arg Glu
                100                 105                 110

Ser Glu Thr Lys Lys Gly Phe Tyr Ser Leu Ser Val Arg His Arg Gln
            115                 120                 125

Val Lys His Tyr Arg Ile Phe Arg Leu Pro Asn Asn Trp Tyr Tyr Ile
    130                 135                 140

Ser Pro Arg Leu Thr Phe Gln Cys Leu Glu Asp Leu Val Thr His Tyr
145                 150                 155                 160

Ser Glu Val Ala Asp Gly Leu Cys Cys Val Leu Thr Thr Pro Cys Leu
                165                 170                 175

Ala Gln Asn Ile Pro Ala Pro Thr Ser His Pro Ser Pro Cys Thr Ser
                180                 185                 190

Pro Gly Ser Pro Val Thr Leu Arg Gln Lys Thr Phe Asp Trp Lys Arg
            195                 200                 205

Val Ser Arg Leu Gln Glu Gly Ser Glu Gly Ala Glu Asn Pro Leu Arg
    210                 215                 220

Val Asp Glu Ser Leu Phe Ser Tyr Gly Leu Arg Glu Ser Ile Ala Ser
225                 230                 235                 240

Tyr Leu Ser Leu Thr Gly Asp Asp Ser Ser Phe Asp Arg Lys Lys
                245                 250                 255

Lys Ser Leu Ser Leu Met Tyr Thr Gly Ser Lys Arg Lys Ser Ser Phe
            260                 265                 270

Phe Ser Ala Pro Gln Tyr Phe Glu Asp
        275                 280

<210> SEQ ID NO 81
<211> LENGTH: 276
<212> TYPE: PRT
<213> ORGANISM: Homo sapiens

<400> SEQUENCE: 81

Met Gly Asn Ser Met Lys Ser Thr Pro Ala Pro Ala Glu Arg Pro Leu
1               5                   10                  15

Pro Asn Pro Glu Gly Leu Asp Ser Asp Phe Leu Ala Val Leu Ser Asp
            20                  25                  30

-continued

```
Tyr Pro Ser Pro Asp Ile Ser Pro Ile Phe Arg Arg Gly Glu Lys
         35                  40                  45
Leu Arg Val Ile Ser Asp Glu Gly Gly Trp Trp Lys Ala Ile Ser Leu
     50                  55                  60
Ser Thr Gly Arg Glu Ser Tyr Ile Pro Gly Ile Cys Val Ala Arg Val
 65                  70                  75                  80
Tyr His Gly Trp Leu Phe Glu Gly Leu Gly Arg Asp Lys Ala Glu Glu
                 85                  90                  95
Leu Leu Gln Leu Pro Asp Thr Lys Val Gly Ser Phe Met Ile Arg Glu
             100                 105                 110
Ser Glu Thr Lys Lys Gly Phe Tyr Ser Leu Ser Val Arg His Arg Gln
         115                 120                 125
Val Lys His Tyr Arg Ile Phe Arg Leu Pro Asn Asn Trp Tyr Tyr Ile
130                 135                 140
Ser Pro Arg Leu Thr Phe Gln Cys Leu Glu Asp Leu Val Asn His Tyr
145                 150                 155                 160
Ser Glu Val Ala Asp Gly Leu Cys Cys Val Leu Thr Thr Pro Cys Leu
                165                 170                 175
Thr Gln Ser Thr Ala Ala Pro Ala Val Arg Ala Ser Ser Ser Pro Val
            180                 185                 190
Thr Leu Arg Gln Lys Thr Val Asp Trp Arg Arg Val Ser Arg Leu Gln
        195                 200                 205
Glu Asp Pro Glu Gly Thr Glu Asn Pro Leu Gly Val Asp Glu Ser Leu
    210                 215                 220
Phe Ser Tyr Gly Leu Arg Glu Ser Ile Ala Ser Tyr Leu Ser Leu Thr
225                 230                 235                 240
Ser Glu Asp Asn Thr Ser Phe Asp Arg Lys Lys Lys Ser Ile Ser Leu
                245                 250                 255
Met Tyr Gly Gly Ser Lys Arg Lys Ser Ser Phe Phe Ser Ser Pro Pro
            260                 265                 270
Tyr Phe Glu Asp
        275
```

<210> SEQ ID NO 82
<211> LENGTH: 5193
<212> TYPE: DNA
<213> ORGANISM: Homo sapiens

<400> SEQUENCE: 82

```
ctccggcgcc cgctctgccc gccgctgggt ccgaccgcgc tcgccttcct tgcagccgcg      60
cctcggcccc atggacgccc tgtgcggttc cggggagctc ggctccaagt tctgggactc     120
caacctgtct gtgcacacag aaaacccgga cctcgctccc tgcttccaga actccctgct     180
ggcctgggtg ccctgcatct acctgtgggt cgccctgccc tgctacttgc tctacctgcg     240
gcaccattgt cgtggctaca tcatcctctc ccacctgtcc aagctcaaga tggtcctggg     300
tgtcctgctg tggtgcgtct cctgggcgga cctttttta tccttccatg gcctggtcca     360
tggccgggcc cctgccctg tttctttgt caccccttg gtggtggggg tcaccatgct     420
gctggccacc ctgctgatac agtatgagcg gctgcagggc gtacagtctt cggggtcct     480
cattatcttc tggttcctgt gtgtggtctg cgccatcgtc ccattccgct ccaagatcct     540
tttagccaag gcagagggtg agatctcaga ccccttccgc ttcaccacct tctacatcca     600
ctttgccctg gtactctctg ccctcatctt ggcctgcttc agggagaaac ctccattttt     660
ctccgcaaag aatgtcgacc ctaaccccta ccctgagacc agcgctggct ttctctcccg     720
```

```
cctgttttc  tggtggttca  caaagatggc  catctatggc  taccggcatc  ccctggagga     780
gaaggacctc  tggtccctaa  aggaagagga  cagatcccag  atggtggtgc  agcagctgct     840
ggaggcatgg  aggaagcagg  aaaagcagac  ggcacgacac  aaggcttcag  cagcacctgg     900
gaaaaatgcc  tccggcgagg  acgaggtgct  gctgggtgcc  cggcccaggc  cccggaagcc     960
ctccttcctg  aaggccctgc  tggccacctt  cggctccagc  ttcctcatca  gtgcctgctt    1020
caagcttatc  caggacctgc  tctccttcat  caatccacag  ctgctcagca  tcctgatcag    1080
gtttatctcc  aacccatgg   ccccctcctg  gtggggcttc  ctggtggctg  ggctgatgtt    1140
cctgtgctcc  atgatgcagt  cgctgatctt  acaaacactat  taccactaca  tctttgtgac    1200
tggggtgaag  tttcgtactg  ggatcatggg  tgtcatctac  aggaaggctc  tggttatcac    1260
caactcagtc  aaacgtgcgt  ccactgtggg  ggaaattgtc  aacctcatgt  cagtggatgc    1320
ccagcgcttc  atggaccttg  ccccttcct   caatctgctg  tggtcagcac  ccctgcagat    1380
catcctggcg  atctacttcc  tctggcagaa  cctaggtccc  tctgtcctgg  ctggagtcgc    1440
tttcatggtc  ttgctgattc  cactcaacgg  agctgtggcc  gtgaagatgc  gcgccttcca    1500
ggtaaagcaa  atgaaattga  aggactcgcg  catcaagctg  atgagtgaga  tcctgaacgg    1560
catcaaggtg  ctgaagctgt  acgcctggga  gcccagcttc  ctgaagcagg  tggagggcat    1620
caggcagggt  gagctccagc  tgctgcgcac  ggcggcctac  ctccacacca  aaccaccttt    1680
cacctgatg   tgcagcccct  tcctggtgac  cctgatcacc  ctctgggtgt  acgtgtacgt    1740
ggacccaaac  aatgtgctgg  acgccgagaa  ggcctttgtg  tctgtgtcct  tgtttaatat    1800
cttaagactt  cccctcaaca  tgctgcccca  gttaatcagc  aacctgactc  aggccagtat    1860
gtctctgaaa  cggatccagc  aattcctgag  ccaagaggaa  cttgaccccc  agagtgtgga    1920
aagaaagacc  atctccccag  gctatgccat  caccatacac  agtggcacct  tcacctgggc    1980
ccaggacctg  ccccccactc  tgcacagcct  agacatccag  gtcccgaaag  ggcactggt    2040
ggccgtggtg  gggcctgtgg  gctgtgggaa  gtcctccctg  gtgtctgccc  tgctgggaga    2100
gatggagaag  ctagaaggca  aagtgcacat  gaagggctcc  gtggcctatg  tgccccagca    2160
ggcatggatc  cagaactgca  ctcttcagga  aaacgtgctt  ttcggcaaag  ccctgaaccc    2220
caagcgctac  cagcagactc  tggaggcctg  tgccttgcta  gctgacctgg  agatgctgcc    2280
tggtggggat  cagacagaga  ttggagagaa  gggcattaac  ctgtctgggg  gccagcggca    2340
gcgggtcagt  ctggctcgag  ctgtttacag  tgatgccgat  attttcttgc  tggatgaccc    2400
actgtccgcg  gtggactctc  atgtggccaa  gcacatcttt  gaccacgtca  tcgggccaga    2460
aggcgtgctg  gcaggcaaga  cgcgagtgct  ggtgacgcac  ggcattagct  tcctgcccca    2520
gacagacttc  atcattgtgc  tagctgatgg  acaggtgtct  gagatgggcc  cgtacccagc    2580
cctgctgcag  cgcaacggct  cctttgccaa  ctttctctgc  aactatgccc  ccgatgagga    2640
ccaagggcac  ctggaggaca  gctggaccgc  gttggaaggt  gcagaggata  aggaggcact    2700
gctgattgaa  gacacactca  gcaaccacac  ggatctgaca  gacaatgatc  cagtcaccta    2760
tgtggtccag  aagcagttta  tgagacagct  gagtgccctg  tcctcagatg  ggagggaca    2820
gggtcggcct  gtaccccgga  ggcacctggg  tccatcagag  aaggtgcagg  tgacagaggc    2880
gaaggcagat  ggggcactga  cccaggagga  gaaagcagcc  attggcactg  tggagctcag    2940
tgtgttctgg  gattatgcca  aggccgtggg  gctctgtacc  acgctggcca  tctgtctcct    3000
gtatgtgggt  caaagtgcgg  ctgccattgg  agccaatgtg  tggctcagtg  cctggacaaa    3060
```

-continued

```
tgatgccatg gcagacagta gacagaacaa cacttccctg aggctgggcg tctatgctgc    3120
tttaggaatt ctgcaagggt tcttggtgat gctggcagcc atggccatgg cagcgggtgg    3180
catccaggct gcccgtgtgt tgcaccaggc actgctgcac aacaagatac gctcgccaca    3240
gtccttcttt gacaccacac catcaggccg catcctgaac tgcttctcca aggacatcta    3300
tgtcgttgat gaggtctggg ccctgtcat cctcatgctg ctcaattcct tcttcaacgc     3360
catctccact cttgtggtca tcatggccag cacgccgctc ttcactgtgg tcatcctgcc    3420
cctggctgtg ctctacacct tagtgcagcg cttctatgca gccacatcac ggcaactgaa    3480
gcggctggaa tcagtcagcc gctcacctat ctactcccac ttttcggaga cagtgactgg    3540
tgccagtgtc atccgggcct acaaccgcag ccgggatttt gagatcatca gtgatactaa    3600
ggtggatgcc aatcagagaa gctgctaccc ctacatcatc tccaaccggt ggctgagcat    3660
cggagtggag ttcgtgggga actgcgtggt gctctttgct gcactatttg ccgtcatcgg    3720
gaggagcagc ctgaacccgg ggctggtggg cctttctgtg tcctactcct gcaggtgac     3780 atttgctctg aactggatga tacgaatgat gccagatttg gaatctaaca tcgtggctgt    3840
ggagagggtc aaggagtact ccaagacaga gacagaggcg ccctgggtgg tggaaggcag    3900
ccgccctccc gaaggttggc ccccacgtgg ggaggtggag ttccggaatt attctgtgcg    3960
ctaccggccg ggcctagacc tggtgctgag agacctgagt ctgcatgtgc acggtggcga    4020
gaaggtgggg atcgtgggcc gcactgggc tggcaagtct tccatgaccc tttgcctgtt     4080
ccgcatcctg gaggcggcaa agggtgaaat ccgcattgat ggcctcaatg tggcagacat    4140
cggcctccat gacctgcgct ctcagctgac catcatcccg caggacccca tcctgttctc    4200
ggggaccctg cgcatgaacc tggacccctt cggcagctac tcagaggagg acatttggtg    4260
ggctttggag ctgtcccacc tgcacacgtt tgtgagctcc cagccggcag gcctggactt    4320
ccagtgctca gagggcgggg agaatctcag cgtgggccag aggcagctcg tgtgcctggc    4380
ccgagccctg ctccgcaaga gccgcatcct ggttttagac gaggccacag ctgccatcga    4440
cctggagact gacaacctca tccaggctac catccgcacc cagtttgata cctgcactgt    4500
cctgaccatc gcacaccggc ttaacactat catggactac accagggtcc tggtcctgga    4560
caaaggagta gtagctgaat tgattctcc agccaacctc attgcagcta gaggcatctt     4620
ctacgggatg ccagagatg ctggacttgc ctaaaatata ttcctgagat ttcctcctgg     4680
cctttcctgg ttttcatcag gaaggaaatg acaccaaata tgtccgcaga atggacttga    4740
tagcaaacac tgggggcacc ttaagatttt gcacctgtaa agtgccttac agggtaactg    4800
tgctgaatgc tttagatgag gaaatgatcc ccaagtggtg aatgacacgc taaggtcac     4860 agctagtttg agccagttag actagtcccc ggtctcccga ttcccaactg agtgttattt    4920
gcacactgca ctgttttcaa ataacgattt tatgaaatga cctctgtcct ccctctgatt    4980
tttcatattt tctaaagttt cgtttctgtt ttttaataaa agctttttc ctcctggaac     5040 agaagacagc tgctgggtca ggccaccct aggaactcag tcctgtactc tggggtgctg     5100
cctgaatcca ttaaaatgg gagtactgat gaaataaaac tacatggtca acagtaaaaa     5160
aaaaaaaaaa aaaaaaaaaa aaaaaaaaaa aaa                                 5193
```

<210> SEQ ID NO 83
<211> LENGTH: 1527
<212> TYPE: PRT
<213> ORGANISM: Homo sapiens

<400> SEQUENCE: 83

```
Met Asp Ala Leu Cys Gly Ser Gly Glu Leu Gly Ser Lys Phe Trp Asp
 1               5                  10                  15

Ser Asn Leu Ser Val His Thr Glu Asn Pro Asp Leu Thr Pro Cys Phe
            20                  25                  30

Gln Asn Ser Leu Leu Ala Trp Val Pro Cys Ile Tyr Leu Trp Val Ala
        35                  40                  45

Leu Pro Cys Tyr Leu Leu Tyr Leu Arg His His Cys Arg Gly Tyr Ile
    50                  55                  60

Ile Leu Ser His Leu Ser Lys Leu Lys Met Val Leu Gly Val Leu Leu
65                  70                  75                  80

Trp Cys Val Ser Trp Ala Asp Leu Phe Tyr Ser Phe His Gly Leu Val
                85                  90                  95

His Gly Arg Ala Pro Ala Pro Val Phe Phe Val Thr Pro Leu Val Val
            100                 105                 110

Gly Val Thr Met Leu Leu Ala Thr Leu Leu Ile Gln Tyr Glu Arg Leu
            115                 120                 125

Gln Gly Val Gln Ser Ser Gly Val Leu Ile Ile Phe Trp Phe Leu Cys
    130                 135                 140

Val Val Cys Ala Ile Val Pro Phe Arg Ser Lys Ile Leu Leu Ala Lys
145                 150                 155                 160

Ala Glu Gly Glu Ile Ser Asp Pro Phe Arg Phe Thr Thr Phe Tyr Ile
                165                 170                 175

His Phe Ala Leu Val Leu Ser Ala Leu Ile Leu Ala Cys Phe Arg Glu
            180                 185                 190

Lys Pro Pro Phe Phe Ser Ala Lys Asn Val Asp Pro Asn Pro Tyr Pro
    195                 200                 205

Glu Thr Ser Ala Gly Phe Leu Ser Arg Leu Phe Phe Trp Trp Phe Thr
    210                 215                 220

Lys Met Ala Ile Tyr Gly Tyr Arg His Pro Leu Glu Glu Lys Asp Leu
225                 230                 235                 240

Trp Ser Leu Lys Glu Glu Asp Arg Ser Gln Met Val Val Gln Gln Leu
                245                 250                 255

Leu Glu Ala Trp Arg Lys Gln Glu Lys Gln Thr Ala Arg His Lys Ala
            260                 265                 270

Ser Ala Ala Pro Gly Lys Asn Ala Ser Gly Glu Asp Glu Val Leu Leu
            275                 280                 285

Gly Ala Arg Pro Arg Pro Arg Lys Pro Ser Phe Leu Lys Ala Leu Leu
    290                 295                 300

Ala Thr Phe Gly Ser Ser Phe Leu Ile Ser Ala Cys Phe Lys Leu Ile
305                 310                 315                 320

Gln Asp Leu Leu Ser Phe Ile Asn Pro Gln Leu Leu Ser Ile Leu Ile
                325                 330                 335

Arg Phe Ile Ser Asn Pro Met Ala Pro Ser Trp Trp Gly Phe Leu Val
            340                 345                 350

Ala Gly Leu Met Phe Leu Cys Ser Met Met Gln Ser Leu Ile Leu Gln
            355                 360                 365

His Tyr Tyr His Tyr Ile Phe Val Thr Gly Val Lys Phe Arg Thr Gly
    370                 375                 380

Ile Met Gly Val Ile Tyr Arg Lys Ala Leu Val Ile Thr Asn Ser Val
385                 390                 395                 400

Lys Arg Ala Ser Thr Val Gly Glu Ile Val Asn Leu Met Ser Val Asp
                405                 410                 415
```

```
Ala Gln Arg Phe Met Asp Leu Ala Pro Phe Leu Asn Leu Leu Trp Ser
            420                 425                 430

Ala Pro Leu Gln Ile Ile Leu Ala Ile Tyr Phe Leu Trp Gln Asn Leu
            435                 440                 445

Gly Pro Ser Val Leu Ala Gly Val Ala Phe Met Val Leu Leu Ile Pro
            450                 455                 460

Leu Asn Gly Ala Val Ala Val Lys Met Arg Ala Phe Gln Val Lys Gln
465                 470                 475                 480

Met Lys Leu Lys Asp Ser Arg Ile Lys Leu Met Ser Glu Ile Leu Asn
            485                 490                 495

Gly Ile Lys Val Leu Lys Leu Tyr Ala Trp Glu Pro Ser Phe Leu Lys
            500                 505                 510

Gln Val Glu Gly Ile Arg Gln Gly Glu Leu Gln Leu Leu Arg Thr Ala
            515                 520                 525

Ala Tyr Leu His Thr Thr Thr Thr Phe Thr Trp Met Cys Ser Pro Phe
            530                 535                 540

Leu Val Thr Leu Ile Thr Leu Trp Val Tyr Val Tyr Val Asp Pro Asn
545                 550                 555                 560

Asn Val Leu Asp Ala Glu Lys Ala Phe Val Ser Val Ser Leu Phe Asn
            565                 570                 575

Ile Leu Arg Leu Pro Leu Asn Met Leu Pro Gln Leu Ile Ser Asn Leu
            580                 585                 590

Thr Gln Ala Ser Val Ser Leu Lys Arg Ile Gln Gln Phe Leu Ser Gln
            595                 600                 605

Glu Glu Leu Asp Pro Gln Ser Val Glu Arg Lys Thr Ile Ser Pro Gly
            610                 615                 620

Tyr Ala Ile Thr Ile His Ser Gly Thr Phe Thr Trp Ala Gln Asp Leu
625                 630                 635                 640

Pro Pro Thr Leu His Ser Leu Asp Ile Gln Val Pro Lys Gly Ala Leu
            645                 650                 655

Val Ala Val Val Gly Pro Val Gly Cys Gly Lys Ser Ser Leu Val Ser
            660                 665                 670

Ala Leu Leu Gly Glu Met Glu Lys Leu Glu Gly Lys Val His Met Lys
            675                 680                 685

Gly Ser Val Ala Tyr Val Pro Gln Gln Ala Trp Ile Gln Asn Cys Thr
            690                 695                 700

Leu Gln Glu Asn Val Leu Phe Gly Lys Ala Leu Asn Pro Lys Arg Tyr
705                 710                 715                 720

Gln Gln Thr Leu Glu Ala Cys Ala Leu Leu Ala Asp Leu Glu Met Leu
            725                 730                 735

Pro Gly Gly Asp Gln Thr Glu Ile Gly Glu Lys Gly Ile Asn Leu Ser
            740                 745                 750

Gly Gly Gln Arg Gln Arg Val Ser Leu Ala Arg Ala Val Tyr Ser Asp
            755                 760                 765

Ala Asp Ile Phe Leu Leu Asp Asp Pro Leu Ser Ala Val Asp Ser His
            770                 775                 780

Val Ala Lys His Ile Phe Asp His Val Ile Gly Pro Glu Gly Val Leu
785                 790                 795                 800

Ala Gly Lys Thr Arg Val Leu Val Thr His Gly Ile Ser Phe Leu Pro
            805                 810                 815

Gln Thr Asp Phe Ile Ile Val Leu Ala Asp Gly Gln Val Ser Glu Met
            820                 825                 830

Gly Pro Tyr Pro Ala Leu Leu Gln Arg Asn Gly Ser Phe Ala Asn Phe
```

-continued

```
                835                 840                 845
Leu Cys Asn Tyr Ala Pro Asp Glu Asp Gln Gly His Leu Glu Asp Ser
    850                 855                 860
Trp Thr Ala Leu Glu Gly Ala Glu Asp Lys Glu Ala Leu Leu Ile Glu
865                 870                 875                 880
Asp Thr Leu Ser Asn His Thr Asp Leu Thr Asp Asn Asp Pro Val Thr
                885                 890                 895
Tyr Val Val Gln Lys Gln Phe Met Arg Gln Leu Ser Ala Leu Ser Ser
            900                 905                 910
Asp Gly Glu Gly Gln Gly Arg Pro Val Pro Arg Arg His Leu Gly Pro
        915                 920                 925
Ser Glu Lys Val Gln Val Thr Glu Ala Lys Ala Asp Gly Ala Leu Thr
    930                 935                 940
Gln Glu Glu Lys Ala Ala Ile Gly Thr Val Glu Leu Ser Val Phe Trp
945                 950                 955                 960
Asp Tyr Ala Lys Ala Val Gly Leu Cys Thr Thr Leu Ala Ile Cys Leu
                965                 970                 975
Leu Tyr Val Gly Gln Ser Ala Ala Ala Ile Gly Ala Asn Val Trp Leu
            980                 985                 990
Ser Ala Trp Thr Asn Asp Ala Met Ala Asp Ser Arg Gln Asn Asn Thr
        995                 1000                1005
Ser Leu Arg Leu Gly Val Tyr Ala Ala Leu Gly Ile Leu Gln Gly Phe
    1010                1015                1020
Leu Val Met Leu Ala Ala Met Ala Met Ala Ala Gly Gly Ile Gln Ala
1025                1030                1035                1040
Ala Arg Val Leu His Gln Ala Leu Leu His Asn Lys Ile Arg Ser Pro
                1045                1050                1055
Gln Ser Phe Phe Asp Thr Thr Pro Ser Gly Arg Ile Leu Asn Cys Phe
            1060                1065                1070
Ser Lys Asp Ile Tyr Val Val Asp Glu Val Leu Ala Pro Val Ile Leu
        1075                1080                1085
Met Leu Leu Asn Ser Phe Phe Asn Ala Ile Ser Thr Leu Val Val Ile
    1090                1095                1100
Met Ala Ser Thr Pro Leu Phe Thr Val Ile Leu Pro Leu Ala Val
1105                1110                1115                1120
Leu Tyr Thr Leu Val Gln Arg Phe Tyr Ala Ala Thr Ser Arg Gln Leu
                1125                1130                1135
Lys Arg Leu Glu Ser Val Ser Arg Ser Pro Ile Tyr Ser His Phe Ser
            1140                1145                1150
Glu Thr Val Thr Gly Ala Ser Val Ile Arg Ala Tyr Asn Arg Ser Arg
        1155                1160                1165
Asp Phe Glu Ile Ile Ser Asp Thr Lys Val Asp Ala Asn Gln Arg Ser
    1170                1175                1180
Cys Tyr Pro Tyr Ile Ile Ser Asn Arg Trp Leu Ser Ile Gly Val Glu
1185                1190                1195                1200
Phe Val Gly Asn Cys Val Val Leu Phe Ala Ala Leu Phe Ala Val Ile
                1205                1210                1215
Gly Arg Ser Ser Leu Asn Pro Gly Leu Val Gly Leu Ser Val Ser Tyr
            1220                1225                1230
Ser Leu Gln Val Thr Phe Ala Leu Asn Trp Met Ile Arg Met Met Ser
        1235                1240                1245
Asp Leu Glu Ser Asn Ile Val Ala Val Glu Arg Val Lys Glu Tyr Ser
    1250                1255                1260
```

-continued

```
Lys Thr Glu Thr Glu Ala Pro Trp Val Val Gly Ser Arg Pro Pro
1265                1270                1275                1280

Glu Gly Trp Pro Pro Arg Gly Glu Val Glu Phe Arg Asn Tyr Ser Val
            1285                1290                1295

Arg Tyr Arg Pro Gly Leu Asp Leu Val Leu Arg Asp Leu Ser Leu His
        1300                1305                1310

Val His Gly Gly Glu Lys Val Gly Ile Val Gly Arg Thr Gly Ala Gly
    1315                1320                1325

Lys Ser Ser Met Thr Leu Cys Leu Phe Arg Ile Leu Glu Ala Ala Lys
1330                1335                1340

Gly Glu Ile Arg Ile Asp Gly Leu Asn Val Ala Asp Ile Gly Leu His
1345                1350                1355                1360

Asp Leu Arg Ser Gln Leu Thr Ile Ile Pro Gln Asp Pro Ile Leu Phe
            1365                1370                1375

Ser Gly Thr Leu Arg Met Asn Leu Asp Pro Phe Gly Ser Tyr Ser Glu
        1380                1385                1390

Glu Asp Ile Trp Trp Ala Leu Glu Leu Ser His Leu His Thr Phe Val
    1395                1400                1405

Ser Ser Gln Pro Ala Gly Leu Asp Phe Gln Cys Ser Glu Gly Gly Glu
    1410                1415                1420

Asn Leu Ser Val Gly Gln Arg Gln Leu Val Cys Leu Ala Arg Ala Leu
1425                1430                1435                1440

Leu Arg Lys Ser Arg Ile Leu Val Leu Asp Glu Ala Thr Ala Ala Ile
            1445                1450                1455

Asp Leu Glu Thr Asp Asn Leu Ile Gln Ala Thr Ile Arg Thr Gln Phe
        1460                1465                1470

Asp Thr Cys Thr Val Leu Thr Ile Ala His Arg Leu Asn Thr Ile Met
    1475                1480                1485

Asp Tyr Thr Arg Val Leu Val Leu Asp Lys Gly Val Val Ala Glu Phe
    1490                1495                1500

Asp Ser Pro Ala Asn Leu Ile Ala Ala Arg Gly Ile Phe Tyr Gly Met
1505                1510                1515                1520

Ala Arg Asp Ala Gly Leu Ala
            1525
```

<210> SEQ ID NO 84
<211> LENGTH: 1527
<212> TYPE: PRT
<213> ORGANISM: Homo sapiens

<400> SEQUENCE: 84

```
Met Asp Ala Leu Cys Gly Ser Gly Glu Leu Gly Ser Lys Phe Trp Asp
1               5                   10                  15

Ser Asn Leu Ser Val His Thr Glu Asn Pro Asp Leu Thr Pro Cys Phe
            20                  25                  30

Gln Asn Ser Leu Leu Ala Trp Val Pro Cys Ile Tyr Leu Trp Val Ala
        35                  40                  45

Leu Pro Cys Tyr Leu Leu Tyr Leu Arg His His Cys Arg Gly Tyr Ile
    50                  55                  60

Ile Leu Ser His Leu Ser Lys Leu Lys Met Val Leu Gly Val Leu Leu
65                  70                  75                  80

Trp Cys Val Ser Trp Ala Asp Leu Phe Tyr Ser Phe His Gly Leu Val
                85                  90                  95

His Gly Arg Ala Pro Ala Pro Val Phe Phe Val Thr Pro Leu Val Val
```

-continued

```
                100                 105                 110
Gly Val Thr Met Leu Leu Ala Thr Leu Leu Ile Gln Tyr Glu Arg Leu
            115                 120                 125

Gln Gly Val Gln Ser Ser Gly Val Leu Ile Ile Phe Trp Phe Leu Cys
            130                 135                 140

Val Val Cys Ala Ile Val Pro Phe Arg Ser Lys Ile Leu Leu Ala Lys
145                 150                 155                 160

Ala Glu Gly Glu Ile Ser Asp Pro Phe Arg Phe Thr Thr Phe Tyr Ile
                165                 170                 175

His Phe Ala Leu Val Leu Ser Ala Leu Ile Leu Ala Cys Phe Arg Glu
            180                 185                 190

Lys Pro Pro Phe Phe Ser Ala Lys Asn Val Asp Pro Asn Pro Tyr Pro
            195                 200                 205

Glu Thr Ser Ala Gly Phe Leu Ser Arg Leu Phe Phe Trp Trp Phe Thr
            210                 215                 220

Lys Met Ala Ile Tyr Gly Tyr Arg His Pro Leu Glu Glu Lys Asp Leu
225                 230                 235                 240

Trp Ser Leu Lys Glu Glu Asp Arg Ser Gln Met Val Val Gln Gln Leu
                245                 250                 255

Leu Glu Ala Trp Arg Lys Gln Glu Lys Gln Thr Ala Arg His Lys Ala
            260                 265                 270

Ser Ala Ala Pro Gly Lys Asn Ala Ser Gly Glu Asp Glu Val Leu Leu
            275                 280                 285

Gly Ala Arg Pro Arg Pro Arg Lys Pro Ser Phe Leu Lys Ala Leu Leu
            290                 295                 300

Ala Thr Phe Gly Ser Ser Phe Leu Ile Ser Ala Cys Phe Lys Leu Ile
305                 310                 315                 320

Gln Asp Leu Leu Ser Phe Ile Asn Pro Gln Leu Leu Ser Ile Leu Ile
                325                 330                 335

Arg Phe Ile Ser Asn Pro Met Ala Pro Ser Trp Trp Gly Phe Leu Val
            340                 345                 350

Ala Gly Leu Met Phe Leu Cys Ser Met Met Gln Ser Leu Ile Leu Gln
            355                 360                 365

His Tyr Tyr His Tyr Ile Phe Val Thr Gly Val Lys Phe Arg Thr Gly
            370                 375                 380

Ile Met Gly Val Ile Tyr Arg Lys Ala Leu Val Ile Thr Asn Ser Val
385                 390                 395                 400

Lys Arg Ala Ser Thr Val Gly Glu Ile Val Asn Leu Met Ser Val Asp
                405                 410                 415

Ala Gln Arg Phe Met Asp Leu Ala Pro Phe Leu Asn Leu Leu Trp Ser
            420                 425                 430

Ala Pro Leu Gln Ile Ile Leu Ala Ile Tyr Phe Leu Trp Gln Asn Leu
            435                 440                 445

Gly Pro Ser Val Leu Ala Gly Val Ala Phe Met Val Leu Leu Ile Pro
            450                 455                 460

Leu Asn Gly Ala Val Ala Val Lys Met Arg Ala Phe Gln Val Lys Gln
465                 470                 475                 480

Met Lys Leu Lys Asp Ser Arg Ile Lys Leu Met Ser Glu Ile Leu Asn
                485                 490                 495

Gly Ile Lys Val Leu Lys Leu Tyr Ala Trp Glu Pro Ser Phe Leu Lys
            500                 505                 510

Gln Val Glu Gly Ile Arg Gln Gly Glu Leu Gln Leu Leu Arg Thr Ala
            515                 520                 525
```

-continued

```
Ala Tyr Leu His Thr Thr Thr Thr Phe Thr Trp Met Cys Ser Pro Phe
        530                 535                 540
Leu Val Thr Leu Ile Thr Leu Trp Val Tyr Val Tyr Val Asp Pro Asn
545                 550                 555                 560
Asn Val Leu Asp Ala Glu Lys Ala Phe Val Ser Val Ser Leu Phe Asn
                565                 570                 575
Ile Leu Arg Leu Pro Leu Asn Met Leu Pro Gln Leu Ile Ser Asn Leu
            580                 585                 590
Thr Gln Ala Ser Val Ser Leu Lys Arg Ile Gln Gln Phe Leu Ser Gln
        595                 600                 605
Glu Glu Leu Asp Pro Gln Ser Val Glu Arg Lys Thr Ile Ser Pro Gly
    610                 615                 620
Tyr Ala Ile Thr Ile His Ser Gly Thr Phe Thr Trp Ala Gln Asp Leu
625                 630                 635                 640
Pro Pro Thr Leu His Ser Leu Asp Ile Gln Val Pro Lys Gly Ala Leu
                645                 650                 655
Val Ala Val Val Gly Pro Val Gly Cys Gly Lys Ser Ser Leu Val Ser
            660                 665                 670
Ala Leu Leu Gly Glu Met Glu Lys Leu Glu Gly Lys Val His Met Lys
        675                 680                 685
Gly Ser Val Ala Tyr Val Pro Gln Gln Ala Trp Ile Gln Asn Cys Thr
    690                 695                 700
Leu Gln Glu Asn Val Leu Phe Gly Lys Ala Leu Asn Pro Lys Arg Tyr
705                 710                 715                 720
Gln Gln Thr Leu Glu Ala Cys Ala Leu Leu Ala Asp Leu Glu Met Leu
                725                 730                 735
Pro Gly Gly Asp Gln Thr Glu Ile Gly Glu Lys Gly Ile Asn Leu Ser
            740                 745                 750
Gly Gly Gln Arg Gln Arg Val Ser Leu Ala Arg Ala Val Tyr Ser Asp
        755                 760                 765
Ala Asp Ile Phe Leu Leu Asp Asp Pro Leu Ser Ala Val Asp Ser His
    770                 775                 780
Val Ala Lys His Ile Phe Asp His Val Ile Gly Pro Glu Gly Val Leu
785                 790                 795                 800
Ala Gly Lys Thr Arg Val Leu Val Thr His Gly Ile Ser Phe Leu Pro
                805                 810                 815
Gln Thr Asp Phe Ile Ile Val Leu Ala Asp Gly Gln Val Ser Glu Met
            820                 825                 830
Gly Pro Tyr Pro Ala Leu Leu Gln Arg Asn Gly Ser Phe Ala Asn Phe
        835                 840                 845
Leu Cys Asn Tyr Ala Pro Asp Glu Asp Gln Gly His Leu Glu Asp Ser
    850                 855                 860
Trp Thr Ala Leu Glu Gly Ala Glu Asp Lys Glu Ala Leu Leu Ile Glu
865                 870                 875                 880
Asp Thr Leu Ser Asn His Thr Asp Leu Thr Asp Asn Asp Pro Val Thr
                885                 890                 895
Tyr Val Val Gln Lys Gln Phe Met Arg Gln Leu Ser Ala Leu Ser Ser
            900                 905                 910
Asp Gly Glu Gly Gln Gly Arg Pro Val Pro Arg Arg His Leu Gly Pro
        915                 920                 925
Ser Glu Lys Val Gln Val Thr Glu Ala Lys Ala Asp Gly Ala Leu Thr
    930                 935                 940
```

-continued

```
Gln Glu Glu Lys Ala Ala Ile Gly Thr Val Glu Leu Ser Val Phe Trp
945                 950                 955                 960

Asp Tyr Ala Lys Ala Val Gly Leu Cys Thr Thr Leu Ala Ile Cys Leu
            965                 970                 975

Leu Tyr Val Gly Gln Ser Ala Ala Ile Gly Ala Asn Val Trp Leu
        980                 985                 990

Ser Ala Trp Thr Asn Asp Ala Met Ala Asp Ser Arg Gln Asn Asn Thr
    995                 1000                1005

Ser Leu Arg Leu Gly Val Tyr Ala Ala Leu Gly Ile Leu Gln Gly Phe
    1010                1015                1020

Leu Val Met Leu Ala Ala Met Ala Met Ala Ala Gly Gly Ile Gln Ala
1025                1030                1035                1040

Ala Arg Val Leu His Gln Ala Leu Leu His Asn Lys Ile Arg Ser Pro
            1045                1050                1055

Gln Ser Phe Phe Asp Thr Thr Pro Ser Gly Arg Ile Leu Asn Cys Phe
            1060                1065                1070

Ser Lys Asp Ile Tyr Val Val Asp Glu Val Leu Ala Pro Val Ile Leu
        1075                1080                1085

Met Leu Leu Asn Ser Phe Phe Asn Ala Ile Ser Thr Leu Val Val Ile
    1090                1095                1100

Met Ala Ser Thr Pro Leu Phe Thr Val Ile Leu Pro Leu Ala Val
1105                1110                1115                1120

Leu Tyr Thr Leu Val Gln Arg Phe Tyr Ala Ala Thr Ser Arg Gln Leu
            1125                1130                1135

Lys Arg Leu Glu Ser Val Ser Arg Ser Pro Ile Tyr Ser His Phe Ser
            1140                1145                1150

Glu Thr Val Thr Gly Ala Ser Val Ile Arg Ala Tyr Asn Arg Ser Arg
    1155                1160                1165

Asp Phe Glu Ile Ile Ser Asp Thr Lys Val Asp Ala Asn Gln Arg Ser
    1170                1175                1180

Cys Tyr Pro Tyr Ile Ile Ser Asn Arg Trp Leu Ser Ile Gly Val Glu
1185                1190                1195                1200

Phe Val Gly Asn Cys Val Val Leu Phe Ala Ala Leu Phe Ala Val Ile
            1205                1210                1215

Gly Arg Ser Ser Leu Asn Pro Gly Leu Val Gly Leu Ser Val Ser Tyr
            1220                1225                1230

Ser Leu Gln Val Thr Phe Ala Leu Asn Trp Met Ile Arg Met Met Ser
    1235                1240                1245

Asp Leu Glu Ser Asn Ile Val Ala Val Glu Arg Val Lys Glu Tyr Ser
1250                1255                1260

Lys Thr Glu Thr Glu Ala Pro Trp Val Val Glu Gly Ser Arg Pro Pro
1265                1270                1275                1280

Glu Gly Trp Pro Pro Arg Gly Glu Val Glu Phe Arg Asn Tyr Ser Val
            1285                1290                1295

Arg Tyr Arg Pro Gly Leu Asp Leu Val Leu Arg Asp Leu Ser Leu His
            1300                1305                1310

Val His Gly Gly Glu Lys Val Gly Ile Val Gly Arg Thr Gly Ala Gly
    1315                1320                1325

Lys Ser Ser Met Thr Leu Cys Leu Phe Arg Ile Leu Glu Ala Ala Lys
    1330                1335                1340

Gly Glu Ile Arg Ile Asp Gly Leu Asn Val Ala Asp Ile Gly Leu His
1345                1350                1355                1360

Asp Leu Arg Ser Gln Leu Thr Ile Ile Pro Gln Asp Pro Ile Leu Phe
```

-continued

```
                1365                1370                1375
Ser Gly Thr Leu Arg Met Asn Leu Asp Pro Phe Gly Ser Tyr Ser Glu
        1380                1385                1390
Glu Asp Ile Trp Trp Ala Leu Glu Leu Ser His Leu His Thr Phe Val
        1395                1400                1405
Ser Ser Gln Pro Ala Gly Leu Asp Phe Gln Cys Ser Glu Gly Gly Glu
    1410                1415                1420
Asn Leu Ser Val Gly Gln Arg Gln Leu Val Cys Leu Ala Arg Ala Leu
1425                1430                1435                1440
Leu Arg Lys Ser Arg Ile Leu Val Leu Asp Glu Ala Thr Ala Ala Ile
            1445                1450                1455
Asp Leu Glu Thr Asp Asn Leu Ile Gln Ala Thr Ile Arg Thr Gln Phe
        1460                1465                1470
Asp Thr Cys Thr Val Leu Thr Ile Ala His Arg Leu Asn Thr Ile Met
        1475                1480                1485
Asp Tyr Thr Arg Val Leu Val Leu Asp Lys Gly Val Val Ala Glu Phe
    1490                1495                1500
Asp Ser Pro Ala Asn Leu Ile Ala Ala Arg Gly Ile Phe Tyr Gly Met
1505                1510                1515                1520
Ala Arg Asp Ala Gly Leu Ala
            1525

<210> SEQ ID NO 85
<211> LENGTH: 1522
<212> TYPE: PRT
<213> ORGANISM: Rattus norvegicus

<400> SEQUENCE: 85

Met Asp Arg Leu Cys Gly Ser Gly Glu Leu Gly Ser Lys Phe Trp Asp
1               5                   10                  15
Ser Asn Leu Thr Val Tyr Thr Asn Thr Pro Asp Leu Thr Pro Cys Phe
            20                  25                  30
Gln Asn Ser Leu Leu Ala Trp Val Pro Cys Ile Tyr Leu Trp Ala Ala
        35                  40                  45
Leu Pro Cys Tyr Leu Phe Tyr Leu Arg His His Arg Leu Gly Tyr Ile
    50                  55                  60
Val Leu Ser Cys Leu Ser Arg Leu Lys Thr Ala Leu Gly Val Leu Leu
65                  70                  75                  80
Trp Cys Ile Ser Trp Val Asp Leu Phe Tyr Ser Phe His Gly Leu Val
                85                  90                  95
His Gly Ser Ser Pro Ala Pro Val Phe Phe Ile Thr Pro Leu Leu Val
            100                 105                 110
Gly Ile Thr Met Leu Leu Ala Thr Leu Leu Ile Gln Tyr Glu Arg Leu
        115                 120                 125
Arg Gly Val Arg Ser Ser Gly Val Leu Ile Ile Phe Trp Leu Leu Cys
    130                 135                 140
Val Ile Cys Ala Ile Ile Pro Phe Arg Ser Lys Ile Leu Leu Ala Leu
145                 150                 155                 160
Ala Glu Gly Lys Ile Leu Asp Pro Phe Arg Phe Thr Thr Phe Tyr Ile
                165                 170                 175
Tyr Phe Ala Leu Val Leu Cys Ala Phe Ile Leu Ser Cys Phe Gln Glu
            180                 185                 190
Lys Pro Pro Leu Phe Ser Pro Glu Asn Leu Asp Thr Asn Pro Cys Pro
        195                 200                 205
```

-continued

Glu Ala Ser Ala Gly Phe Phe Ser Arg Leu Ser Phe Trp Trp Phe Thr
210             215                 220

Lys Leu Ala Ile Leu Gly Tyr Arg Arg Pro Leu Glu Asp Ser Asp Leu
225                 230                 235             240

Trp Ser Leu Ser Glu Glu Asp Cys Ser His Lys Val Val Gln Arg Leu
                245                 250                 255

Leu Glu Ala Trp Gln Lys Gln Thr Gln Ala Ser Gly Pro Gln Thr
        260             265             270

Ala Ala Leu Glu Pro Lys Ile Ala Gly Glu Asp Val Leu Leu Lys
            275             280             285

Ala Arg Pro Lys Thr Lys Lys Pro Ser Phe Leu Arg Ala Leu Val Arg
290             295                 300

Thr Phe Thr Ser Ser Leu Leu Met Gly Ala Cys Phe Lys Leu Ile Gln
305             310                 315                 320

Asp Leu Ser Pro Ser Ser Thr His Ser Cys Ser Ala Ser Ser Ser Gly
                325                 330                 335

Leu Phe Arg Pro His Gly Pro Tyr Trp Trp Gly Phe Leu Leu Ala Gly
            340                 345             350

Leu Met Phe Val Ser Ser Thr Met Gln Thr Leu Ile Leu His Gln His
        355                 360                 365

Tyr His Cys Ile Phe Val Met Ala Leu Arg Ile Arg Thr Ala Ile Ile
    370                 375                 380

Gly Val Ile Tyr Arg Lys Ala Leu Thr Ile Thr Asn Ser Val Lys Arg
385             390                 395                 400

Glu Tyr Thr Val Gly Glu Met Val Asn Leu Met Ser Val Asp Ala Gln
                405                 410                 415

Arg Phe Met Asp Val Ser Pro Phe Ile Asn Leu Leu Trp Ser Ala Pro
            420                 425                 430

Leu Gln Val Ile Leu Ala Ile Tyr Phe Leu Trp Gln Ile Leu Gly Pro
        435                 440                 445

Ser Ala Leu Ala Gly Val Ala Val Ile Val Leu Leu Ile Pro Leu Asn
450                 455                 460

Gly Ala Val Ser Met Lys Met Lys Thr Tyr Gln Val Gln Gln Met Lys
465                 470                 475                 480

Phe Lys Asp Ser Arg Ile Lys Leu Met Ser Glu Ile Leu Asn Gly Ile
                485                 490                 495

Lys Val Leu Lys Leu Tyr Ala Trp Glu Pro Thr Phe Leu Glu Gln Val
            500                 505                 510

Glu Gly Ile Arg Gln Gly Glu Leu Gln Leu Leu Arg Lys Gly Ala Tyr
        515                 520                 525

Leu Gln Ala Ile Ser Thr Phe Ile Trp Val Cys Thr Pro Phe Met Val
    530                 535                 540

Thr Leu Ile Thr Leu Gly Val Tyr Val Cys Val Asp Lys Asn Asn Val
545                 550                 555                 560

Leu Asp Ala Glu Lys Ala Phe Val Ser Leu Ser Leu Phe Asn Ile Leu
                565                 570                 575

Lys Ile Pro Leu Asn Leu Leu Pro Gln Leu Ile Ser Gly Met Thr Gln
            580                 585                 590

Thr Ser Val Ser Leu Lys Arg Ile Gln Asp Phe Leu Asn Gln Asp Glu
        595                 600                 605

Leu Asp Pro Gln Cys Val Glu Arg Lys Thr Ile Ser Pro Gly Arg Ala
    610                 615                 620

Ile Thr Ile His Asn Gly Thr Phe Ser Trp Ser Lys Asp Leu Pro Pro

-continued

```
            625                 630                 635                 640
Thr Leu His Ser Ile Asn Ile Gln Ile Pro Lys Gly Ala Leu Val Ala
                645                 650                 655
Val Val Gly Pro Val Gly Cys Gly Lys Ser Ser Leu Val Ser Ala Leu
                660                 665                 670
Leu Gly Glu Met Glu Lys Leu Glu Gly Ala Val Ser Val Lys Gly Ser
                675                 680                 685
Val Ala Tyr Val Pro Gln Gln Ala Trp Ile Gln Asn Cys Thr Leu Gln
                690                 695                 700
Glu Asn Val Leu Phe Gly Gln Pro Met Asn Pro Lys Arg Tyr Gln Gln
705                 710                 715                 720
Ala Leu Glu Thr Cys Ala Leu Leu Ala Asp Leu Asp Val Leu Pro Gly
                725                 730                 735
Gly Asp Gln Thr Glu Ile Gly Glu Lys Gly Ile Asn Leu Ser Gly Gly
                740                 745                 750
Gln Arg Gln Arg Val Ser Leu Ala Arg Ala Val Tyr Ser Asp Ala Asn
                755                 760                 765
Ile Phe Leu Leu Asp Asp Pro Leu Ser Ala Val Asp Ser His Val Ala
770                 775                 780
Lys His Ile Phe Asp Gln Val Ile Gly Pro Glu Gly Val Leu Ala Gly
785                 790                 795                 800
Lys Thr Arg Val Leu Val Thr His Gly Ile Ser Phe Leu Pro Gln Thr
                805                 810                 815
Asp Phe Ile Ile Val Leu Ala Asp Gly Gln Ile Thr Glu Met Gly His
                820                 825                 830
Tyr Ser Glu Leu Leu Gln His Asp Gly Ser Phe Ala Asn Phe Leu Arg
                835                 840                 845
Asn Tyr Ala Pro Asp Glu Asn Gln Glu Ala Asn Glu Gly Val Leu Gln
850                 855                 860
His Ala Asn Glu Glu Val Leu Leu Leu Glu Asp Thr Leu Ser Thr His
865                 870                 875                 880
Thr Asp Leu Thr Asp Thr Glu Pro Ala Ile Tyr Glu Val Arg Lys Gln
                885                 890                 895
Phe Met Arg Glu Met Ser Ser Leu Ser Ser Glu Gly Glu Gly Gln Asn
                900                 905                 910
Arg Pro Val Leu Lys Arg Tyr Thr Ser Ser Leu Glu Lys Glu Val Pro
                915                 920                 925
Ala Thr Gln Thr Lys Glu Thr Gly Ala Leu Ile Lys Glu Glu Ile Ala
                930                 935                 940
Glu Thr Gly Asn Val Lys Leu Ser Val Tyr Trp Asp Tyr Ala Lys Ser
945                 950                 955                 960
Val Gly Leu Cys Thr Thr Leu Phe Ile Cys Leu Leu Tyr Ala Gly Gln
                965                 970                 975
Asn Ala Val Ala Ile Gly Ala Asn Val Trp Leu Ser Ala Trp Thr Asn
                980                 985                 990
Asp Val Glu Glu His Gly Gln Gln Asn Asn Thr Ser Val Arg Leu Gly
                995                1000                1005
Val Tyr Ala Thr Leu Gly Ile Leu Gln Gly Leu Leu Val Met Leu Ser
            1010                1015                1020
Ala Phe Thr Met Val Val Gly Ala Ile Gln Ala Ala Arg Leu Leu His
1025                1030                1035                1040
Thr Ala Leu Leu His Asn Gln Ile Arg Ala Pro Gln Ser Phe Phe Asp
                1045                1050                1055
```

```
Thr Thr Pro Ser Gly Arg Ile Leu Asn Arg Phe Ser Lys Asp Ile Tyr
        1060                1065                1070

Val Ile His Glu Val Leu Ala Pro Thr Ile Leu Met Leu Phe Asn Ser
    1075                1080                1085

Phe Tyr Thr Ser Ile Ser Thr Ile Val Val Ile Val Ala Ser Thr Pro
1090                1095                1100

Leu Phe Cys Val Val Leu Pro Leu Ala Val Phe Tyr Gly Phe Val
1105                1110                1115                1120

Gln Arg Phe Tyr Val Ala Thr Ser Arg Gln Leu Lys Arg Leu Glu Ser
        1125                1130                1135

Val Ser Arg Ser Pro Ile Phe Ser His Phe Ser Glu Thr Val Thr Gly
        1140                1145                1150

Thr Ser Val Ile Arg Ala Tyr Gly Arg Val Gln Asp Phe Lys Val Leu
        1155                1160                1165

Ser Asp Ala Lys Val Asp Ser Asn Gln Lys Thr Thr Tyr Pro Tyr Ile
        1170                1175                1180

Ala Ser Asn Arg Trp Leu Gly Val His Val Glu Phe Val Gly Asn Cys
1185                1190                1195                1200

Val Val Leu Phe Ser Ala Leu Phe Ala Val Ile Gly Arg Asn Ser Leu
        1205                1210                1215

Asn Pro Gly Leu Val Gly Leu Ser Val Ser Tyr Ala Leu Gln Val Thr
        1220                1225                1230

Leu Ser Leu Asn Trp Met Ile Arg Thr Leu Ser Asp Leu Glu Ser Asn
        1235                1240                1245

Ile Ile Ala Val Glu Arg Val Lys Glu Tyr Ser Lys Thr Glu Thr Glu
        1250                1255                1260

Ala Pro Trp Val Leu Glu Ser Asn Arg Ala Pro Glu Gly Trp Pro Arg
1265                1270                1275                1280

Ser Gly Val Val Glu Phe Arg Asn Tyr Ser Val Arg Tyr Arg Pro Gly
        1285                1290                1295

Leu Glu Leu Val Leu Lys Asn Leu Thr Leu His Val Gln Gly Gly Glu
        1300                1305                1310

Lys Val Gly Ile Val Gly Arg Thr Gly Ala Gly Lys Ser Ser Met Thr
        1315                1320                1325

Leu Cys Leu Phe Arg Ile Leu Glu Ala Ala Glu Gly Glu Ile Phe Ile
        1330                1335                1340

Asp Gly Leu Asn Val Ala His Ile Gly Leu His Asp Leu Arg Ser Gln
1345                1350                1355                1360

Leu Thr Ile Ile Pro Gln Asp Pro Ile Leu Phe Ser Gly Thr Leu Arg
        1365                1370                1375

Met Asn Leu Asp Pro Phe Gly Arg Tyr Ser Asp Glu Asp Ile Trp Arg
        1380                1385                1390

Thr Leu Glu Leu Ser His Leu Ser Ala Phe Val Ser Ser Gln Pro Thr
        1395                1400                1405

Gly Leu Asp Phe Gln Cys Ser Glu Gly Gly Asp Asn Leu Ser Val Gly
        1410                1415                1420

Gln Arg Gln Leu Val Cys Leu Ala Arg Ala Leu Leu Arg Lys Ser Arg
1425                1430                1435                1440

Val Leu Val Leu Asp Glu Ala Thr Ala Ala Ile Asp Leu Glu Thr Asp
        1445                1450                1455

Asp Leu Ile Gln Gly Thr Ile Arg Thr Gln Phe Glu Asp Cys Thr Val
        1460                1465                1470
```

```
Leu Thr Ile Ala His Arg Leu Asn Thr Ile Met Asp Tyr Asn Arg Val
        1475                1480                1485

Leu Val Leu Asp Lys Gly Val Val Ala Glu Phe Asp Ser Pro Val Asn
    1490                1495                1500

Leu Ile Ala Ala Gly Gly Ile Phe Tyr Gly Met Ala Lys Asp Ala Gly
1505                1510                1515                1520

Leu Ala

<210> SEQ ID NO 86
<211> LENGTH: 1531
<212> TYPE: PRT
<213> ORGANISM: Homo sapiens

<400> SEQUENCE: 86

Met Ala Leu Arg Gly Phe Cys Ser Ala Asp Gly Ser Asp Pro Leu Trp
  1               5                  10                  15

Asp Trp Asn Val Thr Trp Asn Thr Ser Asn Pro Asp Phe Thr Lys Cys
              20                  25                  30

Phe Gln Asn Thr Val Leu Val Trp Val Pro Cys Phe Tyr Leu Trp Ala
          35                  40                  45

Cys Phe Pro Phe Tyr Phe Leu Tyr Leu Ser Arg His Asp Arg Gly Tyr
      50                  55                  60

Ile Gln Met Thr Pro Leu Asn Lys Thr Lys Thr Ala Leu Gly Phe Leu
 65                  70                  75                  80

Leu Trp Ile Val Cys Trp Ala Asp Leu Phe Tyr Ser Phe Trp Glu Arg
                  85                  90                  95

Ser Arg Gly Ile Phe Leu Ala Pro Val Phe Leu Val Ser Pro Thr Leu
              100                 105                 110

Leu Gly Ile Thr Thr Leu Leu Ala Thr Phe Leu Ile Gln Leu Glu Arg
          115                 120                 125

Arg Lys Gly Val Gln Ser Ser Gly Ile Met Leu Thr Phe Trp Leu Val
      130                 135                 140

Ala Leu Val Cys Ala Leu Ala Ile Leu Arg Ser Lys Ile Met Thr Ala
145                 150                 155                 160

Leu Lys Glu Asp Ala Gln Val Asp Leu Phe Arg Asp Ile Thr Phe Tyr
                  165                 170                 175

Val Tyr Phe Ser Leu Leu Leu Ile Gln Leu Val Leu Ser Cys Phe Ser
              180                 185                 190

Asp Arg Ser Pro Leu Phe Ser Glu Thr Ile His Asp Pro Asn Pro Cys
          195                 200                 205

Pro Glu Ser Ser Ala Ser Phe Leu Ser Arg Ile Thr Phe Trp Trp Ile
      210                 215                 220

Thr Gly Leu Ile Val Arg Gly Tyr Arg Gln Pro Leu Glu Gly Ser Asp
225                 230                 235                 240

Leu Trp Ser Leu Asn Lys Glu Asp Thr Ser Glu Gln Val Val Pro Val
                  245                 250                 255

Leu Val Lys Asn Trp Lys Lys Glu Cys Ala Lys Thr Arg Lys Gln Pro
              260                 265                 270

Val Lys Val Val Tyr Ser Ser Lys Asp Pro Ala Gln Pro Lys Glu Ser
          275                 280                 285

Ser Lys Val Asp Ala Asn Glu Glu Val Glu Ala Leu Ile Val Lys Ser
      290                 295                 300

Pro Gln Lys Glu Trp Asn Pro Ser Leu Phe Lys Val Leu Tyr Lys Thr
305                 310                 315                 320
```

```
Phe Gly Pro Tyr Phe Leu Met Ser Phe Phe Lys Ala Ile His Asp
            325                 330                 335

Leu Met Met Phe Ser Gly Pro Gln Ile Leu Lys Leu Leu Ile Lys Phe
            340                 345                 350

Val Asn Asp Thr Lys Ala Pro Asp Trp Gln Gly Tyr Phe Tyr Thr Val
            355                 360                 365

Leu Leu Phe Val Thr Ala Cys Leu Gln Thr Leu Val Leu His Gln Tyr
    370                 375                 380

Phe His Ile Cys Phe Val Ser Gly Met Arg Ile Lys Thr Ala Val Ile
385                 390                 395                 400

Gly Ala Val Tyr Arg Lys Ala Leu Val Ile Thr Asn Ser Ala Arg Lys
                405                 410                 415

Ser Ser Thr Val Gly Glu Ile Val Asn Leu Met Ser Val Asp Ala Gln
            420                 425                 430

Arg Phe Met Asp Leu Ala Thr Tyr Ile Asn Met Ile Trp Ser Ala Pro
            435                 440                 445

Leu Gln Val Ile Leu Ala Leu Tyr Leu Leu Trp Leu Asn Leu Gly Pro
    450                 455                 460

Ser Val Leu Ala Gly Val Ala Val Met Val Leu Met Val Pro Val Asn
465                 470                 475                 480

Ala Val Met Ala Met Lys Thr Lys Thr Tyr Gln Val Ala His Met Lys
                485                 490                 495

Ser Lys Asp Asn Arg Ile Lys Leu Met Asn Glu Ile Leu Asn Gly Ile
            500                 505                 510

Lys Val Leu Lys Leu Tyr Ala Trp Glu Leu Ala Phe Lys Asp Lys Val
    515                 520                 525

Leu Ala Ile Arg Gln Glu Glu Leu Lys Val Leu Lys Lys Ser Ala Tyr
    530                 535                 540

Leu Ser Ala Val Gly Thr Phe Thr Trp Val Cys Thr Pro Phe Leu Val
545                 550                 555                 560

Ala Leu Cys Thr Phe Ala Val Tyr Val Thr Ile Asp Glu Asn Asn Ile
                565                 570                 575

Leu Asp Ala Gln Thr Ala Phe Val Ser Leu Ala Leu Phe Asn Ile Leu
            580                 585                 590

Arg Phe Pro Leu Asn Ile Leu Pro Met Val Ile Ser Ser Ile Val Gln
            595                 600                 605

Ala Ser Val Ser Leu Lys Arg Leu Arg Ile Phe Leu Ser His Glu Glu
    610                 615                 620

Leu Glu Pro Asp Ser Ile Glu Arg Arg Pro Val Lys Asp Gly Gly Gly
625                 630                 635                 640

Thr Asn Ser Ile Thr Val Arg Asn Ala Thr Phe Thr Trp Ala Arg Ser
                645                 650                 655

Asp Pro Pro Thr Leu Asn Gly Ile Thr Phe Ser Ile Pro Glu Gly Ala
            660                 665                 670

Leu Val Ala Val Val Gly Gln Val Gly Cys Gly Lys Ser Ser Leu Leu
    675                 680                 685

Ser Ala Leu Leu Ala Glu Met Asp Lys Val Glu Gly His Val Ala Ile
    690                 695                 700

Lys Gly Ser Val Ala Tyr Val Pro Gln Gln Ala Trp Ile Gln Asn Asp
705                 710                 715                 720

Ser Leu Arg Glu Asn Ile Leu Phe Gly Cys Gln Leu Glu Glu Pro Tyr
                725                 730                 735

Tyr Arg Ser Val Ile Gln Ala Cys Ala Leu Leu Pro Asp Leu Glu Ile
```

-continued

```
            740                 745                 750
Leu Pro Ser Gly Asp Arg Thr Glu Ile Gly Glu Lys Gly Val Asn Leu
            755                 760                 765
Ser Gly Gly Gln Lys Gln Arg Val Ser Leu Ala Arg Ala Val Tyr Ser
            770                 775                 780
Asn Ala Asp Ile Tyr Leu Phe Asp Asp Pro Leu Ser Ala Val Asp Ala
785                 790                 795                 800
His Val Gly Lys His Ile Phe Glu Asn Val Ile Gly Pro Lys Gly Met
                    805                 810                 815
Leu Lys Asn Lys Thr Arg Ile Leu Val Thr His Ser Met Ser Tyr Leu
            820                 825                 830
Pro Gln Val Asp Val Ile Ile Val Met Ser Gly Gly Lys Ile Ser Glu
            835                 840                 845
Met Gly Ser Tyr Gln Glu Leu Leu Ala Arg Asp Gly Ala Phe Ala Glu
850                 855                 860
Phe Leu Arg Thr Tyr Ala Ser Thr Glu Gln Glu Gln Asp Ala Glu Glu
865                 870                 875                 880
Asn Gly Val Thr Gly Val Ser Gly Pro Gly Lys Glu Ala Lys Gln Met
                    885                 890                 895
Glu Asn Gly Met Leu Val Thr Asp Ser Ala Gly Lys Gln Leu Gln Arg
                    900                 905                 910
Gln Leu Ser Ser Ser Ser Ser Tyr Ser Gly Asp Ile Ser Arg His His
            915                 920                 925
Asn Ser Thr Ala Glu Leu Gln Lys Ala Glu Ala Lys Lys Glu Glu Thr
            930                 935                 940
Trp Lys Leu Met Glu Ala Asp Lys Ala Gln Thr Gly Gln Val Lys Leu
945                 950                 955                 960
Ser Val Tyr Trp Asp Tyr Met Lys Ala Ile Gly Leu Phe Ile Ser Phe
                    965                 970                 975
Leu Ser Ile Phe Leu Phe Met Cys Asn His Val Ser Ala Leu Ala Ser
                    980                 985                 990
Asn Tyr Trp Leu Ser Leu Trp Thr Asp Asp Pro Ile Val Asn Gly Thr
            995                 1000                1005
Gln Glu His Thr Lys Val Arg Leu Ser Val Tyr Gly Ala Leu Gly Ile
    1010                1015                1020
Ser Gln Gly Ile Ala Val Phe Gly Tyr Ser Met Ala Val Ser Ile Gly
1025                1030                1035                1040
Gly Ile Leu Ala Ser Arg Cys Leu His Val Asp Leu Leu His Ser Ile
                    1045                1050                1055
Leu Arg Ser Pro Met Ser Phe Phe Glu Arg Thr Pro Ser Gly Asn Leu
            1060                1065                1070
Val Asn Arg Phe Ser Lys Glu Leu Asp Thr Val Asp Ser Met Ile Pro
            1075                1080                1085
Glu Val Ile Lys Met Phe Met Gly Ser Leu Phe Asn Val Ile Gly Ala
            1090                1095                1100
Cys Ile Val Ile Leu Leu Ala Thr Pro Ile Ala Ala Ile Ile Ile Pro
1105                1110                1115                1120
Pro Leu Gly Leu Ile Tyr Phe Phe Val Gln Arg Phe Tyr Val Ala Ser
                    1125                1130                1135
Ser Arg Gln Leu Lys Arg Leu Glu Ser Val Ser Arg Ser Pro Val Tyr
            1140                1145                1150
Ser His Phe Asn Glu Thr Leu Leu Gly Val Ser Val Ile Arg Ala Phe
            1155                1160                1165
```

```
Glu Glu Gln Glu Arg Phe Ile His Gln Ser Asp Leu Lys Val Asp Glu
    1170                1175                1180

Asn Gln Lys Ala Tyr Tyr Pro Ser Ile Val Ala Asn Arg Trp Leu Ala
1185                1190                1195                1200

Val Arg Leu Glu Cys Val Gly Asn Cys Ile Val Leu Phe Ala Ala Leu
            1205                1210                1215

Phe Ala Val Ile Ser Arg His Ser Leu Ser Ala Gly Leu Val Gly Leu
        1220                1225                1230

Ser Val Ser Tyr Ser Leu Gln Val Thr Thr Tyr Leu Asn Trp Leu Val
    1235                1240                1245

Arg Met Ser Ser Glu Met Glu Thr Asn Ile Val Ala Val Glu Arg Leu
1250                1255                1260

Lys Glu Tyr Ser Glu Thr Glu Lys Glu Ala Pro Trp Gln Ile Gln Glu
1265                1270                1275                1280

Thr Ala Pro Pro Ser Ser Trp Pro Gln Val Gly Arg Val Glu Phe Arg
            1285                1290                1295

Asn Tyr Cys Leu Arg Tyr Arg Glu Asp Leu Asp Phe Val Leu Arg His
        1300                1305                1310

Ile Asn Val Thr Ile Asn Gly Gly Glu Lys Val Gly Ile Val Gly Arg
    1315                1320                1325

Thr Gly Ala Gly Lys Ser Ser Leu Thr Leu Gly Leu Phe Arg Ile Asn
1330                1335                1340

Glu Ser Ala Glu Gly Glu Ile Ile Ile Asp Gly Ile Asn Ile Ala Lys
1345                1350                1355                1360

Ile Gly Leu His Asp Leu Arg Phe Lys Ile Thr Ile Ile Pro Gln Asp
            1365                1370                1375

Pro Val Leu Phe Ser Gly Ser Leu Arg Met Asn Leu Asp Pro Phe Ser
        1380                1385                1390

Gln Tyr Ser Asp Glu Glu Val Trp Thr Ser Leu Glu Leu Ala His Leu
    1395                1400                1405

Lys Asp Phe Val Ser Ala Leu Pro Asp Lys Leu Asp His Glu Cys Ala
    1410                1415                1420

Glu Gly Gly Glu Asn Leu Ser Val Gly Gln Arg Gln Leu Val Cys Leu
1425                1430                1435                1440

Ala Arg Ala Leu Leu Arg Lys Thr Lys Ile Leu Val Leu Asp Glu Ala
            1445                1450                1455

Thr Ala Ala Val Asp Leu Glu Thr Asp Asp Leu Ile Gln Ser Thr Ile
        1460                1465                1470

Arg Thr Gln Phe Glu Asp Cys Thr Val Leu Thr Ile Ala His Arg Leu
    1475                1480                1485

Asn Thr Ile Met Asp Tyr Thr Arg Val Ile Val Leu Asp Lys Gly Glu
    1490                1495                1500

Ile Gln Glu Tyr Gly Ala Pro Ser Asp Leu Leu Gln Gln Arg Gly Leu
1505                1510                1515                1520

Phe Tyr Ser Met Ala Lys Asp Ala Gly Leu Val
            1525                1530

<210> SEQ ID NO 87
<211> LENGTH: 1515
<212> TYPE: PRT
<213> ORGANISM: Homo sapiens

<400> SEQUENCE: 87

Asp Trp Asn Val Thr Trp Asn Thr Ser Asn Pro Asp Phe Thr Lys Cys
```

-continued

```
  1               5                10               15
Phe Gln Asn Thr Val Leu Val Trp Val Pro Cys Phe Tyr Leu Trp Ala
                 20                25               30

Cys Phe Pro Phe Tyr Phe Leu Tyr Leu Ser Arg His Asp Arg Gly Tyr
             35              40              45

Ile Gln Met Thr Pro Leu Asn Lys Thr Lys Thr Ala Leu Gly Phe Leu
         50              55              60

Leu Trp Ile Val Cys Trp Ala Asp Leu Phe Tyr Ser Phe Trp Glu Arg
65              70              75              80

Ser Arg Gly Ile Phe Leu Ala Pro Val Phe Leu Val Ser Pro Thr Leu
             85              90              95

Leu Gly Ile Thr Thr Leu Leu Ala Thr Phe Leu Ile Gln Leu Glu Arg
            100             105             110

Arg Lys Gly Val Gln Ser Ser Gly Ile Met Leu Thr Phe Trp Leu Val
            115             120             125

Ala Leu Val Cys Ala Leu Ala Ile Leu Arg Ser Lys Ile Met Thr Ala
            130             135             140

Leu Lys Glu Asp Ala Gln Val Asp Leu Phe Arg Asp Ile Thr Phe Tyr
145             150             155             160

Val Tyr Phe Ser Leu Leu Leu Ile Gln Leu Val Leu Ser Cys Phe Ser
                165             170             175

Asp Arg Ser Pro Leu Phe Ser Glu Thr Ile His Asp Pro Asn Pro Cys
            180             185             190

Pro Glu Ser Ser Ala Ser Phe Leu Ser Arg Ile Thr Phe Trp Trp Ile
            195             200             205

Thr Gly Leu Ile Val Arg Gly Tyr Arg Gln Pro Leu Glu Gly Ser Asp
            210             215             220

Leu Trp Ser Leu Asn Lys Glu Asp Thr Ser Glu Gln Val Val Pro Val
225             230             235             240

Leu Val Lys Asn Trp Lys Lys Glu Cys Ala Lys Thr Arg Lys Gln Pro
                245             250             255

Val Lys Val Val Tyr Ser Ser Lys Asp Pro Ala Gln Pro Lys Glu Ser
                260             265             270

Ser Lys Val Asp Ala Asn Glu Glu Val Glu Ala Leu Ile Val Lys Ser
            275             280             285

Pro Gln Lys Glu Trp Asn Pro Ser Leu Phe Lys Val Leu Tyr Lys Thr
            290             295             300

Phe Gly Pro Tyr Phe Leu Met Ser Phe Phe Lys Ala Ile His Asp
305             310             315             320

Leu Met Met Phe Ser Gly Pro Gln Ile Leu Lys Leu Leu Ile Lys Phe
                325             330             335

Val Asn Asp Thr Lys Ala Pro Asp Trp Gln Gly Tyr Phe Tyr Thr Val
            340             345             350

Leu Leu Phe Val Thr Ala Cys Leu Gln Thr Leu Val Leu His Gln Tyr
            355             360             365

Phe His Ile Cys Phe Val Ser Gly Met Arg Ile Lys Thr Ala Val Ile
            370             375             380

Gly Ala Val Tyr Arg Lys Ala Leu Val Ile Thr Asn Ser Ala Arg Lys
385             390             395             400

Ser Ser Thr Val Gly Glu Ile Val Asn Leu Met Ser Val Asp Ala Gln
                405             410             415

Arg Phe Met Asp Leu Ala Thr Tyr Ile Asn Met Ile Trp Ser Ala Pro
            420             425             430
```

```
Leu Gln Val Ile Leu Ala Leu Tyr Leu Leu Trp Leu Asn Leu Gly Pro
        435                 440                 445
Ser Val Leu Ala Gly Val Ala Val Met Val Leu Met Val Pro Val Asn
        450                 455                 460
Ala Val Met Ala Met Lys Thr Lys Thr Tyr Gln Val Ala His Met Lys
465                 470                 475                 480
Ser Lys Asp Asn Arg Ile Lys Leu Met Asn Glu Ile Leu Asn Gly Ile
                485                 490                 495
Lys Val Leu Lys Leu Tyr Ala Trp Glu Leu Ala Phe Lys Asp Lys Val
        500                 505                 510
Leu Ala Ile Arg Gln Glu Leu Lys Val Leu Lys Lys Ser Ala Tyr
        515                 520                 525
Leu Ser Ala Val Gly Thr Phe Thr Trp Val Cys Thr Pro Phe Leu Val
        530                 535                 540
Ala Leu Cys Thr Phe Ala Val Tyr Val Thr Ile Asp Glu Asn Asn Ile
545                 550                 555                 560
Leu Asp Ala Gln Thr Ala Phe Val Ser Leu Ala Leu Phe Asn Ile Leu
                565                 570                 575
Arg Phe Pro Leu Asn Ile Leu Pro Met Val Ile Ser Ser Ile Val Gln
                580                 585                 590
Ala Ser Val Ser Leu Lys Arg Leu Arg Ile Phe Leu Ser His Glu Glu
        595                 600                 605
Leu Glu Pro Asp Ser Ile Glu Arg Arg Pro Val Lys Asp Gly Gly Gly
        610                 615                 620
Thr Asn Ser Ile Thr Val Arg Asn Ala Thr Phe Thr Trp Ala Arg Ser
625                 630                 635                 640
Asp Pro Pro Thr Leu Asn Gly Ile Thr Phe Ser Ile Pro Glu Gly Ala
                645                 650                 655
Leu Val Ala Val Val Gly Gln Val Gly Cys Gly Lys Ser Ser Leu Leu
                660                 665                 670
Ser Ala Leu Leu Ala Glu Met Asp Lys Val Glu Gly His Val Ala Ile
        675                 680                 685
Lys Gly Ser Val Ala Tyr Val Pro Gln Gln Ala Trp Ile Gln Asn Asp
        690                 695                 700
Ser Leu Arg Glu Asn Ile Leu Phe Gly Cys Gln Leu Glu Glu Pro Tyr
705                 710                 715                 720
Tyr Arg Ser Val Ile Gln Ala Cys Ala Leu Leu Pro Asp Leu Glu Ile
                725                 730                 735
Leu Pro Ser Gly Asp Arg Thr Glu Ile Gly Glu Lys Gly Val Asn Leu
                740                 745                 750
Ser Gly Gly Gln Lys Gln Arg Val Ser Leu Ala Arg Ala Val Tyr Ser
        755                 760                 765
Asn Ala Asp Ile Tyr Leu Phe Asp Asp Pro Leu Ser Ala Val Asp Ala
        770                 775                 780
His Val Gly Lys His Ile Phe Glu Asn Val Ile Gly Pro Lys Gly Met
785                 790                 795                 800
Leu Lys Asn Lys Thr Arg Ile Leu Val Thr His Ser Met Ser Tyr Leu
                805                 810                 815
Pro Gln Val Asp Val Ile Ile Val Met Ser Gly Gly Lys Ile Ser Glu
                820                 825                 830
Met Gly Ser Tyr Gln Glu Leu Leu Ala Arg Asp Gly Ala Phe Ala Glu
        835                 840                 845
```

-continued

```
Phe Leu Arg Thr Tyr Ala Ser Thr Glu Gln Glu Gln Asp Ala Glu
    850                 855                 860
Asn Gly Val Thr Gly Val Ser Gly Pro Gly Lys Glu Ala Lys Gln Met
865                 870                 875                 880
Glu Asn Gly Met Leu Val Thr Asp Ser Ala Gly Lys Gln Leu Gln Arg
                    885                 890                 895
Gln Leu Ser Ser Ser Ser Ser Tyr Ser Gly Asp Ile Ser Arg His His
                900                 905                 910
Asn Ser Thr Ala Glu Leu Gln Lys Ala Glu Ala Lys Lys Glu Glu Thr
                915                 920                 925
Trp Lys Leu Met Glu Ala Asp Lys Ala Gln Thr Gly Gln Val Lys Leu
    930                 935                 940
Ser Val Tyr Trp Asp Tyr Met Lys Ala Ile Gly Leu Phe Ile Ser Phe
945                 950                 955                 960
Leu Ser Ile Phe Leu Phe Met Cys Asn His Val Ser Ala Leu Ala Ser
                965                 970                 975
Asn Tyr Trp Leu Ser Leu Trp Thr Asp Asp Pro Ile Val Asn Gly Thr
                980                 985                 990
Gln Glu His Thr Lys Val Arg Leu Ser Val Tyr Gly Ala Leu Gly Ile
                995                 1000                1005
Ser Gln Gly Ile Ala Val Phe Gly Tyr Ser Met Ala Val Ser Ile Gly
    1010                1015                1020
Gly Ile Leu Ala Ser Arg Cys Leu His Val Asp Leu Leu His Ser Ile
1025                1030                1035                1040
Leu Arg Ser Pro Met Ser Phe Phe Glu Arg Thr Pro Ser Gly Asn Leu
                1045                1050                1055
Val Asn Arg Phe Ser Lys Glu Leu Asp Thr Val Asp Ser Met Ile Pro
                1060                1065                1070
Glu Val Ile Lys Met Phe Met Gly Ser Leu Phe Asn Val Ile Gly Ala
                1075                1080                1085
Cys Ile Val Ile Leu Leu Ala Thr Pro Ile Ala Ala Ile Ile Ile Pro
    1090                1095                1100
Pro Leu Gly Leu Ile Tyr Phe Phe Val Gln Arg Phe Tyr Val Ala Ser
1105                1110                1115                1120
Ser Arg Gln Leu Lys Arg Leu Glu Ser Val Ser Arg Ser Pro Val Tyr
                1125                1130                1135
Ser His Phe Asn Glu Thr Leu Leu Gly Val Ser Val Ile Arg Ala Phe
                1140                1145                1150
Glu Glu Gln Glu Arg Phe Ile His Gln Ser Asp Leu Lys Val Asp Glu
                1155                1160                1165
Asn Gln Lys Ala Tyr Tyr Pro Ser Ile Val Ala Asn Arg Trp Leu Ala
    1170                1175                1180
Val Arg Leu Glu Cys Val Gly Asn Cys Ile Val Leu Phe Ala Ala Leu
1185                1190                1195                1200
Phe Ala Val Ile Ser Arg His Ser Leu Ser Ala Gly Leu Val Gly Leu
                1205                1210                1215
Ser Val Ser Tyr Ser Leu Gln Val Thr Thr Tyr Leu Asn Trp Leu Val
                1220                1225                1230
Arg Met Ser Ser Glu Met Glu Thr Asn Ile Val Ala Val Glu Arg Leu
                1235                1240                1245
Lys Glu Tyr Ser Glu Thr Glu Lys Glu Ala Pro Trp Gln Ile Gln Glu
    1250                1255                1260
Thr Ala Pro Pro Ser Ser Trp Pro Gln Val Gly Arg Val Glu Phe Arg
```

-continued

```
              1265                1270                1275                1280
Asn Tyr Cys Leu Arg Tyr Arg Glu Asp Leu Asp Phe Val Leu Arg His
                1285                1290                1295
Ile Asn Val Thr Ile Asn Gly Gly Glu Lys Val Gly Ile Val Gly Arg
            1300                1305                1310
Thr Gly Ala Gly Lys Ser Ser Leu Thr Leu Gly Leu Phe Arg Ile Asn
            1315                1320                1325
Glu Ser Ala Glu Gly Glu Ile Ile Ile Asp Gly Ile Asn Ile Ala Lys
            1330                1335                1340
Ile Gly Leu His Asp Leu Arg Phe Lys Ile Thr Ile Ile Pro Gln Asp
1345                1350                1355                1360
Pro Val Leu Phe Ser Gly Ser Leu Arg Met Asn Leu Asp Pro Phe Ser
                1365                1370                1375
Gln Tyr Ser Asp Glu Glu Val Trp Thr Ser Leu Glu Leu Ala His Leu
            1380                1385                1390
Lys Asp Phe Val Ser Ala Leu Pro Asp Lys Leu Asp His Glu Cys Ala
            1395                1400                1405
Glu Gly Gly Glu Asn Leu Ser Val Gly Gln Arg Gln Leu Val Cys Leu
        1410                1415                1420
Ala Arg Ala Leu Leu Arg Lys Thr Lys Ile Leu Val Leu Asp Glu Ala
1425                1430                1435                1440
Thr Ala Ala Val Asp Leu Glu Thr Asp Asp Leu Ile Gln Ser Thr Ile
                1445                1450                1455
Arg Thr Gln Phe Glu Asp Cys Thr Val Leu Thr Ile Ala His Arg Leu
                1460                1465                1470
Asn Thr Ile Met Asp Tyr Thr Arg Val Ile Val Leu Asp Lys Gly Glu
            1475                1480                1485
Ile Gln Glu Tyr Gly Ala Pro Ser Asp Leu Leu Gln Arg Gly Leu
        1490                1495                1500
Phe Tyr Ser Met Ala Lys Asp Ala Gly Leu Val
1505                1510                1515

<210> SEQ ID NO 88
<211> LENGTH: 1528
<212> TYPE: PRT
<213> ORGANISM: Mus musculus

<400> SEQUENCE: 88

Met Ala Leu Arg Ser Phe Cys Ser Ala Asp Gly Ser Asp Pro Leu Trp
  1               5                  10                  15
Asp Trp Asn Val Thr Trp His Thr Ser Asn Pro Asp Phe Thr Lys Cys
                20                  25                  30
Phe Gln Asn Thr Val Leu Thr Trp Val Pro Cys Phe Tyr Leu Trp Ser
            35                  40                  45
Cys Phe Pro Leu Tyr Phe Tyr Leu Ser Arg His Asp Arg Gly Tyr
        50                  55                  60
Ile Gln Met Thr His Leu Asn Lys Thr Lys Thr Ala Leu Gly Phe Phe
 65                 70                  75                  80
Leu Trp Ile Ile Cys Trp Ala Asp Leu Phe Tyr Ser Phe Trp Glu Arg
                85                  90                  95
Ser Gln Gly Val Leu Arg Ala Pro Val Leu Leu Val Ser Pro Thr Leu
            100                 105                 110
Leu Gly Ile Thr Met Leu Leu Ala Thr Phe Leu Ile Gln Leu Glu Arg
        115                 120                 125
```

-continued

```
Arg Lys Gly Val Gln Ser Ser Gly Ile Met Leu Thr Phe Trp Leu Val
130                 135                 140

Ala Leu Leu Cys Ala Leu Ala Ile Leu Arg Ser Lys Ile Ile Ser Ala
145                 150                 155                 160

Leu Lys Lys Asp Ala His Val Asp Val Phe Arg Asp Ser Thr Phe Tyr
                165                 170                 175

Leu Tyr Phe Thr Leu Val Leu Val Gln Leu Val Leu Ser Cys Phe Ser
                180                 185                 190

Asp Cys Ser Pro Leu Phe Ser Glu Thr Val His Asp Arg Asn Pro Cys
                195                 200                 205

Pro Glu Ser Ser Ala Ser Phe Leu Ser Arg Ile Thr Phe Trp Trp Ile
210                 215                 220

Thr Gly Met Met Val His Gly Tyr Arg Gln Pro Leu Glu Ser Ser Asp
225                 230                 235                 240

Leu Trp Ser Leu Asn Lys Glu Asp Thr Ser Glu Val Val Pro Val
                245                 250                 255

Leu Val Asn Asn Trp Lys Lys Glu Cys Asp Lys Ser Arg Lys Gln Pro
                260                 265                 270

Val Arg Ile Val Tyr Ala Pro Pro Lys Asp Pro Ser Lys Pro Lys Gly
                275                 280                 285

Ser Ser Gln Leu Asp Val Asn Glu Glu Val Glu Ala Leu Ile Val Lys
290                 295                 300

Ser Pro His Lys Asp Arg Glu Pro Ser Leu Phe Lys Val Leu Tyr Lys
305                 310                 315                 320

Thr Phe Gly Pro Tyr Phe Leu Met Ser Phe Leu Tyr Lys Ala Leu His
                325                 330                 335

Asp Leu Met Met Phe Ala Gly Pro Lys Ile Leu Glu Leu Ile Ile Asn
                340                 345                 350

Phe Val Asn Asp Arg Glu Ala Pro Asp Trp Gln Gly Tyr Phe Tyr Thr
                355                 360                 365

Ala Leu Leu Phe Val Ser Ala Cys Leu Gln Thr Leu Ala Leu His Gln
370                 375                 380

Tyr Phe His Ile Cys Phe Val Ser Gly Met Arg Ile Lys Thr Ala Val
385                 390                 395                 400

Val Gly Ala Val Tyr Arg Lys Ala Leu Leu Ile Thr Asn Ala Ala Arg
                405                 410                 415

Lys Ser Ser Thr Val Gly Glu Ile Val Asn Leu Met Ser Val Asp Ala
                420                 425                 430

Gln Arg Phe Met Asp Leu Ala Thr Tyr Ile Asn Met Ile Trp Ser Ala
                435                 440                 445

Pro Leu Gln Val Ile Leu Ala Leu Tyr Phe Leu Trp Leu Ser Leu Gly
450                 455                 460

Pro Ser Val Leu Ala Gly Val Ala Val Met Ile Leu Met Val Pro Leu
465                 470                 475                 480

Asn Ala Val Met Ala Met Lys Thr Lys Thr Tyr Gln Val Ala His Met
                485                 490                 495

Lys Ser Lys Asp Asn Arg Ile Lys Leu Met Asn Glu Ile Leu Asn Gly
                500                 505                 510

Ile Lys Val Leu Lys Leu Tyr Ala Trp Glu Leu Ala Phe Gln Asp Lys
                515                 520                 525

Val Met Ser Ile Arg Gln Glu Glu Leu Lys Val Leu Lys Lys Ser Ala
530                 535                 540

Tyr Leu Ala Ala Val Gly Thr Phe Thr Trp Val Cys Thr Pro Phe Leu
```

```
         545                 550                 555                 560
    Val Ala Leu Ser Thr Phe Ala Val Phe Val Thr Val Asp Glu Arg Asn
                    565                 570                 575

Ile Leu Asp Ala Lys Ala Phe Val Ser Leu Ala Leu Phe Asn Ile
                    580                 585                 590

Leu Arg Phe Pro Leu Asn Ile Leu Pro Met Val Ile Ser Ser Ile Val
                    595                 600                 605

Gln Ala Ser Val Ser Leu Lys Arg Leu Arg Ile Phe Leu Ser His Glu
                    610                 615                 620

Glu Leu Glu Pro Asp Ser Ile Glu Arg Ser Ile Lys Ser Gly Glu
    625                 630                 635                 640

Gly Asn Ser Ile Thr Val Lys Asn Ala Thr Phe Thr Trp Ala Arg Gly
                    645                 650                 655

Glu Pro Pro Thr Leu Asn Gly Ile Thr Phe Ser Ile Pro Glu Gly Ala
                    660                 665                 670

Leu Val Ala Val Val Gly Gln Val Gly Cys Gly Lys Ser Ser Leu Leu
                    675                 680                 685

Ser Ala Leu Leu Ala Glu Met Asp Lys Val Glu Gly His Val Thr Leu
                    690                 695                 700

Lys Gly Ser Val Ala Tyr Val Pro Gln Gln Ala Trp Ile Gln Asn Asp
    705                 710                 715                 720

Ser Leu Arg Glu Asn Ile Leu Phe Gly His Pro Leu Gln Glu Asn Tyr
                    725                 730                 735

Tyr Lys Ala Val Met Glu Ala Cys Ala Leu Leu Pro Asp Leu Glu Ile
                    740                 745                 750

Leu Pro Ser Gly Asp Arg Thr Glu Ile Gly Glu Lys Gly Val Asn Leu
                    755                 760                 765

Ser Gly Gly Gln Lys Gln Arg Val Ser Leu Ala Arg Ala Val Tyr Ser
                    770                 775                 780

Asn Ser Asp Ile Tyr Leu Phe Asp Asp Pro Leu Ser Ala Val Asp Ala
    785                 790                 795                 800

His Val Gly Lys His Ile Phe Glu Lys Val Val Gly Pro Met Gly Leu
                    805                 810                 815

Leu Lys Asn Lys Thr Arg Ile Leu Val Thr His Gly Ile Ser Tyr Leu
                    820                 825                 830

Pro Gln Val Asp Val Ile Ile Val Met Ser Gly Gly Lys Ile Ser Glu
                    835                 840                 845

Met Gly Ser Tyr Gln Glu Leu Leu Asp Arg Asp Gly Ala Phe Ala Glu
                    850                 855                 860

Phe Leu Arg Thr Tyr Ala Asn Ala Glu Gln Asp Leu Ala Ser Glu Asp
    865                 870                 875                 880

Asp Ser Val Ser Gly Ser Gly Lys Glu Ser Lys Pro Val Glu Asn Gly
                    885                 890                 895

Met Leu Val Thr Asp Thr Val Gly Lys His Leu Gln Arg His Leu Ser
                    900                 905                 910

Asn Ser Ser Ser His Ser Gly Asp Thr Ser Gln Gln His Ser Ser Ile
                    915                 920                 925

Ala Glu Leu Gln Lys Ala Gly Ala Lys Glu Glu Thr Trp Lys Leu Met
                    930                 935                 940

Glu Ala Asp Lys Ala Gln Thr Gly Gln Val Gln Leu Ser Val Tyr Trp
    945                 950                 955                 960

Asn Tyr Met Lys Ala Ile Gly Leu Phe Ile Thr Phe Leu Ser Ile Phe
                    965                 970                 975
```

```
Leu Phe Leu Cys Asn His Val Ser Ala Leu Ala Ser Asn Tyr Trp Leu
            980                 985                 990
Ser Leu Trp Thr Asp Pro Pro Val Val Asn Gly Thr Gln Ala Asn
        995                1000                1005
Arg Asn Phe Arg Leu Ser Val Tyr Gly Ala Leu Gly Ile Leu Gln Gly
    1010                1015                1020
Ala Ala Ile Phe Gly Tyr Ser Met Ala Val Ser Ile Gly Gly Ile Phe
1025                1030                1035                1040
Ala Ser Arg Arg Leu His Leu Asp Leu Leu Tyr Asn Val Leu Arg Ser
            1045                1050                1055
Pro Met Ser Phe Phe Glu Arg Thr Pro Ser Gly Asn Leu Val Asn Arg
        1060                1065                1070
Phe Ser Lys Glu Leu Asp Thr Val Asp Ser Met Ile Pro Gln Val Ile
    1075                1080                1085
Lys Met Phe Met Gly Ser Leu Phe Ser Val Ile Gly Ala Val Ile Ile
    1090                1095                1100
Ile Leu Leu Ala Thr Pro Ile Ala Ala Val Ile Pro Pro Leu Gly
1105                1110                1115                1120
Leu Val Tyr Phe Phe Val Gln Arg Phe Tyr Val Ala Ser Ser Arg Gln
            1125                1130                1135
Leu Lys Arg Leu Glu Ser Val Ser Arg Ser Pro Val Tyr Ser His Phe
            1140                1145                1150
Asn Glu Thr Leu Leu Gly Val Ser Val Ile Arg Ala Phe Glu Glu Gln
        1155                1160                1165
Glu Arg Phe Ile His Gln Ser Asp Leu Lys Val Asp Glu Asn Gln Lys
    1170                1175                1180
Ala Tyr Tyr Pro Ser Ile Val Ala Asn Arg Trp Leu Ala Val Arg Leu
1185                1190                1195                1200
Glu Cys Val Gly Asn Cys Ile Val Leu Phe Ala Ala Leu Phe Ala Val
            1205                1210                1215
Ile Ser Arg His Ser Leu Ser Ala Gly Leu Val Gly Leu Ser Val Ser
        1220                1225                1230
Tyr Ser Leu Gln Ile Thr Ala Tyr Leu Asn Trp Leu Val Arg Met Ser
    1235                1240                1245
Ser Glu Met Glu Thr Asn Ile Val Ala Val Glu Arg Leu Lys Glu Tyr
    1250                1255                1260
Ser Glu Thr Glu Lys Glu Ala Pro Trp Gln Ile Gln Glu Thr Ala Pro
1265                1270                1275                1280
Pro Ser Thr Trp Pro His Ser Gly Arg Val Glu Phe Arg Asp Tyr Cys
            1285                1290                1295
Leu Arg Tyr Arg Glu Asp Leu Asp Leu Val Leu Lys His Ile Asn Val
            1300                1305                1310
Thr Ile Glu Gly Gly Lys Val Gly Ile Val Gly Arg Thr Gly Ala
        1315                1320                1325
Gly Lys Ser Ser Leu Thr Leu Gly Leu Phe Arg Ile Asn Glu Ser Ala
    1330                1335                1340
Glu Gly Glu Ile Ile Ile Asp Gly Val Asn Ile Ala Lys Ile Gly Leu
1345                1350                1355                1360
His Asn Leu Arg Phe Lys Ile Thr Ile Ile Pro Gln Asp Pro Val Leu
            1365                1370                1375
Phe Ser Gly Ser Leu Arg Met Asn Leu Asp Pro Phe Ser Gln Tyr Ser
            1380                1385                1390
```

```
Asp Glu Glu Val Trp Met Ala Leu Glu Leu Ala His Leu Lys Gly Phe
        1395                1400                1405
Val Ser Ala Leu Pro Asp Lys Leu Asn His Glu Cys Ala Glu Gly Gly
    1410                1415                1420
Glu Asn Leu Ser Val Gly Gln Arg Gln Leu Val Cys Leu Ala Arg Ala
1425                1430                1435                1440
Leu Leu Arg Lys Thr Lys Ile Leu Val Leu Asp Glu Ala Thr Ala Ala
            1445                1450                1455
Val Asp Leu Glu Thr Asp Asn Leu Ile Gln Ser Thr Ile Arg Thr Gln
        1460                1465                1470
Phe Glu Asp Cys Thr Val Leu Thr Ile Ala His Arg Leu Asn Thr Ile
    1475                1480                1485
Met Asp Tyr Thr Arg Val Ile Val Leu Asp Lys Gly Glu Val Arg Glu
    1490                1495                1500
Cys Gly Ala Pro Ser Glu Leu Leu Gln Gln Arg Gly Ile Phe Tyr Ser
1505                1510                1515                1520
Met Ala Lys Asp Ala Gly Leu Val
            1525
```

<210> SEQ ID NO 89
<211> LENGTH: 1794
<212> TYPE: DNA
<213> ORGANISM: Homo sapiens

<400> SEQUENCE: 89

```
acgcgtagcc acaagaccgg gtccgtttct ggttgccgtt cccgcaggtg acgctgcaga     60
cagaccagag actccagtca ccctcgccat ctgtggaatc atattctggc tgatctttgg    120
tttcaaaagt ccggtggcct ggggctgtat ggtcccaccc cctgggggg ttgaggaagt    180
tgctgtcgtc tgaggtactg ccgtacgtgt agtcctgaaa ccagcttttc tctctccaaa    240
gaagcaccaa gggagcatct ggaccaccag gctgcacacc aacccttccc cagaccgcga    300
ttccgacaag agacggggca cccttcattg caaagagatt tccccagatc ctttctcctt    360
gatctaccaa actttccaga tctttccaaa gctgatatca atgggcagaa tccaaatatc    420
caggtcacca tagaggtggt cgacggtcct gactctgaag cagataaaga tcagcatccg    480
gagaataagc ccagctggtc agtcccatcc cccgactggc gggcctggtg cagaggtcc    540
ctgtccttgg ccagggcaaa cagcggggac caggactaca agtacgacag tacctcagac    600
gacagcaact tcctcaaccc ccccaggggg tggaccata cagccccagg ccaccggact    660
tttgaaacca agatcagcc agaatatgat tccacagatg gcgagggtga ctggagtctc    720
tggtctgtct gcagcgtcac ctgcgggaac ggcaaccaga acggacccg gtcttgtggc    780
tacgcgtgca ctgcaacaga atcgaggacc tgtgaccgtc caaactgccc agcttgcacc    840
ggattcctga ttgtaaagga agcttggtta ggggtggtag tttggcatgt ccctgcacct    900
ccaactggca acccctctgt gcctttgcct gaggtctttc tctggacccg agcccagctg    960
    cgcatgaatg cacagggcat tcctagctgg aaatccagga ccagtcccct gtcagtgatg   1020
    aatgggagct ggtggataaa aactcagatc cccatcaata aaaacaaatc cggactcagt   1080
    aaggagagga tttattcaaa ggattattgc agggaggcaa gggatgttat ctcccctatta   1140
    ttgcaatggg atgaacgctg tgaccataag atctgcaagc atctcaagga cagcctggt   1200
    gtcacatgct ccttgaagca cctcctgtgg gccggttgta cacgcggtga gagggtttct   1260
    cttgtgcctt ttccagacac agacagctgt gagcgctgga tgagcttcaa agcgaggttc   1320
    ttaaagaagt acatgcacaa ggtgatgaat gacctgccca gctgcccctg ctcctacccc   1380
    actgaggtgg cctacagcac ggcgacatc ttcgaccgca tcaagcgcaa ggacttccgc   1440
    tggaaggacg ccagcggcc caaggagaag ctggagatct acaagcccac tgcccggtac   1500
    tgcatccgct ccatgctgtc cctggagagc accacgctgg cggcacagca ctgctgctac   1560
    ggcgacaaca tgcagctcat caccagggggg aaggggcgg gcacgcccaa cctcatcagc   1620
    accgagttct ccgcggagct ccactacaag gtggacgtcc tgccctggat tatctgcaag   1680
```

```
                            ggtgactgga gcaggtataa cgaggcccgg cctcccaaca acggacagaa gtgcacagag  1740
                            agccctcgg acgaggacta catcaagcag ttccaagagg ccagggaata ttaa         1794
```

<210> SEQ ID NO 90
<211> LENGTH: 539
<212> TYPE: PRT
<213> ORGANISM: Homo sapiens

<400> SEQUENCE: 90

```
Gly Ser Cys Cys Arg Leu Arg Tyr Cys Arg Thr Cys Ser Pro Glu Thr
 1               5                  10                  15

Ser Phe Ser Leu Ser Lys Glu Ala Pro Arg Glu His Leu Asp His Gln
             20                  25                  30

Ala Ala His Gln Pro Phe Pro Arg Pro Arg Phe Arg Gln Glu Thr Gly
         35                  40                  45

His Pro Ser Leu Gln Arg Asp Phe Pro Arg Ser Phe Leu Leu Asp Leu
     50                  55                  60

Pro Asn Phe Pro Asp Leu Ser Lys Ala Asp Ile Asn Gly Gln Asn Pro
 65                  70                  75                  80

Asn Ile Gln Val Thr Ile Glu Val Val Asp Gly Pro Asp Ser Glu Ala
                 85                  90                  95

Asp Lys Asp Gln His Pro Glu Asn Lys Pro Ser Trp Ser Val Pro Ser
            100                 105                 110

Pro Asp Trp Arg Ala Trp Trp Gln Arg Ser Leu Ser Leu Ala Arg Ala
        115                 120                 125

Asn Ser Gly Asp Gln Asp Tyr Lys Tyr Asp Ser Thr Ser Asp Asp Ser
130                 135                 140

Asn Phe Leu Asn Pro Pro Arg Gly Trp Asp His Thr Ala Pro Gly His
145                 150                 155                 160

Arg Thr Phe Glu Thr Lys Asp Gln Pro Glu Tyr Asp Ser Thr Asp Gly
                165                 170                 175

Glu Gly Asp Trp Ser Leu Trp Ser Val Cys Ser Val Thr Cys Gly Asn
            180                 185                 190

Gly Asn Gln Lys Arg Thr Arg Ser Cys Gly Tyr Ala Cys Thr Ala Thr
        195                 200                 205

Glu Ser Arg Thr Cys Asp Arg Pro Asn Cys Pro Ala Cys Thr Gly Phe
    210                 215                 220

Leu Ile Val Lys Glu Ala Trp Leu Gly Val Val Trp His Val Pro
225                 230                 235                 240

Ala Pro Pro Thr Gly Asn Pro Ser Val Pro Leu Pro Glu Val Phe Leu
                245                 250                 255

Trp Thr Arg Ala Gln Leu Arg Met Asn Ala Gln Gly Ile Pro Ser Trp
            260                 265                 270

Lys Ser Arg Thr Ser Pro Leu Ser Val Met Asn Gly Ser Trp Trp Ile
        275                 280                 285

Lys Thr Gln Ile Pro Ile Asn Lys Asn Lys Ser Gly Leu Ser Lys Glu
    290                 295                 300

Arg Ile Tyr Ser Lys Asp Tyr Cys Arg Glu Ala Arg Asp Val Ile Ser
305                 310                 315                 320

Leu Leu Leu Gln Trp Asp Glu Arg Cys Asp His Lys Ile Cys Lys His
                325                 330                 335

Leu Lys Glu Gln Pro Gly Val Thr Cys Ser Leu Lys His Leu Leu Trp
            340                 345                 350

Ala Gly Cys Thr Arg Gly Glu Arg Val Ser Leu Trp Pro Phe Pro Asp
        355                 360                 365
```

```
Thr Asp Ser Cys Glu Arg Trp Met Ser Phe Lys Ala Arg Phe Leu Lys
    370                 375                 380
Lys Tyr Met His Lys Val Met Asn Asp Leu Pro Ser Cys Pro Cys Ser
385                 390                 395                 400
Tyr Pro Thr Glu Val Ala Tyr Ser Thr Ala Asp Ile Phe Asp Arg Ile
                405                 410                 415
Lys Arg Lys Asp Phe Arg Trp Lys Asp Ala Ser Gly Pro Lys Glu Lys
            420                 425                 430
Leu Glu Ile Tyr Lys Pro Thr Ala Arg Tyr Cys Ile Arg Ser Met Leu
        435                 440                 445
Ser Leu Glu Ser Thr Thr Leu Ala Ala Gln His Cys Cys Tyr Gly Asp
    450                 455                 460
Asn Met Gln Leu Ile Thr Arg Gly Lys Gly Ala Gly Thr Pro Asn Leu
465                 470                 475                 480
Ile Ser Thr Glu Phe Ser Ala Glu Leu His Tyr Lys Val Asp Val Leu
                485                 490                 495
Pro Trp Ile Ile Cys Lys Gly Asp Trp Ser Arg Tyr Asn Glu Ala Arg
            500                 505                 510
Pro Pro Asn Asn Gly Gln Lys Cys Thr Glu Ser Pro Ser Asp Glu Asp
        515                 520                 525
Tyr Ile Lys Gln Phe Gln Glu Ala Arg Glu Tyr
    530                 535

<210> SEQ ID NO 91
<211> LENGTH: 1238
<212> TYPE: DNA
<213> ORGANISM: Homo sapiens

<400> SEQUENCE: 91
gtacgtgtag tcctgaaacc agcttttctc tctccaaaga agcaccaagg gagcatctgg      60
accaccaggc tgcacaccaa cccttcccca gaccgcgatt ccgacaagag acggggcacc     120
cttcattgca aagagatttc cccagatcct ttctccttga tctaccaaac tttccagatc     180
tttccaaagc tgatatcaat gggcagaatc caaatatcca ggtcaccata gaggtggtcg     240
acggtcctga ctctgaagca gataaagatc agcatccgga gaataagccc agctggtcag     300
tcccatcccc cgactggcgg gcctggtggc agaggtccct gtccttggcc agggcaaaca     360
gcggggacca ggactacaag tacgacagta cctcagacga cagcaacttc ctcaaccccc     420 ccaggggtg ggaccataca gccccaggcc accggacttt tgaaaccaaa gatcagccag      480
aatatgattc cacagatggc gagggtgact ggagtctctg gtctgtctgc agcgtcacct     540
gcgggaacgg caaccagaaa cggacccggt cttgtggcta cgcgtgcact gcaacagaat     600
cgaggacctg tgaccgtcca aactgcccag gaattgaaga cacttttagg acagctgcca     660
ccgaagtgag tctgcttgcg ggaagcgagg agtttaatgc caccaaactg tttgaagttg     720
acacagacag ctgtgagcgc tggatgagct gcaaaagcga gttcttaaag aagtacatgc     780
acaaggtgat gaatgacctg cccagctgcc cctgctccta ccccactgag gtggcctaca     840
gcacggctga catcttcgac cgcatcaagc gcaaggactt ccgctggaag gacgccagcg     900
ggcccaagga gaagctggag atctacaagc ccactgcccg gtactgcatc cgctccatgc     960
tgtccctgga gagcaccacg ctggcggcac agcactgctg ctacggcgac aacatgcagc   1020
    tcatcaccag ggcaaggggg gcgggcacgc ccaacctcat cggcaccgag ttctccgcgg   1080
    agctccacta caaggtggac gtcctgccct ggattatctg caagggtgac tggagcaggt   1140
    ataacgaggc ccggcctccc aacaacggac aggagtgcac agagagcccc tcggacgagg   1200
    actacatcaa gcagttccaa gaggccaggg aatattaa                           1238
```

<210> SEQ ID NO 92
<211> LENGTH: 411
<212> TYPE: PRT
<213> ORGANISM: Homo sapiens

<400> SEQUENCE: 92

```
Thr Cys Ser Pro Glu Thr Ser Phe Ser Leu Ser Lys Glu Ala Pro Arg
  1               5                  10                  15

Glu His Leu Asp His Gln Ala Ala His Gln Pro Phe Pro Arg Pro Arg
             20                  25                  30

Phe Arg Gln Glu Thr Gly His Pro Ser Leu Gln Arg Asp Phe Pro Arg
         35                  40                  45

Ser Phe Leu Leu Asp Leu Pro Asn Phe Pro Asp Leu Ser Lys Ala Asp
     50                  55                  60

Ile Asn Gly Gln Asn Pro Asn Ile Gln Val Thr Ile Glu Val Val Asp
 65                  70                  75                  80

Gly Pro Asp Ser Glu Ala Asp Lys Asp Gln His Pro Glu Asn Lys Pro
                 85                  90                  95

Ser Trp Ser Val Pro Ser Pro Asp Trp Arg Ala Trp Gln Arg Ser
            100                 105                 110

Leu Ser Leu Ala Arg Ala Asn Ser Gly Asp Gln Asp Tyr Lys Tyr Asp
        115                 120                 125

Ser Thr Ser Asp Asp Ser Asn Phe Leu Asn Pro Pro Arg Gly Trp Asp
    130                 135                 140

His Thr Ala Pro Gly His Arg Thr Phe Glu Thr Lys Asp Gln Pro Glu
145                 150                 155                 160

Tyr Asp Ser Thr Asp Gly Glu Gly Asp Trp Ser Leu Trp Ser Val Cys
                165                 170                 175

Ser Val Thr Cys Gly Asn Gly Asn Gln Lys Arg Thr Arg Ser Cys Gly
            180                 185                 190

Tyr Ala Cys Thr Ala Thr Glu Ser Arg Thr Cys Asp Arg Pro Asn Cys
        195                 200                 205

Pro Gly Ile Glu Asp Thr Phe Arg Thr Ala Thr Glu Val Ser Leu
    210                 215                 220

Leu Ala Gly Ser Glu Glu Phe Asn Ala Thr Lys Leu Phe Glu Val Asp
225                 230                 235                 240

Thr Asp Ser Cys Glu Arg Trp Met Ser Cys Lys Ser Glu Phe Leu Lys
                245                 250                 255

Lys Tyr Met His Lys Val Met Asn Asp Leu Pro Ser Cys Pro Cys Ser
            260                 265                 270

Tyr Pro Thr Glu Val Ala Tyr Ser Thr Ala Asp Ile Phe Asp Arg Ile
        275                 280                 285

Lys Arg Lys Asp Phe Arg Trp Lys Asp Ala Ser Gly Pro Lys Glu Lys
    290                 295                 300

Leu Glu Ile Tyr Lys Pro Thr Ala Arg Tyr Cys Ile Arg Ser Met Leu
305                 310                 315                 320

Ser Leu Glu Ser Thr Thr Leu Ala Ala Gln His Cys Cys Tyr Gly Asp
                325                 330                 335

Asn Met Gln Leu Ile Thr Arg Gly Lys Gly Ala Gly Thr Pro Asn Leu
            340                 345                 350

Ile Gly Thr Glu Phe Ser Ala Glu Leu His Tyr Lys Val Asp Val Leu
        355                 360                 365

Pro Trp Ile Ile Cys Lys Gly Asp Trp Ser Arg Tyr Asn Glu Ala Arg
```

```
            370              375              380
Pro Pro Asn Asn Gly Gln Glu Cys Thr Glu Ser Pro Ser Asp Glu Asp
385                 390                 395                 400

Tyr Ile Lys Gln Phe Gln Glu Ala Arg Glu Tyr
            405                 410

<210> SEQ ID NO 93
<211> LENGTH: 391
<212> TYPE: PRT
<213> ORGANISM: Homo sapiens

<400> SEQUENCE: 93

His Gln Ala Ala His Gln Pro Phe Pro Arg Pro Arg Phe Arg Gln Glu
  1               5                  10                  15

Thr Gly His Pro Ser Leu Gln Arg Asp Phe Pro Arg Ser Phe Leu Leu
             20                  25                  30

Asp Leu Pro Asn Phe Pro Asp Leu Ser Lys Ala Asp Ile Asn Gly Gln
         35                  40                  45

Asn Pro Asn Ile Gln Val Thr Ile Glu Val Val Asp Gly Pro Asp Ser
     50                  55                  60

Glu Ala Asp Lys Asp Gln His Pro Glu Asn Lys Pro Ser Trp Ser Val
 65                  70                  75                  80

Pro Ser Pro Asp Trp Arg Ala Trp Trp Gln Arg Ser Leu Ser Leu Ala
                 85                  90                  95

Arg Ala Asn Ser Gly Asp Gln Asp Tyr Lys Tyr Asp Ser Thr Ser Asp
                100                 105                 110

Asp Ser Asn Phe Leu Asn Pro Pro Arg Gly Trp Asp His Thr Ala Pro
            115                 120                 125

Gly His Arg Thr Phe Glu Thr Lys Asp Gln Pro Glu Tyr Asp Ser Thr
        130                 135                 140

Asp Gly Glu Gly Asp Trp Ser Leu Trp Ser Val Cys Ser Val Thr Cys
145                 150                 155                 160

Gly Asn Gly Asn Gln Lys Arg Thr Arg Ser Cys Gly Tyr Ala Cys Thr
                165                 170                 175

Ala Thr Glu Ser Arg Thr Cys Asp Arg Pro Asn Cys Pro Gly Ile Glu
                180                 185                 190

Asp Thr Phe Arg Thr Ala Ala Thr Glu Val Ser Leu Leu Ala Gly Ser
            195                 200                 205

Glu Glu Phe Asn Ala Thr Lys Leu Phe Glu Val Asp Thr Asp Ser Cys
210                 215                 220

Glu Arg Trp Met Ser Cys Lys Ser Glu Phe Leu Lys Lys Tyr Met His
225                 230                 235                 240

Lys Val Met Asn Asp Leu Pro Ser Cys Pro Cys Ser Tyr Pro Thr Glu
                245                 250                 255

Val Ala Tyr Ser Thr Ala Asp Ile Phe Asp Arg Ile Lys Arg Lys Asp
                260                 265                 270

Phe Arg Trp Lys Asp Ala Ser Gly Pro Lys Glu Lys Leu Glu Ile Tyr
            275                 280                 285

Lys Pro Thr Ala Arg Tyr Cys Ile Arg Ser Met Leu Ser Leu Glu Ser
        290                 295                 300

Thr Thr Leu Ala Ala Gln His Cys Cys Tyr Gly Asp Asn Met Gln Leu
305                 310                 315                 320

Ile Thr Arg Gly Lys Gly Ala Gly Thr Pro Asn Leu Ile Ser Thr Glu
                325                 330                 335
```

```
Phe Ser Ala Glu Leu His Tyr Lys Val Asp Val Leu Pro Trp Ile Ile
        340                 345                 350

Cys Lys Gly Asp Trp Ser Arg Tyr Asn Glu Ala Arg Pro Pro Asn Asn
            355                 360                 365

Gly Gln Lys Cys Thr Glu Ser Pro Ser Asp Glu Asp Tyr Ile Lys Gln
        370                 375                 380

Phe Gln Glu Ala Arg Glu Tyr
385                 390

<210> SEQ ID NO 94
<211> LENGTH: 658
<212> TYPE: PRT
<213> ORGANISM: Homo sapiens

<400> SEQUENCE: 94

Met Arg Ala Leu Arg Asp Arg Ala Gly Leu Leu Cys Val Leu Leu
  1               5                  10                  15

Leu Ala Ala Leu Leu Glu Ala Ala Leu Gly Leu Pro Val Lys Lys Pro
                20                  25                  30

Arg Leu Arg Gly Pro Arg Pro Gly Ser Leu Thr Arg Leu Ala Glu Val
            35                  40                  45

Ser Gly Gly Gly Thr Gly Leu Arg Ser Ala Leu Ser Val Pro Pro Pro
        50                  55                  60

Gln Pro Ala Gly Ser Ser Arg Ala Gly Ser Gly Thr Gly Thr His Thr
 65                  70                  75                  80

Gly Ser Asp Pro Pro Met Glu Arg Gly Ala Gly Ala Gly Arg Lys Leu
                 85                  90                  95

Pro Asp Thr Gly Arg Cys Pro Val Thr Glu Gly Ser Thr Val Gln Leu
            100                 105                 110

Ile Ala Pro Trp Asn Ala Ala Asp Val His Ser His Gly Asp Lys Asp
        115                 120                 125

Ser Gln Thr Cys Ile Arg Val Ser Ala Ser Pro Asp Pro Arg Pro Leu
130                 135                 140

Lys Glu Glu Glu Glu Ala Pro Leu Leu Pro Arg Thr His Leu Gln Ala
145                 150                 155                 160

Glu Pro His Gln His Gly Cys Trp Thr Val Thr Glu Pro Ala Ala Met
                165                 170                 175

Thr Pro Gly Asn Ala Thr Pro Pro Arg Thr Pro Glu Val Thr Pro Leu
            180                 185                 190

Arg Leu Glu Leu Gln Lys Leu Pro Gly Leu Ala Asn Thr Thr Leu Ser
        195                 200                 205

Thr Pro Asn Pro Asp Thr Gln Ala Ser Ala Ser Pro Asp Pro Arg Pro
    210                 215                 220

Leu Arg Glu Glu Glu Ala Arg Leu Leu Pro Arg Thr His Leu Gln
225                 230                 235                 240

Ala Glu Leu His Gln His Gly Cys Trp Thr Val Thr Glu Pro Ala Ala
                245                 250                 255

Leu Thr Pro Gly Asn Ala Thr Pro Pro Arg Thr Gln Glu Val Thr Pro
            260                 265                 270

Leu Leu Leu Glu Leu Gln Lys Leu Pro Glu Leu Val His Ala Thr Leu
        275                 280                 285

Ser Thr Pro Asn Pro Asp Asn Gln Val Thr Ile Lys Val Val Glu Asp
    290                 295                 300

Pro Gln Ala Glu Val Ser Ile Asp Leu Leu Ala Glu Pro Ser Asn Pro
305                 310                 315                 320
```

```
Pro Pro Gln Asp Thr Leu Ser Trp Leu Pro Ala Leu Trp Ser Phe Leu
                325                 330                 335
Trp Gly Asp Tyr Lys Gly Glu Lys Asp Arg Ala Pro Gly Glu Lys
            340                 345                 350
Gly Glu Glu Lys Glu Glu Asp Glu Asp Tyr Pro Ser Glu Asp Ile Glu
        355                 360                 365
Gly Glu Asp Gln Glu Asp Lys Glu Glu Asp Glu Glu Gln Ala Leu
        370                 375                 380
Trp Phe Asn Gly Thr Thr Asp Asn Trp Asp Gln Gly Trp Leu Ala Pro
385                 390                 395                 400
Gly Asp Trp Val Phe Lys Asp Ser Val Ser Tyr Asp Tyr Glu Pro Gln
                405                 410                 415
Lys Glu Trp Ser Pro Trp Ser Pro Cys Ser Gly Asn Cys Ser Thr Gly
                420                 425                 430
Lys Gln Gln Arg Thr Arg Pro Cys Gly Tyr Gly Cys Thr Ala Thr Glu
            435                 440                 445
Thr Arg Thr Cys Asp Leu Pro Ser Cys Pro Gly Thr Glu Asp Lys Asp
    450                 455                 460
Thr Leu Gly Leu Pro Ser Glu Glu Trp Lys Leu Leu Ala Arg Asn Ala
465                 470                 475                 480
Thr Asp Met His Asp Gln Asp Val Asp Ser Cys Glu Lys Trp Leu Asn
                485                 490                 495
Cys Lys Ser Asp Phe Leu Ile Lys Tyr Leu Ser Gln Met Leu Arg Asp
                500                 505                 510
Leu Pro Ser Cys Pro Cys Ala Tyr Pro Leu Glu Ala Met Asp Ser Pro
            515                 520                 525
Val Ser Leu Gln Asp Glu His Gln Gly Arg Ser Phe Arg Trp Arg Asp
        530                 535                 540
Ala Ser Gly Pro Arg Glu Arg Leu Asp Ile Tyr Gln Pro Thr Ala Arg
545                 550                 555                 560
Phe Cys Leu Arg Ser Met Leu Ser Gly Glu Ser Ser Thr Leu Ala Ala
                565                 570                 575
Gln His Cys Cys Tyr Asp Glu Asp Ser Arg Leu Leu Thr Arg Gly Lys
            580                 585                 590
Gly Ala Gly Met Pro Asn Leu Ile Ser Thr Asp Phe Ser Pro Lys Leu
        595                 600                 605
His Phe Lys Phe Asp Thr Thr Pro Trp Ile Leu Cys Lys Gly Asp Trp
    610                 615                 620
Ser Arg Leu His Ala Val Leu Pro Pro Asn Asn Gly Arg Ala Cys Thr
625                 630                 635                 640
Asp Asn Pro Leu Glu Glu Tyr Leu Ala Gln Leu Gln Glu Ala Lys
                645                 650                 655
Glu Tyr

<210> SEQ ID NO 95
<211> LENGTH: 60
<212> TYPE: PRT
<213> ORGANISM: Homo sapiens

<400> SEQUENCE: 95

Asn Asn Leu Asn Val Gly Ser Asp Thr Thr Ser Glu Thr Ser Phe Ser
  1               5                  10                  15
Leu Ser Lys Glu Ala Pro Arg Glu His Leu Asp His Gln Ala Ala His
            20                  25                  30
```

Gln Pro Phe Pro Arg Pro Arg Phe Arg Gln Glu Thr Gly His Pro Ser
            35                  40                  45

Leu Gln Arg Asp Phe Pro Arg Ser Phe Leu Leu Asp
    50                  55                  60

<210> SEQ ID NO 96
<211> LENGTH: 660
<212> TYPE: PRT
<213> ORGANISM: Cryptosporidium wrairi

<400> SEQUENCE: 96

Lys Leu Thr His Tyr Ser Val Gly Gly His Ala Ser Thr Ser Arg Val
  1               5                  10                  15

Lys Gly Arg Ser Ser Ser Gly Ser Ser Ser Gly Asp Phe Lys Val Pro
             20                  25                  30

Gly Leu Asn Gly Tyr Leu Cys Pro Ser Tyr Asn Arg Asp Pro Arg Gly
         35                  40                  45

Phe Gly Cys Phe Gly Leu Asn Thr Ala Tyr Thr Val Lys Lys Asn Ser
     50                  55                  60

Trp Gln Glu Cys Ala Asn Gln Cys Tyr Trp Ser Lys Tyr Thr Ile Tyr
 65                  70                  75                  80

Gly Asn Cys Gln Arg Ser Val Tyr Asn Ser Asn Asn Gln Asp Cys His
                 85                  90                  95

Ile Lys Gly Gly Asp Asn Asp Cys Met Lys Ser Pro Asp Gly Met Ile
            100                 105                 110

Leu Thr Asn Arg Gln Ser Tyr Met Ile Gly Glu Cys Ala Thr Thr Cys
        115                 120                 125

Thr Val Ser Ser Trp Ser Ser Trp Thr Pro Cys Ser Gly Val Cys Gly
    130                 135                 140

Glu Met Arg Ser Arg Thr Arg Ser Val Leu Ser Phe Pro Arg Tyr Asp
145                 150                 155                 160

His Glu Tyr Cys Pro His Leu Ile Glu Tyr Ser Asn Cys Val Val Gln
                165                 170                 175

Asn Lys Cys Pro Glu Asn Cys Pro Gln Tyr Gly Val Ser Ile Leu Gly
            180                 185                 190

Trp Gly Cys Gln Phe Glu Ser Met Phe Ser Phe Asn Lys Asn Leu Phe
        195                 200                 205

Val Ser Tyr Glu Glu Asp Trp Lys Gly Cys Met Ser Thr Cys Lys Gln
    210                 215                 220

Asp Pro Phe Cys Val Ala Trp Ser Tyr Asn Ala Thr Leu Ser Glu Gly
225                 230                 235                 240

Pro Asp Ser Val Gly Phe Ser Arg Glu Tyr Arg Pro Cys Tyr Thr His
                245                 250                 255

Arg Phe Ala Ser Gly Cys Gln Ala Leu Ala Pro Gly Trp Val Ser Gly
            260                 265                 270

Asn Lys Tyr Thr Arg Asp Val Asp Cys Glu Thr Gly Thr Cys Ile His
        275                 280                 285

Asn Glu Trp Ser Ser Trp Thr Cys Lys Asp Pro Cys Ser Asn Thr
    290                 295                 300

Glu Thr Met Ser Arg Asn Arg Thr Val Lys Ser Val Ser Gln Asn Trp
305                 310                 315                 320

Ala Ser Thr Thr Cys Arg Asp Glu Ser Gln Ile Gln Leu Cys Ser Glu
                325                 330                 335

Asn Pro Gln Ser Ile Glu Thr Cys Lys Thr Cys Leu Val Gly Ser Trp

-continued

```
                340                 345                 350
Ser Glu Trp Ser Asp Cys Ser Thr Ser Cys Gly Glu Gly Asn Arg Ile
            355                 360                 365
Arg Thr Arg Glu Ser Thr Lys Pro Pro Leu Asn Gly Asp Glu Ser Thr
370                 375                 380
Cys Pro Glu Leu Ile Ala Lys Glu Ser Cys Asn Lys Asp Val Glu Cys
385                 390                 395                 400
Pro Asn Ile Gln Cys Glu Leu Gly Glu Trp Ser Ser Trp Ser Pro Cys
                405                 410                 415
Ser Val Thr Cys Gly Ser Gly Thr Thr Ser Arg Asn Arg Glu Val Lys
            420                 425                 430
Gly Glu Asn Cys Thr Glu Leu Pro Thr Glu Ser Lys Lys Cys Asn Leu
        435                 440                 445
Ala Asn Cys Gly Asp Asn Ser Ala Ser Cys Thr Ala Val Met Ser Val
    450                 455                 460
Trp Ser Glu Trp Ser Ala Cys Ser Glu Lys Cys Asp Gln Gly Leu Val
465                 470                 475                 480
Arg Arg Tyr Arg Asp Phe Asp Phe Ser Lys Ile Gly Val Phe Gly Tyr
                485                 490                 495
Val Pro Pro Gly Lys Ser Glu Gln Asn Lys Val Arg Glu Ile Cys
            500                 505                 510
Lys Asp Thr Pro Thr Leu Glu Glu Pro Cys Thr Ser Gly Val Thr
        515                 520                 525
Cys Thr Pro Gly Cys Lys Tyr Thr Glu Trp Ser Ala Trp Ser Ser Cys
    530                 535                 540
Asp Cys Ser Gly Ser Gln Thr Arg Asp Arg Val Val Thr Phe Pro Glu
545                 550                 555                 560
Gly Ile Ile Asp Ala Ile Cys Gln Ser Ser Lys Asp Thr Arg Ser Cys
                565                 570                 575
Ser Lys Pro Glu Gly Cys Thr Glu Thr Pro Asp Ser Gly Asp Ala
            580                 585                 590
Thr Leu Ala Ile Ala Ile Gly Leu Pro Val Gly Ile Leu Gly Leu Cys
        595                 600                 605
Ile Ile Ala Gly Ser Leu Phe Leu Ile Gly Arg Ser Gly Asn Gln
    610                 615                 620
Glu Glu Asp Glu Thr Ser Tyr Gln Tyr Phe Asp Gln Pro Ser Ala Ala
625                 630                 635                 640
Leu Asp Gln Asp Ser Glu Tyr Val Gln Glu Ile Gly Pro Glu Ser Gln
                645                 650                 655
Asn Trp Ala Ser
            660

<210> SEQ ID NO 97
<211> LENGTH: 831
<212> TYPE: PRT
<213> ORGANISM: Homo sapiens

<400> SEQUENCE: 97

Met Gly Leu Ala Trp Gly Leu Gly Val Leu Phe Leu Met His Val Cys
1               5                   10                  15
Gly Thr Asn Arg Ile Pro Glu Ser Gly Gly Asp Asn Ser Val Phe Asp
            20                  25                  30
Ile Phe Glu Leu Thr Gly Ala Ala Arg Lys Gly Ser Gly Arg Arg Leu
        35                  40                  45
```

-continued

```
Val Lys Gly Pro Asp Pro Ser Ser Pro Ala Phe Arg Ile Glu Asp Ala
 50              55                  60
Asn Leu Ile Pro Pro Val Pro Asp Asp Lys Phe Gln Asp Leu Val Asp
 65              70                  75                  80
Ala Val Arg Thr Glu Lys Gly Phe Leu Leu Ala Ser Leu Arg Gln
                 85                  90                  95
Met Lys Lys Thr Arg Gly Thr Leu Leu Ala Leu Glu Arg Lys Asp His
                100                 105                 110
Ser Gly Gln Val Phe Ser Val Val Ser Asn Gly Lys Ala Gly Thr Leu
                115                 120                 125
Asp Leu Ser Leu Thr Val Gln Gly Lys Gln His Val Val Ser Val Glu
130                 135                 140
Glu Ala Leu Leu Ala Thr Gly Gln Trp Lys Ser Ile Thr Leu Phe Val
145                 150                 155                 160
Gln Glu Asp Arg Ala Gln Leu Tyr Ile Asp Cys Glu Lys Met Glu Asn
                165                 170                 175
Ala Glu Leu Asp Val Pro Ile Gln Ser Val Phe Thr Arg Asp Leu Ala
                180                 185                 190
Ser Ile Ala Arg Leu Arg Ile Ala Lys Gly Gly Val Asn Asp Asn Phe
                195                 200                 205
Gln Gly Val Leu Gln Asn Val Arg Phe Val Phe Gly Thr Thr Pro Glu
210                 215                 220
Asp Ile Leu Arg Asn Lys Gly Cys Ser Ser Ser Thr Ser Val Leu Leu
225                 230                 235                 240
Thr Leu Asp Asn Asn Val Val Asn Gly Ser Ser Pro Ala Ile Arg Thr
                245                 250                 255
Asn Tyr Ile Gly His Lys Thr Lys Asp Leu Gln Ala Ile Cys Gly Ile
                260                 265                 270
Ser Cys Asp Glu Leu Ser Ser Met Val Leu Glu Leu Arg Gly Leu Arg
                275                 280                 285
Thr Ile Val Thr Thr Leu Gln Asp Ser Ile Arg Lys Val Thr Glu Glu
290                 295                 300
Asn Lys Glu Leu Ala Asn Glu Leu Arg Arg Pro Pro Leu Cys Tyr His
305                 310                 315                 320
Asn Gly Val Gln Tyr Arg Asn Asn Glu Glu Trp Thr Val Asp Ser Cys
                325                 330                 335
Thr Glu Cys His Cys Gln Asn Ser Val Thr Ile Cys Lys Lys Val Ser
                340                 345                 350
Cys Pro Ile Met Pro Cys Ser Asn Ala Thr Val Pro Asp Gly Glu Cys
                355                 360                 365
Cys Pro Arg Cys Trp Pro Ser Asp Ser Ala Asp Asp Gly Trp Ser Pro
370                 375                 380
Trp Ser Glu Trp Thr Ser Cys Ser Thr Ser Cys Gly Asn Gly Ile Gln
385                 390                 395                 400
Gln Arg Gly Arg Ser Cys Asp Ser Leu Asn Asn Arg Cys Glu Gly Ser
                405                 410                 415
Ser Val Gln Thr Arg Thr Cys His Ile Gln Glu Cys Asp Lys Arg Phe
                420                 425                 430
Lys Gln Asp Gly Gly Trp Ser His Trp Ser Pro Trp Ser Ser Cys Ser
                435                 440                 445
Val Thr Cys Gly Asp Gly Val Ile Thr Arg Ile Arg Leu Cys Asn Ser
450                 455                 460
Pro Ser Pro Gln Met Asn Gly Lys Pro Cys Glu Gly Glu Ala Arg Glu
```

-continued

```
            465                 470                 475                 480

Thr Lys Ala Cys Lys Lys Asp Ala Cys Pro Ile Asn Gly Gly Trp Gly
                485                 490                 495

Pro Trp Ser Pro Trp Asp Ile Cys Ser Val Thr Cys Gly Gly Gly Val
            500                 505                 510

Gln Lys Arg Ser Arg Leu Cys Asn Asn Pro Thr Pro Gln Phe Gly Gly
        515                 520                 525

Lys Asp Cys Val Gly Asp Val Thr Glu Asn Gln Ile Cys Asn Lys Gln
    530                 535                 540

Asp Cys Pro Ile Asp Gly Cys Leu Ser Asn Pro Cys Phe Ala Gly Val
545                 550                 555                 560

Lys Cys Thr Ser Tyr Pro Asp Gly Ser Trp Lys Cys Gly Ala Cys Pro
                565                 570                 575

Pro Gly Tyr Ser Gly Asn Gly Ile Gln Cys Thr Asp Val Asp Glu Cys
            580                 585                 590

Lys Glu Val Pro Asp Ala Cys Phe Asn His Asn Gly Glu His Arg Cys
        595                 600                 605

Glu Asn Thr Asp Pro Gly Tyr Asn Cys Leu Pro Cys Pro Pro Arg Phe
    610                 615                 620

Thr Gly Ser Gln Pro Phe Gly Gln Gly Val Glu His Ala Thr Ala Asn
625                 630                 635                 640

Lys Gln Val Cys Lys Pro Arg Asn Pro Cys Thr Asp Gly Thr His Asp
                645                 650                 655

Cys Asn Lys Asn Ala Lys Cys Asn Tyr Leu Gly His Tyr Ser Asp Pro
            660                 665                 670

Met Tyr Arg Cys Glu Cys Lys Pro Gly Tyr Ala Gly Asn Gly Ile Ile
        675                 680                 685

Cys Gly Glu Asp Thr Asp Leu Asp Gly Trp Pro Asn Glu Asn Leu Val
    690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
                725                 730                 735

Ala Cys Asp Asp Asp Asp Asn Asp Lys Ile Pro Asp Asp Arg Asp
            740                 745                 750

Asn Cys Pro Phe His Tyr Asn Pro Ala Gln Tyr Asp Tyr Asp Arg Asp
        755                 760                 765

Asp Val Gly Asp Arg Cys Asp Asn Cys Pro Tyr Asn His Asn Pro Asp
    770                 775                 780

Gln Ala Asp Thr Asp Asn Asn Gly Glu Gly Asp Ala Cys Ala Ala Asp
785                 790                 795                 800

Ile Asp Gly Asp Gly Ile Leu Asn Glu Arg Asp Asn Cys Gln Tyr Val
                805                 810                 815

Tyr Asn Val Asp Gln Arg Asp Thr Asp Met Asp Gly Val Gly Asp
            820                 825                 830
```

<210> SEQ ID NO 98
<211> LENGTH: 831
<212> TYPE: PRT
<213> ORGANISM: Mus musculus

<400> SEQUENCE: 98

```
Met Glu Leu Leu Arg Gly Leu Gly Val Leu Phe Leu Leu His Met Cys
 1               5                  10                  15
```

-continued

```
Gly Ser Asn Arg Ile Pro Glu Ser Gly Gly Asp Asn Gly Val Phe Asp
            20                  25                  30
Ile Phe Glu Leu Ile Gly Gly Ala Arg Arg Gly Pro Gly Arg Arg Leu
                35                  40                  45
Val Lys Gly Gln Asp Leu Ser Ser Pro Ala Phe Arg Ile Glu Asn Ala
 50                  55                  60
Asn Leu Ile Pro Ala Val Pro Asp Asp Lys Phe Gln Asp Leu Leu Asp
 65                  70                  75                  80
Ala Val Trp Ala Asp Lys Gly Phe Ile Phe Leu Ala Ser Leu Arg Gln
                 85                  90                  95
Met Lys Lys Thr Arg Gly Thr Leu Leu Ala Val Glu Arg Lys Asp Asn
                100                 105                 110
Thr Gly Gln Ile Phe Ser Val Val Ser Asn Gly Lys Ala Gly Thr Leu
                115                 120                 125
Asp Leu Ser Leu Ser Leu Pro Gly Lys Gln Gln Val Val Ser Val Glu
130                 135                 140
Glu Ala Leu Leu Ala Thr Gly Gln Trp Lys Ser Ile Thr Leu Phe Val
145                 150                 155                 160
Gln Glu Asp Arg Ala Gln Leu Tyr Ile Asp Cys Asp Lys Met Glu Ser
                165                 170                 175
Ala Glu Leu Asp Val Pro Ile Gln Ser Ile Phe Thr Arg Asp Leu Ala
                180                 185                 190
Ser Val Ala Arg Leu Arg Val Ala Lys Gly Asp Val Asn Asp Asn Phe
                195                 200                 205
Gln Gly Val Leu Gln Asn Val Arg Phe Val Phe Gly Thr Thr Pro Glu
                210                 215                 220
Asp Ile Leu Arg Asn Lys Gly Cys Ser Ser Thr Asn Val Leu Leu
225                 230                 235                 240
Thr Leu Asp Asn Asn Val Val Asn Gly Ser Ser Pro Ala Ile Arg Thr
                245                 250                 255
Asn Tyr Ile Gly His Lys Thr Lys Asp Leu Gln Ala Ile Cys Gly Leu
                260                 265                 270
Ser Cys Asp Glu Leu Ser Ser Met Val Leu Glu Leu Lys Gly Leu Arg
                275                 280                 285
Thr Ile Val Thr Thr Leu Gln Asp Ser Ile Arg Lys Val Thr Glu Glu
                290                 295                 300
Asn Arg Glu Leu Val Ser Glu Leu Lys Arg Pro Pro Leu Cys Phe His
305                 310                 315                 320
Asn Gly Val Gln Tyr Lys Asn Asn Glu Glu Trp Thr Val Asp Ser Cys
                325                 330                 335
Thr Glu Cys His Cys Gln Asn Ser Val Thr Ile Cys Lys Lys Val Ser
                340                 345                 350
Cys Pro Ile Met Pro Cys Ser Asn Ala Thr Val Pro Asp Gly Glu Cys
                355                 360                 365
Cys Pro Arg Cys Trp Pro Ser Asp Ser Ala Asp Asp Gly Trp Ser Pro
                370                 375                 380
Trp Ser Glu Trp Thr Ser Cys Ser Ala Thr Cys Gly Asn Gly Ile Gln
385                 390                 395                 400
Gln Arg Gly Arg Ser Cys Asp Ser Leu Asn Asn Arg Cys Glu Gly Ser
                405                 410                 415
Ser Val Gln Thr Arg Thr Cys His Ile Gln Glu Cys Asp Lys Arg Phe
                420                 425                 430
Lys Gln Asp Gly Gly Trp Ser His Trp Ser Pro Trp Ser Ser Cys Ser
```

```
                435                 440                 445
Val Thr Cys Gly Asp Gly Val Ile Thr Arg Ile Arg Leu Cys Asn Ser
    450                 455                 460

Pro Ser Pro Gln Met Asn Gly Lys Pro Cys Glu Gly Glu Ala Arg Glu
465                 470                 475                 480

Thr Lys Ala Cys Lys Lys Asp Ala Cys Pro Ile Asn Gly Gly Trp Gly
                485                 490                 495

Pro Trp Ser Pro Trp Asp Ile Cys Ser Val Thr Cys Gly Gly Gly Val
            500                 505                 510

Gln Arg Arg Ser Arg Leu Cys Asn Asn Pro Thr Pro Gln Phe Gly Gly
        515                 520                 525

Lys Asp Cys Val Gly Asp Val Thr Glu Asn Gln Val Cys Asn Lys Gln
530                 535                 540

Asp Cys Pro Ile Asp Gly Cys Leu Ser Asn Pro Cys Phe Ala Gly Ala
545                 550                 555                 560

Lys Cys Thr Ser Tyr Pro Asp Gly Ser Trp Lys Cys Gly Ala Cys Pro
                565                 570                 575

Pro Gly Tyr Ser Gly Asn Gly Ile Gln Cys Lys Asp Val Asp Glu Cys
            580                 585                 590

Lys Glu Val Pro Asp Ala Cys Phe Asn His Asn Gly Glu His Arg Cys
        595                 600                 605

Lys Asn Thr Asp Pro Gly Tyr Asn Cys Leu Pro Cys Pro Pro Arg Phe
610                 615                 620

Thr Gly Ser Gln Pro Phe Gly Arg Gly Val Glu His Ala Met Ala Asn
625                 630                 635                 640

Lys Gln Val Cys Lys Pro Arg Asn Pro Cys Thr Asp Gly Thr His Asp
                645                 650                 655

Cys Asn Lys Asn Ala Lys Cys Asn Tyr Leu Gly His Tyr Ser Asp Pro
            660                 665                 670

Met Tyr Arg Cys Glu Cys Lys Pro Gly Tyr Ala Gly Asn Gly Ile Ile
        675                 680                 685

Cys Gly Glu Asp Thr Asp Leu Asp Gly Trp Pro Asn Glu Asn Leu Val
690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
                725                 730                 735

Ala Cys Asp Asp Asp Asp Asp Asn Asp Lys Ile Pro Asp Asp Arg Asp
            740                 745                 750

Asn Cys Pro Phe His Tyr Asn Pro Ala Gln Tyr Asp Tyr Asp Arg Asp
        755                 760                 765

Asp Val Gly Asp Arg Cys Asp Asn Cys Pro Tyr Asn His Asn Pro Asp
770                 775                 780

Gln Ala Asp Thr Asp Lys Asn Gly Glu Gly Asp Ala Cys Ala Val Asp
785                 790                 795                 800

Ile Asp Gly Asp Gly Ile Leu Asn Glu Arg Asp Asn Cys Gln Tyr Val
                805                 810                 815

Tyr Asn Val Asp Gln Arg Asp Thr Asp Met Asp Gly Val Gly Asp
            820                 825                 830

<210> SEQ ID NO 99
<211> LENGTH: 2760
<212> TYPE: DNA
<213> ORGANISM: Homo sapiens
```

-continued

```
<400> SEQUENCE: 99
ccgggggcgc agccgcgggc ccacctcggc ctcccctgag cggacgcctc cccgcgcgca      60
ccgggggccc cggagaccgc cttccccgct ccgaacgcac gcggcccggc cccggcgagg     120
tgcctgaacg ctacccgagc tgcggcgggg ctcccggggt gagtgctgca gccccaggcc     180
cgcctgctcc cacaggctcg ggcaatggag accgcggcc gccccgccc cttgaccctg       240 cctcacccct cacgcccgct gccgcccacg acctccgacc ccgctgccgc ccggctcgca     300
gcccggctcg cagcccggct cggcgggcct cacctcccgc gggttccgca ctcctcttcc     360
cgccgtcctg ctcctctcgg ccttctcctc aataggcgc ctagcaccct gagtgggcta      420
caccaatcag agacgaagcg cgctaacgt gactgactaa ctaaccaatc caaagtctca      480
atctccctga gagggcgga gcgtacccgg gccagccctc gccgccgatt ggtgatcgac      540 ctcaggggttg caggggcggt gcccttacac ggattggaga gggcagcgat ggggcggagt    600
tcaagctccg attagtccgc gctccgtggc gggcttggcg attggacgcc ggcgctgtca     660
gccgcgcgcg gaccggggcg gggcgggcgg tgccccgggc tgggcgaggg gccgggtgcg     720
gggccgctgg ccgagaggct gaggcggcgt catgtcctcc gaggtgtccg cgcgccgcga     780
cgccaagaag ctggtgcgct ccccgagcgg cctgcgcatg gtgcccgaac accgcgcctt     840
cggaagcccg ttcggcctgg aggagccgca gtgggtcccg gacaaggagg tgggtgtatg     900
cagtgtgacg ccaagtttga ctttctcacc agaaagcacc actgtcgccg ctgcgggaag     960
tgcttctgcg acaggtgctg cagccagaag gtgccgctgc ggcgcatgtg ctttgtggac  1020
             cccgtgcgca agtgcgcgga gtgcgccctg gtgtcccctca aggaggcgga gttctacgac  1080
             aagcagctca agtgctcct gagcggagcc accttcctcg tcacgtttgg aaactcagag  1140
             aaacctgaaa ctatgacttg tcgtcttttcc aataaccaga gatacttgtt tctggatgga  1200
             gacagccact atgaaatcga aattgtacac atttccaccg tgcagatcct cacagaaggc  1260
             ttccctcctg gagaaaaaga cattcacgct tacaccagcc tccgggggag ccagcctgcc  1320
             tctgaaggag gcaacgcacg ggccacaggc atgttcctgc agtatacagt gccggggacg  1380
             gagggtgtga cccagctgaa gctgacagtg gtgaggacg tgactgtggg caggaggcag  1440
             gcggtggcgt ggctagtgat ctgcaggctg ccaagctcct ctatgaatct cgggaccagt  1500
             aactctacgt ggggctgagc ttggagtacg tgtggtcacc aggactgagt cgcttggaac  1560
             agcagagcct gctccttgcg taccacaggg attaatcctg cttgtgctgg gaaatgcaac  1620
             tcactcatgt atttggagaa acaggagtgt tcacttatct agtgcaatat gttcacagtt  1680
             tattaatgct ttaaacagct tcatgtttta gaatttgtgt attgtcaata cttaattggg  1740
             ggtgggagag actgagctac actactgcta aactattttt agcataatat ataccatttt  1800
             tatgagttcg caggtctact agaaggttct ggcccatcaa tattcatttc atttaattct  1860
             tccacagaac cagtttgggc agtaggaact caggcttctg gtctgcagtg gagcctgttc  1920
             gcctctaata gccagtttac agcacttgcc ttagcctgtt tcacagactt gtccacttac  1980
             cttgtcacta atttgggct tctgggctgt gagtgatcct ttgatacttc accaagggga  2040
             acgtggggc tttgtgtttt gtacttttca ctcactattt cacttttatt agatgactgt  2100
             acagcaattt gtatataaag cttatgatta aaacatacg tgaacatacg acaaggcct   2160
             cgccttcctg tgtccagatc acctgaaccc tcgtgccaca gcgcagtctg ggtccagaaa  2220
             gaagactcac agccgccggg gtgagacggg tttattgtgc acatttacac agcgtcagca  2280
             gcgtctgggc tggcagcgac catgctcctg tggtcgggct gctctacaag ggcgttcact  2340
             tttcttcacc acactatgta cagtcagtgc tccaaggtga tgggctacag tgctgcatca  2400
             gtgagtctgt acacacattt ttacataaat tacacacgac tcatacatga aaaatagagc  2460
             ctaagggcct gtatttttaat gagaaaaaaa aaatttccaa catagttcgg gtagctttga  2520
             atggtctagt caaaaaatac ttttggtata taaaaagcct gtacgtacaa ttcacaccctc  2580
             agtgaagcgc cctccttgcc ttgaggctgg gcctgggaca aggtggcct cacagccagc    2640
             ccaggcaggg agatcggcag agagggtgg ccctgaccc cagctcctct gccccagctg    2700
             ctgctccttg gtggcggccc ctcctgacac caggcgtctg ccatccttca ggcaccaaac   2760

<210> SEQ ID NO 100
<211> LENGTH: 206
<212> TYPE: PRT
<213> ORGANISM: Homo sapiens

<400> SEQUENCE: 100

Met Gln Cys Asp Ala Lys Phe Asp Phe Leu Thr Arg Lys His His Cys
  1               5                  10                  15

Arg Arg Cys Gly Lys Cys Phe Cys Asp Arg Cys Cys Ser Gln Lys Val
             20                  25                  30
```

-continued

```
Pro Leu Arg Arg Met Cys Phe Val Asp Pro Val Arg Gln Cys Ala Glu
         35                  40                  45

Cys Ala Leu Val Ser Leu Lys Glu Ala Glu Phe Tyr Asp Lys Gln Leu
 50                  55                  60

Lys Val Leu Leu Ser Gly Ala Thr Phe Leu Val Thr Phe Gly Asn Ser
 65                  70                  75                  80

Glu Lys Pro Glu Thr Met Thr Cys Arg Leu Ser Asn Asn Gln Arg Tyr
                 85                  90                  95

Leu Phe Leu Asp Gly Asp Ser His Tyr Glu Ile Glu Ile Val His Ile
                100                 105                 110

Ser Thr Val Gln Ile Leu Thr Glu Gly Phe Pro Pro Gly Glu Lys Asp
            115                 120                 125

Ile His Ala Tyr Thr Ser Leu Arg Gly Ser Gln Pro Ala Ser Glu Gly
        130                 135                 140

Gly Asn Ala Arg Ala Thr Gly Met Phe Leu Gln Tyr Thr Val Pro Gly
145                 150                 155                 160

Thr Glu Gly Val Thr Gln Leu Lys Leu Thr Val Val Glu Asp Val Thr
                165                 170                 175

Val Gly Arg Arg Gln Ala Val Ala Trp Leu Val Ile Cys Arg Leu Pro
            180                 185                 190

Ser Ser Ser Met Asn Leu Gly Thr Ser Asn Ser Thr Trp Gly
        195                 200                 205

<210> SEQ ID NO 101
<211> LENGTH: 673
<212> TYPE: DNA
<213> ORGANISM: Homo sapiens

<400> SEQUENCE: 101
gttccaacta ttttgtccgc ccacaggaat tcgcccttgg tgtatgcagt gtgacgccaa      60
gtttgacttt ctcaccagaa agcaccactg tcgccgctgc gggaagtgct tctgcgacag    120
gtgctgcagc cagaaggtgc cgctgcggcg catgtgcttt gtggaccccg tgcggcagtg    180
cgcggagtgc gccctggtgt ccctcaagga ggcggagttc tacgacaagc agctcaaagt    240
gctcctgagc ggagccacct tcctcgtcac gtttggaaac tcagagaaac ctgaaactat    300
gacttgtcgt ctttccaata accagagata cttgtttctg gatggagaca gccactatga    360
aatcgaaatt gtacacattt ccaccgtgca gatcctcaca gaaggcttcc ctcctggaga    420
aaaagacatt cacgcttaca ccagcctccg ggggagccag cctgcctctg aaggaggcaa    480
cgcacaggcc acaggcatgt tcctgcagta tacagtgccg ggacggaggg tgtgacccca    540
gctgaagctg acagtggtgg aggacgtgac tgtgggcagg aggcaggcgg tggcgtggct    600
agtggccatg cacaaggctg ccaagctcct ctatgaatct cgggaccagt aactctacgt    660
ggggctgagc ttg                                                       673

<210> SEQ ID NO 102
<211> LENGTH: 202
<212> TYPE: PRT
<213> ORGANISM: Homo sapiens

<400> SEQUENCE: 102

Met Gln Cys Asp Ala Lys Phe Asp Phe Leu Thr Arg Lys His His Cys
 1               5                  10                  15

Arg Arg Cys Gly Lys Cys Phe Cys Asp Arg Cys Cys Ser Gln Lys Val
             20                  25                  30
```

```
Pro Leu Arg Arg Met Cys Phe Val Asp Pro Val Arg Gln Cys Ala Glu
        35                  40                  45

Cys Ala Leu Val Ser Leu Lys Glu Ala Glu Phe Tyr Asp Lys Gln Leu
 50                  55                  60

Lys Val Leu Leu Ser Gly Ala Thr Phe Leu Val Thr Phe Gly Asn Ser
 65                  70                  75                  80

Glu Lys Pro Glu Thr Met Thr Cys Arg Leu Ser Asn Asn Gln Arg Tyr
                 85                  90                  95

Leu Phe Leu Asp Gly Asp Ser His Tyr Glu Ile Glu Ile Val His Ile
            100                 105                 110

Ser Thr Val Gln Ile Leu Thr Glu Gly Phe Pro Pro Gly Glu Lys Asp
            115                 120                 125

Ile His Ala Tyr Thr Ser Leu Arg Gly Ser Gln Pro Ala Ser Glu Gly
130                 135                 140

Gly Asn Ala Gln Ala Thr Gly Met Phe Leu Gln Tyr Thr Val Pro Gly
145                 150                 155                 160

Thr Glu Gly Val Thr Gln Leu Lys Leu Thr Val Val Glu Asp Val Thr
                165                 170                 175

Val Gly Arg Arg Gln Ala Val Ala Trp Leu Val Ala Met His Lys Ala
                180                 185                 190

Ala Lys Leu Leu Tyr Glu Ser Arg Asp Gln
            195                 200

<210> SEQ ID NO 103
<211> LENGTH: 234
<212> TYPE: PRT
<213> ORGANISM: Homo sapiens

<400> SEQUENCE: 103

Met Ser Ser Glu Val Ser Ala Arg Arg Asp Ala Lys Lys Leu Val Arg
  1               5                  10                  15

Ser Pro Ser Gly Leu Arg Met Val Pro Glu His Arg Ala Phe Gly Ser
                 20                  25                  30

Pro Phe Gly Leu Glu Glu Pro Gln Trp Val Pro Asp Lys Glu Cys Arg
            35                  40                  45

Arg Cys Met Gln Cys Asp Ala Lys Phe Asp Phe Leu Thr Arg Lys His
 50                  55                  60

His Cys Arg Arg Cys Gly Lys Cys Phe Cys Asp Arg Cys Cys Ser Gln
 65                  70                  75                  80

Lys Val Pro Leu Arg Arg Met Cys Phe Val Asp Pro Val Arg Gln Cys
                 85                  90                  95

Ala Glu Cys Ala Leu Val Ser Leu Lys Glu Ala Glu Phe Tyr Asp Lys
            100                 105                 110

Gln Leu Lys Val Leu Leu Ser Gly Ala Thr Phe Leu Val Thr Phe Gly
            115                 120                 125

Asn Ser Glu Lys Pro Glu Thr Met Thr Cys Arg Leu Ser Asn Asn Gln
130                 135                 140

Arg Tyr Leu Phe Leu Asp Gly Asp Ser His Tyr Glu Ile Glu Ile Val
145                 150                 155                 160

His Ile Ser Thr Val Gln Ile Leu Thr Glu Gly Phe Pro Pro Gly Gly
                165                 170                 175

Gly Asn Ala Arg Ala Thr Gly Met Phe Leu Gln Tyr Thr Val Pro Gly
                180                 185                 190

Thr Glu Gly Val Thr Gln Leu Lys Leu Thr Val Val Glu Asp Val Thr
```

```
                195                 200                 205
Val Gly Arg Arg Gln Ala Val Ala Trp Leu Val Ala Met His Lys Ala
        210                 215                 220

Ala Lys Leu Leu Tyr Glu Ser Arg Asp Gln
225                 230

<210> SEQ ID NO 104
<211> LENGTH: 212
<212> TYPE: PRT
<213> ORGANISM: Mus musculus

<400> SEQUENCE: 104

Met Val Pro Glu His Arg Ala Phe Gly Ser Pro Phe Gly Leu Glu Glu
  1               5                  10                  15

Pro Gln Trp Val Pro Asp Lys Glu Cys Pro Arg Cys Met Gln Cys Asp
             20                  25                  30

Ala Lys Phe Asp Phe Ile Thr Arg Lys His Cys Arg Arg Cys Gly
         35                  40                  45

Lys Cys Phe Cys Asp Arg Cys Cys Ser Gln Lys Val Pro Leu Arg Arg
 50                  55                  60

Met Cys Phe Val Asp Pro Val Arg Gln Cys Ala Asp Cys Ala Leu Val
 65                  70                  75                  80

Ser His Arg Glu Ala Glu Phe Tyr Asp Lys Gln Leu Lys Val Leu Leu
                 85                  90                  95

Ser Gly Ala Thr Phe Leu Val Thr Phe Gly Asp Ser Glu Lys Pro Glu
            100                 105                 110

Thr Met Val Cys Arg Leu Ser Asn Asn Gln Arg Cys Leu Val Leu Asp
        115                 120                 125

Gly Asp Ser His Arg Glu Ile Glu Ile Ala His Val Cys Thr Val Gln
130                 135                 140

Ile Leu Thr Glu Gly Phe Thr Pro Gly Ala Gly Ser Thr Leu Ala Thr
145                 150                 155                 160

Gly Met Leu Leu Gln Tyr Thr Val Pro Gly Ala Glu Ala Ala Ala Gln
                165                 170                 175

Leu Arg Leu Met Ala Gly Glu Asp Ala Ser Gly Ser Lys Arg Gln Ala
            180                 185                 190

Ala Ala Trp Leu Ala Ala Met His Lys Ala Thr Lys Leu Leu Tyr Glu
        195                 200                 205

Ser Arg Asp Gln
    210

<210> SEQ ID NO 105
<211> LENGTH: 327
<212> TYPE: PRT
<213> ORGANISM: Homo sapiens

<400> SEQUENCE: 105

Pro Ala Glu Arg Trp Val Ser Val Ser Ser Glu Glu Pro Arg Ala Pro
  1               5                  10                  15

Val Pro Ala Ser Val Arg Ala Pro Glu Arg Pro Leu Pro Gly Leu Arg
             20                  25                  30

Ser Ala Arg Arg Ala Ala Cys Arg Ala Tyr Ser Gly Pro Arg Thr Cys
         35                  40                  45

Pro Ala His Leu Pro Ala Ala Arg Ser Ala Leu Arg Ala Ser Leu Ala
     50                  55                  60

Ser Leu Pro Ala Thr Ala Arg Gly Leu Arg Pro Cys Leu Arg Val Arg
```

-continued

```
            65                  70                  75                  80
Pro Ala Pro Gln Pro Gly Pro Gly Ala Ala Leu Arg Arg Ala Arg Ala
                85                  90                  95
Ala Arg Ser Pro Ala Arg Ala Gly Ala Ala Met Met Asn Arg Phe Arg
            100                 105                 110
Lys Trp Leu Tyr Lys Pro Lys Arg Ser Asp Pro Gln Leu Leu Ala Arg
            115                 120                 125
Phe Tyr Tyr Ala Asp Glu Glu Leu Asn Gln Val Ala Ala Glu Leu Asp
            130                 135                 140
Ser Leu Asp Gly Arg Lys Asp Pro Gln Arg Cys Thr Leu Leu Val Ser
145                 150                 155                 160
Gln Phe Arg Ser Gln Asp Asn Val Leu Asn Ile Ile Asn Gln Ile
            165                 170                 175
Met Asp Glu Cys Ile Pro Gln Asp Arg Ala Pro Arg Asp Phe Cys Val
            180                 185                 190
Lys Phe Pro Glu Glu Ile Arg His Asp Asn Leu Ala Gly Gln Leu Trp
            195                 200                 205
Phe Gly Ala Glu Cys Leu Ala Ala Gly Ser Ile Ile Met Asn Arg Glu
            210                 215                 220
Leu Glu Ser Met Ala Met Arg Pro Leu Ala Lys Glu Leu Thr Arg Ser
225                 230                 235                 240
Leu Glu Asp Val Arg Gly Ala Leu Arg Asp Gln Ala Leu Arg Asp Leu
            245                 250                 255
Asn Thr Tyr Thr Glu Lys Met Arg Glu Ala Leu Arg His Phe Asp Val
            260                 265                 270
Leu Phe Ala Glu Phe Glu Leu Ser Tyr Val Ser Ala Met Val Pro Val
            275                 280                 285
Lys Ser Pro Arg Glu Tyr Tyr Val Gln Gln Glu Val Ile Val Leu Phe
            290                 295                 300
Cys Glu Thr Val Glu Arg Ala Leu Asp Phe Gly Tyr Leu Thr Gln Asp
305                 310                 315                 320
Met Ile Asp Asp Tyr Glu Pro
            325

<210> SEQ ID NO 106
<211> LENGTH: 173
<212> TYPE: PRT
<213> ORGANISM: Homo sapiens

<400> SEQUENCE: 106

Leu His His Lys Trp Leu Asn Ser His Ser Gly Arg Pro Ser Thr Thr
1               5                   10                  15
Ser Ser Pro Asp Gln Pro Ser Arg Ser His Leu Asp Asp Gly Met
            20                  25                  30
Pro Val Tyr Thr Asp Thr Ile Gln Gln Arg Leu Arg Gln Ile Glu Ser
            35                  40                  45
Gly His Gln Gln Glu Val Glu Thr Leu Lys Lys Gln Val Gln Glu Leu
        50                  55                  60
Lys Ser Arg Leu Glu Ser Gln Tyr Leu Thr Ser Ser Leu Arg Phe Asn
65                  70                  75                  80
Gly Asp Phe Gly Asp Glu Val Met Thr Arg Trp Leu Pro Asp His Leu
            85                  90                  95
Ala Ala His Cys Tyr Ala Cys Asp Ser Ala Phe Trp Leu Ala Ser Arg
            100                 105                 110
```

-continued

```
Lys His His Cys Arg Asn Cys Gly Asn Val Phe Cys Ser Ser Cys Cys
        115                 120                 125

Asn Gln Lys Val Pro Val Pro Ser Gln Gln Leu Phe Glu Pro Ser Arg
    130                 135                 140

Val Cys Lys Ser Cys Tyr Ser Ser Leu His Pro Thr Ser Ser Ser Ile
145                 150                 155                 160

Asp Leu Glu Leu Asp Lys Pro Ile Ala Ala Thr Ser Asn
                165                 170
```

<210> SEQ ID NO 107
<211> LENGTH: 597
<212> TYPE: PRT
<213> ORGANISM: Mus musculus

<400> SEQUENCE: 107

```
Met Ala Thr Asp Asp Lys Ser Pro Thr Leu Asp Ser Ala Asn Asp
1               5                   10                  15

Leu Pro Arg Ser Pro Ala Ser Pro Ser His Leu Thr His Phe Lys Pro
            20                  25                  30

Leu Thr Pro Asp Gln Asp Glu Pro Pro Phe Lys Ser Ala Tyr Ser Ser
        35                  40                  45

Phe Val Asn Leu Phe Arg Phe Asn Lys Glu Arg Gly Glu Gly Gly Gln
    50                  55                  60

Gly Glu Gln Gln Ser Pro Ser Ser Ser Trp Ala Ser Pro Gln Ile Pro
65                  70                  75                  80

Ser Arg Thr Gln Ser Val Arg Ser Pro Val Pro Tyr Lys Lys Gln Leu
                85                  90                  95

Asn Glu Glu Leu His Arg Arg Ser Ser Val Leu Glu Asn Thr Leu Pro
            100                 105                 110

His Pro Gln Glu Ser Thr Asp Ser Arg Arg Lys Ala Glu Pro Ala Cys
        115                 120                 125

Gly Gly His Asp Pro Arg Thr Ala Val Gln Leu Arg Ser Leu Ser Thr
    130                 135                 140

Val Leu Lys Arg Leu Lys Glu Ile Met Glu Gly Lys Ser Gln Asp Ser
145                 150                 155                 160

Asp Leu Lys Gln Tyr Trp Met Pro Asp Ser Gln Cys Lys Glu Cys Tyr
                165                 170                 175

Asp Cys Ser Glu Lys Phe Thr Phe Arg Arg Arg His His Cys Arg
            180                 185                 190

Leu Cys Gly Gln Ile Phe Cys Ser Arg Cys Cys Asn Gln Glu Ile Pro
        195                 200                 205

Gly Lys Phe Met Gly Tyr Thr Gly Asp Leu Arg Ala Cys Thr Tyr Cys
    210                 215                 220

Arg Lys Ile Ala Leu Ser Tyr Ala His Ser Thr Asp Ser Asn Ser Ile
225                 230                 235                 240

Gly Glu Asp Leu Asn Ala Leu Ser Asp Ser Thr Cys Ser Val Ser Ile
                245                 250                 255

Leu Asp Pro Ser Glu Pro Arg Thr Pro Val Gly Ser Arg Lys Ala Ser
            260                 265                 270

Arg Asn Ile Phe Leu Glu Asp Leu Ala Trp Gln Ser Leu Ile His
        275                 280                 285

Pro Asp Ser Ser Asn Ser Ala Leu Ser Thr Arg Leu Val Ser Val Gln
    290                 295                 300

Glu Asp Ala Gly Lys Ser Pro Ala Arg Asn Arg Ser Ala Ser Ile Thr
305                 310                 315                 320
```

```
Asn Leu Ser Leu Asp Arg Ser Gly Ser Pro Met Val Pro Ser Tyr Glu
                325                 330                 335

Thr Ser Val Ser Pro Gln Ala Asn Arg Asn Tyr Ile Arg Thr Glu Thr
            340                 345                 350

Thr Glu Asp Glu Arg Lys Ile Leu Leu Asp Ser Ala Gln Leu Lys Asp
        355                 360                 365

Leu Trp Lys Lys Ile Cys His His Thr Ser Gly Met Glu Phe Gln Asp
    370                 375                 380

His Arg Tyr Trp Leu Arg Thr His Pro Asn Cys Ile Val Gly Lys Glu
385                 390                 395                 400

Leu Val Asn Trp Leu Ile Arg Asn Gly His Ile Ala Thr Arg Ala Gln
                405                 410                 415

Ala Ile Ala Ile Gly Gln Ala Met Val Asp Gly Arg Trp Leu Asp Cys
            420                 425                 430

Val Ser His His Asp Gln Leu Phe Arg Asp Glu Tyr Ala Leu Tyr Arg
        435                 440                 445

Pro Leu Gln Ser Thr Glu Phe Ser Glu Thr Pro Ser Pro Asp Ser Asp
    450                 455                 460

Ser Val Asn Ser Val Glu Gly His Ser Glu Pro Ser Trp Phe Lys Asp
465                 470                 475                 480

Ile Lys Phe Asp Asp Ser Asp Thr Glu Gln Ile Ala Glu Glu Gly Asp
                485                 490                 495

Asp Asn Leu Ala Lys Tyr Leu Val Ser Asp Thr Gly Gly Gln Gln Leu
            500                 505                 510

Ser Ile Ser Asp Ala Phe Ile Lys Glu Ser Leu Phe Asn Arg Arg Val
        515                 520                 525

Glu Glu Lys Ser Lys Glu Leu Pro Phe Thr Pro Leu Gly Trp His His
    530                 535                 540

Asn Asn Leu Glu Leu Leu Arg Glu Glu Asn Glu Glu Lys Gln Ala Met
545                 550                 555                 560

Glu Arg Leu Leu Ser Ala Asn His Asn His Met Met Ala Leu Leu Gln
                565                 570                 575

Gln Leu Leu Gln Asn Glu Ser Leu Ser Ser Ser Trp Arg Asp Ile Ile
            580                 585                 590

Val Ser Leu Val Cys
        595

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 108
tggcttgatg atatgtgcct gtag                                            24

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 109
```
ttatagtacg agcaagaact ttgg                                      24

<210> SEQ ID NO 110
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 110
ttattgacag tttatcctgc cgcacct                                   27

<210> SEQ ID NO 111
<211> LENGTH: 26
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 111
aactactcgt gaggctgagg caggag                                    26

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 112
caatccttgc gtgtccttgc agtc                                      24

<210> SEQ ID NO 113
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 113
agcaagcaaa atcaggatgt tttcctc                                   27

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 114
caatccttgc gtgtccttgc agtc                                      24

<210> SEQ ID NO 115
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 115
agcaagcaaa atcaggatgt tttcctc                                   27

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 116
gctaccttca ccacctcctg ctgt                                          24

<210> SEQ ID NO 117
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 117
aagtgcagac ctataggcca atacagg                                       27

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 118
agaacccaag gctccctgga tt                                            22

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 119
catggaatta ttcaaatttg ctctg                                         25

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 120
gtagccacaa gaccgggtcc g                                             21

<210> SEQ ID NO 121
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 121
ccctggcctc ttggaactgc ttgat                                         25

<210> SEQ ID NO 122
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 122
ccgctggccg agaggctga                                              19

<210> SEQ ID NO 123
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 123
tgtttaaagc attaataaa                                              19

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 124
ctgaactcag ttggcaaagg                                             20

<210> SEQ ID NO 125
<211> LENGTH: 26
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 125
tctgtgggta aatcctcttt cacatg                                      26

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 126
agggccacat catgtatgtt ag                                          22

<210> SEQ ID NO 127
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 127
ggtgaacaga acctacctgt tg                                          22

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 128
gctctcgaaa gtgggctata tt                                              22

<210> SEQ ID NO 129
<211> LENGTH: 29
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 129 cactttttgtt ttatcttctc caaccacca                                      29

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 130
tctcctattc aggtgacttt cg                                              22

<210> SEQ ID NO 131
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 131
gccctgatca agttttcata cc                                              22

<210> SEQ ID NO 132
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 132
cacatagctc agcctgctct gagttga                                         27

<210> SEQ ID NO 133
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 133
tgtcaactcc acatgaatca aa                                              22

<210> SEQ ID NO 134

```
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 134
tcctacccag cttctgaatt ct                                            22

<210> SEQ ID NO 135
<211> LENGTH: 26
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 135
tacttgggta ccaccctgcg gacaat                                        26

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 136
aacactctgt tctgcaatga ca                                            22

<210> SEQ ID NO 137
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 137
atatgattga gaaggcccaa ac                                            22

<210> SEQ ID NO 138
<211> LENGTH: 29
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 138
cctttaaaat ttagatctgt gtctcccca                                     29

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 139
ctgtgtctcc agagaggtct ga                                            22

<210> SEQ ID NO 140
<211> LENGTH: 20
```

```
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 140
ctggacaggt tagggctttg                                                     20

<210> SEQ ID NO 141
<211> LENGTH: 26
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 141
ccttctggaa gtctgccagt gtcctt                                              26

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 142
tgagagagtt ctgggtgtcc ta                                                  22

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 143
ctgccctgct acttgctcta c                                                   21

<210> SEQ ID NO 144
<211> LENGTH: 26
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 144
caccattgtc gtggctacat catcct                                              26

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 145
aggaccatct tgagcttgga                                                     20

<210> SEQ ID NO 146
<211> LENGTH: 20
<212> TYPE: DNA
```

```
<213> ORGANISM: Artificial Sequence
<220> FEATURE:
<223> OTHER INFORMATION: Description of Artificial Sequence:
      oligonucleotide primer

<400> SEQUENCE: 146
gacggtcaca ggtcctcgat                                              20

<210> SEQ ID NO 147
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 147
tgcacgcgta gccacaagac cg                                           22

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 148
gggaacggca accagaaac                                               19

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 149
ccagatcctt tctccttgat ct                                           22

<210> SEQ ID NO 150
<211> LENGTH: 28
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 150
ccaaactttc cagatctttc caaagctg                                     28

<210> SEQ ID NO 151
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 151
tgacctggat atttggattc tg                                           22

<210> SEQ ID NO 152
<211> LENGTH: 21
<212> TYPE: DNA
<213> ORGANISM: Artificial Sequence
```

```
<220> FEATURE:
<223> OTHER INFORMATION: Description of Artificial Sequence:
      oligonucleotide primer

<400> SEQUENCE: 152
aacagaatcg aggacctgtg a                                              21

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 153
ccagcttgca ccggattcct gat                                            23

<210> SEQ ID NO 154
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 154
ccctaaccaa gcttccttta ca                                             22

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 155
gagtgggcta caccaatcag                                                20

<210> SEQ ID NO 156
<211> LENGTH: 26
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 156
agcggcgcta acgtgactga ctaact                                         26

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 157
ccctctcagg gagattgaga                                                20

<210> SEQ ID NO 158
<211> LENGTH: 22
<212> TYPE: DNA
```

-continued

```
<213> ORGANISM: Artificial Sequence
<220> FEATURE:
<223> OTHER INFORMATION: Description of Artificial Sequence:
      oligonucleotide primer

<400> SEQUENCE: 158
ccctgaaata cacagaggac at                                             22

<210> SEQ ID NO 159
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 159
atggaatccc tggccctgtc taatg                                          25
```